United States Patent
Sadelain et al.

(10) Patent No.: US 11,753,654 B2
(45) Date of Patent: Sep. 12, 2023

(54) GLOBIN GENE THERAPY FOR TREATING HEMOGLOBINOPATHIES

(71) Applicant: MEMORIAL SLOAN-KETTERING CANCER CENTER, New York, NY (US)

(72) Inventors: Michel Sadelain, New York, NY (US); Annalisa Cabriolu, Villacidro (IT)

(73) Assignee: MEMORIAL SLOAN-KETTERING CANCER CENTER, New York, NY (US)

(*) Notice: Subject to any disclaimer, the term of this patent is extended or adjusted under 35 U.S.C. 154(b) by 427 days.

(21) Appl. No.: 16/890,436

(22) Filed: Jun. 2, 2020

(65) Prior Publication Data
US 2020/0291433 A1 Sep. 17, 2020

Related U.S. Application Data

(63) Continuation of application No. PCT/US2018/064256, filed on Dec. 6, 2018.

(60) Provisional application No. 62/595,277, filed on Dec. 6, 2017.

(51) Int. Cl.
*C12N 15/86* (2006.01)
*A61P 7/00* (2006.01)
*C12N 9/22* (2006.01)

(52) U.S. Cl.
CPC .............. *C12N 15/86* (2013.01); *A61P 7/00* (2018.01); *C12N 9/22* (2013.01); *C12N 2310/20* (2017.05); *C12N 2830/008* (2013.01); *C12N 2830/15* (2013.01); *C12N 2830/30* (2013.01)

(58) Field of Classification Search
None
See application file for complete search history.

(56) References Cited

U.S. PATENT DOCUMENTS

| | | |
|---|---|---|
| 4,873,192 A | 10/1989 | Kunkel |
| 5,399,346 A | 3/1995 | Anderson et al. |
| 5,399,363 A | 3/1995 | Liversidge et al. |
| 5,543,158 A | 8/1996 | Gref et al. |
| 5,641,515 A | 6/1997 | Ramtool |
| 5,725,871 A | 3/1998 | Illum |
| 5,756,353 A | 5/1998 | Debs |
| 5,780,045 A | 7/1998 | McQuinn et al. |
| 5,804,212 A | 9/1998 | Illum |
| 6,797,494 B1 | 9/2004 | Antoniou et al. |
| 7,541,179 B2 | 6/2009 | Sadelain et al. |
| 2009/0054985 A1 | 2/2009 | Anderson |
| 2009/0156534 A1 | 6/2009 | Lisowski et al. |
| 2011/0301073 A1 | 12/2011 | Gregory et al. |
| 2017/0173185 A1 | 6/2017 | Sadelain et al. |
| 2020/0109416 A1* | 4/2020 | Kohn .............. C12N 15/63 |

FOREIGN PATENT DOCUMENTS

| | | | |
|---|---|---|---|
| WO | WO 2015/138852 | 9/2015 | |
| WO | WO-2016037138 A1 * | 3/2016 | ......... A61K 48/0058 |

OTHER PUBLICATIONS

Levasseur et al. Blood, vol. 102, pp. 4312-4319 (Year: 2003).*
Adams et al., "Binding of Disparate Transcriptional Activators to Nucleosomal DNA Is Inherently Cooperative," Molecular and Cellular Biology 15(3):1405-1421 (1995).
Aker et al., "Extended Core Sequences from the cHS4 Insulator Are Necessary for Protecting Retroviral Vectors from Silencing Position Effects," Hum Gene Ther 18:333-343 (2007).
Anderson, "Prospects for Human Gene Therapy," Science 226(4673):401-409 (1984).
Antoniou et al., "The human β-globin gene contains multiple regulatory regions: identification of one promoter and two downstream enhancers," EMBO J., 7(2):377-384 (1988).
Armstrong et al., "NF-E2 Disrupts Chromatin Structure at Human β-Globin Locus Control Region Hypersensitive Site 2 In Vitro," Mol. Cell. Biol. 16(10):5634-5644 (1996).
Arumugam et al., "Genotoxic Potential of Lineage-specific Lentivirus Vectors Carrying the β-Globin Locus Control Region," Mol Ther 17(11):1929-1937 (2009).
Arumugam et al., "Improved Human β-globin Expression from Self-inactivating Lentiviral Vectors Carrying the Chicken Hypersensitive Site-4 (cHS4) Insulator Element," Mol Ther 15(10):1863-1871 (2007).
Atweh et al., "Pharmacological Induction of Fetal Hemoglobin in Sickle Cell Disease and β-Thalassemia," Semin Hematol 38:367-373 (2001).
Bank et al., "A Phase I/II Clinical Trial of β-Globin Gene Therapy for β-Thalassemia," Ann N.Y. Acad. Sci. 1054:308-316 (2005).
Barski et al., "High-Resolution Profiling of Histone Methylations in the Human Genome," Cell 129:823-837 (2007).
Baum et al., "Mutagenesis and Oncogenesis by Chromosomal Insertion of Gene Transfer Vectors," Hum Gene Ther 17:253-263 (2006).
Belfort et al., "Homing endonucleases: keeping the house in order," Nucleic Acids Res., 25(17):3379-3388 (1997).
Bell et al., "The Protein CTCF Is Required for the Enhancer Blocking Activity of Vertebrate Insulators," Cell 98:387-396 (1999).
Benton et al., "Screening lambdagt recombinant clones by hybridization to single plaques in situ," Science, 196(4286):180-182 (1977).
Blomer et al., "Highly Efficient and Sustained Gene Transfer in Adult Neurons with a Lentivirus Vector," Journal of Virology 71:6641-6649 (1997).

(Continued)

*Primary Examiner* — Brian Whiteman
(74) *Attorney, Agent, or Firm* — Baker Botts L.L.P.

(57) ABSTRACT

The presently disclosed subject matter provides for expression cassettes that allow for expression of a globin gene or a functional portion thereof, vectors comprising thereof, and cells transduced with such expression cassettes and vectors. The presently disclosed subject matter further provides methods for treating a hemoglobinopathy in a subject comprising administering an effective amount of such transduced cells to the subject.

14 Claims, 21 Drawing Sheets
Specification includes a Sequence Listing.

(56) References Cited

OTHER PUBLICATIONS

Borgna-Pignatti et al., "Survival and complications in patients with thalassemia major treated with transfusion and deferoxamine," Haematologica 89:1187-1193 (2004).
Boulad et al., "Bone Marrow Transplantation for Homozygous β-Thalassemia. The Memorial Sloan-Kettering Cancer Center Experience," Ann NY Acad Sci 850:498-502 (1998).
Braun et al., "Gene Therapy for Wiskott-Aldrich Syndrome-Long-Term Efficacy and Genotoxicity," Sci Transl Med 6:227ra33 (2014).
Bregni, et al., "Human Peripheral Blood Hematopoietic Progenitors Are Optimal Targets of Retroviral-Mediated Gene Transfer," Blood 80(6):1418-1422 (1992).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Brownell et al., "Special HATs for special occasions: linking histone acetylation to chromatin assembly and gene activation," Curr Opin Genet Dev 6:176-184 (1996).
Bulger et al., "Conservation of sequence and structure flanking the mouse and human β-globin loci: The β-globin genes are embedded within an array of odorant receptor genes," Proc. Natl. Acad. Sci. 96:5129-5134 (1999).
Bungert et al., "Hypersensitive Site 2 Specifies a Unique Function within the Human β-Globin Locus Control Region To Stimulate Globin Gene Transcription," Mol. and Cell Biol. 19(4):3062-3072 (1999).
Burgess-Beusse et al., "The insulation of genes from external enhancers and silencing chromatin," PNAS USA 99(Suppl 4):16433-16437 (2002).
Caterina et al., "Multiple elements in human β-globin locus control region 5' HS 2 are involved in enhancer activity and position-independent, transgene expression," Nucleic Acids Res. 22(6):1006-1011 (1994).
Cavazzana-Calvo et al., "Transfusion independence and HMGA2 activation after gene therapy of human β-thalassaemia," Nature 467:318-322 (2010).
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).
Chang et al., "Correction of the sickle cell mutation in embryonic stem cells," Proc Natl Acad Sci 103(4):1036-1040 (2006).
Chang et al., "Epigenetic Modifications and Chromosome Conformations of the Beta Globin Locus throughout Development," Stem Cell Rev and Rep 9:397-407 (2013).
Chang et al., "Lentiviral siRNAs targeting multiple highly conserved RNA sequences of human immunodeficiency virus type 1," Gene Ther 12:1133-1144 (2005).
Chang et al., "The Genetic Engineering of Hematopoietic Stem Cells: the Rise of Lentiviral Vectors, the Conundrum of the LTR, and the Promise of Lineage-Restricted Vectors," Mol Ther 15(3):445-456 (2007).
Charache et al., "Hydroxyurea: Effects on Hemoglobin F Production in Patients With Sickle Cell Anemia," Blood 79(10):2555-2565 (1992).
Chung et al. "A 5' Element of the Chicken β-Globin Domain Serves as an Insulator in Human Erythroid Cells and Protects against Position Effect in *Drosophila*," Cell, 74: 505-514 (1993).
Chung et al., "Characterization of the chicken β-globin insulator," PNAS USA 94:575-580 (1997).
Collis et al., "Definition of the minimal requirements within the human β-globin gene and the dominant control region for high level expression," The EMBO Journal 9(1):233-240 (1990).
Cooley, T.B. & Lee, P., "A Series of Cases of Splenomegaly in Children with Anemia and Peculiar Bone Changes," Trans. Am. Pediatr. Soc. 37:29 (1925).
Cornetta et al., "Gene Transfer into Primates and Prospects for Gene Therapy in Humans," Nucleic Acid Research and Molecular Biology 36:311-322 (1987).

Danos, et al., "Safe and efficient generation of recombinant retroviruses with amphotropic and ecotropic host ranges," Proc. Natl. Acad. Sci. USA 85:6460-6464 (1988).
Dayhoff et al., "A Model of Evolutionary Change in Proteins," Atlas of Protein Sequence and Structure, pp. 345-352 (1978).
Dickson et al., "VEZF1 Elements Mediate Protection from DNA Methylation," PLoS Genet 6:e1000804 (2010).
Dorschner et al., "High-throughput localization of functional elements by quantitative chromatin profiling," Nat Methods 1(3):219-225 (2004).
Dull et al., "A Third-Generation Lentivirus Vector with a Conditional Packaging System," Journal of Virology 72(11):8463-8471 (1998).
Eglitis et al., "Retroviral Vectors for Introduction of Genes into Mammalian Cells," BioTechniques 6(7):608-614 (1988).
Elgin, "DNAase I-Hypersensitive Sites of Chromatin," Cell 27:413-415 (1981).
Elgin, S.C., "Molecular Biology. Anatomy of hypersensitive sites," Nature 309:213-214 (1984).
Ellis et al., "A Dominant chromatin-opening activity in 5' hypersensitive site 3 of the human β-globin locus control region," The EMBO Journal 15(3):562-568 (1996).
Elnitski et al., "Conserved E Boxes Function as Part of the Enhancer in Hypersensitive Site 2 of the β-Globin Locus Control Region," The Journal of Biological Chemistry 272(1):369-378 (1997).
Emery et al., "A chromatin insulator protects retrovirus vectors from chromosomal position effects," PNAS USA 97(16):9150-9155 (2000).
Emery et al., "Development of a Condensed Locus Control Region Cassette and Testing in Retrovirus Vectors for $^A\gamma$-Globin," Blood Cells, Molecules, and Diseases 24(16):322-339 (1998).
Emery et al., "Development of virus vectors for gene therapy of β chain hemoglobinopathies: flanking with a chromatin insulator reduces γ-globin gene silencing in vivo," Blood 100:2012-2019 (2002).
Emery, "The Use of Chromatin Insulators to Improve the Expression and Safety of Integrating Gene Transfer Vectors," Hum Gene Ther 22:761-774 (2011).
Evans-Galea et al., "Suppression of Clonal Dominance in Cultured Human Lymphoid Cells by Addition of the cHS4 Insulator to a Lentiviral Vector," Mol Ther 15(4):801-809 (2007).
Feigner et al., "Lipofection: A highly efficient, lipid-mediated DNA-transfection procedure," Proc. Natl. Acad. Sci. USA 84:7413-7417 (1987).
Felsenfeld et al., "Chromatin structure and gene expression," PNAS USA 93:9384-9388 (1996).
Felsenfeld et al., "Controlling the double helix," Nature 421:448-453 (2003).
Felsenfeld, "Chromatin as an essential part of the transcriptional mechanism," Nature 355:219-224 (1992).
Follenzi et al., "Gene transfer by lentiviral vectors is limited by nuclear translocation and rescued by HIV-1 pol sequences," Nature Genetics 25:217-222 (2000).
Fraser et al., "Each hypersensitive site of the human β-globin locus control region confers a different developmental pattern of expression on the globin genes," Genes & Development 7:106-113 (1993).
Friedmann, "Progress Toward Human Gene Therapy," Science 244(4910):1275-1281 (1989).
Gaszner et al., "Insulators: exploiting transcriptional and epigenetic mechanisms," Nat Rev Genet 7:703-713 (2006).
Giardina et al., "Chelation Therapy in β-Thalassemia: An Optimistic Update," Semin Hematol 38:360-366 (2001).
Giardini et al., "Bone marrow transplantation in the treatment of thalassemia," Current Opinion in Hematology 1:170-176 (1994).
Giles et al., "Chromatin Boundaries, Insulators, and Long-Range Interactions in the Nucleus," Cold Spring Harbor Symposia on Quantitative Biology 75:79-85 (2010).
Gross et al., "Nuclease Hypersensitive Sites in Chromatin," Ann Rev Biochem 57:159-197 (1988).
Grosveld et al., "Position-Independent, High-Level Expression of the Human β-Globin Gene in Transgenic Mice," Cell 51:975-985 (1987).

(56) References Cited

OTHER PUBLICATIONS

Grunstein et al., "Colony hybridization: A method for the isolation of cloned DNAs that contain a specific gene," Proc. Natl. Acad. Sci. USA 72(10):3961-3965 (1975).
Hanawa et al., "Optimized Lentiviral Vector Design Improves Titer and Transgene Expression of Vectors Containing the Chicken β-Globin Locus HS4 Insulator Element," Mol Ther 17(4):667-674 (2009).
Hanna et al., Treatment of Sickle Cell Anemia Mouse Model with iPS Cells Generated from Autologous Skin, Science 318:1920-1923 (2007).
Hardison et al., "Locus control regions of mammalian β-globin gene clusters: combining phylogenetic analyses and experimental results to gain functional insights," Gene 205:73-94 (1997).
Hino et al., "Sea urchin insulator protects lentiviral vector from silencing by maintaining active chromatin structure," Gene Ther 11:819-828 (2004).
Horak et al., "GATA-1 binding sites mapped in the β-globin locus by using mammalian chip-chip analysis," PNAS 99(5):2924-2929 (2002).
Hug et al., "Analysis of Mice Containing a Targeted Deletion of β-Globin Locus Control Region 5' Hypersensitive Site 3," Mol. and Cell Biol. 16(6):2906-2912 (1996).
Hughes et al., "Retroviral Gene Transfer to Primitive Normal and Leukemic Hematopoietic Cells Using Clinically Applicable Procedures," J. Clin. Invest. 89:1817-1824 (1992).
International Search Report dated May 14, 2019 in International Application No. PCT/US18/64256.
Jakobsson et al., "Dynamics of transgene expression in a neural stem cell line transduced with lentiviral vectors incorporating the cHS4 insulator," Experimental Cell Research 298:611-623 (2004).
Jinek et al., A Programmable Dual-RNA-Guided DNA Endonuclease in Adaptive Bacterial Immunity, Science 337:816-821 (2012).
Johnson et al., "Highly Restricted Localization of RNA Polymerase II within a Locus Control Region of a Tissue-Specific Chromatin Domain," Molecular and Cellular Biology 23(18):6484-6493 (2003).
Johnson, "Gene Therapy for Cystic Fibrosis," Chest 107(2):77S-83S (1995).
Kadonaga, "Eukaryotic Transcription: An Interlaced Network of Transcription Factors and Chromatin-Modifying Machines," Cell 92:307-313 (1998).
Kido et al., "Use of retroviral vector with an internal opsin promoter to direct gene expression to retinal photoreceptor cells," Current Eye Research 15:833-844 (1996).
Kim et al., "Analysis of the Vertebrate Insulator Protein CTCF-Binding Sites in the Human Genome," Cell 128:1231-1245 (2007).
Kim et al., "Hybrid restriction enzymes: Zinc finger fusions to Fok I cleavage domain" Proc. Natl. Acad. Sci. USA 93:1156-1160(1996).
Kimmel, "[54] Identification and Characterization of Specific Clones: Strategy for Confirming the Validity of Presumptive Clones," Methods in Enzymology 152:507-511 (1987).
Kingston et al., "ATP-dependent remodeling and acetylation as regulators of chromatin fluidity," Genes & Development 13:2339-2352 (1999).
Kunkel et al., "Rapid and Efficient Site-Specific Mutagenesis without Phenotypic Selection," Methods in Enzymol, 154:367-382 (1987).
Kunkel, "Rapid and efficient site-specific mutagenesis without phenotypic selection," Proc. Natl. Acad. Sci. USA 82:488-492 (1985).
Ladis et al., "Survival in a large cohort of Greek patients with transfusion-dependent beta thalassaemia and mortality ratios compared to the general population," European Journal of Haematology 86:332-338 (2011).
Le Gal La Salle et al., "An Adenovirus Vector for Gene Transfer into Neurons and Glia in the Brain," Science 259:988-990 (1993).
Leboulch et al., "Mutagenesis of retroviral vectors transducing human β-globin gene and β-globin locus control region derivatives results in stable transmission of an active transcriptional structure," EMBO J 13(13):3065-3076 (1994).
Levings et al., "Recruitment of transcription complexes to the β-globin locus control region and transcription of hypersensitive site 3 prior to erythroid differentiation of murine embryonic stem cells," The FEBS Journal 273:746-755 (2006).
Ley et al., "Reduced β-Globin Gene Expression in Adult Mice Containing Deletions of Locus Control Region 5' HS-2 or 5' HS-3a," Ann. N.Y. Acad. Sci. 850:45-53 (1998).
Li et al., "Evidence that DNase I hypersensitive site 5 of the human β-globin locus control region functions as a chromosomal insulator in transgenic mice," Nucleic Acids Res 30(11):2484-2491 (2002).
Li et al., "Genomic and Functional Assays Demonstrate Reduced Gammaretroviral Vector Genotoxicity Associated With Use of the cHS4 Chromatin Insulator," Mol Ther 17(4):716-724 (2009).
Li et al., "Hypersensitive Site 5 of the Human β Locus Control Region Functions as a Chromatin Insulator," Blood 84(5):1399-1401 (1994).
Li et al., "Primary Structure of the Goat β-Globin Locus Control Region," Genomics 9:488-499 (1991).
Li et al., "The cHS4 chromatin insulator reduces gammaretroviral vector silencing by epigenetic modifications of integrated provirus," Gene Ther 15:49-53 (2008).
Li et al., "Nucleotide Sequence of 16-Kilobase Pairs of DNA 5' to the Human ε-Globin Gene," J. Biol. Chem. 260(28):14901-14910 (1985).
Li et al., "β-Globin locus activation regions: Conservation of organization, structure, and function," Proc. Natl. Acad. Sci. USA 87:8207-8211 (1990).
Lisowski et al., "Locus control region elements HS1 and HS4 enhance the therapeutic efficacy of globin gene transfer in β-thalassemic mice," Blood 110(13):4175-4178 (2007).
Lowrey et al., "Mechanism of DNase I hypersensitive site formation within the human globin locus control region," PNAS USA 89:1143-1147 (1992).
Lucarelli et al., "Bone Marrow Transplantation in Adult Thalassemic Patients," Blood 93(4):1164-1167 (1999).
Luzzatto et al., "Sickle cell anaemia. A simple disease with no cure," Nature 337:17-18 (1989).
Ma et al., "High-Level Sustained Transgene Expression in Human Embryonic Stem Cells Using Lentiviral Vectors," Stem Cells 21:111-117 (2003).
Mancuso et al., "A Prospective Study of Hepatocellular Carcinoma Incidence in Thalassemia," Hemoglobin 30(1):119-124 (2006).
Margot et al., "Complete Nucleotide Sequence of the Rabbit β-like Globin Gene Cluster: Analysis of Intergenic Sequences and Comparison with the Human β-like Globin Gene Cluster," J. Mol. Biol. 205:15-40 (1989).
Maurano et al., "Systematic Localization of Common Disease-Associated Variation in Regulatory DNA," Science 337:1190-1195 (2012).
May et al., "Successful treatment of murine β-thalassemia intermedia by transfer of the human β-globin gene," Blood 99:1902-1908 (2002).
May et al., "Therapeutic haemoglobin synthesis in β-thalassaemic mice expressing lentivirus-encoded human β-globin," Nature 406:82-86 (2000).
McArthur et al., "Quantification of DNaseI-sensitivity by Real-time PCR: Quantitative Analysis of DNaseI-hypersensitivity of the Mouse β-Globin LCR," J Mol Biol 313:27-34 (2001).
McGhee et al., "A 200 Base Pair Region at the 5' End of the Chicken Adult β-Globin Gene Is Accessible to Nuclease Digestion," Cell 27:45-55 (1981).
Meissner et al., "Direct reprogramming of genetically unmodified fibroblasts into pluripotent stem cells," Nature Biotechnology 25:1177-1181 (2007).
Miccio et al., "In vivo selection of genetically modified erythroblastic progenitors leads to long-term correction of β-thalassemia," PNAS USA 105(30):10547-10552 (2008).
Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).

(56) References Cited

OTHER PUBLICATIONS

Miller et al., "Improved Retroviral Vectors for Gene Transfer and Expression," Biotechniques 7(9):980-990 (1989).
Miller et al., "Redesign of retrovirus packaging cell lines to avoid recombination leading to helper virus production," Mol. Cell. Biol. 6(8):2895-2902 (1986).
Miller, "Retrovirus Packaging Cells," Human Gene Therapy 1:5-14 (1990).
Miyoshi et al., "Development of a Self-Inactivating Lentivirus Vector," J. Virol. 72(10):8150-8157 (1998).
Miyoshi et al., "Stable and efficient gene transfer into the retina using an HIV-based lentiviral vector," Proc. Natl. Acad. Sci. USA 94:10319-10323 (1997).
Moen, "Directions in Gene Therapy," Blood Cells 17:407-416 (1991).
Moi et al., "Synergistic enhancement of globin gene expression by activator protein-1-like proteins," PNAS USA 87:9000-9004 (1990).
Moi et al., "Towards the genetic treatment of β-thalassemia: new disease models, new vectors, new cells," Haematologica 93(3):325-330 (2008).
Nagel et al., "Structural bases of the inhibitory effects of hemoglobin F and hemoglobin A2 on the polymerization of hemoglobin S," PNAS USA 76(2):670-672 (1979).
Nakagawa et al., "Generation of induced pluripotent stem cells without Myc from mouse and human fibroblasts," Nat Biotechnol 26:101-106 (2008).
Naldini et al., "In Vivo Gene Delivery and Stable Transduction of Nondividing Cells by a Lentiviral Vector," Science 272:263-267 (1996).
Naldini et al., "Efficient transfer, integration, and sustained long-term expression ofthe transgene in adult rat brains injected with a lentiviralvector," Proc. Natl. Acad. Sci. USA 93:11382-11388 (1996).
Navas et al., "Developmental specificity of the Interaction between the Locus Control Region and Embryonic or Fetal Globin Genes in Transgenic Mice with an HS3 Core Deletion," Molecular and Cellular Biology 18(7):4188-4196 (1998).
Neph et al., "An expansive human regulatory lexicon encoded in transcription factor footprints," Nature 489:83-90 (2012).
Neph et al., "Circuitry and Dynamics of Human Transcription Factor Regulatory Networks," Cell 150:1274-1286 (2012).
Ney et al., "Tandem AP-1-binding sites within the human β-globin dominant control region function as an inducible enhancer in erythroid cells," Genes & Dev. 4:993-1006 (1990).
Nienhuis et al., "Genotoxicity of Retroviral Integration In Hematopoietic Cells," Mol Ther 13(6):1031-1049 (2006).
Nienhuis, "Development of gene therapy for blood disorders: an update," Blood 122(9):1556-1564 (2013).
Nishino et al. "Partial correction of murine β-thalassemia with a gammaretrovirus vector for human γ-globin," Blood Cells Mol Dis 37:1-7 (2006).
Okita et al., "Generation of germline-competent induced pluripotent stem cells," Nature 448:313-317 (2007).
Ono et al., "Plasmid DNAs directly injected into mouse brain with lipofectin can be incorporated and expressed by brain cells," Neuroscience Letters 117:259-263 (1990).
Papapetrou et al., "Genomic safe harbors permit high β-globin transgene expression in thalassemia induced pluripotent stem cells," Nat Biotechnol. 29(1):73-78 (2011).
Papayannopoulou et al., "Hemopoietic lineage commitment decisions: in vivo evidence from a transgenic mouse model harboring μLCR-βpro-LacZ as a transgene," Blood 95:1274-1282 (2000).
Park et al., "Reprogramming of human somatic cells to pluripotency with defined factors," Nature 451:141-146 (2007).
Pauling et al., "Sickle Cell Anemia, a Molecular Disease," Science 110:543-548 (1949).
Pawliuk et al., "Correction of Sickle Cell Disease in Transgenic Mouse Models by Gene Therapy," Science 294:2368-2371 (2001).
Perrine et al., "Induction of Fetal Globin in β-Thalassemia: Cellular Obstacles and Molecular Progress," Ann, N.Y. Acad. Sci. 1054:257-265 (2005).
Persons et al., "Gene Therapy for the Hemoglobin Disorders," Semin Hematol 41:279-286 (2004).
Persons, "The challenge of obtaining therapeutic levels of genetically modified hematopoietic stem cells in β-thalassemia patients," Ann NY Acad Sci 1202:69-74 (2010).
Perumbeti et al., "Therapy for β-globinopathies: a brief review and determinants for successful and safe correction," Ann NY Acad Sci 1202:36-44 (2010).
Pestina et al., "Correction of Murine Sickle Cell Disease Using γ-Globin Lentiviral Vectors to Mediate High-Level Expression of Fetal Hemoglobin," Molecular Therapy 17(2):245-252 (2009).
Phillips et al., "CTCF: Master Weaver of the Genome," Cell 137:1194-1211 (2009).
Pikaart et al., "Loss of transcriptional activity of a transgene is accompanied by DNA methylation and histone deacetylation and is prevented by insulators," Genes & Development 12:2852-2862 (1998).
Platt et al., "Hydroxyurea Enhances Fetal Hemoglobin Production in Sickle Cell Anemia," J. Clin. Invest. 74:652-656 (1984).
Pluta et al., "Tight control of transgene expression by lentivirus vectors containing second-generation tetracycline-responsive promoters," J Gene Med 7:803-817 (2005).
Prioleau et al., "An insulator element and condensed chromatin region separate the chicken β-globin locus from an independently regulated erythroid-specific folate receptor gene," EMBO J. 18(14):4035-4048 (1999).
Pruzina et al., "Hypersensitive site 4 of the human β globin locus control region," Nucleic Acids Research 19(7):1413-1419 (1991).
Puthenveetil et al., "Successful correction of the human β-thalassemia major phenotype using a lentiviral vector," Blood 104:3445-3453 (2004).
Ramezani et al., "Combinatorial Incorporation of Enhancer-Blocking Components of the Chicken β-Globin 5'HS4 and Human T-cell Receptor α/δBEAD-1 Insulators in SelfInactivating Retroviral Vectors Reduces Their Genotoxic Potential," Stem Cells 26:3257-3266 (2008).
Ramezani et al., "Performance- and safety-enhanced lentiviral vectors containing the human interferon-β scaffold attachment region and the chicken β-globin insulator," Blood 101:4717-4724 (2003).
Ramezani et al., "Stable Gammaretroviral Vector Expression during Embryonic Stem Cell-Derived In Vitro Hematopoietic Development," Mol Ther 14(2):245-254 (2006).
Recillas-Targa et al., "Position-effect protection and enhancer blocking by the chicken β-globin insulator are separable activities," PNAS USA 99(10):6883-6888 (2002).
Renda et al., "Critical DNA Binding Interactions Of The Insulator Protein CTCF: A Small No. of Zinc Fingers Mediate Strong Binding, and a Single Finger-DNA Interaction Controls Binding at Imprinted Loci," J Biol Chem 282(46):33336-33345 (2007).
Rivella et al., "A novel murine model of Cooley anemia and its rescue by lentiviral-mediated human β-globin gene transfer," Blood 101:2932-2939 (2003).
Rivella et al., "The cHS4 Insulator Increases the Probability of Retroviral Expression at Random Chromosomal Integration Sites," J Virol 74(10):4679-4687 (2000).
Rosenberg et al., "Gene Transfer into Humans—Immunotherapy of Patients with Advanced Melanoma, Using Tumor-Infiltrating Lymphocytes Modified by Retroviral Gene Transduction," N. Engl. J. Med 323(9):570-578 (1990).
Ryu et al., "A chromatin insulator blocks interactions between globin regulatory elements and cellular promoters in erythroid cells," Blood Cells Mol Dis 3 9:221-228 (2007).
Ryu et al., "An experimental system for the evaluation of retroviral vector design to diminish the risk for proto-oncogene activation," Blood 111(4):1866-1875 (2008).
Sabo et al., "Discovery of functional noncoding elements by digital analysis of chromatin structure," PNAS USA 101(48):16837-16842 (2004).
Sabo et al., "Genome-scale mapping of DNase I sensitivity in vivo using tiling DNA microarrays," Nat Methods 3(7):511-518 (2006).
Sabo et al., "Genome-wide identification of DNaseI hypersensitive sites using active chromatin sequence libraries," PNAS USA 101(13):4537-4542 (2004).

(56) References Cited

OTHER PUBLICATIONS

Sadelain et al., "Safe Harbours for the integration of new DNA in the human genome," Nature Reviews 12:51-58 (2012).
Sadelain et al., "Generation of a high-titer retroviral vector capable of expressing high levels of the human β-globin gene," PNAS USA 92:6728-6732 (1995).
Sadelain et al., "Stem Cell Engineering for the Treatment of Severe Hemoglobinopathies," Curr Mol Med 8:690-697 (2008).
Sadelain et al., "Therapeutic Options for Patients with Severe β-Thalassemia: The Need for Globin Gene Therapy," Hum Gene Ther 18:1-9 (2007).
Sadelain, "Genetic Treatment of the Haemoglobinopathies: Recombinations and New Combinations," Br J Haematol 98:247-253 (1997).
Sadelain, "Recent advances in globin gene transfer for the treatment of beta-thalassemia and sickle cell anemia," Current Opinion in Hematology 13:142-148 (2006).
Samakoglu et al., "A genetic strategy to treat sickle cell anemia by coregulating globin transgene expression and RNA interference," Nat. Biotechnol 24:89-94 (2006).
Schmidt et al., "Waves of Retrotransposon Expansion Remodel Genome Organization and CTCF Binding in Multiple Mammalian Lineages," Cell 148:335-348 (2012).
Sharp, The Lancet 337:1277-1278 (1991).
Shehee et al., "Nucleotide Sequence of the BALB/c Mouse β-Globin Complex," J. Mol. Biol. 205:41-62(1989).
Shimotsuma et al., "DNase I Hypersensitivity and e-Globin Transcriptional Enhancement Are Separable in Locus Control Region (LCR) HS1 Mutant Human β-Globin YAC Transgenic Mice," Journal of Biological Chemistry 285(19):14495-14503 (2010).
Shivdasani et al., "Transcription Factor NF-E2 is Required for Platelet Formation Independent of the Actions of Thrombopoietin/MGDF in Megakaryocyte Development," Cell 81:695-704 (1995).
Stamatoyannopoulos, "Prospects for developing a molecular cure for thalassemia," Hematology 10(Suppl 1):255-257 (2005).
Stergachis et al., "Developmental Fate and Cellular Maturity Encoded in Human Regulatory DNA Landscapes," Cell 154:888-903 (2013).
Stergachis et al., "Exonic Transcription Factor Binding Directs Codon Choice and Affects Protein Evolution," Science 342:1367-1372 (2013).
Straubinger et al., "[32] Liposomes as Carriers for Intracellular Delivery of Nucleic Acids," Methods in Enzymology 101:512-527 (1983).
Struhl, "Histone acetylation and transcriptional regulatory mechanisms," Genes & Development 12:599-606 (1998).
Swank et al., "Fetal gene reactivation," Curr Opin Genet Dev 8:366-370 (1998).
Taboit-Dameron et al., "Association of the 5' HS4 sequence of the chicken β-globin locus control region with human EF1α gene promoter induces ubiquitous and high expression of human CD55 and CD59 cDNAs in transgenic rabbits," Transgenic Research, 8:223-235 (1999).
Takahashi et al., "Induction of Pluripotent Stem Cells from Adult Human Fibroblasts by Defined Factors," Cell 131:861-872 (2007).
Takahashi et al., "Induction of pluripotent, stem cells from fibroblast cultures," Nature Protocols 2(12):3081-3089 (2007).
Takahashi et al., Induction of Pluripotent Stem Cells from Mouse Embryonic and Adult Fibroblast Cultures by Defined Factors, Cell 126:663-676 (2006).
Talbot et al., "A dominant control region from the human β-globin locus conferring integration site-independent gene expression," Nature 338:352-355 (1989).
Talbot et al., "The 5'HS2 of the globin locus control region enhances transcription through the interaction of a multimeric complex binding at two functionally distinct NF-E2 binding sites," EMBO J 10(6): 1391-1398 (1991).
Telfer et al. "Improved survival in thalassemia major patients on switching from desferrioxamine to combined chelation therapy with desferrioxamine and deferiprone," Haematologica 94(12):1777-1778 (2009).

Thurman et al., "The accessible chromatin landscape of the human genome," Nature 489:75-82 (2012).
Tisdale et al., "Toward Gene Therapy for Disorders of Globin Synthesis," Semin Hematol 38(4):382-392 (2001).
Tolstoshev et al., Gene expression using retroviral vectors, Current Opinion in Biotechnology 1:55-61 (1990).
Trudel et al., "A 3' enhancer contributes to the stage-specific expression of the human β-globin gene," Genes & Development 1:954-961 (1987).
Trudel et al., "Upstream Gγ-Globin and Downstream P-Globin Sequences Required for Stage-Specific Expression in Transgenic Mice," Molecular and Cellular Biology 7(11):4024-4029 (1987).
Tsukiyama et al., "Chromatin remodeling and transcription," Curr Opin Genet Dev 7:182-191 (1997).
Vermylen et al., "Haematopoietic stem cell transplantation for sickle cell anaemia: the first 50 patients transplanted in Belgium," Bone Marrow Transplant 22:1-6 (1998).
Vieira et al., "Recruitment of Transcription Complexes to the β-Globin Gene Locus in Vivo and in Vitro," J Biol Chem 279(48):50350-50357 (2004).
Wahl et al., Molecular Hybridization of Immobilized Nucleic Acids: Theoretical Concepts and Practical Considerations, Methods in Enzymology 152:399-407 (1987).
Wallace et al., "We gather together: insulators and genome organization," Curr Opin Genet Dev 17:400-407 (2007).
Wang et al., "Ligand-inducible and liver-specific target gene expression in transgenic mice," Nature Biotechnology 15:239-243 (1997).
Wang et al., "Widespread plasticity in CTCF occupancy linked to DNA methylation," Genome Research 22:1680-1688 (2012).
Weatherall, "Phenotype-Genotype Relationships In Monogenic Disease: Lessons From The Thalassaemias," Nature Reviews Genetics 2:245-255 (2001).
Wernig et al., "In vitro reprogramming of fibroblasts into a pluripotent ES-cell-like state," Nature 448:318-324 (2007).
Wilber et al., "Transcriptional regulation of fetal to adult hemoglobin switching: new therapeutic opportunities," Blood 117(15):3945-3953 (2011).
Wolff et al., "Direct Gene Transfer into Mouse Muscle in Vivo," Science 247(4949):1465-1468 (1990).
Wolffe et al., "Activators and repressors: making use of chromatin to regulate transcription," Genes to Cells 2:291-302 (1997).
Wu et al., "Receptor-mediated Gene Delivery and Expression in Vivo," The Journal of Biological Chemistry 263(29):14621-14624 (1988).
Wu et al., "Targeting Genes: Delivery and Persistent Expression of a Foreign Gene Driven by Mammalian Regulatory Elements in Vivo," The Journal of Biological Chemistry 264(29):16985-16987 (1989).
Wu, "The 5' ends of *Drosophila* heat shock genes in chromatin are hypersensitive to DNase I," Nature 286:854-860 (1980).
Xu et al., Correction of the enzyme deficiency in hematopoietic cells of Gaucher patients using a clinically acceptable retroviral supernatant transduction protocol, Experimental Hematology 22:223-230 (1994).
Yannaki et al., "Gene therapy for β-thalassaemia: the continuing challenge," Expert Reviews in Molecular Medicine 12:e31 (2010).
Yannaki et al., "Topological Constraints Governing the Use of the Chicken HS4 Chromatin Insulator in Oncoretrovirus Vectors," Mol Ther 5(5):589-598 (2002).
Yao et al., "Retrovirus silencer blocking by the cHS4 insulator is CTCF independent," Nucleic Acids Res 31(18):5317-5323 (2003).
Yu et al., "Induced Pluripotent Stem Cell Lines Derived from Human Somatic Cells," Science 318:1917-1920 (2007).
Yusufzai et al., "The 5'-HS4 chicken β-globin insulator is a CTCF-dependent nuclear matrix-associated element," PNAS USA 101(23):8620-8624 (2004).
Zufferey et al., "Self-Inactivating Lentivirus Vector for Safe and Efficient In Vivo Gene Delivery," Journal of Virology 72(12):9873-9880 (1998).

* cited by examiner

- ALAS Intron 1:

XhoI_PacI~TCTCCCACGCCCTGGTCTCAGCCTTGGGGAGTGGTCAGACCCCAATGGCGATAAACTCTGGCAACTTTATCTGTGcaCTGCAGGCTCAGCCCCA
  AcaGCTTTAGCTTTCACAAGCAGGCAGGGAAGGGAAACACATATCTCCAGATATGAGG-PacI (TTAAT/TAA)

- ALAS Intron 8:

SdaI~CTAAACCCCTCCCCCACCCTAGCCCCAAGCTTCATCTTAGCTCCACTCCTGACCCTATCCAGCCCTAAAGGTCCCCACCCAGCTCCTGCCTATCTAGTCAT
  TGCATATGGCAAGACTTGAAAGTCCTATCTCAAAGCAGCAGAATTATCAGCTACGACT-SdaI (CCTGCA/GG)

- BLVRB:

PaiI~CCATCCCCCAGCACTCCCTGCCCCCACAGCCCAGACTTGACCAACTCCCAGCTccGCCTGGGACTTCCAGATATGGGGCCCCACCCTTGCAGGCCCTTGG
  GGACGCTGAAGATATTGACTATCTGCGTGCCggAAAAGGGTG-PaiI (TTA|TAA)

- PPOX

AgeI_AAAGGCTGGGGGTGGGAGTAGCCGGATTTGAAGCACTTGTTGGCCTACAGAGGTGTGGCAAGCAGAGCACCTCAGAACTCAGGCGTACTGCCCGCCGCCC
  GAGCCCTGCGAGGGCCGATAGCGAGGGTGTGGCCCTTATCTGCACCCAGCAGAGAGCGGGCGCCGGGGGTACGGTC-AgeI(a/ccggt)

- Spectrin-alpha

Xma_CAGTTGCCTCAGCTGAGTATGTCTTCTAAAGATAATGTCGATTGTCGATGGCTGATGGGATTCTAGGACCAAGCAAGCAAGAGGTTTTTTTTTCCCCACATACTTA
  ACGTTTCTATATTTCTATTTGAATTCGACTGGACAGTTCCATTTGAATTATTTCTCTCTCTCTCTCTGACACATTTATCTTGCCA-Xma (c/ccggg)-XhoI

FIG. 8

Average of total Hb: (TNS9.B87.A1 n=4, SNS23.2.B87.A1 n=5 SNS26.B87.A1=5 SNS27.2.B87.A1=5 TH3/+mock n=1)

Average of ΔHb normalized per VCN: (TNS9.B87.A1 n=4, SNS23.2.B87.A1 n=5 SNS26.B87.A1=5 SNS27.2.B87.A1=5 TH3/+mock n=1)

SEQUENCE LISTING

```
<160> NUMBER OF SEQ ID NOS: 78

<210> SEQ ID NO 1
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
tccttccttt ctaaatgacg agagagacag aagaattctt caaggttagt gtgtccagca      60
tgcaaccttt ccttcctgga tgagcatccc tggagtagga gagccagcct gcctcctgcg     120
ctggcacaga gcccggttcc ctagacaact gcctctccaa atctgatgtc cagcgccacc     180
tggtgtccac atcaagcaga cacaattaat agtcaacctg ttcaggaaaa ctgtgagggg     240 gaaaaaaag aaagaggatt tatgaaggga aagaaagtt tagaggatat gccacgattg       300
gctag                                                                 305

<210> SEQ ID NO 2
<211> LENGTH: 1074
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aagtaaactt ccacaaccgc aagcttattg aggctaaggc atctgtgaag gaaagaaaca      60
tctcctctaa accactatgc tgctagagcc tcttttctgt actcaagcct cattcagaca     120
ctagtgtcac cagtctcctc atatacctat tgtattttct tcttcttgct ggtttagtca     180
tgttttctgg gagcttaggg gcttatttta ttttgttttg ttttctaatc aacagagatg     240
ggcaaaccca ttatttttttt ctttagactt gggatggtga tagctgggca gcgtcagaaa    300
ctgtgtgtgg atatagataa gagctcggac tatgctgagc tgtgatgagg gagggaccta    360
gccaaaggca gtgagagtca gaatgctcct gctattgcct tctcagtccc cacgcttggt    420
ttctacacaa gtagatacat agaaaaggct ataggttagt gtttgagagt cctgcatgag    480
ttagttgctc agaaatgccc gataaatatg ttatgtgtgt ttatgtatat atatgtttta    540
tatatatata tgtgtgtgtg tgtgtgtgtg tgtgttgtgt ttacaaatat gtgattatca    600
tcaaaacgtg agggctaaag tgaccagata acttgcaggt cctaggatac caggaaaata    660
aattacattc caaaaattta actgagactt taaaaaaaaa aaaaaaaaaa aaaaaaaaac    720
cagtgatcca tggacacagg gaggggaaca tcacacactg gggcctgttg ggggtggggg    780
gctaggggaa ggatagcatt aggagaaata cctaatgtag atgacgggtt gatgggtgca    840
gcaaaccacc atggcacatg tacccccagaa cttaaagcat attaaaaaaa cagtgatcat    900
aaaagaagct caaatttaac tataagagac ggaatggctc ccacaattct taactataat    960
```
cttacagaat attctcattg aatagaagta tgcttatcat tagagatttg gacagccagg    1020
aaagcacaga aaaaaaaaaa aggagctctg ttgccttata gcctagaggt gttt          1074

<210> SEQ ID NO 3
<211> LENGTH: 602
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ggcatctgtg aaggaaagaa acatctcctc taaaccacta tgctgctaga gcctcttttc      60
tgtactcaag cctcattcag acactagtgt caccagtctc ctcatatacc tattgtattt     120
tcttcttctt gctggtttag tcatgttttc tgggagctta ggggcttatt ttattttgtt     180
ttgttttcta atcaacagag atgggcaaac ccattatttt tttctttaga cttgggatgg     240
tgatagctgg gcagcgtcag aaactgtgtg tggatataga taagagctcg gactatgctg     300
agctgtgatg agggagggac ctagccaaag gcagtgagag tcagaatgct cctgctattg     360
ccttctcagt ccccacgctt ggtttctaca caagtagata catagaaaag gctataggtt     420
agtgtttgag agtcctgcat gagttagttg ctcagaaatg cccgataaat atgttatgtg     480
tgtttatgta tatatatgtt ttatatatat atatgtgtgt gtgtgtgtgt gtgtgtgttg     540
tgtttacaaa tatgtgatta tcatcaaaac gtgagggcta aagtgaccag ataacttgca     600
gg                                                                    602

<210> SEQ ID NO 4
<211> LENGTH: 489
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ggcatctgtg aaggaaagaa acatctcctc taaaccacta tgctgctaga gcctcttttc      60
tgtactcaag cctcattcag acactagtgt caccagtctc ctcatatacc tattgtattt     120
tcttcttctt gctggtttag tcatgttttc tgggagctta ggggcttatt ttattttgtt     180
ttgttttcta atcaacagag atgggcaaac ccattatttt tttctttaga cttgggatgg     240
tgatagctgg gcagcgtcag aaactgtgtg tggatataga taagagctcg gactatgctg     300
agctgtgatg agggagggac ctagccaaag gcagtgagag tcagaatgct cctgctattg     360
ccttctcagt ccccacgctt ggtttctaca caagtagata catagaaaag gctataggtt     420
agtgtttgag agtcctgcat gagttagttg ctcagaaatg cccgataaat atgttatgtg     480
tgtttatgt                                                             489

<210> SEQ ID NO 5
<211> LENGTH: 1301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
aagctttcat taaaaaaagt ctaaccagct gcattcgact ttgactgcag cagctggtta      60

```
gaaggttcta ctggaggagg gtcccagccc attgctaaat taacatcagg ctctgagact    120
ggcagtatat ctctaacagt ggttgatgct atcttctgga acttgcctgc tacattgaga    180
ccactgaccc atacatagga agcccatagc tctgtcctga actgttaggc cactggtcca    240
gagagtgtgc atctcctttg atcctcataa taaccctatg agatagacac aattattact    300

cttactttat agatgatgat cctgaaaaca taggagtcaa ggcacttgcc cctagctggg    360
ggtatagggg agcagtccca tgtagtagta gaatgaaaaa tgctgctatg ctgtgcctcc    420
cccacctttc ccatgtctgc cctctactca tggtctatct ctcctggctc ctgggagtca    480
tggactccac ccagcaccac caacctgacc taaccaccta tctgagcctg ccagcctata    540
acccatctgg gccctgatag ctggtggcca gccctgaccc caccccaccc tccctggaac    600
ctctgataga cacatctggc acaccagctc gcaaagtcac cgtgagggtc ttgtgtttgc    660
tgagtcaaaa ttccttgaaa tccaagtcct tagagactcc tgctcccaaa tttacagtca    720
tagacttctt catggctgtc tcctttatcc acagaatgat tcctttgctt cattgcccca    780
tccatctgat cctcctcatc agtgcagcac agggcccatg agcagtagct gcagagtctc    840
acataggtct ggcactgcct ctgacatgtc cgaccttagg caaatgcttg actcttctga    900
gctcagtctt gtcatggcaa aataaagata ataatagtgt ttttttatgg agttagcgtg    960
aggatggaaa acaatagcaa aattgattag actataaaag gtctcaacaa atagtagtag   1020
attttatcat ccattaatcc ttccctctcc tctcttactc atcccatcac gtatgcctct   1080
taattttccc ttacctataa taagagttat tcctcttatt atattcttct tatagtgatt   1140
ctggatatta aagtgggaat gaggggcagg ccactaacga agaagatgtt tctcaaagaa   1200
gccattctcc ccacatagat catctcagca gggttcagga agataaagga ggatcaaggt   1260
cgaaggtagg aactaaggaa gaacactggg caagtggatc c                       1301
```

<210> SEQ ID NO 6
<211> LENGTH: 1065
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
tgagcccctt ttcctctaac tgaaagaagg aaaaaaaaaa tggaacccaa aatattctac     60
atagtttcca tgtcacagcc agggctgggc agtctcctgt tatttctttt aaaataaata    120
tatcatttaa atgcataaat aagcaaaccc tgctcgggaa tgggagggag agtctctgga    180
gtccacccct tctcggccct ggctctgcag atagtgctat caaagccctg acagagccct    240
gcccattgct gggccttgga gtgagtcagc ctagtagaga ggcagggcaa gccatctcat    300
agctgctgag tgggagagag aaaagggctc attgtctata aactcaggtc atggctattc    360
ttattctcac actaagaaaa agaatgagat gtctacatat accctgcgtc ccctcttgtg    420
tactggggcc cccaagagct ctctaaaagt gatggcaaag tcattgcgct agatgccatc    480
ccatctatta taaacctgca tttgtctcca cacaccagtc atggacaata accctcctcc    540
caggtccacg tgcttgtctt tgtataatac tcaagtaatt tcggaaaatg tattctttca    600
atcttgttct gttattcctg tttcaatggc ttagtagaaa aagtacatac ttgttttccc    660
ataaattgac aatagacaat ttcacatcaa tgtctatatg ggtcgttgtg tttgctgtgt    720
ttgcaaaaac tcacaataac tttatattgt tactactcta agaaagttac aacatggtga    780
```

```
atacaagaga aagctattac aagtccagaa ataaaagtt atcatcttga ggcctcagct      840
ttctaggaat aatatcaata ttacaaaatt taatctaaca attatgaaca gcaatgagat     900
aatatgtaca aagtacccag acctatgtgg tagagcatca aggaagcgca ttgcggagca     960
gttttttgtt tgtttgtttt tgtattctgt ttcgtgaggc aaggtttcac tctgctgtcc    1020
aggctggagt gcagtggcaa gatcatgtct cactgcagcc ttgac                    1065
```

<210> SEQ ID NO 7
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
tgagcccctt ttcctctaac tgaaagaagg aaaaaaaaaa tggaacccaa atattctac       60 atagtttcca tgtcacagcc agggctgggc agtctcctgt tatttctttt aaaataaata     120
tatcattaaa tgcataaata agcaaaccct gctcgggaat gggagggaga gtctctggag     180 tccaccccctt ctcggccctg gctctgcaga tagtgctatc aaagccctga cagagccctg   240
cccattgctg ggccttggag tgagtcagcc tagtagagag gcagggcaag ccatctcata    300
gctgctgagt gggagagaga aaagggctca ttgtctataa actcaggtca tggctattct    360
tattctcaca ctaagaaaaa gaatgagatg tctacatata ccctgcgtcc cctcttgtgt    420 actgggccc ccaagagctc tctaaaagtg atggcaaagt cattgcgcta gatgccatcc     480
catctattat aaacctgcat ttgtctccac acaccagtca tggacaataa ccctcctccc    540
aggtccacgt gcttgtcttt gtataatact caagtaattt cggaaaatgt attctttcaa    600
tcttgttctg ttattcctgt ttcaatggct tagtagaaaa agtacatact tgttttccca    660
taaattgaca atagacaatt tcacatcaat gtctatatgg gtcgttgtgt ttgctgtgtt    720
tgcaaaaact cacaataact ttatattgtt actactctaa gaaagttaca acatggtgaa    780
tacaagagaa agctattaca agtccagaaa ataaaagtta tcatcttgag gcctcagctt    840
tctaggaata atatcaatat tacaaaatta atctaacaat tatgaacagc aatgagataa    900
tatgtacaaa gtacccagac ctatgtggta gagcatcaag gaagcgcatt gcggagcagt    960 ttttgtttg tttgttttg tattctgttt cgtgaggcaa ggtttcactc tgctgtccag     1020
gctggagtgc agtggcaaga tcatgtctca ctgcagcctt gacac                   1065
```

<210> SEQ ID NO 8
<211> LENGTH: 446
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
tggaacccaa atattctac atagtttcca tgtcacagcc agggctgggc agtctcctgt      60
tatttctttt aaaataaata tatcatttaa atgcataaat aagcaaaccc tgctcgggaa    120
tgggagggag agtctctgga gtccaccccct ctcggccctg gctctgcag atagtgctat    180 caaagccctg acagagccct gcccattgct gggccttgga gtgagtcagc ctagtagaga    240
ggcagggcaa gccatctcat agctgctgag tgggagagag aaaagggctc attgtctata    300
aactcaggtc atggctattc ttattctcac actaagaaaa agaatgagat gtctacatat    360
```

```
acctgcgtc ccctcttgtg tactggggtc cccaagagct ctctaaaagt gatggcaaag    420
tcattgcgct agatgccatc ccatct                                        446

<210> SEQ ID NO 9
<211> LENGTH: 860
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gtatatgtgt atatatatat atatatattc aggaaataat atattctaga atatgtcaca     60
ttctgtctca ggcatccatt ttctttatga tgccgtttga ggtggagttt tagtcaggtg    120
gtcagcttct cctttttttt gccatctgcc ctgtaagcat cctgctgggg acccagatag    180
gagtcatcac tctaggctga aacatctgg gcacacaccc taagcctcag catgactcat     240
catgactcag cattgctgtg cttgagccag aaggtttgct tagaaggtta cacagaacca    300
gaaggcgggg gtggggcact gaccccgaca ggggcctggc cagaactgct catgcttgga    360
ctatgggagg tcactaatgg agacacacag aaatgtaaca ggaactaagg aaaaactgaa    420
gcttatttaa tcagagatga gatgctggaa gggatagagg gagctgagct tgtaaaaagt    480
atagtaatca ttcagcaaat ggttttgaag cacctgctgg atgctaaaca ctattttcag    540
tgcttgaatc ataaataaga ataaaacatg tatcttattc cccacaagag tccaagtaaa    600
aaataacagt taattataat gtgctctgtc ccccaggctg gagtgcagtg gcacgatctc    660
agctcactgc aacctccgcc tcccgggttc aagcaattct cctgcctcag ccaccctaat    720
agctgggatt acaggtgcac accaccatgc caggctaatt tttgtacttt ttgtagaggc    780
agggtatcac catgttgtcc aagatggtct tgaactcctg agctccaagc agtccaccca    840
cctcagcctc ccaaagtgct                                               860

<210> SEQ ID NO 10
<211> LENGTH: 613
<212> TYPE: DNA
<213> ORGANISM: Homo sapiens

<400> SEQUENCE: 10
aagcaataga tggctctgcc ctgacttta tgcccagccc tggctcctgc cctccctgct      60
cctgggagta gattggccaa ccctagggtg tggctccaca gggtgaggtc taagtgatga    120
cagccgtacc tgtccttggc tcttctggca ctggcttagg agttggactt caaaccctca    180
gccctccctc taagatatat ctcttggccc cataccatca gtacaaattg ctactaaaaa    240
catcctcctt tgcaagtgta tttacgtaat atttggaatc acagcttggt aagcatattg    300
aagatcgttt tcccaatttt cttattacac aaataagaaa ttgatgcact aaaagtggaa    360
gagttttgtc taccataatt cagctttggg atatgtagat ggatctcttc ctgcgtctcc    420
agaatatgca aaatacttac aggacagaat ggatgaaaac tctacctcag ttctaagcat    480
atcttctcct tatttggatt aaaaccttct ggtaagaaaa gaaaaaaaat atatatatat    540
atgtgtatat atacacacat acatatacat atatatgcat tcatttgttg ttgttttct    600 taatttgctc atg                                                      613

<210> SEQ ID NO 11
<211> LENGTH: 265
```

```
<212> TYPE: DNA
<213> ORGANISM: Homo sapiens

<400> SEQUENCE: 11
aagcaataga tggctctgcc ctgacttta tgcccagccc tggctcctgc cctccctgct      60
cctgggagta gattggccaa ccctagggtg tggctccaca gggtgaggtc taagtgatga    120
cagccgtacc tgtccttggc tcttctggca ctggcttagg agttggactt caaaccctca    180 gccctcctc taagatatat ctcttggccc cataccatca gtacaaattg ctactaaaaa     240
catcctcctt tgcaagtgta tttac                                          265

<210> SEQ ID NO 12
<211> LENGTH: 879
<212> TYPE: DNA
<213> ORGANISM: Homo sapiens

<400> SEQUENCE: 12
taggtattga ataagaaaaa tgaagttaag gtggttgatg gtaacactat gctaataact     60
gcagagccag aagcaccata agggacatga taagggagcc agcagacctc tgatctcttc    120
ctgaatgcta atcttaaaca tcctgaggaa gaatgggact tccatttggg gtgggcctat    180 gataggtaa taagacagta gtgaatatca agctacaaaa agcccccttt caaattcttc     240
tcagtcctaa cttttcatac taagcccagt ccttccaaag cagactgtga aagagtgata    300
gttccgggag actagcactg cagattccgg gtcactgtga gtggggagg cagggaagaa     360 gggctcacag gacagtcaaa ccatgccccc tgttttcct tcttcaagta gacctctata    420
agacaacaga gacaactaag gctgagtggc caggcgagga gaaaccatct cgccgtaaaa    480
catggaagga acacttcagg ggaaaggtgg tatctctaag caagagaact gagtggagtc    540
aaggctgaga gatgcaggat aagcaaatgg gtagtgaaaa gacattcatg aggacagcta    600
aaacaataag taatgtaaaa tacagcatag caaaacttta acctccaaat caagcctcta    660
cttgaatcct tttctgaggg atgaataagg cataggcatc aggggctgtt gccaatgtgc    720
attagctgtt tgcagcctca ccttctttca tggagtttaa gatatagtgt atttcccaa     780 ggtttgaact agctcttcat ttctttatgt tttaaatgca ctgacctccc acattccctt    840
tttagtaaaa tattcagaaa taatttaaat acatcattg                           879

<210> SEQ ID NO 13
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
tctcccacgc cctggtctca gcttggggag tggtcagacc ccaatggcga taaactctgg     60
caactttatc tgtgcactgc aggctcagcc ccaacagctt tagctttcac aagcaggcag    120
gggaagggaa acacatatct ccagatatga gg                                  152

<210> SEQ ID NO 14
<211> LENGTH: 157
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 14
ctaaacccct cccccaccct agccccaagc ttcatcttag ctccactcct gaccctatcc        60
agctaaaggt ccccacccag ctcctgccta tctagtcatt gcatatggca agacttgaaa       120
gtcctatctc aaagcagcag aattatcagc tacgact                                157

<210> SEQ ID NO 15
<211> LENGTH: 141
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
ccatccccca gcactccctg cccccacagc ccagacttga ccaactccca gctccgcctg        60
ggacttccag atatggggcc ccaccccttgc aggccttggg gacgctgaag atattgacta      120
tctgcgtgcc ggaaaagggt g                                                 141

<210> SEQ ID NO 16
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
aaaggctggg ggtgggagta gcggatttga agcacttgtt ggcctacaga ggtgtggcaa        60
gcagagcacc tcagaactca ggcgtactgc ccgccgcccg agccctgcga gggccgatag       120
cgagggtgtg gcccttatct gcacccagca gagcgccggc ggggtacggt c                171

<210> SEQ ID NO 17
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
cagttgcctc agctgagtat gtcttctaaa gataatgtcg attgtgtatg gctgatggga        60
ttctaggacc aagcaagagg ttttttttttt tcccccacat acttaacgtt tctatatttc      120
tatttgaatt cgactggaca gttccatttg aattatttct ctctctctct ctctctgaca       180
cattttatct tgcca                                                        195

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
caccaggtgg cgct                                                          14

<210> SEQ ID NO 19
<211> LENGTH: 81706
<212> TYPE: DNA
<213> ORGANISM: Homo sapiens

```
<400> SEQUENCE: 19
ggatcctcac atgagttcag tatataattg taacagaata aaaaatcaat tatgtattca      60
agttgctagt gtcttaagag gttcacattt ttatctaact gattatcaca aaaatacttc     120
gagttacttt tcattataat tcctgactac acatgaagag actgacacgt aggtgcctta     180
cttaggtagg ttaagtaatt tatccaaaac cacacaatgt agaacctaag ctgattcggc     240
catagaaaca caatatgtgg tataaatgag acagagggat ttctctcctt cctatgctgt     300
cagatgaata ctgagataga atatttagtt catctatcac acattaaacg ggactttaca     360
tttctgtctg ttgaagattt gggtgtgggg ataactcaag gtatcatatc caagggatgg     420
atgaaggcag gtgactctaa cagaaaggga aaggatgttg gcaaggctat gttcatgaaa     480
gtatatgtaa aatccacatt aagcttcttt ctgcatgcat tggcaatgtt tatgaataat     540
gtgtatgtaa aagtgtgctg tatattcaaa agtgtttcat gtgcctaggg gtgtcaaata     600
ctttgagttt gtaagtatat acttctctgt aatgtgtctg aatatctcta tttacttgat     660
tctcaataag taggtatcat agtgaacatc tgacaaatgt ttgaggaaca atttagtgtt     720
tacctattca ccaaaattta ttaaatgcct aatctgtatc agatatacaa ttatctggcg     780
aaatctgtaa ttcctaattt aaacagctgt gtagcctaat tagggataaa ggcatgcaaa     840
cccataattt gtgtaggttg aaatgagcta tagaaaaatg cagtatattt atcagaagtc     900
tttagggtca tgaaaaggaa tggtcaactg acactgccag ggactcatat gtaagagata     960
actaatgtga agtgacttta aaggagaaat tagcagaagt tttctttcca tgtctcctca    1020
tcatgttaca ataacggaag agattaaaac aacaaataca tttagacagc aatgtttatc    1080
ctggttagat gttttaatct aaatctatct tggagtgtta aaatgcattt gctcacctac    1140
tttaaaatat aaatgaaggt aggaacctgt agatacaaaa agttggagaa aaaaagacaa    1200
taaagatgac aaaaatctat taatccttga tagaaaatga gaagagataa aacactggtt    1260
tacataaaga aaataagatg gatagatagc agatccttat aaaagtgata atttgagaaa    1320
aaaaatactc catattctga gtttcttcac ataaaataat acaaatctgc tgtggtaagt    1380
tacaaagaga tagatttttt atcattatat aaaagatatt ttaaacagag ttatacaaca    1440
aaggaacaga ctatgtcata tattctcact tatcactata aacatctcag aaaaatctgc    1500
aaaatcattt catagcattt taaatagtta ggaataatgt agaaaactga acagttcta     1560
agtttcccac aaacttagag tctcaaatgt tgcattacct aacttacctg caaatatttt    1620
atacaaattt gcacatgcta ctctagtcaa aaatatatgt acattatggg tattttctgt    1680
gtgtaacttg gttctagttg cttctttcag aaatagcctc tattttttgat ttacctgata    1740
aaatcacatt cctctccaaa gccttctaaa tacttccaga ctaactactt tttagtacat    1800
ctaagaagaa aagagttttg tctcttatcc acctctgagt caaaaagcag catgtccatc    1860
aattggtaca tagttcccac agccccactt agctctggat tggagttcta cttggcattg    1920
tttgcaacta catggacgta aaatgcatgg attctcttga aaaaatgttt ctgccatgat    1980
gttctctgaa agagactaac cttccctcgc tttgcagaga aagactcgtg taatccttga    2040
caatgtcatc tcatctattt attcccatgt ctacccatat gtgaccttca tgtctttgct    2100
ctaagcccct acatcctcaa tctacacact aggatagtat aaaagtaata gtaataatag    2160
tagtaatagt aataacaata caatgattat ggcttatact atacacaaga cactgttgat    2220
atattatttc atttagtatt cacagtaact ctgtgcctca agtactattg taatacccttt   2280
```

```
taagaggagg aaactgaggc acagggccct aaagtaatat tccaagatga agtggctact    2340
aactgacaga gggcataatt caactcatga tatttggctc tagaatacat gctctgaatc    2400
attatacaat aataattcat gaggaaacat tttttaaagc ctaagttatt tgctctgaaa    2460
taagacataa tttggggtga gaaagcttag attccatgaa gtattacagc atttggtagt    2520 cttttttgcac tccaggtctt attttttactg cttaaacata ataaaacata tggttcagta    2580
tgcctttgat tttacaataa tattcctgtt attttttggaa gcacagggtg tgggataatg    2640
ctaattacta gtgattagta ttgagaggtg acagcgtgct ggcagtcctc acagccctcg    2700
ctcgctcttg gcgcctcctc tgcctgggct cccacattgg tggcacttga ggagcccttc    2760
agccggccgc tgcactgtgg gagccctttt ctgggctggc caaggccaga gccggctccc    2820
tcagcttgcc aggaggtgtg gagggacaga cgcgggcagg aaccgggctg tgcgccgtgc    2880
ttgagggagt tccgggtggg catgggctcc gaggaccccg cactcggagc cgccagccgg    2940
ccccaccggc cgcgggcagt gaggggctta gcacctgggc cagcagctgc tgtgctcaat    3000
tcctcgccgg gccttagctg ccttcctgcg gggcagggct cgggacctgc agcgcgccat    3060
gcctgagcct ccccaccttc atgggctcct gtgcggcccg agcctcgccg acgagcgccg    3120 cccccctgctc cagggcaccc agtcccatcg accacccaag ggctgaagag tgcgggcgca    3180
cggcagggga ctggcaggca gctccccctg cagcccaggt gcgggatcca ctgggtgaag    3240
ccggctaggc tcctgagttt gctggggatg cgaagaaccc ttatgtctag ataagggatt    3300
gtaaatacac caattggcac tctgtatcta gctcaaggtt tgtaaacaca ccaatcagca    3360
ccctgtgtct agctcagggt tgtgaatgc accaatcaac actctatcta gctactctgg    3420
tggggccttg gagaaccttt atgtctagct cagggattgt aaatacacca atcggcagtc    3480
tgtatctagc tcaaggtttg taaacacacc aatcagcacc ctgtgtctag ctcagggttt    3540
gtgaatgcac caatcaacac tctgtatcta gctactctgg tggggacgtg gagaaccttt    3600
atgtctagct cagggattgt aaatacacca ctcggcagtc tgtatctagc tcaaggtttg    3660
taaacacacc aatcagcacc ctgtgtctag ctcagggttt gtgaatgcac caatcaacac    3720
tctgtatcta gctactctgg tggggacttg gagaaccttt gtgtggacac tctgtatcta    3780
gctaatctgg tggggacgtg gagaaccttt gtgtctagct catggattgt aaatgcacca    3840
atcagtgccc tgtcaaaaca gaccactggg ctctaccaat cagcaggatg tgggtggggc    3900
cagataagag aataaaagca ggctgcccga gccagcagtg gcaacccgct cgggtcccct    3960
tccacactgt ggaagctttg ttctttcgct ctttgcaata aatcttgctg ctgctcactg    4020
tttgggtcta cactgccttt atgagctgta acgctcaccg cgaaggtctg cagcttcact    4080
cttgaagcca gcgagaccac gaacccaccg ggaggaacga acaactccag aggcgccgcc    4140
ttaagagctg gaacgttcac tgtgaaggtc tgcagcttca ctcctgagcc agcgagacca    4200
cgaacccatc agaaggaaga aactccgaac acatccaaac atcagaacga acaaactcca    4260
cacacgcagc ctttaagaac tgtaacactc accacgaggg tccccggctt cattcttgaa    4320
gtcagtgaaa ccaagaaccc accaattccg gacacagtat gtcagaaaca atatgagtca    4380
ctaaatcaat atacttctca acaatttcca acagcccttg caattaactt ggccatgtga    4440
ctggttgtga ctaaaataat gtggagataa taatgtgtta ctccctaagg cagagtgccc    4500
ttctatcatt ctctttccct tcctctatgt ggcagaaagt aaaagattct gaaatgataa    4560
agtcaatcac aggaaggcac ctggactcct ggcccactgc ttgggaggaga gcactcagga    4620 ccatgaacat ctgactgtga cgtagcaata aagaaaccca cgtttcatat gaaactgctt    4680
```

```
aaaattaatg gcacaagtca tgttttttgat gttgcacatt tgtctttatt tgtggcttgt    4740
tttgcttcca catcaatcca ctcaaggcct acattctgct ataatgcaat ttcaagttct     4800
ttacaggccg agaaaaatga atctgaattc ctgacctcca aaagtgatca agatatttt     4860 agttcaggct ccaaaatttt ctcatttttca taggttttcc tcgattgatc attattcatg   4920
atttgcaagg aatcattcaa tgttttctaa atctattact gcatcctgac acatatgaca    4980
ttttaactat gttccagatt tttgaatgaa gagtgtaaat tttaaatgtt ttcaccacaa    5040
aaaataagta tgtgaagtgg tggatttgtt aattagcctt atttaaccat ttaatattgt    5100
acacgtacac caaagcatca tgttgtaccc catgaataca cacaattatt atttgtcaat    5160
ttaaaatgaa ataataaaaa ataacaaagg cattagcctc tgcattgcct ttaccggtca    5220
tcctcacggt gactaacgca aaaaacgttc tatttcatcc ttacaaacat ccctatcttt    5280
gatgcctctt tgtctagatc tctatcccct cctgttttct ctacgttatt tatatgggta    5340
tcatcaccat cctggacaac atcaggacag atatccctca ccaagccaat gttcctctct    5400
atgttggctc aaatgtcctt gaactttcct ttcaccaccc tttccacagt caaaaggata    5460 ttgtagtttta atgcctcaga gttcagcttt taagcttctg acaaattatt cttcctcttt    5520
aggttctcct ttatggaatc ttctgtactg atggccatgt cctttaacta ctatgtagat    5580
atctgctact acctgtatta tgcctctacc tttattagca gagttatctg tactgttggc    5640
atgacaatca tttgttaata tgacttgcct ttccttttc tgctattctt gatcaaatgg     5700
ctcctctttc ttgctcctct catttctcct gccttcactt ggacgtgctt cacgtagtct    5760
gtgcttatga ctggattaaa aattgatatg gacttatcct aatgttgttc gtcataatat    5820 gggtttttatg gtccattatt atttcctatg cattgatctg gagaaggctt caatcctttt   5880
actctttgtg gaaaatatct gtaaaccttc tggttcactc tgctatagca atttcagttt    5940
aggctagtaa gcatgaggat gcctccttct ctgatttttc ccacagtctg ttggtcacag    6000
aataacctga gtgattactg atgaaagagt gagaatgtta ttgatagtca caatgacaaa     6060
aaacaaacaa ctacagtcaa aatgtttctc tttttattag tggattatat ttcctgacct    6120
atatctggca ggactcttta gagaggtagc tgaagctgct gttatgacca ctagagggaa    6180
gaagatacct gtggagctaa tggtccaaga tggtggagcc ccaagcaagg aagttgttaa    6240
ggagcccttt tgattgaagg tgggtgcccc caccttacag ggacaggaca tctggatact    6300
cctcccagtt tctccagttt ccctttttcc taatatatct cctgataaaa tgtctatact    6360
cacttcccca tttctaataa taaagcaaag gctagttagt aagacatcac cttgcatttt    6420
gaaaatgcca tagactttca aaattatttc atacatcggt ctttctttat ttcaagagtc    6480
cagaaatggc aacattacct ttgattcaat gtaatggaaa gagctctttc aagagacaga    6540
gaaaagaata atttaatttc tttccccaca cctccttccc tgtctcttac cctatcttcc    6600
ttccttctac cctccccatt tctctctctc atttctcaga agtatatttt gaaaggattc    6660
atagcagaca gctaaggctg gttttttcta agtgaagaag tgatattgag aaggtagggt    6720
tgcatgagcc ctttcagttt tttagtttat atacatctgt attgttagaa tgtttttataa   6780 tataaataaa attattctc agttatatac tagctatgta acctgtggat atttccttaa     6840
gtattacaag ctatacttaa ctcacttgga aaactcaaat aaatacctgc ttcatagtta    6900
ttaataagga ttaagtgaga taatgccccat aagattccta ttaataacag ataaatacat   6960
acacacacac acacattgaa aggattctta ctttgtgcta ggaactataa taagttcatt    7020
```

```
gatgcattat atcattaagt tctaatttca acactagaag gcaggtatta tctaaatttc    7080
atactggata cctccaaact cataaagata attaaattgc cttttgtcat atatttattc    7140
aaaagggtaa actcaaacta tggcttgtct aattttatat atcaccctac tgaacatgac    7200
cctattgtga tattttataa aattattctc aagttattat gaggatgttg aaagacagag    7260 aggatgggt gctatgcccc aaatcagcct cacaattaag ctaagcagct aagagtcttg    7320
cagggtagtg tagggaccac agggttaagg gggcagtaga attatactcc cactttagtt    7380
tcatttcaaa caatccatac acacacagcc ctgagcactt acaaattata ctacgctcta    7440 tacttttgt ttaaatgtat aaataagtgg atgaaagaat agatagatag atagacagat    7500
agatgataga tagaataaat gcttgccttc atagctgtct ccctaccttg ttcaaaatgt    7560
tcctgtccag accaaagtac cttgccttca cttaagtaat caattcctag gttatattct    7620
gatgtcaaag gaagtcaaaa gatgtgaaaa acaatttctg acccacaact catgctttgt    7680
agatgactag atcaaaaaat ttcagccata tcttaacagt gagtgaacag gaaatctcct    7740 cttttccta catctgagat cccagcttct aagaccttca attctcactc ttgatgcaac    7800
agaccttgga agcatacagg agagctgaac ttggtcaaca aaggagaaaa gtttgttggc    7860
ctccaaaggc acagctcaaa cttttcaagc cttctctaat cttaaaggta aacaagggtc    7920
tcatttcttt gagaacttca gggaaaatag acaaggactt gcctggtgct tttggtaggg    7980
gagcttgcac tttcccctt tctggaggaa atatttatcc ccaggtagtt cccttttgc    8040 accagtggtt ctttgaagag acttccacct gggaacagtt aaacagcaac tacagggcct    8100
tgaactgcac actttcagtc cggtcctcac agttgaaaag acctaagctt gtgcctgatt    8160
taagcctttt tggtcataaa acattgaatt ctaatctccc tctcaaccct acagtcaccc    8220
atttggtata ttaaagatgt gttgtctact gtctagtatc cctcaagtag tgtcaggaat    8280
tagtcattta aatagtctgc aagccaggag tggtggctca tgtctgtaat tccagcactt    8340
gagaggtaga agtgggagga ctgcttgagc tcaagagttt gatattatcc tggacaacat    8400
agcaagacct cgtctctact taaaaaaaaa aaaaaaatta gccaggcatg tgatgtacac    8460
ctgtagtccc agctactcag gaggccgaaa tgggaggatc ccttgagctc aggaggtcaa    8520
ggctgcagtg agacatgatc ttgccactgc actccagcct ggacagcaga gtgaaacctt    8580
gcctcacgaa acagaataca aaaacaaaca aacaaaaaac tgctccgcaa tgcgcttcct    8640
tgatgctcta ccacataggt ctgggtactt tgtacacatt atctcattgc tgttcataat    8700
tgttagatta atttttgtaat attgatatta ttcctagaaa gctgaggcct caagatgata    8760 actttttattt tctggacttg taatagcttt ctcttgtatt caccatgttg taacttctt    8820 agagtagtaa caatataaag ttattgtgag tttttgcaaa cacagcaaac acaacgaccc    8880
atatagacat tgatgtgaaa ttgtctattg tcaatttatg ggaaaacaag tatgtacttt    8940
ttctactaag ccattgaaac aggaataaca gaacaagatt gaaagaatac attttccgaa    9000
attacttgag tattatacaa agacaagcac gtggacctgg gaggaggggtt attgtccatg    9060 actggtgtgt ggagacaaat gcaggtttat aatagatggg atggcatcta gcgcaatgac    9120
tttgccatca cttttagaga gctcttgggg accccagtac acaagagggg acgcagggta    9180
tatgtagaca tctcattctt tttcttagtg tgagaataag aatagccatg acctgagttt    9240
atagacaatg agccctttc tctctcccac tcagcagcta tgagatggct tgccctgcct    9300
ctctactagg ctgactcact ccaaggccca gcaatgggca gggctctgtc agggctttga    9360
tagcactatc tgcagagcca gggccgagaa ggggtggact ccagagactc tccctcccat    9420
```

-continued

```
tcccgagcag ggtttgctta tttatgcatt taaatgatat atttattta  aaagaaataa  9480
caggagactg cccagccctg gctgtgacat ggaaactatg tagaatattt tgggttccat  9540
ttttttttcc ttctttcagt tagaggaaaa ggggctcact gcacatacac tagacagaaa  9600
gtcaggagct ttgaatccaa gcctgatcat ttccatgtca tactgagaaa gtccccaccc  9660
ttctctgagc ctcagtttct cttttataa  gtaggagtct ggagtaaatg atttccaatg  9720
gctctcattt caatacaaaa tttccgttta ttaaatgcat gagcttctgt tactccaaga  9780
ctgagaagga aattgaacct gagactcatt gactggcaag atgtcccag  aggctctcat  9840
tcagcaataa aattctcacc ttcacccagg cccactgagt gtcagatttg catgcactag  9900
ttcacgtgtg taaaaggag  gatgcttctt tcctttgtat tctcacatac ctttaggaaa  9960
gaacttagca cccttcccac acagccatcc caataactca tttcagtgac tcaacccttg 10020
actttataaa agtcttgggc agtatagagc agagattaag agtacagatg ctggagccag 10080
accacctgag tgattagtga ctcagtttct cttagtagtt gtatgactca gtttcttcat 10140
ctgtaaaatg gagggttttt taattagttt gttttgaga  aagggtctca ctctgtcacc 10200
caaatgggag tgtagtggca aaatctcggc tcactgcaac ttgcacttcc caggctcaag 10260
cggtcctccc acctcaacat cctgagtagc tggaaccaca ggtacacacc accatacctc 10320
gctaatttt  tgtattttg  gtagagatgg ggtttcacat gttacacagg atggtctcag 10380
actccggagc tcaagcaatc tgcccacctc agccttccaa agtgctggga ttataagcat 10440
gattacagga gttttaacag gctcataaga ttgttctgca gcccgagtga gttaatacat 10500
gcaaagagtt taaagcagtg acttataaat gctaactact ctagaaatgt tgctagtat  10560
tttttgttta actgcaatca ttcttgctgc aggtgaaaac tagtgttctg tactttatgc 10620
ccattcatct ttaactgtaa taataaaat  aactgacatt tattgaaggc tatcagagac 10680
tgtaattagt gctttgcata attaatcata tttaatactc ttggattctt tcaggtagat 10740
actattatta tccccatttt actacagtta aaaaaactac ctctcaactt gctcaagcat 10800
acactctcac acacacaaac ataaactact agcaaatagt agaattgaga tttggtccta 10860
attatgtctt tgctcactat ccaataaata tttattgaca tgtacttctt ggcagtctgt 10920
atgctggatg ctggggatac aaagatgttt aaatttaagc tccagtctct gcttccaaag 10980
gcctcccagg ccaagttatc cattcagaaa gcattttta  ctctttgcat tccactgttt 11040
ttcctaagtg actaaaaaat tacactttat tcgtctgtgt cctgctctgg gatgatagtc 11100
tgactttcct aacctgagcc taacatccct gacatcagga aagactacac catgtggaga 11160
aggggtggtg gttttgattg ctgctgtctt cagttagatg gttaactttg tgaagttgaa 11220
aactgtggct ctctggttga ctgttagagt tctggcactt gtcactatgc ctattattta 11280
acaaatgcat gaatgcttca gaatatggga atattatctt ctggaatagg gaatcaagtt 11340
atattatgta acccaggatt agaagattct tctgtgtgta agaatttcat aaacattaag 11400
ctgtctagca aaagcaaggg cttggaaaat ctgtgagctc ctcaccatat agaaagcttt 11460
taacccatca ttgaataaat ccctataggg gatttctacc ctgagcaaaa ggctggtctt 11520
gattaattcc caaactcata tagctctgag aaagtctatg ctgttaacgt tttcttgtct 11580
gctaccccat catatgcaca acaataaatg caggcctagg catgactgaa ggctctctca 11640
taattcttgg ttgcatgaat cagattatca acagaaatgt tgagacaaac tatggggaag 11700
cagggtatga aagagctctg aatgaaatgg aaaccgcaat gcttcctgcc cattcagggc 11760
```

```
tccagcatgt agaaatctgg ggctttgtga agactggctt aaaatcagaa gccccattgg   11820
ataagagtag ggaagaacct agagcctacg ctgagcaggt ttccttcatg tgacagggag   11880
cctcctgccc cgaacttcca gggatcctct cttaagtgtt tcctgctgga atctcctcac   11940
ttctatctgg aaatggtttc tccacagtcc agccctggc tagttgaaag agttacccat    12000
gcagaggccc tcctagcatc cagagactag tgcttagatt cctactttca gcgttggaca   12060
acctggatcc acttgcccag tgttcttcct tagttcctac cttcgacctt gatcctcctt   12120
tatcttcctg aaccctgctg agatgatcta tgtggggaga atggcttctt tgagaaacat   12180
cttcttcgtt agtggcctgc ccctcattcc cactttaata tccagaatca ctataagaag   12240
aatataataa gaggaataac tcttattata ggtaagggaa aattaagagg catacgtgat   12300
gggatgagta agagaggaga gggaaggatt aatggacgat aaaatctact actatttgtt   12360
gagacctttt atagtctaat caattttgct attgttttcc atcctcacgc taactccata   12420
aaaaaacact attattatct ttattttgcc atgacaagac tgagctcaga agagtcaagc   12480
atttgcctaa ggtcggacat gtcagaggca gtgccagacc tatgtgagac tctgcagcta   12540
ctgctcatgg gccctgtgct gcactgatga ggaggatcag atggatgggg caatgaagca   12600
aaggaatcat tctgtggata aaggagacag ccatgaagaa gtctatgact gtaaatttgg   12660
gagcaggagt ctctaaggac ttggatttca aggaattttg actcagcaaa cacaagaccc   12720
tcacggtgac tttgcgagct ggtgtgccag atgtgtctat cagaggttcc agggagggtg   12780
gggtggggtc agggctggcc accagctatc agggcccaga tgggttatag gctggcaggc   12840
tcagataggt ggttaggtca ggttggtggt gctgggtgga gtccatgact cccaggagcc   12900
aggagagata gaccatgagt agagggcaga catgggaaag gtgggggagg cacagcatag   12960
cagcattttt cattctacta ctacatggga ctgctcccct ataccccag ctaggggcaa    13020 gtgccttgac tcctatgttt tcaggatcat catctataaa gtaagagtaa taattgtgtc   13080
tatctcatag ggttattatg aggatcaaag gagatgcaca ctctctggac cagtggccta   13140
acagttcagg acagagctat gggcttccta tgtatgggtc agtggtctca atgtagcagg   13200
caagttccag aagatagcat caaccactgt tagagatata ctgccagtct cagagcctga   13260
tgttaattta gcaatgggct gggaccctcc tccagtagaa ccttctaacc agctgctgca   13320
gtcaaagtcg aatgcagctg gttagacttt ttttaatgaa agcttagctt tcattaaaga   13380
ttaagctcct aagcagggca cagatgaaat tgtctaacag caactttgcc atctaaaaaa   13440
atctgacttc actggaaaca tggaagccca aggttctgaa catgagaaat ttttaggaat   13500
ctgcacagga gttgagaggg aaacaagatg gtgaagggac tagaaaccac atgagagaca   13560
cgaggaaata tgtagatttt aggctggagg taaatgaaag agaagtggga attaatactt   13620
actgaaatct ttctatatgt caggtgccat tttatgatat ttaataatct cattacatat   13680
ggtaattctg tgagatatgt attattgaac atactataat taatactaat gataagtaac   13740
acctcttgag tacttagtat atgctagaat caaatttaag tttatcatat gaggccgggc   13800
acggtggctc atatatggga ttacatgcct gtaatcccag cactttggga ggccaaggca   13860
attggatcac ctgaggtcag gagttccaga ccagcctggc caacatggtg aaacccttc    13920 tctactaaaa aatacaaaaa atcagccagg tgtggtggca cgcgtctata atcccagcta   13980
ctcaggaggc tgaggcagga gaatcacttg aacccaggag gtggaggttg cagtgagcta   14040
agattgcacc actgcactcc agcctaggcg acagagtgag actccatctc aaaaaaaaaa   14100
aaagaagttt attatatgaa ttaacttagt tttactcaca ccaatactca gaagtagatt   14160
```

-continued

```
attacctcat ttattgatga ggagcccaat gtacttgtag tgtagatcaa cttattgaaa    14220
gcacaagcta ataagtagac aattagtaat tagaagtcag atggtctgag ctctcctact    14280
gtctacatta catgagctct tattaactgg ggactcgaaa atcaaagaca tgaaataatt    14340
tgtccaagct tacagaacca ccaagtagta aggctaggat gtagacccag ttctgctacc    14400
tctgaagaca gtgttttttc cacagcaaaa cacaaactca gatattgtgg atgcgagaaa    14460
ttagaagtag atattcctgc cctgtggccc ttgcttctta cttttacttc ttgtcgattg    14520
gaagttgtgg tccaagccac agttgcagac catacttcct caaccataat tgcatttctt    14580
caggaaagtt tgagggagaa aaaggtaaag aaaaatttag aaacaacttc agaataaaga    14640
gattttctct tgggttacag agattgtcat atgacaaatt ataagcagac acttgagaaa    14700
actgaaggcc catgcctgcc caaattaccc tttgacccct tggtcaagct gcaactttgg    14760
ttaaagggag tgtttatgtg ttatagtgtt catttactct tctggtctaa cccattggct    14820
ccgtcttcat cctgcagtga cctcagtgcc tcagaaacat acatatgttt gtctagttta    14880
agtttgtgtg aaattctaac tagcgtcaag aactgagggc cctaaactat gctaggaata    14940
gtgctgtggt gctgtgatag gtacacaaga aatgagaaga aactgcagat tctctgcatc    15000
tccctttgcc gggtctgaca acaaagtttc cccaaatttt accaatgcaa gccatttctc    15060
catatgctaa ctactttaaa atcatttggg gcttcacatt gtctttctca tctgtaaaaa    15120
gaatggaaga actcattcct acagaactcc ctatgtcttc cctgatgggc tagagttcct    15180
ctttctcaaa aattagccat tattgtattt ccttctaagc caaagctcag aggtcttgta    15240
ttgcccagtg acatgcacac tggtcaaaag taggctaagt agaagggtac tttcacagga    15300
acagagagca aaagaggtgg gtgaatgaga gggtaagtga gaaagacaaa atgaagagtt    15360
acaacatgat ggcttgttgt ctaaatatct cctagggaat tattgtgaga ggtctgaata    15420
gtgttgtaaa ataagctgaa tctgctgcca acattaacag tcaagaaata cctccgaata    15480
actgtacctc caattattct ttaaggtagc atgcaactgt aatagttgca tgtatatatt    15540
tatcataata ctgtaacaga aaacacttac tgaatatata ctgtgtccct agttctttac    15600
acaataaact aatctcatcc tcataattct attagctaat acatattatc atcctatatt    15660
tcagagactt caagaagtta agcaacttgc tcaagatcat ctaagaagta ggtggtatt    15720 ctgggctcat ttggcccctc ctaatctctc atggcaacat ggctgcctaa agtgttgatt    15780
gccttaattc atcagggatg ggctcatact cactgcagac cttaactggc atcctctttt    15840
cttatgtgat ctgcctgacc ctagtagact tatgaaattt ctgatgagaa aggagagagg    15900
agaaaggcag agctgactgt gatgagtgat gaaggtgcct tctcatctgg gtaccagtgg    15960
ggcctctaag actaagtcac tctgtctcac tgtgtcttag ccagttcctt acagcttgcc    16020
ctgatgggag atagagaatg ggtatcctcc aacaaaaaaa taaattttca tttctcaagg    16080
tccaacttat gtttttcttaa tttttaaaaa aatcttgacc attctccact ctctaaaata    16140
atccacagtg agagaaacat tcttttcccc catcccataa atacctctat taaatatgga    16200
aaatctgggc atggtgtctc acacctgtaa tcccagcact ttgggaggct gaggtgggtg    16260
gactgcttgg agctcaggag ttcaagacca tcttggacaa catggtgata ccctgcctct    16320
acaaaaagta caaaaattag cctggcatgg tggtgtgcac ctgtaatccc agctattagg    16380
gtggctgagg caggagaatt gcttgaaccc gggaggcgga ggttgcagtg agctgagatc    16440
gtgccactgc actccagcct gggggacaga gcacattata attaactgtt attttttact    16500
```

```
tggactcttg tggggaataa gatacatgtt ttattcttat ttatgattca agcactgaaa    16560
atagtgttta gcatccagca ggtgcttcaa aaccatttgc tgaatgatta ctatacttt     16620 tacaagctca gctccctcta tcccttccag catcctcatc tctgattaaa taagcttcag    16680
ttttccttta gttcctgtta catttctgtg tgtctccatt agtgacctcc catagtccaa    16740
gcatgagcag ttctggccag gcccctgtcg gggtcagtgc cccaccccg ccttctggtt     16800 ctgtgtaacc ttctaagcaa accttctggc tcaagcacag caatgctgag tcatgatgag    16860
tcatgctgag gcttagggtg tgtgcccaga tgttctcagc ctagagtgat gactcctatc    16920
tgggtcccca gcaggatgct tacagggcag atggcaaaaa aaaggagaag ctgaccacct    16980
gactaaaact ccacctcaaa cggcatcata agaaaatgg atgcctgaga cagaatgtga     17040
catattctag aatatattat ttcctgaata tatatatata tatacacata tacgtatata    17100
tatatatata tatatatttg ttgttatcaa ttgccataga atgattagtt attgtgaatc    17160
aaatatttat cttgcaggtg gcctctatac ctagaagcgg cagaatcagg ctttattaat    17220
acatgtgtat agattttag gatctataca catgtattaa tatgaaacaa ggatatggaa     17280
gaggaaggca tgaaaacagg aaaagaaaac aaaccttgtt tgccatttta aggcacccct    17340
ggacagctag gtggcaaaag gcctgtgctg ttagaggaca catgctcaca tacggggtca    17400
gatctgactt ggggtgctac tgggaagctc tcatcttaag gatacatctc aggccagtct    17460
tggtgcatta ggaagatgta ggcaactctg atcctgagag gaagaaaca ttcctccagg     17520 agagctaaaa gggttcacct gtgtgggtaa ctgtgaagga ctacaagagg atgaaaaaca    17580
atgacagaca gacataatgc ttgtgggaga aaaacagga ggtcaagggg atagagaagg     17640
cttccagaag aatggctttg aagctggctt ctgtaggagt tcacagtggc aaagatgttt    17700
cagaaatgtg acatgactta aggaactata caaaaggaa caaatttaag gagaggcaga     17760
taaattagtt caacagacat gcaaggaatt ttcagatgaa tgttatgtct ccactgagct    17820
tcttgaggtt agcagctgtg aggtttttgc aggcccagga cccattacag gacctcacgt    17880
atacttgaca ctgttttttg tattcatttg tgaatgaatg acctcttgtc agtctactcg    17940
gtttcgctgt gaatgaatga tgtcttgtca gcctacttgg tttcgctaag agcacagaga    18000
gaagatttag tgatgctatg taaaaacttc cttttggtt caagtgtatg tttgtgatag     18060
aaatgaagac aggctacatg atgcatatct aacataaaca caaacattaa gaaaggaaat    18120
caacctgaag agtatttata cagataacaa aatacagaga gtgagttaaa tgtgtaataa    18180
ctgtggcaca ggctggaata tgagccattt aaatcacaaa ttaattagaa aaaaacagt     18240 ggggaaaaaa ttccatggat gggtctagaa agactagcat tgttttaggt tgagtggcag    18300
tgtttaaagg gtgatatcag actaaacttg aaatatgtgg ctaaataact agaatactct    18360 ttatttttc gtatcatgaa tagcagatat agcttgatgg ccccatgctt ggtttaacat     18420
ccttgctgtt cctgacatga aatccttaat ttttgacaaa ggggctattc attttcattt    18480
tatattgggc ctagaaatta tgtagatggt cctgaggaaa agtttatagc ttgtctattt    18540
ctctctctaa catagttgtc agcacaatgc ctaggctata ggaagtactc aaagcttgtt    18600
aaattgaatt ctatccttct tattcaattc tacacatgga ggaaaaactc atcagggatg    18660
gaggcacgcc tctaaggaag gcaggtgtgg ctctgcagtg tgattgggta cttgcaggac    18720
gaagggtggg gtgggagtgg ctaaccttcc attcctagtg cagaggtcac agcctaaaca    18780
tcaaattcct tgaggtgcgg tggctcactc ctgtaatcac agcagtttgg gacgccaagg    18840
tgggcagatc acttgaggtc aggagttgga caccagccca gccaacatag tgaaacctgg    18900
```

```
tctctgctta aaaatataaa aattagctgg acgtggtgac gggagcctgt aatccaacta   18960
cttgggaggc tgaggcagga gaatcgcttg aaccggggga gtggagtttg cactgagcag   19020
agatcatgcc attgcactcc agcctccaga gcgagactct gtctaaagaa aaacgaaaac   19080
aaacaaacaa acaaacaaac aaaacccatc aaattccctg accgaacaga attctgtctg   19140
attgttctct gacttatcta ccatttccc tccttaaaga aactgtgaac ttccttcagc    19200
tagaggggcc tggctcagaa gcctctggtc agcatccaag aaatacttga tgtcactttg   19260
gctaaaggta tgatgtgtag acaagctcca gagatggttt ctcatttcca tatccaccca   19320
cccagctttc caattttaaa gccaattctg aggtagagac tgtgatgaac aaacaccttg   19380
acaaaattca acccaaagac tcactttgcc tagcttcaaa atccttactc tgacatatac   19440
tcacagccag aaattagcat gcactagagt gtgcatgagt gcaacacaca cacacaccaa   19500
ttccatattc tctgtcagaa aatcctgttg gttttcgtg aaaggatgtt ttcagaggct     19560
gaccccttgc cttcacctcc aatgctacca ctctggtcta agtcactgtc accaccacct   19620
aaattatagc tgttgactca taacaatctt cctgcttcta ccactgcccc actacaattt   19680
cttcccaata tactatccaa attagtcttt tcaaaatgta agtcatatat ggtcacctct   19740
ttgttcaaag tcttctgata gtttcctata tcatttataa taaaaccaaa tccttacaat   19800
tctctacaat agttgttcat gcatatatta tgtttattac agatacatat atatagctct   19860
catataaata aatatatata tttatgtgta tgtgtgtaga gtgttttttc ttacaactct   19920
atgatgtagg tattattagt gtcccaaatt ttataattta ggacttctat gatctcatct   19980
tttattctcc ccttcaccga atctcatcct acattggcct tattgatatt ccttgaaaat   20040
tctaagcatc ttcacatcttt agggtattta catttgccat tccctatgcc ctaaatattt    20100
aatcatagtt tcatataaat gggttcctca tcatctatgg gtactctctc aggtgttaac   20160
tttatagtga ggactttcct gccatactac ttaaagtagc gatacccttt caccctgtcc   20220
taatcacact ctggccttca tttcagtttt ttttttttct ccatagcacc taatctcatt   20280
ggtatataac atgtttcatt tgcttattta atgtcaagct cttcccacta tcaagtccat   20340
gaaaacagga actttattcc tctattctgt ttttgtgctg tattcttagc aattttacaa   20400
ttttgaatga atgaatgagc agtcaaacac atatacaact ataattaaaa ggatgtatgc   20460
tgacacatcc actgctatgc acacacaaag aaatcagtgg agtagagctg gaagtgctaa   20520
gcctgcatag agctagttag ccctccgcag gcagagcctt gatgggatta ctgagttcta   20580
gaattggact catttgtttt gtaggctgag atttgctctt gaaaacttgt tctgaccaaa    20640
ataaaaggct caaagatgaa atatcgaaac cagggtgttt tttacactgg aatttataac   20700
tagagcactc atgtttatgt aagcaattaa ttgtttcatc agtcaggtaa agtaaagaa      20760 aaactgtgcc aaggcaggta gcctaatgca atatgccact aaagtaaaca ttatttcata   20820
ggtgtcagat atggcttatt catccatctt catgggaagg atggccttgg cctggacatc   20880
agtgttatgt gaggttcaaa acacctctag gctataaggc aacagagctc ctttttttt    20940 tttctgtgct ttcctggctg tccaaatctc taatgataag catacttcta ttcaatgaga   21000
atattctgta agattatagt taagaattgt gggagccatt ccgtctctta tagttaaatt    21060
tgagcttctt ttatgatcac tgttttttta atatgcttta agttctgggg tacatgtgcc    21120
atggtggttt gctgcaccca tcaaccccgtc atctacatta ggtatttctc ctaatgctat   21180
ccttccccta gccccccacc cccaacaggc cccagtgtgt gatgttcccc tccctgtgtc    21240
```

```
catggatcac tggttttttt ttgttttttt tttttttta aagtctcagt taaattttg    21300 gaatgtaatt tattttcctg gtatcctagg acttgcaagt tatctggtca ctttagccct    21360
cacgttttga tgataatcac atatttgtaa acacaacaca cacacacaca cacacacaca    21420
tatatatata tataaaacat atatatacat aaacacacat aacatattta tcgggcattt    21480
ctgagcaact aatcatgcag gactctcaaa cactaaccta tagcctttc tatgtatcta    21540 cttgtgtaga aaccagcgt ggggactgag aaggcaatag caggagcatt ctgactctca    21600
ctgcctttag ctaggcccct ccctcatcac agctcagcat agtcctgagc tcttatctat    21660
atccacacac agtttctgac gctgcccagc tatcaccatc ccaagtctaa agaaaaaat    21720 aatgggtttg cccatctctg ttgattagaa aacaaaacaa aataaaataa gccctaagc    21780 tcccagaaaa catgactaaa ccagcaagaa gaagaaaata caataggtat atgaggagac    21840
tggtgacact agtgtctgaa tgaggcttga gtacagaaaa gaggctctag cagcatagtg    21900
gtttagagga gatgtttctt tccttcacag atgccttagc ctcaataagc ttgcggttgt    21960
ggaagtttac tttcagaaca aactcctgtg gggctagaat tattgatggc taaaagaagc    22020 ccggggagg gaaaaatcat tcagcatcct caccctagt gacacaaaac agagggggcc    22080
tggttttcca tattcctca tgatggatga tctcgttaat gaaggtggtc tgacgagatc    22140
attgcttctt ccatttaagc cttgctcact tgccaatcct cagttttaac cttctccaga    22200
gaaatacaca ttttttattc aggaaacata ctatgttata gtttcaatac taaataatca    22260
aagtactgaa gatagcatgc ataggcaaga aaagtcctt agctttatgt tgctgttgtt    22320
tcagaattta aaaagatca ccagtcaag gacttctcag ttctagcact agaggtggaa    22380
tcttagcata taatcagagg tttttcaaaa tttctagaca taagattcaa agccctgcac    22440
ttaaaatagt ctcatttgaa ttaactcttt atataaattg aaagcacatt ctgaactact    22500
tcagagtatt gttttatttc tatgttctta gttcataaat acattaggca atgcaattta    22560
attaaaaaaa cccaagaatt tcttagaatt ttaatcatga aaataaatga aggcatcttt    22620
acttactcaa ggtcccaaaa ggtcaaagaa accaggaaag taaagctata tttcagcgga    22680
aaatgggata tttatgagtt ttctaagttg acagactcaa gttttaacct tcagtgccca    22740
tcatgtagga aagtgtggca taactggctg attctggctt tctactcctt tttcccatta    22800
aagatccctc ctgcttaatt aacattcaca agtaactctg gttgtacttt aggcacagtg    22860
gctcccgagg tcagtcacac aataggatgt ctgtgctcca agttgccaga gagagagatt    22920
actcttgaga atgagcctca gccctggctc aaactcacct gcaaacttcg tgagagatga    22980
ggcagaggta cactacgaaa gcaacagtta gaagctaaat gatgagaaca catggactca    23040
tagagggaaa caacgcatac tggggcctat cagagggtgg agggtgagag aaggagagga    23100
tcaggaaaaa tcactaatgg atgctaagcg taatacctga gtgatgagat catctataca    23160 acaaccccc ttgacattca tttatctatg taacaaacct gcacatcctg tacatgtacc    23220
cctgaactta aaataaaagt tgaaaacaag aaagcaacag tttgaacact tgttatggtc    23280
tattctctca ttctttacaa ttacactaga aaatagccac aggcttcctg caaggcagcc    23340
acagaattta tgacttgtga tatccaagtc attcctggat aatgcaaaat ctaacacaaa    23400
atctagtaga atcatttgct tacatctatt tttgttctga gaatatagat ttagatacat    23460
aatggaagca gaataattta aaatctggct aatttagaat cctaagcagc tcttttccta    23520
tcagtggttt acaagccttg tttatatttt tcctatttta aaaataaaaa taagtaagt    23580 tatttgtggt aaagaatatt cattaaagta tttatttctt agataatacc atgaaaaaca    23640
```

```
ttcagtgaag tgaagggcct actttactta acaagaatct aatttatata attttttcata    23700
ctaatagcat ctaagaacag tacaatattt gactcttcag gttaaacata tgtcataaat    23760
tagccagaaa gatttaagaa aatattggat gtttccttgt ttaaattagg catcttacag    23820
tttttagaat cctgcataga acttaagaaa ttacaaatgc taaagcaaac ccaaacaggc    23880
aggaattaat cttcatcgaa tttgggtgtt tctttctaaa agtcctttat acttaaatgt    23940
cttaagacat acatagattt tattttacta attttaatta tatagacaat aaatgaatat    24000
tcttactgat tactttttct gactgtctaa tctttctgat ctatcctgga tggccataac    24060
acttatctct ctgaactttg ggcttttaat ataggaaaga aaagcaataa tccatttttc    24120
atggtatctc atatgataaa caaataaaat gcttaaaaat gagcaggtga agcaatttat    24180
cttgaaccaa caagcatcga agcaataatg agactgcccg cagcctacct gacttctgag    24240
tcaggattta taagccttgt tactgagaca caaacctggg cctttcaatg ctataacctt    24300
tcttgaagct cctccctacc acctttagcc ataaggaaac atggaatggg tcagatccct    24360
ggatgcaagc caggtctgga accataggca gtaaggagag aagaaaatgt gggctctgca    24420
actggctccg agggagcagg agaggatcaa ccccatactc tgaatctaag agaagactgg    24480
tgtccatact ctgaatggga agaatgatgg gattacccat agggcttgtt ttagggagaa    24540
acctgttctc caaactcttg gccttgagat acctggtcct tattccttgg actttggcaa    24600
tgtctgaccc tcacattcaa gttctgagga agggccactg ccttcatact gtggatctgt    24660
agcaaattcc ccctgaaaac ccagagctgt atcttaattg gttaaaaaaa attatattat    24720
ctcaacgact gttcttctct gagtagccaa gctcagcttg gttcaagcta caagcagctg    24780
agctgctttt tgtctagtca ttgttctttt atttcagtgg atcaaatacg ttctttccaa    24840
acctaggatc ttgtcttcct aggctatata ttttgtccca ggaagtctta atctggggtc    24900
cacagaacac tagggggctg gtgaagttta tagaaaaaaa atctgtattt ttacttacat    24960
gtaactgaaa tttagcattt tcttctactt tgaatgcaaa ggacaaacta gaatgacatc    25020
atcagtacct attgcatagt tataaagaga aaccacagat attttcatac tacaccatag    25080
gtattgcaga tcttttgtt tttgtttttg tttgagatgg agtttcgctc ttattgccca    25140
ggctggagtg cagtggcatg atttcggctc actgcaacct ccccttcctg cattcaagca    25200
attctcctgc cttggcctcc tgagtagctg ggattacag gcacctgcca ccatgccagt    25260
ctaattttg tatttttagt agagatgggg tttcgccatg ttggccaggc tggtcttgaa    25320
ctcctgacct cagatgatct gcccgccttg gcctcctgaa gtgctgggat tataggtgtg    25380
agccaccacg cctggcccat tgcagatatt tttaattcac atttatctgc atcactactt    25440
ggatcttaag gtagctgtag acccaatcct agatctaatg ctttcataaa gaagcaaata    25500
taataaatac tataccacaa atgtaatgtt tgatgtctga taatgatatt tcagtgtaat    25560
taaacttagc actcctatgt atattatttg atgcaataaa aacatatttt tttagcactt    25620
acagtctgcc aaactggcct gtgacacaaa aaaagtttag gaattcctgg ttttgtctgt    25680
gttagccaat ggttagaata tatgctcaga aagataccat tggttaatag ctaaaagaaa    25740
atggagtaga aattcagtgg cctggaataa taacaatttg ggcagtcatt aagtcaggtg    25800
aagacttctg gaatcatggg agaaaagcaa gggagacatt cttacttgcc acaagtgttt    25860
ttttttttt ttttttttat cacaaacata agaaaatata ataaataaca aagtcaggtt    25920
atagaagaga gaaacgctct tagtaaactt ggaatatgga atccccaaag gcacttgact    25980
```

```
tgggagacag gagccatact gctaagtgaa aaagacgaag aacctctagg gcctgaacat   26040
acaggaaatt gtaggaacag aaattcctag atctggtggg gcaaggggag ccataggaga   26100
aagaaatggt agaaatggat ggagacggag gcagaggtgg gcagatcatg aggtcaagag   26160
atcgagacca tcctggcaaa catggtgaaa tcccgtctct actaaaaata aaaaaattag   26220
ctgggcatgg tggcatgcgc ctgtagtccc agctgctcgg gaggctgagg caggagaatc   26280
gtttgaaccc aggaggcgaa ggttgcagtg agctgagata gtgccattgc actccagtct   26340
ggcaacagag tgagactccg tctcaaaaaa aaaaaaaaa gaaagaaaga aaagaaaaag   26400
aaaaaagaaa aaataaatgg atgtagaaca agccagaagg aggaactggg ctggggcaat   26460
gagattatgg tgatgtaagg gacttttata gaattaacaa tgctggaatt tgtggaactc   26520
tgcttctatt attcccccaa tcattacttc tgtcacattg atagttaaat aatttctgtg   26580
aatttattcc ttgattctaa aatatgagga taatgacaat ggtattataa gggcagatta   26640
agtgatatag catgagcaat attcttcagg cacatggatc gaattgaata cactgtaaat   26700
cccaacttcc agtttcagct ctaccaagta aagagctagc aagtcatcaa aatggggaca   26760
tacagaaaaa aaaaggaca ctagaggaat aatataccct gactcctagc ctgattaata   26820
tatcgattca ctttttctc tgtttgatga caaattctgg cttttaaataa ttttaggatt   26880 ttaggcttct cagctcccctt cccagtgaga agtataagca ggacagacag gcaagcaaga   26940
agagagcccc aggcaatact cacaaagtag ccaatgtccc ctgtggtcat agagaaatga   27000
aaagagagag gattctctgg aagcactgga tgtaatcttt tctgtctgtc ctctctaggg   27060
aatcacccca aggtactgta ctttgggatt aaggctttag tcccactgtg gactacttgc   27120
tattctgttc agtttctaga aggaactatg tacggttttt gtctccctag agaaactaag   27180
gtacagaagt tttgtttaca atgcactcct taagagagct agaactgggt gagattctgt   27240
tttaacagct ttatttctt ttccttggcc ctgtttttgt cactgtcacc acctttaagg   27300
caaatgttaa atgcgctttg gctgaaactt ttttcctat tttgagattt gctccttat    27360 atgaggcttt cttggaaaag gagaatggga gagatggata tcattttgga agatgatgaa   27420
gagggtaaaa aaggggacaa atggaaattt gtgttgcaga tagatgagga gccaacaaaa   27480
aagagcctca ggatccagca cacattatca caaacttagt gtccatccat cactgctgac   27540
cctctccgga cctgactcca cccctgaggg acacaggtca gccttgacca atgacttta    27600 agtaccatgg agaacagggg gccagaactt cggcagtaaa gaataaaagg ccagacagag   27660
aggcagcagc acatatctgc ttccgacaca gctgcaatca ctagcaagct tcaggcctg    27720 gcatcatggt gcattttact gctgaggaga aggctgccgt cactagcctg tggagcaaga   27780
tgaatgtgga agaggctgga ggtgaagcct tgggcaggta agcattggtt tcaatgcat    27840 gggaatgaag ggtgaatatt accctagcaa gttgattggg aaagtcctca agatttttg    27900 catctctaat tttgtatctg atatggtgtc atttcataga ctcctcgttg tttacccctg   27960
gacccagaga ttttttgaca gctttggaaa cctgtcgtct ccctctgcca tcctgggcaa   28020
ccccaaggtc aaggcccatg gcaagaaggt gctgacttcc tttggagatg ctattaaaaa   28080 catgacaac ctcaagcccg cctttgctaa gctgagtgag ctgcactgtg acaagctgca    28140
tgtggatcct gagaacttca aggtgagttc aggtgctggt gatgtgattt tttggcttta   28200
tattttgaca ttaattgaag ctcataatct tattggaaag accaacaaag atctcagaaa   28260
tcatgggtcg agcttgatgt tagaacagca gacttctagt gagcataacc aaaacttaca   28320
tgattcagaa ctagtgacag taaaggacta ctaacagcct gaattggctt aacttttcag   28380
```

```
gaaatcttgc cagaacttga tgtgtttatc ccagagaatt gtattataga attgtagact   28440
tgtgaaagaa gaatgaaatt tggcttttgg tagatgaaag tccatttcaa ggaaatagaa   28500
atgccttatt ttatgtgggt catgataatt gaggtttaga agagattttt tgcaaaaaaa   28560
ataaaagatt tgctcaaaga aaaataagac acattttcta aaatatgtta aatttcccat   28620
cagtattgtg accaagtgaa ggcttgtttc cgaatttgtt ggggatttta aactcccgct   28680
gagaactctt gcagcactca cattctacat ttacaaaaat tagacaattg cttaaagaaa   28740
aacagggaga gagggaaccc aataatactg gtaaaatggg gaaggggtg agggtgtagg    28800 taggtagaat gttgaatgta gggctcatag aataaaattg aacctaagct catctgaatt   28860 tttgggtgg gcacaaacct tggaacagtt tgaggtcagg gttgtctagg aatgtaggta    28920
taaagccgtt tttgtttgtt tgtttgtttt ttcatcaagt tgttttcgga aacttctact   28980
caacatgcct gtgtgttatt ttgtcttttg cctaacagct cctgggtaac gtgatggtga   29040
ttattctggc tactcacttt ggcaaggagt tcacccctga agtgcaggct gcctggcaga   29100
agctggtgtc tgctgtcgcc attgccctgg cccataagta ccactgagtt ctcttccagt   29160
ttgcaggtgt tcctgtgacc ctgacaccct ccttctgcac atgggactg ggcttggcct    29220 tgagagaaag ccttctgttt aataaagtac attttcttca gtaatcaaaa attgcaattt   29280
tatcttctcc atcttttact cttgtgttaa aggaaaaag tgttcatggg ctgagggatg    29340
gagagaaaca taggaagaac caagagcttc cttaagaaat gtatggggc ttgtaaaatt    29400 aatgtggatg ttatgggaga attccaggat tccaaggagg atgatatgat ggagaaaaat   29460
ctttatcggg gtgggaaaat ggttaattaa gtggacagag actcctaggc agtttttact   29520
gcaccgggga aagaaggagc tgttagtggt acctgagaaa gcagatttgt ggtacatgtc   29580
acttttcatt aaaaacaaaa acaaaacaaa acaaacttc atagatatcc aagatatagg    29640
ctagaattac tattttaatt tactcttatt tacattttga agtagctagc ttgtcacatg   29700
ttttatgaaa ttgatttgga gataagatga gtgtgtatca acaatagcct gctctttcca   29760
tgaaggattc cattatttca tgggttagct gaagctaaga cacatgatat cattgtgcat   29820
tatcttctga tagaatgtaa catgcactaa aataaagtta gagttaggac ctgagtggga   29880
aagttttggg agagtgtgat gaagactttc cgtgggagat agaatactaa taaaggctta   29940
aattctaaaa ccagcaagct agggcttcgt gacttgcatg aaactggctc tctggaagta   30000
gaagggagag taagacatac gtagaggact aggaaagacc agatagtaca gggcctggct   30060
acaaaaatac aagcttttac tatgctattg caatactaaa cgataagcat taggatgtta   30120
agtgactcag gaaataagat tttgggaaaa agtaatctgc ttatgtgcac aaaatggatt   30180
caagtttgca gataaaataa aatatggatg atgattcaag gggacagata caatggttca   30240
aacccaagag gagcagtgag tctgtggaat ttgaaggatg acaaaggtg gggtgagaaa    30300 gacatagtat tcgactgact gtgggagatg agaaggaaga aggaggtgat aaatgactga   30360
aagctcccag actggtgaag ataacaggag gaaaccatgc actgacctgg tgactctcat   30420
gtgtgaaggg tagagggata ttaacagatt tactttttag gaagtgctag attggtcagg   30480
gagttttgac cttcaggtct tgtgtctttc atatcaagga acctttgcat tttccaagtt   30540
agagtgccat attttggcaa atataacttt attagtaatt ttatagtgct ctcacattga   30600
tcagactttt tcctgtgaat tacttttgaa tttggctgta tatatccaga atatgggaga   30660
gagacaaata attattgtag ttgcaggcta tcaacaatac tggtctctct gagccttata   30720
```

```
accttccaat atgcccataa acagagtaaa cagggattat tcatggcact aaatattttc    30780
acctagtcag tcaacaaatg ggagcaatgt gcatttttg atacatattt ttatatattt     30840
atggggtaca tgtgatactt acatgcctag aacatgtgat gattaagtct agatatttag    30900
gatatccatt gctttgagca tttatcattt ctatgtattg agaaaatttc aaatcctcat    30960
ttctagccat tttgaaatat ataataaata gtaattaact atagtcaccc tactcaaata    31020
tcaaacatta tggcttaatc cttctatcca actgtgtttg tacctattaa ccaacatctc    31080
ttaaatcccc tcccatacac actcacactt tttccagcct ctgataacta tcattctact    31140
ctctaccacc atgagaccca ctttttttagc tcccacagat gaataaaaac atgtgatatt   31200
tgactttctg tatctggctt attttattat ctatctcttt ggcataccaa gagtttgttt    31260
ttgttctgct tcagggcttt caattaacat aatgacctct ggttccatcc atgttgctac    31320
aaatgacaag atttcattct ttttcatggc aaaatagtac tgtgcaaaaa tacaattttt    31380
taatccgttc atctgttgat agacacttag gttgatccca aaccttaact attgtgaata    31440
gtgcttcaat aaacatgagt gtaatgtgtc cattggatat actgatttcc tttcttttgg    31500
ataaataacc actagtgaga ttgctggatt gtatgatagt tctgtttta gtttactgag      31560
aaatcttcat actgttttcc ataatggttg tactatttta cattcccacc aacagtgtgt    31620
aagaaagagt tccctttttct ccatatcctc acaaggatct gttattttt gtcttttttg     31680
ttaatagccg ttttaactag agtaagtaga tatctcattg tagttttgat ttgcatttcc    31740
ctgatcatta gtgatgttga aatttttttc atatgtttgt tggtcatttg tatatctttt    31800
tctgagaatt gtctgttcat gtccttagcc tactttttat tgggattgtt tgttatttttc   31860
ttgataatct atttgtgttc atttagagc ctggatatta ttcttttgtc agatgtatag      31920
attgtgaaga ttttctccca ctctgtgggt tgtctgttta ttctgcagac tcttcctttt   31980
gccatgcaaa agctctttag tttaatttag tcccagatat tttctttgtt tttatgtatt    32040
tgcatttgtg ttcttggtca tgaaatcctt tcctaagcca atgtgtagaa gggttttttcc   32100
gatgttattt tctagaattg ttacagtttc agggcttaga tttaagtcct tgatccatct    32160
tgagttgatt tttgtataag gtgagagatg aagatccagt ttcattctcc tacatgtagc   32220
ttgccagcta tccccgcacc atttgttgaa tagggtgccc tttccccact ttatgttttt    32280
gtttgctttg tcaaagatca gttggatgta agtatttgag tttatttctg ggttctctat    32340
tctgttccat tggtcgatgt gcctatttgt acaccagcat catgctgttt tggtgactat    32400
ggccttattg tatagtttga aatgaggtaa tgtaatgcct tcagatttgt tcttttttttt   32460
agacttgctt gtttattggg ctctttttg gttccataag aattttagga ttgttttttc     32520
tagttctgtg aagactaatg gtggtatttt gatgggaatt gcaatgaatt tgtaggttgc    32580
ttctggcatt atggccattt tcacaatatt gattctaccc atctatgaga atggcatgtg    32640
tttccatttg tttgtgtctt atatgattac tttcagccgt gtttttgtagt tttccttgta   32700
gatgtctttc acctccttgg ttaggtatat attcctaagt ttttgttttg ttttgttttg   32760
tttttttgcag ctattgtaaa aggggttgag ttcttgattt tattctcagc ttggtcattg   32820
ctggtatgta agaaagcaac tcattggtgt acgttaattt tgtatccaga aactttgctg    32880
aattatttta tcagttctag ggggttttgg aggagtcttt agagttttct acatacacaa    32940
tcatatcatc agcaaacagt gacagtttga cttctctttt aacaatttgg atgtgcttta    33000
cttgtttctc ttgtctgatt gctccttgcta ggacttccag taatatgtta agagaagtg    33060
gtgagagtgg gtatccttgt ctcattccag ttttcagaca gaatgctttt aacttttttcc   33120
```

```
cattcaatat aatgttggct gtgtgtttac catagctggc ttttattaca ttgaggtatg   33180
tcctttgtaa accgattttg ctgagtttta gtcataaagt gatgttgaat tttgttgaat   33240
gcagtttctg tggctattga gataatcaca tgattttgt ttccaattct ctttatgttg    33300
tgtatcacac ttattgactt gcgtatgtta aaccatccgt gcatccctcg catgaaaccc   33360
acttgatcat gggttttgat atgctgtcgg atgctattag ctagtatttt gtcaaggatg   33420
ttggcatcta tgttcatcag ggatattgat ctgtagtgtt ttttttttt ggttatgttc    33480 tttcccagtt ttggtattaa ggtgatactg gcttcataga atgatttagg gaggattctc   33540
tctttctcta tcttgtagaa tactgtcaat aggattggta tcaattcttc tttgaatgtc   33600
tggtagaatt cagctgtgaa tctatctggt cctggacttt tttgttgttg gtaaattttt   33660
attatcattt cagtcttgct gcttattact ggtctgttca gggtatctaa ttcttcctga   33720
cttaagctag agccctgtat cttcccagga attcgaacgt ctcctttagg ttttctagtt   33780
tatgcatgta aaggtgttca tagtagcctt gaataatctt ttgtatttct gtggtatcag   33840
taatagtatc tcctgttttg tttctaattg agtttatttg cacttctctc ctcttttctt   33900
ggttaatctt gctaatggtc tatcagtttt atttatcttt tcaaagaacc agctttttat   33960
ttcatttagc ttttgtattt ttttgcagtt gttttaattt catttagttc tcctcttatc   34020
ttagttattc ccttctttt gctgggtttt ggttctgttt gttttttgttt ctctagtttc   34080 ttgtggtgtg accttatatt gtctgtctgt cctctttcag actctttgac atcgacattt   34140
agggctgtga actttccttt tagcaccatc tttgctgtat cctagaggtt ttgataggtt   34200
gtgtcactat tgtcggtcag ttcaagtaat tttgttgttc ttattatact ttaagttctg   34260
ggatacatgt gcagaatgtg caggtttgtt acataggtat agatgtgcca tggtggtttg   34320
ctgcacccat caacctgtca tctacattag gtatttcttt taatgttatc cctctcctaa   34380 cccctcacc ccccgacagg ccctggtgtg tgatgttccc ctccctgtgt ccatgtgttc    34440
tcattgttca actcccactt atgagtgaga acgtgtggtg tttggtttct ctgttcctgt   34500
gttagtttgc tcagaatgat ggtttccacc ttcatccatg tccctgcaaa gacatgaact   34560 catcatttt atggctgcat agtattccat ggtgtatatg tgccacattt tctttatcca    34620
ttatatcgct gatggccatt tgggttggtt ccaagtcttt gctattgtga atagtgccac   34680
aataaacata cgtgtgcacg tgtctttata gtagaatgat ttctaattct ttgggtatat   34740
acccagtaat gggattgctg ggtcaaacag tatttctggt tctagatcct tgaggaatcg   34800
ccacactgtc ttccacaatg gttgaactaa tttacacacc catcaacagt gtaaatttt    34860 tcctattctt ccacatcctc tccagcacct tttgtttcct gacttttttaa taattgccat   34920 tctaactggc atgagatggt atctcattgt ggttttgatt tgcatttctc taatgaccag   34980
tgatgatgag cttcttttca tgtgtttctt ggccacataa atgacttctt tagagaagca   35040
tctgttcata tccttgtcc actttttgat gggtcgtta ggttttttct tgtaaatttg     35100
ttgaagttct ttgtagattt tggatgttag cccttgtca gatggataga ttgcaaaaat    35160
tttctcccat tctgtaggtt gcctgttcac tctgatgata gtcttttgct gtgcagaagc   35220
tctttagttt aattagatcc catatgtcaa ttttggcctt tgttgtcatt gcttttgatg   35280
ttttagtcgt gaattttgc ccatgcctat gtcctgaatg gtattgccta ggttatcttc    35340
taggattttt atggttttag gttgcacatt taagtcttta atccaccttg agttaatttt   35400
tgtataaggt gtaaggaagg ggtacagttt cagttttatg catattgcta gccagttttt   35460
```

```
ccagcaccat ttattaaata gggaattctt tctccattgc ttttgtgatg tttgtcaaag    35520
atcagatggt cgtagatgtg tggcattatt tctgaggctt ctgttctgtt ccactggtct    35580
atatatctgt tttggtacca gtaccatgct gtttttgtta ctgtagcctt gtagtatagt    35640
ttgaagtcag gtagcatcat gcctccagct ttgttctttt tgtttaggat tgtcttggct    35700
atatgggctc tttttgatt ccatatgaca tttaaagtag ttttttctaa ttctttgaaa     35760
aaagtcagtg gtagcttgat ggggatagca ttgaatctat aaattacttt gggcagtatg    35820 gccatttaa agatattgat tctttctatc tatgagcatg gaatgttttt ccatttgttt     35880
gtgtcctctc ttatttcctt gagcagtgag tggtttgtag ctctccttga agaggttctt    35940
cacatccctt agaagttgta tttctaggta ttttatttta ttctctttgc agcaattgtg    36000
aatgggagtt cacccatgat ttggctctct gcttgtctat tattggtgta taggaacgct    36060
tgtgatttct gcacactgat tttgtatctt gagactttgc tgaagctgtt tatcagctta    36120
agattttggg ctgagatgac agggtcttct aaatatacaa tcatgtcatc tgcaaacaga    36180
gacaatttga cttcctctct tcctatttga atatgcttta tttctttctc ttgcctgatt    36240
gtcctggcga gaacttccaa tactatgttg agtaagagtg gcgagagggc atccttgtct    36300
tgtgccggtt ttcaaagcaa atgatttta aatttccatc ttgatttcat tgttgaccca     36360
atgatcattc aggagcaggt tatttaattt ccctgtattt gcatggtttt gaaggttcct    36420
tttgtagttg atttccaatt ttattctact gtggtctgag agagtgcttg atataatttc    36480
aatttttaaa aatttattga ggcttgtttt gtggcatatc atatggccta tcttggagaa    36540
agttccatgt gctgatgaat agaatgtgta ttctgcagtt gttgggtaga atgtcctgta    36600
aatatctgtt aagtccattt gttctttaaa tccattgttt cttgtagac tgtcttgatg     36660 acctgcctag tgcagtcagt ggagtattga agtcccccac tattattatg ttgctgtcta    36720
gtctagtagt aattgtttta taaatttggg atctccagta ttagatgcat atatattaag    36780
aattgtaata ttctcccatt ggacaagggc ttttatcatt tatgatgtc cctctttgtc     36840 tttttaact gctgtttctt taaagtttgt tttgtctgac ataagaatag ctgctttggc     36900
tcgcttttgg tgtccatttg tgtggaatgt cattttccac cccttacct taagtttatg     36960 tgagtcctta tgtgttaggt gagtctcctg aaggcggcag ataactggtt ggtgaattct    37020
tattcattct gcaattctgt atcttttaag tggagcattt agtccattta cattcaacat    37080
cagtattgag gtgtgaggta ctattccatt cttcgtggta tttgttgcct gtgtatcttt    37140
ttatctgtat ttttgttgta tatgtccatc gggattatg ctttaaagag gttctgtttt    37200
gatgtgcttc cagggtttat ttcaagattt agagctcctt ttatcagttc ttgtagtgtt    37260
ggcttggtag tgccgaattc tctcagcatt tgtttttctg aaaaacactg tgtattttct    37320
tcatttgtga agcttagttt cactggatat aaaattcttg gctgataatt gttttgttta    37380
agaaggctga agataggggcc atattcactt ctagctttta cggtttctgc tgagaaatct    37440
gctgttaatc tgataggttt tctttcatag gttacctggt agtttcacct cacagctctt    37500
aagattctct ttgtctttag ataactttgg atactctgat gacaatgtac ctaggcaatg    37560 atattttgc aatgaatttc ccaggtgttt attgagcttc ttgtatttgg atatctaggt     37620
ctctagcaag gtgggggaag ttttccttga ttatttccct ggataagttt tccaaacttt    37680
tagatttctc ttcttttctca ggaatgctga ttattcttag gtttgattgt ttaacataat   37740
cccagatttc ttggaggctt tgttcatatt ttccttattct ttttcttttg tctttgttgg   37800
attgggttaa ttcaaaaact ttgtcttcaa gctctgaatt tcttctgctt ggattctatt    37860
```

```
gctgagactt tctagagcat tttgcatttc tataagtgca tccattcatc cattgtttcc    37920
tgaagttttg aatgttttt atttatgcta tctctttaac tgaagatttc tcccctcatt    37980
tcttgtatca tattttggt ttttttaaaa ttggacttca ccttcctcgg atgcctcctt    38040
gattagctta ataactgacc ttctgaatta tttttcaggt aaatcaggga tttcttcttg    38100
gtttggatgc attgctggtg agctagtatg atttttggg gggtgttaaa gaaccttgtt    38160
tttcatatta ccagagttag ttttctggtt ccttctcact tgggtaggct ctgtcagagg    38220
gaaagtctag gcctcaaggc tgagactttt gtcccatgag gtgttccctt gatgtagcac    38280 agtcccctt ttcctaggcg tggggcttcc tgagagccga actgtagtga ttgttatctc    38340
tcttctggat ctagccaccc atcaggtcta ccagactcca ggctggtact ggggtttgtc    38400
tgcacagagt cttgtgacgt gaaccatctg tgggtctctc agccatagat acaaccacct    38460
gctccaatgg aggtggcaga ggatgaaatg gactctgtga gggtccttac ttttggttgt    38520
tcaatgcact attttgtgc tggttggcct cctgccagga ggtggcactt tctagaaagc    38580
atcagcagag gcagtcaggt ggtggtggct gggggggctg gggcacccta gaactcccaa    38640
gaatatatgc cctttgtctt cagctaccag ggtgagtaag gaaggaccat caggtggggg    38700
caggactagt cgtgtctgag ctcagagtct ccttgggcag gtctttctgt ggctactgtg    38760
ggaggatggg ggtgtagttt ccaggtcaat ggatttatgt tcctaggaca attatggctg    38820
cctctgctgt gtcatgcagg tcatcaggaa agtgggggaa agcaagcagt cacgtgactt    38880
gcccagctcc catgcaactc aaaaggttgg tctcacttcc agcgtgcacc ctcccccgca    38940
acagcaccga atctgtttcc atgcagtcag tgagcaaggc tgagaacttg ccccaggcta    39000
ccagctgcga aaccaagtag ggctgtccta cttccctgcc agtggagtct gcacaccaaa    39060
ttcatgtccc cccaccaacc cccccactgc ccagcccta gatctggcca ggtggagatt    39120 ttcttttcc tgtcatcttt tcccagttcc tctggcagcc ctcccaaatg accctgtga    39180 ggcaaggcag aaatggcttc ctaggggacc cagagagccc acgggctttt tcccgctgct    39240
tcctctaccc ctgtattttg cttggccctc taaattgact cagctccagg taaggtcaga    39300
atcttctcct gtggtctaga tcttcaggtt ccccagtgag gatgtgtgtt tgggggtaga    39360
cggtccccct tttccacttc cacagtttgg gcactcacaa tatttggggt gtttcccggg    39420
tcctgcagga gcaatctgct tctttcagag ggtgtgtgcg ttctctcagc tttcttgatt    39480
tatttctgca ggtggttctg caaaaaaaat tcctgatggg agacttcaca tgctgctctg    39540
tgcatccgag tgggagctgc aatgtacttc tgctgcctcc catctgccat caccctctaa    39600
tttgtcggta atatgcattt ttaatcaatc ttttttctc tctctctctt tttcttctcc    39660
cccaaaacta tactgccctt tgatatcaag gaatcaagga cgtgatgttg aggggtgggc    39720
agtggataca ctctttaccc cttagggagc tatatctaga tttagatatt gccaattcaa    39780
gataacttaa ttgaaagcaa attcataatg aatacacaca cacacacaca catctgcatg    39840
acaagatttt taatagttga aagaataact aataattgtc cacaggcaat aagggctttt    39900
taagcaaaac agttgtgata aacaggtcat tcttagaata gtaatccagc caatagtaca    39960
ggttgcttag agattatgtc attaccagag ttaaaattct ataatggctt ctcactccct    40020
accactgagg acaagtttat gtccttaggt ttatgcttcc ctgaaacaat accacctgct    40080
attctccact ttacatatca acggcactgg ttctttatct aactctctgg cacagcagga    40140
gtttgttttc ttctgcttca gagctttgaa tttactattt cagcttctaa actttatttg    40200
```

```
gcaatgcctt cccatggcag attccttctg tcattttgcc tctgttcgaa tactttctcc  40260
ttaatttcat tcttagttaa taatatctga aattattttg ttgtttaact taattattaa  40320
ttttatgtat gttctaccta gattataatc ttcagaggaa agttttattc tctgacttat  40380
ttaacttaaa tgcccactac tttaaaaatt atgacattta tttaacagat atttgctgaa  40440
caaatgtttg aaaatacatg ggaagaatg cttgaaaaca cttgaaattg cttgtgtaaa  40500
gaaacagttt tatcagttag gatttaatca atgtcagaag caatgatata ggaaaaatcg  40560
aggaataaga cagttatgga taaggagaaa tcaacaaact cttaaaagat attgcctcaa  40620
aagcataaga ggaaataagg gtttatacat gacttttaga acactgcctt ggttttggga  40680
taaatgggga agttgtttga aaacaggagg gatcctagat attccttagt ctgaggagga  40740
gcaattaaga ttcacttgtt tagaggctgg gagtggtggc tcacgcctgt aatcccagaa  40800 tttgggagg ccaaggcagg cagatcacct gaggtcaaga gttcaagacc aacctggcca  40860
acatggtgaa atcccatctc tacaaaaata caaaaattag acaggcatga tggcaagtgc  40920
ctgtaatccc agctacttgg gaggctgagg aaggagaatt gcttgaacct ggaaggcagg  40980
agttgcagtg agccgagatc ataccactgc actccagcct gggtgacaga acaagactct  41040
gtctcaaaaa aaaaaagag agattcaaaa gattcacttg tttaggcctt agcgggctta  41100
gacaccagtc tctgacacat tcttaaaggt caggctctac aaatggaacc caaccagact  41160
ctcagatatg gccaaagatc tatacacacc catctcacag atcccctatc ttaaagagac  41220
cctaatttgg gttcacctca gtctctataa tctgtaccag cataccaata aaaatctttc  41280
tcacccatcc ttagattgag agaagtcact tattattatg tgagtaactg gaagatactg  41340
ataagttgac aaatcttttt ctttcctttc ttattcaact tttatttaa cttccaaaga  41400 acaagtgcaa tatgtgcagc tttgttgcgc aggtcaacat gtatctttct ggtcttttag  41460
ccgcctaaca ctttgagcag atataagcct tacacaggat tatgaagtct gaaaggattc  41520
caccaatatt attataattc ctatcaacct gataggttag gggaaggtag agctctcctc  41580
caataagcca gatttccaga gtttctgacg tcataatcta ccaaggtcat ggatcgagtt  41640
cagagaaaaa acaaaagcaa aaccaaacct accaaaaaat aaaaatccca aagaaaaaat  41700
aaagaaaaaa acagcatgaa tacttcctgc catgttaagt ggccaatatg tcagaaacag  41760
cactgagtta cagataaaga tgtctaaact acagtgacat cccagctgtc acagtgtgtg  41820
gactattagt caataaaaca gtccctgcct cttaagagtt gttttccatg caaatacatg  41880
tcttatgtct tagaataaga ttccctaaga agtgaaccta gcatttatac aagataatta  41940
attctaatcc atagtatctg gtaaagagca ttctaccatc atctttaccg agcatagaag  42000
agctacacca aaaccctggg tcatcagcca gcacatacac ttatccagtg ataaatacac  42060
atcatcgggt gcctacatac ataccctgaat ataaaaaaa tacttttgct gagatgaaac  42120
aggcgtgatt tatttcaaat aggtacggat aagtagatat tgaagtaagg attcagtctt  42180
atattatatt acataacatt aatctattcc tgcactgaaa ctgttgcttt ataggatttt  42240
tcactacact aatgagaact taagagataa tggcctaaaa ccacagagag tatattcaaa  42300
gataagtata gcacttctta tttggaaacc aatgcttact aaatgagact aagacgtgtc  42360
ccatcaaaaa tcctggacct atgcctaaaa cacatttcac aatccctgaa cttttcaaaa  42420
attggtacat gctttaactt taaactacag gcctcactgg agctacagac aagaaggtga  42480
aaaacggctg acaaaagaag tcctggtatc ttctatggtg ggagagaaa actagctaaa  42540 gggaagaata aattagagaa aaattggaat gactgaatcg gaacaaggca aaggctataa  42600
```

```
aaaaaattaa gcagcagtat cctcttgggg gcccttccc cacactatct caatgcaaat    42660
atctgtctga aacggtccct ggctaaactc cacccatggg ttggccagcc ttgccttgac    42720
caatagcctt gacaaggcaa acttgaccaa tagtcttaga gtatccagtg aggccagggg    42780
ccggcggctg gctagggatg aagaataaaa ggaagcaccc ttcagcagtt ccacacactc    42840
gcttctggaa cgtctgaggt tatcaataag ctcctagtcc agacgccatg ggtcatttca    42900
cagaggagga caaggctact atcacaagcc tgtggggcaa ggtgaatgtg aaagatgctg    42960
gaggagaaac cctgggaagg taggctctgg tgaccaggac aagggaggga aggaaggacc    43020
ctgtgcctgg caaagtcca ggtcgcttct caggatttgt ggcaccttct gactgtcaaa    43080
ctgttcttgt caatctcaca ggctcctggt tgtctaccca tggacccaga ggttctttga    43140
cagctttggc aacctgtcct ctgcctctgc catcatgggc aaccccaaag tcaaggcaca    43200
tggcaagaag gtgctgactt ccttgggaga tgccataaag cacctggatg atctcaaggg    43260 caccttgcc cagctgagtg aactgcactg tgacaagctg catgtggatc ctgagaactt    43320
caaggtgagt ccaggagatg tttcagcact gttgccttta gtctcgaggc aacttagaca    43380
actgagtatt gatctgagca cagcaggtg tgagctgttt gaagatactg gggttgggag    43440
tgaagaaact gcagaggact aactgggctg agacccagtg gcaatgtttt agggcctaag    43500
gagtgcctct gaaaatctag atggacaact ttgactttga gaaagagag gtggaaatga    43560 ggaaaatgac ttttctttat tagatttcgg tagaagaac tttcaccttt ccctatttt    43620 tgttattcgt tttaaaacat ctatctggag gcaggacaag tatggtcatt aaaagatgc    43680 aggcagaagg catatattgg ctcagtcaaa gtggggaact ttggtggcca acatacatt    43740 gctaaggcta ttcctatatc agctggacac atataaaatg ctgctaatgc ttcattacaa    43800
acttatatcc tttaattcca gatgggggca aagtatgtcc aggggtgagg aacaattgaa    43860
acatttgggc tggagtagat tttgaaagtc agctctgtgt gtgtgtgtgt gtgtgtgcgc    43920
gcgtgtgttt gtgtgtgtgt gagagcgtgt gtttctttta acgttttcag cctacagcat    43980
acagggttca tggtggcaag aagataacaa gatttaaatt atggccagtg actagtgctg    44040
caagaagaac aactacctgc atttaatggg aaagcaaaat ctcaggcttt gagggaagtt    44100
aacataggct tgattctggg tggaagcttg gtgtgtagtt atctggaggc caggctggag    44160
ctctcagctc actatgggtt catctttatt gtctcctttc atctcaacag ctcctgggaa    44220
atgtgctggt gaccgttttg gcaatccatt tcggcaaaga attcacccct gaggtgcagg    44280
cttcctggca gaagatggtg actggagtgg ccagtgccct gtcctccaga taccactgag    44340
ctcactgccc atgatgcaga gctttcaagg ataggcttta ttctgcaagc aatcaaataa    44400
taaatctatt ctgctaagag atcacacatg gttgtcttca gttcttttt tatgtctttt    44460 taaatatatg agccacaaag ggttttatgt tgagggatgt gtttatgtgt atttatacat    44520
ggctatgtgt gtttgtgtca tgtgcacact ccacactttt ttgtttacgt tagatgtggg    44580
ttttgatgag caaataaaag aactaggcaa taaagaaact tgtacatggg agttctgcaa    44640
gtgggagtaa aaggtgcagg agaaatctgg ttggaagaaa gacctctata ggacaggact    44700
cctcagaaac agatgttttg gaagagatgg ggaaaggttc agtgaagggg gctgaaccc    44760 cttccctgga ttgcagcaca gcagcgagga aggggctcaa cgaagaaaaa gtgttccaag    44820
ctttaggaag tcaaggttta ggcagggata gccattctat tttattaggg gcaatactat    44880
ttccaacggc atctggcttt tctcagccct tgtgaggctc tacagggagg ttgaggtgtt    44940
```

-continued

```
agagatcaga gcaggaaaca ggttttctt tccacggtaa ctacaatgaa gtgatcctta    45000
ctttactaag gaactttca ttttaagtgt tgacgcatgc ctaaagaggt gaaattaatc    45060
ccatacctt aagtctacag actggtcaca gcatttcaag gaggagacct cattgtaagc    45120
ttctagggag gtggggactt aggtgaagga aatgagccag cagaagctca caagtcagca    45180
tcagcgtgtc atgtctcagc agcagaacag cacggtcaga tgaaaatata gtgtgaagaa    45240
tttgtataac attaattgag aaggcagatt cactggagtt cttatataat tgaaagttaa    45300
tgcacgttaa taagcaagag tttagtttaa tgtgatggtg ttatgaactt aacgcttgtg    45360
tctccagaaa attcacatgc tgaatcccca actcccaatt ggctccattt gtggggagg    45420
ctttggaaaa gtaatcaggt ttagaggagc tcatgagagc agatccccat catagaatta    45480
tttcctcat cagaagcaga gagattagcc atttctcttc cttctggtga ggacacagtg    45540
ggaagtcagc cacctgcaac ccaggaagag agccctgacc aggaaccagc agaaaagtga    45600
gaaaaatcc tgttgttgaa gtcacccagt ctatgctatt ttgttatagc accttgcact    45660
aagtaaggca gatgaagaaa gagaaaaaaa taagcttcgg tgttcagtgg attagaaacc    45720
atgtttatct caggtttaca aatctccact tgtcctctgt gtttcagaat aaaataccaa    45780
ctctactact ctcatctgta agatgcaaat agtaagcctg agcccttctg tctaactttg    45840
aattctattt tttcttcaac gtactttagg cttgtaatgt gtttatatac agtgaaatgt    45900
caagttcttt ctttatattt cttctttct tttttttcct cagcctcaga gttttccaca    45960
tgcccttcct actttcagga acttctttct ccaaacgtct tctgcctggc tccatcaaat    46020
cataaaggac ccacttcaaa tgccatcact cactaccatt tcacaattcg cactttcttt    46080
ctttgtcctt tttttttta gtaaaacaag tttataaaaa attgaaggaa taaatgaatg    46140
gctacttcat aggcagagta gacgcaaggg ctactggttg ccgatttta ttgttatttt    46200
tcaatagtat gctaaacaag gggtagatta tttatgctgc ccattttag accataaaag    46260
ataacttcct gatgttgcca tggcattttt ttccttttaa ttttatttca tttcatttta    46320
atttcgaagg tacatgtgca ggatgtgcag gcttgttaca tgggtaaatg tgtgtctttc    46380
tggccttta gccatctgta tcaatgagca gatataagct ttacacagga tcatgaagga    46440
tgaaagaatt tcaccaatat tataataatt tcaatcaacc tgatagctta ggggataaac    46500
taatttgaag atacagcttg cctccgataa gccagaattc cagagcttct ggcattataa    46560
tctagcaagg ttagagatca tggatcactt tcagagaaaa acaaaaacaa actaaccaaa    46620
agcaaaacag aaccaaaaaa ccaccataaa tacttcctac cctgttaatg gtccaatatg    46680
tcagaaacag cactgtgtta gaaataaagc tgtctaaagt acactaatat tcgagttata    46740
atagtgtgtg gactattagt caataaaaac aaccccttgcc tctttagagt tgttttccat    46800
gtacacgcac atcttatgtc ttagagtaag attccctgag aagtgaacct agcatttata    46860
caagataatt aattctaatc cacagtacct gccaaagaac attctaccat catctttact    46920
gagcatagaa gagctacgcc aaaaccctgg gtcatcagcc agcacacaca cttatccagt    46980
ggtaaataca catcatctgg tgtatacata catacctgaa tatggaatca atatttttc    47040
taagatgaaa cagtcatgat ttatttcaaa taggtacgga taagtagata ttgaggtaag    47100
cattaggtct tatattatgt aacactaatc tattactgcg ctgaaactgt ggctttatag    47160
aaattgtttt cactgcacta ttgagaaatt aagagataat ggcaaagtc acaagagta    47220
tattcaaaaa gaagtatagc acttttttcct tagaaaccac tgctaactga aagagactaa    47280
gatttgtccc gtcaaaaatc ctggacctat gcctaaaaca catttcacaa tccctgaact    47340
```

```
tttcaaaaat tggtacatgc tttagcttta aactacaggc ctcactggag ctagagacaa    47400
gaaggtaaaa aacggctgac aaaagaagtc ctggtatcct ctatgatggg agaaggaaac    47460
tagctaaagg gaagaataaa ttagagaaaa actggaatga ctgaatcgga acaaggcaaa    47520
ggctataaaa aaaattagca gtatcctctt gggggcccct tccccacact atctcaatgc    47580
aaatatctgt ctgaaacggt ccctggctaa actccaccca tgggttggcc agccttgcct    47640
tgaccaatag ccttgacaag gcaaacttga ccaatagtct tagagtatcc agtgaggcca    47700
ggggccggcg gctggctagg gatgaagaat aaaaggaagc acccttcagc agttccacac    47760
actcgcttct ggaacgtctg aggttatcaa taagctccta gtccagacgc catgggtcat    47820
ttcacagagg aggacaaggc tactatcaca agcctgtggg gcaaggtgaa tgtggaagat    47880
gctggaggag aaaccctggg aaggtaggct ctggtgacca ggacaaggga gggaaggaag    47940
gaccctgtgc ctggcaaaag tccaggtcgc ttctcaggat tgtggcacc ttctgactgt     48000 caaactgttc ttgtcaatct cacaggctcc tggttgtcta cccatggacc cagaggttct    48060
ttgacagctt tggcaacctg tcctctgcct ctgccatcat gggcaacccc aaagtcaagg    48120
cacatggcaa gaaggtgctg acttccttgg gagatgccac aaagcacctg gatgatctca    48180
agggcacctt tgcccagctg agtgaactgc actgtgacaa gctgcatgtg gatcctgaga    48240
acttcaaggt gagtccagga gatgtttcag ccctgttgcc tttagtctcg aggcaactta    48300
gacaacggag tattgatctg agcacagcag ggtgtgagct gtttgaagat actggggttg    48360
ggggtgaaga aactgcagag gactaactgg gctgagaccc agtggtaatg ttttagggcc    48420
taaggagtgc ctctaaaaat ctagatggac aattttgact ttgagaaaag agaggtggaa    48480
atgaggaaaa tgacttttct ttattagatt ccagtagaaa gaactttcat cttccctca     48540 tttttgttgt tttaaaacat ctatctggag gcaggacaag tatggtcgtt aaaaagatgc    48600
aggcagaagg catatattgg ctcagtcaaa gtggggaact ttggtggcca acatacatt     48660 gctaaggcta ttcctatatc agctggacac atataaaatg ctgctaatgc ttcattacaa    48720
acttatatcc tttaattcca gatgggggca aagtatgtcc aggggtgagg aacaattgaa    48780
acatttgggc tggagtagat tttgaaagtc agctctgtgt gtgtgtgtgt gtgtgcgcgc    48840
gcgcgtgtgt gtgtgtgtgt cagcgtgtgt ttcttttaac gtcttcagcc tacaacatac    48900
agggttcatg gtggcaagaa gatagcaaga tttaaattat ggccagtgac tagtgcttga    48960
aggggaacaa ctacctgcat ttaatgggaa ggcaaaatct caggctttga gggaagttaa    49020
cataggcttg attctgggtg gaagcttggt gtgtagttat ctggaggcca ggctggagct    49080
ctcagctcac tatgggttca tctttattgt ctcctttcat ctcaacagct cctgggaaat    49140
gtgctggtga ccgttttggc aatccatttc ggcaaagaat tcacccctga ggtgcaggct    49200
tcctggcaga agatggtgac tgcagtggcc agtgccctgt cctccagata ccactgagct    49260
cactgcccat gattcagagc tttcaaggat aggcttatt ctgcaagcaa tacaaataat     49320
aaatctattc tgctgagaga tcacacatga ttttcttcag ctctttttt tacatctttt     49380 taaatatatg agccacaaag ggtttatatt gagggaagtg tgtatgtgta tttctgcatg    49440
cctgtttgtg tttgtggtgt gtgcatgctc ctcatttatt tttatatgag atgtgcattt    49500
tgatgagcaa ataaaagcag taaagacact tgtacacggg agttctgcaa gtgggagtaa    49560
atggtgtagg agaaatccgg tgggaagaaa gacctctata ggacaggact tctcagaaac    49620
agatgttttg gaagagatgg gaaaaggttc agtgaagacc tggggctgg attgattgca     49680
```

```
gctgagtagc aaggatggtt cttaaggaag ggaaagtgtt ccaagcttta ggaattcaag    49740
gtttagtcag gtgtagcaat tctatttat taggaggaat actatttcta atggcactta    49800
gcttttcaca gcccttgtgg atgcctaaga aagtgaaatt aatcccatgc cctcaagtgt    49860
gcagattggt cacagcattt caagggagag acctcattgt aagactctgg gggaggtggg    49920
gacttaggtg taagaaatga atcagcagag gctcacaagt cagcatgagc atgttatgtc    49980
tgagaaacag accagcactg tgagatcaaa atgtagtggg aagaatttgt acaacattaa    50040
ttggaaggct tacttaatgg aattttgta tagttggatg ttagtgcatc tctataagta    50100
agagtttaat atgatggtgt tacggaccta atgtttgtgt ctcctcaaaa ttcacatgct    50160
gaatccccaa ctcccaactg accttatctg tggggaggc ttttgaaaag taattaggtt    50220
tagatgagct cataagagca gatccccatc ataaaattat tttccttatc agaagcagag    50280
agacaagcca tttctctttc ctcccggtga ggacacagtg agaagtccgc catctgcaat    50340
ccaggaagag aaccctgacc acgagtcagc cttcagaaat gtgagaaaaa actctgttgt    50400
tgaagccacc cagtcttttg tattttgtta tagcaccttg cactgagtaa ggcagatgaa    50460
gaaggagaaa aaaataagct tgggttttga gtggactaca gaccatgttt atctcaggtt    50520
tgcaaagctc ccctcgtccc ctatgtttca gtataaaata cctactctac tactctcatc    50580
tataagaccc aaataataag cctgcgccct tctctctaac tttgattct cctattttta    50640 cttcaacatg ctttactcta gccttgtaat gtctttacat acagtgaaat gtaaagttct    50700
ttattctttt tttctttctt tctttttct cctcagcctc agaatttggc acatgcccctt    50760 ccttctttca ggaacttctc caacatctct gcctggctcc atcatatcat aaaggtccca    50820
cttcaaatgc agtcactacc gtttcagaat atgcactttc tttcttttt gttttttgtt    50880 tttttaagt caaagcaaat tcttgagag agtaaagaaa taacgaatg actactgcat    50940 aggcagagca gccccgaggg ccgctggttg ttccttttat ggttatttct tgatgatatg    51000
ttaaacaagt tttggattat ttatgccttc tcttttagg ccatataggg taactttctg    51060
acattgccat ggcatttttc ttttaattta atttactgtt accttaaatt cagggtaca    51120 cgtacaggat atgcaggttt gttttatagg taaaagtgtg ccatggtttt aatgggtttt    51180 tttttcttg taaagttgtt taagtttctt gtttactctg gatattaggc ctttgtcaga    51240
agaatagatt ggaaaatctt tttcccatte tgtagattgt ctttcgctct gatggtagtt    51300
tcttttgctg agcaggagct ctttagttta attagattcc attggtcaat ttttgctttt    51360
gctgcaattg cttttcacgc tttcatcatg aaatctgtgc ccgtgtttat atcatgaata    51420
gtattgcctt gattttttc taggctttt atagtttggg gttttcatt taagtctcta    51480 atccatctgg agttaatttt ggataaggta taaggaagga gtccagtttc attttcagc    51540 atatggctag ccagttctcc cccatcattt attaaattga aaatcctttc cccattgctt    51600
gcttttgtca ggtttctaaa agaccagatg gttgtaggta caatatgcag tttcttcaag    51660
tcatataata ccatctgaaa tctcttatta attcatttct tttagtatgt atgctggtct    51720
cctctgctca ctatagtgag ggcaccatta gccagagaat ctgtctgtct agttcatgta    51780
agattctcag aattaagaaa aatgatggc atatgaatga aacttcatgg atgacatatg    51840
gaatctaata tgtatttgtt gaattaatgc ataagatgca acagagagaa gttgacaact    51900
gcaatgataa cctggtattg atgatataag agtctataga tcacagtaga agcaataatc    51960
atggaaaaca attggaaatg gggaacagcc acaaacaaga aagaatcaat acttccagga    52020
aagtgactgc aggtcacttt tcctggagcg ggtgagagaa aagtggaagt tagcagtaac    52080
```

```
tgctgaattc ctggttggct gatggaaaga tggggcagct gttcactggt acgcagggtt    52140
ttagatgtat gtacctaagg atatgaggta tggcaatgaa cagaaattct tttgggaatg    52200
agttttaggg ccattaaagg acatgacctg aagtttcctc tgaggccagt ccccacaact    52260
caatataaat gtgtttcctg catatagtca aagttgccac ttcttttcct tcatatcatc    52320
gatctctgct cttaaagata atcttggttt tgcctcaaac tgtttgtcac tacaaacttt    52380
ccccatgttc ctaagtaaaa caggtaactg cctctcaact atatcaagta gactaaaata    52440
ttgtgtctct aatatcagaa attcagcttt aatatattgg gtttaactct ttgaaattta    52500
gagtctcctt gaaatacaca tgggggtgat ttcctaaact ttatttcttg taaggattta    52560
tctcaggggt aacacacaaa ccagcatcct gaacctctaa gtatgaggac agtaagcctt    52620
aagaatataa aataaactgt tcttctctct gccggtggaa gtgtgccctg tctattcctg    52680
aaattgcttg tttgagacgc atgagacgtg cagcacatga gacacgtgca gcagcctgtg    52740
gaatattgtc agtgaagaat gtcttttgcct gattagatat aaagacaagt taaacacagc    52800
attagactat agatcaagcc tgtgccagac acaaatgacc taatgcccag cacgggccac    52860
ggaatctcct atcctcttgc ttgaacagag cagcacactt ctcccccaac actattagat    52920
gttctggcat aattttgtag atatgtagga tttgacatgg actattgttc aatgattcag    52980
aggaaatctc ctttgttcag ataagtacac tgactactaa atggattaaa aaacacagta    53040
ataaaaccca gttttcccct tacttcccta gtttgtttct tattctgctt tcttccaagt    53100
tgatgctgga tagaggtgtt tatttctatt ctaaaaagtg atgaaattgg ccgggcgcgg    53160
tggctcacac ctgtaatccc agcactttgg gaggctgagg tgggcggatc acgaggtcag    53220
gagatcaaga ccatcctggc taacatggtg aaaccccatc tctactaaaa atacaaaaaa    53280
ttagccagag acagtggcgg gtgcctgtag tcccagctac tcgggaggct gaggcaggag    53340
aatggcgtga acctgggagg cagagcttgc ggtgagcaga gatcgcgcca ctgcacactc    53400
cagcctgggt gacaaagcga gactccatct caaaaaaaaa aaaaaaaaa agaaaaagaa    53460 agaaagaaag aaaaaaaaac tgatgaaatt gtgtattcaa tgtagtctca agagaattga    53520
aaaccaagaa aggctgtggc ttcttccaca taaagcctgg atgaataaca ggataacacg    53580
ttgttacatt gtcacaactc ctgatccagg aattgatggc taagatattc gtaattctta    53640
tccttttcag ttgtaactta ttcctatttg tcagcattca ggttattagc ggctgctggc    53700
gaagtccttg agaaataaac tgcacactgg atggtggggg tagtgtagga aaatggaggg    53760
gaaggaagta aagtttcaaa ttaagcctga acagcaaagt tcccctgaga aggccacctg    53820
gattctatca gaaactcgaa tgtccatctt gcaaaacttc cttgcccaaa ccccacccct    53880
ggagtcacaa cccaccccttg accaatagat tcattttact gagggaggca aagggctggt    53940
caatagattc atttcactgg gagaggcaaa gggctggggg ccagagagga gaagtaaaaa    54000
gccacacatg aagcagcaat gcaggcatgc ttctggctca tctgtgatca ccaggaaact    54060
cccagatctg acactgtagt gcatttcact gctgacaaga aggctgctgc caccagcctg    54120
tgaagcaagg ttaaggtgag aaggctggag gtgagattct gggcaggtag gtactggaag    54180
ccgggacaag gtgcagaaag gcagaaagtg tttctgaaag agggattagc ccgttgtctt    54240
acatagtctg actttgcacc tgctctgtga ttatgactat cccacagtct cctggttgtc    54300
tacccatgga cctagaggta ctttgaaagt tttggatatc tgggctctga ctgtgcaata    54360
atgggcaacc ccaaagtcaa ggcacatggc aagaaggtgc tgatctcctt cggaaaagct    54420
```

```
gttatgctca cggatgacct caaaggcacc tttgctacac tgagtgacct gcactgtaac    54480
aagctgcacg tggaccctga gaacttcctg gtgagtagta agtacactca cgctttcttc    54540
tttacccttg gatatttgca ctatgggtac ttttgaaagc agaggtggct ttctcttgtg    54600
ttatgagtca gctatgggat atgatatttc agcagtggga ttttgagagt tatgttgctg    54660
taaataacat aactaaaatt tggtagagca aggactatga ataatggaag gccacttacc    54720
atttgatagc tctgaaaaac acatcttata aaaaattctg gccaaaatca aactgagtgt    54780
ttttggatga gggaacagaa gttgagatag agaaaataac atctttcctt tggtcagcga    54840
aattttctat aaaaattaat agtcactttt ctgcatagtc ctggaggtta gaaaagatc    54900 aactgaacaa agtagtggga agctgttaaa aagaggattg tttccctccg aatgatgatg    54960
gtatactttt gtacgcatgg tacaggattc tttgttatga gtgtttggga aaattgtatg    55020
tatgtatgta tgtatgtatg tgatgactgg ggacttatcc tatccattac tgttccttga    55080
agtactatta tcctactttt taaaaggacg aagtctctaa aaaaaaaatg aaacaatcac    55140
aatatgttgg ggtagtgagt tggcatagca agtaagagaa ggataggaca caatgggagg    55200
tgcagggctg ccagtcatat tgaagctgat atctagccca taatggtgag agttgctcaa    55260
actctggtga aaaaggatgt aagtgttata tctatttact gcaagtccag cttgaggcct    55320
tctattcact atgtaccatt ttcttttta tcttcactcc ctccccagct cttaggcaac    55380
gtgatattga ttgttttggc aacccacttc agcgaggatt ttaccctaca gatacaggct    55440
tcttggcagt aactaacaaa tgctgtggtt aatgctgtag cccacaagac cactgagttc    55500
cctgtccact atgtttgtac ctatggtcca ctatgtttgt acctatgtcc caaaatctca    55560
tctcctttag atggggagg ttggggagaa gagcagtatc ctgcctgctg attcagttcc    55620
tgcatgataa aaatagaata aagaaatatg ctctctaaga aatatcattg tactcttttt    55680
ctgtctttat attttacccct gattcagcca aaaggacgca ctatttctga tggaaatgag    55740
aatgttggag aatgggagtt taaggacaga gaagatactt tcttgcaatc ctgcaagaaa    55800
agagagaact cgtgggtgga tttagtgggg tagttactcc taggaagggg aaatcgtctc    55860
tagaataaga caatgttttt acagaaaggg aggtcaatgg aggtactctt tggaggtgta    55920
agaggattgt tggtagtgtg tagaggtatg ttaggactca aattagaagt tctgtatagg    55980
ctattatttg tatgaaactc aggatatagc tcatttggtg actgcagttc acttctactt    56040
attttaaaca acatattttt tattatttat aatgaagtgg ggatggggct tcctagagac    56100
caatcagggg ccaaaccttg aactttctct taacgtcttc aatggtatta atagagaatt    56160
atctctaagg catgtgaact ggctgtcttg gttttcatct gtacttcatc tgctacctct    56220
gtgacctgaa acatatttat aattccatta agctgtgcat atgatagatt tatcatatgt    56280
attttcctta aaggattttt gtaagaacta attgaattga tacctgtaaa gtctttatca    56340
cactacccaa taataataa atctctttgt tcagctctct gtttctataa atatgtacaa    56400
gttttattgt ttttagtggt agtgatttta ttctctttct atatatatac acacacatgt    56460
gtgcattcat aaatatatac aattttatg aataaaaaat tattagcaat caatattgaa    56520
aaccactgat ttttgtttat gtgagcaaac agcagattaa aaggctgaga tttaggaaac    56580
agcacgttaa gtcaagttga tagaggagaa tatggacatt taaagaggc aggatgatat    56640 aaaattaggg aaactggatg cagagaccag atgaagtaag aaaaatagct atcgttttga    56700
gcaaaaatca ctgaagtttc ttgcatatga gagtgacata ataaataggg aaacgtgaaa    56760
aattgattca catgtatata tatatataga actgattaga caaagtctaa cttgggtata    56820
```

```
gtcagaggag cttgctgtaa ttatattgag gtgatggata aagaactgaa gttgatggaa    56880
acaatgaagt taagaaaaaa aatcgagtaa gagaccattg tggcagtgat tgcacagaac    56940
tggaaaacat tgtgaaacag agagtcagag atgacagcta aaatccctgt ctgtgaatga    57000
aaagaaggaa atttattgac agaacagcaa atgcctacaa gccccctgtt tggatctggc    57060
aatgaacgta gccattctgt ggcaatcact tcaaactcct gtacccaaga cccttaggaa    57120
gtatgtagca ccctcaaacc taaaacctca agaaagagg ttttagaaga tataataccc     57180
tttcttctcc agtttcatta atcccaaaac ctctttctca aagtatttcc tctatgtgtc    57240 cacccccaaag agctcacctc accatatctc ttgagtggga gcacatagat aggcggtgct   57300
accatctaac agcttctgaa attcctttgt catattttg agtccccact aataacccac     57360
aaagcagaat aaataccagt tgctcatgta caataatcac tcaactgctg tcttgtagca    57420
tacattaatt aagcacattc tttgaataat tactgtgtcc aaacaatcac actttaaaat    57480
ctcacacttg tgctatccct tgcccttctg aatgtcactc tgtattttaa atgaagagat    57540
gagggttgaa tttcctgtgt tacttattgt tcatttctcg atgaggagtt ttcacattca    57600
cctttagtgg aaaacacata agtacacatc ttacaggaaa aatataccaa actgacatgt    57660
agcatgaatg cttgtgcatg tagtcatata aaatcttgta gcaatgtaaa cattctctga    57720
tatacacata cagatgtgtc tatatgtcta cacaatttct tatgctccat gaacaaacat    57780
tccatgcaca cataagaaca cacactgtta cagatgcata cttgagtgca ttgacaaaat    57840
taccccagtc aatctagaga atttggattt ctgcatttga ctctgttagc tttgtacatg    57900
ctgttcattt actctgggtg atgtctttcc ctcattttgc cttgtctatc ttgtactcat    57960
actttaagtc ctaacttata tgttatctca actaagaagc tattttttt taattttaac    58020 tgggcttaaa gccctgtcta taaactctgc tacaattatg ggctctttct tataatattt    58080 agtgttttc ctactaatgt acttaatctg ctcattgtat attcctacca ctaaattta     58140 acctctttta tggtagagac attgtcttgt aaactcttat ttccctagta tttggagatg    58200 aaaaaaaga ttaaattatc caaaattaga tctctcttt ctacattatg agtattacac     58260
tatccataga gaagtttgtt tgagacctaa actgaggaac ctttggttct aaaatgacta    58320
tgtgatatct tagtatttat aggtcatgag gttccttcct ctgcctctgc tatagtttga    58380
ttagtcaaca agcatgtgtc atgcatttat tcacatcaga atttcataca ctaataagac    58440
atagtatcag aagtcagttt attagttata tcagttaggg tccatcaagg aaaggacaaa    58500
ccattatcag ttactcaacc tagaattaaa tacagctctt aatagttaat tatccttgta    58560
ttggaagagc taaaatatca aataaggac agtgcagaaa tctagatgtt agtaacatca     58620
gaaaacctct tccgccatta ggcctagaag ggcagaagga gaaatgtttt ataccaccag    58680
agtccagaac cagagcccat aaccagaggt ccactggatt cagtgagcta gtgggtgctc    58740
cttggagaga gccagaactg tctaatgggg gcatcaaagt atcagccata aaaaaccata    58800
aaaaagactg tctgctgtag gagatccgtt cagagagaga gagagaccag aaataatctt    58860
gcttatgctt tccctcagcc agtgtttacc attgcagaat gtacatgcga ctgaaagggt    58920
gaggaaacct gggaaatgtc agttcctcaa atacagaaa cactgaggga aggatgagaa     58980
ataaatgtga aagcagacat gaatggtaat tgacagaagg aaactaggat gtgtccagta    59040
aatgaataat tacagtgtgc agtgattatt gcaatgatta atgtattgat aagataatat    59100
gaaaacacag aattcaaaca gcagtgaact gagattagaa ttgtggagag cactggcatt    59160
```

| | |
|---|---|
| taagaatgtc acacttagaa tgtgtctcta ggcattgttc tgtgcatata tcatctcaat | 59220 |
| attcattatc tgaaaattat gaattaggta caaagctcaa ataatttatt ttttcaggtt | 59280 |
| agcaagaact tttttttttt ttttctgaga tagagcattg ctatggttgc ccaggctgga | 59340 |
| gtgcaatggc atgatccagg ctcactgcaa catctgcctc ccaggttcaa gcgattctcc | 59400 |
| tgcctcagcc tcccaagtag ctggcactac aggcatgtgc caccaccatg cctggctaat | 59460 |
| tttctatttt tagtagatag ggggtttcac catgttggtc aggctgatct cgaactccta | 59520 |
| acatcaggtg atccaccctc ctcggcctct gaaagtgctg ggatcacagg cgtgagccac | 59580 |
| cacacccagc caagaatgtg aattttgtag aaggatataa cccatatttc tctgacccta | 59640 |
| gagtccttag tatacctccc ataccatgtg gctcatcctc cttacataca tttcccatct | 59700 |
| ttcaccctac cttttccttt tgtttcagc ttttcactgt gtcaaaatct agaaccttat | 59760 |
| ctcctacctg ctctgaaacc aacagcaagt tgacttccat tctaacccac attggcatta | 59820 |
| cactaattaa aatcgatact gagttctaaa atcatcgggg attttgggga ctatgtctta | 59880 |
| cttcatactt cctgagatt tcacattaaa tgttggtgtt cattaaaggt ccttcattta | 59940 |
| actttgtatt catcacactc ttggattcac agttatatct aaactcttaa atacagcctg | 60000 |
| tataatccca attcccaact ctgatttcta acctctgacc tccaacctca gtgccaaacc | 60060 |
| catatatcaa acaatgtact gggcttattt atatagatgt cctataggca cctcagactc | 60120 |
| agcatgggta tttcacttgt tatactaaaa ctgtttctct tccagtgttt tccattttag | 60180 |
| tcattagata gctacttgcc cattcaccaa ggtcacagat taaaatcatt tccctacctc | 60240 |
| taatcaacag ttcgattctg cttcaatttg tccctatcta ttaatcacca ctcttactgc | 60300 |
| ccagtcaggt cctcattgtt tcctgaacaa gagtagatgc tattctttcc acttttagac | 60360 |
| cttatcctgg ctggatgcgg tggctcaggc ttgtaaaccc agcactttgg gaggccaagg | 60420 |
| caggcagatc acttgaggtc aggagttcaa gaccagcctg accaacatgg tgaaacccca | 60480 |
| tctctactaa aaatacaaaa tcagccgggc gtgtggtgca tgcctgcagt cccagctatt | 60540 |
| caggtggctg aggcaggaga attgcttgaa cccaggaggc agaggttgcg gtgagcctag | 60600 |
| attgcaccat tgcactctag cttgggcaat agggatgaaa ctccatctca gaagagaaaa | 60660 |
| gaaaaaaga ccttattctg ttatacaaat cctctcaatg caatccatat agaataaaca | 60720 |
| tgtaaccaga tctcccaatg tgtaaaatca tttcaggtag aacagaatta aagtgaaaag | 60780 |
| ccaagtcttt ggaattaaca gacaaagatc aaataacagt cctcatggcc ttaagaattt | 60840 |
| acctaacatt ttttttagaa tcaattttct tatatatgaa ttggaaacat aattcctccc | 60900 |
| tcacaaacac attctaagat tttaaggaga tattgatgaa gtacatcatc tgtcattttt | 60960 |
| aacaggtagt ggtagtgatt cacacagcac attatgatct gttcttgtat gttcgtgttcc | 61020 |
| attctgtatt cttgacctgg ttgtattctt tctgagctcc agatccacat atctaagtac | 61080 |
| atcttttgc atttacaag agtgcataca atacaatgta tccaagactg tatttctgat | 61140 |
| tttatcgtac cactaaactc acaaatgtgg ccctattctt gtgttcacga ctgacatcac | 61200 |
| cgtcatggtc caagtctgat aatagaaatg gcattgtcac tttcttccct actgcaacag | 61260 |
| aagcccagct atttgtctcc cattttctct acttctaaaa tacatttctt cactaagtga | 61320 |
| gaataatctt ttaaagacac aaatcaaacc atgccaccac cttcttgaa ttattcaata | 61380 |
| tctttcgttg gcttccaggt tacagaaaaa taacttgtaa caaagtttaa aggtcattca | 61440 |
| tggctcctct ctaccctatt ttataacatt tcccctgtg atcagaatct caggcacatc | 61500 |
| atccatcttt ctatatacaa ataaagtcat atagtttgaa ctcacctctg gttactttta | 61560 |

```
atcaaccaaa tgctgtaaaa tgcatttgta tcgctacgtg ttaagcagta gttgattctt    61620
ttcatttctg tgtaatattc tattctttga ctataccgta atttatcaat tctactgttg    61680
gtaagcattt aagtggctac cggtttgagg tttttatgat tattgctgtc ataagcattt    61740
ctatacatgt ctttggatac acacatgcat gtgtttctga atatctaaaa atgtaattgc    61800
taggtaatag acttatcaag catccagcat ttgtggatac tattaaaggt tttccaaagg    61860
ggttatacta ttgtacagtg tcaccaacag agtttgagtt tctattgatc catatccacca   61920
ccaaaatttg aactgtcagt cttatctctt ctcttgtctc ttttttcctc ttttttttcc    61980
ttcccttccc ctctcttcgt ttcttttctc tcctcttctc ttctttcctc tcttcccttc    62040
cctttctctt tctcttccct atcccttctc ctctcctctc ccctcctttt ttctcctctc    62100
ctctccatta tttattttc cttcttctcc tccatccctt ccatcctctc tcttcccctc    62160
ttccttcctt cctttctcca tttcttcctc ctctttcctt caatccttcc ttttggatat    62220
gctcatgggt gtgtatttgt ctgccattgt ggcattattt gaattcagaa aagagtgaaa    62280
aactactggg atcttcattc ctgggtctaa ttccacattt ttttttaaga acacatctgt    62340
aaaaatgttc tgtactagca tattcccagg aacttcgtta aatttaatct ggctgaatat    62400
ggtaaatcta cttttcactt tgcattcttt ctttagtcat accataattt taaacattca    62460
aaatatttgt atataatatt tgattttatc tgtcattaaa atgttaacct taaaattcat    62520
gtttccagaa cctatttcaa taactggtaa ataaacacta ttcattttt aaatattctt    62580
ttaatggata tttatttcaa tataataaaa aattagagtt ttattatagg aagaatttac    62640
caaagaagg aggaagcaag caagtttaaa ctgcagcaat agatttgtcc attccaacct    62700
ctcaaaattc ccttggagac aaaaatctct agaggcaaag aagaacttta tattgagtca    62760
acttgttaaa acatctgctt ttagataagt tttcttagta taaagtgaca gaaacaaata    62820
agttaaactc taagatacat tccactatat tagcctaaaa cacttctgca aaaatgaaac    62880
taggaggata ttttttagaaa caactgctga aagagatgcg gtggggagat atgtagagga    62940
gaacagggtt tctgagtcaa gacacacatg acagaacagc caatctcagg gcaagttaag    63000
ggaatagtgg aatgaaggtt cattttttcat tctcacaaac taatgaaacc ctgcttatct    63060
taaaccaacc tgctcactgg agcagggagg acaggaccag cataaaaggc agggcagagt    63120
cgactgttgc ttacactttc ttctgacata acagtgttca ctagcaacct caaacagaca    63180
ccatggtgca tctgactcct gaggagaaga ctgctgtcaa tgccctgtgg ggcaaagtga    63240
acgtggatgc agttggtggt gaggccctgg gcaggttggt atcaaggtta taagagaggc    63300
tcaaggaggc aaatggaaac tgggcatgtg tagacagaga agactcttgg gtttctgata    63360
ggcactgact ctctgtccct tgggctgttt tcctaccctc agattactgg tggtctaccc    63420
ttggacccag aggttctttg agtcctttgg ggatctgtcc tctcctgatg ctgttatggg    63480
caaccctaag gtgaaggctc atggcaagaa ggtgctaggt gcctttagtg atggcctggc    63540
tcacctggac aacctcaagg gcacttttttc tcagctgagt gagctgcact gtgacaagct    63600
gcacgtggat cctgagaact tcaggggtgag tccaggagat gcttcacttt tctcttttta    63660
ctttctaatc ttcattttg gttcttttac ctacctgctc ttctcccaca ttttgtcat    63720
tttactatat tttatcattt aatgcttcta aaattttgtt aatttttttat ttaaatattc    63780
tgcattttt ccttcctcac aatcttgcta ttttaaatta tttaatatcc tgtctttctc    63840
tcccaacccc ctcccttcat ttttccttct ctaacaacaa ctcaaattat gcataccagc    63900
```

```
tctcacctgc taattctgca cttagaataa tccttttgtc tctccacatg ggtatgggag    63960
aggctccaac tcaaagatga gaggcataga atactgtttt agaggctata aatcatttta    64020
caataaggaa taattggaat tttataaatt ctgtagtaaa tggaatggaa aggaaagtga    64080
atatttgatt atgaaagact aggcagttac actggaggtg gggcagaagt cgttgctagg    64140
agacagccca tcatcacact gattaatcaa ttaatttgta tctattaatc tgtttatagt    64200
aattaatttg tatatgctat atacacatac aaaattaaaa ctaatttgga attaatttgt    64260
atatagtatt atacagcata tatagcatat atgtacatat atagactaca tgctagttaa    64320
gtacatagag gatgtgtgtg tatagatata tgttatatgt atgcattcat atatgtactt    64380
atttatgctg atgggaataa cctggggatc agttttgtct aagatttggg cagaaaaaaa    64440
tgggtgttgg ctcagtttct cagaagccag tctttatttc tctgttaacc atatgcatgt    64500
atctgcctac ctcttctccg cagctcttgg gcaatgtgct ggtgtgtgtg ctggcccgca    64560
actttggcaa ggaattcacc ccacaaatgc aggctgccta tcagaaggtg gtggctggtg    64620
tggctaatgc cctggctcac aagtaccatt gagatcctgg actgtttcct gataaccata    64680
agaagaccct atttccctag attctatttt ctgaacttgg gaacacaatg cctacttcaa    64740
gggtatggct tctgcctaat aaagaatgtt cagctcaact tcctgattaa tttcacttat    64800 ttcattttt tgtccaggtg tgtaagaagg ttcctgaggc tctacagata gggagcactt    64860
gtttatttta caaagagtac atgggaaaag agaaaagcaa gggaaccgta caaggcatta    64920
atgggtgaca cttctacctc caaagagcag aaattatcaa gaactcttga tacaaagata    64980
atactggcac tgcagaggtt ctagggaaga cctcaaccct aagacatagc ctcaagggta    65040
atgctacgat taaactccaa caattactga gaaaataatg tgctcaatta aaggcataat    65100
gattactcaa gacaatgtta tgttgtcttt cttcctcctt cctttgcctg cacattgtag    65160
cccataatac tataccccat caagtgttcc tgctccaaga aatagcttcc tcctcttact    65220
tgccccagaa catctctgta aagaatttcc tcttatcttc ccatatttca gtcaagattc    65280
attgctcacg tattacttgt gacctctctt gaccccagcc acaataaact tctctatact    65340
acccaaaaaa tctttccaaa ccctccccca caccattttt tatattttta tatttttctt    65400
atttatttca tgcacacaca cacactccgt gctttataag caattctgcc tattctctac    65460
cttcttacat gcctactgtg cctcatatta aattcatcaa tgggcagaaa gaaaatattt    65520
attcaagaaa acagtgaatg aatgaacgaa tgagtaaatg agtaaatgaa ggaatgatta    65580
ttccttgctt tagaacttct ggaattagag gacaatatta ataataccat cgcacagtgt    65640
ttctttgttg ttaatgctac aacatacaaa gaggaagcat gcagtaaaca accgaacagt    65700
tatttccttt ctgatcatag gagtaatatt ttttccttg agcaccattt ttgccatagg    65760
taaaattaga aggattttta gaactttctc agttgtatac attttaaaa atctgtatta    65820 tatgcatgtt gattaatttt aaacttactt gaatacctaa acagaatctg ttgtttcctt    65880
gtgtttgaaa gtgctttcac agtaactctg tctgtactgc cagaatatac tgacaatgtg    65940
ttatagttaa ctgttttgat cacaacattt tgaattgact ggcagcagaa gctctttat    66000 atccatgtgt tttccttaag tcattataca tagtaggcac tgagaactct ttatatctga    66060
ataagatatt taggaaccac tggtttacat atcagaagca gagctactca gggcattttg    66120
gggaagatca ctttcacatt cctgagcata gggaagttct cataagagta agatattaaa    66180
aggagatact tgtgtggtat tcgaaagaca gtaagagaga ttgtagacct tatgatcttg    66240
atagggaaaa caaactacat tcctttctcc aaaagtcaaa aaaaaagagc aaatatagct    66300
```

```
tactatacct tctattccta caccattaga agtagtcagt gagtctaggc aagatgttgg    66360
ccctaaaaat ccaaataccq gagaattcat gagaacatca cctggatggg acatgtgccg    66420
agcacacaca attactatat gctaggcatt gctatcttca tattgaagat gaggaggtca    66480
agagatgaaa aaagacttgg caccttgttg ttatattaaa attatttgtt agagtagagc    66540
ttttgtaaga gtctaggagt gtgggagcta aatgatgata cacatggaca caaaaaatag    66600
atcaacagac acccaggcct acttgagggt tgagggtggg aagagggaga cgatgaaaaa    66660
gaacctattg ggtattaagt tcatcactga gtgatgaaat aatctgtaca tcaagaccca    66720
gtgatatgca atttacctat ataacttgta catgtacccc caaatttaaa atgaaagtta    66780
aaacaaagta taggaatgga attaattcct caagatttgg ctttaatttt atttgataat    66840
ttatcaaatg gttgttttc ttttctcact atggcgttgc tttataaact atgttcagta    66900
tgtctgaatg aaagggtgtg tgtgtgtgtg aaagagaggg agagaggaag ggaagagagg    66960
acgtaataat gtgaatttga gttcatgaaa attttcaat aaaataattt aatgtcagga    67020
gaattaagcc taatagtctc ctaaatcatc catctcttga gcttcagagc agtcctctga    67080
attaatgcct acatgtttgt aaagggtgtt cagactgaag ccaagattct acctctaaag    67140
agatgcaatc tcaaatttat ctgaagactg tacctctgct ctccataaat tgacaccatg    67200
gcccacttaa tgaggttaaa aaaagctaa ttctgaatga aatctgagc ccagtggagg    67260 aaatattaat gaacaaggtg cagactgaaa tataaatttt tctgtaataa ttatgcatat    67320
actttagcaa agttctgtct atgttgactt tattgctttt tggtaagaaa tacaactttt    67380
taaagtgaac taaactatcc tatttccaaa ctattttgtg tgtgtgcggt ttgtttctat    67440
gggttctggt tttcttggag catttttatt tcattttaat taattaattc tgagagctgc    67500
tgagttgtgt ttactgagag attgtgtatc tgcgagagaa gtctgtagca agtagctaga    67560
ctgtgcttga cctaggaaca tatacagtag attgctaaaa tgtctcactt ggggaatttt    67620
agactaaaca gtagagcatg tataaaaata ctctagtcaa gtgctgcttt tgaaacaaat    67680
gataaaacca cactcccata gatgagtgtc atgattttca tggaggaagt taatattcat    67740
cctctaagta tacccagact agggccattc tgatataaaa cattaggact taagaaagat    67800
taatagactg gagtaaagga aatggacctc tgtctctctc gctgtctctt ttttgaggac    67860
ttgtgtgtgt gtgtgtgtgt gtgtgtgtgt gtgtgttgtg gtcagtgggg ctggaataaa    67920
agtagaatag acctgcacct gctgtggcat ccattcacag agtagaagca agctcacaat    67980
agtgaagatg tcagtaagct tgaatagttt ttcaggaact ttgaatgctg atttagattt    68040
gaaactgagg ctctgaccat aaccaaattt gcactattta ttgcttcttg aaacttattt    68100
gcctggtatg cctgggcttt tgatggtctt agtatagctt gcagccttgt ccctgcaggg    68160
tattatgggt aatagaaaga aaagtctgcg ttacactcta gtcacactaa gtaactacca    68220
ttggaaaagc aacccctgcc ttgaagccag gatgatggta tctgcagcag ttgccaacac    68280
aagagaagga tccatagttc atcatttaaa aaagaaaaca aaatagaaaa aggaaaacta    68340
tttctgagca taagaagttg tagggtaagt ctttaagaag gtgacaattt ctgccaatca    68400
ggatttcaaa gctcttgctt tgacaatttt ggtctttcag aatactataa atataaccta    68460
tattataatt tcataaagtc tgtgcatttt ctttgaccca ggatatttgc aaaagacata    68520
ttcaaacttc cgcagaacac tttatttcac atatacatgc ctcttatatc agggatgtga    68580
aacagggtct tgaaaactgt ctaaatctaa aacaatgcta atgcaggttt aaatttaata    68640
```

```
aaataaaatc caaaatctaa cagccaagtc aaatctgcat gttttaacat ttaaaatatt    68700
ttaaagacgt cttttcccag gattcaacat gtgaaatctt ttctcaggga tacacgtgtg    68760
cctagatcct cattgcttta gttttttaca gaggaatgaa tataaaaaga aaatacttaa    68820
attttatccc tcttacctct ataatcatac ataggcataa ttttttaacc taggctccag    68880
atagccatag aagaaccaaa cactttctgc gtgtgtgaga ataatcagag tgagattttt    68940
tcacaagtac ctgatgaggg ttgagacagg tagaaaagt gagagatctc tatttattta     69000
gcaataatag agaaagcatt taagagaata aagcaatgga aataagaaat ttgtaaattt    69060
ccttctgata actagaaata gaggatccag tttcttttgg ttaacctaaa ttttatttca    69120
ttttattgtt ttatttatt ttattttatt ttattttgtg taatcgtagt ttcagagtgt     69180
tagagctgaa aggaagaagt aggagaaaca tgcaaagtaa aagtataaca ctttccttac    69240
taaaccgaca tgggtttcca ggtaggggca ggattcagga tgactgacag ggcccttagg    69300
gaacactgag accctacgct gacctcataa atgcttgcta cctttgctgt tttaattaca    69360
tcttttaata gcaggaagca gaactctgca cttcaaaagt ttttcctcac ctgaggagtt    69420
aatttagtac aaggggaaaa agtcaggggg gatgggagaa aggcgatcac gttgggaagc    69480
tatagagaaa gaagagtaaa ttttagtaaa ggaggtttaa acaaacaaaa tataaagaga    69540
aataggaact tgaatcaagg aaatgatttt aaaacgcagt attcttagtg gactagagga    69600
aaaaaataat ctgagccaag tagaagacct ttttcccctcc tacccctact ttctaagtca    69660
cagaggcttt ttgttccccc agacactctt gcagattagt ccaggcagaa acagttagat    69720
gtccccagtt aacctcctat ttgacaccac tgattacccc attgatagtc acactttggg    69780
ttgtaagtga cttttatttt atttgtattt ttgactgcat taagaggtct ctagttttttt   69840 atctcttgtt tcccaaaacc taataagtaa ctaatgcaca gagcacattg atttgtattt    69900
attctatttt tagacataat ttattagcat gcatgagcaa attaagaaaa acaacaacaa    69960
atgaatgcat atatatgtat atgtatgtgt gtatatatac acacatatat atatatattt    70020
tttcttttct taccagaagg ttttaatcca aataaggaga agatatgctt agaaccgagg    70080
tagagttttc atccattctg tcctgtaagt attttgcata ttctggagac gcaggaagag    70140
atccatctac atatcccaaa gctgaattat ggtagacaaa actcttccac ttttagtgca    70200
tcaacttctt atttgtgtaa taagaaaatt gggaaaacga tcttcaatat gcttaccaag    70260
ctgtgattcc aaatattacg taaatacact tgcaaaggag gatgttttta gtagcaattt    70320
gtactgatgg tatggggcca agagatatat cttagaggga gggctgaggg tttgaagtcc    70380
aactcctaag ccagtgccag aagagccaag gacaggtacg gctgtcatca cttagacctc    70440
accctgtgga gccacaccct agggttggcc aatctactcc caggagcagg gagggcagga    70500
gccagggctg ggcataaaag tcagggcaga gccatctatt gcttacattt gcttctgaca    70560
caactgtgtt cactagcaac ctcaaacaga caccatggtg catctgactc ctgaggagaa    70620
gtctgccgtt actgccctgt ggggcaaggt gaacgtggat gaagttggtg gtgaggccct    70680
gggcaggttg gtatcaaggt tacaagacag gtttaaggag accaatagaa actgggcatg    70740
tggagacaga gaagactctt gggtttctga taggcactga ctctctctgc ctattggtct    70800
attttcccac ccttaggctg ctggtggtct accctttggac ccagaggttc tttgagtcct   70860
ttggggatct gtccactcct gatgctgtta tgggcaaccc taaggtgaag gctcatggca    70920
agaaagtgct cggtgccttt agtgatggcc tggctcacct ggacaacctc aagggcacct    70980
ttgccacact gagtgagctg cactgtgaca agctgcacgt ggatcctgag aacttcaggg    71040
```

```
tgagtctatg ggacgcttga tgttttcttt cccttctttt tctatggtta agttcatgtc   71100
ataggaaggg gataagtaac agggtacagt ttagaatggg aaacagacga atgattgcat   71160
cagtgtggaa gtctcaggat cgttttagtt tcttttattt gctgttcata acaattgttt   71220
tcttttgttt aattcttgct ttctttttt tccttctccg caatttttac tattatactt    71280
aatgccttaa cattgtgtat aacaaaagga aatatctctg agatacatta agtaacttaa   71340
aaaaaaactt tacacagtct gcctagtaca ttactatttg aatatatgt gtgcttattt    71400
gcatattcat aatctcccta ctttatttc ttttatttt aattgataca taatcattat     71460
acatatttat gggttaaagt gtaatgtttt aatatgtgta cacatattga ccaaatcagg   71520
gtaattttgc atttgtaatt ttaaaaaatg ctttcttctt ttaatatact ttttttgttta  71580
tcttatttct aatactttcc ctaatctctt tctttcaggg caataatgat acaatgtatc   71640
atgcctcttt gcaccattct aaagaataac agtgataatt tctgggttaa ggcaatagca   71700
atatctctgc atataaatat ttctgcatat aaattgtaac tgatgtaaga ggtttcatat   71760
tgctaatagc agctacaatc cagctaccat tctgctttta ttttatggtt gggataaggc   71820
tggattattc tgagtccaag ctaggccctt ttgctaatca tgttcatacc tcttatcttc   71880
ctcccacagc tcctgggcaa cgtgctggtc tgtgtgctgg cccatcactt tggcaaagaa   71940
ttcaccccac cagtgcaggc tgcctatcag aaagtggtgg ctggtgtggc taatgccctg   72000
gcccacaagt atcactaagc tcgctttctt gctgtccaat ttctattaaa ggttcctttg   72060
ttccctaagt ccaactacta aactgggga tattatgaag ggccttgagc atctggattc    72120
tgcctaataa aaaacattta ttttcattgc aatgatgtat ttaaattatt tctgaatatt   72180
ttactaaaaa gggaatgtgg gaggtcagtg catttaaaac ataaagaaat gaagagctag   72240
ttcaaacctt gggaaaatac actatatctt aaactccatg aaagaaggtg aggctgcaaa   72300
cagctaatgc acattggcaa cagcccctga tgcatatgcc ttattcatcc ctcagaaaag   72360
gattcaagta gaggcttgat ttggaggtta aagttttgct atgctgtatt ttacattact   72420
tattgtttta gctgtcctca tgaatgtctt ttcactaccc atttgcttat cctgcatctc   72480
tcagccttga ctccactcag ttctcttgct tagagatacc cctttcccc tgaagtgttc    72540
cttccatgtt ttacggcgag atggtttctc ctcgcctggc cactcagcct tagttgtctc   72600
tgttgtctta tagaggtcta cttgaagaag gaaaaacagg ggtcatggtt tgactgtcct   72660
gtgagccctt cttccctgcc tcccccactc acagtgaccc ggaatctgca gtgctagtct   72720
cccggaacta tcactctttc acagtctgct ttggaaggac tgggcttagt atgaaaagtt   72780
aggactgaga agaatttgaa aggcggcttt ttgtagcttg atattcacta ctgtcttatt   72840
accctgtcat aggcccaccc caaatggaag tccattctt cctcaggatg tttaagatta    72900
gcattcagga agagatcaga ggtctgctgg ctcccttatc atgtccctta tggtgcttct   72960
ggctctgcag ttattagcat agtgttacca tcaaccacct taacttcatt tttcttattc   73020
aatacctagg taggtagatg ctagattctg gaaataaaat atgagtctca agtggtcctt   73080
gtcctctctc ccagtcaaat tctgaatcta gttggcaaga ttctgaaatc aaggcatata   73140
atcagtaata agtgatgata gaagggtata tagaagaatt ttattatatg agagggtgaa   73200
accctcaaaa tgaaatgaaa tcagacccct gtcttacacc ataaacaaaa ataaatttga   73260
atgggttaaa gaattaaact aagacctaaa accataaaaa ttttttaaaga aatcaaaaga  73320
agaaaattct aatattcacg ttgcagccgt tttttgaatt tgatatgaga agcaaaggca   73380
```

-continued

```
acaaaaggaa aaataaagaa gtgaggctac atcaaactaa aaaatttcca cacaaaaaac    73440
aaaacaatga acaaatgaaa ggtgaaccat gaaatggcat atttgcaaac caaatatttc    73500
ttaaatattt tggttaatat ccaaaatata taagaaacac agatgattca ataacaaaca    73560
aaaaattaaa aataggaaaa taaaaaaatt aaaaagaaga aaatcctgcc atttatggca    73620
gaattgatga acctggagga tgtaaaacta agaaaaataa gcctgacaca aaaagacaaa    73680
tactacacaa ccttgctcat atgtgaaaca taaaaaagtc actctcatgg aaacagacag    73740
tagaggtatg gtttccaggg gttggggtg ggagaatcag gaaactatta ctcaaagggt    73800
ataaaatttc agttatgtgg gatgaataaa ttctagatat ctaatgtaca gcatcgtgac    73860
tgtagttaat tgtactgtaa gtatatttaa aatttgcaaa gagagtagat tttttttttt    73920
ttttagatgg agttttgctc ttgttgtcca ggctggagtg caatggcaag atcttggctc    73980
actgcaacct ccgcctcctg ggttcaagca atctcctgc ctcagcctcc cgagtagctg    74040
ggattacagg catgcgacac catgcccagc taattttgta tttttagtag agacggggtt    74100
tctccatgtt ggtcaggctg atccgcctgc ctcggccacc caaagggctg ggattacagg    74160
cgtgagccac cgggcctggc cgagagtaga tcttaaaagc atttaccaca agaaaaaggt    74220
aactatgtga gataatgggt atgttaatta gcttgattgt ggtaatcatt tcacaaggta    74280
tacatatatt aaaacatcat gttgtacacc ttaaatatat acaatttta tttgtgaatg    74340
ataactcaat aaagttgaag aataataaaa aagaatagac atcacatgaa ttaaaaaact    74400
aaaaaataaa aaaatgcatc ttgatgatta gaattgcatt cttgattttt cagatacaaa    74460
tatccatttg actgtttact cttttccaaa acaatacaat aaattttagc actttatctt    74520
catttccc ttcccaatct ataattatat atatatatat tttagatatt ttgtatagtt    74580
ttactcccta gattttctag tgttattatt aaatagtgaa gaaatgttta cacttatgta    74640
caaaatgttt tgcatgcttt tcttcatttc taacattctc tctaagttta ttctattttt    74700
ttctgattat ccttaatatt atctctttct gctggaaata cattgttact tttggtttat    74760
ctaaaaatgg cttcatttc ttcattctaa aatcatgtta aattaatacc actcatgtgt    74820
aagtaagata gtggaataaa tagaaatcca aaaactaaat ctcactaaaa tataataatg    74880
tgatatataa aaatatagct tttaaattta gcttggaaat aaaaaacaaa cagtaattga    74940
acaactatac tttttgaaaa gagtaaagtg aaatgcttaa ctgcatatac cacaatcgat    75000
tacacaatta ggtgtgaagg taaaattcag tcacgaaaaa actagaataa aaatatggga    75060
agacatgtat ataatcttag agataacact gttatttaat tatcaaccca aagtagaaac    75120
tatcaaggga gaaataaatt cagtcaacaa taaaagcatt taagaagtta ttctaggctg    75180
ggagcggtgg ctcacacctg caattgcagc actttgggag gcctagacag gcggatcacg    75240
acgtcaggag ttcaagatca gcctggccaa catagtgaaa cctcatcgct actaaaaata    75300
taaaaactta gcctggcgtg gtggcaggca tgtgtaatcc cagcaatttg ggaggctgag    75360
gcaggagaat cgcttgatcc tgggaggcag aggttgcagt gagccaagat tgtgccactg    75420
cattccagcc caggtgacag catgagactc cgtcacaaaa aaaaagaaaa aaaaagggg    75480
ggggggggagc ggtggagcca agatgaccga ataggaacag ctccagtcta tagctcccat    75540
cgtgagtgac gcagaagacg ggtgatttct gcatttccaa ctgaggtacc aggttcatct    75600
cacagggaag tgccaggcag tgggtgcagg acagtaggtg cagtgcactg tgcatgagcc    75660
aaagcagggc gaggcatcac ctcacccggg aagcacaagg ggtcagggaa ttcccttttcc    75720
tagtcaaaga aaagggtgac agatggcacc tggaaaatcg ggtcactccc gccctaatac    75780
```

```
tgcgctcttc caacaagctt aacaaatggc acaccaggag attatatccc atgcctggct    75840
cagagggtcc tacgcccatg gagcctcgct cattgctagc acagcagtct gaggtcaaac    75900
tgcaaggtgg cagtgaggct gggggagggg tgcccaccat tgtccaggct tgagcaggta    75960
aacaaagccg cctggaagct cgaactgggt ggagcccacc acagctcaag gaggcctgcc    76020
tgcctctgta ggctccacct ctaggggcag ggcacagaca aacaaaagac aacaagaacc    76080
tctgcagact taaatgtccc tgtctgacag ctttgaagag agtagtggtt ctcccagcac    76140
atagcttcag atctgagaac aggcagactg cctcctcaag tgggtccctg accccgagt    76200 agcctaactg ggaggcatcc cccagtaggg gcagactgac acctcacatg gctggtactc    76260
ctctaagaca aaacttccag aggaatgatc aggcagcagc atttgcggtt caccaatatc    76320
cactgttctg cagccaccgc tgttgatacc caggaaaaca gcttctggag tggacctcca    76380
gtaaactcca acagacctgc agctgagggt cctgactgtt agaaggaaaa ctaacaaaca    76440
gaaaggacat ccacaccaaa aacccatctg tacatcgcca tcatcaaaga ccaaaggtag    76500
ataaaaccat aaagatgggg aaaaagcaga gcagaaaaac tggacactct aaaaatgaga    76560
gtgcctctcc tcctccaaag taacgcagct cctcaccagc aatggaacaa agctgggcag    76620
agaatgactt tgacgagttg agagaggaag gcttcagaag atcaaactac tccaagctaa    76680
aggaggaagt tcgaacaaac ggcaaagaag taaaaaactt tgaaaaaaaa ttagatgaat    76740
ggataactag aataaccaat gcacagaagt ccttaaagga cctgatggag ctgaaaacca    76800
aggcaggaga actacgtgac aaatacacaa gcctcagtaa ccgatgagat caactggaag    76860
aaagggtatc aatgacgaaa gatgaaatga atgaaatgaa gcatgaagag aagtttagag    76920 aaaaagaat aaaaagaaac gaacaaagcc tccaagaaat atgggactat gtgaaaagac    76980
caaatctaca tctaattggt gtagctgaaa gtgatgggga gaatggaacc aagttggaaa    77040
acactctgca ggatattatc caggagaact tccccaatct agcaaggcaa gcccaaattc    77100
acattcagga aatacagaga acgccacaaa gatactccta gagaaaagca actccaagac    77160
acataactgt cagattcacc aaagttgaaa tgaaggaaaa aatgttaagg gcagccagag    77220
agaaaggtcg ggttacccac aaagggaagc ccatcagact aacagctgat ctatcggcag    77280
aaactctaca agccagaaga agtgggggc caatattcaa cattgttaaa gaaaagaatt    77340
ttcaacccag aatttcatat ccagccaaac taagcttcat aagtgaagga gaaataaaat    77400
cctttacaga caagcaaatg ctgagagatt ttgtcaccac caggcctgcc ctacaagagc    77460
tcctgaagga agcactaaac atggaaagga caaactagta tcagccactg caaaaacatg    77520
ccaaattgta aagaccatca aggctaggaa gaaactgcat caacgagcaa ataaccagc    77580 taacatcata atgacaggat caaattcata cataacaata ctcaccttaa atgtaaatag    77640
gctaaatgct ccaattaaaa gacacagact ggcaaattgg ataaggagtc aagacccatc    77700
tgtgttctgt attcaggaaa cccatctcac gtgcagagac acacataggc tcgaaataaa    77760
aggatggagg aatatctacc aagcaaatgg aaaacaaaaa aaggcagggg ttgcaatcct    77820
agtctctgat aaaacagatt ttaaaccaac aaagatcaaa agagacaaag aaggccatta    77880
cataatggca aagggatcta ttcaagaaga gaactaact atactaaata tatatgcacc    77940
caatacagga gcacccagat tcataaaaca agtcctgagt gacctacaaa gagacttaga    78000
tgcccacaca ataataatgg gagactttaa caccccactg tcaacattag acagatcaac    78060
gagacagaaa gttaacaagg atatccagga attggactca gctctgcacc aagcagacct    78120
```

```
aatagacatc tacagaactc tccaccccaa atcaacagaa tatacattct tttcagcacc   78180
acaccacacc tattccaaaa ctgaccacat agttggaagt aaagctctcc tcagcaaatg   78240
taaaagaaca gaaactataa caaactgtct ctcagaccac agtgcaatca aactagaact   78300
caggattaag aaactcactc aaaaccactc agctacatgg aaactgaaca gcctgctcct   78360
gaatgactac tgggtacata caaaatgaa ggcagaaata aagatgttct ttgaaaccaa   78420
cgagaacaaa gacacaacac accagaatct ctgagacaca ttcaaagcag tgtgtagagg   78480
gaaatttata gcactaaatg cccacaaggg aaagcaggaa agatctaaaa ttgacaccct   78540
aacatcacaa ttaaaaaact agagaagcag gagcaaacac attcaaaagc taacagaaga   78600
caagaaataa ctaagatcag agcagaagtg aaggacatag agacacaaaa aaacccttca   78660
aaaaaatcaa tgaatccaga agctgttttt ttgaaaagat caacaaaatt gatagactgc   78720
tagcaagact aataaagaag aaaagagaga agaatcaaat agacgcaata aaaaatgaca   78780
cggggtatca ccactgatcc cacagaaata caaactaccg tcagagaata ctataaacac   78840
ctctacgcaa ataaactaga aaatctagaa gaaatggata aattcctcga cacatacact   78900
ctgccaagac taaaccagga agaagttgta tctctgaata gaccaataac aggctctgaa   78960
attgaggcaa taattaatag cttatcaacc aaaaaaagtc cgggaccagt aggattcata   79020
gccgaattct accagaggta caaggaggag ctggtaccat tccttctgaa actattccaa   79080
tcaatagaaa aagagggaat cctccctaac tcattttatg aggccagcat catcctgata   79140
ccaaagcctg acagagacac aacaaaaaaa gagaatgtta caccaatatc cttgatgaac   79200
attgatgcaa aaatcctcaa taaaatactg gcaaactgat ccaccatgat caagtgggct   79260
tcatccctgc catgcaaggc tggttcaaca tacgaaaatc aataaacata atccagcata   79320
taaacagaac caaagacaca aaccatatga ttatctcaat agatgcagaa aaggcctttg   79380
acaaaattca caacgcttc atgctaaaaa ctctcaataa attaggtatt gatgggacat   79440
atctcaaaat aataagagct atctatgaca aacccacagc caatatcata ctgagtggac   79500
aaaaactgga agcattccct ttgaaaactg gcacaaggca gggatgccct ctctcaccac   79560
tcctattcaa catagtgttg taagttctgg ccagggcaat caggcaggag aaggaaataa   79620
agggcattca attaggaaaa gaggaagtga aattgtccct gtttgcagat gacatgattg   79680
tatatctaga aaaccccatt gtctcagccc aaaatctcct taagctgata agcaacttca   79740
gcaaagtctc aggatataaa atcagtgtgc aaaaatcaca agtattccta tgcaccaata   79800
acagacaaac agagagccaa atcatgagtg aactcccatt cacaattgct tcaaagagaa   79860
taaaatacct aggaatccaa cttacaaggg atgtgaagga cctcttcaag gagaactaca   79920
aaccactgct caatgaaata aaagaggata caaacaaatg gaagaacatt ccatgctcat   79980
gggtaggaag aatcaatatc gtgaaaatgg tcatactgcc caaggtaatt tatagattca   80040
atgccatccc catcaagcta ccaatgactt tcttcacaga actggaaaaa actacttaa   80100
agttcatatg gaaccaaaaa agagcccaca tcaccaaggc aatcctaagc caaagaaca   80160
aagctggagg catcacgcta cctgacttca aactatacta caatgctacg gtaaccaaaa   80220
cagcatggta ctggtaccaa aacagagatc tagaccaatg gaacagaaca gagccctcag   80280
aaataatgcc gcatatctac aactatctga tctttgacaa acctgagaga aacaagcaat   80340
ggggaaagga ttccctattt aataaatggt gctgggaaaa ctggctagcc atatgtagaa   80400
agctgaaact ggatcccttc cttacacctt atacaaaaat taattcaaga tggattaaag   80460
acttacatgt tagacctaaa accataaaaa ccctagaaaa aaacctaggc aataccattc   80520
```

```
aggacatagg catgggcaag gacttcatgt ctaaaacacc aaaagcaatg gcaacaaaag    80580
acaaaatgga caaacgggat ctaattaaac taaagagctt ctgcacagct aaagaaacta    80640
ccatcagagt gaacaggcaa cctacaaaat gggagaaaat ttttgcaatc tactcatctg    80700
acaaagggct aatatccaga atctacaatg aactcaaaca aatttacaag aaaaaacaaa    80760
caaccccatc aaaaagtggg caaggatat gaacagacac ttcgcaaaag aagacattta     80820
tgtaatcaaa aaacacatga aaaaatgctc atcatcacta gccatcagag aaatgcaaat    80880
caaaaccaca atgagatacc atctcacacc agttagaatg gcgatcatta aaaagtcagg    80940
aaacaacagg tgctggagag gatgtggaga acaggaaca acttttacac tgttggtggg     81000
actgtaaact agttcaacca ttgcggaagt cagtgtggca attcctcagg aatctagaac    81060
tagaaatacc atttgaccca gccatcccat tactgggtac atacccaaag gattataaat    81120
catgctgcta taaagacaca tgcacacgta tgtttattgc agcactattc acaatagcaa    81180
agacttggaa ccaacccaaa tgtccaacaa cgatagactg gattaagaaa atgtggcaca    81240
tatacaccat ggaatactat gcagccataa aaatgatga gttcatgtcc tttgtaggga     81300
catggatgaa gctggaaact atcattctca gcaaactatc acaaggagaa taaaccaaac    81360
accgcatgtt ctcactcata ggtgggaatt gaacaatgag aacacatgga cacatgaaga    81420
ggaacatcac actctgggga ctgttatggg gtgggggca ggggcaggga tagcactagg     81480
agatatacct aatgctaaat gacgagttaa tgggtgcagc acaccaacat ggcacatgta    81540
tacatatata acaaacctgc atgttgtgca catgtacct aaaacttgaa gtataataat     81600 aaaaaaagt tatcctatta aaactgatct cacacatccg tagagccatt atcaagtctt     81660
tctctttgaa atagacagaa atttagtgtt ttctcagtca gttaac                  81706

<210> SEQ ID NO 20
<211> LENGTH: 388
<212> TYPE: DNA
<213> ORGANISM: Homo sapiens

<400> SEQUENCE: 20
taagcttcag ttttttcctta gttcctgtta catttctgtg tgtctccatt agtgacctcc       60
catagtccaa gcatgagcag ttctggccag gcccctgtcg gggtcagtgc cccaccccg       120 ccttctggtt ctgtgtaacc ttctaagcaa accttctggc tcaagcacag caatgctgag      180
tcatgatgag tcatgctgag gcttagggtg tgtgcccaga tgttctcagc ctagagtgat      240
gactcctatc tgggtcccca gcaggatgct tacagggcag atggcaaaaa aaaggagaag     300
ctgaccacct gactaaaact ccacctcaaa cggcatcata agaaaatgg atgcctgaga      360 cagaatgtga catattctag aatatatt                                         388

<210> SEQ ID NO 21
<211> LENGTH: 387
<212> TYPE: DNA
<213> ORGANISM: Homo sapiens

<400> SEQUENCE: 21
taagcttcag ttttttcctta gttcctgtta catttctgtg tgtctccatt agtgacctcc       60
catagtccaa gcatgagcag ttctggccag gcccctgtcg gggtcagtgc cccaccccg       120 ccttctggtt ctgtgtaacc ttctaagcaa accttctggc tcaagcacag caatgctgag      180
tcatgatgag tcatgctgag gctagggtgt gtgcccagat gttctcagcc tagagtgatg     240
```

```
actcctatct gggtccccag caggatgctt acagggcaga tggcaaaaaa aaggagaagc      300
tgaccacctg actaaaactc cacctcaaac ggcatcataa agaaaatgga tgcctgagac      360
agaatgtgac atattctaga atatatt                                          387

<210> SEQ ID NO 22
<211> LENGTH: 286
<212> TYPE: DNA
<213> ORGANISM: Homo sapiens

<400> SEQUENCE: 22
ctgagcaact aactcatgca ggactctcaa acactaacct atagccttt  ctatgtatct      60 acttgtgtag aaaccaagcg tggggactga aaggcaata gcaggagcat tctgactctc       120
actgcctttg ctaggtccc tccctcatca cagctcagca tagtccgagc tcttatctat       180
atccacacac agtttctgac gctgcccagc tatcaccatc ccaagtctaa agaaaaaaat      240
aatgggtttg cccatctctg ttgattagaa acaaaacaa aataaa                      286

<210> SEQ ID NO 23
<211> LENGTH: 286
<212> TYPE: DNA
<213> ORGANISM: Homo sapiens

<400> SEQUENCE: 23
ctgagcaact aatcatgcag gactctcaaa cactaaccta tagccttttc tatgtatcta      60
cttgtgtaga aaccaagcgt ggggactgag aaggcaatag caggagcatt ctgactctca      120
ctgcctttag ctaggcccct ccctcatcac agctcagcat agtcctgagc tcttatctat      180
atccacacac agtttctgac gctgcccagc tatcaccatc ccaagtctaa agaaaaaaat      240
aatgggtttg cccatctctg ttgattagaa acaaaacaa aataaa                      286

<210> SEQ ID NO 24
<211> LENGTH: 301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
ccaatcgtgg catatcctct aaactttctt ttcccttcat aaatcctctt tcttttttt       60 cccctcaca gttttcctga acaggttgac tattaattgt gtctgcttga tgtggacacc       120
aggtggcgct ggacatcaga tttggagagg cagttgtcta gggaaccggg ctctgtgcca      180
gcgcaggagg caggctggct ctcctattcc agggatgctc atccaggaag gaaaggttgc      240
atgctggaca cactaacctt gaagaattct tctgtctctc tcgtcattta gaaaggaagg      300
a                                                                     301

<210> SEQ ID NO 25
<211> LENGTH: 305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ctagccaatc gtggcatatc ctctaaactt tcttttccct tcataaatcc tcttttcttttt    60 ttttcccccct cacagttttc ctgaacaggt tgactattaa ttgtgtctgc ttgatgtgga    120
```

```
caccaggtgg cgctggacat cagatttgga gaggcagttg tctagggaac cgggctctgt      180
gccagcgcag gaggcaggct ggctctccta ctccagggat gctcatccag gaaggaaagg      240
ttgcatgctg acacactaa ccttgaagaa ttcttctgtc tctctcgtca tttagaaagg       300
aagga                                                                  305
```

<210> SEQ ID NO 26
<211> LENGTH: 896
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
ctcgagttaa ttaatctccc acgccctggt ctcagcttgg ggagtggtca gaccccaatg       60
gcgataaact ctggcaactt tatctgtgca ctgcaggctc agccccaaca gctttagctt      120
tcacaagcag gcaggggaag ggaaacacat atctccagat atgaggttaa ttaacctgca      180
ggctaaaccc ctccccacc ctagcccaa gcttcatctt agctccactc ctgaccctat       240
ccagctaaag gtccccaccc agctcctgcc tatctagtca ttgcatatgg caagacttga      300
aagtcctatc tcaaagcagc agaattatca gctacgactc ctgcaggtta taaccatccc      360
ccagcactcc ctgcccccac agcccagact tgaccaactc ccagctccgc ctgggacttc      420
cagatatggg gcccaccct tgcaggcctt ggggacgctg aagatattga ctatctgcgt      480 gccgaaaag ggtgttataa accggtaaag gctgggggtg ggagtagcgg atttgaagca      540
cttgttggcc tacagaggtg tggcaagcag agcacctcag aactcaggcg tactgcccgc      600
cgcccgagcc ctgcgagggc cgatagcgag ggtgtggccc ttatctgcac ccagcagagc      660
gccggcgggg tacggtcacc ggtcccgggc agttgcctca gctgagtatg tcttctaaag      720
ataatgtcga ttgtgtatgg ctgatgggat tctaggacca agcaagaggt tttttttttt      780
cccccacata cttaacgttt ctatatttct atttgaattc gactggacag ttccatttga      840
attatttctc tctctctctc tctctgacac attttatctt gccacccggg ctcgag         896
```

<210> SEQ ID NO 27
<211> LENGTH: 320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27

```
ctggttctac tcattacatt ccaatcgtgg catatcctct aaactttctt ttcccttcat       60
aaatcctctt tcttttttt cccctcaca gttttcctga acaggttgac tattaattgt       120
gtctgcttga tgtggacacc aggtggcgct ggacatcaga tttggagagg cagttgtcta      180
gggaaccggg ctctgtgcca gcgcaggagg caggctggct ctcctattcc agggatgctc      240
atccaggaag gaaaggttgc atgctggaca cactaacctt gaagaattct tctgtctctc      300
tcgtcattta gaaggaagg                                                   320
```

<210> SEQ ID NO 28
<211> LENGTH: 300
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 28

```
ccaatcgtgg catatcctct aaactttctt ttcccttcat aaatcctctt tctttttttt    60 cccccctcaca gttttcctga acaggttgac tattaattgt gtctgcttga tgtggacacc   120
aggtggcgct ggacatcaga tttggagagg cagttgtcta gggaaccggg ctctgtgcca   180
gcgcaggagg caggctggct ctcctattcc agggatgctc atccaggaag gaaaggttgc   240
atgctggaca cactaacctt gaagaattct tctgtctctc tcgtcattta gaaaggaagg   300
```

<210> SEQ ID NO 29
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
tcataaatcc tctttctttt ttttccccct cacagttttc ctgaacaggt tgactattaa    60
ttgtgtctgc ttgatgtgga caccaggtgg cgctggacat cagatttgga gaggcagttg   120
```

<210> SEQ ID NO 30
<211> LENGTH: 170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30

```
tcataaatcc tctttctttt ttttccccct cacagttttc ctgaacaggt tgactattaa    60
ttgtgtctgc ttgatgtgga caccaggtgg cgctggacat cagatttgga gaggcagttg   120
tctagggaac cgggctctgt gccagcgcag gaggcaggct ggctctccta                170
```

<210> SEQ ID NO 31
<211> LENGTH: 240
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
tcataaatcc tctttctttt ttttccccct cacagttttc ctgaacaggt tgactattaa    60
ttgtgtctgc ttgatgtgga caccaggtgg cgctggacat cagatttgga gaggcagttg   120
tctagggaac cgggctctgt gccagcgcag gaggcaggct ggctctccta ttccagggat   180
gctcatccag gaaggaaagg ttgcatgctg gacacactaa ccttgaagaa ttcttctgtc   240
```

<210> SEQ ID NO 32
<211> LENGTH: 320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
ctggttctac tcattacatt ccaatcgtgg catatcctct aaactttctt ttcccttcat    60
```

```
aaatcctctt tctttttttt ccccctcaca gttttcctga acaggttgac tattaattgt    120
gtctgcttga tgtggacacc aggtggcgct ggacatcaga tttggagagg cagttgtcta    180
gggaaccggg ctctgtgcca gcgcaggagg caggctggct ctcctattcc agggatgctc    240
atccaggaag gaaaggttgc atgctggaca cactaacctt gaagaattct tctgtctctc    300
tcgtcattta gaaaggaagg                                                320
```

<210> SEQ ID NO 33
<211> LENGTH: 816
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
tctagaatat gtcacattct gtctcaggca tccatttcct ttatgatgcc gtttgaggtg    60
gagttttagt caggtggtca gcttctcctt tttttgcca tctgccctgt aagcatcctg    120
ctggggaccc agataggagt catcactcta ggctgagaac atctgggcac acccctaag    180 cctcagcatg actcatcatg actcagcatt gctgtgcttg agccagaagg tttgcttaga    240
aggttacaca gaaccagaag gcgggggtgg ggcactgacc ccgacagggg cctggccaga    300
actgctcatg cttggactat ggaggtcac taatggagac acacagaaat gtaacaggaa    360
ctaaggaaaa actgaagctt atttaatcag agatgagatg ctggaaggga tagagggagc    420
tgagcttgta aaagtatag taatcattca gcaaatggtt ttgaagcacc tgctggatgc    480
taaacactat tttcagtgct tgaatcataa ataagaacaa acatgtatc ttattcccca    540 caagagtcca agtaaaaaat aacagttaat tataatgtgc tctgtccccc aggctggagt    600
gcagtggcac gatctcagct cactgcaacc tccgcctccc gggttcaagc aattctcctg    660
cctcagccac cctaatagct gggattacag gtgcacacca ccatgccagg ctaattttg    720 tacttttgt agaggcaggg tatcaccatg ttgtccaaga tggtcttgaa ctcctgagct    780
ccaagcagtc cacccacctc agcctcccaa agtgct                              816
```

<210> SEQ ID NO 34
<211> LENGTH: 1301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
aagctttcat caaaaaaagt ctaaccagct gcattcgact ttgactgcag cagctggtta    60
gaaggttcta ctggaggagg gtcccagccc attgctaaat taacatcagg ctctgagact    120
ggcagtatat ctctaacagt ggttgatgct atcttctgga acttgcctgc tacattgaga    180
ccactgaccc atacatagga agcccatagc tctgtcctga actgttaggc cactggtcca    240
gagagtgtgc atctccttg atcctcataa taaccctatg agatagacac aattattact    300
cttactttat agatgatgat cctgaaaaca taggagtcaa ggcacttgcc cctagctggg    360
ggtatagggg agcagtccca tgtagtagta gaatgaaaaa tgctgctatg ctgtgcctcc    420
cccacctttc ccatgtctgc cctctactca tggtctatct ctcctggctc ctggagtca    480 tggactccac ccagcaccac caacctgacc taaccaccta tctgagcctg ccagcctata    540
acccatctgg gccctgatag ctggtggcca gccctgaccc cacccacccc tccctggaac    600
```

```
ctctgataga cacatctggc acaccagctc gcaaagtcac cgtgagggtc ttgtgtttgc    660
tgagtcaaaa ttccttgaaa tccaagtcct tagagactcc tgctcccaaa tttacagtca    720
tagacttctt catggctgtc tcctttatcc acagaatgat tcctttgctt cattgcccca    780
tccatctgat cctcctcatc agtgcagcac agggcccatg agcagtagct gcagagtctc    840
acataggtct ggcactgcct ctgacatgtc cgaccttagg caaatgcttg actcttctga    900
gctcagtctt gtcatggcaa acaaagata ataatagtgt ttttttatgg agttagcgtg     960
aggatggaaa acaatagcaa aattgattag actataaaag gtctcaacaa atagtagtag   1020
attttatcat ccattaatcc ttccctctcc tctcttactc atcccatcac gtatgcctct   1080
taattttccc ttacctataa taagagttat tcctcttatt atattcttct tatagtgatt   1140
ctggatatca aagtgggaat gaggggcagg ccactaacga agaagatgtt tctcaaagaa   1200
gccattctcc ccacatagat catctcagca gggttcagga agataaagga ggatcaaggt   1260
cgaaggtagg aactaaggaa gaacactggg caagtggatc c                       1301
```

<210> SEQ ID NO 35
<211> LENGTH: 754
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
taaatatatc atttaaatgc ataaataagc aaaccctgct cgggaatggg agggagagtc     60
tctggagtcc accccttctc ggccctggct ctgcagatag tgctatcaaa gccctgacag    120
agccctgccc attgctgggc cttggagtga gtcagcctag tagagaggca gggcaagcca    180
tctcatagct gctgagtggg agagagaaaa gggctcattg tctataaact caggtcatgg    240
ctattcttat tctcacacta agaaaaagaa tgagatgtct acatataccc tgcgtccct      300 cttgtgtact ggggccccca agagctctct aaaagtgatg gcaaagtcat tgcgctagat    360
gccatcccat ctattataaa cctgcatttg tctccacaca ccagtcatgg acaataaccc    420
tcctcccagg tccacgtgct tgtctttgta taatactcaa gtaatttcgg aaaatgtatt    480
ctttcaatct tgttctgtta ttcctgtttc aatggcttag tagaaaaagt acatacttgt    540
tttcccataa attgacaata gacaatttca catcaatgtc tatatgggtc gttgtgtttg    600
ctgtgtttgc aaaaactcac aataacttta tattgttact actctaagaa agttacaaca    660
tggtgaatac aagagaaagc tattacaagt ccagaaaaca aaagttatca tcttgaggcc    720
tcagctttct aggaataata tcaatattac aaaa                                 754
```

<210> SEQ ID NO 36
<211> LENGTH: 1232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 36

```
gcaatgaaaa taaatgtttt ttattaggca gaatccagat gctcaaggcc cttcataata     60
tcccccagtt tagtagttgg acttagggaa caaaggaacc tttaatagaa attggacagc    120
aagaaagcga gcttagtgat acttgtgggc cagggcatta gccacaccag ccaccacttt    180
```

```
ctgataggca gcctgcactg gtggggtgaa ttctttgcca aagtgatggg ccagcacaca    240
gaccagcacg ttgcccagga gctgtgggag gaagataaga ggtatgaaca tgattagcaa    300
aagggcctag cttggactca gaataatcca gccttatccc aaccataaaa taaaagcaga    360
atggtagctg gattgtagct gctattagca atatgaaacc tcttacatca gttacaattt    420
atatgcagaa atatttatat gcagaaatat tgctattgcc ttaacccaga aattatcact    480
gttattcttt agaatggtgc aaagaggcat gatacattgt atcattattg ccctgaaaga    540
aagagattag ggaaagtatt agaaataaga taaacaaaaa agtatattaa aagaagaaag    600 catttttta aattacaaat gcaaaattac cctgatttgg tcaatatgtg taccctgtta    660
cttctcccct tcctatgaca tgaacttaac catagaaaag aaggggaaag aaaacatcaa    720
gggtcccata gactcaccct gaagttctca ggatccacgt gcagcttgtc acagtgcagc    780
tcactcagct gggcaaaggt gcccttgagg ttgtccaggt gagccaggcc atcactaaag    840
gcaccgagca ctttcttgcc atgagccttc accttagggt tgcccataac agcatcagga    900
gtggacagat ccccaaagga ctcaaagaac ctctgggtcc aagggtagac caccagcagc    960
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aacttcatcc acgttcacct tgccccacag   1140
ggcagtaacg gcagacttct cctcaggagt caggtgcacc atggtgtctg tttgaggttg   1200
ctagtgaaca cagttgtgtc agaagcaaat gt                                 1232
```

<210> SEQ ID NO 37
<211> LENGTH: 12142
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37

```
attggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
acggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccggggt ctctctggtt agaccagatc tgagcctggg agctctctgg    720
ctaactaggg aacccactgc ttaagcctca ataaagcttg ccttgagtgc ttcaagtagt    780
gtgtgcccgt ctgttgtgtg actctggtaa ctagagatcc ctcagaccct tttagtcagt    840
gtggaaaatc tctagcagtg gcgcccgaac agggacttga aagcgaaagg gaaaccagag    900
gagctctctc gacgcaggac tcggcttgct gaagcgcgca cggcaagagg cgaggggcgg    960
```

```
cgactggtga gtacgccaaa aatttgact agcggaggct agaaggagag agacgggtgc      1020
gagagcgtca gtattaagcg ggggtgaata agatcgcgat gggaaaaaat tcggttaagg      1080
ccagggggaa agaaaaaata taaattaaaa catatagtat gggcaagcag ggagctagaa      1140
cgattcgcag ttaatcctgg cctgttagaa acatcagaag gctgtagaca aatactggga      1200
cagctacaac catcccttca gacaggatca gaagaactta gatcattata taatacagta      1260
gcaaccctct attgtgtgca tcaaggata gagataaaag acaccaagga agctttagac       1320
aagatagagg aagagcaaaa caaaagtaag accaccgcac agcaagcggc cgctgatctt      1380
cagacctgga ggaggagata tgagggacaa ttggagaagt gaattatata aatataaagt      1440
agtaaaaatt gaaccattag gagtagcacc caccaaggca aagagaagag tggtgcagag      1500
agaaaaaaga gcagtgggaa taggagcttt gttccttggg ttcttgggag cagcaggaag      1560
cactatgggc gcagcgtcaa tgacgctgac ggtacaggcc agacaattat tgtctggtat      1620
agtgcagcag cagaacaatt tgctgagggc tattgaggcg caacagcatc tgttgcaact      1680
cacagtctgg ggcatcaagc agctccaggc aagaatcctg ctgtggaaaa gatacctaaa      1740
ggatcaacag ctcctgggga tttggggttg ctctggaaaa ctcatttgca ccactgctgt      1800
gccttggaat gctagttgga gtaataaatc tctggaacag atttggaatc acacgacctg      1860
gatggagtgg gacagagaaa ttaacaatta cacaagctta atacactcct taattgaaga      1920
atcgcaaaac cagcaagaaa agaatgaaca agaattattg gaattagata atgggcaag       1980 tttgtggaat tggtttaaca taacaaattg gctgtggtat ataaaattat tcataatgat      2040
agtaggaggc ttggtaggtt taagaatagt ttttgctgta ctttctatag tgaatagagt      2100
taggcaggga tattcaccat tatcgtttca gacccacctc ccaaccccga ggggacccga      2160
caggcccgaa ggaatagaag aagaaggtgg agagagagac agagacagat ccattcgatt      2220
agtgaacgga tctcgacggt atcgttttaa agaaaaggg gggattgggg ggtacagtgc       2280
aggggaaaga atagtagaca taatagcaac agacatacaa actaaagaat tacaaaaaca      2340
aattacaaaa attcaaaatt ttatcggcgt gttgggggtg gaccatcctc taggtattga     2400
ataagaaaaa tgaagttaag gtggttgatg gtaacactat gctaataact gcagagccag      2460
aagcaccata agggacatga taagggagcc agcagacctc tgatctcttc ctgaatgcta      2520
atcttaaaca tcctgaggaa gaatgggact tccatttggg gtgggcctat gatagggtaa      2580
taagacagta gtgaatatca agctacaaaa agccccttt caaattcttc tcagtcctaa       2640
cttttcatac taagcccagt ccttccaaag cagactgtga aagagtgata gttccgggag      2700
actagcactg cagattccgg gtcactgtga gtggggagg cagggaagaa gggctcacag       2760
gacagtcaaa ccatgccccc tgttttcct tcttcaagta gacctctata agacaacaga       2820
gacaactaag gctgagtggc caggcgagga gaaaccatct cgccgtaaaa catggaagga      2880
acacttcagg ggaaaggtgg tatctctaag caagagaact gagtggagtc aaggctgaga      2940
gatgcaggat aagcaaatgg gtagtgaaaa gacattcatg aggacagcta aaacaataag      3000
taatgtaaaa tacagcatag caaaacttta acctccaaat caagcctcta cttgaatcct      3060
tttctgaggg atgaataagg cataggcatc aggggctgtt gccaatgtgc attagctgtt      3120
tgcagcctca ccttctttca tggagtttaa gatatagtgt attttcccaa ggtttgaact      3180
agctcttcat ttctttatgt tttaaatgca ctgacctccc acattccctt tttagtaaaa      3240
tattcagaaa taatttaaat acatcattgc aatgaaaata aatgttttt attaggcaga       3300 atccagatgc tcaaggccct tcataatatc ccccagttta gtagttggac ttagggaaca      3360
```

```
aaggaacctt taatagaaat tggacagcaa gaaagcgagc ttagtgatac ttgtgggcca    3420
gggcattagc cacaccagcc accactttct gataggcagc ctgcactggt ggggtgaatt    3480
ctttgccaaa gtgatgggcc agcacacaga ccagcacgtt gcccaggagc tgtgggagga    3540
agataagagg tatgaacatg attagcaaaa gggcctagct tggactcaga ataatccagc    3600
cttatcccaa ccataaaata aaagcagaat ggtagctgga ttgtagctgc tattagcaat    3660
atgaaacctc ttcatcagt tacaatttat atgcagaaat atttatatgc agaaatattg    3720
ctattgcctt aacccagaaa ttatcactgt tattctttag aatggtgcaa agaggcatga    3780
tacattgtat cattattgcc ctgaaagaaa gagattaggg aaagtattag aaataagata    3840
aacaaaaaag tatattaaaa gaagaaagca ttttttaaaa ttacaaatgc aaaattaccc    3900
tgatttggtc aatatgtgta ccctgttact tctcccctcc ctatgacatg aacttaacca    3960
tagaaaagaa ggggaaagaa aacatcaagg gtcccataga ctcaccctga agttctcagg    4020
atccacgtgc agcttgtcac agtgcagctc actcagctgg gcaaaggtgc ccttgaggtt    4080
gtccaggtga gccaggccat cactaaaggc accgagcact tcttgccat gagccttcac    4140 cttagggttg cccataacag catcaggagt ggacagatcc ccaaaggact caaagaacct    4200
ctgggtccaa gggtagacca ccagcagcct aagggtggga aaatagacca ataggcagag    4260
agagtcagtg cctatcagaa acccaagagt cttctctgtc tccacatgcc cagtttctat    4320
tggtctcctt aaacctgtct tgtaaccttg ataccaacct gcccagggcc tcaccaccaa    4380
cttcatccac gttcaccttg ccccacaggg cagtaacggc agacttctcc tcaggagtca    4440
ggtgcaccat ggtgtctgtt tgaggttgct agtgaacaca gttgtgtcag aagcaaatgt    4500
aagcaataga tggctctgcc ctgactttta tgcccagccc tggctcctgc cctccctgct    4560
cctgggagta gattggccaa ccctagggtg tggctccaca gggtgaggtc taagtgatga    4620
cagccgtacc tgtccttggc tcttctggca ctggcttagg agttggactt caaaccctca    4680
gccctccctc taagatatat ctcttggccc cataccatca gtacaaattg ctactaaaaa    4740
catcctcctt tgcaagtgta tttacgtaat atttggaatc acagcttggt aagcatattg    4800
aagatcgttt tcccaatttt cttattacac aaataagaaa ttgatgcact aaaagtggaa    4860
gagttttgtc taccataatt cagctttggg atatgtagat ggatctcttc ctgcgtctcc    4920
agaatatgca aaatacttac aggacagaat ggatgaaaac tctacctcag ttctaagcat    4980
atcttctcct tatttggatt aaaaccttct ggtaagaaaa gaaaaaaaat atatatatat    5040
atgtgtatat atacacacat acatatacat atatatgcat tcatttgttg ttgttttttct    5100 taatttgctc atggtatatg tgtatatata tatatatata ttcaggaaat aatatattct    5160
agaatatgtc acattctgtc tcaggcatcc attttcttta tgatgccgtt tgaggtggag    5220
ttttagtcag gtggtcagct tctcctttt tttgccatct gccctgtaag catcctgctg    5280
gggacccaga taggagtcat cactctaggc tgagaacatc tgggcacaca ccctaagcct    5340
cagcatgact catcatgact cagcattgct gtgcttgagc cagaaggttt gcttagaagg    5400
ttacacagaa ccagaaggcg ggggtggggc actgaccccg acaggggcct ggccagaact    5460
gctcatgctt ggactatggg aggtcactaa tggagacaca cagaaatgta acaggaacta    5520
aggaaaaact gaagcttatt taatcagaga tgagatgctg gaagggatag agggagctga    5580
gcttgtaaaa agtatagtaa tcattcagca aatggttttg aagcacctgc tggatgctaa    5640
acactatttt cagtgcttga atcataaata agaataaaac atgtatctta ttccccacaa    5700
```

```
gagtccaagt aaaaaataac agttaattat aatgtgctct gtcccccagg ctggagtgca    5760
gtggcacgat ctcagctcac tgcaacctcc gcctcccggg ttcaagcaat tctcctgcct    5820
cagccaccct aatagctggg attacaggtg cacaccacca tgccaggcta attttttgtac   5880
ttttttgtaga ggcagggtat caccatgttg tccaagatgg tcttgaactc ctgagctcca   5940
agcagtccac ccacctcagc ctcccaaagt gctatctgcg gccgcctatc tgtaccacta    6000
gtctcgagaa gctttcatta aaaaaagtct aaccagctgc attcgacttt gactgcagca    6060
gctggttaga aggttctact ggaggagggt cccagcccat tgctaaatta acatcaggct    6120
ctgagactgg cagtatatct ctaacagtgg ttgatgctat cttctggaac ttgcctgcta    6180
cattgagacc actgacccat acataggaag cccatagctc tgtcctgaac tgttaggcca    6240
ctggtccaga gagtgtgcat ctcctttgat cctcataata accctatgag atagacacaa    6300
ttattactct tactttatag atgatgatcc tgaaaacata ggagtcaagg cacttgcccc    6360
tagctggggg tataggggag cagtcccatg tagtagtaga atgaaaaatg ctgctatgct    6420
gtgcctcccc cacctttccc atgtctgccc tctactcatg gtctatctct cctggctcct    6480
gggagtcatg gactccaccc agcaccacca acctgaccta accacctatc tgagcctgcc    6540
agcctataac ccatctgggc cctgatagct ggtggccagc cctgaccca ccccacccctc    6600
cctggaacct ctgatagaca catctggcac accagctcgc aaagtcaccg tgagggtctt    6660
gtgtttgctg agtcaaaatt ccttgaaatc caagtcctta gagactcctg ctcccaaatt    6720
tacagtcata gacttcttca tggctgtctc ctttatccac agaatgattc ctttgcttca    6780
ttgccccatc catctgatcc tcctcatcag tgcagcacag ggcccatgag cagtagctgc    6840
agagtctcac ataggtctgg cactgcctct gacatgtccg accttaggca aatgcttgac    6900
tcttctgagc tcagtcttgt catggcaaaa taaagataat aatagtgttt ttttatggag    6960
ttagcgtgag gatggaaaac aatagcaaaa ttgattagac tataaaaggt ctcaacaaat    7020
agtagtagat tttatcatcc attaatcctt ccctctcctc tcttactcat cccatcacgt    7080
atgcctctta atttttccctt acctataata agagttattc ctcttattat attcttctta    7140
tagtgattct ggatattaaa gtgggaatga ggggcaggcc actaacgaag aagatgtttc    7200
tcaaagaagc cattctcccc acatagatca tctcagcagg gttcaggaag ataaaggagg    7260
atcaaggtcg aagtaggaa ctaaggaaga acactgggca agtggatcct gagcccttt     7320
tcctctaact gaaagaagga aaaaaaaat ggaacccaaa atattctaca tagttttccat   7380
gtcacagcca gggctgggca gtctcctgtt atttcttta aaataaatat atcatttaaa    7440
tgcataaata agcaaaccct gctcgggaat gggagggaga gtctctggag tccaccccttt  7500
ctcggccctg gctctgcaga tagtgctatc aaagccctga cagagccctg cccattgctg    7560
ggccttggag tgagtcagcc tagtagagag gcagggcaag ccatctcata gctgctgagt    7620
gggagagaga aaagggctca ttgtctataa actcaggtca tggctattct tattctcaca    7680
ctaagaaaaa gaatgagatg tctacatata ccctgcgtcc cctcttgtgt actggggccc    7740
ccaagagctc tctaaaagtg atggcaaagt cattgcgcta gatgccatcc catctattat    7800
aaacctgcat ttgtctccac acaccagtca tggacaataa ccctcctccc aggtccacgt    7860
gcttgtcttt gtataatact caagtaattt cggaaaatgt attctttcaa tcttgttctg    7920
ttattcctgt ttcaatggct tagtagaaaa agtacatact tgttttccca taaattgaca    7980
atagacaatt tcacatcaat gtctatatgg gtcgttgtgt ttgctgtgtt tgcaaaaact    8040
cacaataact ttatattgtt actactctaa gaaagttaca acatggtgaa tacaagagaa    8100
```

```
agctattaca agtccagaaa ataaaagtta tcatcttgag gcctcagctt tctaggaata    8160
atatcaatat tacaaaattt aatctaacaa ttatgaacag caatgagata atatgtacaa    8220
agtacccaga cctatgtggt agagcatcaa ggaagcgcat tgcggagcag ttttttgttt    8280
gtttgttttt gtattctgtt tcgtgaggca aggtttcact ctgctgtcca ggctggagtg    8340
cagtggcaag atcatgtctc actgcagcct tgacacgcgt cgacggtacc gttaacgatc    8400
ttagccactt tttaaaagaa aaggggggac tggaagggct aattcactcc caacgaagac    8460
aagatatcct gctagtcctt cctttctaaa tgacgagaga gacagaagaa ttcttcaagg    8520
ttagtgtgtc cagcatgcaa cctttccttc ctggatgagc atccctggag taggagagcc    8580
agcctgcctc ctgcgctggc acagagcccg gttccctaga caactgcctc tccaaatctg    8640
atgtccagcg ccacctggtg tccacatcaa gcagacacaa ttaatagtca acctgttcag    8700
gaaaactgtg aggggaaaa aaaagaaaga ggatttatga agggaaaaga aagtttagag    8760
gatatgccac gattggctag cagctgcttt ttgcctgtac tgggtctctc tggttagacc    8820
agatctgagc ctgggagctc tctggctaac tagggaaccc actgcttaag cctcaataaa    8880
gcttgccttg agtgcttcat ccggaatcaa cctctggatt acaaaatttg tgaaagattg    8940
actggtattc ttaactatgt tgctcctttt acgctatgtg gatacgctgc tttaatgcct    9000
ttgtatcatg ctattgcttc ccgtatggct ttcattttct cctccttgta taaatcctgg    9060
ttgctgtctc tttatgagga gttgtggccc gttgtcaggc aacgtggcgt ggtgtgcact    9120
gtgtttgctg acgcaacccc cactggtgg ggcattgcca ccacctgtca gctccttttcc    9180
gggactttcg ctttccccct cccattgcc acggcggaac tcatcgccgc ctgccttgcc    9240
cgctgctgga caggggctcg gctgttgggc actgacaatt ccgtggtgtt gtcggggaag    9300
ctgacgtcct ttccatggct gctcgcctgt gttgccacct ggattctgcg cgggacgtcc    9360
ttctgctacg tccccttcggc cctcaatcca cggaccttc cttcccgcgg cctgctgccg    9420
gctctgcggc ctcttccgcg tcttcgcctt cgccctcaga cgagtcggat ctcccttttgg    9480
gccgcctccc cgcctgtccg gtagcttgcc agcctcgact gtgccttcta gttgccagcc    9540
gtctgttgtt tgcccctccc ccgtgccttc cttgaccctg gaaggtgcca ctcccactgt    9600
cctttcctaa taaaatgagg aaattgcatc gcattgtctg agtaggtgtc attctattct    9660
ggggggtggg gtggggcagg acagcaaggg ggaggattgg gaagacaata gcaggcatgc    9720
aagcttggcg taatcatggt catagctgtt tcctgtgtga aattgttatc cgctcacaat    9780
tccacacaac atacgagccg gaagcataaa gtgtaaagcc tggggtgcct aatgagtgag    9840
ctaactcaca ttaattgcgt tgcgctcact gcccgctttc cagtcgggaa acctgtcgtg    9900
ccagctgcat taatgaatcg gccaacgcgc ggggagaggc ggtttgcgta ttgggcgctc    9960
ttccgcttcc tcgctcactg actcgctgcg ctcggtcgtt cggctgcggc gagcggtatc   10020
agctcactca aaggcggtaa tacggttatc cacagaatca ggggataacg caggaaagaa   10080
catgtgagca aaaggccagc aaaaggccag gaaccgtaaa aaggccgcgt tgctggcgtt   10140
tttccatagg ctccgccccc ctgacgagca tcacaaaaat cgacgctcaa gtcagaggtg   10200
gcgaaacccg acaggactat aaagatacca ggcgtttccc cctggaagct ccctcgtgcg   10260
ctctcctgtt ccgaccctgc cgcttaccgg atacctgtcc gcctttctcc cttcgggaag   10320
cgtggcgctt tctcatagct cacgctgtag gtatctcagt tcggtgtagg tcgttcgctc   10380
caagctgggc tgtgtgcacg aaccccccgt tcagcccgac cgctgcgcct tatccggtaa   10440
```

```
ctatcgtctt gagtccaacc cggtaagaca cgacttatcg ccactggcag cagccactgg   10500
taacaggatt agcagagcga ggtatgtagg cggtgctaca gagttcttga agtggtggcc   10560
taactacggc tacactagaa gaacagtatt tggtatctgc gctctgctga agccagttac   10620
cttcggaaaa agagttggta gctcttgatc cggcaaacaa accaccgctg gtagcggtgg   10680
tttttttgtt tgcaagcagc agattacgcg cagaaaaaaa ggatctcaag aagatccttt   10740
gatcttttct acggggtctg acgctcagtg gaacgaaaac tcacgttaag ggattttggt   10800
catgagatta tcaaaaagga tcttcaccta gatccttta aattaaaaat gaagttttaa   10860
atcaatctaa agtatatatg agtaaacttg gtctgacagt taccaatgct taatcagtga   10920
ggcacctatc tcagcgatct gtctatttcg ttcatccata gttgcctgac tccccgtcgt   10980
gtagataact acgatacggg agggcttacc atctggcccc agtgctgcaa tgataccgcg   11040
agacccacgc tcaccggctc cagatttatc agcaataaac cagccagccg gaagggccga   11100
gcgcagaagt ggtcctgcaa ctttatccgc ctccatccag tctattaatt gttgccggga   11160
agctagagta agtagttcgc cagttaatag tttgcgcaac gttgttgcca ttgctacagg   11220
catcgtggtg tcacgctcgt cgtttggtat ggcttcattc agctccggtt cccaacgatc   11280
aaggcgagtt acatgatccc ccatgttgtg caaaaaagcg gttagctcct tcggtcctcc   11340
gatcgttgtc agaagtaagt tggccgcagt gttatcactc atggttatgg cagcactgca   11400
taattctctt actgtcatgc catccgtaag atgcttttct gtgactggtg agtactcaac   11460
caagtcattc tgagaatagt gtatgcggcg accgagttgc tcttgcccgg cgtcaatacg   11520
ggataatacc gcgccacata gcagaacttt aaaagtgctc atcattggaa aacgttcttc   11580
ggggcaaaac tctcaaggat cttaccgctg ttgagatcca gttcgatgta acccactcgt   11640
gcacccaact gatcttcagc atcttttact ttcaccagcg tttctgggtg agcaaaaaca   11700
ggaaggcaaa atgccgcaaa aaagggaata agggcgacac ggaaatgttg aatactcata   11760
ctcttccttt ttcaatatta ttgaagcatt tatcagggtt attgtctcat gagcggatac   11820
atatttgaat gtatttagaa aaataaacaa ataggggttc cgcgcacatt tccccgaaaa   11880
gtgccacctg acgtctaaga aaccattatt atcatgacat taacctataa aaataggcgt   11940
atcacgaggc cctttcgtct cgcgcgtttc ggtgatgacg gtgaaaacct ctgacacatg   12000 cagctccccgg agacggtcac agcttgtctg taagcggatg ccgggagcag acaagcccgt   12060
cagggcgcgt cagcgggtgt tggcgggtgt cggggctggc ttaactatgc ggcatcagag   12120
cagattgtac tgagagtgca cc                                            12142
```

<210> SEQ ID NO 38  
<211> LENGTH: 12040  
<212> TYPE: DNA  
<213> ORGANISM: Artificial Sequence  
<220> FEATURE:  
<223> OTHER INFORMATION: Description of Artificial Sequence: Synthetic  
       polynucleotide

<400> SEQUENCE: 38

```
attggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
```

```
cccacttggc agtacatcaa gtgtatcata tgccaagtac gccccctatt gacgtcaatg    360
acggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg gcggtaggc gtgtacggtg gaggtctat ataagcagag      660 ctcgtttagt gaaccggggt ctctctggtt agaccagatc tgagcctggg agctctctgg    720
ctaactaggg aacccactgc ttaagcctca ataaagcttg ccttgagtgc ttcaagtagt    780
gtgtgcccgt ctgttgtgtg actctggtaa ctagagatcc ctcagaccct tttagtcagt    840
gtggaaaatc tctagcagtg gcgcccgaac agggacttga agcgaaagg gaaaccagag     900 gagctctctc gacgcaggac tcggcttgct gaagcgcgca cggcaagagg cgaggggcgg    960
cgactggtga gtacgccaaa aattttgact agcggaggct agaaggagag agacgggtgc   1020
gagagcgtca gtattaagcg ggggtgaata agatcgcgat gggaaaaaat tcggttaagg   1080
ccagggggaa agaaaaaata taaattaaaa catatagtat gggcaagcag ggagctagaa   1140
cgattcgcag ttaatcctgg cctgttagaa acatcagaag gctgtagaca atactgggga   1200
cagctacaac catcccttca gacaggatca gaagaactta gatcattata taatacagta   1260
gcaaccctct attgtgtgca tcaaggata gagataaaag acaccaagga agctttagac    1320
aagatagagg aagagcaaaa caaaagtaag accaccgcac agcaagcggc cgctgatctt   1380
cagacctgga ggaggagata tgagggacaa ttggagaagt gaattatata aatataaagt   1440
agtaaaaatt gaaccattag gagtagcacc caccaaggca agagaagag tggtgcagag    1500 agaaaaaaga gcagtgggaa taggagcttt gttccttggg ttcttgggag cagcaggaag   1560
cactatgggc gcagcgtcaa tgacgctgac ggtacaggcc agacaattat tgtctggtat   1620
agtgcagcag cagaacaatt tgctgagggc tattgaggcg caacagcatc tgttgcaact   1680
cacagtctgg ggcatcaagc agctccaggc aagaatcctg gctgtggaaa gatacctaaa   1740
ggatcaacag ctcctgggga tttggggttg ctctggaaaa ctcatttgca ccactgctgt   1800
gccttggaat gctagttgga gtaataaatc tctggaacag atttggaatc acacgacctg   1860
gatggagtgg gacagagaaa ttaacaatta cacaagctta atacactcct taattgaaga   1920
atcgcaaaac cagcaagaaa agaatgaaca agaattattg gaattagata atgggcaag    1980 tttgtggaat tggtttaaca taacaaattg gctgtggtat ataaaattat tcataatgat   2040
agtaggaggc ttggtaggtt taagaatagt ttttgctgta ctttctatag tgaatagagt   2100
taggcaggga tattcaccat tatcgtttca gacccacctc ccaaccccga ggggaccccga   2160 caggcccgaa ggaatagaag aagaaggtgg agagagagac agagacagat ccattcgatt   2220
agtgaacgga tctcgacggt atcgttttaa aagaaaggg gggattgggg ggtacagtgc    2280 agggaaaga atagtagaca aatagcaac agacatacaa actaaagaat tacaaaaaca     2340
aattacaaaa attcaaaatt ttatcggcgt gttgggggtg gaccatcctc taggtattga   2400
ataagaaaaa tgaagttaag gtggttgatg gtaacactat gctaataact gcagagccag   2460
aagcaccata agggacatga taagggagcc agcagacctc tgatctcttc ctgaatgcta   2520
atcttaaaca tcctgaggaa gaatgggact ccatttggg gtgggcctat gatagggtaa    2580
taagacagta gtgaatatca agctacaaaa agccccttt caaattcttc tcagtcctaa    2640
cttttcatac taagcccagt ccttccaaag cagactgtga aagagtgata gttccgggag   2700
```

```
actagcactg cagattccgg gtcactgtga gtggggagg cagggaagaa gggctcacag    2760
gacagtcaaa ccatgccccc tgtttttcct tcttcaagta gacctctata agacaacaga    2820
gacaactaag gctgagtggc caggcgagga gaaaccatct cgccgtaaaa catggaagga    2880
acacttcagg ggaaaggtgg tatctctaag caagagaact gagtggagtc aaggctgaga    2940
gatgcaggat aagcaaatgg gtagtgaaaa gacattcatg aggacagcta aaacaataag    3000
taatgtaaaa tacagcatag caaaacttta acctccaaat caagcctcta cttgaatcct    3060
tttctgaggg atgaataagg cataggcatc aggggctgtt gccaatgtgc attagctgtt    3120
tgcagcctca ccttctttca tggagtttaa gatatagtgt attttcccaa ggtttgaact    3180
agctcttcat ttctttatgt tttaaatgca ctgacctccc acattccctt tttagtaaaa    3240
tattcagaaa taatttaaat acatcattgc aatgaaaata aatgtttttt attaggcaga    3300
atccagatgc tcaaggccct tcataatatc ccccagttta gtagttggac ttagggaaca    3360
aaggaacctt taatagaaat tggacagcaa gaaagcgagc ttagtgatac ttgtgggcca    3420
gggcattagc cacaccagcc accactttct gataggcagc ctgcactggt ggggtgaatt    3480
ctttgccaaa gtgatgggcc agcacacaga ccagcacgtt gcccaggagc tgtggagga    3540
agataagagg tatgaacatg attagcaaaa gggcctagct tggactcaga ataatccagc    3600
cttatcccaa ccataaaata aaagcagaat ggtagctgga ttgtagctgc tattagcaat    3660
atgaaacctc ttacatcagt tacaatttat atgcagaaat atttatatgc agaaatattg    3720
ctattgcctt aacccagaaa ttatcactgt tattctttag aatggtgcaa agaggcatga    3780
tacattgtat cattattgcc ctgaaagaaa gagattaggg aaagtattag aaataagata    3840
aacaaaaaag tatattaaaa gaagaaagca tttttaaaaa ttacaaatgc aaaattaccc    3900
tgatttggtc aatatgtgta ccctgttact tctccccttc ctatgacatg aacttaacca    3960
tagaaaagaa ggggaaagaa aacatcaagg gtcccataga ctcaccctga agttctcagg    4020
atccacgtgc agcttgtcac agtgcagctc actcagctgg gcaaaggtgc ccttgaggtt    4080
gtccaggtga gccaggccat cactaaaggc accgagcact ttcttgccat gagccttcac    4140
cttagggttg cccataacag catcaggagt ggacagatcc ccaaaggact caaagaacct    4200
ctgggtccaa gggtagacca ccagcagcct aagggtggga aaatagacca ataggcagag    4260
agagtcagtg cctatcagaa acccaagagt cttctctgtc tccacatgcc cagtttctat    4320
tggtctcctt aaacctgtct tgtaaccttg ataccaacct gcccagggcc tcaccaccaa    4380
cttcatccac gttcaccttg ccccacaggg cagtaacggc agacttctcc tcaggagtca    4440
ggtgcaccat ggtgtctgtt tgaggttgct agtgaacaca gttgtgtcag aagcaaatgt    4500
aagcaataga tggctctgcc ctgacttta tgcccagccc tggctcctgc cctccctgct    4560
cctgggagta gattggccaa ccctagggtg tggctccaca gggtgaggtc taagtgatga    4620
cagccgtacc tgtccttggc tcttctggca ctggcttagg agttggactt caaaccctca    4680
gccctccctc taagatatat ctcttggccc cataccatca gtacaaattg ctactaaaaa    4740
catcctcctt tgcaagtgta tttacggcat ctgtgaagga aagaaacatc tcctctaaac    4800
cactatgctg ctagagcctc ttttctgtac tcaagcctca ttcagacact agtgtcacca    4860
gtctcctcat atacctattg tattttcttc ttcttgctgg tttagtcatg ttttctggga    4920
gcttaggggc ttatttttatt ttgttttgtt ttctaatcaa cagagatggg caaacccatt    4980
atttttttct ttagacttgg gatggtgata gctgggcagc gtcagaaact gtgtgtggat    5040
```

```
atagataaga gctcggacta tgctgagctg tgatgaggga gggacctagc caaaggcagt     5100
gagagtcaga atgctcctgc tattgccttc tcagtcccca cgcttggttt ctacacaagt     5160
agatacatag aaaaggctat aggttagtgt ttgagagtcc tgcatgagtt agttgctcag     5220
aaatgcccga taaatatgtt atgtgtgttt atgtatatat atgttttata tatatatatg     5280
tgtgtgtgtg tgtgtgtgtg tgttgtgttt acaaatatgt gattatcatc aaaacgtgag     5340
ggctaaagtg accagataac ttgcaggtct agaatatgtc acattctgtc tcaggcatcc     5400
attttcttta tgatgccgtt tgaggtggag ttttagtcag gtggtcagct tctccttttt     5460
tttgccatct gccctgtaag catcctgctg gggacccaga taggagtcat cactctaggc     5520
tgagaacatc tgggcacaca ccctaagcct cagcatgact catcatgact cagcattgct     5580
gtgcttgagc cagaaggttt gcttagaagg ttacacagaa ccagaaggcg ggggtggggc     5640
actgaccccg cagggggcct ggccagaact gctcatgctt ggactatggg aggtcactaa     5700
tggagacaca cagaaatgta acaggaacta aggaaaaact gaagcttatt taatcagaga     5760
tgagatgctg gaagggatag agggagctga gcttgtaaaa agtatagtaa tcattcagca     5820
aatggttttg aagcacctgc tggatgctaa acactatttt cagtgcttga atcataaata     5880
agaacaaaac atgtatctta ttccccacaa gagtccaagt aaaaaataac agttaattat     5940
aatgtgctct gtcccccagg ctggagtgca gtggcacgat ctcagctcac tgcaacctcc     6000
gcctcccggg ttcaagcaat tctcctgcct cagccaccct aatagctggg attacaggtg     6060
cacaccacca tgccaggcta attttttgtac tttttgtaga ggcagggtat caccatgttg     6120
tccaagatgg tcttgaactc ctgagctcca agcagtccac ccacctcagc ctcccaaagt     6180
gctatctgcg gccgcctatc tgtaccacta gtctcgagaa gctttcatca aaaaaagtct     6240
aaccagctgc attcgacttt gactgcagca gctggttaga aggttctact ggaggagggt     6300
cccagcccat tgctaaatta acatcaggct ctgagactgg cagtatatct ctaacagtgg     6360
ttgatgctat cttctggaac ttgcctgcta cattgagacc actgacccat acataggaag     6420
cccatagctc tgtcctgaac tgttaggcca ctggtccaga gagtgtgcat ctcctttgat     6480
cctcataata accctatgag atagacacaa ttattactct tactttatag atgatgatcc     6540
tgaaaacata ggagtcaagg cacttgcccc tagctggggg tatagggggag cagtcccatg     6600 tagtagtaga atgaaaaatg ctgctatgct gtgcctcccc cacctttccc atgtctgccc     6660
tctactcatg gtctatctct cctggctcct gggagtcatg gactccaccc agcaccacca     6720
acctgaccta accacctatc tgagcctgcc agcctataac ccatctgggc cctgatagct     6780
ggtggccagc cctgacccca ccccacccctc cctggaacct ctgatagaca catctggcac     6840
accagctcgc aaagtcaccg tgagggtctt gtgtttgctg agtcaaaatt ccttgaaatc     6900
caagtcctta gagactcctg ctcccaaatt tacagtcata gacttcttca tggctgtctc     6960
ctttatccac agaatgattc ctttgcttca ttgccccatc catctgatcc tcctcatcag     7020
tgcagcacag ggcccatgag cagtagctgc agagtctcac ataggtctgg cactgcctct     7080
gacatgtccg accttaggca aatgcttgac tcttctgagc tcagtcttgt catggcaaaa     7140
caaagataat aatagtgttt ttttatggag ttagcgtgag gatggaaaac aatagcaaaa     7200
ttgattagac tataaaaggt ctcaacaaat agtagtagat tttatcatcc attaatcctt     7260
ccctctcctc tcttactcat cccatcacgt atgcctctta attttccctt acctataata     7320
agagttattc ctcttattat attcttctta tagtgattct ggatatcaaa gtgggaatga     7380
ggggcaggcc actaacgaag aagatgtttc tcaaagaagc cattctcccc acatagatca     7440
```

-continued

```
tctcagcagg gttcaggaag ataaaggagg atcaaggtcg aaggtaggaa ctaaggaaga    7500
acactgggca agtggatcct aaatatatca tttaaatgca taaataagca aaccctgctc    7560
gggaatggga gggagagtct ctggagtcca ccccttctcg gccctggctc tgcagatagt    7620
gctatcaaag ccctgacaga gccctgccca ttgctgggcc ttggagtgag tcagcctagt    7680
agagaggcag ggcaagccat ctcatagctg ctgagtggga gagagaaaag ggctcattgt    7740
ctataaactc aggtcatggc tattcttatt ctcacactaa gaaaagaat gagatgtcta     7800 catataccct gcgtcccctc ttgtgtactg gggcccccaa gagctctcta aaagtgatgg    7860
caaagtcatt gcgctagatg ccatcccatc tattataaac ctgcatttgt ctccacacac    7920
cagtcatgga caataaccct cctcccaggt ccacgtgctt gtctttgtat aatactcaag    7980
taatttcgga aaatgtattc tttcaatctt gttctgttat tcctgtttca atggcttagt    8040
agaaaaagta catacttgtt ttcccataaa ttgacaatag acaatttcac atcaatgtct    8100
atatgggtcg ttgtgtttgc tgtgtttgca aaaactcaca ataactttat attgttacta    8160
ctctaagaaa gttacaacat ggtgaataca agagaaagct attacaagtc cagaaaacaa    8220
aagttatcat cttgaggcct cagctttcta ggaataatat caatattaca aaacgcgtcg    8280
acggtaccgt taacgatctt agccactttt taaaagaaaa ggggggactg aagggctaa     8340 ttcactccca acgaagacaa gatatcctgc tagtccttcc tttctaaatg acgagagaga    8400
cagaagaatt cttcaaggtt agtgtgtcca gcatgcaacc tttccttcct ggatgagcat    8460
ccctggagta ggagagccag cctgcctcct gcgctggcac agagcccggt tccctagaca    8520
actgcctctc caaatctgat gtccagcgcc acctggtgtc cacatcaagc agacacaatt    8580
aatagtcaac ctgttcagga aaactgtgag ggggaaaaaa aagaaagagg atttatgaag    8640
ggaaaagaaa gtttagagga tatgccacga ttggctagca gctgcttttt gcctgtactg    8700
ggtctctctg gttagaccag atctgagcct gggagctctc tggctaacta gggaacccac    8760
tgcttaagcc tcaataaagc ttgccttgag tgcttcatcc ggaatcaacc tctggattac    8820
aaaatttgtg aaagattgac tggtattctt aactatgttg ctccttttac gctatgtgga    8880
tacgctgctt taatgccttt gtatcatgct attgcttccc gtatggcttt cattttctcc    8940
tccttgtata aatcctggtt gctgtctctt tatgaggagt tgtggcccgt tgtcaggcaa    9000
cgtggcgtgg tgtgcactgt gtttgctgac gcaaccccca ctggttgggg cattgccacc    9060
acctgtcagc tcctttccgg gactttcgct ttccccctcc ctattgccac ggcggaactc    9120
atcgccgcct gccttgcccg ctgctggaca ggggctcggc tgttgggcac tgacaattcc    9180
gtggtgttgt cggggaagct gacgtccttt ccatggctgc tcgcctgtgt tgccacctgg    9240
attctgcgcg gacgtccttt ctgctacgtc ccttcggccc tcaatccagc ggaccttcct    9300
tcccgcggcc tgctgccggc tctgcggcct cttccgcgtc ttcgccttcg ccctcagacg    9360
agtcggatct ccctttgggc cgcctccccg cctgtccggt agcttgccag cctcgactgt    9420
gccttctagt tgccagccgt ctgttgtttg cccctcccc gtgccttcct tgaccctgga    9480
aggtgccact cccactgtcc tttcctaata aaatgaggaa attgcatcgc attgtctgag    9540
taggtgtcat tctattctgg ggggtggggt ggggcaggac agcaagggg aggattggga     9600 agacaatagc aggcatgcaa gcttggcgta atcatggtca tagctgtttc ctgtgtgaaa    9660
ttgttatccg ctcacaattc cacacaacat acgagccgga agcataaagt gtaaagcctg    9720
gggtgcctaa tgagtgagct aactcacatt aattgcgttg cgctcactgc ccgctttcca    9780
```

```
gtcgggaaac ctgtcgtgcc agctgcatta atgaatcggc caacgcgcgg ggagaggcgg    9840
tttgcgtatt gggcgctctt ccgcttcctc gctcactgac tcgctgcgct cggtcgttcg    9900
gctgcggcga gcggtatcag ctcactcaaa ggcggtaata cggttatcca cagaatcagg    9960
ggataacgca ggaaagaaca tgtgagcaaa aggccagcaa aaggccagga accgtaaaaa   10020
ggccgcgttg ctggcgtttt tccataggct ccgcccccct gacgagcatc acaaaaatcg   10080
acgctcaagt cagaggtggc gaaacccgac aggactataa agataccagg cgtttccccc   10140
tggaagctcc ctcgtgcgct ctcctgttcc gaccctgccg cttaccggat acctgtccgc   10200
ctttctccct tcgggaagcg tggcgctttc tcatagctca cgctgtaggt atctcagttc   10260
ggtgtaggtc gttcgctcca agctgggctg tgtgcacgaa ccccccgttc agcccgaccg   10320
ctgcgcctta tccggtaact atcgtcttga gtccaacccg gtaagacacg acttatcgcc   10380
actggcagca gccactggta acaggattag cagagcgagg tatgtaggcg gtgctacaga   10440
gttcttgaag tggtggccta actacggcta cactagaaga acagtatttg gtatctgcgc   10500
tctgctgaag ccagttacct tcggaaaaag agttggtagc tcttgatccg gcaaacaaac   10560
caccgctggt agcggtggtt tttttgtttg caagcagcag attacgcgca gaaaaaaagg   10620
atctcaagaa gatcctttga tcttttctac ggggtctgac gctcagtgga acgaaaactc   10680
acgttaaggg attttggtca tgagattatc aaaaaggatc ttcacctaga tccttttaaa   10740
ttaaaaatga agttttaaat caatctaaag tatatatgag taaacttggt ctgacagtta   10800
ccaatgctta atcagtgagg cacctatctc agcgatctgt ctatttcgtt catccatagt   10860
tgcctgactc cccgtcgtgt agataactac gatacgggag gcttaccatc tggccccag   10920
tgctgcaatg ataccgcgag acccacgctc accggctcca gatttatcag caataaacca   10980
gccagccgga agggccgagc gcagaagtgg tcctgcaact ttatccgcct ccatccagtc   11040
tattaattgt tgccgggaag ctagagtaag tagttcgcca gttaatagtt tgcgcaacgt   11100
tgttgccatt gctacaggca tcgtggtgtc acgctcgtcg tttggtatgg cttcattcag   11160
ctccggttcc caacgatcaa ggcgagttac atgatccccc atgttgtgca aaaaagcggt   11220
tagctccttc ggtcctccga tcgttgtcag aagtaagttg gccgcagtgt tatcactcat   11280
ggttatggca gcactgcata attctcttac tgtcatgcca tccgtaagat gcttttctgt   11340
gactggtgag tactcaacca agtcattctg agaatagtgt atgcggcgac cgagttgctc   11400
ttgcccggcg tcaatacggg ataataccgc gccacatagc agaactttaa aagtgctcat   11460
cattggaaaa cgttcttcgg ggcaaaactc tcaaggatct taccgctgtt gagatccagt   11520
tcgatgtaac ccactcgtgc acccaactga tcttcagcat cttttacttt caccagcgtt   11580
tctgggtgag caaaaacagg aaggcaaaat gccgcaaaaa agggaataag ggcgacacgg   11640
aaatgttgaa tactcatact cttcctttt caatattatt gaagcattta tcagggttat   11700
tgtctcatga gcggatacat atttgaatgt atttagaaaa ataaacaaat aggggttccg   11760
cgcacatttc cccgaaaagt gccacctgac gtctaagaaa ccattattat catgacatta   11820
acctataaaa ataggcgtat cacgaggccc tttcgtctcg cgcgtttcgg tgatgacggt   11880
gaaaacctct gacacatgca gctcccggag acggtcacag cttgtctgta agcggatgcc   11940
gggagcagac aagcccgtca gggcgcgtca gcgggtgttg gcgggtgtcg ggctggctt   12000
aactatgcgg catcagagca gattgtactg agagtgcacc                         12040
```

<210> SEQ ID NO 39
<211> LENGTH: 11438

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 39

```
attggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact tccattgac gtcaatgggt ggagtattta cggtaaactg      300
cccacttggc agtacatcaa gtgtatcata tgccaagtac gccccctatt gacgtcaatg     360
acggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg gaggtctat ataagcagag      660
ctcgtttagt gaaccggggt ctctctggtt agaccagatc tgagcctggg agctctctgg     720
ctaactagga acccactgc ttaagcctca ataaagcttg ccttgagtgc ttcaagtagt      780
gtgtgcccgt ctgttgtgtg actctggtaa ctagagatcc ctcagaccct tttagtcagt     840
gtggaaaatc tctagcagtg gcgcccgaac agggacttga aagcgaaagg gaaaccagag     900
gagctctctc gacgcaggac tcggcttgct gaagcgcgca cggcaagagg cgaggggcgg     960
cgactggtga gtacgccaaa aattttgact agcggaggct agaaggagag agacgggtgc    1020
gagagcgtca gtattaagcg ggggtgaata agatcgcgat gggaaaaaat tcggttaagg    1080
ccaggggaa agaaaaaata taaattaaaa catatagtat gggcaagcag ggagctagaa      1140
cgattcgcag ttaatcctgg cctgttagaa acatcagaag gctgtagaca atactggga     1200
cagctacaac catcccttca gacaggatca gaagaactta gatcattata taatacagta    1260
gcaaccctct attgtgtgca tcaaaggata gagataaaag acaccaagga agctttagac    1320
aagatagagg aagagcaaaa caaaagtaag accaccgcac agcaagcggc cgctgatctt    1380
cagacctgga ggaggagata tgagggacaa ttggagaagt gaattatata aatataaagt    1440
agtaaaaatt gaaccattag gagtagcacc caccaaggca aagagaagag tggtgcagag    1500
agaaaaaaga gcagtgggaa taggagcttt gttccttggg ttcttgggag cagcaggaag    1560
cactatgggc gcagcgtcaa tgacgctgac ggtacaggcc agacaattat tgtctggtat    1620
agtgcagcag cagaacaatt tgctgagggc tattgaggcg caacagcatc tgttgcaact    1680
cacagtctgg ggcatcaagc agctccaggc aagaatcctg ctgtggaaa gatacctaaa     1740
ggatcaacag ctcctgggga tttggggttg ctctggaaaa ctcatttgca ccactgctgt    1800
gccttggaat gctagttgga gtaataaatc tctggaacag atttggaatc acacgacctg    1860
gatggagtgg gacagagaaa ttaacaatta cacaagctta atacactcct taattgaaga    1920
atcgcaaaac cagcaagaaa agaatgaaca agaattattg gaattagata aatgggcaag    1980
tttgtggaat tggtttaaca taacaaattg gctgtggtat ataaaattat tcataatgat    2040
agtaggaggc ttggtaggtt taagaatagt ttttgctgta ctttctatag tgaatagagt    2100
taggcaggga tattcaccat tatcgtttca gacccacctc ccaaccccga ggggacccga    2160
```

```
caggcccgaa ggaatagaag aagaaggtgg agagagagac agagacagat ccattcgatt    2220
agtgaacgga tctcgacggt atcgttttaa aagaaaaggg gggattgggg ggtacagtgc    2280 agggggaaaga atagtagaca taatagcaac agacatacaa actaaagaat tacaaaaaca   2340
aattacaaaa attcaaaatt ttatcggcgt gttgggggtg gaccatcctc taggtattga    2400
ataagaaaaa tgaagttaag gtggttgatg gtaacactat gctaataact gcagagccag    2460
aagcaccata agggacatga taagggagcc agcagacctc tgatctcttc ctgaatgcta    2520
atcttaaaca tcctgaggaa gaatgggact tccatttggg gtgggcctat gatagggtaa    2580
taagacagta gtgaatatca agctacaaaa agccccttt caaattcttc tcagtcctaa     2640
cttttcatac taagcccagt ccttccaaag cagactgtga aagagtgata gttccgggag    2700
actagcactg cagattccgg gtcactgtga gtggggagg cagggaagaa gggctcacag     2760
gacagtcaaa ccatgccccc tgttttttcct tcttcaagta gacctctata agacaacaga   2820
gacaactaag gctgagtggc caggcgagga gaaaccatct cgccgtaaaa catggaagga    2880
acacttcagg ggaaaggtgg tatctctaag caagagaact gagtggagtc aaggctgaga    2940
gatgcaggat aagcaaatgg gtagtgaaaa gacattcatg aggacagcta aaacaataag    3000
taatgtaaaa tacagcatag caaaacttta acctccaaat caagcctcta cttgaatcct    3060
tttctgaggg atgaataagg cataggcatc aggggctgtt gccaatgtgc attagctgtt    3120
tgcagcctca ccttctttca tggagtttaa gatatagtgt atttttcccaa ggtttgaact   3180 agctcttcat ttctttatgt tttaaatgca ctgacctccc acattccctt tttagtaaaa    3240
tattcagaaa taatttaaat acatcattgc aatgaaaata aatgtttttt attaggcaga    3300
atccagatgc tcaaggccct tcataatatc ccccagttta gtagttggac ttagggaaca    3360
aaggaacctt taatagaaat tggacagcaa gaaagcgagc ttagtgatac ttgtgggcca    3420
gggcattagc cacaccagcc accactttct gataggcagc ctgcactggt ggggtgaatt    3480 cttttgccaaa gtgatgggcc agcacacaga ccagcacgtt gcccaggagc tgtgggagga    3540
agataagagg tatgaacatg attagcaaaa gggcctagct tggactcaga ataatccagc    3600
cttatcccaa ccataaaata aaagcagaat ggtagctgga ttgtagctgc tattagcaat    3660
atgaaacctc ttacatcagt tacaatttat atgcagaaat atttatatgc agaaatattg    3720
ctattgcctt aacccagaaa ttatcactgt tattctttag aatggtgcaa agaggcatga    3780
tacattgtat cattattgcc ctgaaagaaa gagattaggg aaagtattag aaataagata    3840
aacaaaaaag tatattaaaa gaagaaagca ttttttaaaa ttacaaatgc aaaattaccc    3900
tgatttggtc aatatgtgta ccctgttact tctcccttc ctatgacatg aacttaacca     3960
tagaaaagaa gggaaagaa aacatcaagg gtcccataga ctcaccctga agttctcagg     4020
atccacgtgc agcttgtcac agtgcagctc actcagctgg gcaaaggtgc ccttgaggtt    4080
gtccaggtga gccaggccat cactaaaggc accgagcact ttcttgccat gagccttcac    4140
cttagggttg cccataacag catcaggagt ggacagatcc ccaaaggact caaagaacct    4200
ctgggtccaa gggtagacca ccagcagcct aagggtggga aaatagacca ataggcagag    4260
agagtcagtg cctatcagaa acccaagagt cttctctgtc tccacatgcc cagtttctat    4320
tggtctcctt aaacctgtct tgtaaccttg ataccaacct gcccagggcc tcaccaccaa    4380
cttcatccac gttcaccttg ccccacaggg cagtaacggc agacttctcc tcaggagtca    4440
ggtgcaccat ggtgtctgtt tgaggttgct agtgaacaca gttgtgtcag aagcaaatgt    4500
```

```
aagcaataga tggctctgcc ctgactttta tgcccagccc tggctcctgc cctccctgct   4560
cctgggagta gattggccaa ccctagggtg tggctccaca gggtgaggtc taagtgatga   4620
cagccgtacc tgtccttggc tcttctggca ctggcttagg agttggactt caaaccctca   4680
gccctccctc taagatatat ctcttggccc cataccatca gtacaaattg ctactaaaaa   4740
catcctcctt tgcaagtgta tttactctag aatatgtcac attctgtctc aggcatccat   4800
tttcttttatg atgccgtttg aggtggagtt ttagtcaggt ggtcagcttc tcctttttttt   4860
tgccatctgc cctgtaagca tcctgctggg gacccagata ggagtcatca ctctaggctg   4920
agaacatctg ggcacacacc ctaagcctca gcatgactca tcatgactca gcattgctgt   4980
gcttgagcca gaaggtttgc ttagaaggtt acacagaacc agaaggcggg ggtggggcac   5040
tgaccccgac aggggcctgg ccagaactgc tcatgcttgg actatgggag gtcactaatg   5100
gagacacaca gaaatgtaac aggaactaag gaaaaactga agcttattta atcagagatg   5160
agatgctgga agggatagag ggagctgagc ttgtaaaaag tatagtaatc attcagcaaa   5220
tggttttgaa gcacctgctg gatgctaaac actattttca gtgcttgaat cataaataag   5280
aacaaaacat gtatcttatt ccccacaaga gtccaagtaa aaaataacag ttaattataa   5340
tgtgctctgt cccccaggct ggagtgcagt ggcacgatct cagctcactg caacctccgc   5400
ctcccgggtt caagcaattc tcctgcctca gccaccctaa tagctgggat tacaggtgca   5460
caccaccatg ccaggctaat ttttgtactt tttgtagagg cagggtatca ccatgttgtc   5520
caagatggtc ttgaactcct gagctccaag cagtccaccc acctcagcct cccaaagtgc   5580
tatctgcggc cgcctatctg taccactagt ctcgagaagc tttcatcaaa aaagtctaa    5640
ccagctgcat tcgactttga ctgcagcagc tggttagaag gttctactgg aggagggtcc   5700
cagcccattg ctaaattaac atcaggctct gagactggca gtatatctct aacagtggtt   5760
gatgctatct tctggaactt gcctgctaca ttgagaccac tgacccatac ataggaagcc   5820
catagctctg tcctgaactg ttaggccact ggtccagaga gtgtgcatct cctttgatcc   5880
tcataataac cctatgagat agacacaatt attactctta ctttatagat gatgatcctg   5940
aaaacatagg agtcaaggca cttgccccta gctgggggta taggggagca gtcccatgta   6000
gtagtagaat gaaaaatgct gctatgctgt gcctcccccca cctttcccat gtctgccctc   6060
tactcatggt ctatctctcc tggctcctgg gagtcatgga ctccacccag caccaccaac   6120
ctgacctaac cacctatctg agcctgccag cctataaccc atctgggccc tgatagctgg   6180
tggccagccc tgaccccacc ccaccctccc tggaacctct gatagacaca tctggcacac   6240
cagctcgcaa agtcaccgtg agggtcttgt gtttgctgag tcaaaattcc ttgaaatcca   6300
agtccttaga gactcctgct cccaaattta cagtcataga cttcttcatg gctgtctcct   6360
ttatccacag aatgattcct ttgcttcatt gccccatcca tctgatcctc ctcatcagtg   6420
cagcacaggg cccatgagca gtagctgcag agtctcacat aggtctggca ctgcctctga   6480
catgtccgac cttaggcaaa tgcttgactc ttctgagctc agtcttgtca tggcaaaaca   6540
aagataataa tagtgttttt ttatggagtt agcgtgagga tggaaaacaa tagcaaaatt   6600
gattagacta taaaggtct caacaaatag tagtagattt tatcatccat taatccttcc    6660
ctctcctctc ttactcatcc catcacgtat gcctcttaat tttcccttac ctataataag   6720
agttattcct cttattatat tcttcttata gtgattctgg atatcaaagt gggaatgagg   6780
ggcaggccac taacgaagaa gatgtttctc aaagaagcca ttctccccac atagatcatc   6840
tcagcagggt tcaggaagat aaaggaggat caaggtcgaa ggtaggaact aaggaagaac   6900
```

```
actgggcaag tggatcctaa atatatcatt taaatgcata aataagcaaa ccctgctcgg    6960
gaatgggagg gagagtctct ggagtccacc ccttctcggc cctggctctg cagatagtgc    7020
tatcaaagcc ctgacagagc cctgcccatt gctgggcctt ggagtgagtc agcctagtag    7080
agaggcaggg caagccatct catagctgct gagtgggaga gagaaaaggg ctcattgtct    7140
ataaactcag gtcatggcta ttcttattct cacactaaga aaagaatga gatgtctaca    7200 tataccctgc gtcccctctt gtgtactggg gcccccaaga gctctctaaa agtgatggca    7260
aagtcattgc gctagatgcc atcccatcta ttataaacct gcatttgtct ccacacacca    7320
gtcatggaca ataaccctcc tcccaggtcc acgtgcttgt ctttgtataa tactcaagta    7380
atttcggaaa atgtattctt tcaatcttgt tctgttattc ctgtttcaat ggcttagtag    7440
aaaaagtaca tacttgtttt cccataaatt gacaatagac aatttcacat caatgtctat    7500
atgggtcgtt gtgtttgctg tgtttgcaaa aactcacaat aactttatat tgttactact    7560
ctaagaaagt tacaacatgg tgaatacaag agaaagctat tacaagtcca gaaaacaaaa    7620
gttatcatct tgaggcctca gctttctagg aataatatca atattacaaa acgcgtcgac    7680
ggtaccgtta acgatcttag ccactttta aagaaaagg ggggactgga agggctaatt    7740
cactcccaac gaagacaaga tatcctgcta gtccttcctt tctaaatgac gagagagaca    7800
gaagaattct tcaaggttag tgtgtccagc atgcaacctt tccttcctgg atgagcatcc    7860
ctggagtagg agagccagcc tgcctcctgc gctggcacag agcccggttc cctagacaac    7920
tgcctctcca aatctgatgt ccagcgccac ctggtgtcca catcaagcag acacaattaa    7980
tagtcaacct gttcaggaaa actgtgaggg ggaaaaaaaa gaaagaggat ttatgaaggg    8040
aaaagaaagt ttagaggata tgccacgatt ggctagcagc tgcttttgc ctgtactggg    8100 tctctctggt tagaccagat ctgagcctgg gagctctctg gctaactagg gaacccactg    8160
cttaagcctc aataaagctt gccttgagtg cttcatccgg aatcaacctc tggattacaa    8220
aatttgtgaa agattgactg gtattcttaa ctatgttgct cctttacgc tatgtggata    8280 cgctgcttta atgcctttgt atcatgctat tgcttcccgt atggctttca ttttctcctc    8340
cttgtataaa tcctggttgc tgtctcttta tgaggagttg tggcccgttg tcaggcaacg    8400
tggcgtggtg tgcactgtgt ttgctgacgc aaccccact ggttgggca ttgccaccac    8460 ctgtcagctc ctttccggga cttttcgcttt ccccctccct attgccacgg cggaactcat    8520
cgccgcctgc cttgcccgct gctggacagg ggctcggctg ttgggcactg acaattccgt    8580
ggtgttgtcg gggaagctga cgtccttcc atggctgctc gcctgtgttg ccacctggat    8640
tctgcgcggg acgtccttct gctacgtccc ttcggccctc aatccagcgg accttccttc    8700
ccgcggcctg ctgccggctc tcggcctct tccgcgtctt cgccttcgcc ctcagacgag    8760
tcggatctcc ctttgggccg cctccccgcc tgtccggtag cttgccagcc tcgactgtgc    8820
cttctagttg ccagccgtct gttgtttgcc cctccccgt gccttccttg accctggaag    8880
gtgccactcc cactgtcctt tcctaataaa atgaggaaat tgcatcgcat tgtctgagta    8940
ggtgtcattc tattctgggg ggtggggtgg ggcaggacag caaggggag gattgggaag    9000 acaatagcag gcatgcaagc ttggcgtaat catggtcata gctgtttcct gtgtgaaatt    9060
gttatccgct cacaattcca cacaacatac gagccggaag cataaagtgt aaagcctggg    9120
gtgcctaatg agtgagctaa ctcacattaa ttgcgttgcg ctcactgccc gctttccagt    9180
cgggaaacct gtcgtgccag ctgcattaat gaatcggcca acgcgcgggg agaggcggtt    9240
```

```
tgcgtattgg gcgctcttcc gcttcctcgc tcactgactc gctgcgctcg gtcgttcggc    9300
tgcggcgagc ggtatcagct cactcaaagg cggtaatacg gttatccaca gaatcagggg    9360
ataacgcagg aaagaacatg tgagcaaaag gccagcaaaa ggccaggaac cgtaaaaagg    9420
ccgcgttgct ggcgttttc cataggctcc gcccccctga cgagcatcac aaaaatcgac     9480
gctcaagtca gaggtggcga acccgacag gactataaag ataccaggcg tttccccctg     9540
gaagctccct cgtgcgctct cctgttccga cctgccgct taccggatac ctgtccgcct     9600
ttctcccttc gggaagcgtg gcgctttctc atagctcacg ctgtaggtat ctcagttcgg    9660
tgtaggtcgt tcgctccaag ctgggctgtg tgcacgaacc ccccgttcag cccgaccgct    9720
gcgccttatc cggtaactat cgtcttgagt ccaacccggt aagacacgac ttatcgccac    9780
tggcagcagc cactggtaac aggattagca gagcgaggta tgtaggcggt gctacagagt    9840
tcttgaagtg gtggcctaac tacggctaca ctagaagaac agtatttggt atctgcgctc    9900
tgctgaagcc agttaccttc ggaaaaagag ttggtagctc ttgatccggc aaacaaacca    9960
ccgctggtag cggtggtttt tttgtttgca agcagcagat tacgcgcaga aaaaaggat    10020 ctcaagaaga tcctttgatc ttttctacgg ggtctgacgc tcagtggaac gaaaactcac    10080
gttaagggat tttggtcatg agattatcaa aaaggatctt cacctagatc cttttaaatt    10140
aaaaatgaag ttttaaatca atctaaagta tatatgagta aacttggtct gacagttacc    10200
aatgcttaat cagtgaggca cctatctcag cgatctgtct atttcgttca tccatagttg    10260
cctgactccc cgtcgtgtag ataactacga tacgggaggg cttaccatct ggccccagtg    10320
ctgcaatgat accgcgagac ccacgctcac cggctccaga tttatcagca ataaaccagc    10380
cagccggaag ggccgagcgc agaagtggtc ctgcaacttt atccgcctcc atccagtcta    10440
ttaattgttg ccgggaagct agagtaagta gttcgccagt taatagtttg cgcaacgttg    10500
ttgccattgc tacaggcatc gtggtgtcac gctcgtcgtt tggtatggct tcattcagct    10560
ccggttccca acgatcaagg cgagttacat gatccccat gttgtgcaaa aaagcggtta    10620
gctccttcgg tcctccgatc gttgtcagaa gtaagttggc cgcagtgtta tcactcatgg    10680
ttatggcagc actgcataat tctcttactg tcatgccatc cgtaagatgc ttttctgtga    10740
ctggtgagta ctcaaccaag tcattctgag aatagtgtat gcggcgaccg agttgctctt    10800
gcccggcgtc aatacgggat aataccgcgc cacatagcag aactttaaaa gtgctcatca    10860
ttggaaaacg ttcttcgggg caaaactctc aaggatctta ccgctgttga tccagttc     10920 gatgtaaccc actcgtgcac ccaactgatc ttcagcatct tttactttca ccagcgtttc    10980
tgggtgagca aaaacaggaa ggcaaaatgc cgcaaaaaag gaataagggc gacacggaa    11040 atgttgaata ctcatactct tccttttca atattattga gcatttatc agggttattg    11100 tctcatgagc ggatacatat ttgaatgtat ttagaaaaat aaacaaatag gggttccgcg    11160
cacatttccc cgaaaagtgc cacctgacgt ctaagaaacc attattatca tgacattaac    11220
ctataaaaat aggcgtatca cgaggccctt tcgtctcgcg cgtttcggtg atgacggtga    11280
aaacctctga cacatgcagc tcccggagac ggtcacagct tgtctgtaag cggatgccgg    11340
gagcagacaa gcccgtcagg gcgcgtcagc gggtgttggc gggtgtcggg gctggcttaa    11400
ctatgcggca tcagagcaga ttgtactgag agtgcacc                           11438
```

<210> SEQ ID NO 40
<211> LENGTH: 11342
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
attggccatt gcatacgttg tatccatatc ataatatgta catttatatt ggctcatgtc      60
caacattacc gccatgttga cattgattat tgactagtta ttaatagtaa tcaattacgg     120
ggtcattagt tcatagccca tatatggagt tccgcgttac ataacttacg gtaaatggcc     180
cgcctggctg accgcccaac gacccccgcc cattgacgtc aataatgacg tatgttccca     240
tagtaacgcc aatagggact ttccattgac gtcaatgggt ggagtattta cggtaaactg     300
cccacttggc agtacatcaa gtgtatcata tgccaagtac gccccctatt gacgtcaatg     360
acggtaaatg gcccgcctgg cattatgccc agtacatgac cttatgggac tttcctactt     420
ggcagtacat ctacgtatta gtcatcgcta ttaccatggt gatgcggttt tggcagtaca     480
tcaatgggcg tggatagcgg tttgactcac ggggatttcc aagtctccac cccattgacg     540
tcaatgggag tttgttttgg caccaaaatc aacgggactt tccaaaatgt cgtaacaact     600
ccgccccatt gacgcaaatg ggcggtaggc gtgtacggtg ggaggtctat ataagcagag     660
ctcgtttagt gaaccgggt ctctctggtt agaccagatc tgagcctggg agctctctgg     720
ctaactaggg aacccactgc ttaagcctca ataaagcttg ccttgagtgc ttcaagtagt     780
gtgtgcccgt ctgttgtgtg actctggtaa ctagagatcc ctcagaccct tttagtcagt     840
gtggaaaatc tctagcagtg gcgcccgaac agggacttga agcgaaagg gaaaccagag      900
gagctctctc gacgcaggac tcggcttgct gaagcgcgca cggcaagagg cgaggggcgg     960
cgactggtga gtacgccaaa attttgact agcggaggct agaaggagag agacgggtgc    1020
gagagcgtca gtattaagcg ggggtgaata agatcgcgat gggaaaaaat tcggttaagg    1080
ccaggggga agaaaaaata taaattaaaa catatagtat gggcaagcag ggagctagaa    1140
cgattcgcag ttaatcctgg cctgttagaa acatcagaag gctgtagaca aatactggga    1200
cagctacaac catcccttca gacaggatca gaagaactta gatcattata taatacagta    1260
gcaaccctct attgtgtgca tcaaaggata gagataaaag acaccaagga agctttagac    1320
aagatagagg aagagcaaaa caaaagtaag accaccgcac agcaagcggc cgctgatctt    1380
cagacctgga ggaggagata tgagggacaa ttggagaagt gaattatata aatataaagt    1440
agtaaaaatt gaaccattag gagtagcacc caccaaggca agagaagag tggtgcagag    1500
agaaaaaaga gcagtgggaa taggagcttt gttccttggg ttcttgggag cagcaggaag    1560
cactatgggc gcagcgtcaa tgacgctgac ggtacaggcc agacaattat tgtctggtat    1620
agtgcagcag cagaacaatt tgctgagggc tattgaggcg caacagcatc tgttgcaact    1680
cacagtctgg ggcatcaagc agctccaggc aagaatcctg gctgtggaaa gatacctaaa    1740
ggatcaacag ctcctgggga tttgggttg ctctggaaaa ctcatttgca ccactgctgt    1800
gccttggaat gctagttgga gtaataaatc tctggaacag atttggaatc acacgacctg    1860
gatggagtgg gacagagaaa ttaacaatta cacaagctta atacactcct taattgaaga    1920
atcgcaaaac cagcaagaaa agaatgaaca agaattattg gaattagata atgggcaag    1980
tttgtggaat tggtttaaca taacaaattg gctgtggtat ataaaattat tcataatgat    2040
agtaggaggc ttggtaggtt taagaatagt ttttgctgta ctttctatag tgaatagagt    2100
taggcaggga tattcaccat tatcgtttca gacccacctc ccaaccccga ggggacccga    2160
caggcccgaa ggaatagaag aagaaggtgg agagagagac agagacagat ccattcgatt    2220
```

```
agtgaacgga tctcgacggt atcgttttaa aagaaaaggg gggattgggg ggtacagtgc   2280 agggaaaga atagtagaca taatagcaac agacatacaa actaaagaat tacaaaaaca    2340
aattacaaaa attcaaaatt ttatcggcgt gttggggggtg gaccatcctc taggtattga  2400
ataagaaaaa tgaagttaag gtggttgatg gtaacactat gctaataact gcagagccag   2460
aagcaccata agggacatga taagggagcc agcagacctc tgatctcttc ctgaatgcta   2520
atcttaaaca tcctgaggaa gaatgggact tccatttggg gtgggcctat gatagggtaa   2580
taagacagta gtgaatatca agctacaaaa agccccctttt caaattcttc tcagtcctaa  2640
cttttcatac taagcccagt ccttccaaag cagactgtga aagagtgata gttccgggag   2700
actagcactg cagattccgg gtcactgtga gtgggggagg cagggaagaa gggctcacag   2760
gacagtcaaa ccatgccccc tgttttttcct tcttcaagta gacctctata agacaacaga  2820
gacaactaag gctgagtggc caggcgagga gaaaccatct cgccgtaaaa catggaagga   2880
acacttcagg ggaaaggtgg tatctctaag caagagaact gagtggagtc aaggctgaga  2940
gatgcaggat aagcaaatgg gtagtgaaaa gacattcatg aggacagcta aaacaataag   3000
taatgtaaaa tacagcatag caaaacttta acctccaaat caagcctcta cttgaatcct   3060
tttctgaggg atgaataagg cataggcatc aggggctgtt gccaatgtgc attagctgtt   3120
tgcagcctca ccttctttca tggagtttaa gatatagtgt attttcccaa ggtttgaact   3180
agctcttcat ttcttatgt tttaaatgca ctgacctccc acattccctt tttagtaaaa    3240
tattcagaaa taatttaaat acatcattgc aatgaaaata aatgtttttt attaggcaga   3300
atccagatgc tcaaggccct tcataatatc ccccagttta gtagttggac ttagggaaca   3360
aaggaacctt taatagaaat tggacagcaa gaaagcgagc ttagtgatac ttgtgggcca   3420
gggcattagc cacaccagcc accactttct gataggcagc ctgcactggt ggggtgaatt   3480
ctttgccaaa gtgatgggcc agcacacaga ccagcacgtt gcccaggagc tgtgggagga   3540
agataagagg tatgaacatg attagcaaaa gggcctagct tggactcaga ataatccagc   3600
cttatcccaa ccataaaata aaagcagaat ggtagctgga ttgtagctgc tattagcaat   3660
atgaaacctc ttacatcagt tacaatttat atgcagaaat atttatatgc agaaatattg   3720
ctattgcctt aacccagaaa ttatcactgt tattctttag aatggtgcaa agaggcatga   3780
tacattgtat cattattgcc ctgaaagaaa gagattaggg aaagtattag aaataagata   3840
aacaaaaaag tatattaaaa gaagaaagca tttttttaaaa ttacaaatgc aaaattaccc  3900
tgatttggtc aatatgtgta ccctgttact tctccccttc ctatgacatg aacttaacca   3960
tagaaaagaa ggggaaagaa aacatcaagg gtcccataga ctcaccctga agttctcagg   4020
atccacgtga agcttgtcac agtgcagctc actcagctgg gcaaaggtgc ccttgaggtt   4080
gtccaggtga gccaggccat cactaaaggc accgagcact ttcttgccat gagccttcac   4140 cttaggggttg cccataacag catcaggagt ggacagatcc ccaaaggact caaagaacct   4200
ctgggtccaa gggtagacca ccagcagcct aagggtggga aaatagacca ataggcagag   4260
agagtcagtg cctatcagaa acccaagagt cttctctgtc tccacatgcc cagtttctat   4320
tggtctcctt aaacctgtct tgtaaccttg ataccaacct gcccagggcc tcaccaccaa   4380
cttcatccac gttcaccttg ccccacaggg cagtaacggc agacttctcc tcaggagtca   4440
ggtgcaccat ggtgtctgtt tgaggttgct agtgaacaca gttgtgtcag aagcaaatgt   4500
aagcaataga tggctctgcc ctgacttta tgcccagccc tggctcctgc cctccctgct    4560
```

```
cctgggagta gattggccaa ccctagggtg tggctccaca gggtgaggtc taagtgatga   4620
cagccgtacc tgtccttggc tcttctggca ctggcttagg agttggactt caaaccctca   4680
gccctccctc taagatatat ctcttggccc cataccatca gtacaaattg ctactaaaaa   4740
catcctcctt tgcaagtgta tttacggcat ctgtgaagga agaaacatc tcctctaaac    4800
cactatgctg ctagagcctc ttttctgtac tcaagcctca ttcagacact agtgtcacca   4860
gtctcctcat atacctattg tatttcttc ttccttgctgg tttagtcatg ttttctggga   4920
gcttagggc ttattttatt ttgttttgtt ttctaatcaa cagagatggg caaacccatt    4980
atttttttct ttagacttgg gatggtgata gctgggcagc gtcagaaact gtgtgtggat   5040
atagataaga gctcggacta tgctgagctg tgatgaggga gggacctagc caaaggcagt   5100
gagagtcaga atgctcctgc tattgccttc tcagtcccca cgcttggttt ctacacaagt   5160
agatacatag aaaaggctat aggttagtgt ttgagagtcc tgcatgagtt agttgctcag   5220
aaatgcccga taaatatgtt atgtgtgttt atgtatatat atgttttata tatatatg     5280
tgtgtgtgtg tgtgtgtgtg tgttgtgttt acaaatatgt gattatcatc aaaacgtgag   5340
ggctaaagtg accagataac ttgcaggtct agacaccctt ttccggcacg cagatagtca   5400
atatcttcag cgtccccaag gcctgcaagg gtggggcccc atatctggaa gtcccaggcg   5460
gagctgggag ttggtcaagt ctgggctgtg ggggcaggga gtgctggggg atggctcgag   5520
aagctttcat caaaaaaagt ctaaccagct gcattcgact ttgactgcag cagctggtta   5580
gaaggttcta ctggaggagg gtcccagccc attgctaaat taacatcagg ctctgagact   5640
ggcagtatat ctctaacagt ggttgatgct atcttctgga acttgcctgc tacattgaga   5700
ccactgaccc atacatagga agcccatagc tctgtcctga actgttaggc cactggtcca   5760
gagagtgtgc atctcctttg atcctcataa taacccctatg agatagacac aattattact   5820
cttactttat agatgatgat cctgaaaaca taggagtcaa ggcacttgcc cctagctggg   5880
ggtataggg agcagtccca tgtagtagta gaatgaaaaa tgctgctatg ctgtgcctcc    5940
cccacctttc ccatgtctgc cctctactca tggtctatct ctcctggctc ctgggagtca   6000
tggactccac ccagcaccac caacctgacc taaccaccta tctgagcctg ccagcctata   6060
acccatctgg gccctgatag ctggtggcca gccctgaccc caccccaccc tccctggaac   6120
ctctgataga cacatctggc acaccagctc gcaaagtcac cgtgagggtc ttgtgtttgc   6180
tgagtcaaaa ttccttgaaa tccaagtcct tagagactcc tgctcccaaa tttacagtca   6240
tagacttctt catggctgtc tccttatcc acagaatgat tcctttgctt cattgcccca    6300
tccatctgat cctcctcatc agtgcagcac agggcccatg agcagtagct gcagagtctc   6360
acataggtct ggcactgcct ctgacatgtc cgacccttagg caaatgcttg actcttctga   6420
gctcagtctt gtcatggcaa aacaaagata ataatagtgt ttttttatgg agttagcgtg   6480
aggatggaaa acaatagcaa aattgattag actataaaag gtctcaacaa atagtagtag   6540
attttatcat ccattaatcc ttccctctcc tctcttactc atcccatcac gtatgcctct   6600
taattttccc ttacctataa taagagttat tcctcttatt atattcttct tatagtgatt   6660
ctggatatca aagtgggaat gaggggcagg ccactaacga agaagatgtt tctcaaagaa   6720
gccattctcc ccacatagat catctcagca gggttcagga agataaagga ggatcaaggt   6780
cgaaggtagg aactaaggaa gaacactggg caagtggatc ctaaatatat catttaaatg   6840
cataaataag caaaccctgc tcgggaatgg gagggagagt ctctggagtc cacccccttct  6900
cggccctggc tctgcagata gtgctatcaa agccctgaca gagccctgcc cattgctggg   6960
```

```
ccttggagtg agtcagccta gtagagaggc agggcaagcc atctcatagc tgctgagtgg    7020
gagagagaaa agggctcatt gtctataaac tcaggtcatg gctattctta ttctcacact    7080
aagaaaaaga atgagatgtc tacatatacc ctgcgtcccc tcttgtgtac tggggccccc    7140
aagagctctc taaaagtgat ggcaaagtca ttgcgctaga tgccatccca tctattataa    7200
acctgcattt gtctccacac accagtcatg gacaataacc ctcctcccag gtccacgtgc    7260
ttgtctttgt ataatactca agtaatttcg gaaaatgtat tctttcaatc ttgttctgtt    7320
attcctgttt caatggctta gtagaaaaag tacatacttg ttttcccata aattgacaat    7380
agacaatttc acatcaatgt ctatatgggt cgttgtgttt gctgtgtttg caaaaactca    7440
caataacttt atattgttac tactctaaga aagttacaac atggtgaata caagagaaag    7500
ctattacaag tccagaaaac aaaagttatc atcttgaggc ctcagctttc taggaataat    7560
atcaatatta caaaacgcgt cgacggtacc gttaacgatc ttagccactt tttaaaagaa    7620
aaggggggac tggaagggct aattcactcc caacgaagac aagatatcct gctagtcctt    7680
cctttctaaa tgacgagaga gacagaagaa ttcttcaagg ttagtgtgtc cagcatgcaa    7740
cctttccttc ctggatgagc atccctggag taggagagcc agcctgcctc ctgcgctggc    7800
acagagcccg gttccctaga caactgcctc tccaaatctg atgtccagcg ccacctggtg    7860
tccacatcaa gcagacacaa ttaatagtca acctgttcag gaaaactgtg aggggggaaaa    7920 aaaagaaaga ggatttatga agggaaaaga aagtttagag gatatgccac gattggctag    7980
cagctgcttt ttgcctgtac tgggtctctc tggttagacc agatctgagc ctgggagctc    8040
tctggctaac tagggaaccc actgcttaag cctcaataaa gcttgccttg agtgcttcat    8100
ccggaatcaa cctctggatt acaaaatttg tgaaagattg actggtattc ttaactatgt    8160
tgctcctttt acgctatgtg gatacgctgc tttaatgcct ttgtatcatg ctattgcttc    8220
ccgtatggct ttcattttct cctccttgta taaatcctgg ttgctgtctc tttatgagga    8280
gttgtggccc gttgtcaggc aacgtggcgt ggtgtgcact gtgtttgctg acgcaacccc    8340
cactggttgg ggcattgcca ccacctgtca gctcctttcc gggactttcg ctttccccct    8400
ccctattgcc acggcggaac tcatcgccgc ctgccttgcc cgctgctgga caggggctcg    8460
gctgttgggc actgacaatt ccgtggtgtt gtcggggaag ctgacgtcct ttccatggct    8520
gctcgcctgt gttgccacct ggattctgcg cgggacgtcc ttctgctacg tcccttcggc    8580
cctcaatcca gcggaccttc cttcccgcgg cctgctgccg gctctgcggc ctcttccgcg    8640
tcttcgcctt cgccctcaga cgagtcggat ctccctttgg gccgcctccc cgcctgtccg    8700
gtagcttgcc agcctcgact gtgccttcta gttgccagcc gtctgttgtt gccccctccc    8760
ccgtgccttc cttgaccctg gaaggtgcca ctcccactgt cctttcctaa taaaatgagg    8820
aaattgcatc gcattgtctg agtaggtgtc attctattct ggggggtggg gtggggcagg    8880
acagcaaggg ggaggattgg gaagacaata gcaggcatgc aagcttggcg taatcatggt    8940
catagctgtt tcctgtgtga aattgttatc cgctcacaat tccacacaac atacgagccg    9000
gaagcataaa gtgtaaagcc tggggtgcct aatgagtgag ctaactcaca ttaattgcgt    9060
tgcgctcact gcccgctttc cagtcgggaa acctgtcgtg ccagctgcat taatgaatcg    9120
gccaacgcgc ggggagaggc ggtttgcgta ttgggcgctc ttccgcttcc tcgctcactg    9180
actcgctgcg ctcggtcgtt cggctgcggc gagcggtatc agctcactca aaggcggtaa    9240
tacggttatc cacagaatca ggggataacg caggaaagaa catgtgagca aaaggccagc    9300
```

```
aaaaggccag gaaccgtaaa aaggccgcgt tgctggcgtt tttccatagg ctccgcccccc    9360
ctgacgagca tcacaaaaat cgacgctcaa gtcagaggtg gcgaaacccg acaggactat    9420
aaagatacca ggcgtttccc cctggaagct ccctcgtgcg ctctcctgtt ccgaccctgc    9480
cgcttaccgg atacctgtcc gcctttctcc cttcgggaag cgtggcgctt tctcatagct    9540
cacgctgtag gtatctcagt tcggtgtagg tcgttcgctc caagctgggc tgtgtgcacg    9600
aaccccccgt tcagcccgac cgctgcgcct tatccggtaa ctatcgtctt gagtccaacc    9660
cggtaagaca cgacttatcg ccactggcag cagccactgg taacaggatt agcagagcga    9720
ggtatgtagg cggtgctaca gagttcttga agtggtggcc taactacggc tacactagaa    9780
gaacagtatt tggtatctgc gctctgctga agccagttac cttcggaaaa agagttggta    9840
gctcttgatc cggcaaacaa accaccgctg gtagcggtgg tttttttgtt tgcaagcagc    9900
agattacgcg cagaaaaaaa ggatctcaag aagatccttt gatcttttct acggggtctg    9960
acgctcagtg gaacgaaaac tcacgttaag ggattttggt catgagatta tcaaaaagga   10020
tcttcaccta gatcctttta aattaaaaat gaagttttaa atcaatctaa agtatatatg   10080
agtaaacttg gtctgacagt taccaatgct taatcagtga ggcacctatc tcagcgatct   10140
gtctatttcg ttcatccata gttgcctgac tccccgtcgt gtagataact acgatacggg   10200
agggcttacc atctggcccc agtgctgcaa tgataccgcg agacccacgc tcaccggctc   10260
cagatttatc agcaataaac cagccagccg aagggccga gcgcagaagt ggtcctgcaa   10320
ctttatccgc ctccatccag tctattaatt gttgccggga agctagagta agtagttcgc   10380
cagttaatag tttgcgcaac gttgttgcca ttgctacagg catcgtggtg tcacgctcgt   10440
cgtttggtat ggcttcattc agctccggtt cccaacgatc aaggcgagtt acatgatccc   10500
ccatgttgtg caaaaaagcg gttagctcct tcggtcctcc gatcgttgtc agaagtaagt   10560
tggccgcagt gttatcactc atggttatgg cagcactgca taattctctt actgtcatgc   10620
catccgtaag atgcttttct gtgactggtg agtactcaac caagtcattc tgagaatagt   10680
gtatgcggcg accgagttgc tcttgcccgg cgtcaatacg ggataatacc gcgccacata   10740
gcagaacttt aaaagtgctc atcattggaa aacgttcttc ggggcaaaac tctcaaggat   10800
cttaccgctg ttgagatcca gttcgatgta acccactcgt gcacccaact gatcttcagc   10860
atcttttact tcaccagcg tttctgggtg agcaaaaaca ggaaggcaaa atgccgcaaa   10920
aaagggaata agggcgacac ggaaatgttg aatactcata ctcttccttt ttcaatatta   10980
ttgaagcatt tatcagggtt attgtctcat gagcggatac atatttgaat gtatttagaa   11040
aaataaacaa atagggggttc cgcgcacatt tccccgaaaa gtgccacctg acgtctaaga   11100
aaccattatt atcatgacat taacctataa aaataggcgt atcacgaggc ctttcgtct   11160
cgcgcgtttc ggtgatgacg gtgaaaacct ctgacacatg cagctcccgg agacggtcac   11220
agcttgtctg taagcggatg ccgggagcag acaagcccgt cagggcgcgt cagcgggtgt   11280
tggcgggtgt cggggctggc ttaactatgc ggcatcagag cagattgtac tgagagtgca   11340
cc                                                                  11342
```

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic probe

```
<400> SEQUENCE: 41
acagccttct gatgtttcta acaggccagg                                          30

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggagctagaa cgattcgcag tt                                                  22

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gttgtagctg tcccagtatt tgtc                                                24

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
tgctgaaaca ttcaccttcc atgcagt                                             27

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgaaacatac gttcccaaag agttt                                               25

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ctctccttct cagaaagtgt gcatat                                              26

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
```
tacgagggct atgctctccc tcacgc                                            26

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tcacccacac tgtgcccat                                                    19

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agccaggtcc agacgcag                                                     18

<210> SEQ ID NO 50
<211> LENGTH: 114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
tgagcccctt ttcctctaac tgaaagaagg aaaaaaaaaa tggaacccaa aatattctac       60
atagtttcca tgtcacagcc agggctgggc agtctcctgt tatttctttt aaaa            114

<210> SEQ ID NO 51
<211> LENGTH: 197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
tttaatctaa caattatgaa cagcaatgag ataatatgta caaagtaccc agacctatgt       60
ggtagagcat caaggaagcg cattgcggag cagttttttg tttgtttgtt tttgtattct      120
gtttcgtgag gcaaggtttc actctgctgt ccaggctgga gtgcagtggc aagatcatgt      180
ctcactgcag ccttgac                                                    197

<210> SEQ ID NO 52
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gtatatgtgt atatatatat atatatattc aggaaataat atat                        44

<210> SEQ ID NO 53
<211> LENGTH: 1232

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
gcaatgaaaa taaatgttttt ttattaggca gaatccagat gctcaaggcc cttcataata      60
tcccccagtt tagtagttgg acttagggaa caaaggaacc tttaatagaa attggacagc     120
aagaaagcga gcttagtgat acttgtgggc cagggcatta gccacaccag ccaccacttt     180
ctgataggca gcctgcactg gtggggtgaa ttctttgcca aagtgatggg ccagcacaca     240
gaccagcacg ttgcccagga gctgtgggag gaagataaga ggtatgaaca tgattagcaa     300
aagggcctag cttggactca gaataatcca gccttatccc aaccataaaa taaaagcaga     360
atggtagctg gattgtagct gctattagca atatgaaacc tcttacatca gttacaattt     420
atatgcagaa atatttatat gcagaaatat tgctattgcc ttaacccaga aattatcact     480
gttattcttt agaatggtgc aaagaggcat gatacattgt atcattattg ccctgaaaga     540
aagagattag ggaaagtatt agaaataaga taaacaaaaa agtatattaa aagaagaaag     600
cattttttaa aattacaaat gcaaaattac cctgatttgg tcaatatgtg taccctgtta     660
cttctcccct tcctatgaca tgaacttaac catagaaaag aaggggaaag aaaacatcaa     720
gggtcccata gactcacccct gaagttctca ggatccacgt gcagcttgtc acagtgcagc     780
tcactcagtt gggcaaaggt gcccttgagg ttgtccaggt gagccaggcc atcactaaag     840
gcaccgagca ctttcttgcc atgagccttc accttagggt tgcccataac agcatcagga     900
gtggacagat ccccaaagga ctcaaagaac ctctgggtcc aagggtagac caccagcagc     960
ctaagggtgg gaaatagac caataggcag agagagtcag tgcctatcag aaacccaaga    1020
gtcttctctg tctccacatg cccagtttct attggtctcc ttaaacctgt cttgtaacct    1080
tgataccaac ctgcccaggg cctcaccacc aacttcatcc acgttcacct tgccccacag    1140
ggcagtaacg gcagacttct cctcaggagt caggtgcacc atggtgtctg tttgaggttg    1200
ctagtgaaca cagttgtgtc agaagcaaat gt                                   1232
```

<210> SEQ ID NO 54
<211> LENGTH: 1232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 54

```
gcaatgaaaa taaatgttttt ttattaggca gaatccagat gctcaaggcc cttcataata      60
tcccccagtt tagtagttgg acttagggaa caaaggaacc tttaatagaa attggacagc     120
aagaaagcga gcttagtgat acttgtgggc cagggcatta gccacaccag ccaccacttt     180
ctgataggca gcctgcactg gtggggtgaa ttctttgcca aagtgatggg ccagcacaca     240
gaccagcacg ttgcccagga gctgtgggag gaagataaga ggtatgaaca tgattagcaa     300
aagggcctag cttggactca gaataatcca gccttatccc aaccataaaa taaaagcaga     360
atggtagctg gattgtagct gctattagca atatgaaacc tcttacatca gttacaattt     420
atatgcagaa atatttatat gcagaaatat tgctattgcc ttaacccaga aattatcact     480
gttattcttt agaatggtgc aaagaggcat gatacattgt atcattattg ccctgaaaga     540
```

```
aagagattag ggaaagtatt agaaataaga taaacaaaaa agtatattaa aagaagaaag      600
cattttttaa aattacaaat gcaaaattac cctgatttgg tcaatatgtg taccctgtta      660
cttctcccct tcctatgaca tgaacttaac catagaaaag aaggggaaag aaaacatcaa      720
gggtcccata gactcaccct gaagttctca ggatccacgt gcagcttgtc acagtgcagc      780
tcactcagtg tggcaaaggt gcccttgagg ttgtccaggt gagccaggcc atcactaaag      840
gcaccgagca ctttcttgcc atgagccttc accttagggt tgcccataac agcatcagga      900
gtggacagat ccccaaagga ctcaaagaac ctctgggtcc aagggtagac caccagcagc      960
ctaagggtgg gaaatagac caataggcag agagagtcag tgcctatcag aaacccaaga     1020
gtcttctctg tctccacatg cccagtttct attggtctcc ttaaacctgt cttgtaacct     1080
tgataccaac ctgcccaggg cctcaccacc aacggcatcc acgttcacct tgccccacag     1140
ggcagtaacg gcagacttct cctcaggagt caggtgcacc atggtgtctg tttgaggttg     1200
ctagtgaaca cagttgtgtc agaagcaaat gt                                   1232
```

<210> SEQ ID NO 55
<211> LENGTH: 1232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
gcaatgaaaa taaatgtttt ttattaggca gaatccagat gctcaaggcc cttcataata       60
tcccccagtt tagtagttgg acttagggaa caaaggaacc tttaatagaa attggacagc      120
aagaaagcga gcttagtgat acttgtgggc cagggcatta gccacaccag ccaccacttt      180
ctgataggca gcctgcactg gtggggtgaa ttctttgcca aagtgatggg ccagcacaca      240
gaccagcacg ttgcccagga gctgtgggag gaagataaga ggtatgaaca tgattagcaa      300
aagggcctag cttggactca gaataatcca gccttatccc aaccataaaa taaaagcaga      360
atggtagctg gattgtagct gctattagca atatgaaacc tcttacatca gttacaattt      420
atatgcagaa atatttatat gcagaaatat tgctattgcc ttaacccaga aattatcact      480
gttattcttt agaatggtgc aaagaggcat gatacattgt atcattattg ccctgaaaga      540
aagagattag ggaaagtatt agaaataaga taaacaaaaa agtatattaa aagaagaaag      600
cattttttaa aattacaaat gcaaaattac cctgatttgg tcaatatgtg taccctgtta      660
cttctcccct tcctatgaca tgaacttaac catagaaaag aaggggaaag aaaacatcaa      720
gggtcccata gactcaccct gaagttctca ggatccacgt gcagcttgtc acagtgcagc      780
tcactcagtg tggcaaaggt gcccttgagg ttgtccaggt gagccaggcc atcactaaag      840
gcaccgagca ctttcttgcc atgagccttc accttagggt tgcccataac agcatcagga      900
gtggacagat ccccaaagga ctcaaagaac ctctgggtcc aagggtagac caccagcagc      960
ctaagggtgg gaaatagac caataggcag agagagtcag tgcctatcag aaacccaaga     1020
gtcttctctg tctccacatg cccagtttct attggtctcc ttaaacctgt cttgtaacct     1080
tgataccaac ctgcccaggg cctcaccacc aactgcatcc acgttcacct tgccccacag     1140
ggcagtaacg gcagacttct cctcaggagt caggtgcacc atggtgtctg tttgaggttg     1200
ctagtgaaca cagttgtgtc agaagcaaat gt                                   1232
```

<210> SEQ ID NO 56

<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
gcaatgaaaa taaatgttttt ttattaggca gaatccagat gctcaaggcc cttcataata      60
tcccccagtt tagtagttgg acttagggaa caaaggaacc tttaatagaa attggacagc     120
aagaaagcga gcttagtgat acttgtgggc cagggcatta gccacaccag ccaccacttt     180
ctgataggca gcctgcactg gtggggtgaa ttctttgcca aagtgatggg ccagcacaca     240
gaccagcacg ttgcccagga gctgtgggag gaagataaga ggtatgaaca tgattagcaa     300
aagggcctag cttggactca gaataatcca gccttatccc aaccataaaa taaaagcaga     360
atggtagctg gattgtagct gctattagca atatgaaacc tcttacatca gttacaattt     420
atatgcagaa atatttatat gcagaaatat tgctattgcc ttaacccaga aattatcact     480
gttattcttt agaatggtgc aaagaggcat gatacattgt atcattattg ccctgaaaga     540
aagagattag ggaaagtatt agaaataaga taaacaaaaa agtatattaa aagaagaaag     600
catttttaa aattacaaat gcaaaattac cctgatttgg tcaatatgtg taccctgtta     660
cttctcccct tcctatgaca tgaacttaac catagaaaag aaggggaaag aaaacatcaa     720
gggtcccata gactcaccct gaagttctca ggatccacgt gcagcttgtc acagtgcagc     780
tcactcagtg tggcaaaggt gcccttgagg ttgtccaggt gagccaggcc atcactaaag     840
gcaccgagca ctttcttgcc atgagccttc accttagggt tgcccataac agcatcagga     900
gtggacagat ccccaaagga ctcaaagaac ctctgggtcc aagggtagac caccagcagc     960
ctaagggtgg gaaatagac caataggcag agagagtcag tgcctatcag aaacccaaga    1020
gtcttctctg tctccacatg cccagttttct attggtctcc ttaaacctgt cttgtaacct    1080
tgataccaac ctgcccaggg cctcaccacc aacagcatcc acgttcacct tgccccacag    1140
ggcagtaacg gcagacttct cctcaggagt caggtgcacc atggtgtctg tttgaggttg    1200
ctagtgaaca cagttgtgtc agaagcaaat gt                                   1232
```

<210> SEQ ID NO 57
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
gcaatgaaaa taaatgttttt ttattaggca gaatccagat gctcaaggcc cttcataata      60
tcccccagtt tagtagttgg acttagggaa caaaggaacc tttaatagaa attggacagc     120
aagaaagcga gcttagtgat acttgtgggc cagggcatta gccacaccag ccaccacttt     180
ctgataggca gcctgcactg gtggggtgaa ttctttgcca aagtgatggg ccagcacaca     240
gaccagcacg ttgcccagga gctgtgggag gaagataaga ggtatgaaca tgattagcaa     300
aagggcctag cttggactca gaataatcca gccttatccc aaccataaaa taaaagcaga     360
atggtagctg gattgtagct gctattagca atatgaaacc tcttacatca gttacaattt     420
atatgcagaa atatttatat gcagaaatat tgctattgcc ttaacccaga aattatcact     480
gttattcttt agaatggtgc aaagaggcat gatacattgt atcattattg ccctgaaaga     540
```

```
aagagattag ggaaagtatt agaaataaga taaacaaaaa agtatattaa aagaagaaag      600
cattttttaa aattacaaat gcaaaattac cctgatttgg tcaatatgtg taccctgtta      660
cttctcccct tcctatgaca tgaacttaac catagaaaag aaggggaaag aaaacatcaa      720
gggtcccata gactcaccct gaagttctca ggatccacgt gcagcttgtc acagtgcagc      780
tcactcagtg tggcaaaggt gcccttgagg ttgtccaggt gagccaggcc atcactaaag      840
gcaccgagca ctttcttgcc atgagccttc accttagggt tgcccataac agcatcagga      900
gtggacagat ccccaaagga ctcaaagaac ctctgggtcc aagggtagac caccagcagc      960
ctaagggtgg gaaaatagac caataggcag agagagtcag tgcctatcag aaacccaaga     1020
gtcttctctg tctccacatg cccagtttct attggtctcc ttaaacctgt cttgtaacct     1080
tgataccaac ctgcccaggg cctcaccacc aaccgcatcc acgttcacct tgccccacag     1140
ggcagtaacg gcagacttct cctcaggagt caggtgcacc atggtgtctg tttgaggttg     1200
ctagtgaaca cagttgtgtc agaagcaaat gt                                   1232
```

<210> SEQ ID NO 58
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

```
gcaatgaaaa taaatgtttt ttattaggca gaatccagat gctcaaggcc cttcataata       60
tcccccagtt tagtagttgg acttagggaa caaaggaacc tttaatagaa attggacagc      120
aagaaagcga gcttagtgat acttgtgggc cagggcatta gccacaccag ccaccacttt      180
ctgataggca gcctgcactg gtggggtgaa ttctttgcca aagtgatggg ccagcacaca      240
gaccagcacg ttgcccagga gctgtgggag aagataaga ggtatgaaca tgattagcaa       300
aagggcctag cttggactca gaataatcca gccttatccc aaccataaaa taaaagcaga      360
atggtagctg gattgtagct gctattagca atatgaaacc tcttacatca gttacaattt      420
atatgcagaa atatttatat gcagaaatat tgctattgcc ttaacccaga aattatcact      480
gttattcttt agaatggtgc aaagaggcat gatacattgt atcattattg ccctgaaaga      540
aagagattag ggaaagtatt agaaataaga taaacaaaaa agtatattaa aagaagaaag      600
cattttttaa aattacaaat gcaaaattac cctgatttgg tcaatatgtg taccctgtta      660
cttctcccct tcctatgaca tgaacttaac catagaaaag aaggggaaag aaaacatcaa      720
gggtcccata gactcaccct gaagttctca ggatccacgt gcagcttgtc acagtgcagc      780
tcactcagtg tggcaaaggt gcccttgagc ttgtccaggt gagccaggcc atcactaaag      840
gcaccgagca ctttcttgcc atgagccttc accttagggt tgcccataac agcatcagga      900
gtggacagat ccccaaagga ctcaaagaac ctctgggtcc aagggtagac caccagcagc      960
ctaagggtgg gaaaatagac caataggcag agagagtcag tgcctatcag aaacccaaga     1020
gtcttctctg tctccacatg cccagtttct attggtctcc ttaaacctgt cttgtaacct     1080
tgataccaac ctgcccaggg cctcaccacc aacttcatcc acgttcacct tgccccacag     1140
ggcagtaacg gcagacttct cctcaggagt caggtgcacc atggtgtctg tttgaggttg     1200
ctagtgaaca cagttgtgtc agaagcaaat gt                                   1232
```

<210> SEQ ID NO 59
<211> LENGTH: 1232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

| | | | | | |
|---|---|---|---|---|---|
| gcaatgaaaa | taaatgttttt | ttattaggca | gaatccagat | gctcaaggcc | cttcataata | 60 |
| tcccccagtt | tagtagttgg | acttagggaa | caaaggaacc | tttaatagaa | attggacagc | 120 |
| aagaaagcga | gcttagtgat | acttgtgggc | cagggcatta | gccacaccag | ccaccactt | 180 |
| ctgataggca | gcctgcactg | gtggggtgaa | ttctttgcca | aagtgatggg | ccagcacaca | 240 |
| gaccagcacg | ttgcccagga | gctgtgggag | gaagataaga | ggtatgaaca | tgattagcaa | 300 |
| aagggcctag | cttggactca | gaataatcca | gccttatccc | aaccataaaa | taaaagcaga | 360 |
| atggtagctg | gattgtagct | gctattagca | atatgaaacc | tcttacatca | gttacaattt | 420 |
| atatgcagaa | atatttatat | gcagaaatat | tgctattgcc | ttaacccaga | aattatcact | 480 |
| gttattcttt | agaatggtgc | aaagaggcat | gatacattgt | atcattattg | ccctgaaaga | 540 |
| aagagattag | ggaaagtatt | agaaataaga | taaacaaaaa | agtatattaa | aagaagaaag | 600 |
| catttttttaa | aattacaaat | gcaaaattac | cctgatttgg | tcaatatgtg | taccctgtta | 660 |
| cttctcccct | tcctatgaca | tgaacttaac | catagaaaag | aaggggaaag | aaaacatcaa | 720 |
| gggtcccata | gactcaccct | gaagttctca | ggatccacgt | gcagcttgtc | acagtgcagc | 780 |
| tcactcagtg | tggcaaaggt | gcccttgagt | ttgtccaggt | gagccaggcc | atcactaaag | 840 |
| gcaccgagca | ctttcttgcc | atgagccttc | accttagggt | tgcccataac | agcatcagga | 900 |
| gtggacagat | ccccaaagga | ctcaaagaac | ctctgggtcc | aagggtagac | caccagcagc | 960 |
| ctaagggtgg | gaaaatagac | caataggcag | agagagtcag | tgcctatcag | aaacccaaga | 1020 |
| gtcttctctg | tctccacatg | cccagtttct | attggtctcc | ttaaacctgt | cttgtaacct | 1080 |
| tgataccaac | ctgcccaggg | cctcaccacc | aacttcatcc | acgttcacct | tgccccacag | 1140 |
| ggcagtaacg | gcagacttct | cctcaggagt | caggtgcacc | atggtgtctg | tttgaggttg | 1200 |
| ctagtgaaca | cagttgtgtc | agaagcaaat | gt | | | 1232 |

<210> SEQ ID NO 60
<211> LENGTH: 1232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

| | | | | | |
|---|---|---|---|---|---|
| gcaatgaaaa | taaatgttttt | ttattaggca | gaatccagat | gctcaaggcc | cttcataata | 60 |
| tcccccagtt | tagtagttgg | acttagggaa | caaaggaacc | tttaatagaa | attggacagc | 120 |
| aagaaagcga | gcttagtgat | acttgtgggc | cagggcatta | gccacaccag | ccaccactt | 180 |
| ctgataggca | gcctgcactg | gtggggtgaa | ttctttgcca | aagtgatggg | ccagcacaca | 240 |
| gaccagcacg | ttgcccagga | gctgtgggag | gaagataaga | ggtatgaaca | tgattagcaa | 300 |
| aagggcctag | cttggactca | gaataatcca | gccttatccc | aaccataaaa | taaaagcaga | 360 |
| atggtagctg | gattgtagct | gctattagca | atatgaaacc | tcttacatca | gttacaattt | 420 |
| atatgcagaa | atatttatat | gcagaaatat | tgctattgcc | ttaacccaga | aattatcact | 480 |

```
gttattctttagaatggtgcaaagaggcatgatacattgtatcattattgccctgaaaga    540 aagagattagggaaagtattagaaataagataaacaaaaaagtatattaaaagaagaaag    600 cattttttaaaattacaaatgcaaaattaccctgatttggtcaatatgtgtaccctgtta    660 cttctcccctttcctatgacatgaacttaaccatagaaaagaagggggaaagaaaacatcaa    720 gggtcccatagactcaccctgaagttctcaggatccacgtgcagcttgtcacagtgcagc    780 tcactcagtgtggcaaaggtgcccttgagcttgtccaggtgagccaggccatcactaaag    840 gcaccgagcactttcttgccatgagccttcaccttagggtgcccataacagcatcagga    900 gtggacagatccccaaaggactcaaagaacctctgggtccaagggtagacaccagcagc    960 ctaagggtgggaaaatagaccaataggcagagagagtcagtgcctatcagaaacccaaga    1020 gtcttctctgtctccacatgcccagtttctattggtctccttaaacctgtcttgtaacct    1080 tgataccaacctgcccagggcctcaccaccaacggcatccacgttcacctgccccacag    1140 ggcagtaacggcagacttctcctcaggagtcaggtgcaccatggtgtctgtttgaggttg    1200 ctagtgaacacagttgtgtcagaagcaaatgt    1232
```

<210> SEQ ID NO 61
<211> LENGTH: 1232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
gcaatgaaaataaatgttttttattaggcagaatccagatgctcaaggccttcataata    60 tcccccagttttagtagttggacttaggggaacaaaggaacctttaatagaaattggacagc    120 aagaaagcgagcttagtgatacttgtgggccagggcattagccacaccagccaccactttt    180 ctgataggcagcctgcactggtggggtgaattctttgccaaagtgatgggccagcacaca    240 gaccagcacgttgcccaggagctgtgggaggaagataagaggtatgaacatgattagcaa    300 aagggcctagcttggactcagaataatccagccttatcccaaccataaaataaaagcaga    360 atggtagctggattgtagctgctattagcaatatgaaacctcttacatcagttacaattt    420 atatgcagaaatatttatatgcagaaatatgctattgccttaacccagaaattatcact    480 gttattctttagaatggtgcaaagaggcatgatacattgtatcattattgccctgaaaga    540 aagagattagggaaagtattagaaataagataaacaaaaaagtatattaaaagaagaaag    600 cattttttaaaattacaaatgcaaaattaccctgatttggtcaatatgtgtaccctgtta    660 cttctcccctttcctatgacatgaacttaaccatagaaaagaagggggaaagaaaacatcaa    720 gggtcccatagactcaccctgaagttctcaggatccacgtgcagcttgtcacagtgcagc    780 tcactcagtgtggcaaaggtgcccttgagtttgtccaggtgagccaggccatcactaaag    840 gcaccgagcactttcttgccatgagccttcaccttagggtgcccataacagcatcagga    900 gtggacagatccccaaaggactcaaagaacctctgggtccaagggtagacaccagcagc    960 ctaagggtgggaaaatagaccaataggcagagagagtcagtgcctatcagaaacccaaga    1020 gtcttctctgtctccacatgcccagtttctattggtctccttaaacctgtcttgtaacct    1080 tgataccaacctgcccagggcctcaccaccaacggcatccacgttcacctgccccacag    1140 ggcagtaacggcagacttctcctcaggagtcaggtgcaccatggtgtctgtttgaggttg    1200 ctagtgaacacagttgtgtcagaagcaaatgt    1232
```

<210> SEQ ID NO 62
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

| | | | | | |
|---|---|---|---|---|---|
| gcaatgaaaa | taaatgttttt | ttattaggca | gaatccagat | gctcaaggcc | cttcataata | 60 |
| tcccccagtt | tagtagttgg | acttagggaa | caaaggaacc | tttaatagaa | attggacagc | 120 |
| aagaaagcga | gcttagtgat | acttgtgggc | cagggcatta | gccacaccag | ccaccacttt | 180 |
| ctgataggca | gcctgcactg | gtggggtgaa | ttctttgcca | aagtgatggg | ccagcacaca | 240 |
| gaccagcacg | ttgcccagga | gctgtgggag | gaagataaga | ggtatgaaca | tgattagcaa | 300 |
| aagggcctag | cttggactca | gaataatcca | gccttatccc | aaccataaaa | taaaagcaga | 360 |
| atggtagctg | gattgtagct | gctattagca | atatgaaacc | tcttacatca | gttacaattt | 420 |
| atatgcagaa | atatttatat | gcagaaatat | tgctattgcc | ttaacccaga | aattatcact | 480 |
| gttattcttt | agaatggtgc | aaagaggcat | gatacattgt | atcattattg | ccctgaaaga | 540 |
| aagagattag | ggaaagtatt | agaaataaga | taaacaaaaa | agtatattaa | aagaagaaag | 600 |
| catttttta | aattacaaat | gcaaaattac | cctgatttgg | tcaatatgtg | taccctgtta | 660 |
| cttctcccct | tcctatgaca | tgaacttaac | catagaaaag | aaggggaaag | aaaacatcaa | 720 |
| gggtcccata | gactcaccct | gaagttctca | ggatccacgt | gcagcttgtc | acagtgcagc | 780 |
| tcactcagtg | tggcaaaggt | gcccttgagc | ttgtccaggt | gagccaggcc | atcactaaag | 840 |
| gcaccgagca | ctttcttgcc | atgagccttc | accttagggt | tgcccataac | agcatcagga | 900 |
| gtggacagat | ccccaaagga | ctcaaagaac | ctctgggtcc | aagggtagac | caccagcagc | 960 |
| ctaagggtgg | gaaatagac | caataggcag | agagagtcag | tgcctatcag | aaacccaaga | 1020 |
| gtcttctctg | tctccacatg | cccagtttct | attggtctcc | ttaaacctgt | cttgtaacct | 1080 |
| tgataccaac | ctgcccaggg | cctcaccacc | aactgcatcc | acgttcacct | tgccccacag | 1140 |
| ggcagtaacg | gcagacttct | cctcaggagt | caggtgcacc | atggtgtctg | tttgaggttg | 1200 |
| ctagtgaaca | cagttgtgtc | agaagcaaat | gt | | | 1232 |

<210> SEQ ID NO 63
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

| | | | | | |
|---|---|---|---|---|---|
| gcaatgaaaa | taaatgttttt | ttattaggca | gaatccagat | gctcaaggcc | cttcataata | 60 |
| tcccccagtt | tagtagttgg | acttagggaa | caaaggaacc | tttaatagaa | attggacagc | 120 |
| aagaaagcga | gcttagtgat | acttgtgggc | cagggcatta | gccacaccag | ccaccacttt | 180 |
| ctgataggca | gcctgcactg | gtggggtgaa | ttctttgcca | aagtgatggg | ccagcacaca | 240 |
| gaccagcacg | ttgcccagga | gctgtgggag | gaagataaga | ggtatgaaca | tgattagcaa | 300 |
| aagggcctag | cttggactca | gaataatcca | gccttatccc | aaccataaaa | taaaagcaga | 360 |
| atggtagctg | gattgtagct | gctattagca | atatgaaacc | tcttacatca | gttacaattt | 420 |
| atatgcagaa | atatttatat | gcagaaatat | tgctattgcc | ttaacccaga | aattatcact | 480 |

```
gttattctttt agaatggtgc aaagaggcat gatacattgt atcattattg ccctgaaaga        540
aagagattag ggaaagtatt agaaataaga taaacaaaaa agtatattaa aagaagaaag        600
cattttttaa aattacaaat gcaaaattac cctgatttgg tcaatatgtg taccctgtta        660
cttctcccct tcctatgaca tgaacttaac catagaaaag aaggggaaag aaaacatcaa        720
gggtcccata gactcaccct gaagttctca ggatccacgt gcagcttgtc acagtgcagc        780
tcactcagtg tggcaaaggt gcccttgagc ttgtccaggt gagccaggcc atcactaaag        840
gcaccgagca ctttcttgcc atgagccttc accttagggt tgcccataac agcatcagga        900
gtggacagat ccccaaagga ctcaagaac ctctgggtcc aagggtagac caccagcagc        960
ctaagggtgg gaaaatagac caataggcag agagagtcag tgcctatcag aaacccaaga       1020
gtcttctctg tctccacatg cccagtttct attggtctcc ttaaacctgt cttgtaacct       1080
tgataccaac ctgcccaggg cctcaccacc aacagcatcc acgttcacct tgccccacag       1140
ggcagtaacg gcagacttct cctcaggagt caggtgcacc atggtgtctg tttgaggttg       1200
ctagtgaaca cagttgtgtc agaagcaaat gt                                     1232
```

<210> SEQ ID NO 64
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

```
gcaatgaaaa taaatgtttt ttattaggca gaatccagat gctcaaggcc cttcataata         60
tcccccagtt tagtagttgg acttaggaa caaaggaacc tttaatgaaa attggacagc        120
aagaaagcga gcttagtgat acttgtgggc cagggcatta gccacaccag ccaccacttt       180
ctgataggca gcctgcactg gtggggtgaa ttctttgcca aagtgatggg ccagcacaca       240
gaccagcacg ttgcccagga gctgtgggag gaagataaga ggtatgaaca tgattagcaa       300
aagggcctag cttggactca gaataatcca gccttatccc aaccataaaa taaaagcaga       360
atggtagctg gattgtagct gctattagca atatgaaacc tcttacatca gttacaattt       420
atatgcagaa atatttatat gcagaaatat tgctattgcc ttaacccaga aattatcact       480 gttattctttt agaatggtgc aaagaggcat gatacattgt atcattattg ccctgaaaga      540
aagagattag ggaaagtatt agaaataaga taaacaaaaa agtatattaa aagaagaaag       600
cattttttaa aattacaaat gcaaaattac cctgatttgg tcaatatgtg taccctgtta       660
cttctcccct tcctatgaca tgaacttaac catagaaaag aaggggaaag aaaacatcaa       720
gggtcccata gactcaccct gaagttctca ggatccacgt gcagcttgtc acagtgcagc       780
tcactcagtg tggcaaaggt gcccttgagc ttgtccaggt gagccaggcc atcactaaag       840
gcaccgagca ctttcttgcc atgagccttc accttagggt tgcccataac agcatcagga       900
gtggacagat ccccaaagga ctcaagaac ctctgggtcc aagggtagac caccagcagc        960
ctaagggtgg gaaaatagac caataggcag agagagtcag tgcctatcag aaacccaaga      1020
gtcttctctg tctccacatg cccagtttct attggtctcc ttaaacctgt cttgtaacct      1080
tgataccaac ctgcccaggg cctcaccacc aaccgcatcc acgttcacct tgccccacag      1140
ggcagtaacg gcagacttct cctcaggagt caggtgcacc atggtgtctg tttgaggttg      1200
ctagtgaaca cagttgtgtc agaagcaaat gt                                    1232
```

<210> SEQ ID NO 65
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

| | | |
|---|---|---|
| gcaatgaaaa taaatgttttt ttattaggca gaatccagat gctcaaggcc cttcataata | 60 |
| tcccccagtt tagtagttgg acttagggaa caaaggaacc tttaatagaa attggacagc | 120 |
| aagaaagcga gcttagtgat acttgtgggc cagggcatta gccacaccag ccaccacttt | 180 |
| ctgataggca gcctgcactg gtggggtgaa ttctttgcca aagtgatggg ccagcacaca | 240 |
| gaccagcacg ttgcccagga gctgtgggag gaagataaga ggtatgaaca tgattagcaa | 300 |
| aagggcctag cttggactca gaataatcca gccttatccc aaccataaaa taaaagcaga | 360 |
| atggtagctg gattgtagct gctattagca atatgaaacc tcttacatca gttacaattt | 420 |
| atatgcagaa atatttatat gcagaaatat tgctattgcc ttaacccaga aattatcact | 480 |
| gttattcttt agaatggtgc aaagaggcat gatacattgt atcattattg ccctgaaaga | 540 |
| aagagattag ggaaagtatt agaaataaga taaacaaaaa agtatattaa aagaagaaag | 600 |
| catttttttaa aattacaaat gcaaaattac cctgatttgg tcaatatgtg taccctgtta | 660 |
| cttctcccct tcctatgaca tgaacttaac catagaaaag aaggggaaag aaaacatcaa | 720 |
| gggtcccata gactcaccct gaagttctca ggatccacgt gcagcttgtc acagtgcagc | 780 |
| tcactcagtg tggcaaaggt gcccttgagt ttgtccaggt gagccaggcc atcactaaag | 840 |
| gcaccgagca ctttcttgcc atgagccttc accttagggt tgcccataac agcatcagga | 900 |
| gtggacagat ccccaaagga ctcaaagaac ctctgggtcc aagggtagac caccagcagc | 960 |
| ctaagggtgg gaaatagac caataggcag agagagtcag tgcctatcag aaacccaaga | 1020 |
| gtcttctctg tctccacatg cccagtttct attggtctcc ttaaacctgt cttgtaacct | 1080 |
| tgataccaac ctgcccaggg cctcaccacc aactgcatcc acgttcacct tgccccacag | 1140 |
| ggcagtaacg gcagacttct cctcaggagt caggtgcacc atggtgtctg tttgaggttg | 1200 |
| ctagtgaaca cagttgtgtc agaagcaaat gt | 1232 |

<210> SEQ ID NO 66
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 66

| | | |
|---|---|---|
| gcaatgaaaa taaatgttttt ttattaggca gaatccagat gctcaaggcc cttcataata | 60 |
| tcccccagtt tagtagttgg acttagggaa caaaggaacc tttaatagaa attggacagc | 120 |
| aagaaagcga gcttagtgat acttgtgggc cagggcatta gccacaccag ccaccacttt | 180 |
| ctgataggca gcctgcactg gtggggtgaa ttctttgcca aagtgatggg ccagcacaca | 240 |
| gaccagcacg ttgcccagga gctgtgggag gaagataaga ggtatgaaca tgattagcaa | 300 |
| aagggcctag cttggactca gaataatcca gccttatccc aaccataaaa taaaagcaga | 360 |
| atggtagctg gattgtagct gctattagca atatgaaacc tcttacatca gttacaattt | 420 |

```
atatgcagaa atatttatat gcagaaatat tgctattgcc ttaacccaga aattatcact    480
gttattcttt agaatggtgc aaagaggcat gatacattgt atcattattg ccctgaaaga    540
aagagattag ggaaagtatt agaaataaga taaacaaaaa agtatattaa aagaagaaag    600
cattttttaa aattacaaat gcaaaattac cctgatttgg tcaatatgtg taccctgtta    660
cttctcccct tcctatgaca tgaacttaac catagaaaag aaggggaaag aaaacatcaa    720
gggtcccata gactcaccct gaagttctca ggatccacgt gcagcttgtc acagtgcagc    780
tcactcagtg tggcaaaggt gcccttgagt tgtccaggt gagccaggcc atcactaaag    840
gcaccgagca ctttcttgcc atgagccttc accttagggt tgcccataac agcatcagga    900
gtggacagat ccccaaagga ctcaaagaac ctctgggtcc aagggtagac caccagcagc    960
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aacagcatcc acgttcacct tgccccacag   1140
ggcagtaacg gcagacttct cctcaggagt caggtgcacc atggtgtctg tttgaggttg   1200
ctagtgaaca cagttgtgtc agaagcaaat gt                                 1232
```

<210> SEQ ID NO 67
<211> LENGTH: 1232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
gcaatgaaaa taaatgtttt ttattaggca gaatccagat gctcaaggcc cttcataata     60
tcccccagtt tagtagttgg acttagggaa caaaggaacc tttaatagaa attggacagc    120
aagaaagcga gcttagtgat acttgtgggc cagggcatta gccacaccag ccaccacttt    180
ctgataggca gcctgcactg gtggggtgaa ttctttgcca aagtgatggg ccagcacaca    240
gaccagcacg ttgcccagga gctgtgggag gaagataaga ggtatgaaca tgattagcaa    300
aagggcctag cttggactca gaataatcca gcctatccc aaccataaaa taaaagcaga    360
atggtagctg gattgtagct gctattagca atatgaaacc tcttacatca gttacaattt    420
atatgcagaa atatttatat gcagaaatat tgctattgcc ttaacccaga aattatcact    480
gttattcttt agaatggtgc aaagaggcat gatacattgt atcattattg ccctgaaaga    540
aagagattag ggaaagtatt agaaataaga taaacaaaaa agtatattaa aagaagaaag    600
cattttttaa aattacaaat gcaaaattac cctgatttgg tcaatatgtg taccctgtta    660
cttctcccct tcctatgaca tgaacttaac catagaaaag aaggggaaag aaaacatcaa    720
gggtcccata gactcaccct gaagttctca ggatccacgt gcagcttgtc acagtgcagc    780
tcactcagtg tggcaaaggt gcccttgagt tgtccaggt gagccaggcc atcactaaag    840
gcaccgagca ctttcttgcc atgagccttc accttagggt tgcccataac agcatcagga    900
gtggacagat ccccaaagga ctcaaagaac ctctgggtcc aagggtagac caccagcagc    960
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aacagcatcc acgttcacct tgccccacag   1140
ggcagtaacg gcagacttct cctcaggagt caggtgcacc atggtgtctg tttgaggttg   1200
```

```
ctagtgaaca cagttgtgtc agaagcaaat gt                                    1232
```

<210> SEQ ID NO 68
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 68

```
gcaatgaaaa taaatgttttt ttattaggca gaatccagat gctcaaggcc cttcataata      60
tcccccagtt tagtagttgg acttagggaa caaaggaacc tttaatagaa attggacagc     120
aagaaagcga gcttagtgat acttgtgggc cagggcatta gccacaccag ccaccacttt     180
ctgataggca gcctgcactg gtggggtgaa ttctttgcca aagtgatggg ccagcacaca     240
gaccagcacg ttgcccagga gctgtgggag gaagataaga ggtatgaaca tgattagcaa     300
aagggcctag cttggactca gaataatcca gccttatccc aaccataaaa taaaagcaga     360
atggtagctg gattgtagct gctattagca atatgaaacc tcttacatca gttacaatttt    420
atatgcagaa atatttatat gcagaaatat tgctattgcc ttaacccaga aattatcact     480
gttattcttt agaatggtgc aaagaggcat gatacattgt atcattattg ccctgaaaga     540
aagagattag ggaaagtatt agaaataaga taaacaaaaa agtatattaa agaagaaag      600
cattttttaa aattacaaat gcaaaattac cctgatttgg tcaatatgtg taccctgtta     660
cttctcccct tcctatgaca tgaacttaac catagaaaag aagggaaag aaaacatcaa      720
gggtcccata gactcaccct gaagttctca ggatccacgt gcagcttgtc acagtgcagc     780
tcactcagct gggcaaaggt gcccttgagg ttgtccaggt gagccaggcc atcactaaag     840
gcaccgagca cttttcttgcc atgagccttc accttagggt tgcccataac agcatcagga     900
gtggacagat ccccaaagga ctcaaagaac ctctgggtcc aagggtagac caccagcagc     960
ctaagggtgg gaaatagac caataggcag agagagtcag tgcctatcag aaacccaaga    1020
gtcttctctg tctccacatg cccagtttct attggtctcc ttaaacctgt cttgtaacct    1080
tgataccaac ctgcccaggg cctcaccacc aacggcatcc acgttcacct tgccccacag    1140
ggcagtaacg gcagacttct cctcaggagt caggtgcacc atggtgtctg tttgaggttg    1200
ctagtgaaca cagttgtgtc agaagcaaat gt                                 1232
```

<210> SEQ ID NO 69
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
gcaatgaaaa taaatgttttt ttattaggca gaatccagat gctcaaggcc cttcataata      60
tcccccagtt tagtagttgg acttagggaa caaaggaacc tttaatagaa attggacagc     120
aagaaagcga gcttagtgat acttgtgggc cagggcatta gccacaccag ccaccacttt     180
ctgataggca gcctgcactg gtggggtgaa ttctttgcca aagtgatggg ccagcacaca     240
gaccagcacg ttgcccagga gctgtgggag gaagataaga ggtatgaaca tgattagcaa     300
aagggcctag cttggactca gaataatcca gccttatccc aaccataaaa taaaagcaga     360
atggtagctg gattgtagct gctattagca atatgaaacc tcttacatca gttacaatttt    420
```

```
atatgcagaa atatttatat gcagaaatat tgctattgcc ttaacccaga aattatcact      480
gttattcttt agaatggtgc aaagaggcat gatacattgt atcattattg ccctgaaaga      540
aagagattag ggaaagtatt agaaataaga taaacaaaaa agtatattaa aagaagaaag      600
cattttttaa aattacaaat gcaaaattac cctgatttgg tcaatatgtg taccctgtta      660
cttctcccct tcctatgaca tgaacttaac catagaaaag aaggggaaag aaaacatcaa      720
gggtcccata gactcaccct gaagttctca ggatccacgt gcagcttgtc acagtgcagc      780
tcactcagtt gggcaaaggt gcccttgagg ttgtccaggt gagccaggcc atcactaaag      840
gcaccgagca ctttcttgcc atgagccttc accttagggt tgcccataac agcatcagga      900
gtggacagat ccccaaagga ctcaaagaac ctctgggtcc aagggtagac caccagcagc      960
ctaagggtgg gaaaatagac caataggcag agagagtcag tgcctatcag aaacccaaga     1020
gtcttctctg tctccacatg cccagtttct attggtctcc ttaaacctgt cttgtaacct     1080
tgataccaac ctgcccaggg cctcaccacc aacggcatcc acgttcacct tgccccacag     1140
ggcagtaacg gcagacttct cctcaggagt caggtgcacc atggtgtctg tttgaggttg     1200
ctagtgaaca cagttgtgtc agaagcaaat gt                                    1232
```

<210> SEQ ID NO 70
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

```
gcaatgaaaa taaatgtttt ttattaggca gaatccagat gctcaaggcc cttcataata       60
tcccccagtt tagtagttgg acttagggaa caaaggaacc tttaatagaa attggacagc      120
aagaaagcga gcttagtgat acttgtgggc cagggcatta gccacaccag ccaccacttt      180
ctgataggca gcctgcactg gtggggtgaa ttctttgcca aagtgatggg ccagcacaca      240
gaccagcacg ttgcccagga gctgtgggag gaagataaga ggtatgaaca tgattagcaa      300
aagggcctag cttggactca gaataatcca gccttatccc aaccataaaa taaaagcaga      360
atggtagctg gattgtagct gctattagca atatgaaacc tcttacatca gttacaattt      420
atatgcagaa atatttatat gcagaaatat tgctattgcc ttaacccaga aattatcact      480
gttattcttt agaatggtgc aaagaggcat gatacattgt atcattattg ccctgaaaga      540
aagagattag ggaaagtatt agaaataaga taaacaaaaa agtatattaa aagaagaaag      600
cattttttaa aattacaaat gcaaaattac cctgatttgg tcaatatgtg taccctgtta      660
cttctcccct tcctatgaca tgaacttaac catagaaaag aaggggaaag aaaacatcaa      720
gggtcccata gactcaccct gaagttctca ggatccacgt gcagcttgtc acagtgcagc      780
tcactcagct gggcaaaggt gcccttgagg ttgtccaggt gagccaggcc atcactaaag      840
gcaccgagca ctttcttgcc atgagccttc accttagggt tgcccataac agcatcagga      900
gtggacagat ccccaaagga ctcaaagaac ctctgggtcc aagggtagac caccagcagc      960
ctaagggtgg gaaaatagac caataggcag agagagtcag tgcctatcag aaacccaaga     1020
gtcttctctg tctccacatg cccagtttct attggtctcc ttaaacctgt cttgtaacct     1080
tgataccaac ctgcccaggg cctcaccacc aactgcatcc acgttcacct tgccccacag     1140
ggcagtaacg gcagacttct cctcaggagt caggtgcacc atggtgtctg tttgaggttg     1200
```
ctagtgaaca cagttgtgtc agaagcaaat gt                         1232

<210> SEQ ID NO 71
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
gcaatgaaaa taaatgtttt ttattaggca gaatccagat gctcaaggcc cttcataata    60
tcccccagtt tagtagttgg acttagggaa caaaggaacc tttaatagaa attggacagc   120
aagaaagcga gcttagtgat acttgtgggc cagggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600
cattttttaa aattacaaat gcaaaattac cctgatttgg tcaatatgtg taccctgtta   660
cttctcccct tcctatgaca tgaacttaac catagaaaag aagggggaaag aaaacatcaa   720 gggtcccata gactcaccct gaagttctca ggatccacgt gcagcttgtc acagtgcagc   780
tcactcagct gggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagttttct attggtctcc ttaaacctgt cttgtaacct  1080
tgataccaac ctgcccaggg cctcaccacc aacagcatcc acgttcacct tgccccacag  1140
ggcagtaacg gcagacttct cctcaggagt caggtgcacc atggtgtctg tttgaggttg  1200
ctagtgaaca cagttgtgtc agaagcaaat gt                                1232

<210> SEQ ID NO 72
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
gcaatgaaaa taaatgtttt ttattaggca gaatccagat gctcaaggcc cttcataata    60
tcccccagtt tagtagttgg acttagggaa caaaggaacc tttaatagaa attggacagc   120
aagaaagcga gcttagtgat acttgtgggc cagggcatta gccacaccag ccaccacttt   180
ctgataggca gcctgcactg gtggggtgaa ttctttgcca aagtgatggg ccagcacaca   240
gaccagcacg ttgcccagga gctgtgggag gaagataaga ggtatgaaca tgattagcaa   300
aagggcctag cttggactca gaataatcca gccttatccc aaccataaaa taaaagcaga   360

```
atggtagctg gattgtagct gctattagca atatgaaacc tcttacatca gttacaattt    420
atatgcagaa atatttatat gcagaaatat tgctattgcc ttaacccaga aattatcact    480
gttattcttt agaatggtgc aaagaggcat gatacattgt atcattattg ccctgaaaga    540
aagagattag ggaaagtatt agaaataaga taaacaaaaa agtatattaa aagaagaaag    600 catttttttaa aattacaaat gcaaaattac cctgatttgg tcaatatgtg taccctgtta   660
cttctcccct tcctatgaca tgaacttaac catagaaaag aaggggaaag aaaacatcaa    720
gggtcccata gactcaccct gaagttctca ggatccacgt gcagcttgtc acagtgcagc    780
tcactcagct gggcaaaggt gcccttgagg ttgtccaggt gagccaggcc atcactaaag    840
gcaccgagca ctttcttgcc atgagccttc accttagggt tgcccataac agcatcagga    900
gtggacagat ccccaaagga ctcaaagaac ctctgggtcc aagggtagac caccagcagc    960
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aaccgcatcc acgttcacct tgccccacag   1140
ggcagtaacg gcagacttct cctcaggagt caggtgcacc atggtgtctg tttgaggttg   1200
ctagtgaaca cagttgtgtc agaagcaaat gt                                  1232
```

<210> SEQ ID NO 73
<211> LENGTH: 1232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

```
gcaatgaaaa taaatgtttt ttattaggca gaatccagat gctcaaggcc cttcataata    60
tcccccagtt tagtagttgg acttaggtaa caaaggaacc tttaatagaa attggacagc   120
aagaaagcga gcttagtgat acttgtgggc cagggcatta gccacaccag ccaccacttt   180
ctgataggca gcctgcactg gtggggtgaa ttctttgcca agtgatggg ccagcacaca    240 gaccagcacg ttgcccagga gctgtgggag gaagataaga ggtatgaaca tgattagcaa   300
aagggcctag cttggactca gaataatcca gccttatccc aaccataaaa taaaagcaga   360
atggtagctg gattgtagct gctattagca atatgaaacc tcttacatca gttacaattt   420
atatgcagaa atatttatat gcagaaatat tgctattgcc ttaacccaga aattatcact   480
gttattcttt agaatggtgc aaagaggcat gatacattgt atcattattg ccctgaaaga   540
aagagattag ggaaagtatt agaaataaga taaacaaaaa agtatattaa aagaagaaag   600 catttttttaa aattacaaat gcaaaattac cctgatttgg tcaatatgtg taccctgtta   660
cttctcccct tcctatgaca tgaacttaac catagaaaag aaggggaaag aaaacatcaa   720
gggtcccata gactcaccct gaagttctca ggatccacgt gcagcttgtc acagtgcagc   780
tcactcagtt gggcaaaggt gcccttgagg ttgtccaggt gagccaggcc atcactaaag   840
gcaccgagca ctttcttgcc atgagccttc accttagggt tgcccataac agcatcagga   900
gtggacagat ccccaaagga ctcaaagaac ctctgggtcc aagggtagac caccagcagc   960
ctaagggtgg gaaaatagac caataggcag agagagtcag tgcctatcag aaacccaaga  1020
gtcttctctg tctccacatg cccagtttct attggtctcc ttaaacctgt cttgtaacct  1080
tgataccaac ctgcccaggg cctcaccacc aactgcatcc acgttcacct tgccccacag  1140
```

```
ggcagtaacg gcagacttct cctcaggagt caggtgcacc atggtgtctg tttgaggttg    1200
ctagtgaaca cagttgtgtc agaagcaaat gt                                  1232
```

<210> SEQ ID NO 74
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
gcaatgaaaa taaatgtttt ttattaggca gaatccagat gctcaaggcc cttcataata      60
tcccccagtt tagtagttgg acttagggaa caaaggaacc tttaatagaa attggacagc     120
aagaaagcga gcttagtgat acttgtgggc cagggcatta gccacaccag ccaccacttt     180
ctgataggca gcctgcactg gtggggtgaa ttctttgcca aagtgatggg ccagcacaca     240
gaccagcacg ttgcccagga gctgtgggag gaagataaga ggtatgaaca tgattagcaa     300
aagggcctag cttggactca gaataatcca gccttatccc aaccatgaaaa taaaagcaga     360 atggtagctg gattgtagct gctattagca atatgaaacc tcttacatca gttacaattt     420
atatgcagaa atatttatat gcagaaatat tgctattgcc ttaacccaga aattatcact     480
gttattcttt agaatggtgc aaagaggcat gatacattgt atcattattg ccctgaaaga     540
aagagattag ggaaagtatt agaaataaga taaacaaaaa agtatattaa aagaagaaag     600
cattttttaa aattacaaat gcaaaattac cctgatttgg tcaatatgtg taccctgtta     660
cttctcccct tcctatgaca tgaacttaac catagaaaag aaggggaaag aaaacatcaa     720
gggtcccata gactcaccct gaagttctca ggatccacgt gcagcttgtc acagtgcagc     780
tcactcagtt gggcaaaggt gcccttgagg ttgtccaggt gagccaggcc atcactaaag     840
gcaccgagca ctttcttgcc atgagccttc accttagggt tgcccataac agcatcagga     900
gtggacagat cccaaaagga ctcaaagaac ctctgggtcc aagggtagac caccagcagc     960
ctaagggtgg gaaaatagac caataggcag agagagtcag tgcctatcag aaacccaaga    1020
gtcttctctg tctccacatg cccagtttct attggtctcc ttaaacctgt cttgtaacct    1080
tgataccaac ctgcccaggg cctcaccacc aacagcatcc acgttcacct tgccccacag    1140
ggcagtaacg gcagacttct cctcaggagt caggtgcacc atggtgtctg tttgaggttg    1200
ctagtgaaca cagttgtgtc agaagcaaat gt                                  1232
```

<210> SEQ ID NO 75
<211> LENGTH: 1232
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75

```
gcaatgaaaa taaatgtttt ttattaggca gaatccagat gctcaaggcc cttcataata      60
tcccccagtt tagtagttgg acttagggaa caaaggaacc tttaatagaa attggacagc     120
aagaaagcga gcttagtgat acttgtgggc cagggcatta gccacaccag ccaccacttt     180
ctgataggca gcctgcactg gtggggtgaa ttctttgcca aagtgatggg ccagcacaca     240
gaccagcacg ttgcccagga gctgtgggag gaagataaga ggtatgaaca tgattagcaa     300
aagggcctag cttggactca gaataatcca gccttatccc aaccatgaaaa taaaagcaga     360
```

```
atggtagctg gattgtagct gctattagca atatgaaacc tcttacatca gttacaattt    420
atatgcagaa atatttatat gcagaaatat tgctattgcc ttaacccaga aattatcact    480
gttattcttt agaatggtgc aaagaggcat gatacattgt atcattattg ccctgaaaga    540
aagagattag ggaaagtatt agaaataaga taaacaaaaa agtatattaa agaagaaag     600 cattttttaa aattacaaat gcaaaattac cctgatttgg tcaatatgtg taccctgtta    660
cttctcccct tcctatgaca tgaacttaac catagaaaag aaggggaaag aaaacatcaa    720
gggtcccata gactcaccct gaagttctca ggatccacgt gcagcttgtc acagtgcagc    780
tcactcagtt gggcaaaggt gcccttgagg ttgtccaggt gagccaggcc atcactaaag    840
gcaccgagca ctttcttgcc atgagccttc acctttaggg tgcccataac agcatcagga    900
gtggacagat ccccaaagga ctcaaagaac ctctgggtcc aagggtagac caccagcagc    960
ctaagggtgg gaaaatagac caataggcag agagagtcag tgcctatcag aaacccaaga   1020
gtcttctctg tctccacatg cccagtttct attggtctcc ttaaacctgt cttgtaacct   1080
tgataccaac ctgcccaggg cctcaccacc aaccgcatcc acgttcacct tgccccacag   1140
ggcagtaacg gcagacttct cctcaggagt caggtgcacc atggtgtctg tttgaggttg   1200
ctagtgaaca cagttgtgtc agaagcaaat gt                                 1232

<210> SEQ ID NO 76
<211> LENGTH: 8674
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
attggccatt gcatacgttg tatccatatc ataatatgta catttatatt ggctcatgtc     60
caacattacc gccatgttga cattgattat tgactagtta ttaatagtaa tcaattacgg    120
ggtcattagt tcatagccca tatatggagt tccgcgttac ataacttacg gtaaatggcc    180
cgcctggctg accgcccaac gacccccgcc cattgacgtc aataatgacg tatgttccca    240
tagtaacgcc aatagggact ttccattgac gtcaatgggt ggagtattta cggtaaactg    300
cccacttggc agtacatcaa gtgtatcata tgccaagtac gccccctatt gacgtcaatg    360
acggtaaatg gcccgcctgg cattatgccc agtacatgac cttatgggac tttcctactt    420
ggcagtacat ctacgtatta gtcatcgcta ttaccatggt gatgcggttt tggcagtaca    480
tcaatgggcg tggatagcgg tttgactcac ggggatttcc aagtctccac cccattgacg    540
tcaatgggag tttgttttgg caccaaaatc aacgggactt tccaaaatgt cgtaacaact    600
ccgccccatt gacgcaaatg ggcggtaggc gtgtacggtg ggaggtctat ataagcagag    660
ctcgtttagt gaaccggggt ctctctggtt agaccagatc tgagcctggg agctctctgg    720
ctaactaggg aacccactgc ttaagcctca ataaagcttg ccttgagtgc ttcaagtagt    780
gtgtgcccgt ctgttgtgtg actctggtaa ctagagatcc ctcagaccct tttagtcagt    840
gtggaaaatc tctagcagtg gcgcccgaac agggacttga agcgaaagg gaaaccagag    900 gagctctctc gacgcaggac tcggcttgct gaagcgcgca cggcaagagg cgaggggcgg    960
cgactggtga gtacgccaaa aattttgact agcggaggct agaaggagag agacgggtgc   1020
gagagcgtca gtattaagcg ggggtgaata agatcgcgat gggaaaaaat tcggttaagg   1080
ccagggggaa agaaaaaata taaattaaaa catatagtat gggcaagcag ggagctagaa   1140
```

```
cgattcgcag ttaatcctgg cctgttagaa acatcagaag gctgtagaca aatactggga    1200
cagctacaac catcccttca gacaggatca gaagaactta gatcattata taatacagta    1260
gcaaccctct attgtgtgca tcaaaggata gagataaaag acaccaagga agctttagac    1320
aagatagagg aagagcaaaa caaaagtaag accaccgcac agcaagcggc cgctgatctt    1380
cagacctgga ggaggagata tgagggacaa ttggagaagt gaattatata aatataaagt    1440
agtaaaaatt gaaccattag gagtagcacc caccaaggca agagaagag tggtgcagag    1500 agaaaaaaga gcagtgggaa taggagcttt gttccttggg ttcttgggag cagcaggaag    1560
cactatgggc gcagcgtcaa tgacgctgac ggtacaggcc agacaattat tgtctggtat    1620
agtgcagcag cagaacaatt tgctgagggc tattgaggcg caacagcatc tgttgcaact    1680
cacagtctgg ggcatcaagc agctccaggc aagaatcctg gctgtggaaa gatacctaaa    1740
ggatcaacag ctcctgggga tttggggttg ctctggaaaa ctcatttgca ccactgctgt    1800
gccttggaat gctagttgga gtaataaatc tctggaacag atttggaatc acacgacctg    1860
gatggagtgg gacagagaaa ttaacaatta cacaagctta atacactcct taattgaaga    1920
atcgcaaaac cagcaagaaa agaatgaaca agaattattg gaattagata atgggcaag    1980 tttgtggaat tggtttaaca taacaaattg gctgtggtat ataaaattat tcataatgat    2040
agtaggaggc ttggtaggtt taagaatagt ttttgctgta cttctctatag tgaatagagt    2100 taggcaggga tattcaccat tatcgtttca gacccacctc ccaaccccga ggggacccga    2160
caggcccgaa ggaatagaag aagaaggtgg agagagagac agagacagat ccattcgatt    2220
agtgaacgga tctcgacggt atcgttttaa agaaaaggg gggattgggg ggtacagtgc    2280
aggggaaaga atagtagaca taatagcaac agacatacaa actaaagaat tacaaaaaca    2340
aattacaaaa attcaaaatt ttatcggcgt gttggggtg gaccatcctc taggtattga    2400
ataagaaaaa tgaagttaag gtggttgatg gtaacactat gctaataact gcagagccag    2460
aagcaccata agggacatga taagggagcc agcagacctc tgatctcttc ctgaatgcta    2520
atcttaaaca tcctgaggaa gaatgggact tccatttggg gtgggcctat gatagggtaa    2580
taagacagta gtgaatatca agctacaaaa agccccttt caaattcttc tcagtcctaa    2640
cttttcatac taagcccagt ccttccaaag cagactgtga agagtgata gttccgggag    2700 actagcactg cagattccgg gtcactgtga gtggggagg cagggaagaa gggctcacag    2760
gacagtcaaa ccatgccccc tgttttcct tcttcaagta gacctctata agacaacaga    2820
gacaactaag gctgagtggc caggcgagga gaaaccatct cgccgtaaaa catgaaggaa    2880
acacttcagg ggaaaggtgg tatctctaag caagagaact gagtggagtc aaggctgaga    2940
gatgcaggat aagcaaatgg gtagtgaaaa gacattcatg aggacagcta aaacaataag    3000
taatgtaaaa tacagcatag caaaacttta acctccaaat caagcctcta cttgaatcct    3060
tttctgaggg atgaataagg cataggcatc agggctgtt gccaatgtgc attagctgtt    3120
tgcagcctca ccttctttca tggagtttaa gatatagtgt attttcccaa ggtttgaact    3180
agctcttcat ttctttatgt tttaaatgca ctgacctccc acattcctt tttagtaaaa    3240 tattcagaaa taatttaaat acatcattgc aatgaaaata aatgtttttt attaggcaga    3300
atccagatgc tcaaggccct tcataatatc ccccagttta gtagttggac ttagggaaca    3360
aaggaacctt taatagaaat tggacagcaa gaaagcgagc ttagtgatac ttgtgggcca    3420
gggcattagc cacaccagcc accactttct gataggcagc ctgcactggt ggggtgaatt    3480
```

```
ctttgccaaa gtgatgggcc agcacacaga ccagcacgtt gcccaggagc tgtgggagga    3540
agataagagg tatgaacatg attagcaaaa gggcctagct tggactcaga ataatccagc    3600
cttatcccaa ccataaaata aaagcagaat ggtagctgga ttgtagctgc tattagcaat    3660
atgaaacctc ttacatcagt tacaatttat atgcagaaat atttatatgc agaaatattg    3720
ctattgcctt aacccagaaa ttatcactgt tattctttag aatggtgcaa agaggcatga    3780
tacattgtat cattattgcc ctgaaagaaa gagattaggg aaagtattag aaataagata    3840
aacaaaaaag tatattaaaa gaagaaagca ttttttaaaa ttacaaatgc aaaattaccc    3900
tgatttggtc aatatgtgta ccctgttact tctccccttc ctatgacatg aacttaacca    3960
tagaaaagaa ggggaaagaa aacatcaagg gtcccataga ctcaccctga agttctcagg    4020
atccacgtgc agcttgtcac agtgcagctc actcagctgg gcaaaggtgc ccttgaggtt    4080
gtccaggtga gccaggccat cactaaaggc accgagcact ttcttgccat gagccttcac    4140
cttagggttg cccataacag catcaggagt ggacagatcc ccaaaggact caaagaacct    4200
ctgggtccaa gggtagacca ccagcagcct aagggtggga aaatagacca ataggcagag    4260
agagtcagtg cctatcagaa acccaagagt cttctctgtc tccacatgcc cagtttctat    4320
tggtctcctt aaacctgtct tgtaaccttg ataccaacct gcccagggcc tcaccaccaa    4380
cttcatccac gttcaccttg ccccacaggg cagtaacggc agacttctcc tcaggagtca    4440
ggtgcaccat ggtgtctgtt tgaggttgct agtgaacaca gttgtgtcag aagcaaatgt    4500
aagcaataga tggctctgcc ctgacttttt agcccagccc tggctcctgc cctccctgct    4560
cctgggagta gattggccaa ccctagggtg tggctccaca gggtgaggtc taagtgatga    4620
cagccgtacc tgtccttggc tcttctggca ctggcttagg agttggactt caaaccctca    4680
gccctccctc taagatatat ctcttggccc cataccatca gtacaaattg ctactaaaaa    4740
catcctcctt tgcaagtgta tttaccaccc ttttccggca cgcagatagt caatatcttc    4800
agcgtcccca aggcctgcaa gggtggggcc ccatatctgg aagtcccagg cggagctggg    4860
agttggtcaa gtctgggctg tggggcagg gagtgctggg ggatggacgc gtcgacggta    4920
ccgttaacga tcttagccac tttttaaaag aaaggggggg actggaaggg ctaattcact    4980
cccaacgaag acaagatatc ctgctagtcc ttccttttcta aatgacgaga gagacagaag    5040
aattcttcaa ggttagtgtg tccagcatgc aacctttcct tcctggatga gcatccctgg    5100
agtaggagag ccagcctgcc tcctgcgctg gcacagagcc cggttcccta gacaactgcc    5160
tctccaaatc tgatgtccag cgccacctgg tgtccacatc aagcagacac aattaatagt    5220
caacctgttc aggaaaactg tgaggggaa aaaaagaaa gaggatttat gaagggaaaa    5280
gaaagtttag aggatatgcc acgattggct agcagctgct ttttgcctgt actgggtctc    5340
tctggttaga ccagatctga gcctgggagc tctctggcta actagggaac ccactgctta    5400
agcctcaata aagcttgcct tgagtgcttc atccggaatc aacctctgga ttacaaaatt    5460
tgtgaaagat tgactggtat tcttaactat gttgctcctt ttacgctatg tggatacgct    5520
gctttaatgc ctttgtatca tgctattgct tcccgtatgg ctttcatttt ctcctccttg    5580
tataaatcct ggttgctgtc tctttatgag gagttgtggc ccgttgtcag gcaacgtggc    5640
gtggtgtgca ctgtgtttgc tgacgcaacc cccactggtt ggggcattgc caccacctgt    5700
cagctccttt ccgggacttt cgctttcccc ctccctattg ccacggcgga actcatcgcc    5760
gcctgccttg cccgctgctg acagggggct cggctgttgg gcactgacaa ttccgtggtg    5820
ttgtcgggga agctgacgtc ctttccatgg ctgctcgcct gtgttgccac ctggattctg    5880
```

```
cgcgggacgt ccttctgcta cgtcccttcg gccctcaatc cagcggacct tccttcccgc   5940
ggcctgctgc cggctctgcg gcctcttccg cgtcttcgcc ttcgccctca gacgagtcgg   6000
atctcccttt gggccgcctc cccgcctgtc cggtagcttg ccagcctcga ctgtgccttc   6060
tagttgccag ccgtctgttg tttgcccctc ccccgtgcct tccttgaccc tggaaggtgc   6120
cactcccact gtcctttcct aataaaatga ggaaattgca tcgcattgtc tgagtaggtg   6180
tcattctatt ctgggggtg gggtggggca ggacagcaag ggggaggatt gggaagacaa   6240
tagcaggcat gcaagcttgg cgtaatcatg gtcatagctg tttcctgtgt gaaattgtta   6300
tccgctcaca attccacaca acatacgagc cggaagcata aagtgtaaag cctggggtgc   6360
ctaatgagtg agctaactca cattaattgc gttgcgctca ctgcccgctt tccagtcggg   6420
aaacctgtcg tgccagctgc attaatgaat cggccaacgc gcgggagag gcggtttgcg   6480
tattgggcgc tcttccgctt cctcgctcac tgactcgctg cgctcggtcg ttcggctgcg   6540
gcgagcggta tcagctcact caaaggcggt aatacggtta ccacagaat caggggataa   6600
cgcaggaaag aacatgtgag caaaaggcca gcaaaaggcc aggaaccgta aaaaggccgc   6660
gttgctggcg ttttttccata ggctccgccc ccctgacgag catcacaaaa atcgacgctc   6720
aagtcagagg tggcgaaacc cgacaggact ataaagatac caggcgtttc ccctggaag   6780
ctccctcgtg cgctctcctg ttccgaccct gccgcttacc ggatacctgt ccgcctttct   6840
cccttcggga agcgtggcgc tttctcatag ctcacgctgt aggtatctca gttcggtgta   6900
ggtcgttcgc tccaagctgg gctgtgtgca cgaaccccc gttcagcccg accgctgcgc   6960
cttatccggt aactatcgtc ttgagtccaa cccggtaaga cacgacttat cgccactggc   7020
agcagccact ggtaacagga ttagcagagc gaggtatgta ggcggtgcta cagagttctt   7080
gaagtggtgg cctaactacg gctacactag aagaacagta tttggtatct gcgctctgct   7140
gaagccagtt accttcggaa aaagagttgg tagctcttga tccggcaaac aaaccaccgc   7200
tggtagcggt ggttttttttg tttgcaagca gcagattacg cgcagaaaaa aaggatctca   7260
agaagatcct ttgatctttt ctacggggtc tgacgctcag tggaacgaaa actcacgtta   7320
agggattttg gtcatgagat tatcaaaaag gatcttcacc tagatccttt taaattaaaa   7380
atgaagtttt aaatcaatct aaagtatata tgagtaaact tggtctgaca gttaccaatg   7440
cttaatcagt gaggcaccta tctcagcgat ctgtctattt cgttcatcca tagttgcctg   7500
actccccgtc gtgtagataa ctacgatacg ggagggctta ccatctggcc ccagtgctgc   7560
aatgataccg cgagacccac gctcaccggc tccagattta tcagcaataa accagccagc   7620
cggaagggcc gagcgcagaa gtggtcctgc aactttatcc gcctccatcc agtctattaa   7680
ttgttgccgg gaagctagag taagtagttc gccagttaat agtttgcgca acgttgttgc   7740
cattgctaca ggcatcgtgg tgtcacgctc gtcgtttggt atggcttcat tcagctccgg   7800
ttcccaacga tcaaggcgag ttacatgatc ccccatgttg tgcaaaaaag cggttagctc   7860
cttcggtcct ccgatcgttg tcagaagtaa gttggccgca gtgttatcac tcatggttat   7920
ggcagcactg cataattctc ttactgtcat gccatccgta agatgctttt ctgtgactgg   7980
tgagtactca accaagtcat tctgagaata gtgtatgcgg cgaccgagtt gctcttgccc   8040
ggcgtcaata cgggataata ccgcgccaca tagcagaact ttaaaagtgc tcatcattgg   8100
aaaacgttct cggggcaaa actctcaagg atcttaccgc tgttgagatc cagttcgatg   8160
taacccactc gtgcacccaa ctgatcttca gcatctttta ctttcaccag cgtttctggg   8220
```

| | |
|---|---|
| tgagcaaaaa caggaaggca aaatgccgca aaaaagggaa taagggcgac acggaaatgt | 8280 |
| tgaatactca tactcttcct ttttcaatat tattgaagca tttatcaggg ttattgtctc | 8340 |
| atgagcggat acatatttga atgtatttag aaaaataaac aaatagggt tccgcgcaca | 8400 |
| tttccccgaa aagtgccacc tgacgtctaa gaaaccatta ttatcatgac attaacctat | 8460 |
| aaaaataggc gtatcacgag gccctttcgt ctcgcgcgtt tcggtgatga cggtgaaaac | 8520 |
| ctctgacaca tgcagctccc ggagacggtc acagcttgtc tgtaagcgga tgccgggagc | 8580 |
| agacaagccc gtcagggcgc gtcagcgggt gttggcgggt gtcggggctg gcttaactat | 8640 |
| gcggcatcag agcagattgt actgagagtg cacc | 8674 |

<210> SEQ ID NO 77
<211> LENGTH: 10011
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77

| | |
|---|---|
| attggccatt gcatacgttg tatccatatc ataatatgta catttatatt ggctcatgtc | 60 |
| caacattacc gccatgttga cattgattat tgactagtta ttaatagtaa tcaattacgg | 120 |
| ggtcattagt tcatagccca tatatggagt tccgcgttac ataacttacg gtaaatggcc | 180 |
| cgcctggctg accgcccaac gacccccgcc cattgacgtc aataatgacg tatgttccca | 240 |
| tagtaacgcc aatagggact ttccattgac gtcaatgggt ggagtattta cggtaaactg | 300 |
| cccacttggc agtacatcaa gtgtatcata tgccaagtac gccccctatt gacgtcaatg | 360 |
| acggtaaatg gcccgcctgg cattatgccc agtacatgac cttatgggac tttcctactt | 420 |
| ggcagtacat ctacgtatta gtcatcgcta ttaccatggt gatgcggttt tggcagtaca | 480 |
| tcaatgggcg tggatagcgg tttgactcac ggggatttcc aagtctccac cccattgacg | 540 |
| tcaatgggag tttgttttgg caccaaaatc aacgggactt tccaaaatgt cgtaacaact | 600 |
| ccgccccatt gacgcaaatg gcggtaggc gtgtacggtg gaggtctat ataagcagag | 660 |
| ctcgtttagt gaaccggggt ctctctggtt agaccagatc tgagcctggg agctctctgg | 720 |
| ctaactaggg aacccactgc ttaagcctca ataaagcttg ccttgagtgc ttcaagtagt | 780 |
| gtgtgcccgt ctgttgtgtg actctggtaa ctagagatcc ctcagaccct tttagtcagt | 840 |
| gtggaaaatc tctagcagtg gcgcccgaac agggacttga aagcgaaagg gaaaccagag | 900 |
| gagctctctc gacgcaggac tcggcttgct gaagcgcgca cggcaagagg cgaggggcgg | 960 |
| cgactggtga gtacgccaaa aattttgact agcggaggct agaaggagag agacgggtgc | 1020 |
| gagagcgtca gtattaagcg ggggtgaata agatcgcgat gggaaaaaat tcggttaagg | 1080 |
| ccagggggaa agaaaaaata taattaaaa catatagtat gggcaagcag ggagctagaa | 1140 |
| cgattcgcag ttaatcctgg cctgttagaa acatcagaag gctgtagaca atactggga | 1200 |
| cagctacaac catcccttca gacaggatca gaagaactta gatcattata taatacagta | 1260 |
| gcaaccctct attgtgtgca tcaaaggata gagataaaag acaccaagga agctttagac | 1320 |
| aagatagagg aagagcaaaa caaaagtaag accaccgcac agcaagcggc cgctgatctt | 1380 |
| cagacctgga ggaggagata tgagggacaa ttggagaagt gaattatata aatataaagt | 1440 |
| agtaaaaatt gaaccattag gagtagcacc caccaaggca aagagaagag tggtgcagag | 1500 |
| agaaaaaaga gcagtgggaa taggagcttt gttccttggg ttcttgggag cagcaggaag | 1560 |

-continued

```
cactatgggc gcagcgtcaa tgacgctgac ggtacaggcc agacaattat tgtctggtat    1620
agtgcagcag cagaacaatt tgctgagggc tattgaggcg caacagcatc tgttgcaact    1680
cacagtctgg ggcatcaagc agctccaggc aagaatcctg gctgtggaaa gatacctaaa    1740
ggatcaacag ctcctgggga tttggggttg ctctggaaaa ctcatttgca ccactgctgt    1800
gccttggaat gctagttgga gtaataaatc tctggaacag atttggaatc acacgacctg    1860
gatggagtgg gacagagaaa ttaacaatta cacaagctta atacactcct taattgaaga    1920
atcgcaaaac cagcaagaaa agaatgaaca agaattattg gaattagata aatgggcaag    1980
tttgtggaat tggtttaaca taacaaattg gctgtggtat ataaaattat tcataatgat    2040
agtaggaggc ttggtaggtt taagaatagt ttttgctgta ctttctatag tgaatagagt    2100
taggcaggga tattcaccat tatcgtttca gacccacctc ccaacccccga ggggacccga    2160 caggcccgaa ggaatagaag aagaaggtgg agagagagac agagacagat ccattcgatt    2220
agtgaacgga tctcgacggt atcgttttaa agaaaaggg gggattgggg gtacagtgc     2280 aggggaaaga atagtagaca taatagcaac agacatacaa actaaagaat acaaaaaca    2340 aattacaaaa attcaaaatt ttatcggcgt gttgggggtg gaccatcctc taggtattga    2400
ataagaaaaa tgaagttaag gtggttgatg gtaacactat gctaataact gcagagccag    2460
aagcaccata agggacatga taagggagcc agcagacctc tgatctcttc ctgaatgcta    2520
atcttaaaca tcctgaggaa gaatgggact tccatttggg gtgggcctat gatagggtaa    2580
taagacagta gtgaatatca agctacaaaa agccccctttt caaattcttc tcagtcctaa    2640
cttttcatac taagcccagt ccttccaaag cagactgtga aagagtgata gttccgggag    2700
actagcactg cagattccgg gtcactgtga gtggggagg cagggaagaa gggctcacag    2760
gacagtcaaa ccatgcccccc tgttttttcct tcttcaagta gacctctata agacaacaga    2820
gacaactaag gctgagtggc caggcgagga gaaaccatct cgccgtaaaa catggaagga    2880
acacttcagg ggaaaggtgg tatctctaag caagagaact gagtggagtc aaggctgaga    2940
gatgcaggat aagcaaatgg gtagtgaaaa gacattcatg aggacagcta aaacaataag    3000
taatgtaaaa tacagcatag caaaacttta acctccaaat caagcctcta cttgaatcct    3060
tttctgaggg atgaataagg cataggcatc aggggctgtt gccaatgtgc attagctgtt    3120
tgcagcctca ccttctttca tggagtttaa gatatagtgt atttttcccaa ggtttgaact    3180 agctcttcat ttctttatgt tttaaatgca ctgacctccc acattccctt tttagtaaaa    3240
tattcagaaa taatttaaat acatcattgc aatgaaaata aatgtttttt attaggcaga    3300
atccagatgc tcaaggccct tcataatatc ccccagttta gtagttggac ttagggaaca    3360
aaggaacctt taatagaaat tggacagcaa gaaagcgagc ttagtgatac ttgtgggcca    3420
gggcattagc cacaccagcc accactttct gataggcagc ctgcactggt ggggtgaatt    3480
ctttgccaaa gtgatgggcc agcacacaga ccagcacgtt gcccaggagc tgtgggagga    3540
agataagagg tatgaacatg attagcaaaa gggcctagct tggactcaga ataatccagc    3600
cttatcccaa ccataaaata aaagcagaat ggtagctgga ttgtagctgc tattagcaat    3660
atgaaacctc ttcatcagt tacaatttat atgcagaaat atttatatgc agaaatattg    3720
ctattgcctt aacccagaaa ttatcactgt tattctttag aatggtgcaa agaggcatga    3780
tacattgtat cattattgcc ctgaaagaaa gagattaggg aaagtattag aaataagata    3840
aacaaaaaag tatattaaaa gaagaaagca ttttttaaaa ttacaaatgc aaaattaccc    3900
tgatttggtc aatatgtgta ccctgttact tctccccttc ctatgacatg aacttaacca    3960
```

```
tagaaaagaa gggaaagaa aacatcaagg gtcccataga ctcaccctga agttctcagg    4020
atccacgtgc agcttgtcac agtgcagctc actcagctgg gcaaaggtgc ccttgaggtt    4080
gtccaggtga gccaggccat cactaaaggc accgagcact ttcttgccat gagccttcac    4140
cttagggttg cccataacag catcaggagt ggacagatcc ccaaaggact caaagaacct    4200
ctgggtccaa gggtagacca ccagcagcct aagggtggga aaatagacca ataggcagag    4260
agagtcagtg cctatcagaa acccaagagt cttctctgtc tccacatgcc cagttttctat   4320
tggtctcctt aaacctgtct tgtaaccttg ataccaacct gcccagggcc tcaccaccaa    4380
cttcatccac gttcaccttg ccccacaggg cagtaacggc agacttctcc tcaggagtca    4440
ggtgcaccat ggtgtctgtt tgaggttgct agtgaacaca gttgtgtcag aagcaaatgt    4500
aagcaataga tggctctgcc ctgactttta tgcccagccc tggctcctgc cctccctgct    4560
cctgggagta gattggccaa ccctagggtg tggctccaca gggtgaggtc taagtgatga    4620
cagccgtacc tgtccttggc tcttctggca ctggcttagg agttggactt caaaccctca    4680
gccctccctc taagatatat ctcttggccc cataccatca gtacaaattg ctactaaaaa    4740
catcctcctt tgcaagtgta tttaccaccc ttttccggca cgcagatagt caatatcttc    4800
agcgtcccca aggcctgcaa gggtggggcc ccatatctgg aagtcccagg cggagctggg    4860
agttggtcaa gtctgggctg tggggggcagg gagtgctggg ggatggacgc gtatctgcgg   4920
ccgcctatct gtaccactag tctcgagaag cttttcatcaa aaaaagtcta accagctgca   4980
ttcgactttg actgcagcag ctggttagaa ggttctactg gaggagggtc ccagcccatt    5040
gctaaattaa catcaggctc tgagactggc agtatatctc taacagtggt tgatgctatc    5100
ttctggaact tgcctgctac attgagacca ctgacccata cataggaagc ccatagctct    5160
gtcctgaact gttaggccac tggtccagag agtgtgcatc tcctttgatc ctcataataa    5220
ccctatgaga tagacacaat tattactctt actttataga tgatgatcct gaaaacatag    5280
gagtcaaggc acttgcccct agctgggggt ataggggagc agtcccatgt agtagtagaa    5340
tgaaaaatgc tgctatgctg tgcctccccc acctttccca tgtctgccct ctactcatgg    5400
tctatctctc ctggctcctg ggagtcatgg actccaccca gcaccaccaa cctgacctaa    5460
ccacctatct gagcctgcca gcctataacc catctgggcc ctgatagctg gtggccagcc    5520
ctgaccccac cccaccctcc ctggaacctc tgatagacac atctggcaca ccagctcgca    5580
aagtcaccgt gagggtcttg tgtttgctga gtcaaaattc cttgaaatcc aagtccttag    5640
agactcctgc tcccaaattt acagtcatag acttcttcat ggctgtctcc tttatccaca    5700
gaatgattcc tttgcttcat tgccccatcc atctgatcct cctcatcagt gcagcacagg    5760
gcccatgagc agtagctgca gagtctcaca taggtctggc actgcctctg acatgtccga    5820
ccttaggcaa atgcttgact cttctgagct cagtcttgtc atggcaaaac aaagataata    5880
atagtgtttt tttatggagt tagcgtgagg atggaaaaca atagcaaaat tgattagact    5940
ataaaaggtc tcaacaaata gtagtagatt ttatcatcca ttaatccttc cctctcctct    6000
cttactcatc ccatcacgta tgcctcttaa ttttcccctta cctataataa gagttattcc    6060
tcttattata ttcttcttat agtgattctg gatatcaaag tgggaatgag gggcaggcca    6120
ctaacgaaga agatgtttct caaagaagcc attctcccca catagatcat ctcagcaggg    6180
ttcaggaaga taaggagga tcaaggtcga aggtaggaac taaggaagaa cactgggcaa    6240
gtgacgcgtc gacggtaccg ttaacgatct tagccacttt ttaaaagaaa aggggggact    6300
```

```
ggaagggcta attcactccc aacgaagaca agatatcctg ctagtccttc ctttctaaat    6360
gacgagagag acagaagaat tcttcaaggt tagtgtgtcc agcatgcaac ctttccttcc    6420
tggatgagca tccctggagt aggagagcca gcctgcctcc tgcgctggca cagagcccgg    6480
ttccctagac aactgcctct ccaaatctga tgtccagcgc cacctggtgt ccacatcaag    6540
cagacacaat taatagtcaa cctgttcagg aaaactgtga gggggaaaaa aagaaagag    6600 gatttatgaa gggaaaagaa agtttagagg atatgccacg attggctagc agctgctttt    6660
tgcctgtact gggtctctct ggttagacca gatctgagcc tgggagctct ctggctaact    6720
agggaaccca ctgcttaagc ctcaataaag cttgccttga gtgcttcatc cggaatcaac    6780
ctctggatta caaaatttgt gaaagattga ctggtattct taactatgtt gctccttta    6840 cgctatgtgg atacgctgct ttaatgcctt tgtatcatgc tattgcttcc cgtatggctt    6900
tcattttctc ctccttgtat aaatcctggt tgctgtctct ttatgaggag ttgtggcccg    6960
ttgtcaggca acgtggcgtg gtgtgcactg tgtttgctga cgcaaccccc actggttggg    7020
gcattgccac cacctgtcag ctcctttccg ggactttcgc tttccccctc cctattgcca    7080
cggcggaact catcgccgcc tgccttgccc gctgctggac aggggctcgg ctgttgggca    7140
ctgacaattc cgtggtgttg tcggggaagc tgacgtcctt tccatggctg ctcgcctgtg    7200
ttgccacctg gattctgcgc gggacgtcct tctgctacgt cccttcggcc ctcaatccag    7260
cggaccttcc ttcccgcggc ctgctgccgg ctctgcggcc tcttccgcgt cttcgccttc    7320
gccctcagac gagtcggatc tccctttggg ccgcctcccc gcctgtccgg tagcttgcca    7380
gcctcgactg tgccttctag ttgccagccg tctgttgttt gcccctcccc cgtgccttcc    7440
ttgaccctgg aaggtgccac tcccactgtc ctttcctaat aaaatgagga aattgcatcg    7500
cattgtctga gtaggtgtca ttctattctg ggggtgggg tggggcagga cagcaagggg    7560
gaggattggg aagacaatag caggcatgca agcttggcgt aatcatggtc atagctgttt    7620
cctgtgtgaa attgttatcc gctcacaatt ccacacaaca tacgagccgg aagcataaag    7680
tgtaaagcct ggggtgccta atgagtgagc taactcacat taattgcgtt gcgctcactg    7740
cccgctttcc agtcgggaaa cctgtcgtgc cagctgcatt aatgaatcgg ccaacgcgcg    7800
gggagaggcg gtttgcgtat tgggcgctct tccgcttcct cgctcactga ctcgctgcgc    7860
tcggtcgttc ggctgcggcg agcggtatca gctcactcaa aggcggtaat acggttatcc    7920
acagaatcag gggataacgc aggaaagaac atgtgagcaa aaggccagca aaaggccagg    7980
aaccgtaaaa aggccgcgtt gctggcgttt ttccataggc tccgccccc tgacgagcat    8040 cacaaaaatc gacgctcaag tcagaggtgg cgaaacccga caggactata agataccag    8100 gcgtttcccc ctggaagctc cctcgtgcgc tctcctgttc cgaccctgcc gcttaccgga    8160
tacctgtccg cctttctccc ttcgggaagc gtggcgcttt ctcatagctc acgctgtagg    8220
tatctcagtt cggtgtaggt cgttcgctcc aagctgggct gtgtgcacga accccccgtt    8280
cagcccgacc gctgcgcctt atccggtaac tatcgtcttg agtccaaccc ggtaagacac    8340
gacttatcgc cactggcagc agccactggt aacaggatta gcagagcgag gtatgtaggc    8400
ggtgctacag agttcttgaa gtggtggcct aactacggct acactagaag aacagtattt    8460
ggtatctgcg ctctgctgaa gccagttacc ttcggaaaaa gagttggtag ctcttgatcc    8520
ggcaaacaaa ccaccgctgg tagcggtggt tttttgttt gcaagcagca gattacgcgc    8580
agaaaaaaag gatctcaaga agatcctttg atcttttcta cggggtctga cgctcagtgg    8640
aacgaaaact cacgttaagg gattttggtc atgagattat caaaaaggat cttcacctag    8700
```

| | | | | |
|---|---|---|---|---|
| atccttttaa | attaaaaatg | aagtttaaa | tcaatctaaa | gtatatatga | gtaaacttgg | 8760 |
| tctgacagtt | accaatgctt | aatcagtgag | gcacctatct | cagcgatctg | tctatttcgt | 8820 |
| tcatccatag | ttgcctgact | ccccgtcgtg | tagataacta | cgatacggga | gggcttacca | 8880 |
| tctggcccca | gtgctgcaat | gataccgcga | gacccacgct | caccggctcc | agatttatca | 8940 |
| gcaataaacc | agccagccgg | aagggccgag | cgcagaagtg | gtcctgcaac | tttatccgcc | 9000 |
| tccatccagt | ctattaattg | ttgccgggaa | gctagagtaa | gtagttcgcc | agttaatagt | 9060 |
| ttgcgcaacg | ttgttgccat | tgctacaggc | atcgtggtgt | cacgctcgtc | gtttggtatg | 9120 |
| gcttcattca | gctccggttc | ccaacgatca | aggcgagtta | catgatcccc | catgttgtgc | 9180 |
| aaaaaagcgg | ttagctcctt | cggtcctccg | atcgttgtca | gaagtaagtt | ggccgcagtg | 9240 |
| ttatcactca | tggttatggc | agcactgcat | aattctctta | ctgtcatgcc | atccgtaaga | 9300 |
| tgcttttctg | tgactggtga | gtactcaacc | aagtcattct | gagaatagtg | tatgcggcga | 9360 |
| ccgagttgct | cttgcccggc | gtcaatacgg | gataataccg | cgccacatag | cagaacttta | 9420 |
| aaagtgctca | tcattggaaa | acgttcttcg | gggcaaaact | ctcaaggatc | ttaccgctgt | 9480 |
| tgagatccag | ttcgatgtaa | cccactcgtg | cacccaactg | atcttcagca | tcttttactt | 9540 |
| tcaccagcgt | ttctgggtga | gcaaaaacag | gaaggcaaaa | tgccgcaaaa | aagggaataa | 9600 |
| gggcgacacg | gaaatgttga | atactcatac | tcttcctttt | tcaatattat | tgaagcattt | 9660 |
| atcagggtta | ttgtctcatg | agcggataca | tatttgaatg | tatttagaaa | aataaacaaa | 9720 |
| taggggttcc | gcgcacattt | ccccgaaaag | tgccacctga | cgtctaagaa | accattatta | 9780 |
| tcatgacatt | aacctataaa | aataggcgta | tcacgaggcc | ctttcgtctc | gcgcgtttcg | 9840 |
| gtgatgacgg | tgaaaacctc | tgacacatgc | agctcccgga | gacggtcaca | gcttgtctgt | 9900 |
| aagcggatgc | cgggagcaga | caagcccgtc | agggcgcgtc | agcgggtgtt | ggcgggtgtc | 9960 |
| ggggctggct | taactatgcg | gcatcagagc | agattgtact | gagagtgcac | c | 10011 |

<210> SEQ ID NO 78
<211> LENGTH: 879
<212> TYPE: DNA
<213> ORGANISM: Homo sapiens

<400> SEQUENCE: 78

| | | | | |
|---|---|---|---|---|
| ctaggtattg | aataagaaaa | atgaagttaa | ggtggttgat | ggtaacacta | tgctaataac | 60 |
| tgcagagcca | gaagcaccat | aagggacatg | ataaggagc | cagcagacct | ctgatctctt | 120 |
| cctgaatgct | aatcttaaac | atcctgagga | agaatgggac | ttccatttgg | ggtgggccta | 180 |
| tgatagggta | ataagacagt | agtgaatatc | aagctacaaa | aagccccctt | tcaaattctt | 240 |
| ctcagtccta | acttttcata | ctaagcccag | tccttccaaa | gcagactgtg | aaagagtgat | 300 |
| agttccggga | gactagcact | gcagattccg | ggtcactgtg | agtggggag | gcagggaaga | 360 |
| agggctcaca | ggacagtcaa | accatgcccc | ctgttttcc | ttcttcaagt | agacctctat | 420 |
| aagacaacag | agacaactaa | ggctgagtgg | ccaggcgagg | agaaaccatc | tcgccgtaaa | 480 |
| acatggaagg | aacacttcag | gggaaaggtg | gtatctctaa | gcaagagaac | tgagtggagt | 540 |
| caaggctgag | agatgcagga | taagcaaatg | ggtagtgaaa | agacattcat | gaggacagct | 600 |

-continued

```
aaaacaataa gtaatgtaaa atacagcata gcaaaacttt aacctccaaa tcaagcctct    660
acttgaatcc ttttctgagg gatgaataag gcataggcat caggggctgt tgccaatgtg    720
cattagctgt ttgcagcctc accttctttc atggagttta agatatagtg tattttccca    780
aggtttgaac tagctcttca tttctttatg ttttaaatgc actgacctcc cacattccct    840
ttttagtaaa atattcagaa ataatttaaa tacatcatt                          879
```

GLOBIN GENE THERAPY FOR TREATING HEMOGLOBINOPATHIES

CROSS-REFERENCE TO RELATED APPLICATIONS

This application is a Continuation of International Patent Application No. PCT/US18/064256 filed on Dec. 6, 2018, which claims priority to U.S. Provisional Application No. 62/595,277 filed on Dec. 6, 2017, the content of each of which is incorporated by reference in its entirety, and to each of which priority is claimed.

SEQUENCE LISTING

The specification further incorporates by reference the Sequence Listing submitted herewith via EFS on Jun. 2, 2020. Pursuant to 37 C.F.R. § 1.52(e)(5), the Sequence Listing text file, identified as 0727341087_SL.txt, is 268,531 bytes and was created on May 31, 2020. The Sequence Listing, electronically filed herewith, does not extend beyond the scope of the specification and thus does not contain new matter.

INTRODUCTION

The presently disclosed subject matter provides expression cassettes and vectors comprising such expression cassettes that express a globin protein, e.g., a human β-globin protein. The presently disclosed subject matter further provides expression cassettes that comprise a globin gene or a functional portion thereof operably linked to a β-globin locus control region (LCR) comprising a plurality of Dnase I hypersensitive sites. The expression cassettes of the presently disclosed subject matter comprise one or more insulators that counteract the effect of enhancer elements. The insulators disclosed herein do not substantially adversely impact the titer of a vector that comprises the presently disclosed expression cassettes. The expression cassettes and vectors can be used for treating a hemoglobinopathy, e.g., β-thalassemia, and sickle cell anemia.

BACKGROUND

β-thalassemia and sickle cell anemia are severe congenital anemias that are caused by defective production of the β chain of hemoglobin. In β-thalassemia, the β chain deficit leads to the intracellular precipitation of excess α-globin chains, causing ineffective erythropoiesis and hemolytic anemia (Weatherall and Clegg (1981), Stamatoyannopoulos et al., (1994), Weatherall (2001), Steinberg (2001)). In the most severe forms found in homozygotes or compound heterozygotes, anemia is lethal within the first years of life in the absence of any treatment (Cooley and Lee (1925)). Lifelong transfusion therapy is needed to correct anemia, suppress ineffective erythropoiesis and inhibit gastrointestinal iron absorption (Weatherall and Clegg (1981), Stamatoyannopoulos et al. (1994), Weatherall (2001), Steinberg (2001)). However, transfusion therapy itself leads to iron overload, which is lethal if untreated. The prevention and treatment of iron overload are the major goals of current patient management (Giardina (2001)). The only current curative treatment to cure β-thalassemia is to provide erythroid precursors harboring normal globin genes through allogeneic bone marrow transplantation (BMT) (Giardini and Lucarelli (1994), Boulad et al. (1998), Lucarelli et al. (1999), Tisdale and Sadelain (2001)).

In sickle cell anemia, the hemoglobin β chain is mutated at amino acid position 6 (Glu→Val), leading to the synthesis of $β^S$ instead of the normal $β^A$ chain (Steinberg (2001), Pauling et al. (1949)). The resulting hemoglobin, HbS, causes accelerated red cell destruction, erythroid hyperplasia and painful vaso-occlusive 'crises' (Steinberg (2001)). Vaso-occlusion can damage organs, eventually causing long-term disabilities (e.g. following stroke or bone necrosis), and sometimes sudden death. While a very serious disorder, the course of sickle cell disease is typically unpredictable (Steinberg (2001)). By increasing production of fetal hemoglobin (Swank and Stamatoyannopoulos (1998)) and suppressing hematopoiesis, hydroxyurea can produce a measurable clinical benefit (Platt et al. (1984)), Charache et al. (1992), Atweh and Loukopoulos (2001)). Since hydroxyurea is a cytotoxic agent, there is a great need for alternative, less toxic drugs to induce γ-globin gene expression (Perrine et al. (2005), Stamatoyannopoulos (2005)). As for β-thalassemia, allogeneic bone marrow transplantation (BMT) is at present the only curative therapy for sickle cell disease (Tisdale and Sadelain (2001), Vermylen et al. (1998), Luzzatto and Goodfellow (1989)).

BMT, however, is not available as a therapeutic option to most patients suffering from β-thalassemia or sickle cell disease, due to the lack of an HLA-matched bone marrow donor for most individuals. Furthermore, although potentially curative, allogeneic BMT is not devoid of complications. Safe transplantation requires the identification of a histo-compatible donor to minimize the risks of graft rejection and graft-versus-host disease (Tisdale and Sadelain (2001), Vermylen et al. (1998), Luzzatto and Goodfellow (1989)). Because of the greater risks associated with matched-unrelated or mismatched transplants, most patients have to settle for life-long transfusion therapy, which does not correct ineffective erythropoiesis and exacerbates systemic iron accumulation. Moreover, despite the considerable improvement in life expectancy in the last decades (Borgna-Pignatti et al. (2004), Telfer et al. (2009), Ladis et al. (2011)), the risk of some serious complications arising over the long term from viral infections, iron toxicity and liver cirrhosis, remain (Mancuso et al. (2006)). These medical risks, together with the socio-economic cost of chronic β-thalassemia, underscore the need for safe, effective and curative therapies.

The only means to cure rather than treat severe β-thalassemia is to provide the patient with healthy hematopoietic stem cells (HSCs). HSCs normally give rise to all blood cell types, including 20 billion RBCs per day in adults. HSCs can be harvested from a donor with wild-type β-globin genes to yield long-lived red blood cells (RBCs) with a normal content in hemoglobin. Alternatively, one may genetically correct the patient's own HSCs, which at once resolves the search for a donor and eliminates the risks of graft-versus-host disease and graft rejection associated with allogeneic BMT (Sadelain (1997), Sadelain et al. (2007)). Globin gene transfer aims to restore the capacity of the β-thalassemic subject's own blood-forming stem cells to generate RBCs with a sufficient hemoglobin content Sadelain et al. (2007), Persons and Tisdale (2004), Sadelain (2006)). The goal in patients with sickle cell anemia is to prevent sickling, which can be achieved by diluting the endogenous HbS with a non-sickling Hb that incorporates the vector-encoded globin chain. The patient's own HSCs are the cells that have to be genetically modified to ensure long-lasting therapeutic benefits and achieve a curative stem cell-based therapy.

The implementation of globin gene transfer for the treatment of severe β-thalassemia and sickle cell anemia requires the efficient introduction of a regulated human β- or β-like globin gene in HSCs. The β-globin gene (or β-like variant) must be expressed in erythroid-specific fashion and at high level, especially for the treatment of transfusion-dependent beta-zero thalassemias.

The globin vectors developed to date present shortcomings that may limit or even preclude their safe use in thalassemia and sickle cell patients. Some of the β-globin locus control region (LCR) components contained in the vectors, in particular Dnase I hypersensitive site-2 (HS2), may have non-erythroid activity, exposing patients to the risk of insertional oncogenesis as seen with non-specific expression vectors. Further, the use of large LCR segments can be detrimental to the production of high titer vectors and the efficient transduction of patients HSCs. Accordingly, there is a need for novel globin expression cassettes that allow for therapeutic expression of a globin gene (e.g., human β-globin gene) in erythroid-specific and differentiation stage-specific fashion with minimal risk of insertional oncogenesis, and that enable high level transduction, thus improving their safety when used in treating thalassemia and sickle cell patients.

SUMMARY OF THE INVENTION

The presently disclosed subject matter generally provides enhancer blocking insulators, and certain insulators additionally possess barrier insulator activity. The presently disclosed subject matter also provides expression cassettes comprising one or more insulators and allows for expression of a globin gene (e.g., a human β globin gene). Also provided are vectors comprising such expression cassettes, cells transduced with such expression cassettes or such vectors, and uses of such expression cassettes for treating hemoglobinopathies (e.g., β-thalassemia and sickle cell anemia).

In certain non-limiting embodiments, the presently disclosed subject matter provides an expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, which is provided below.

[SEQ ID NO: 50]
TGAGCCCCTTTTCCTCTAACTGAAAGAAGGAAAAAAAAAATGGAACCCAA

AATATTCTACATAGTTTCCATGTCACAGCCAGGGCTGGGCAGTCTCCTGT

TATTTCTTTTAAAA

In certain embodiments, the HS2 region does not comprise the nucleotide sequence set forth in SEQ ID NO: 52, which is provided below.

[SEQ ID NO: 52]
GTATATGTGTATATATATATATATATATTCAGGAAATAATATAT

In certain embodiments, the HS2 region has nucleotides 45-860 of SEQ ID NO: 9. In certain embodiments, the HS2 region has the nucleotide sequence set forth in SEQ ID NO: 33.

In certain embodiments, the expression cassette further comprises a Dnase I hypersensitive site-1 (HS1) region.

The presently disclosed subject matter also provides an expression cassette comprising a globin gene or a functional portion thereof operably linked to a β-globin locus control region (LCR) that comprises a HS1 region, a HS3 region, and a HS4 region and does not comprise a core sequence of HS2 region, wherein the HS4 region has a length of less than about 800 bp and does not comprise the nucleotide sequence set forth in SEQ ID NO: 50. In certain embodiments, the core sequence of HS2 has the nucleotide sequence set forth in SEQ ID NO:20 or SEQ ID NO:21. In certain embodiments, the β-globin LCR does not comprise a HS2 region that sustains the enhancer activity of HS2.

In various of these embodiments, the HS4 region has a length of between about 700 bp and about 800 bp. In certain embodiments, the HS4 region has a length of about 750 bp. In certain embodiments, the HS4 region does not comprise the nucleotide sequence set forth in SEQ ID NO: 51, which is provided below.

[SEQ ID NO: 51]
TTTAATCTAACAATTATGAACAGCAATGAGATAATATGTACAAAGTACCC

AGACCTATGTGGTAGAGCATCAAGGAAGCGCATTGCGGAGCAGTTTTTTG

TTTGTTTGTTTTTGTATTCTGTTTCGTGAGGCAAGGTTTCACTCTGCTGT

CCAGGCTGGAGTGCAGTGGCAAGATCATGTCTCACTGCAGCCTTGAC

In various of these embodiments, the HS3 region has a length of about 1300 bp. In certain embodiments, the HS3 region has the nucleotide sequence set forth in SEQ ID NO: 5. In certain embodiments, the HS3 region has the nucleotide sequence set forth in SEQ ID NO: 34.

In various of these embodiments, the HS1 region has a length of about 600 bp. In certain embodiments, the HS1 region has the nucleotide sequence set forth in SEQ ID NO: 3.

In certain embodiments, the β-globin LCR comprises or consists essentially of a HS2 region having nucleotides 45-860 of SEQ ID NO: 9, a HS3 region having the nucleotide sequence set forth in SEQ ID NO: 5, and a HS4 region having nucleotides 115-868 of SEQ ID NO: 6.

In certain embodiments, the β-globin LCR comprises or consists essentially of a HS2 region having the nucleotide sequence set forth in SEQ ID NO: 33, a HS3 region having the nucleotide sequence set forth in SEQ ID NO: 34, and a HS4 region having the nucleotide sequence set forth in SEQ ID NO: 35.

In certain embodiments, the β-globin LCR comprises or consists essentially of a HS1 region having the nucleotide sequence set forth in SEQ ID NO: 3, a HS3 region having the nucleotide sequence set forth in SEQ ID NO: 5, and a HS4 region having nucleotides 115-868 of SEQ ID NO: 6.

In certain embodiments, the β-globin LCR comprises or consists essentially of a HS1 region having the nucleotide sequence set forth in SEQ ID NO: 3, a HS3 region having the nucleotide sequence set forth in SEQ ID NO: 34, and a HS4 region having the nucleotide sequence set forth in SEQ ID NO: 35.

In certain embodiments, the β-globin LCR comprises or consists essentially of a HS1 region having the nucleotide sequence set forth in SEQ ID NO: 3, a HS2 region having nucleotides 45-860 of SEQ ID NO: 9, a HS3 region having the nucleotide sequence set forth in SEQ ID NO: 5, and a HS4 region having nucleotides 115-868 of SEQ ID NO: 6.

In certain embodiments, the β-globin LCR comprises or consists essentially of a HS1 region having the nucleotide sequence set forth in SEQ ID NO: 3, a HS2 region having the nucleotide sequence set forth in SEQ ID NO: 33, a HS3 region having the nucleotide sequence set forth in SEQ ID NO: 34, and a HS4 region having the nucleotide sequence set forth in SEQ ID NO: 35.

In various of these embodiments, the expression cassette further comprises at least one an insulator comprising the CTCF binding site sequence set forth in SEQ ID NO:18. In certain embodiments, the at least one insulator has the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, or SEQ ID NO: 31. In certain embodiments, the expression cassette comprises two insulators, each comprising the CTCF binding site sequence set forth in SEQ ID NO:18, for example, but not limited to, where one or both insulators comprise the nucleotide sequence set forth in SEQ ID NO: 1, SEQ ID NO: 24, SEQ ID NO:25, SEQ ID NO: 27, SEQ ID NO: 28, SEQ ID NO: 29, SEQ ID NO: 30, or SEQ ID NO: 31.

In certain embodiments, the expression cassette further comprises at least one erythroid-specific enhancer. In certain embodiments, the at least one erythroid-specific enhancer is positioned within the β-globin LCR. In certain embodiments, the at least one erythroid-specific enhancer is positioned between the HS1 region and the HS3 region of the β-globin LCR. In certain embodiments, the at least one erythroid-specific enhancer has the nucleotide sequence set forth in SEQ ID NO: 13, SEQ ID NO: 14, SEQ ID NO: 15, SEQ ID NO: 16, or SEQ ID NO: 17. In certain embodiments, the at least one erythroid-specific enhancer has the nucleotide sequence set forth in SEQ ID NO: 15. In certain embodiments, the at least one erythroid-specific enhancer is between about 100 and about 200 bp in length. In certain embodiments, the expression cassette comprises one, two or three erythroid-specific enhancers.

The presently disclosed subject matter also provides an expression cassette comprising at least one erythroid-specific enhancer disclosed herein and a globin gene or a functional portion thereof, wherein the expression cassette does not comprise a β-globin locus control region (LCR).

The presently disclosed subject matter further provides an expression cassette comprising at least one erythroid-specific enhancer disclosed herein and a globin gene or a functional portion thereof that is operatively linked to a β-globin locus control region (LCR) that comprises a HS3 region, and does not comprise a core sequence of a HS1 region, a core sequence of a HS2 region, or a core sequence of a HS4 region.

In certain embodiments, the globin gene is selected from the group consisting of β-globin gene, γ-globin gene, and δ-globin gene. In certain non-limiting embodiments, the globin gene is human β-globin gene. In certain non-limiting embodiments, the human β-globin gene is a wild-type human β-globin gene. In certain non-limiting embodiments, the human β-globin gene is a non-wild-type human β-globin gene, including, but not limited to, a human β-globin gene comprising one or more deletions of intron sequences, a human β-globin gene encoding at least one (e.g., one or two) anti-sickling amino acid residue (e.g., a human β-globin gene encoding anti-sickling hemoglobin 1 (HB AS1), and a human β-globin gene encoding anti-sickling hemoglobin 2 (HB AS2)), and a human β-globin gene comprising one or more deletions of intron sequences and encoding at least one anti-sickling amino acid residue. In certain non-limiting embodiments, the human β-globin gene is a human $β^A$-globin gene encoding a threonine to glutamine mutation at codon 87 ($β^{A-T87Q}$). In certain non-limiting embodiments, the human β-globin gene is a human $β^A$-globin gene encoding a threonine to glutamine mutation at codon 87 ($β^{A-T87Q}$) and comprising a deletion in intron 2. In certain non-limiting embodiments, the human β-globin gene is a human $β^A$-globin gene encoding a glutamic acid to alanine mutation at codon 22 ($β^{A-E22A}$). In certain non-limiting embodiments, the human β-globin gene is a human $β^A$-globin gene encoding a glutamic acid to alanine mutation at codon 22 ($β^{A-E22A}$) and comprising a deletion in intron 2. In certain non-limiting embodiments, the human β-globin gene is a human $β^A$-globin gene encoding an asparagine to lysine mutation at codon 80 ($β^{-N80K}$). In certain non-limiting embodiments, the human β-globin gene is a human $β^A$-globin gene encoding an asparagine to lysine mutation at codon 80 ($β^{-N80K}$) and comprising a deletion in intron 2. In certain non-limiting embodiments, the human β-globin gene is a human $β^A$-globin gene encoding a glutamic acid to alanine mutation at codon 22 and an asparagine to lysine mutation at codon 80. In certain non-limiting embodiments, the human β-globin gene is a human $β^A$-globin gene encoding a glutamic acid to alanine mutation at codon 22 and an asparagine to lysine mutation at codon 80 and comprising a deletion in intron 2. In certain non-limiting embodiments, the human β-globin gene is a human $β^A$-globin gene encoding a glutamic acid to alanine mutation at codon 22 and a threonine to glutamine mutation at codon 87. In certain non-limiting embodiments, the human β-globin gene is a human $β^A$-globin gene encoding a glutamic acid to alanine mutation at codon 22 and a threonine to glutamine mutation at codon 87 and comprising a deletion in intron 2. In certain embodiments, the deletion in intro 2 is a deletion of about 370 bp.

In certain embodiments, the expression cassette further comprises a β-globin promoter. In certain embodiments, the β-globin promoter is positioned between the globin gene or functional portion thereof and β-globin LCR. In certain non-limiting embodiments, the β-globin promoter is a human β-globin promoter that is about 265 bp in length. In certain non-limiting embodiments, the β human β-globin promoter has the nucleotide sequence set forth in SEQ ID NO:11.

In certain embodiments, the expression cassette further comprises a human β-globin 3' enhancer. In certain embodiments, the human β-globin 3' enhancer is positioned in the upstream of the globin gene or functional portion thereof. In certain embodiments, the β-globin 3' enhancer is between about 700 and about 900 bp in length, e.g., between about 800 and 900 bp in length. In certain embodiments, the human β-globin 3' enhancer is about 880 bp in length. In certain embodiments, the human β-globin 3' enhancer has the nucleotide sequence set forth in SEQ ID NO:12.

In certain embodiments, the expression cassette allows for expression of the globin gene or functional portion thereof in a mammal. In certain embodiments, the expression cassette allows for expression of a human β-globin gene. In certain embodiments, the expression of the globin gene or functional portion thereof is restricted to erythroid tissue.

The presently disclosed subject matter also provides recombinant vectors comprising the above-described expression cassettes. In certain embodiments, the recombinant vector is a retroviral vector. In certain embodiments, the retroviral vector is a lentivirus vector. In certain embodiments, the expression cassette comprised in the recombinant vector comprises one insulator. In certain embodiments, the expression cassette comprised in the recombinant vector comprises two insulators, e.g., two of the insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32. In certain embodiments, the recombinant vector further comprises a Woodchuck hepatitis post-regulatory element (WPRE) in the 3' long terminal repeat (LTR) of the vector. In certain embodiments, the recombinant vector further comprises a bovine growth hormone polyadenylation signal in the 3' long terminal repeat (LTR) of the vector.

In addition, the presently disclosed subject matter provides non-naturally occurring or engineered nucleases comprising the above-described expression cassettes. In certain embodiments, the nuclease is selected from the group consisting of a non-naturally occurring or engineered zinc-finger nuclease (ZFN), a non-naturally occurring or engineered meganuclease, and a non-naturally occurring or engineered transcription activator-like effector nuclease (TALEN). In certain embodiments, the nuclease comprises a DNA binding domain and a nuclease cleavage domain. In certain embodiments, the nuclease binds to a genomic safe harbor site. In certain embodiments, the nuclease generates a double strand break (DSB) at the genomic safe harbor site. In certain embodiments, the expression cassette comprised in the nuclease comprises two insulators, e.g., two of the insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32. In certain embodiments, the nuclease allows for targeted delivery of the expression cassette. The presently disclosed subject matter also provides polynucleotides encoding the above-described nucleases, and vectors comprising the polynucleotides. In certain embodiments, the vector is a lentiviral vector.

Furthermore, the presently disclosed subject matter provides non-naturally occurring or engineered CRISPR-Cas systems comprising the above-described expression cassettes. In certain embodiments, the CRISPR-Cas system comprises a CRISPR-Cas nuclease and single-guide RNA. In certain embodiments, the CRISPR-Cas system binds to a genomic safe harbor site. In certain embodiments, the CRISPR-Cas system generates a double strand break (DSB) at the genomic safe harbor site. In certain embodiments, the expression cassette comprised in the CRISPR-Cas system comprises two insulators, e.g., two of the insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32. In certain embodiments, the CRISPR-Cas allows for targeted delivery of the expression cassette. The presently disclosed subject matter also provides polynucleotides encoding the above-described CRISPR-Cas systems, and vectors comprising the polynucleotides. In certain non-limiting embodiments, the vector is a lentiviral vector.

In certain embodiments, the genomic safe harbor site is an extragenic genomic safe harbor site. In certain embodiments, the genomic safe harbor site is located on chromosome 1. In certain embodiments, the genomic safe harbor meets all of the following five criteria: (1) distance of at least 50 kb from the 5' end of any gene (e.g., from the 5' end of the gene), (ii) distance of at least 300 kb from any cancer-related gene, (iii) within an open/accessible chromatin structure (measured by DNA cleavage with natural or engineered nucleases), (iv) location outside a gene transcription unit and (v) location outside ultraconserved regions (UCRs), microRNA or long non-coding RNA of the human genome.

Additionally, the presently disclosed subject matter provides cells transduced with the above-described expression cassettes, cells transduced with the above-described recombinant vectors, cells transduced with the above-described nucleases, cells transduced with the above-described CRISPR-Cas systems. In addition, the presently disclosed subject matter provides cells transduced with the above-described vectors. In certain embodiments, the cell is selected from the group consisting of a hematopoietic stem cell, an embryonic stem cell, an induced pluripotent stem cell, and a hemogenic endothelium cell. In certain non-limiting embodiments, the hematopoietic stem cell is a $CD34^+$ hematopoietic stem cell. In certain embodiments, the cell is transduced ex vivo.

Also provided are pharmaceutical compositions comprising an effective amount of the above-described cells and a pharmaceutically acceptable carrier. The presently disclosed subject matter also provides pharmaceutical compositions for treating a hemoglobinopathy comprising an effective amount of the above-described cells and a pharmaceutically acceptable carrier.

Furthermore, the presently disclosed subject matter provides kits for treating a hemoglobinopathy comprising the above-described cells. In certain embodiments, the kits further comprise written instructions for using the cell for treating a subject having a hemoglobinopathy.

In addition, the presently disclosed subject matter provides methods of treating a hemoglobinopathy in a subject, comprising administering an effective amount of the above-described cells to the subject, thereby restoring the subject's ability to produce red blood cells containing normal hemoglobin. In certain embodiments, a therapeutically relevant level of hemoglobin is produced in the subject following administering the cell to the subject. In certain amendments, the method comprises administering an effective amount of the cell transduced with the above-described recombinant vector. In certain embodiments, the vector copy number of the recombinant vector in the cell that provides for the therapeutically relevant level of hemoglobin in the subject is about 0.5-2 vector copy number per cell. In certain embodiments, the method corrects ineffective erythropoiesis in the subject. In certain embodiments, the method does not incur the risk of graft-versus-host disease in the subject. In certain embodiments, the method does not comprise administering an immunosuppressive agent. In certain embodiments, the cell is selected from the group consisting of a hematopoietic stem cell, an embryonic stem cell, an induced pluripotent stem cell, and a hemogenic endothelium cell. In certain non-limiting embodiments, the subject is a human. In certain embodiments, the cell is from the subject. In certain non-limiting embodiments, the cell is from bone marrow of the subject.

In accordance with the presently disclosed subject matter, the hemoglobinopathy can be selected from the group consisting of hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease. In certain non-limiting embodiments, the hemoglobinopathy is β-thalassemia. In certain non-limiting embodiments, the hemoglobinopathy is sickle cell anemia.

BRIEF DESCRIPTION OF THE FIGURES

The following Detailed Description, given by way of example, but not intended to limit the invention to specific embodiments described, may be understood in conjunction with the accompanying drawings.

"RRE" represents for "Rev Response Element". cPPT represents for "Central Polypurine tract".

Figure 2:
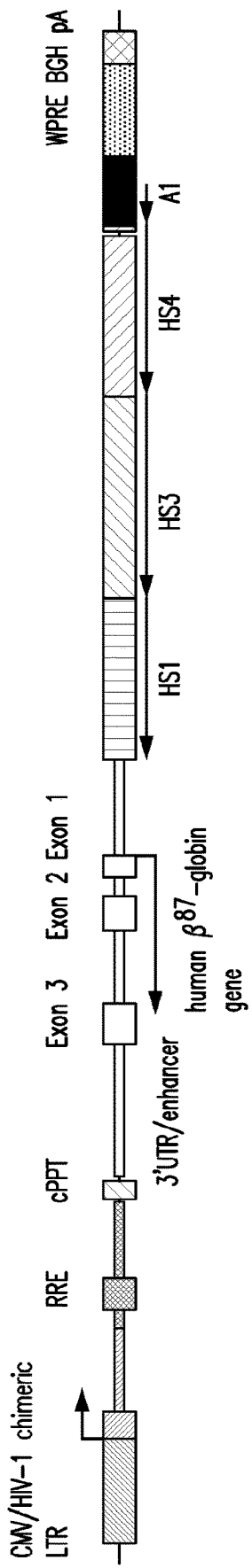

FIG. 2 depicts a recombinant vector an expression cassette in accordance with one non-limiting embodiment of the presently disclosed subject matter.

Figure 3:
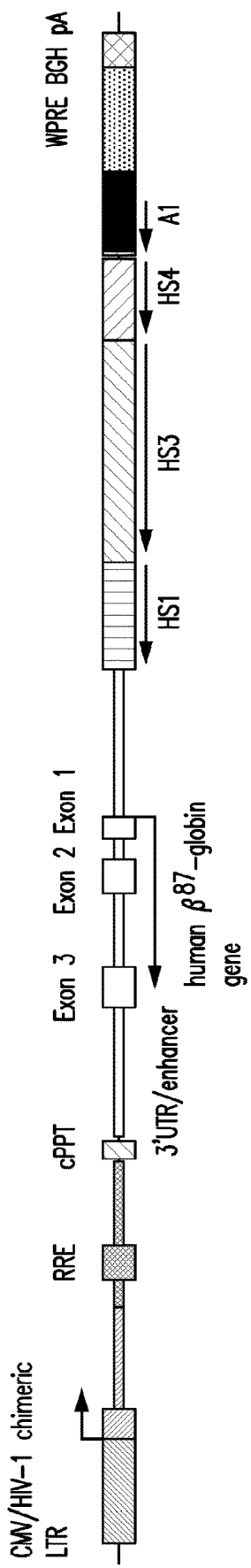

FIG. 3 depicts a recombinant vector an expression cassette in accordance with one non-limiting embodiment of the presently disclosed subject matter.

Figure 4:
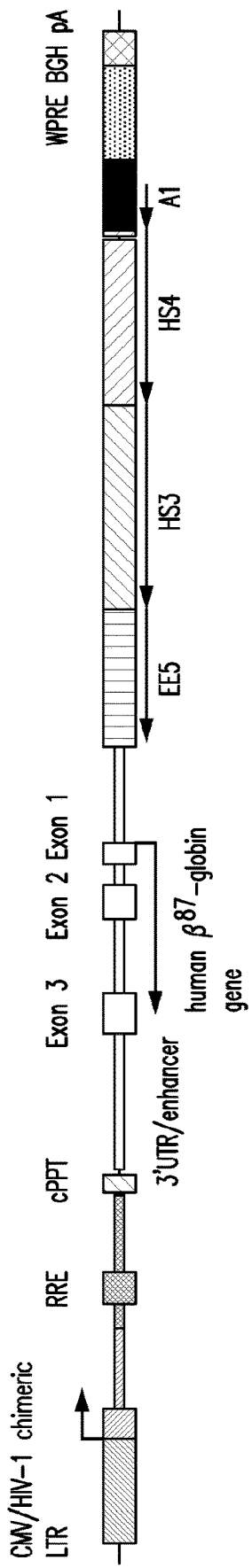

FIG. 4 depicts a recombinant vector an expression cassette in accordance with one non-limiting embodiment of the presently disclosed subject matter.

Figures 5A, 5B, 5C:
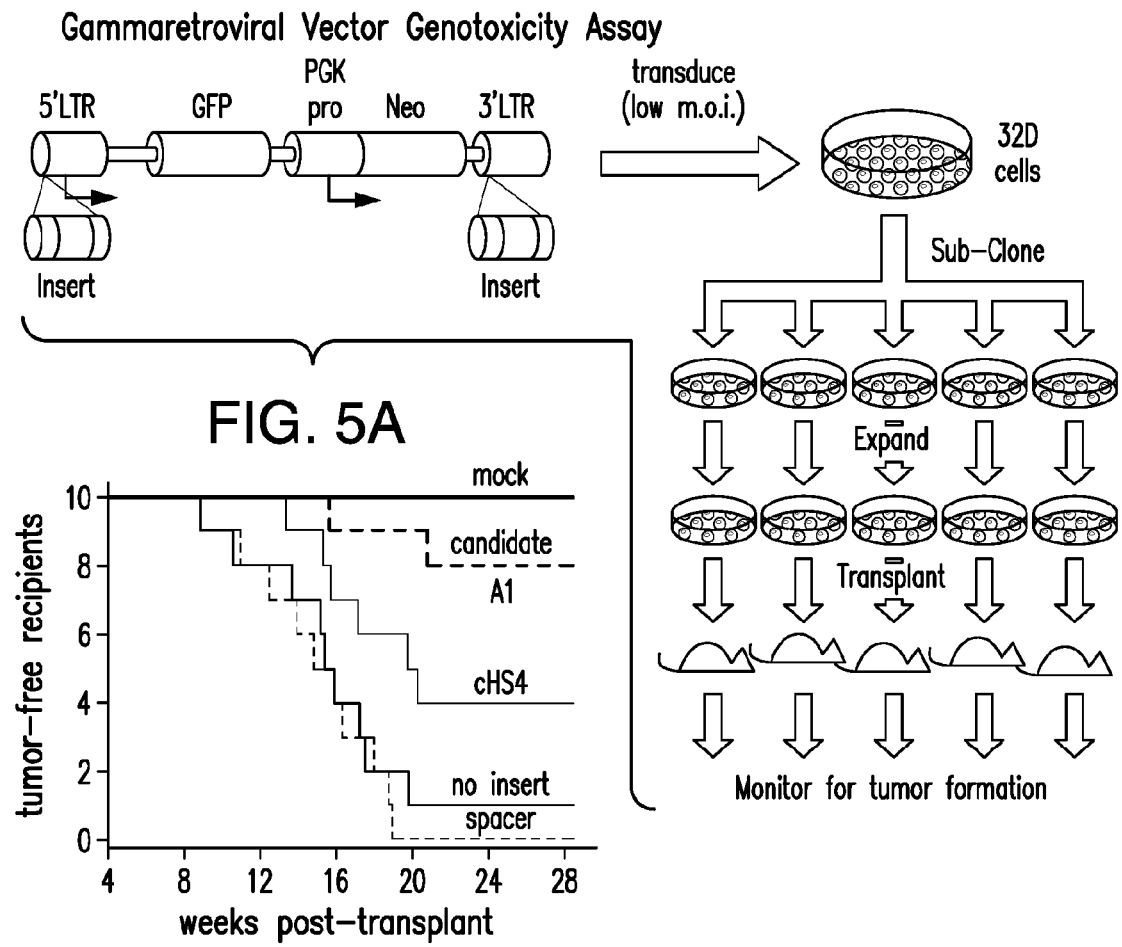

FIGS. 5A-5C represent the genotoxicity of insulator A1. FIG. 5A demonstrates the gammaretroviral vector genotoxicity assay used. FIG. 5B notices the increased survival of mice receiving 32D cells transduced with insulated gammaretroviral vector. Also notice the results obtained with cHS4 and with the uninsulated control. FIG. 5C shows that insulator A1 decreased the risk of genotoxicity.

Figure 6:
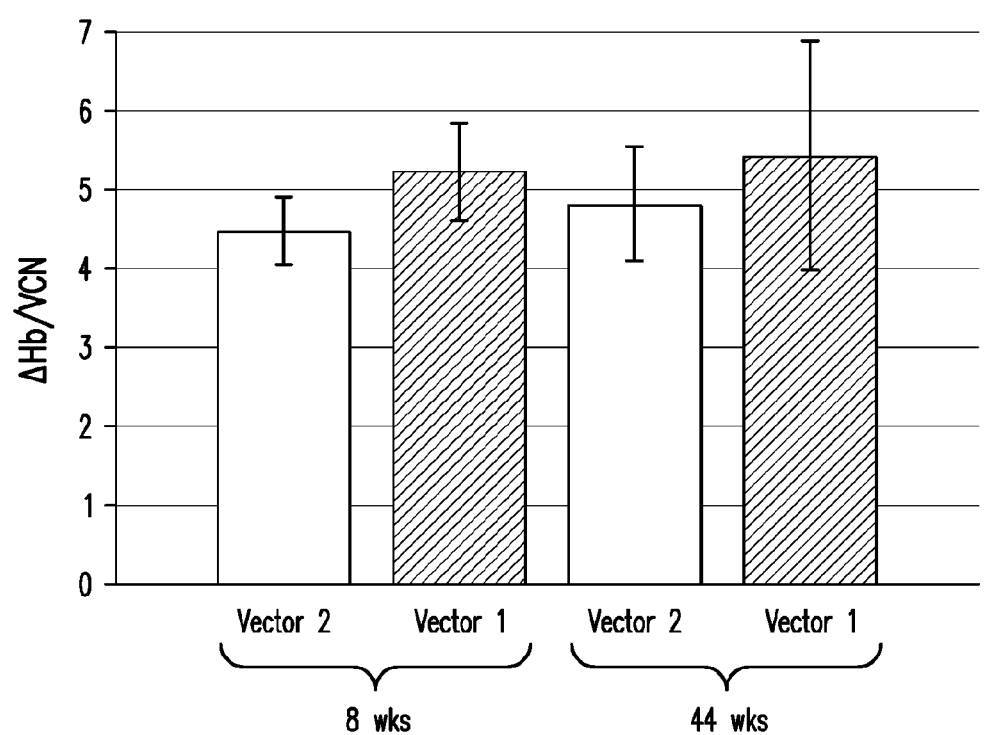

FIG. 6 represents normalized β chain expression in thalassemic $Hbb^{th3/+}$ mice 8 and 44 weeks post-treatment.

Figure 7:
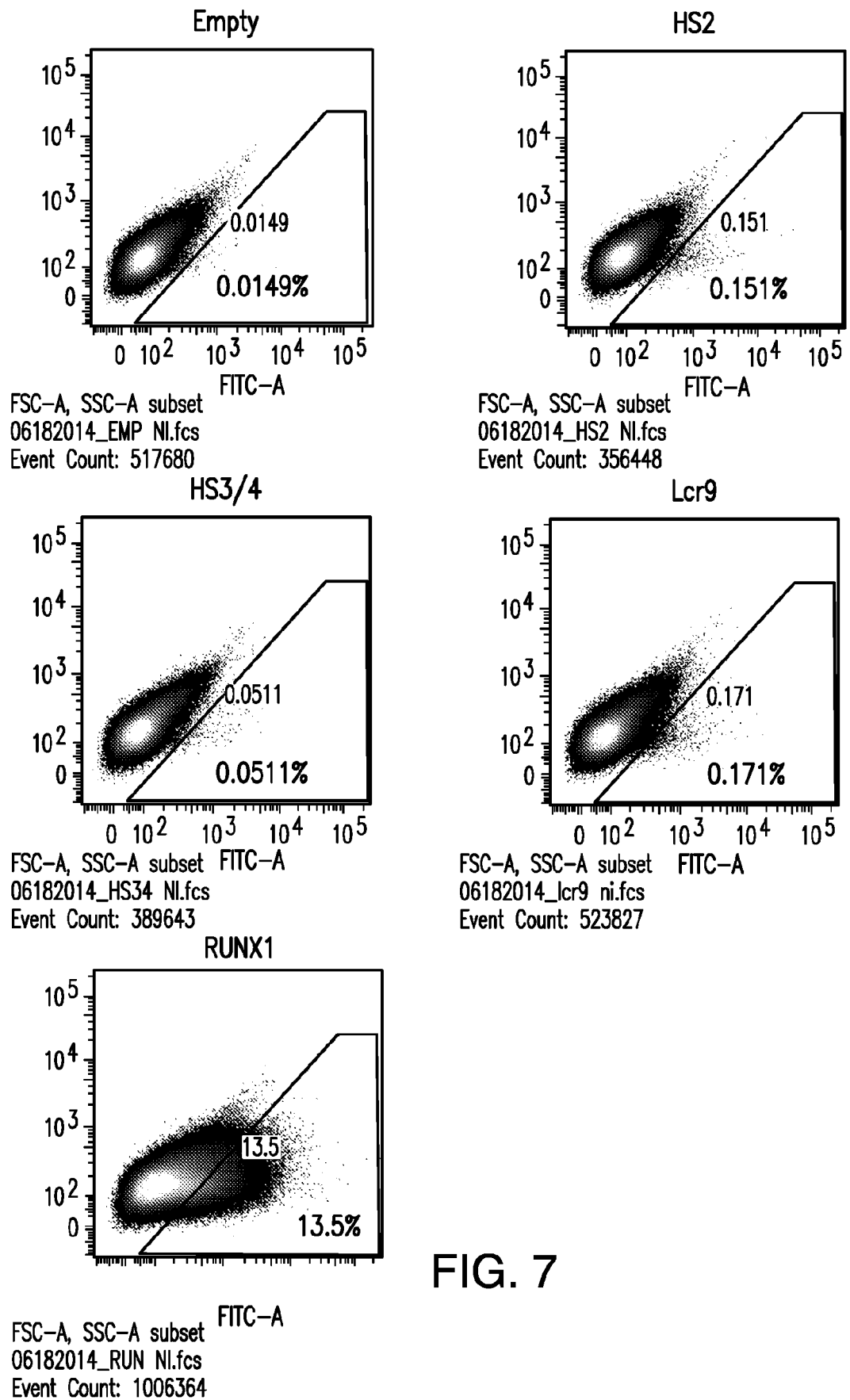

FIG. 7 represents the evaluation of enhancer activity in non-erythroid K562 cells.

FIG. 8 represents the erythroid-specific enhancers in accordance with certain embodiments of the presently disclosed subject matter (SEQ ID NOS 13-17, respectively, in order of appearance).

Figure 9:
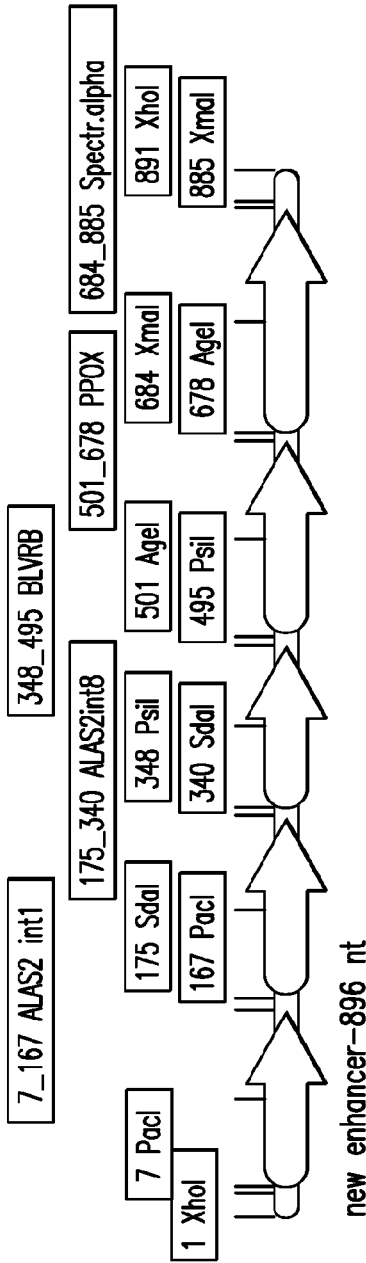

FIG. 9 represents the erythroid-specific enhancers in accordance with certain embodiments of the presently disclosed subject matter (SEQ ID NO: 26).

Figure 10A:
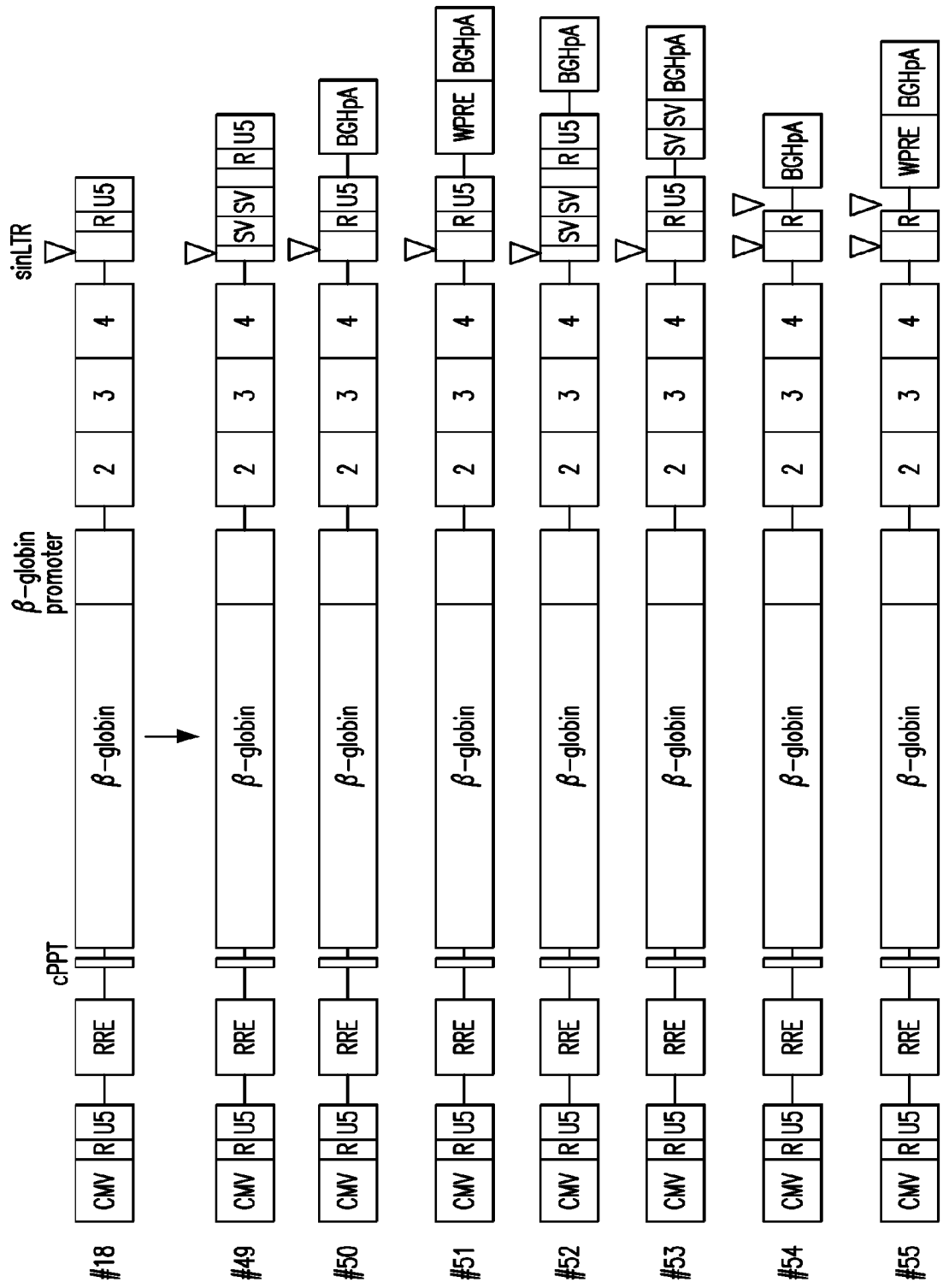
Figure 10B:
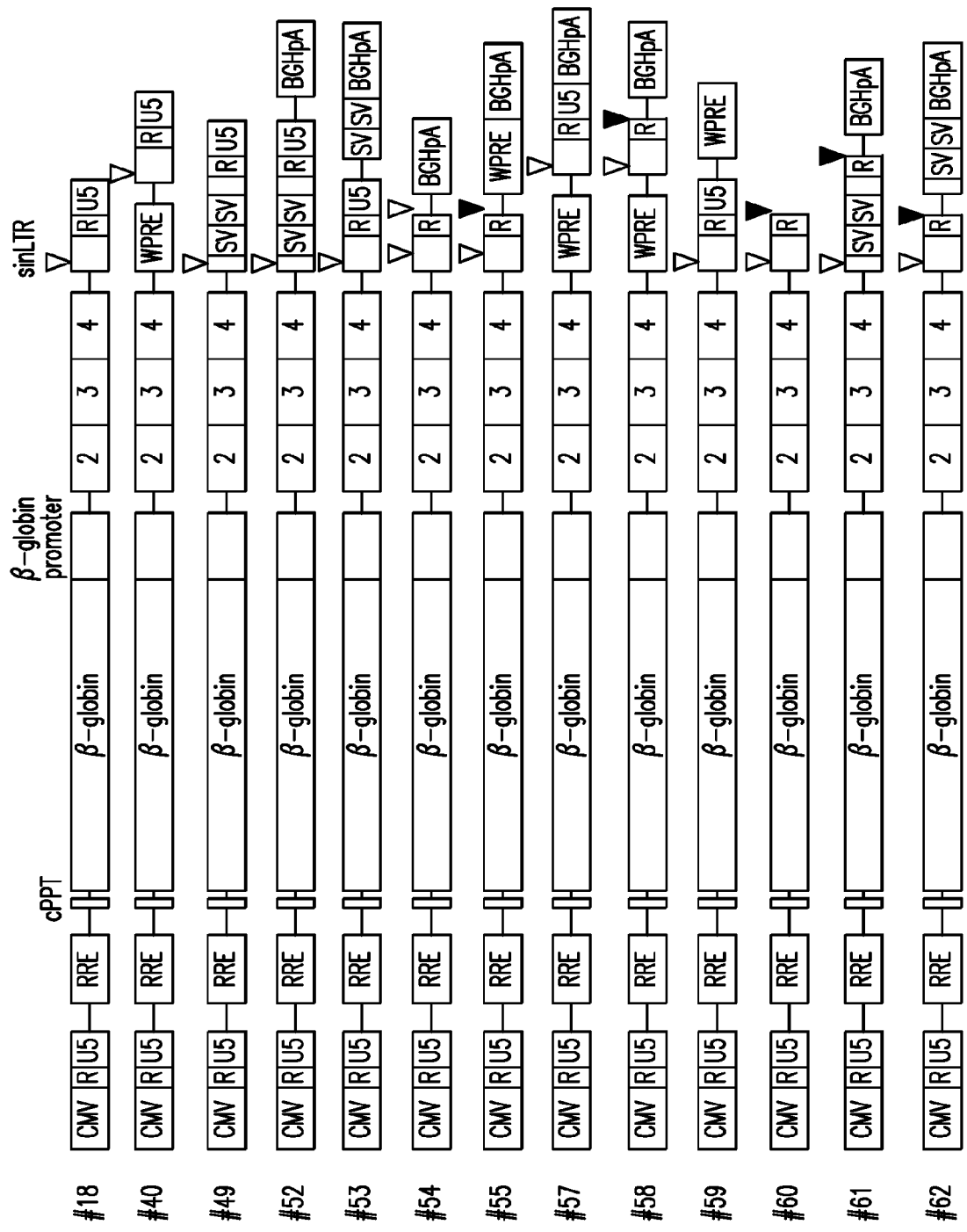

FIGS. 10A-10B depict various recombinant vectors comprising the presently disclosed expression cassettes. FIG. 10A depicts recombinant vector #18, and #49-#55. FIG. 10B shows recombinant vector #18, #40, #49, #52-#55, and #57-#62.

Figure 11:
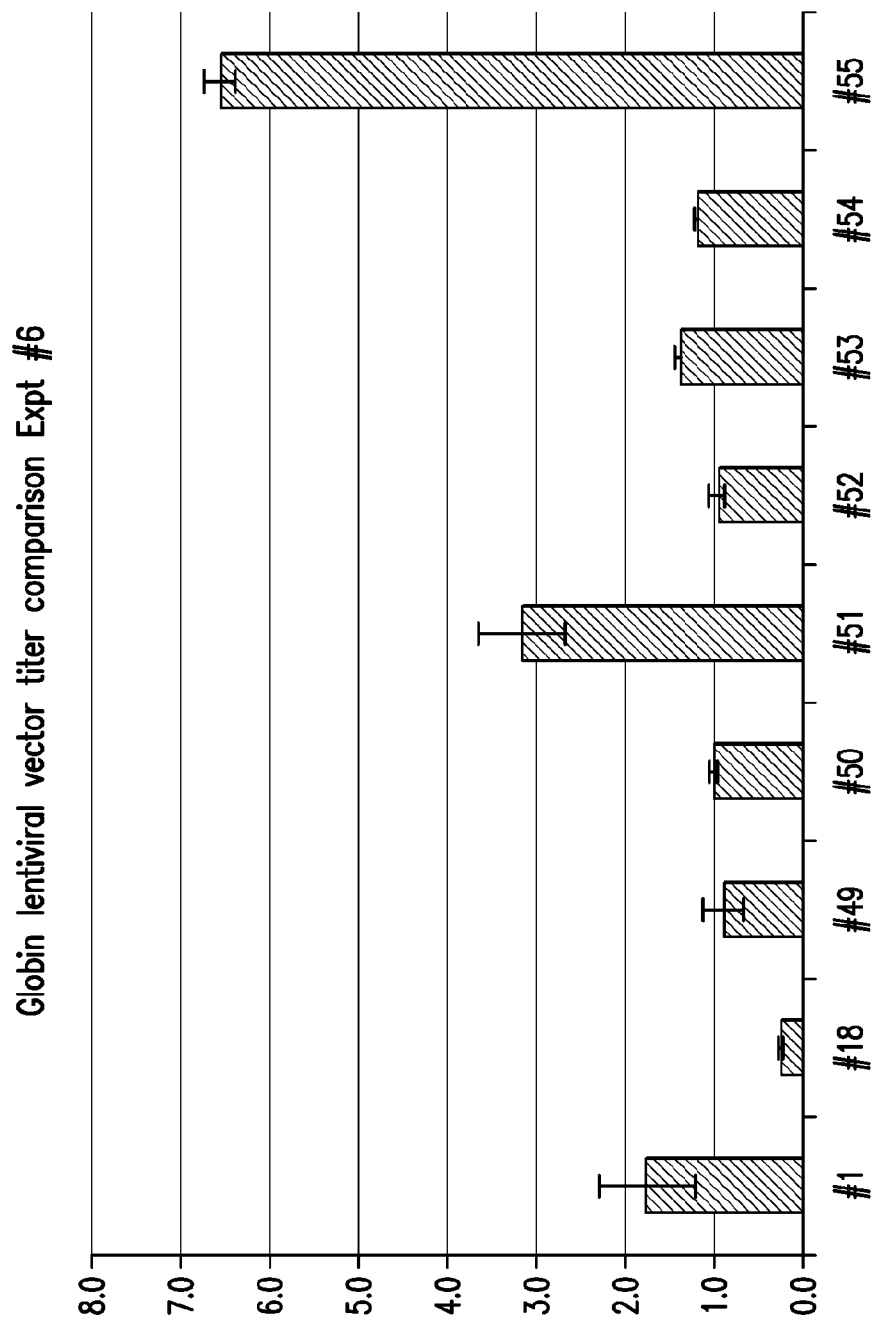

FIG. 11 represents the titer of the recombinant vectors comprising the presently disclosed expression cassettes.

Figure 12:
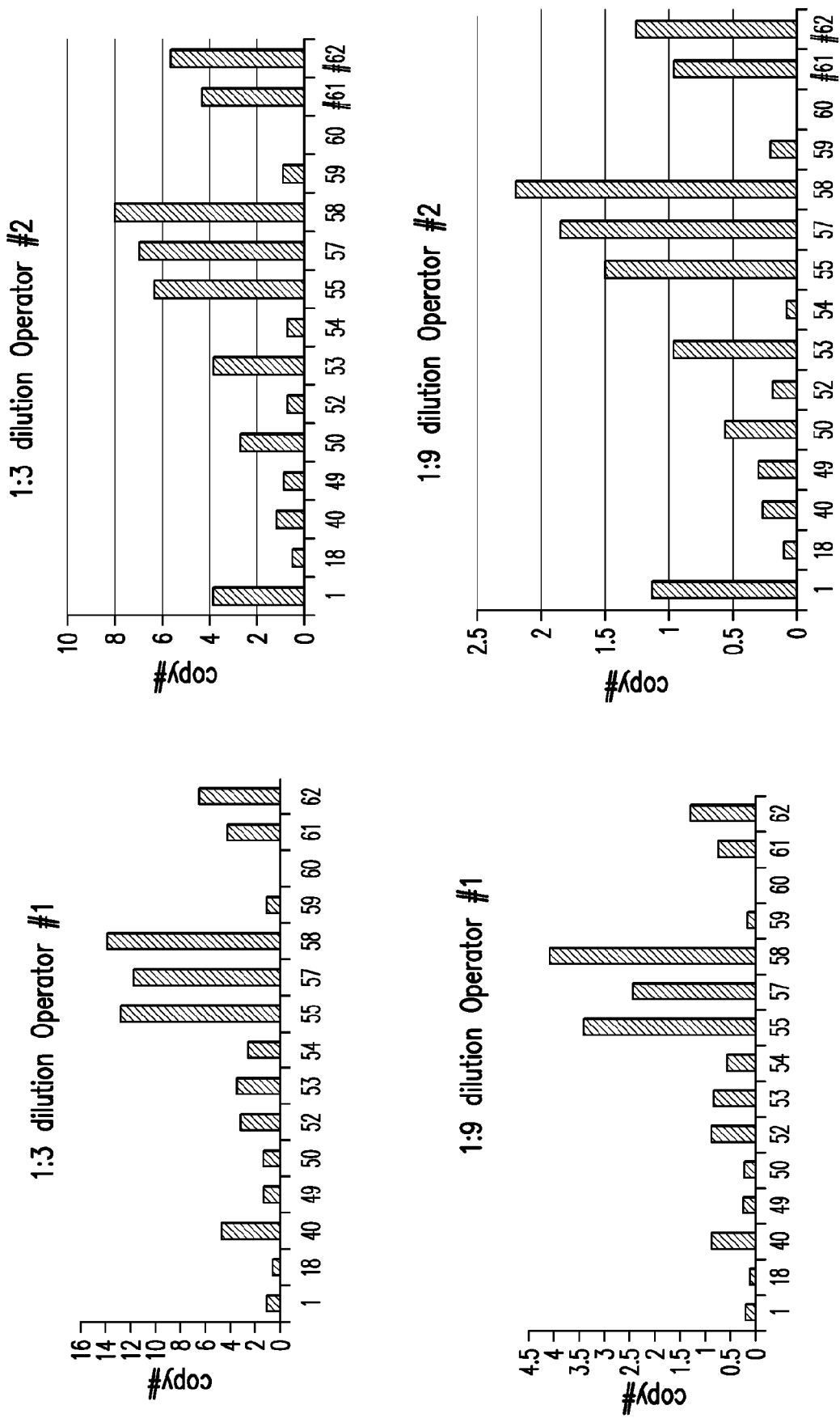

FIG. 12 represents the titer of the recombinant vectors comprising the presently disclosed expression cassettes.

Figure 13:
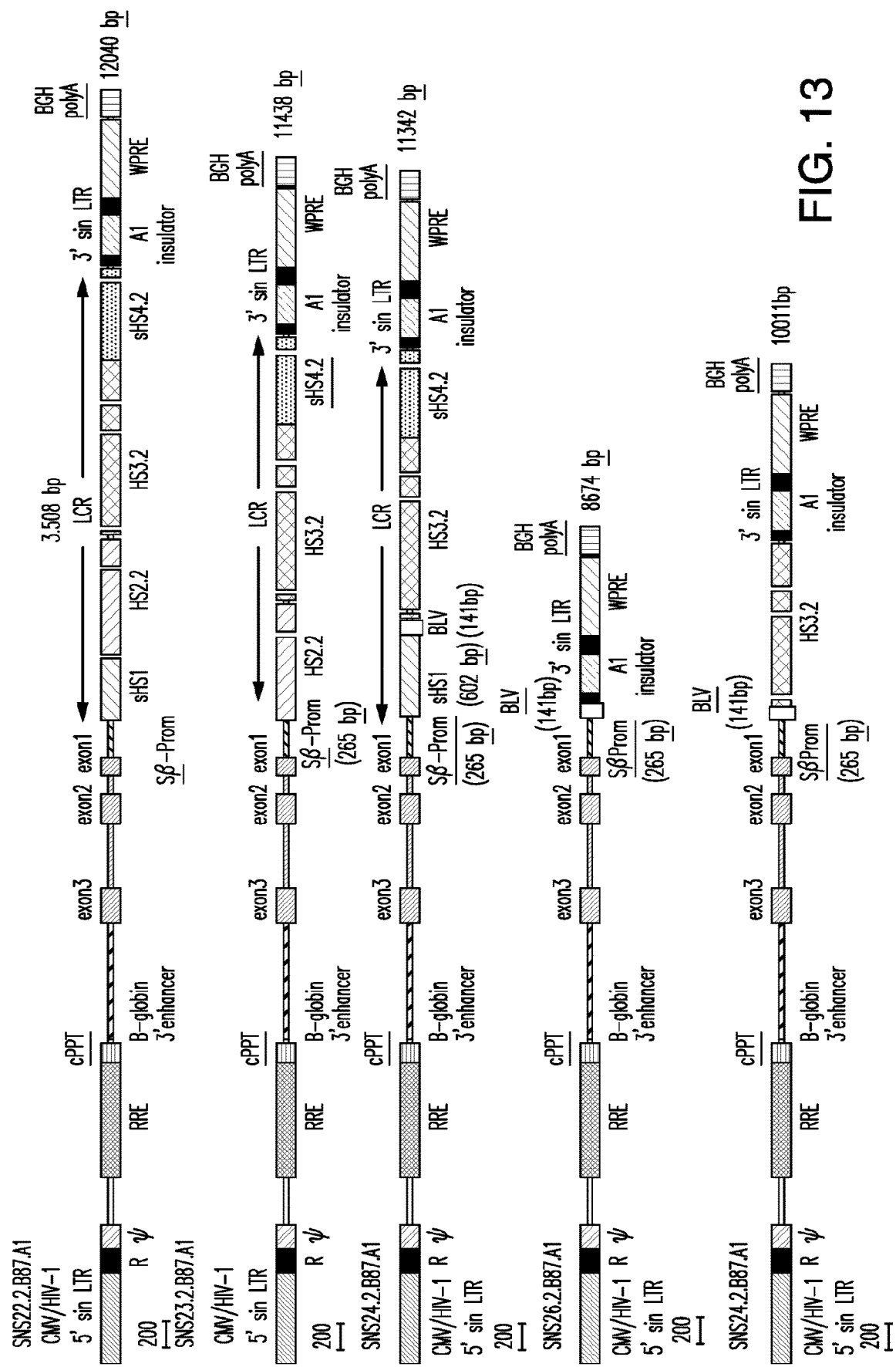

FIG. 13 depicts recombinant vectors comprising expression cassettes in accordance with certain non-limiting embodiments of the presently disclosed subject matter.

Figure 14:
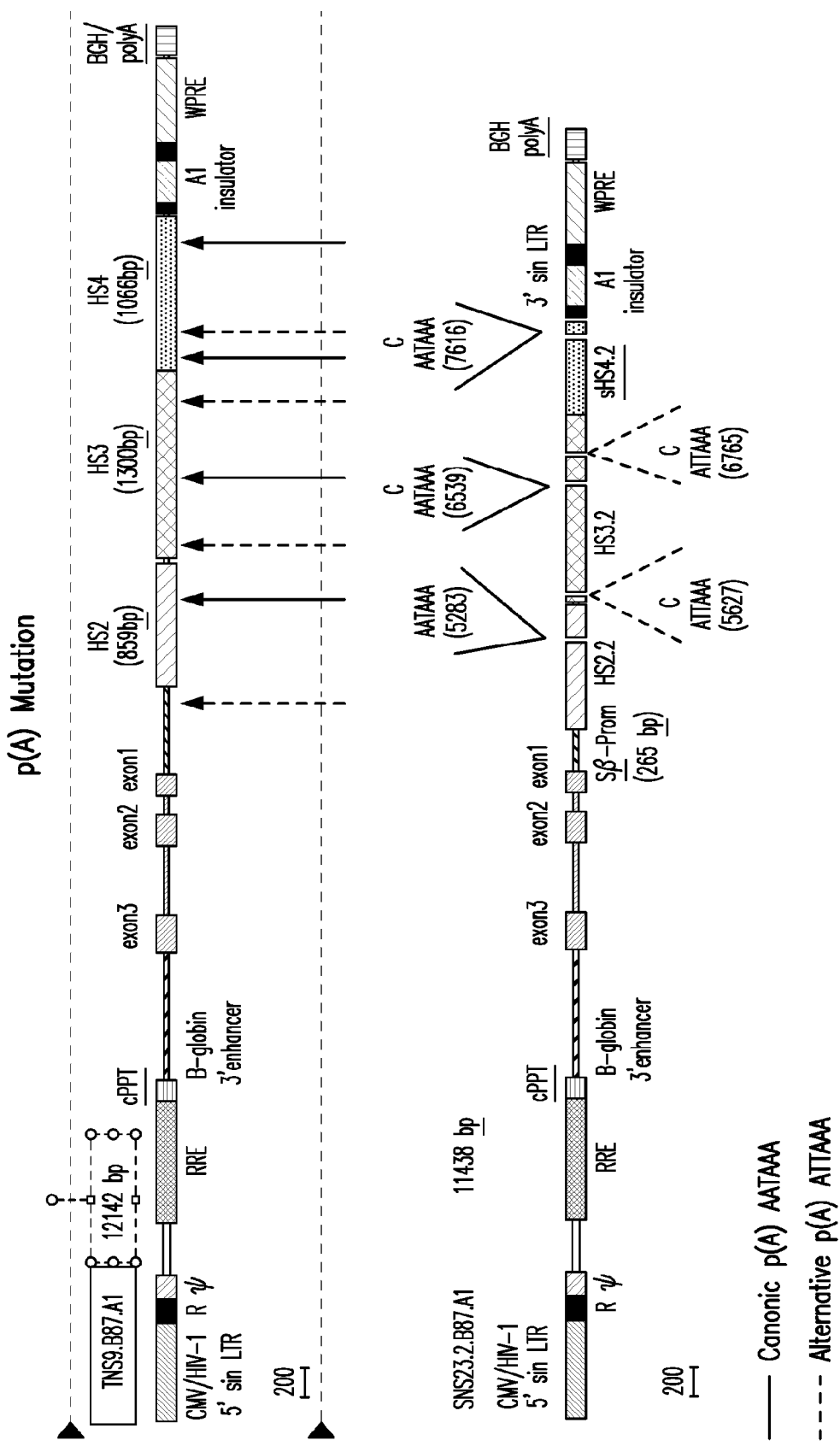

FIG. 14 depicts recombinant vectors comprising expression cassettes in accordance with certain non-limiting embodiments of the presently disclosed subject matter.

Figure 15:
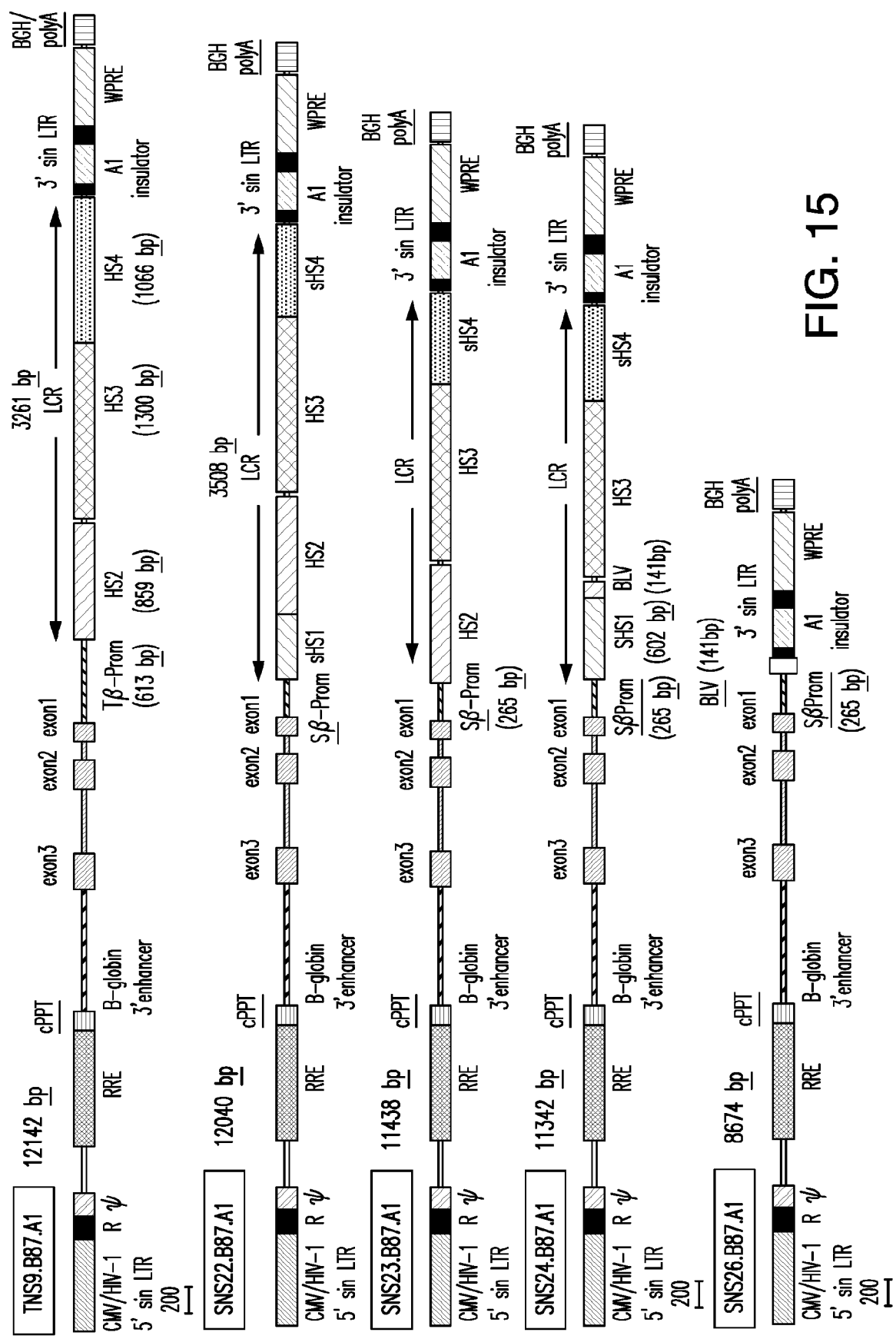

FIG. 15 depicts recombinant vectors comprising expression cassettes in accordance with certain non-limiting embodiments of the presently disclosed subject matter.

Figure 16:
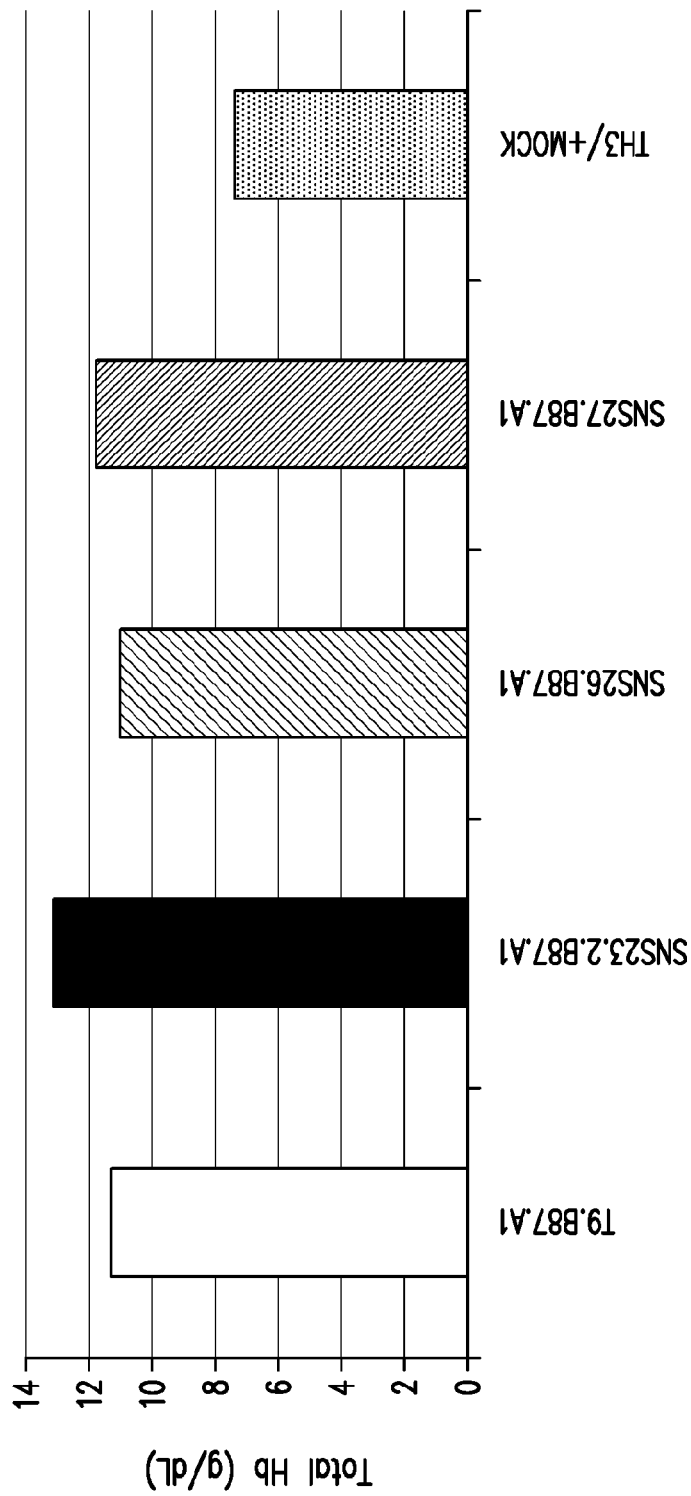

FIG. 16 depicts the average Hb production for vectors (TNS9.B87.A1 SNS23.2.B87.A1, SNS26.B87.A1, and SNS27.2B.87.A1).

Figure 17:
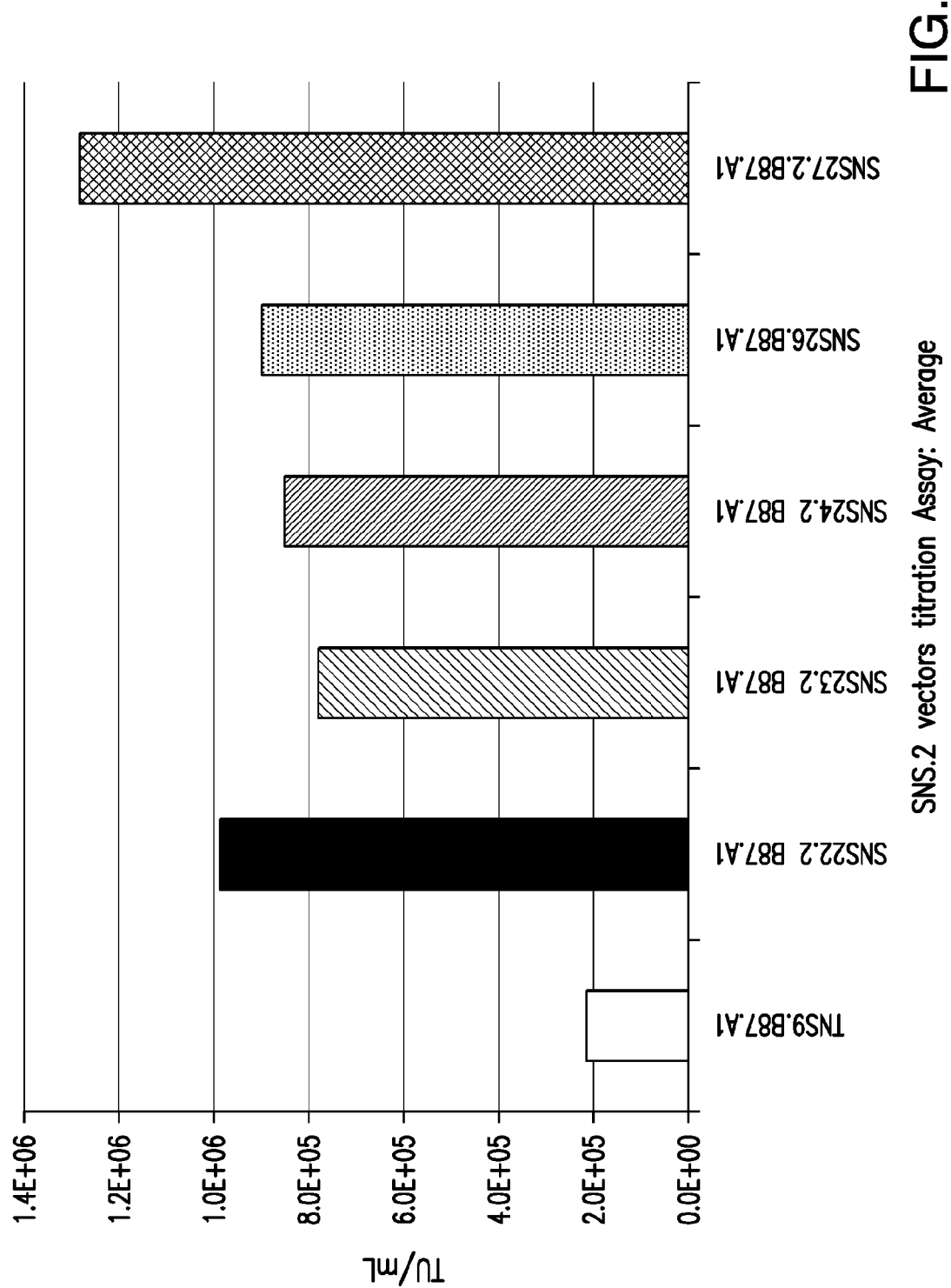

FIG. 17 depicts the titration assay relative to various vectors.

Figure 18:
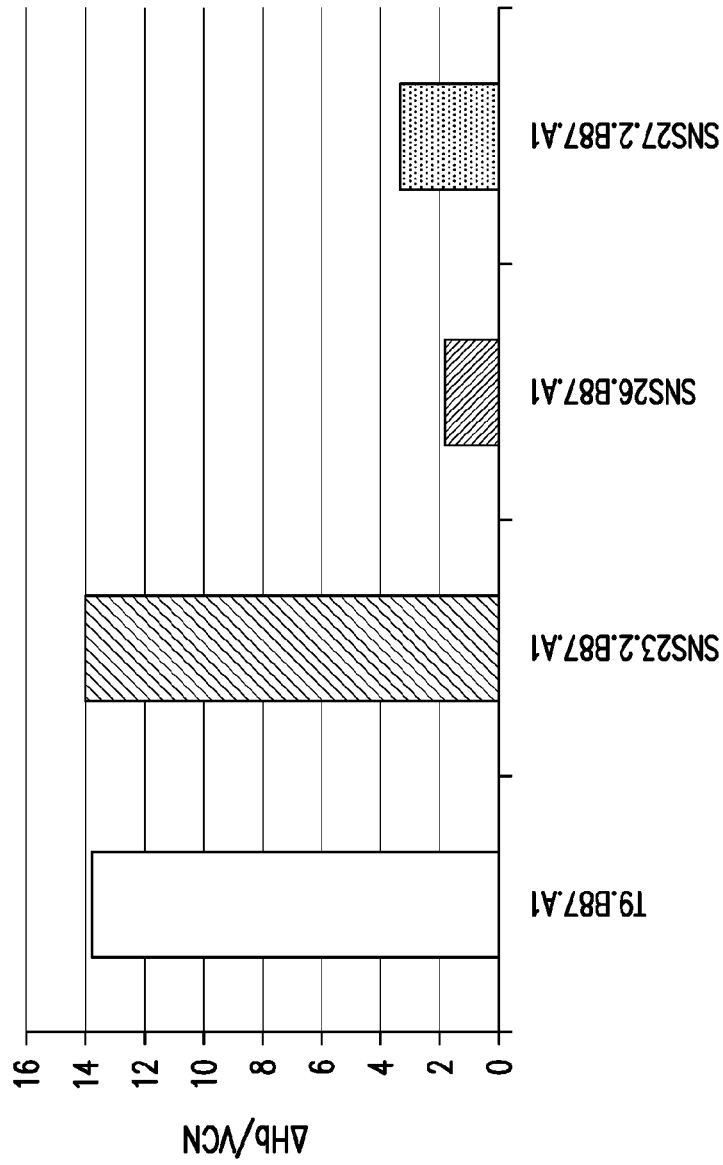

FIG. 18 depicts the average of ΔHb normalized per VCN for various vectors.

Figure 19:
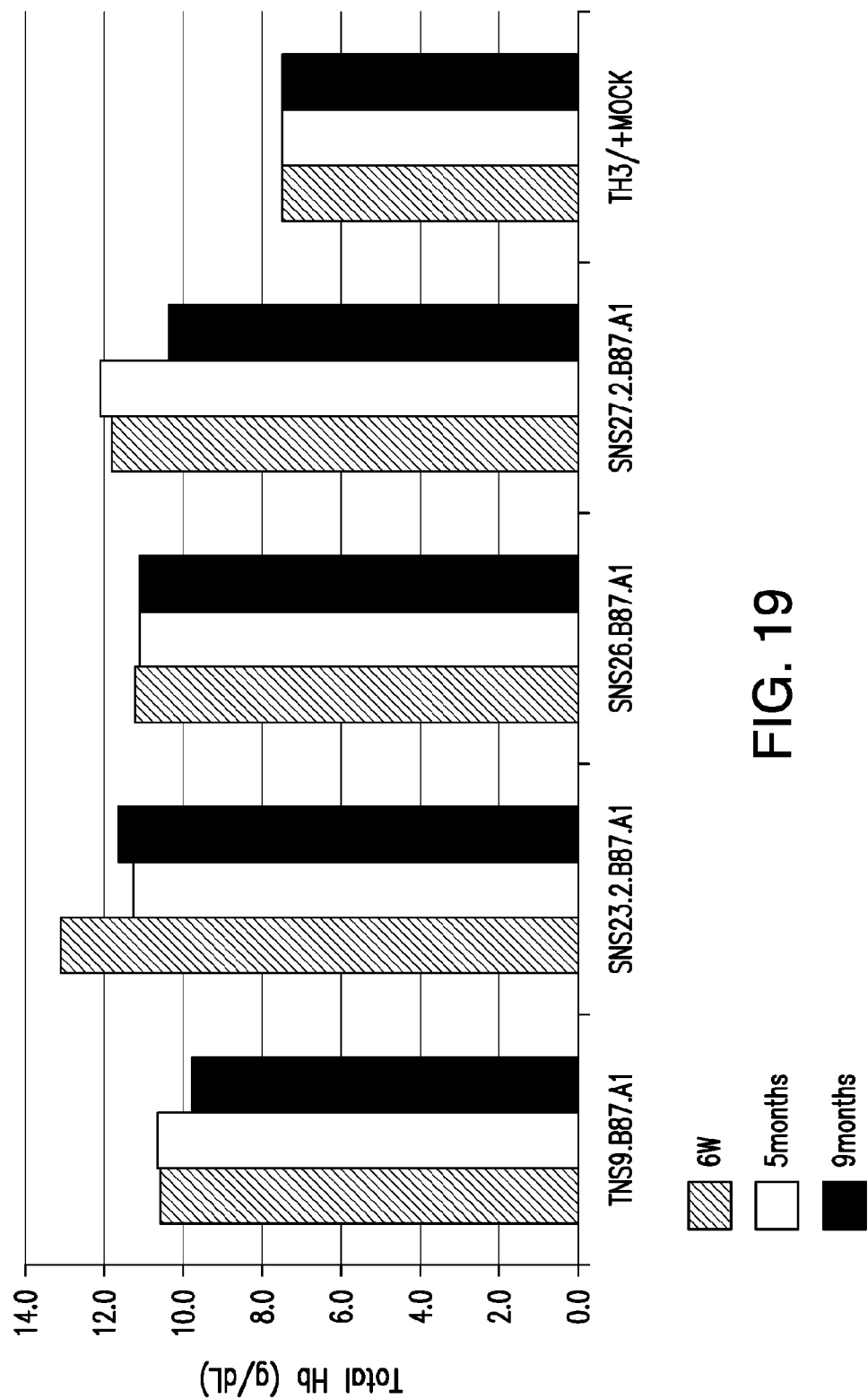

FIG. 19 depicts the average of total Hemoglobin (Hb) in thalassemic mouse peripheral blood at time points of 6-week, 5-month, and 9-month.

Figure 20:
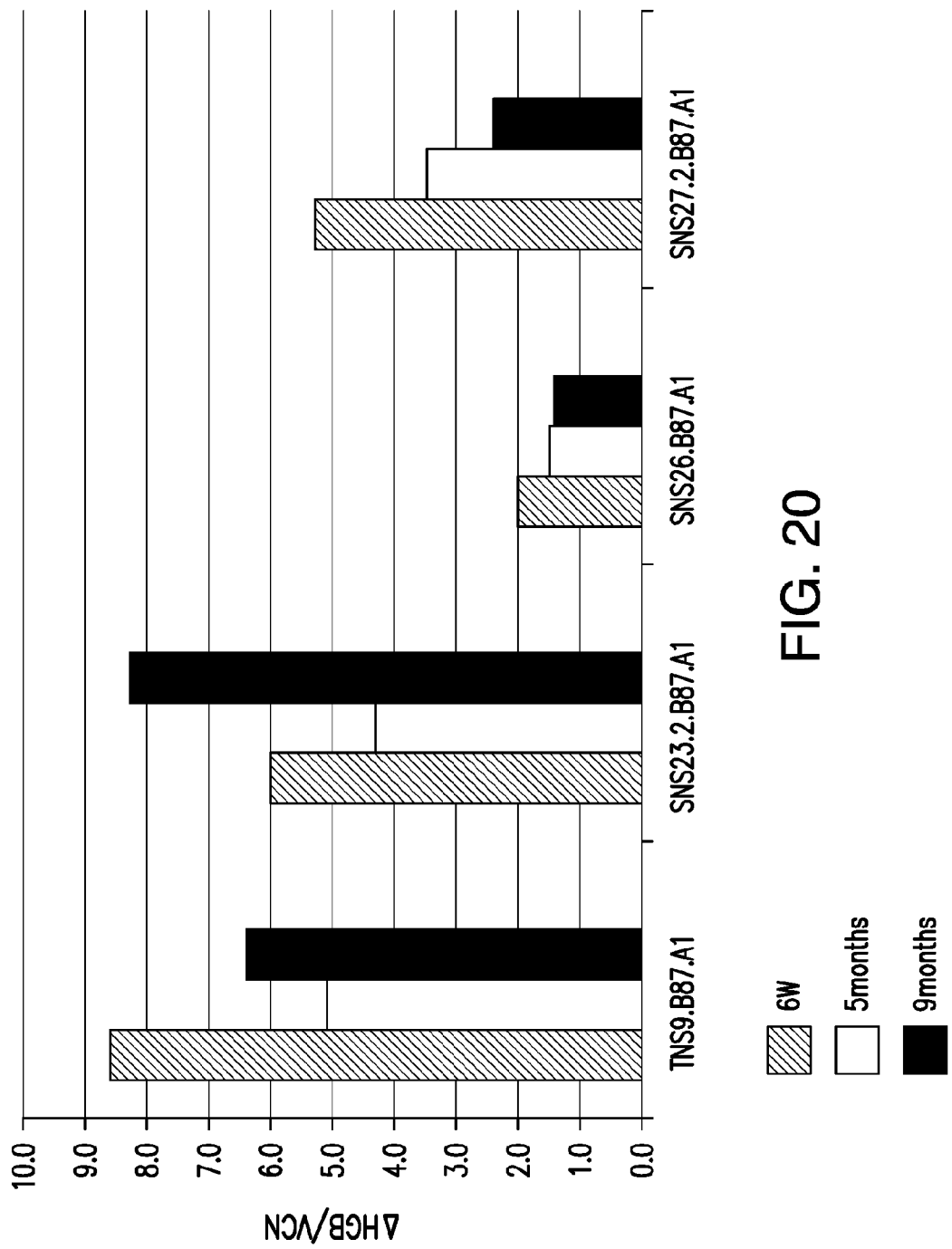

FIG. 20 depicts the average gain in Hb level (ΔHb) normalized to vector copy (VCN) at time points of 6-week, 5-month, and 9-month. ΔHb=Hb level−7.5 (baseline level in thalassemic mice).

DETAILED DESCRIPTION OF THE INVENTION

The presently disclosed subject matter generally provides expression cassettes that allow for expression of a globin gene (e.g., human β-globin gene). In certain non-limiting embodiments, the expression cassette comprises at least one insulator comprising the CTCF binding site sequence set forth in SEQ ID NO:18, for example, but not limited to, an insulator comprising the nucleotide sequence set forth in SEQ ID NO: 1, SEQ ID NO: 24, SEQ ID NO: 25, or SEQ ID NO: 27 and a globin gene or a functional portion thereof operably linked to a β-globin locus control region (LCR). The expression of the globin gene induced by the presently disclosed expression cassettes is erythroid-specific, differentiation stage-specific, high-level, and sustained. The presently disclosed subject matter also provides recombinant vectors, non-naturally occurring or engineered nucleases, and non-naturally occurring or engineered CRISPR-Cas systems comprising such expression cassettes, and cells transduced with such expression cassettes, recombinant vectors, nucleases and CRISPR-Cas systems. The presently disclosed expression cassettes and vectors comprising thereof provide for a safe gene transfer therapy as therapeutic transgene expression is achieved (e.g., a therapeutically relevant level of hemoglobin is produced) with a low vector copy number per cell (e.g., 0.5-2, 1-2, or even 0.5-1). In addition, the presently disclosed subject matter provides methods of using such transduced cells for treating a hemoglobinopathy (e.g., β-thalassemia and sickle cell anemia).

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "expression cassette" refers to a nucleic acid construct, generated recombinantly or synthetically, with a series of specified nucleic acid elements, which permit transcription of a particular nucleic acid in a target cell. The expression cassette can be incorporated into a plasmid, chromosome, mitochondrial DNA, plastid DNA, virus or nucleic acid region. The expression cassette portion can include a gene to be transcribed and elements that control the expression of the gene (e.g., a promoter).

As used herein, the term "β-globin locus control region (LCR)" refers to a polynucleotide composed of one or more Dnase I hypersensitive site (HS) regions, including a HS1 region, a HS2 region, a HS3 region, and a HS4 region. The structure of many LCRs of the β-globin genes have been published, e.g., human (Li et al., *J. Biol. Chem.* (1985); 260:14,901; Li et al., *Proc. Natl. Acad. Sci.* (1990) 87:8207); mouse (Shehee et al., *J. Mol. Biol.* (1989); 205:41); rabbit (Margot et al., J. Mol. Biol. (1989); 205:15); and goat (Li, Q., et al., *Genomics* (1991); 9:488), each of which are incorporated by reference herein. In certain embodiments, the β-globin LCR comprises a HS2 region (e.g., a β-globin LCR comprising a HS2 region, a HS3 region and a HS4 region; and a β-globin LCR comprising a HS1 region, a HS2 region, a HS3 region and a HS4 region). In certain embodiments, the β-globin LCR does not comprise a HS2 region (e.g., a β-globin LCR comprising or consisting essentially of a HS1 region, a HS3 region, a HS4 region). In certain embodiments, the β-globin LCR does not comprise a HS2 region or a HS1 region (e.g., a β-globin LCR comprising or consisting essentially of a HS3 region and a HS4 region). In certain embodiments, the β-globin LCR does not comprise a HS1 region, a HS2 region or a HS4 region (e.g., a β-globin LCR comprising or consisting essentially of a HS3 region).

As used herein, the term "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention or may have reduced or eliminated expression of a native gene.

As used herein, the term "globin" refers to a family of heme-containing proteins that are involved in the binding and transport of oxygen. Subunits of vertebrate and invertebrate hemoglobins, vertebrate and invertebrate myoglobins or mutants thereof are included by the term globin.

As used herein, the term "wild-type" refers to the normal gene, virus, or organism found in nature without any mutation or modification.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene region, loci (locus) defined from linkage analysis, exons, introns, messenger RNA (mRNA), transfer RNA, ribosomal RNA, short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide can comprise one or more modified nucleotides, such as methylated nucleotides and nucleotide analogs. In particular embodiments, the presently disclosed subject matter provides polynucleotides encoding one or more globin genes or functional portions thereof. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. Such polynucleotides need not be about 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152: 507).

For example, stringent salt concentration can ordinarily be less than about 750 mM NaCl and 75 mM trisodium citrate, e.g., less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, e.g., at least about 50% formamide. Stringent temperature conditions can ordinarily include temperatures of at least about 30° C., e.g., of at least about 37° C. or of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In certain embodiments, hybridization occurs at 37° C. in 500 mM NaCl, 50 mM trisodium citrate, 1% SDS, 35% formamide, and 100 µg/ml denatured salmon sperm DNA (ssDNA). In certain embodiments, hybridization occurs at 42° C. in 250 mM NaCl, 25 mM trisodium citrate, 1% SDS, 50% formamide, and 200 µg/ml ssDNA. Useful variations on these conditions can be readily apparent to those skilled in the art.

For most applications, washing steps that follow hybridization can also vary in stringency. Wash stringency conditions can be defined by salt concentration and by temperature. As above, wash stringency can be increased by decreasing salt concentration or by increasing temperature. For example, stringent salt concentration for the wash steps can be less than about 30 mM NaCl and 3 mM trisodium citrate, e.g., less than about 15 mM NaCl and 1.5 mM trisodium citrate. Stringent temperature conditions for the wash steps can ordinarily include a temperature of at least about 25° C., e.g., of at least about 42° C., or of at least about 68° C. In certain embodiments, wash steps occur at 25° C. in 30 mM NaCl, 3 mM trisodium citrate, and 0.1% SDS. In certain embodiments, wash steps occur at 42° C. in 15 mM NaCl, 1.5 mM trisodium citrate, and 0.1% SDS. In certain embodiments, wash steps occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Rogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

As used herein, the terms "polypeptide" and "protein" are used interchangeably to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. Particular embodiments of the presently disclosed subject matter also include polypeptide "variants." Polypeptide "variant" refers to polypeptides that are distinguished from a reference polypeptide by the addition, deletion, truncations, and/or substitution of at least one amino acid residue, and that retain a biological activity. In certain embodiments, a polypeptide variant is distinguished from a reference polypeptide by one or more substitutions, which may be conservative or non-conservative, as known in the art. In certain embodiments, a variant polypeptide includes an amino acid sequence having at least about 50%, 55%, 60%, 65%, 70%, 75%, 80%, 85%, 90%, 91%, 92%, 93%, 94%, 95%, 96%, 97%, 98%, 99% or more sequence identity or similarity to a corresponding sequence of a reference polypeptide. In certain embodiments, the amino acid additions or deletions occur at the C-terminal end and/or the N-terminal end of the reference polypeptide. In certain embodiments, the amino acid deletions include C-terminal truncations of about 1, about 2, about 3, about 4, about 5, about 6, about 7, about 8, about 9, about 10, about 15, about 20, about 25, about 30, about 35, about 40, about 45, 50, about 55, about 60, about 65, about 70, about 75, about 80, about 85, about 90, about 95, about 100, about 105, about 110, about 115, about 120, about 125, about 130, about 135, about 140, about 145, about 150, about 155, about 160, about 165, about 170, or about 175 or more amino acids, including all intervening numbers of amino acids, e.g., 25, 26, 27, 29, 30 . . . 100, 101, 102, 103, 104, 105 . . . 170, 171, 172, 173, 174, etc.

As noted above, polypeptides of the presently disclosed subject matter may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, Proc. Natl. Acad. Sci. USA. 82: 488-492), Kunkel et al., (1987, Methods in Enzymol, 154: 367-382), U.S. Pat. No. 4,873,192, Watson, J. D. et al., Molecular Biology of the Gene, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

As used herein, the term "substantially identical" refers to a polypeptide or a polynucleotide exhibiting at least 50% identity to a reference amino acid sequence (for example, any one of the amino acid sequences described herein) or a nucleic acid sequence (for example, any one of the nucleic acid sequences described herein). Preferably, such a sequence is at least about 60%, e.g., about 80%, about 85%, about 90%, about 95%, or about 99% identical at the amino acid level or nucleic acid to the sequence used for comparison.

Sequence identity or homology is typically measured using sequence analysis software (for example, Sequence Analysis Software Package of the Genetics Computer Group, University of Wisconsin Biotechnology Center, 1710 University Avenue, Madison, Wis. 53705, BLAST, BEST-FIT, GAP, or PILEUP/PRETTYBOX programs). Such software matches identical or similar sequences by assigning degrees of homology to various substitutions, deletions, and/or other modifications. In an exemplary approach to determining the degree of identity or homology, a BLAST program may be used, with a probability score between e-3 and e-100 indicating a closely related sequence. The percentage of identity between two sequences can also be determined with programs such as DNAMAN (Lynnon Biosoft, version 3.2). Using this program two sequences can be aligned using the optimal alignment algorithm (Smith and Waterman, 1981). After alignment of the two sequences the percentage identity can be calculated by dividing the number of identical nucleotides between the two sequences by the length of the aligned sequences minus the length of all gaps.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation.

As used herein, a "single guide RNA" or a "synthetic guide RNA" refers to the polynucleotide sequence comprising the guide sequence, the tracr sequence and the tracr mate sequence. The term "guide sequence" refers to the about 20 bp sequence within the guide RNA that specifies the target site and may be used interchangeably with the terms "guide" or "spacer". The term "tracr mate sequence" may also be used interchangeably with the term "direct repeat(s)".

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

As used herein, the term "expression" refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" or "individual" refers to a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys. The term "immunocompromised" as used herein refers to a subject who has an immunodeficiency. The subject is very vulnerable to opportunistic infections, infections caused by organisms that usually do not cause disease in a person with a healthy immune system, but can affect people with a poorly functioning or suppressed immune system.

As used herein, the term "isolated cell" refers to a cell that is separated from the molecular and/or cellular components that naturally accompany the cell. As used herein, the term "isolated" refers to material that is free, substantially free, or essentially free to varying degrees from components which normally accompany it as found in its native state. "Isolate" denotes a degree of separation from original source or surroundings.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, at least about $10^3$ cells, at least about $10^4$ cells, at least about $10^5$ cells, at least about $10^6$ cells, at least about $10^7$ cells, or at least about $10^8$ cells expressing similar or different phenotypes.

As used herein, the term "cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

As used herein, the term "cleavage half-domain" refers to a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

As used herein, the term "chromosome" refers to a chromatin complex comprising all or a portion of the genome of a cell. The genome of a cell is often characterized by its karyotype, which is the collection of all the chromosomes that comprise the genome of the cell. The genome of a cell can comprise one or more chromosomes.

As used herein, the term "gene" includes a DNA region encoding a gene product, as well as all DNA regions which regulate the production of the gene product, whether or not such regulatory sequences are adjacent to coding and/or transcribed sequences. Accordingly, a gene includes, but is not limited to, promoter sequences, terminators, translational regulatory sequences such as ribosome binding sites and internal ribosome entry sites, enhancers, silencers, insulators, boundary elements, replication origins, matrix attachment sites and locus control regions The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

A "functional region" or "functional portion" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional region can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. The ability of a protein to interact with another protein can be determined, for example, by co-immunoprecipitation, two-hybrid assays or complementation, both genetic and biochemical.

As used herein, the term "promoter" refers to a recognition site of a polynucleotide (DNA or RNA) to which an RNA polymerase binds. The term "enhancer" refers to a segment of DNA which contains sequences capable of providing enhanced transcription and in some instances can function independent of their orientation relative to another control sequence. An enhancer can function cooperatively or additively with promoters and/or other enhancer elements.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

As used herein, the term "modulate" refers to altering positively or negatively. Exemplary modulations include an about 1%, about 2%, about 5%, about 10%, about 25%, about 50%, about 75%, or about 100% change.

As used herein, the term "increase" refers to alter positively by at least about 5%, including, but not limited to, alter positively by about 5%, by about 10%, by about 25%, by about 30%, by about 50%, by about 75%, or by about 100%.

As used herein, the term "reduce" refers to alter negatively by at least about 5% including, but not limited to, alter negatively by about 5%, by about 10%, by about 25%, by about 30%, by about 50%, by about 75%, or by about 100%.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value.

II. Insulators

Several cases of vector-related malignant transformation have been reported in clinical settings, associated with the activation of cellular oncogenes by vector-encoded enhancers (Baum et al. (2006), Nienhuis et al. (2006), Ramezani et al. (2006)) and various vector modifications have been performed or proposed to reduce vector genotoxicity (Baum et al. (2006), Nienhuis et al. (2006), Ramezani et al. (2006)). A class of DNA elements known as chromatin insulators has been recognized as one approach to improve vector safety and performance (Emery (2011)).

Insulators are naturally occurring DNA elements that help from the functional boundaries between adjacent chromatin domains. Insulators bind proteins that modify chromatin and alter regional gene expression. The placement of insulators in the vectors described herein offer various potential benefits including, but not limited to, 1) shielding of the vector from positional effect variegation of expression by flanking chromosomes (i.e., barrier activity, which may decrease position effects and vector silencing); and 2) shielding flanking chromosomes from insertional transactivation of endogenous gene expression by the vector (enhancer blocking). There are two basic classes of chromatin insulators: (a) barrier insulators that block the encroachment of silencing heterochromatin into adjoining regions of open chromatin that are transcriptionally permissive, and (b) enhancer blocking insulators that prevent enhancer-mediated transcriptional activation of adjoining regions. The sequences that mediate these activities are physically separable and mechanistically distinct (Recillas-Targa et al. (2002)). Chromatin insulators do not exhibit inherent transcriptional enhancing or repressing activities on their own. As such, they make ideal elements for reducing the interaction between gene transfer vectors and the target cell genome. Insulators can help to preserve the independent function of genes or transcription units embedded in a genome or genetic context in which their expression may otherwise be influenced by regulatory signals within the genome or genetic context (see, e.g., Burgess-Beusse et al. (2002) *Proc. Nat'l Acad. Sci. USA,* 99: 16433; and Zhan et al. (2001) *Hum. Genet.,* 109: 471).

The problems created by insertional mutagenesis of viral vectors are widely known (Nienhuis (2013), Baum et al. (2006), Nienhuis et al. (2006)) as is the evidence that the risks of genotoxicity can be reduced by the use of chromatin insulators (Arumugam et al. (2007), Emery (2011), Evans-Galea et al. (2007), Rivella et al. (2000), Emery et al. (2000), Emery et al. (2002), Yannaki et al. (2002), Hino et al. (2004), Ramezani et al. (2003), Ramezani et al. (2008)). The presently disclosed subject matter provides novel insulators that are powerful enhancer blocking insulators, and certain insulators additionally possess barrier insulator activity. In vertebrates, the function of enhancer blocking insulators is mediated through the zinc-finger DNA-binding factor CTCF (Gaszner and Felsenfeld (2006), Wallace and Felsenfeld (2007)). In general, these elements are thought to function through physical loop structures, which are established by CTCF-mediated interactions between adjacent insulator elements or through CTCF-mediated tethering of the chromatin fiber to structural elements within the nucleus. The first characterized vertebrate chromatin insulator is located within the chicken β-globin locus control region. This element, which contains a DNase-I hypersensitive site-4 (cHS4), appears to constitute the 5' boundary of the chicken β-globin locus (Prioleau et al. (1999) EMBO J. 18: 4035-4048). A 1.2-kb region containing the cHS4 element displays classic insulator activities, including the ability to block the interaction of globin gene promoters and enhancers in cell lines (Chung et al. (1993) Cell, 74: 505-514), and the ability to protect expression cassettes in *Drosophila* (Id.), transformed cell lines (Pikaart et al. (1998) *Genes Dev.* 12: 2852-2862), and transgenic mammals (Wang et al. (1997) *Nat. Biotechnol.,* 15: 239-243; Taboit-Dameron et al. (1999) Transgenic Res., 8: 223-235) from position effects. Much of this activity is contained in a 250-bp region. Within this stretch is a 49-bp cHS4 element (Chung et al. (1997) *Proc. Natl. Acad. Sci., USA,* 94: 575-580) that interacts with the zinc finger DNA binding protein CTCF implicated in enhancer-blocking assays (Bell et al. (1999) *Cell,* 98: 387-396).

Insulators, such as cHS4, can block the interaction between enhancers and promoters when placed between these elements (Evans-Galea et al. (2007), Chung et al. (1997), Bell et al. (1999), Ryu et al. (2007), Ryu et al. (2008)). Several studies have demonstrated the ability of the cHS4 insulator to reduce position-effect silencing of gammaretroviral vectors (Evans-Galea et al. (2007), Rivella et al. (2000), Emery et al. (2000), Emery et al. (2002), Yannaki et al. (2002), Hino et al. (2004), Ramezani et al. (2006), Yao et al. (2003), Nishino et al. (2006), Aker et al. (2007), Li and Emery (2008)), and lentiviral vectors (Bank et al. (2005), Arumugam et al. (2007), Puthenveetil et al. (2004), Evans-Galea et al. (2007), Ramezani et al. (2003), Aker et al. (2007), Ma et al. (2003), Chang et al. (2005), Pluta et al. (2005)). Those appropriately designed studies demonstrated that inclusion of the 1.2 kb version of the cHS4 insulator increased the likelihood and/or consistency of vector transgene expression in at least some settings (Arumugam et al. (2007), Emery (2011), Evans-Galea et al. (2007), Emery et al. (2002), Yannaki et al. (2002), Hino et al. (2004), Ramezani et al. (2006), Aker et al. (2007), Li and Emery (2008), Pluta et al. (2005). Jakobsson et al. (2004)). Nevertheless, the degree of protection afforded by the cHS4 insulator is far from complete. In addition, the inclusion of the 1.2 Kb cHS4 can adversely affect vector titers while the smallest cHS4 core has been proven ineffective (Aker et al. (2007), Jakobsson et al. (2004)). By contrast, the insulators of the presently disclosed subject matter do not affect adversely the titers of viral vectors, and are more powerful and effective than the cHS4 insulator.

The presently disclosed insulators are identified through genomic approaches, e.g., using genomic approaches to identify insulators that are powerful enhancer blockers as well as barrier insulators of the human genome. The presently disclosed insulators enhance the safety of gene therapy (e.g., stem cell gene therapy, globin gene therapy). For gene therapy of the hemoglobinopathies, powerful enhancers are required to achieve therapeutic levels of globin gene expression. Powerful insulators therefore represent one means to protect the genomic environment from the powerful enhancers of the integrating vectors.

The presently disclosed insulators possess powerful enhancer blocking activity. For example, and not by way of limitation, an insulator of the present disclosure can reduce the activity of an enhancer element by at least about 10%, at least about 20%, at least about 30%, at least about 40%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98% or at least about 99%. In certain embodiments, the insulators possess barrier activity in addition to enhancer blocking activity. The presently disclosed insulators substantially decrease the risks of insertional mutagenesis and genotoxicity associated with viral vectors. Furthermore, when at least one presently disclosed insulator is incorporated into a vector, the insulator(s) does not adversely effect vector titers of the vector. In certain embodiments, the presently disclosed insulators (e.g., insulator A1) increase the in vivo expression of the globin gene or functional portion thereof.

In certain embodiments, the insulator comprises a Transcriptional repressor CTCF binding site, which has the nucleotide sequence set forth in SEQ ID NO: 18, which is provided below:

[SEQ ID NO: 18]
CACCAGGTGGCGCT.

In certain embodiments, the insulator has the nucleotide sequence set forth in SEQ ID NO:1, which is provided below, or a sequence which is at least about 80%, about 85%, about 90%, about 95%, about 98, about 99% or about 100% % identical (homologous), to SEQ ID NO:1. SEQ ID NO: 1 is provided below.

[SEQ ID NO: 1]
TCCTTCCTTTCTAAATGACGAGAGAGACAGAAGAATTCTTCAAGGTTAGT

GTGTCCAGCATGCAACCTTTCCTTCCTGGATGAGCATCCCTGGAGTAGGA

GAGCCAGCCTGCCTCCTGCGCTGGCACAGAGCCCGGTTCCCTAGACAACT

GCCTCTCCAAATCTGATGTCCAGCGCCACCTGGTGTCCACATCAAGCAGA

CACAATTAATAGTCAACCTGTTCAGGAAAACTGTGAGGGGGAAAAAAAAG

AAAGAGGATTTATGAAGGGAAAAGAAAGTTTAGAGGATATGCCACGATTG

GCTAG

In certain embodiments, the insulator comprises or has the nucleotide sequence as set forth in SEQ ID NO:24, or a sequence which is at least about 80%, about 85%, about 90%, about 95%, about 98, about 99% or about 100% identical (homologous), to SEQ ID NO: 24. SEQ ID NO: 24 is provided below.

[SEQ ID NO: 24]
CCAATC GTGGCATATC CTCTAAACTT TCTTTTCCCT

TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG

TCTAGGGAAC CGGGCTCTGT GCCAGCGCAG GAGGCAGGCT

GGCTCTCCTA TTCCAGGGAT GCTCATCCAG GAAGGAAAGG

TTGCATGCTG GACACACTAA CCTTGAAGAA TTCTTCTGTC

TCTCTCGTCA TTTAGAAAGG AAGGA.

In certain embodiments, the insulator comprises or has the nucleotide sequence as set forth in SEQ ID NO:25 (which is the reverse complement of SEQ ID NO: 1), or a sequence which is at least about 80%, about 85%, about 90%, about 95%, about 98, about 99% or about 100% identical (homologous), to SEQ ID NO: 25. SEQ ID NO: 25 is provided below.

[SEQ ID NO: 25]
CTAGCCAATCGTGGCATATCCTCTAAACTTTCTTTTCCCTTCATAAATCC

TCTTTCTTTTTTTCCCCCTCACAGTTTTCCTGAACAGGTTGACTATTAA

TTGTGTCTGCTTGATGTGGACACCAGGTGGCGCTGGACATCAGATTTGGA

GAGGCAGTTGTCTAGGGAACCGGGCTCTGTGCCAGCGCAGGAGGCAGGCT

GGCTCTCCTACTCCAGGGATGCTCATCCAGGAAGGAAAGGTTGCATGCTG

GACACACTAACCTTGAAGAATTCTTCTGTCTCTCTCGTCATTTAGAAAGG

AAGGA

In certain embodiments, the insulator comprises or has the nucleotide sequence as set forth in SEQ ID NO: 27, or a sequence which is at least about 80%, about 85%, about 90%, about 95%, about 98, about 99% or about 100% identical (homologous), to SEQ ID NO: 27. SEQ ID NO: 27 is provided below.

[SEQ ID NO: 27]
ctggttctac tcattacatt ccaatcgtgg catatcctct aaactttctt ttcccttcat aaatcctctt tctttttttt cccctcaca gttttcctga acaggttgac tattaattgt gtctgcttga tgtggacacc aggtggcgct ggacatcaga tttggagagg cagttgtcta gggaaccggg ctctgtgcca gcgcaggagg caggctggct ctcctattcc agggatgctc atccaggaag gaaaggttgc atgctggaca cactaacctt gaagaattct tctgtctctc tcgtcattta gaaaggaagg In certain embodiments, the insulator comprises or has the nucleotide sequence as set forth in SEQ ID NO: 28, or a sequence which is at least about 80%, about 85%, about 90%, about 95%, about 98, about 99% or about 100% identical (homologous), to SEQ ID NO: 28. SEQ ID NO: 28 is provided below.

[SEQ ID NO: 28]
CCAATC GTGGCATATC CTCTAAACTT TCTTTTCCCT

TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG

TCTAGGGAAC CGGGCTCTGT GCCAGCGCAG GAGGCAGGCT

GGCTCTCCTA TTCCAGGGAT GCTCATCCAG GAAGGAAAGG

TTGCATGCTG GACACACTAA CCTTGAAGAA TTCTTCTGTC

TCTCTCGTCA TTTAGAAAGG AAGG

In certain embodiments, the insulator comprises or has the nucleotide sequence as set forth in hg18 coordinates 76229933 to 76230115 of chromosome 1.

In certain embodiments, the insulator comprises or has the nucleotide sequence between residues 68041 and 68160 (or SEQ ID NO: 29 provided below), or between residues and 68041 and 68210 (or SEQ ID NO: 30 provided below), or between residues 68041 and 68280 (or SEQ ID NO: 31 provided below), or between residues 68005 and 68305 (or SEQ ID NO: 24), of Homo sapiens chromosome 1 clone RP11-550H2, GenBank Accession No. AC092813.2, or a sequence at least about 80%, about 85%, about 90%, about 95%, about 98, about 99% or about 100% identical (homologous) thereto.

```
                                            (SEQ ID NO: 29)
TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG (SEQ ID NO: 30)
TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG

TCTAGGGAAC CGGGCTCTGT GCCAGCGCAG GAGGCAGGCT

GGCTCTCCTA (SEQ ID NO: 31)
TCATAAATCC TCTTTCTTTT TTTTCCCCCT CACAGTTTTC

CTGAACAGGT TGACTATTAA TTGTGTCTGC TTGATGTGGA

CACCAGGTGG CGCTGGACAT CAGATTTGGA GAGGCAGTTG

TCTAGGGAAC CGGGCTCTGT GCCAGCGCAG GAGGCAGGCT

GGCTCTCCTA TTCCAGGGAT GCTCATCCAG GAAGGAAAGG

TTGCATGCTG GACACACTAA CCTTGAAGAA TTCTTCTGTC
```

III. Expression Cassettes

The presently disclosed subject matter provides expression cassettes comprising one or more insulators. In certain embodiments, an expression cassette comprises at least one insulator disclosed in Section II, and a globin gene or a functional portion thereof. In certain embodiments, an expression cassette comprises at least one insulator comprising or having the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, or SEQ ID NO: 31, and a globin gene or a functional portion thereof.

In certain embodiments, an expression cassette comprises a globin gene or a functional portion thereof, and at least one insulator disclosed in International Patent Publication No. WO2015/138852. WO2015/138852 is herein incorporated by reference in its entirety. In certain embodiments, an expression cassette comprises a globin gene or a functional portion thereof operably and at least one insulator comprising or having the nucleotide sequence set forth in SEQ ID NO: 32, or a fragment thereof (e.g., nucleotides 1 to 320, 10 to 320, 20 to 320, 21 to 320, 55 to 320, 55 to 300, 57 to 300, 57 to 296, 57 to 226, 57 to 200, or 57 to 176 of SEQ ID NO: 32). SEQ ID NO:32 is provided below.

In certain embodiments, the globin gene or functional portion thereof is operably linked to a β-globin LCR, e.g., a β-globin LCR disclosed in section 3.1.

In certain embodiments, the expression cassette does not comprise a β-globin LCR. In certain embodiments, the expression cassette comprises at least one insulator (e.g., one disclosed in Section II and 3.6), and does not comprise a β-globin LCR. In certain embodiments, the expression cassette comprises at least one insulator comprising or having the nucleotide sequence set forth in SEQ ID NO: 1, and does not comprise a β-globin LCR. In certain embodiments, the expression cassette comprises an erythroid-specific enhancer (e.g., an erythroid-specific enhancer disclosed in section 3.5) and does not comprise a β-globin LCR. In certain embodiments, the expression cassette comprises an erythroid-specific enhancer having the nucleotide sequence set forth in SEQ ID NO:15, and does not comprise a β-globin LCR. In certain embodiments, the expression cassette comprises at least one insulator comprising or having the nucleotide sequence set forth in SEQ ID NO: 1, and an erythroid-specific enhancer having the nucleotide sequence set forth in SEQ ID NO:15, and does not comprise a β-globin LCR.

3.1. β-Globin LCR

The human β-globin gene cluster consists of five genes embedded within one of many olfactory receptor gene arrays (Bulger et al., PNAS (1999); 96:5129-5134). The cluster spans over 80 kb on chromosome 11p15.4, and includes the five expressed β-like genes and cis-acting regulatory elements that direct their stage-specific expression during ontogeny (Forget (2001), Molecular Mechanism of Beta Thalassemia. Steinberg M H et al., Eds. Disorders of Hemoglobin. Genetics, Pathophysiology and Clinical Management, Cambridge University Press, Cambridge). The genes are arranged in the order of their developmental expression (Stamatoyannopoulos et al., (2001) Hemoglobin Switching. In: Stamatoyannopoulos G, et al., Eds. Molecular Basis of Blood Disorders, W.B. Saunders, Philadelphia, Pa.), 5'-ε-$^G$γ-$^A$γ-ψη-δ-β-3'. The α-like globin gene cluster (5'-ξ2-ψξ1-ψα2-ψα1-α2-α1-θ-3') is located very close to the telomere of the short arm of chromosome 16 and spans about 40 kb. The expression of genes encoded within these two independent clusters is limited to erythroid cells and balanced so that the output of the β-globin-like chains matches that of the α-chains. This fine-tuned balance is regulated at the transcriptional, posttranscriptional and posttranslational levels.

Developmental stage-specific expression is controlled by a number of proximal or distal cis-acting elements and the transcriptional factors that bind to them. In the case of the β-globin gene (HBB), the proximal regulatory elements comprise the β-globin promoter and two downstream enhancers, one located in the second intron of β-globin and the other approximately 800 bp downstream of the gene

```
                                                                    (SEQ ID NO: 32)
CTGGTTCTAC TCATTACATT CCAATCGTGG CATATCCTCT AAACTTTCTT TTCCCTTCAT   60

AAATCCTCTT TCTTTTTTTT CCCCCTCACA GTTTTCCTGA ACAGGTTGAC TATTAATTGT  120

GTCTGCTTGA TGTGGACACC AGGTGGCGCT GGACATCAGA TTTGGAGAGG CAGTTGTCTA  180

GGGAACCGGG CTCTGTGCCA GCGCAGGAGG CAGGCTGGCT CTCCTATTCC AGGGATGCTC  240

ATCCAGGAAG GAAAGGTTGC ATGCTGGACA CACTAACCTT GAAGAATTCT TCTGTCTCTC  300

TCGTCATTTA GAAAGGAAGG                                              320
```

(Antoniou et al., *EMBO J.* (1988); 7:377-384; Trudel et al., *Genes Dev.* (1987); 1:954-961; Trudel et al., *Mol. Cell. Biol.* (1987); 7:4024-4029). The most prominent distal regulatory element is the β-globin LCR, located 50-60 kb upstream of the HBB and composed of several sub-regions with heightened sensitivity to DNaseI in erythroid cells (Forget (2001); Grosveld et al., *Cell* (1987); 51:975-985; Talbot et al., *Nature* (1989); 338:352). The most prominent property of the LCR is its strong, transcription-enhancing activity. An exemplary nucleotide sequence of the human β-globin region on chromosome 11 is set forth in SEQ ID NO:19 (GenBank Access No.: NG_000007.3), which is provided below:

[SEQ ID NO: 19]

```
ggatcctcacatgagttcagtatataattgtaacagaataaaaaatcaattatgtattcaagttgctagtgtcttaagaggttcacatt
tttatctaactgattatcacaaaaatacttcgagttacttttcattataattcctgactacacatgaagagactgacacgtaggtgcct
tacttaggtaggttaagtaatttatccaaaaccacacaatgtagaacctaagctgattcggccatagaaacacaatatgtggtataaat
gagacagagggatttctctccttcctatgctgtcagatgaatactgagatagaatatttagttcatctatcacacattaaacgggactt
tacatttctgtctgttgaagatttgggtgtgggataactcaaggtatcatatccaagggatggatgaaggcaggtgactctaacagaa
agggaaaggatgttggcaaggctatgttcatgaaagtatatgtaaaatccacattaagcttctttctgcatgcattggcaatgtttatg
aataatgtgtatgtaaaagtgtgctgtatattcaaaagtgtttcatgtgcctaggggtgtcaaatactttgagtttgtaagtatatact
tctctgtaatgtgtctgaatatctctatttacttgattctcaataagtaggtatcatagtgaacatctgacaaatgtttgaggaacaat
ttagtgtttacctattcaccaaaatttattaaatgcctaatctgtatcagatatacaattatctggcgaaatctgtaattcctaattta
aacagctgtgtagcctaattagggataaaggcatgcaaacccataatttgtgtaggttgaaatgagctatagaaaaatgcagtatattt
atcagaagtctttagggtcatgaaaaggaatggtcaactgacactgccagggactcatatgtaagagataactaatgtgaagtgactt
aaaggagaaattagcagaagttttctttccatgtctcctcatcatgttacaataacggaagagattaaaacaacaaatacatttagaca
gcaatgtttatcctggttagatgttttaatctaaatctatcttggagtgttaaaatgcatttgctcacctacttaaaatataaatgaa
ggtaggaacctgtagatacaaaagttggagaaaaaagacaataaagatgacaaaaatctattaatcctgatagaaatgagaagag
ataaaacactggtttacataaagaaaataagatggatagatagcagatccttataaaagtgataatttgagaaaaaaaatactccatat
tctgagtttcttcacataaaataatacaaatctgctgtggtaagttacaaagagatagatttttttatcattatataaaagatattttaa
acagagttatacaacaaaggaacagactatgtcatatattctcacttatcactataaacatctcagaaaaatctgcaaaatcatttcat
agcattttaaatagttaggaataatgtagaaaactgaaacagttctaagtttcccacaaacttagagtctcaaatgttgcattacctaa
cttacctgcaaatattttatacaaatttgcacatgctactctagtcaaaaatatatgtacattatgggtattttctgtgtgtaacttgg
ttctagttgcttctttcagaaatagcctctattttttgatttacctgataaaatcacattcctctccaaagccttctaaatacttccaga
ctaactacttttttagtacatctaagaagaaaagagttttgtctcttatccacctctgagtcaaaaagcagcatgtccatcaattggtac
atagttcccacagcccacttagctctggattggagttctacttggcattgtttgcaactacatggacgtaaaatgcatggattctctt
gaaaaaatgtttctgccatgatgttctctgaaagagactaaccttccctcgctttgcagagaaagactcgtgtaatccttgacaatgtc
atctcatctatttattcccatgtctacccatatgtgaccttcatgtctttgctctaagccctacatcctcaatctacacactaggata
gtataaaagtaatagtaataatagtagtaatagtaataacaatacaatgattatggcttatactatacaagacactgttgatatatt
atttcatttagtattcacagtaactctgtgcctcaagtactattgtaatacccttaagaggaggaaactgaggcacagggccctaaag
taatattccaagatgaagtggctactaactgacagagggcataattcaactcatgatatttggctctagaatacatgctctgaatcatt
atacaataataattcatgaggaaacatttttaaagcctaagttatttgctctgaaataagacataatttggggtgagaaagcttagat
tccatgaagtattacagcatttggtagtcttttttgcactccaggtcttattttactgcttaaacataataaaacatatggttcagtat
gcctttgattttacaataatattcctgttattttttggaagcacagggtgtgggataatgctaattactagtgattagtattgagaggtg
acagcgtgctggcagtcctcacagccctcgctcgctcttggcgctcctctgcctgggctcccacattggtggcacttgaggagcccctt
cagccggccgctgcactgtgggagcccttttctgggctggccaaggccagagccggctccctcagcttgccaggaggtgtggagggaca
gacgcgggcaggaaccgggctgtgcgccgtgcttgagggagttccgggtgggcatgggctccgaggacccgcactcggagccgccagc
cggccccaccggccgcgggcagtgagggcttagcacctgggccagcagctgctgtgctcaattcctcgccgggccttagctgccttcc
tgcggggcagggctcgggacctgcagcgcgccatgcctgagcctccccaccttcatgggctcctgtgcggcccgagcctcgccgacgag
cgccgccccctgctccagggcacccagtcccatcgaccacccaagggctgaagagtgcgggcgcacgcaggggactggcaggcagctc
```

-continued

```
cccctgcagcccaggtgcgggatccactgggtgaagccggctaggctcctgagtttgctggggatgcgaagaacccttatgtctagata
agggattgtaaatacaccaattggcactctgtatctagctcaaggtttgtaaacacaccaatcagcaccctgtgtctagctcagggttt
gtgaatgcaccaatcaacactctatctagctactctggtggggccttggagaacctttatgtctagctcagggattgtaaatacaccaa
tcggcagtctgtatctagctcaaggtttgtaaacacaccaatcagcaccctgtgtctagctcagggtttgtgaatgcaccaatcaacac
tctgtatctagctactctggtggggacgtggagaacctttatgtctagctcagggattgtaaatacaccactcggcagtctgtatctag
ctcaaggtttgtaaacacaccaatcagcaccctgtgtctagctcagggtttgtgaatgcaccaatcaacactctgtatctagctactct
ggtggggacttggagaacctttgtgtggacactctgtatctagctaatctggtggggacgtggagaacctttgtgtctagctcatggat
tgtaaatgcaccaatcagtgccctgtcaaaacagaccactgggctctaccaatcagcaggatgtgggtggggccagataagagaataaa
agcaggctgcccgagccagcagtggcaacccgctcgggtccccttccacactgtggaagctttgttctttcgctctttgcaataaatct
tgctgctgctcactgtttgggtctacactgcctttatgagctgtaacgctcaccgcgaaggtctgcagcttcactcttgaagccagcga
gaccacgaacccaccgggaggaacgaacaactccagaggcgccgccttaagagctggaacgttcactgtgaaggtctgcagcttcactc
ctgagccagcgagaccacgaacccatcagaaggaagaaactccgaacacatccaaacatcagaacgaacaaactccacacacgcagcct
taagaactgtaacactcaccacgagggtccccggcttcattcttgaagtcagtgaaaccaagaacccaccaattccggacacagtatg
tcagaaacaatatgagtcactaaatcaatatacttctcaacaatttccaacagcccttgcaattaacttggccatgtgactggttgtga
ctaaaataatgtggagataataatgtgttactccctaaggcagagtgcccttctatcattctctttcccttcctctatgtggcagaaag
taaaagattctgaaatgataaagtcaatcacaggaaggcacctggactcctggcccactgcttggaggagagcactcaggaccatgaac
atctgactgtgacgtagcaataaagaaacccacgtttcatatgaaactgcttaaaattaatggcacaagtcatgtttttgatgttgcac
atttgtctttatttgtggcttgttttgcttccacatcaatccactcaaggcctacattctgctataatgcaatttcaagttctttacag
gccgagaaaatgaatctgaattcctgacctccaaaagtgatcaagatattttagttcaggctccaaaattttctcattttcataggt
tttcctcgattgatcattattcatgatttgcaaggaatcattcaatgttttctaaatctattactgcatcctgacacatatgacattttt
aactatgttccagattttgaatgaagagtgtaaatttaaatgttttcaccacaaaaataagtatgtgaagtggtggatttgttaat
tagccttatttaaccatttaatattgtacacgtacaccaaagcatcatgttgtacccatgaatacacacaattattatttgtcaattt
aaaatgaataataaaaataacaaaggcattagcctctgcattgcctttaccggtcatcctcacggtgactaacgcaaaaaacgttct
atttcatccttacaaacatccctatctttgatgcctctttgtctagatctctatcccctcctgttttctctacgttatttatatgggta
tcatcaccatcctggacaacatcaggacagatatccctccaagccaatgttcctctctatgttggctcaaatgtccttgaactttcc
tttcaccacccttttccacagtcaaaaggatattgtagtttaatgcctcagagttcagcttttaagcttctgacaaattattcttcctct
ttaggttctcctttatggaatcttctgtactgatggccatgtcctttaactactatgtagatatctgctactacctgtattatgcctct
acctttattagcagagttatctgtactgttggcatgacaatcatttgttaatatgacttgcctttccttttctgctattcttgatcaa
atggctcctcttttcttgctcctctcatttctcctgccttcacttggacgtgcttcacgtagtctgtgcttatgactggattaaaaattg
atatggacttatcctaatgttgttcgtcataatatgggttttatggtccattattatttcctatgcattgatctggagaaggcttcaat
ccttttactctttgtggaaaatatctgtaaacctctggttcactctgctatagcaatttcagtttaggctagtaagcatgaggatgcc
tccttctctgattttcccacagtctgttggtcacagaataacctgagtgattactgatgaaagagtgagaatgttattgatagtcaca
atgacaaaaacaaacaactacagtcaaaatgtttctcttttattagtggattatatttcctgacctatatctggcaggactctttag
agaggtagctgaagctgctgttatgaccactagagggaagaagatacctgtggagctaatggtccaagatggtggagccccaagcaagg
aagttgttaaggagcccttttgattgaaggtgggtgccccaccttacagggacaggacatctggatactcctcccagtttctccagtt
tcccttttcctaatatatctcctgataaaatgtctatactcacttccccatttctaataataaagcaaaggctagttagtaagacatc
accttgcatttgaaaatgccatagactttcaaaattatttcatacatcggtctttctttatttcaagagtccagaaatggcaacatta
cctttgattcaatgtaatggaaagagctctttcaagagacagagaaaagaataatttaatttcttteceecacacctecttececctgtctc
ttaccctatcttccttccttctaccctccccatttctctctctcatttctcagaagtatattttgaaaggattcatagcagacagctaa
ggctggttttttctaagtgaagaagtgatattgagaaggtaggggttgcatgagccctttcagttttttagtttatatacatctgtattg
```

-continued

```
ttagaatgttttataatataaataaaattatttctcagttatatactagctatgtaacctgtggatatttccttaagtattacaagcta
tacttaactcacttggaaaactcaaataaatacctgcttcatagttattaataaggattaagtgagataatgcccataagattcctatt
aataacagataaatacatacacacacacacattgaaaggattcttactttgtgctaggaactataataagttcattgatgcattata
tcattaagttctaatttcaacactagaaggcaggtattatctaaatttcatactggatacctccaaactcataaagataattaaattgc
cttttgtcatatatttattcaaaagggtaaactcaaactatggcttgtctaattttatatatccccctactgaacatgaccctattgtg
atattttataaaattattctcaagttattatgaggatgttgaaagacagagaggatggggtgctatgccccaaatcagcctcacaatta
agctaagcagctaagagtcttgcagggtagtgtagggaccacagggttaaggggcagtagaattatactcccactttagtttcatttc
aaacaatccatacacacacagccctgagcacttacaaattatactacgctctatactttttgtttaaatgtataaataagtggatgaaa
gaatagatagatagatagacagatagatgatagatagaataaatgcttgccttcatagctgtctccctaccttgttcaaaatgttcctg
tccagaccaaagtaccttgccttcacttaagtaatcaattcctaggttatattctgatgtcaaaggaagtcaaaagatgtgaaaaacaa
tttctgacccacaactcatgctttgtagatgactagatcaaaaaatttcagccatatcttaacagtgagtgaacaggaaatctcctctt
ttccctacatctgagatcccagcttctaagaccttcaattctcactcttgatgcaacagaccttggaagcatacaggagagctgaactt
ggtcaacaaggagaaaagtttgttggcctccaaaggcacagctcaaacttttcaagccttctctaatcttaaaggtaaacaagggtct
cattctcttgagaacttcagggaaaatagacaaggacttgcctggtgcttttggtagggagcttgcactttccccctttctggaggaa
atatttatccccaggtagttcccttttttgcaccagtggttctttgaagagacttccacctgggaacagttaaacagcaactacagggcc
ttgaactgcacactttcagtccggtcctcacagttgaaaagacctaagcttgtgcctgatttaagcctttttggtcataaaacattgaa
ttctaatctccctctcaaccctacagtcacccatttggtatattaaagatgtgttgtctactgtctagtatccctcaagtagtgtcagg
aattagtcatttaaatagtctgcaagccaggagtggtggctcatgtctgtaattccagcacttgagaggtagaagtgggaggactgctt
gagctcaagagtttgatattatcctggacaacatagcaagacctcgtctctacttaaaaaaaaaaaaaaaaaattagccaggcatgtgatg
tacacctgtagtcccagctactcaggaggccgaaatgggaggatcccttgagctcaggaggtcaaggctgcagtgagacatgatcttgc
cactgcactccagcctggacagcagagtgaaaccttgcctcacgaaacagaatacaaaaacaaacaaacaaaaaactgctccgcaatgc
gcttccttgatgctctaccacataggtctgggtactttgtacacattatctcattgctgttcataattgttagattaattttgtaatat
tgatattattcctagaaagctgaggcctcaagatgataacttttattttctggacttgtaatagctttctcttgtattcaccatgttgt
aactttcttagagtagtaacaatataaagttattgtgagttttgcaaacacagcaaacacaacgacccatatagacattgatgtgaaa
ttgtctattgtcaatttatgggaaaacaagtatgtactttttctactaagccattgaaacaggaataacagaacaagattgaaagaata
cattttccgaaattacttgagtattatacaaagacaagcacgtggacctgggaggagggttattgtccatgactggtgtgtggagacaa
atgcaggtttataatagatgggatggcatctagcgcaatgactttgccatcacttttagagagctcttggggaccccagtacacaagag
gggacgcagggtatatgtagacatctcattctttttcttagtgtgagaataagaatagccatgacctgagtttatagacaatgagccct
tttctctctcccactcagcagctatgagatggcttgccctgcctctctactaggctgactcactccaaggcccagcaatgggcagggct
ctgtcagggctttgatagcactatctgcagagccagggccgagaaggggtggactccagagactctccctcccattcccgagcagggtt
tgcttatttatgcatttaaatgatatatttatttttaaaagaaataacaggagactgcccagccctggctgtgacatggaaactatgtag
aatattttgggttccattttttttttccttcttcagttagaggaaaaggggctcactgcacatacactagacagaaagtcaggagctttt
gaatccaagcctgatcatttccatgtcatactgagaaagtccccaccttctctgagcctcagtttctcttttttataagtaggagtctg
gagtaaatgatttccaatggctctcatttcaatacaaaatttccgtttattaaatgcatgagcttctgttactccaagactgagaagga
aattgaacctgagactcattgactggcaagatgtccccagaggctctcattcagcaataaaattctcaccttcacccaggcccactgag
tgtcagatttgcatgcactagttcacgtgtgtaaaaaggaggatgcttctttccttgtattctcacatacctttaggaaagaacttag
cacccttcccacacagccatcccaataactcatttcagtgactcaacccttgactttataaaagtcttgggcagtatagagcagagatt
aagagtacagatgctggagccagaccacctgagtgattagtgactcagtttctcttagtagttgtatgactcagtttcttcatctgtaa
aatggagggttttttaattagtttgttttttgagaaagggtctcactctgtcacccaaatgggagtgtagtggcaaaatctcggctcact
gcaacttgcacttcccaggctcaagcggtcctcccacctcaacatcctgagtagctggaaccacaggtacacaccaccatacctcgcta
atttttttgtatttttggtagagatgggggtttcacatgttacacaggatggtctcagactccggagctcaagcaatctgcccacctcagc
```

-continued cttccaaagtgctgggattataagcatgattacaggagttttaacaggctcataagattgttctgcagcccgagtgagttaatacatgc aaagagtttaaagcagtgacttataaatgctaactactctagaaatgtttgctagtattttttgtttaactgcaatcattcttgctgca ggtgaaaactagtgttctgtactttatgcccattcatctttaactgtaataataaaaataactgacatttattgaaggctatcagagac tgtaattagtgctttgcataattaatcatatttaatactcttggattctttcaggtagatactattattatccccattttactacagtt aaaaaaactacctctcaacttgctcaagcatacactctcacacacacaaacataaactactagcaaatagtagaattgagatttggtcc taattatgtctttgctcactatccaataaatatttattgacatgtacttcttggcagtctgtatgctggatgctgggatacaaagatg tttaaatttaagctccagtctctgcttccaaaggcctcccaggccaagttatccattcagaaagcattttttactctttgcattccact gttttcctaagtgactaaaaaattacactttattcgtctgtgtcctgctctgggatgatagtctgactttcctaacctgagcctaaca tccctgacatcaggaaagactacaccatgtggagaaggggtggtggttttgattgctgctgtcttcagttagatggttaactttgtgaa gttgaaaactgtggctctctggttgactgttagagttctggcacttgtcactatgcctattatttaacaaatgcatgaatgcttcagaa tatgggaatattatcttctggaatagggaatcaagttatattatgtaacccaggattagaagattcttctgtgtgtaagaatttcataa acattaagctgtctagcaaaagcaagggcttggaaaatctgtgagctcctccaccatatagaaagcttttaacccatcattgaataaatc cctataggggatttctaccctgagcaaaaggctggtcttgattaattcccaaactcatatagctctgagaaagtctatgctgttaacgt tttcttgtctgctaccccatcatatgcacaacaataaatgcaggcctaggcatgactgaaggctctctcataattcttggttgcatgaa tcagattatcaacagaaatgttgagacaaactatggggaagcagggtatgaaagagctctgaatgaaatggaaaccgcaatgcttcctg cccattcagggctccagcatgtagaaatctgggctttgtgaagactggcttaaaatcagaagcccattggataagagtagggaagaa cctagagcctacgctgagcaggtttccttcatgtgacagggagcctcctgccccgaacttccagggatcctctcttaagtgtttcctgc tggaatctcctcacttctatctggaaatggtttctccacagtccagcccctggctagttgaaagagttacccatgcagaggccctccta gcatccagagactagtgcttagattcctactttcagcgttggacaacctggatccacttgcccagtgttcttccttagttcctaccttc gaccttgatcctcctttatcttcctgaaccctgctgagatgatctatgtggggagaatggcttctttgagaaacatcttcttcgttagt ggcctgcccctcattcccactttaatatccagaatcactataagaagaatataataagaggaataactcttattataggtaagggaaaa ttaagaggcatacgtgatgggatgagtaagagaggagagggaaggattaatggacgataaaatctactactatttgttgagacctttta tagtctaatcaattttgctattgttttccatcctcacgctaactccataaaaaaacactattattatctttatttttgccatgacaagac tgagctcagaagagtcaagcatttgcctaaggtcggacatgtcagaggcagtgccagacctatgtgagactctgcagctactgctcatg ggccctgtgctgcactgatgaggaggatcagatggatggggcaatgaagcaaaggaatcattctgtggataaaggagacagccatgaag aagtctatgactgtaaatttgggagcaggagtctctaaggacttggatttcaaggaattttgactcagcaaacacaagaccctcacggt gactttgcgagctggtgtgccagatgtgtctatcagaggttccagggagggtggggtggggtcagggctggccaccagctatcagggcc cagatgggttataggctggcaggctcagataggtggttaggtcaggttggtggtgctgggtggagtccatgactcccaggagccaggag agatagaccatgagtagagggcagacatgggaaaggtgggggaggcacagcatagcagcattttcattctactactacatgggactgc tcccctataccccagctaggggcaagtgccttgactcctatgttttcaggatcatcatctataaagtaagagtaataattgtgtctat ctcataggttattatgaggatcaaaggagatgcacactctctggaccagtggcctaacagttcaggacagagctatgggcttcctatg tatgggtcagtggtctcaatgtagcaggcaagttccagaagatagcatcaaccactgttagagatatactgccagtctcagagcctgat gttaatttagcaatgggctgggaccctcctccagtagaaccttctaaccagctgctgcagtcaaagtcgaatgcagctggttagacttt ttttaatgaaagcttagctttcattaaagattaagctcctaagcagggcacagatgaaattgtctaacagcaactttgccatctaaaaa aatctgacttcactggaaacatggaagcccaaggttctgaacatgagaaattttaggaatctgcacaggagttgagagggaaacaaga tggtgaagggactagaaaccacatgagagacacgaggaaatagtgtagatttaggctggaggtaaatgaaagagaagtgggaattaata cttactgaaatctttctatatgtcaggtgccattttatgatatttaataatctcattacatatggtaattctgtgagatatgtattatt gaacatactataattaatactaatgataagtaacacctcttgagtacttagtatatgctagaatcaaatttaagtttatcatatgaggc cgggcacggtggctcatatatgggattacatgcctgtaatcccagcactttgggaggccaaggcaattggatcacctgaggtcaggagt tccagaccagcctggccaacatggtgaaaccccttctctactaaaaaatacaaaaaatcagccaggtgtggtggcacgcgtctataatc -continued

```
ccagctactcaggaggctgaggcaggagaatcacttgaacccaggaggtggaggttgcagtgagctaagattgcaccactgcactccag
cctaggcgacagagtgagactccatctcaaaaaaaaaaaagaagtttattatatgaattaacttagttttactcacaccaatactcag
aagtagattattacctcatttattgatgaggagcccaatgtacttgtagtgtagatcaacttattgaaagcacaagctaataagtagac
aattagtaattagaagtcagatggtctgagctctcctactgtctacattacatgagctcttattaactggggactcgaaaatcaaagac
atgaaataatttgtccaagcttacagaaccaccaagtagtaaggctaggatgtagacccagttctgctacctctgaagacagtgttttt
tccacagcaaaacacaaactcagatattgtggatgcgagaaattagaagtagatattcctgccctgtgggcccttgcttcttacttttac
ttcttgtcgattggaagttgtggtccaagccacagttgcagaccatacttcctcaaccataattgcatttcttcaggaaagtttgaggg
agaaaaaggtaaagaaaaatttagaaacaacttcagaataaagagattttctcttgggttacagagattgtcatatgacaaattataag
cagacacttgagaaaactgaaggcccatgcctgcccaaattacccctttgaccccttggtcaagctgcaactttggttaaagggagtgtt
tatgtgttatagtgttcatttactcttctggtctaacccattggctccgtcttcatcctgcagtgacctcagtgcctcagaaacataca
tatgtttgtctagtttaagtttgtgtgaaattctaactagcgtcaagaactgagggccctaaaactatgctaggaatagtgctgtggtgc
tgtgataggtacacaagaaatgagaagaaactgcagattctctgcatctccctttgccgggtctgacaacaaagtttccccaaatttta
ccaatgcaagccatttctccatatgctaactactttaaaatcatttgggggcttcacattgtctttctcatctgtaaaaagaatggaaga
actcattcctacagaactccctatgtcttccctgatgggctagagttcctctttctcaaaaattagccattattgtatttccttctaag
ccaaagctcagaggtcttgtattgcccagtgacatgcacactggtcaaaagtaggctaagtagaagggtactttcacaggaacagagag
caaaagaggtgggtgaatgagagggtaagtgagaaaagacaaatgagaagttacaacatgatggcttgttgtctaaatatctcctaggg
aattattgtgagaggtctgaatagtgttgtaaaataagctgaatctgctgccaacattaacagtcaagaaatacctccgaataactgta
cctccaattattcttttaaggtagcatgcaactgtaatagttgcatgtatatatttatcataatactgtaacagaaaacacttactgaat
atatactgtgtccctagttctttacacaataaactaatctcatcctcataattctattagctaatacatattatcatcctatatttcag
agacttcaagaagttaagcaacttgctcaagatcatctaagaagtaggtggtatttctgggctcatttggcccctcctaatctctcatg
gcaacatggctgcctaaagtgttgattgccttaattcatcagggatgggctcatactcactgcagaccttaactggcatcctcttttct
tatgtgatctgcctgaccctagtagacttatgaaatttctgatgagaaaggagagaggagaaaggcagagctgactgtgatgagtgatg
aaggtgccttctcatctgggtaccagtggggcctctaagactaagtcactctgtctcactgtgtcttagccagttccttacagcttgcc
ctgatgggagatagagaatgggtatcctccaacaaaaaaataaattttcatttctcaaggtccaacttatgtttttcttaattttttaaaa
aaatcttgaccattctccactctctaaaataatccacagtgagagaaacattcttttcccccatcccataaatacctctattaaatatg
gaaaatctgggcatggtgtctcacacctgtaatcccagcactttgggaggctgaggtgggtggactgcttggagctcaggagttcaaga
ccatcttggacaacatggtgataccctgcctctacaaaaagtacaaaaattagcctggcatggtggtgtgcacctgtaatcccagctat
tagggtggctgaggcaggagaattgcttgaacccgggaggcggaggttgcagtgagctgagatcgtgccactgcactccagcctggggg
acagagcacattataattaactgttatttttttacttggactcttgtggggaataagatacatgttttattcttatttatgattcaagca
ctgaaaatagtgtttagcatccagcaggtgcttcaaaaccatttgctgaatgattactatacttttttacaagctcagctccctctatcc
cttccagcatcctcatctctgattaaataagcttcagttttttccttagttcctgttacatttctgtgtgtctccattagtgacctccca
tagtccaagcatgagcagttctggccaggcccctgtcggggtcagtgccccaccccgccttctggttctgtgtaaccttctaagcaaa
ccttctggctcaagcacagcaatgctgagtcatgatgagtcatgctgaggcttagggtgtgtgcccagatgttctcagcctagagtgat
gactcctatctgggtccccagcaggatgcttacagggcagatggcaaaaaaaggagaagctgaccacctgactaaaactccacctcaa
acggcatcataaagaaaatggatgcctgagacagaatgtgacatattctagaatatattatttcctgaatatatatatatatatacaca
tatacgtatatatatatatatatatatttgttgttatcaattgccatagaatgattagttattgtgaatcaaatatttatcttgcag
gtggcctctataccctagaagcggcagaatcaggctttattaatacatgtgtatagattttaggatctatacacatgtattaatatgaa
acaaggatatggaagaggaaggcatgaaaacaggaaaagaaaacaaaccttgtttgccattttaaggcacccctggacagctaggtggc
aaaaggcctgtgctgttagaggacacatgctcacatacgggtcagatctgacttgggtgctactgggaagctctcatcttaaggata
catctcaggccagtcttggtgcattaggaagatgtaggcaactctgatcctgagaggaaagaaacattcctccaggagagctaaaaggg
ttcacctgtgtgggtaactgtgaaggactacaagaggatgaaaaacaatgacagacagacataatgcttgtgggagaaaaaacaggagg
```

-continued

```
tcaagggatagagaaggcttccagaagaatggctttgaagctggcttctgtaggagttcacagtggcaaagatgtttcagaaatgtga catgacttaaggaactatacaaaaaggaacaaatttaaggagaggcagatgaaattagttcaacagacatgcaaggaattttcagatgaa tgttatgtctccactgagcttcttgaggttagcagctgtgagggttttgcaggcccaggacccattacaggacctcacgtatacttgac actgttttttgtattcatttgtgaatgaatgacctcttgtcagtctactcggtttcgctgtgaatgaatgatgtcttgtcagcctactt ggtttcgctaagagcacagagagaagatttagtgatgctatgtaaaaacttccttttttggttcaagtgtatgtttgtgatagaaatgaa gacaggctacatgatgcatatctaacataaacacaaacattaagaaaggaaatcaacctgaagagtatttatacagataacaaaataca gagagtgagttaaatgtgtaataactgtggcacaggctggaatatgagccatttaaatcacaaattaattagaaaaaaaacagtgggga aaaaattccatggatgggtctagaaagactagcattgttttaggttgagtggcagtgtttaaagggtgatatcagactaaacttgaaat atgtggctaaataactagaatactctttatttttttcgtatcatgaatagcagatatagcttgatggcccatgcttggtttaacatcct tgctgttcctgacatgaaatccttaattttttgacaaaggggctattcattttcattttatattgggcctagaaattatgtagatggtcc tgaggaaaagtttatagcttgtctatttctctctctaacatagttgtcagcacaatgcctaggctataggaagtactcaaagcttgtta aattgaattctatccttcttattcaattctacacatggaggaaaaactcatcagggatggaggcacgcctctaaggaaggcaggtgtgg ctctgcagtgtgattgggtacttgcaggacgaagggtggggtgggagtggctaaccttccattcctagtgcagaggtcacagcctaaac atcaaattccttgaggtgcggtggctcactcctgtaatcacagcagtttgggacgccaaggtgggcagatcacttgaggtcaggagttg gacaccagcccagccaacatagtgaaacctggtctctgcttaaaaatataaaaattagctggacgtggtgacgggagcctgtaatccaa ctacttgggaggctgaggcaggagaatcgcttgaaccggggaggtggagtttgcactgagcagagatcatgccattgcactccagcctc cagagcgagactctgtctaaagaaaaacgaaaacaaacaaacaaacaaacaaacccatcaaattccctgaccgaacagaattct gtctgattgttctctgacttatctaccattttccctccttaaagaaactgtgaacttccttcagctagaggggcctggctcagaagcct ctggtcagcatccaagaaatacttgatgtcactttggctaaaggtatgatgtgtagacaagctccagagatggtttctcatttccatat ccacccacccagctttccaattttaaagccaattctgaggtagagactgtgatgaacaaacaccttgacaaaattcaacccaaagactc actttgcctagcttcaaaatccttactctgacatatactcacagccagaaattagcatgcactagagtgtgcatgagtgcaacacacac acacaccaattccatattctctgtcagaaaatcctgttggtttttcgtgaaaggatgttttcagaggctgacccttgccttcacctcc aatgctaccactctggtctaagtcactgtcaccaccacctaaattatagctgttgactcataacaatcttcctgcttctaccactgccc cactacaatttcttcccaatatactatccaaattagtcttttcaaaatgtaagtcatatatggtcacctctttgttcaaagtcttctga tagtttcctatatcatttataataaaaccaaatccttacaattctctacaatagttgttcatgcatatattatgtttattacagataca tatatatagctctcatataaataaatatatatatttatgtgtatgtgtgtagagtgttttttcttacaactctatgatgtaggtattat tagtgtcccaaattttataatttaggacttctatgatctcatctttttattctccccttcaccgaatctcatcctacattggccttattg atattccttgaaaattctaagcatcttacatctttagggtatttacatttgccattccctatgccctaaatatttaatcatagtttcat ataaatgggttcctcatcatctatgggtactctctcaggtgttaactttatagtgaggacttcctgccatactacttaaagtagcgat acccttcaccctgtcctaatcacactctggccttcatttcagttttttttttttctccatagcacctaatctcattggtatataacat gtttcatttgcttatttaatgtcaagctctttccactatcaagtccatgaaaacaggaacttttattcctctattctgttttttgtgctgt attcttagcaattttacaattttgaatgaatgaatgagcagtcaaacacatatacaactataattaaaaggatgtatgctgacacatcc actgctatgcacacacaaagaaatcagtggagtagagctggaagtgctaagcctgcatagagctagttagccctccgcaggcagagcct tgatgggattactgagttctagaattggactcatttgttttgtaggctgagatttgctcttgaaaacttgttctgaccaaaataaaagg ctcaaaagatgaatatcgaaaccagggtgtttttacactggaatttataactagagcactcatgtttatgtaagcaattaattgtttc atcagtcaggtaaaagtaaagaaaaactgtgccaaggcaggtagcctaatgcaatatgccactaaagtaaacattatttcataggtgtc agatatggcttattcatccatcttcatgggaaggatggccttggcctggacatcagtgttatgtgaggttcaaaacacctctaggctat aaggcaacagagctcctttttttttttttctgtgctttcctggctgtccaaatctctaatgataagcatacttctattcaatgagaatat tctgtaagattatagttaagaattgtgggagccattccgtctcttatagttaaatttgagcttcttttatgatcactgtttttttaata tgctttaagttctggggtacatgtgccatggtggtttgctgcacccatcaacccgtcatctacattaggtatttctcctaatgctatcc
```

-continued

```
ttccccctagccccccaccccccaacaggccccagtgtgtgatgttcccctccctgtgtccatggatcactggttttttttttgtttttttt
ttttttttaaagtctcagttaaatttttggaatgtaatttattttcctggtatcctaggacttgcaagttatctggtcactttagccct
cacgttttgatgataatcacatatttgtaaacacaacacacacacacacacacacacacatatatatatataaaacatatatataca
taaacacacataacatatttatcgggcatttctgagcaactaatcatgcaggactctcaaacactaacctatagccttttctatgtatc
tacttgtgtagaaaccaagcgtggggactgagaaggcaatagcaggagcattctgactctcactgcctttagctaggcccctccctcat
cacagctcagcatagtcctgagctcttatctatatccacacacagtttctgacgctgcccagctatcaccatcccaagtctaaagaaaa
aaataatgggtttgcccatctctgttgattagaaaacaaaacaaaataaaataagcccctaagctcccagaaaacatgactaaaccagc
aagaagaagaaaatacaataggtatatgaggagactggtgacactagtgtctgaatgaggcttgagtacagaaaagaggctctagcagc
atagtggtttagaggagatgtttctttccttcacagatgccttagcctcaataagcttgcggttgtggaagtttactttcagaacaaac
tcctgtggggctagaattattgatggctaaaagaagcccgggggagggaaaaatcattcagcatcctcacccttagtgacacaaaacag
agggggcctggttttccatatttcctcatgatggatgatctcgttaatgaaggtggtctgacgagatcattgcttcttccatttaagcc
ttgctcacttgccaatcctcagttttaaccttctccagagaaatacacatttttattcaggaaacatactatgttatagtttcaatac
taaataatcaaagtactgaagatagcatgcataggcaagaaaaagtccttagctttatgttgctgttgtttcagaatttaaaaaagatc
accaagtcaaggacttctcagttctagcactagaggtggaatcttagcatataatcagaggttttttcaaaatttctagacataagattc
aaagccctgcacttaaaatagtctcatttgaattaactctttatataaattgaaagcacattctgaactacttcagagtattgttttat
ttctatgttcttagttcataaatacattaggcaatgcaatttaattaaaaaaacccaagaatttcttagaattttaatcatgaaaataa
atgaaggcatctttacttactcaaggtcccaaaaggtcaaagaaaccaggaaagtaaagctatatttcagcggaaatgggatatttat
gagttttctaagttgacagactcaagttttaaccttcagtgcccatcatgtaggaaagtgtggcataactggctgattctggctttcta
ctcctttttcccattaaagatccctcctgcttaattaacattcacaagtaactctggttgtactttaggcacagtggctcccgaggtca
gtcacacaataggatgtctgtgctccaagttgccagagagagagattactcttgagaatgagcctcagccctggctcaaactcacctgc
aaacttcgtgagagatgaggcagaggtacactacgaaagcaacagttagaagctaaatgatgagaacacatggactcatagagggaaac
aacgcatactggggcctatcagagggtggagggtgagagaaggagaggatcaggaaaaatcactaatggatgctaagcgtaatacctga
gtgatgagcatctatacaacaaaccccccttgacattcatttatctatgtaacaaacctgcacatcctgtacatgtacccctgaactt
aaaataaaagttgaaaacaagaaagcaacagtttgaacacttgttatggtctattctctcattcttttacaattacactagaaaatagcc
acaggcttcctgcaaggcagccacagaatttatgacttgtgatatccaagtcattcctggataatgcaaaatctaacacaaaatctagt
agaatcatttgcttacatctatttttgttctgagaatatagatttagatacataatggaagcagaataatttaaaatctggctaattta
gaatcctaagcagctctttttcctatcagtggtttacaagccttgtttatattttttcctattttaaaaataaaaaataaagtaagttatttt
gtggtaaagaatattcattaaagtatttatttcttagataataccatgaaaaacattcagtgaagtgaagggcctactttacttaacaa
gaatctaatttatataattttttcatactaatagcatctaagaacagtacaatatttgactcttcaggttaaacatatgtcataaattag
ccagaaagatttaagaaaatattggatgtttccttgtttaaattaggcatcttacagttttttagaatcctgcatagaacttaagaaatt
acaaatgctaaagcaaacccaaacaggcaggaattaatcttcatcgaatttgggtgtttcttctaaaagtcctttatacttaaatgtc
ttaagacatacatagatttattttactaattttaattatatagacaataaatgaatattcttactgattacttttctgactgtctaa
tctttctgatctatcctggatggccataacacttatctctctgaactttgggcttttaatataggaaagaaaagcaataatccattttt
catggtatctcatatgataaacaaataaaatgcttaaaaatgagcaggtgaagcaatttatcttgaaccaacaagcatcgaagcaataa
tgagactgcccgcagcctacctgacttctgagtcaggatttataagccttgttactgagacacaaacctgggcctttcaatgctataac
ctttcttgaagctcctccctaccacctttagccataaggaaacatggaatgggtcagatccctggatgcaagccaggtctggaaccata
ggcagtaaggagagaagaaaatgtgggctctgcaactggctccgagggagcaggagaggatcaaccccatactctgaatctaagagaag
actggtgtccatactctgaatgggaagaatgatgggattaccatagggcttgttttagggagaaacctgttctccaaactcttggcct
tgagatacctggtccttattccttggactttggcaatgtctgaccctcacattcaagttctgaggaagggccactgccttcatactgtg
gatctgtagcaaattccccctgaaaacccagagctgtatcttaattggtaaaaaaaattatattatctcaacgactgttcttctctga
gtagccaagctcagcttggttcaagctacaagcagctgagctgcttttgtctagtcattgttctttttatttcagtggatcaaatacgt
```

-continued

```
tctttccaaacctaggatcttgtcttcctaggctatatattttgtcccaggaagtcttaatctggggtccacagaacactaggggctg gtgaagtttatagaaaaaaaatctgtattttacttacatgtaactgaaatttagcattttcttctacttttgaatgcaaaggacaaact agaatgacatcatcagtacctattgcatagttataaagagaaaccacagatattttcatactacaccataggtattgcagatctttttg tttttgtttttgtttgagatggagtttcgctcttattgcccaggctggagtgcagtggcatgatttcggctcactgcaacctccccttc ctgcattcaagcaattctcctgccttggcctcctgagtagctgggattacaggcacctgccaccatgccagtctaattttttgtatttt tagtagagatggggtttcgccatgttggccaggctggtcttgaactcctgacctcagatgatctgcccgccttggcctcctgaagtgct gggattataggtgtgagccaccacgcctggcccattgcagatattttaattcacatttatctgcatcactacttggatcttaaggtag ctgtagacccaatcctagatctaatgctttcataaagaagcaaatataataaatactataccacaaatgtaatgtttgatgtctgataa tgatatttcagtgtaattaaacttagcactcctatgtatattatttgatgcaataaaaacatattttttttagcacttacagtctgccaa actgcctgtgacacaaaaaaagtttaggaattcctggtttttgtctgtgttagccaatggttagaatatatgctcagaaagataccatt ggttaatagctaaaagaaaatggagtagaaattcagtggcctggaataataacaatttgggcagtcattaagtcaggtgaagacttctg gaatcatgggagaaaagcaaggaggagacattcttacttgccacaagtgttttttttttttttttttttttatcacaaacataagaaaatat aataaataacaaagtcaggttatagaagagagaaacgctcttagtaaacttggaatatggaatccccaaaggcacttgacttgggagac aggagccatactgctaagtgaaaaagacgaagaacctctagggcctgaacatacaggaaattgtaggaacagaaattcctagatctggt ggggcaaggggagccataggagaaagaaatggtagaaatggatggagacggaggcagaggtgggcagatcatgaggtcaagagatcgag accatcctggcaaacatggtgaaatcccgtctctactaaaaataaaaaaattagctgggcatggtggcatgcgcctgtagtcccagctg ctcgggaggctgaggcaggagaatcgtttgaacccaggaggcgaaggttgcagtgagctgagatagtgccattgcactccagtctggca acagagtgagactccgtctcaaaaaaaaaaaaaaagaaagaaagaaaagaaaaagaaaaagaaaaaataaatggatgtagaacaagc cagaaggaggaactgggctgggcaatgagattatggtgatgtaagggacttttatagaattaacaatgctggaatttgtggaactctg cttctattattcccccaatcattacttctgtcacattgatagttaaataatttctgtgaatttattccttgattctaaaatatgaggat aatgacaatggtattataagggcagattaagtgatatagcatgagcaatattcttcaggcacatggatcgaattgaatacactgtaaat cccaacttccagtttcagctctaccaagtaaagagctagcaagtcatcaaaatggggacatacagaaaaaaaaaggacactagaggaa taatatatccctgactcctagcctgattaatatatcgattcactttttctctgtttgatgacaaattctggctttaaataattttagga ttttaggcttctcagctcccttcccagtgagaagtataagcaggacagacaggcaagcaagaagagagccccaggcaatactcacaaag tagccaatgtcccctgtggtcatagagaaatgaaaagagagaggattctctggaagcactggatgtaatcttttctgtctgtcctctct agggaatcaccccaaggtactgtactttgggattaaggctttagtcccactgtggactacttgctattctgttcagtttctagaaggaa ctatgtacggttttttgtctccctagagaaactaaggtacagaagttttgtttacaatgcactccttaagagagctagaactgggtgaga ttctgttttaacagctttatttctttttccttggccctgttttgtcactgtcaccacctttaaggcaaatgttaaatgcgctttggct gaaacttttttttcctatttttgagatttgctccttttatatgaggctttcttggaaaaggagaatgggagagatggatatcattttggaag atgatgaagagggtaaaaaaggggacaaatggaaatttgtgttgcagatagatgaggagccaacaaaaaagagcctcaggatccagcac acattatcacaaacttagtgtccatccatcactgctgaccctctccggacctgactccaccctgagggacacaggtcagccttgacca atgacttttaagtaccatggagaacaggggccagaacttcggcagtaaagaataaaaggccagacagagaggcagcagcacatatctg cttccgacacagctgcaatcactagcaagctctcaggcctggcatcatggtgcattttactgctgaggagaaggctgccgtcactagcc tgtggagcaagatgaatgtggaagaggctggaggtgaagccttgggcaggtaagcattggttctcaatgcatgggaatgaagggtgaat attaccctagcaagttgattgggaaagtcctcaagattttttgcatctctaattttgtatctgatatggtgtcatttcatagactcctc gttgtttacccctggacccagagattttttgacagctttggaaacctgtcgtctccctctgccatcctgggcaacccaaggtcaaggc ccatggcaagaaggtgctgacttcctttggagatgctattaaaaacatggacaacctcaagcccgccttttgctaagctgagtgagctgc actgtgacaagctgcatgtggatcctgagaacttcaaggtgagttcaggtgctggtgatgtgatttttttggctttatattttgacatta attgaagctcataatcttattggaaagaccaacaaagatctcagaaatcatgggtcgagcttgatgttagaacagcagacttctagtga gcataaccaaaacttacatgattcagaactagtgacagtaaaggactactaacagcctgaattggcttaacttttcaggaaatcttgcc
```

-continued

```
agaacttgatgtgtttatcccagagaattgtattatagaattgtagacttgtgaaagaagaatgaaatttggcttttggtagatgaaag
tccatttcaaggaaatagaaatgccttattttatgtgggtcatgataattgaggtttagaaagagattttttgcaaaaaaaataaaagat
ttgctcaaagaaaaataagacacatttttctaaaatatgttaaatttcccatcagtattgtgaccaagtgaaggcttgtttccgaatttg
ttggggattttaaactcccgctgagaactcttgcagcactcacattctacatttacaaaaattagacaattgcttaaagaaaaacaggg
agagagggaacccaataatactggtaaaatggggaaggggtgagggtgtaggtaggtagaatgttgaatgtagggctcatagaataaa
attgaacctaagctcatctgaattttttgggtgggcacaaaccttggaacagtttgaggtcagggttgtctaggaatgtaggtataaag
ccgttttttgtttgtttgtttgtttttttcatcaagttgttttcggaaacttctactcaacatgcctgtgtgttattttgtcttttgccta
acagctcctgggtaacgtgatggtgattattctggctactcactttggcaaggagttcacccctgaagtgcaggctgcctggcagaagc
tggtgtctgctgtcgccattgccctggcccataagtaccactgagttctcttccagtttgcaggtgttcctgtgaccctgacaccctcc
ttctgcacatggggactgggcttggccttgagagaaagccttctgtttaataaagtacattttcttcagtaatcaaaaattgcaatttt
atcttctccatctttttactcttgtgttaaaaggaaaaagtgttcatgggctgagggatggagagaaacataggaagaaccaagagcttc
cttaagaaatgtatgggggcttgtaaaattaatgtggatgttatgggagaattccaggattccaaggaggatgatatgatggagaaaaa
tctttatcggggtgggaaaatggttaattaagtggacagagactcctaggcagttttttactgcaccggggaaagaaggagctgttagtg
gtacctgagaaagcagatttgtggtacatgtcacttttcattaaaaacaaaaacaaaacaaaacaaaacttcatagatatccaagatat
aggctagaattactattttaatttactcttatttacattttgaagtagctagcttgtcacatgttttatgaaattgatttggagataag
atgagtgtgtatcaacaatagcctgctcttccatgaaggattccattatttcatgggttagctgaagctaagacacatgatatcattg
tgcattatcttctgatagaatgtaacatgcactaaaataaagttagagttaggacctgagtgggaaagtttttggagagtgtgatgaag
actttccgtgggagatagaatactaataaaggcttaaattctaaaaccagcaagctagggcttcgtgacttgcatgaaactggctctct
ggaagtagaagggagagtaagacatacgtagaggactaggaaagaccagatagtacagggcctggctacaaaaatacaagcttttacta
tgctattgcaatactaaacgataagcattaggatgttaagtgactcaggaaataagatttttgggaaaaagtaatctgcttatgtgcaca
aaatggattcaagtttgcagataaaataaaatatggatgatgattcaaggggacagatacaatggttcaaacccaagaggagcagtgag
tctgtggaatttgaaggatggacaaaggtggggtgagaaagacatagtattcgactgactgtgggagatgagaaggaagaaggaggtga
taaatgactgaaagctcccagactggtgaagataacaggaggaaaccatgcactgacctggtgactctcatgtgtgaagggtagaggga
tattaacagatttacttttttaggaagtgctagattggtcagggagttttgaccttcaggtcttgtgtctttcatatcaaggaacctttg
cattttccaagttagagtgccatattttggcaaatataactttattagtaattttatagtgctctcacattgatcagacttttttcctgt
gaattacttttgaatttggctgtatatatccagaatatgggagagagacaaataattattgtagttgcaggctatcaacaatactggtc
tctctgagccttataacctttcaatatgcccataaacagagtaaacagggattattcatggcactaaatattttcacctagtcagtcaa
caaatgggagcaatgtgcattttttgatacatatttttatatatttatggggtacatgtgatacttacatgcctagaacatgtgatgat
taagtctagatatttaggatatccattgctttgagcatttatcatttctatgtattgagaaaatttcaaatcctcatttctagccattt
tgaaatatataataaatagtaattaactatagtcaccctactcaaatatcaaacattatggcttaatccttctatccaactgtgtttgt
acctattaaccaacatctcttaaatcccctcccatacacactcactttttccagcctctgataactatcattctactctctaccacc
atgagacccactttttttagctcccacagatgaataaaaacatgtgatatttgactttctgtatctggcttatttttattatctatctctt
tggcataccaagagtttgttttttgttctgcttcagggctttcaattaacataatgacctctggttccatccatgttgctacaaatgaca
agatttcattcttttttcatggcaaaatagtactgtgcaaaaatacaattttttaatccgttcatctgttgatagacacttaggttgatc
ccaaaccttaactattgtgaatagtgcttcaataaacatgagtgtaatgtgtccattggatatactgatttcctttcttttggataaat
aaccactagtgagattgctggattgtatgatagttctgttttttagtttactgagaaatcttcatactgttttccataatggttgtacta
ttttacattcccaccaacagtgtgtaagaaagagttccctttttctccatatcctcacaaggatctgttatttttttgtctttttttgttaa
tagccgttttaactagagtaagtagatatctcattgtagttttgatttgcatttccctgatcattagtgatgttgagaattttttcata
tgtttgttggtcatttgtatatcttttttctgagaattgtctgttcatgtccttagcctacttttttattgggattgtttgttattttctt
gataatctatttgtgttcatttagagcctggatattattcttttgtcagatgtatagattgtgaagattttctcccactctgtgggtt
gtctgtttattctgcagactcttccttttgccatgcaaaagctctttagtttaatttagtcccagatattttctttgttttttatgtatt
```

-continued

```
tgcatttgtgttcttggtcatgaaatcctttcctaagccaatgtgtagaagggttttccgatgttattttctagaattgttacagttt cagggcttagatttaagtccttgatccatcttgagttgattttgtataaggtgagagatgaagatccagtttcattctcctacatgta gcttgccagctatccccgcaccatttgttgaatagggtgccctttccccactttatgttttgtttgctttgtcaaagatcagttggat gtaagtatttgagtttatttctgggttctctattctgttccattggtcgatgtgcctatttgtacaccagcatcatgctgttttggtga ctatggccttattgtatagtttgaaatgaggtaatgtaatgccttcagatttgttcttttttttagacttgcttgtttattgggctctt ttttggttccataagaattttaggattgttttttctagttctgtgaagactaatggtggtattttgatgggaattgcaatgaatttgta ggttgcttctggcattatggccatttttcacaatattgattctacccatctatgagaatggcatgtgtttccatttgtttgtgtcttata tgattactttcagccgtgttttgtagttttccttgtagatgtctttcacctccttggttaggtatatattcctaagttttttgttttgtt ttgttttgtttttttgcagctattgtaaaaggggttgagttcttgattttattctcagcttggtcattgctggtatgtaagaaagcaact cattggtgtacgttaattttgtatccagaaacttgctgaattattttatcagttctaggggggttttggaggagtctttagagttttct acatacacaatcatatcatcagcaaacagtgacagtttgactttctcttttaacaatttggatgtgctttacttgtttctcttgtctgat tgctcttgctaggacttccagtaatatgttaaagagaagtggtgagagtgggtatccttgtctcattccagttttcagacagaatgctt ttaactttttcccattcaatataatgttggctgtgtgtttaccatagctggcttttattacattgaggtatgtcctttgtaaaccgatt ttgctgagttttagtcataaagtgatgttgaattttgttgaatgcagttctgtggctattgagataatcacatgattttttgtttccaa ttctctttatgttgtgtatcacacttattgacttgcgtatgttaaaccatccgtgcatccctcgcatgaaacccacttgatcatgggtt ttgatatgctgtcggatgctattagctagtattttgtcaaggatgttggcatctatgttcatcagggatattgatctgtagtgtttttt tttttggttatgttctttcccagttttggtattaaggtgatactggcttcatagaatgatttagggaggattctctctttctctatct tgtagaatactgtcaataggattggtatcaattcttctttgaatgtctggtagaattcagctgtgaatctatctggtcctggacttttt tgttgttggtaaattttttattatcatttcagtcttgctgcttattactggtctgttcagggtatctaattcttcctgacttaagctaga gccctgtatctttccaggaattcgaacgtctcctttaggttttctagtttatgcatgtaaaggtgttcatagtagccttgaataatctt ttgtatttctgtggtatcagtaatagtatctcctgttttgtttctaattgagtttatttgcacttctctcctcttttcttggttaatct tgctaatggtctatcagttttatttatctttcaaagaaccagcttttatttcatttagcttttgtattttttgcagttgttttaat ttcatttagttctcctcttatcttagttattcccttcttttgctgggttttggttctgtttgtttttgtttctctagtttcttgtggt gtgacccttatattgtctgtctgtcctcttttcagactctttgacatcgacatttagggctgtgaactttccttttagcaccatctttgct gtatcctagaggttttgataggttgtgtcactattgtcggtcagttcaagtaattttgttgttcttattatactttaagttctgggata catgtgcagaatgtgcaggtttgttacataggtatagatgtgccatggtggtttgctgcacccatcaacctgtcatctacattaggtat ttcttttaatgttatccctctcctaacccccctcaccccccgacaggcctggtgtgtgatgttcccctccctgtgtccatgtgttctca ttgttcaactcccacttatgagtgagaacgtgtggtgtttggtttctctgttcctgtgttagtttgctcagaatgatggtttccacctt catccatgtccctgcaaagacatgaactcatcattttatggctgcatagtattccatggtgtatatgtgccacatttctcttttatccat tatatcgctgatggccatttgggttggttccaagtctttgctattgtgaatagtgccacaataaacatacgtgtgcacgtgtctttata gtagaatgatttctaattctttgggtatatacccagtaatgggattgctgggcaaacagtatttctggttctagatccttgaggaatc gccacactgtcttccacaatggttgaactaatttacacacccatcaacagtgtaaaattttcctattcttccacatcctctccagcac cttttgtttcctgacttttaataattgccattctaactggcatgagatggtatctcattgtggttttgatttgcatttctctaatgac cagtgatgatgagcttcttttcatgtgtttcttggccacataaatgacttctttagagaagcatctgttcatatcctttgtccacttt tgatggggtcgttaggttttttcttgtaaatttgttgaagttctttgtagattttggatgttagccctttgtcagatggatagattgca aaaattttctcccattctgtaggttgcctgttcactctgatgatagtcttttgctgtgcagaagctctttagtttaattagatcccata tgtcaatttggcctttgttgtcattgcttttgatgttttagtcgtgaattttgcccatgcctatgtcctgaatggtattgcctaggt tatcttctaggattttatggttttaggttgcacatttaagtctttaatccaccttgagttaattttttgtataaggtgtaaggaagggg tacagtttcagtttatgcatattgctagccagttttttccagcaccatttattaaatagggaattctttctccattgcttttgtgatgt ttgtcaaagatcagatggtcgtagatgtgtggcattatttctgaggcttctgttctgttccactggtctatatatctgttttggtacca
```

-continued

```
gtaccatgctgttttttgttactgtagccttgtagtatagtttgaagtcaggtagcatcatgcctccagctttgttcttttgtttagga
ttgtcttggctatatgggctcttttttgattccatatgacatttaaagtagttttttctaattctttgaaaaaagtcagtggtagcttg
atggggatagcattgaatctataaattactttgggcagtatggccattttaaagatattgattctttctatctatgagcatggaatgtt
tttccatttgtttgtgtcctctcttatttccttgagcagtgagtggtttgtagctctccttgaagaggttcttcacatcccttagaagt
tgtatttctaggtatttatttttattctctttgcagcaattgtgaatgggagttcacccatgatttggctctctgcttgtctattattg
gtgtataggaacgcttgtgatttctgcacactgattttgtatcttgagactttgctgaagctgtttatcagcttaagattttggctga
gatgacagggtcttctaaatatacaatcatgtcatctgcaaacagagacaatttgacttcctctcttcctatttgaatatgctttattt
cttctcttgcctgattgtcctggcgagaacttccaatactatgttgagtaagagtggcgagagggcatccttgtcttgtgccggtttt
caaagcaaatgattttttaaatttccatcttgatttcattgttgacccaatgatcattcaggagcaggttatttaatttccctgtatttg
catggttttgaaggttccttttgtagttgatttccaattttattctactgtggtctgagagagtgcttgatataatttcaattttttaaa
aatttattgaggcttgttttgtggcatatcatatggcctatcttggagaaagttccatgtgctgatgaatagaatgtgtattctgcagt
tgtttgggtagaatgtcctgtaaatatctgttaagtccatttgttctttaaatccattgtttctttgtagactgtcttgatgacctgcct
agtgcagtcagtggagtattgaagtcccccactattattatgttgctgtctagtctagtagtaattgttttataaatttgggatctcca
gtattagatgcatatatattaagaattgtaatattctcccattggacaagggcttttatcattatatgatgtccctctttgtctttttt
aactgctgtttcttaaagtttgttttgtctgacataagaatagctgctttggctcgcttttggtgtccatttgtgtggaatgtcattt
tccaccccttttaccttaagtttatgtgagtccttatgtgttaggtgagtctcctgaaggcggcagataactggttggtgaattcttatt
cattctgcaattctgtatcttttaagtggagcatttagtccatttacattcaacatcagtattgaggtgtgaggtactattccattctt
cgtggtatttgttgcctgtgtatctttttatctgtatttttgttgtatatgtcctatgggatttatgctttaaagaggttctgttttga
tgtgcttccagggttatttcaagatttagagctccttttatcagttcttgtagtgttggcttggtagtgccgaattctctcagcatttt
gttttctgaaaaacactgtgtatttcttcatttgtgaagcttagtttcactggatataaaattcttggctgataattgttttgttta
agaaggctgaagataggccatattcacttctagcttttacggtttctgctgagaaatctgctgttaatctgataggttttcttcata
ggttacctggtagtttcacctcacagctcttaagattctctttgtctttagataactttggatactctgatgacaatgtacctaggcaa
tgatattttgcaatgaatttcccaggtgtttattgagcttcttgtatttggatatctaggtctctagcaaggtgggggaagttttcct
tgattatttccctggataagttttccaaacttttagatttctcttctttctcaggaatgctgattattcttaggtttgattgtttaaca
taatcccagatttcttggaggctttgttcatattttcttattctttttctttgtctttgttggattgggttaattcaaaaacttttgtc
ttcaagctctgaatttcttctgcttggattctattgctgagactttctagagcattttgcatttctataagtgcatccattcatccatt
gtttcctgaagttttgaatgttttttatttatgctatctctttaactgaagattctcccctcatttcttgtatcatatttttggtttt
tttaaaattggacttcaccttcctcggatgcctccttgattagcttaataactgaccttctgaattattttcaggtaaatcagggatt
tcttcttggtttggatgcattgctggtgagctagtatgatttttggggggtgttaaagaaccttgttttttcatattaccagagttagt
tttctggttccttctcacttgggtaggctctgtcagagggaaagtctaggcctcaaggctgagacttttgtcccatgaggtgttccctt
gatgtagcacagtccccctttttcctaggcgtgggggcttcctgagagccgaactgtagtgattgttatctctcttctggatctagccacc
catcaggtctaccagactccaggctggtactgggg tttgtctgcacagagtcttgtgacgtgaaccatctgtgggtctctcagccatag
atacaaccacctgctccaatggaggtggcagaggatgaaatggactctgtgagggtccttacttttggttgttcaatgcactattttg
tgctggttggcctcctgccaggaggtggcactttctagaaagcatcagcagaggcagtcaggtggtggtggctgggggggctgggcac
cctagaactcccaagaatatatgccctttgtcttcagctaccagggtgagtaaggaaggaccatcaggtgggggcaggactagtcgtgt
ctgagctcagagtctccttgggcaggtctttctgtggctactgtgggaggatgggggtgtagtttccaggtcaatggatttatgttcct
aggacaattatggctgcctctgctgtgtcatgcaggtcatcaggaaagtgggggaaagcaagcagtcacgtgacttgcccagctccat
gcaactcaaaaggttggtctcacttccagcgtgcaccctcccccgcaacagcaccgaatctgtttccatgcagtcagtgagcaaggctg
agaacttgccccaggctaccagctgcgaaaccaagtagggctgtcctacttccctgccagtggagtctgcacaccaaattcatgtcccc
ccaccaaccccccactgcccagccctagatctggccaggtggagattttcttttcctgtcatcttttcccagttcctctggcagcc
ctcccaaatgacccctgtgaggcaaggcagaaatggcttcctaggggacccagagagcccacagggcttttcccgctgcttcctctacc
```

-continued

```
cctgtattttgcttggccctctaaattgactcagctccaggtaaggtcagaatcttctcctgtggtctagatcttcaggttccccagtg aggatgtgtgtttgggggtagacggtcccccttttccacttccacagtttgggcactcacaatatttggggtgtttcccgggtcctgca ggagcaatctgcttctttcagagggtgtgtgcgttctctcagctttcttgatttatttctgcaggtggttctgcaaaaaaaattcctga tgggagacttcacatgctgctctgtgcatccgagtgggagctgcaatgtacttctgctgcctcccatctgccatcaccctctaatttgt cggtaatatgcattttaatcaatcttttttctctctctctcttttcttctcccccaaaactatactgcccttgatatcaaggaat caaggacgtgatgttgaggggtgggcagtggatacactcttacccttagggagctatatctagatttagatattgccaattcaagat aacttaattgaaagcaaattcataatgaataCaCaCaCaCaCacacatctgcatgacaagatttttaatagttgaaagaataactaa taattgtccacaggcaataagggctttttaagcaaaacagttgtgataaacaggtcattcttagaatagtaatccagccaatagtacag gttgcttagagattatgtcattaccagagttaaaattctataatggcttctcactccctaccactgaggacaagtttatgtccttaggt ttatgcttccctgaaacaataccacctgctattctccacttacatatcaacggcactggttctttatctaactctctggcacagcagg agtttgttttcttctgcttcagagctttgaatttactatttcagcttctaaactttatttggcaatgccttcccatggcagattccttc tgtcatttgcctctgttcgaatacttctccttaatttcattcttagttaataatatctgaaattattttgttgtttaacttaattat taattttatgtatgttctacctagattataatcttcagaggaaagttttattctctgacttatttaacttaaatgcccactactttaaa aattatgacatttatttaacagatatttgctgaacaaatgtttgaaaatacatgggaaagaatgcttgaaaacacttgaaattgcttgt gtaaagaaacagttttatcagttaggatttaatcaatgtcagaagcaatgatataggaaaaatcgaggaataagacagttatggataag gagaaatcaacaaactcttaaaagatattgcctcaaaagcataagaggaaataagggtttatacatgacttttagaacactgccttggt ttttggataaatggggaagttgtttgaaaacaggagggatcctagatattccttagtctgaggaggagcaattaagattcacttgttta gaggctgggagtggtggctcacgcctgtaatcccagaattttgggaggccaaggcaggcagatcacctgaggtcaagagttcaagacca acctggccaacatggtgaaatcccatctctacaaaaatacaaaaattagacaggcatgatggcaagtgcctgtaatcccagctacttgg gaggctgaggaaggagaattgcttgaacctgggaaggcaggagttgcagtgagccgagatcataccactgcactccagcctgggtgacag aacaagactctgtctcaaaaaaaaaaaagagagattcaaaagattcacttgtttaggccttagcgggcttagacaccagtctctgacac attcttaaaggtcaggctctacaaatggaacccaaccagactctcagatatggccaaagatctatacacacccatctcacagatcccct atcttaaagagaccctaatttgggttcacctcagtctctataatctgtaccagcataccaataaaaatctttctcacccatccttagat tgagagaagtcacttattattatgtgagtaactggaagatactgataagttgacaaatcttttctttcctttcttattcaacttttat tttaacttccaaagaacaagtgcaatatgtgcagctttgttgcgcaggtcaacatgtatctttctggtcttttagccgcctaacacttt gagcagatataagccttacacaggattatgaagtctgaaaggattccaccaatattattataattcctatcaacctgataggttagggg aaggtagagctctcctccaataagccagatttccagagtttctgacgtcataatctaccaaggtcatggatcgagttcagagaaaaaac aaaagcaaaaccaaacctaccaaaaaataaaaatcccaaagaaaaaataaagaaaaaaacagcatgaatacttcctgccatgttaagtg gccaatatgtcagaaacagcactgagttacagataaagatgtctaaactacagtgacatcccagctgtcacagtgtgtggactattagt caataaaacagtccctgcctcttaagagttgttttccatgcaaatacatgtcttatgtcttagaataagattccctaagaagtgaacct agcatttatacaagataattaattctaatccatagtatctggtaaagagcattctaccatcatctttaccgagcatagaagagctacac caaaaccctgggtcatcagccagcacatacacttatccagtgataaatacacatcatcgggtgcctacatacatacctgaatataaaaa aaatactttgctgagatgaaacaggcgtgatttatttcaaataggtacggataagtagatattgaagtaaggattcagtcttatatta tattacataacattaatctattcctgcactgaaactgttgctttataggattttcactacactaatgagaacttaagagataatggcc taaaaccacagagagtatattcaaagataagtatagcacttcttatttggaaaccaatgcttactaaatgagactaagacgtgtcccat caaaaatcctggacctatgcctaaaacacatttcacaatccctgaacttttcaaaaattggtacatgctttaactttaaactacaggcc tcactggagctacagacaagaaggtgaaaaacggctgacaaaagaagtcctggtatcttctatggtgggagaagaaaactagctaaagg gaagaataaattagagaaaaattggaatgactgaatcggaacaaggcaaaggctataaaaaaaattaagcagcagtatcctcttgggg cccctttccccacactatctcaatgcaaatatctgtctgaaacggtccctggctaaactccacccatgggttggccagccttgccttgac caatagccttgacaaggcaaacttgaccaatagtcttagagtatccagtgaggccaggggccggcggctggctagggatgaagaataaa
```

-continued

```
aggaagcacccttcagcagttccacacactcgcttctggaacgtctgaggttatcaataagctcctagtccagacgccatgggtcattt
cacagaggaggacaaggctactatcacaagcctgtggggcaaggtgaatgtggaagatgctggaggagaaaccctgggaaggtaggctc
tggtgaccaggacaagggagggaaggaaggaccctgtgcctggcaaaagtccaggtcgcttctcaggatttgtggccacttctgactgt
caaactgttcttgtcaatctcacaggctcctggttgtctacccatggacccagaggttctttgacagctttggcaacctgtcctctgcc
tctgccatcatgggcaaccccaaagtcaaggcacatggcaagaaggtgctgacttccttgggagatgccataaagcacctggatgatct
caagggcacctttgcccagctgagtgaactgcactgtgacaagctgcatgtggatcctgagaacttcaaggtgagtccaggagatgttt
cagcactgttgcctttagtctcgaggcaacttagacaactgagtattgatctgagcacagcagggtgtgagctgtttgaagatactggg
gttgggagtgaagaaactgcagaggactaactgggctgagacccagtggcaatgttttagggcctaaggagtgcctctgaaaatctaga
tggacaactttgactttgagaaaagagaggtggaaatgaggaaaatgacttttctttattagatttcggtagaaagaactttcacctt
cccctatttttgttattcgttttaaaacatctatctggaggcaggacaagtatggtcattaaaaagatgcaggcagaaggcatatattg
gctcagtcaaagtggggaactttggtggccaaacatacattgctaaggctattcctatatcagctggacacatataaaatgctgctaat
gcttcattacaaacttatatcctttaattccagatggggcaaagtatgtccaggggtgaggaacaattgaaacatttgggctggagta
gattttgaaagtcagctctgtgtgtgtgtgtgtgtgtgcgcgcgtgtgtttgtgtgtgtgtgagagcgtgtgtttcttttaacgttt
tcagcctacagcatacaggttcatggtggcaagaagataacaagatttaaattatggccagtgactagtgctgcaagaagaacaacta
cctgcatttaatgggaaagcaaaatctcaggctttgagggaagttaacataggcttgattctgggtggaagcttggtgtgtagttatct
ggaggccaggctggagctctcagctcactatgggttcatctttattgtctcctttcatctcaacagctcctgggaaatgtgctggtgac
cgttttggcaatccatttcggcaaagaattcacccctgaggtgcaggcttcctggcagaagatggtgactggagtggccagtgccctgt
cctccagataccactgagctcactgcccatgatgcagagctttcaaggataggctttattctgcaagcaatcaaataataaatctattc
tgctaagagatcacacatggttgtcttcagttctttttttatgtcttttaaatatgagccacaaagggttttatgttgagggatgt
gtttatgtgtatttatacatggctatgtgtgtttgtgtcatgtgcacactccacactttttgtttacgttagatgtgggttttgatga
gcaaataaaagaactaggcaataaagaaacttgtacatgggagttctgcaagtgggagtaaaaggtgcaggagaaatctggttggaaga
aagacctctataggacaggactcctcagaaacagatgttttggaagagatggggaaaggttcagtgaaggggctgaaccccttccct
ggattgcagcacagcagcgaggaagggctcaacgaagaaaaagtgttccaagctttaggaagtcaaggtttaggcagggatagccatt
ctattttattaggggcaatactatttccaacggcatctggcttttctcagcccttgtgaggctctacagggaggttgaggtgttagaga
tcagagcaggaaacaggttttctttccacggtaactacaatgaagtgatccttacttttactaaggaacttttcattttaagtgttgac
gcatgcctaaagaggtgaaattaatcccatacccttaagtctacagactggtcacagcatttcaaggaggagacctcattgtaagcttc
tagggaggtggggacttaggtgaaggaaatgagccagcagaagctcacaagtcagcatcagcgtgtcatgtctcagcagcagaacagca
cggtcagatgaaaatatagtgtgaagaatttgtataacattaattgagaaggcagattcactggagttcttatataattgaaagttaat
gcacgttaataagcaagagtttagtttaatgtgatggtgttatgaacttaacgcttgtgtctccagaaaattcacatgctgaatcccca
actcccaattggctccatttgtggggaggctttggaaaagtaatcaggtttagaggagctcatgagagcagatccccatcatagaatt
attttcctcatcagaagcagagagattagccatttctcttccttctggtgaggacacagtgggaagtcagccacctgcaacccaggaag
agagccctgaccaggaaccagcagaaaagtgagaaaaaatcctgttgttgaagtcacccagtctatgctattttgttatagcaccttgc
actaagtaaggcagatgaagaagagaaaaaaataagcttcggtgttcagtggattagaaaccatgtttatctcaggtttacaaatctc
cacttgtcctctgtgtttcagaataaaataccaactctactactctcatctgtaagatgcaaatagtaagcctgagcccttctgtctaa
ctttgaattctatttttcttcaacgtactttaggcttgtaatgtgtttatatacagtgaaatgtcaagttctttctttatatttcttt
cttctttttttttcctcagcctcagagttttccacatgcccttcctactttcaggaacttctttctccaaacgtcttctgcctggctcc
atcaaatcataaaggacccacttcaaatgccatcactcactaccatttcacaattcgcactttctttctttgtccttttttttttagt
aaaacaagtttataaaaaattgaaggaataaatgaatggctacttcataggcagagtagacgcaagggctactggttgccgattttat
tgttatttttcaatagtatgctaaacaaggggtagattatttatgctgcccatttttagaccataaaagataacttcctgatgttgcca
tggcattttttttccttttaatttttatttcattttaatttcgaaggtacatgtgcaggatgtgcaggcttgttacatgggtaaat
gtgtgtctttctggccttttagccatctgtatcaatgagcagatataagctttacacaggatcatgaaggatgaaagaatttcaccaat
```

-continued

```
attataataatttcaatcaacctgatagcttaggggataaactaatttgaagatacagcttgcctccgataagccagaattccagagct
tctggcattataatctagcaaggttagagatcatggatcactttcagagaaaaacaaaaacaaactaaccaaaagcaaaacagaaccaa
aaaaccaccataaatacttcctaccctgttaatggtccaatatgtcagaaacagcactgtgttagaaataaagctgtctaaagtacact
aatattcgagttataatagtgtgtggactattagtcaataaaaacaacccttgcctcttagagttgttttccatgtacacgcacatct
tatgtcttagagtaagattccctgagaagtgaacctagcatttatacaagataattaattctaatccacagtacctgccaaagaacatt
ctaccatcatctttactgagcatagaagagctacgccaaaaccctgggtcatcagccagcacacacacttatccagtggtaaatacaca
tcatctggtgtatacatacatacctgaatatggaatcaaatattttctaagatgaaacagtcatgatttatttcaaataggtacggat
aagtagatattgaggtaagcattaggtcttatattatgtaacactaatctattactgcgctgaaactgtggctttatagaaattgtttt
cactgcactattgagaaattaagagataatggcaaaagtcacaaagagtatattcaaaaagaagtatagcacttttccttagaaacca
ctgctaactgaaagagactaagatttgtcccgtcaaaaatcctggacctatgcctaaaacacatttcacaatccctgaacttttcaaaa
attggtacatgctttagctttaaactacaggcctcactggagctagagacaagaaggtaaaaaacggctgacaaaagaagtcctggtat
cctctatgatgggagaaggaaactagctaaagggaagaataaattagagaaaaactggaatgactgaatcggaacaaggcaaaggctat
aaaaaaaattagcagtatcctcttgggggccccttccccacactatctcaatgcaaatatctgtctgaaacggtccctggctaaactcc
acccatgggttggccagccttgccttgaccaatagccttgacaaggcaaacttgaccaatagtcttagagtatccagtgaggccagggg
ccggcggctggctagggatgaagaataaaaggaagcacccttcagcagttccacacactcgcttctggaacgtctgaggttatcaataa
gctcctagtccagacgccatgggtcatttcacagaggaggacaaggctactatcacaagcctgtgggcaaggtgaatgtggaagatgc
tggaggagaaaccctgggaaggtaggctctggtgaccaggacaagggagggaaggaaggaccctgtgcctggcaaaagtccaggtcgct
tctcaggatttgtggcaccttctgactgtcaaactgttcttgtcaatctcacaggctcctggttgtctacccatggacccagaggttct
ttgacagctttggcaacctgtcctctgcctctgccatcatgggcaaccccaaagtcaaggcacatggcaagaaggtgctgacttccttg
ggagatgccacaaagcacctggatgatctcaagggcacctttgcccagctgagtgaactgcactgtgacaagctgcatgtggatcctga
gaacttcaaggtgagtccaggagatgtttcagccctgttgcctttagtctcgaggcaacttagacaacggagtattgatctgagcacag
cagggtgtgagctgtttgaagatactggggttgggggtgaagaaactgcagaggactaactgggctgagacccagtggtaatgttttag
ggcctaaggagtgcctctaaaaatctagatggacaattttgactttgagaaaagagaggtggaaatgaggaaaatgacttttctttatt
agattccagtagaaagaactttcatctttccctcattttgttgttttaaaacatctatctggaggcaggacaagtatggtcgttaaaa
agatgcaggcagaaggcatatattggctcagtcaaagtggggaacttggtggccaaacatacattgctaaggctattcctatatcagc
tggacacatataaaatgctgctaatgcttcattacaaacttatatcctttaattccagatgggggcaaagtatgtccaggggtgaggaa
caattgaaacatttgggctggagtagattttgaaagtcagctctgtgtgtgtgtgtgtgtgcgcgcgcgcgtgtgtgtgtgtgtgtc
agcgtgtgtttctttttaacgtcttcagcctacaacatacagggttcatggtggcaagaagatagcaagatttaaattatggccagtgac
tagtgcttgaagggaacaactacctgcatttaatgggaaggcaaaatctcaggctttgagggaagttaacataggcttgattctggt
ggaagcttggtgtgtagttatctggaggccaggctggagctctcagctcactatgggttcatctttattgtctcctttcatctcaacag
ctcctgggaaatgtgctggtgaccgttttggcaatccattcggcaaagaattcaccccctgaggtgcaggcttcctggcagaagatggt
gactgcagtggccagtgccctgtcctccagataccactgagctcactgcccatgattcagagctttcaaggataggctttattctgcaa
gcaatacaaataataaatctattctgctgagagatcacacatgattttcttcagctcttttttttacatcttttttaaatatatgagcca
caaagggtttatattgagggaagtgtgtatgtgtatttctgcatgcctgtttgtgtttgtggtgtgtgcatgctcctcatttatttttta
tatgagatgtgcattttgatgagcaaataaaagcagtaaagacacttgtacacgggagttctgcaagtgggagtaaatggtgtaggaga
aatccggtgggaagaaagacctctataggacaggacttctcagaaacagatgttttggaagagatgggaaaaggttcagtgaagacctg
ggggctggattgattgcagctgagtagcaaggatggttcttaaggaagggaaagtgttccaagcttaggaattcaaggtttagtcagg
tgtagcaattctattttattaggaggaatactatttctaatggcacttagcttttcacagcccttgtggatgcctaagaaagtgaaatt
aatcccatgccctcaagtgtgcagattggtcacagcatttcaagggagagacctcattgtaagactctggggagggtgggacttaggt
gtaagaaatgaatcagcagaggctcacaagtcagcatgagcatgttatgtctgagaaacagaccagcactgtgagatcaaaatgtagtg
```

-continued

```
ggaagaattttgtacaacattaattggaaggcttacttaatggaattttttgtatagttggatgttagtgcatctctataagtaagagttt
aatatgatggtgttacggacctaatgtttgtgtctcctcaaaattcacatgctgaatccccaactcccaactgaccttatctgtggggg
aggcttttgaaaagtaattaggtttagatgagctcataagagcagatccccatcataaaattattttccttatcagaagcagagagaca
agccatttctctttcctcccggtgaggacacagtgagaagtccgccatctgcaatccaggaagagaaccctgaccacgagtcagccttc
agaaatgtgagaaaaaactctgttgttgaagccacccagtcttttgtattttgttatagccttgcactgagtaaggcagatgaagaa
ggagaaaaaataagctttgggttttgagtggactacagaccatgtttatctcaggtttgcaaagctccctcgtcccctatgtttcagt
ataaaatacctactctactactctcatctataagacccaaataataagcctgcgcccttctctctaactttgatttctcctattttttac
ttcaacatgctttactctagccttgtaatgtcttacatacagtgaaatgtaaagttctttattctttttttctttctttctttttttct
cctcagcctcagaatttggcacatgcccttccttctttcaggaacttctccaacatctctgcctggctccatcatatcataaaggtccc
acttcaaatgcagtcactaccgtttcagaatatgcactttctttctttttttgttttttgttttttttaagtcaaagcaaatttcttgag
agagtaaagaaataaacgaatgactactgcataggcagagcagccccgagggccgctggttgttccttttatggttatttcttgatgat
atgttaaacaagttttggattatttatgccttctctttttaggccatatagggtaactttctgacattgccatggcattttcttttaa
tttaatttactgttaccttaaattcaggggtacacgtacaggatatgcaggtttgttttataggtaaaagtgtgccatggttttaatgg
gtttttttttcttgtaaagttgtttaagtttcttgtttactctggatattaggcctttgtcagaagaatagattggaaaatcttttc
ccattctgtagattgtcttcgctctgatggtagtttcttttgctgagcaggagctctttagtttaattagattccattggtcaatttt
tgcttttgctgcaattgcttttcacgctttcatcatgaaatctgtgcccgtgtttatatcatgaatagtattgccttgatttttttcta
ggcttttatagtttgggggttttcatttaagtctctaatccatctggagttaattttggataaggtataaggaaggagtccagtttca
tttttcagcatatggctagccagttctcccccatcatttattaaattgaaaatcctttccccattgcttgcttttgtcaggtttctaaa
agaccagatggttgtaggtacaatatgcagtttcttcaagtcatataataccatctgaaatctcttattaattcatttcttttagtatg
tatgctggtctcctctgctcactatagtgagggcaccattagccagagaatctgtctgtctagttcatgtaagattctcagaattaaga
aaaatggatggcatatgaatgaaacttcatggatgacatatggaatctaatatgtatttgttgaattaatgcataagatgcaacagaga
gaagttgacaactgcaatgataacctggtattgatgatataagagtctatagatcacagtagaagcaataatcatggaaaacaattgga
aatggggaacagccacaaacaagaaagaatcaatacttccaggaaagtgactgcaggtcacttttcctggagcgggtgagagaaagtg
gaagttagcagtaactgctgaattcctggttggctgatggaaagatggggcagctgttcactggtacgcagggttttagatgtatgtac
ctaaggatatgaggtatggcaatgaacagaaattcttttgggaatgagttttagggccattaaaggacatgacctgaagtttcctctga
ggccagtccccacaactcaatataaatgtgtttcctgcatatagtcaaagttgccacttctttttcttcatatcatcgatctctgctct
taaagataatcttggttttgcctcaaactgtttgtcactacaaactttcccatgttcctaagtaaaacaggtaactgcctctcaacta
tatcaagtagactaaaatattgtgtctctaatatcagaaattcagctttaatatattgggtttaactctttgaaatttagagtctcctt
gaaatacacatgggggtgatttcctaaactttatttcttgtaaggatttatctcaggggtaacacacaaaccagcatcctgaacctcta
agtatgaggacagtaagccttaagaatataaaataaactgttcttctctctgccggtggaagtgtgccctgtctattcctgaaattgct
tgtttgagacgcatgagacgtgcagcacatgagacacgtgcagcagcctgtggaatattgtcagtgaagaatgtctttgcctgattaga
tataaagacaagttaaacacagcattagactatagatcaagcctgtgccagacacaaatgacctaatgcccagcacgggccacggaatc
tcctatcctcttgcttgaacagagcagcacacttctcccccaacactattagatgttctggcataattttgtagatatgtaggatttga
catggactattgttcaatgattcagaggaaatctcctttgttcagataagtacactgactactaaatggattaaaaaacacagtaataa
aacccagttttccccttacttccctagtttgtttcttattctgctttcttccaagttgatgctggatagaggtgtttatttctattcta
aaaagtgatgaaattggccgggcgcggtggctcacacctgtaatcccagcactttgggaggctgaggtgggcggatcacgaggtcagga
gatcaagaccatcctggctaacatggtgaaaccccatctctactaaaaatacaaaaaattagccagagacagtggcgggtgcctgtagt
cccagctactcgggaggctgaggcaggagaatggcgtgaacctgggaggcagagcttgcggtgagcagagatcgcgccactgcacactc
cagcctgggtgacaaagcgagactccatctcaaaaaaaaaaaaaaaaagaaaagaaagaaagaaaaaaaactgatgaaat
tgtgtattcaatgtagtctcaagagaattgaaaaccaagaaaggctgtggcttcttccacataaagcctggatgaataacaggataaca
cgttgttacattgtcacaactcctgatccaggaattgatggctaagatattcgtaattcttatccttttcagttgtaacttattcctat
```

-continued

```
ttgtcagcattcaggttattagcggctgctggcgaagtccttgagaaataaactgcacactggatggtgggggtagtgtaggaaaatgg aggggaaggaagtaaagtttcaaattaagcctgaacagcaaagttcccctgagaaggccacctggattctatcagaaactcgaatgtcc atcttgcaaaacttccttgcccaaaccccacccctggagtcacaacccacccttgaccaatagattcattttactgagggaggcaaagg gctggtcaatagattcatttcactgggagaggcaaagggctgggggccagagaggagaagtaaaaagccacacatgaagcagcaatgca ggcatgcttctggctcatctgtgatcaccaggaaactcccagatctgacactgtagtgcatttcactgctgacaagaaggctgctgcca ccagcctgtgaagcaaggttaaggtgagaaggctggaggtgagattctgggcaggtaggtactggaagccgggacaaggtgcagaaagg cagaaagtgtttctgaaagagggattagcccgttgtcttacatagtctgactttgcacctgctctgtgattatgactatcccacagtct cctggttgtctacccatggacctagaggtactttgaaagttttggatatctgggctctgactgtgcaataatgggcaaccccaaagtca aggcacatggcaagaaggtgctgatctccttcggaaaagctgttatgctcacggatgacctcaaaggcacctttgctacactgagtgac ctgcactgtaacaagctgcacgtggaccctgagaacttcctggtgagtagtaagtacactcacgctttcttctttacccttagatattt gcactatgggtacttttgaaagcagaggtggctttctcttgtgttatgagtcagctatgggatatgatatttcagcagtgggattttga gagttatgttgctgtaaataacataactaaaatttggtgagagcaaggactatgaataatggaaggccacttaccatttgatagctctga aaaacacatcttataaaaaattctggccaaaatcaaactgagtgtttttggatgagggaacagaagttgagatagagaaaataacatct ttcctttggtcagcgaaattttctataaaaattaatagtcacttttctgcatagtcctggaggttagaaaaagatcaactgaacaaagt agtgggaagctgttaaaagaggattgtttccctccgaatgatgatggtatacttttgtacgcatggtacaggattctttgttatgagt gtttgggaaaattgtatgtatgtatgtatgtatgtgatgactgggggacttatcctatccattactgttccttgaagtactattat cctactttttaaaggacgaagtctctaaaaaaaaaatgaaacaatcacaatatgttggggtagtgagttggcatagcaagtaagagaa ggataggacacaatgggaggtgcagggctgccagtcatattgaagctgatatctagcccataatggtgagagttgctcaaactctggtg aaaaaggatgtaagtgttatatctatttactgcaagtccagcttgaggccttctattcactatgtaccattttcttttttatcttcact ccctccccagctcttaggcaacgtgatattgattgttttggcaacccacttcagcgaggattttaccctacagatacaggcttcttggc agtaactaacaaatgctgtggttaatgctgtagcccacaagaccactgagttccctgtccactatgtttgtacctatggtccactatgt ttgtacctatgtcccaaaatctcatctccttagatgggggaggttggggagaagagcagtatcctgcctgctgattcagttcctgcat gataaaaatagaataaagaaatatgctctctaagaaatatcattgtactctttttctgtctttatattttaccctgattcagccaaaag gacgcactatttctgatggaaatgagaatgttggagaatgggagtttaaggacagagaagatacttcttgcaatcctgcaagaaaaga gagaactcgtgggtggatttagtggggtagttactcctaggaaggggaaatcgtctctagaataagacaatgttttacagaaagggag gtcaatggaggtactctttggaggtgtaagaggattgttggtagtgtgtagaggtatgttaggactcaaattagaagttctgtataggc tattatttgtatgaaactcaggatatagctcatttggtgactgcagttcacttctacttattttaaacaacatattttttattatttat aatgaagtggggatggggcttcctagagaccaatcaagggccaaaccttgaactttctcttaacgtcttcaatggtattaatagagaat tatctctaaggcatgtgaactggctgtcttggttttcatctgtacttcatctgctacctctgtgacctgaaacatatttataattccat taagctgtgcatatgatagatttatcatatgtattttccttaaaggattttgtaagaactaattgaattgatacctgtaaagtcttta tcacactacccaataaataataaatctctttgttcagctctctgtttctataaatatgtacaagttttattgttttagtggtagtgat tttattctctttctatatatatacacacacatgtgtgcattcataaatatatacaatttttatgaataaaaaattattagcaatcaata ttgaaaaccactgattttgtttatgtgagcaaacagcagattaaaaggctgagatttaggaaacagcacgttaagtcaagttgataga ggagaatatggacatttaaaagaggcaggatgatataaaattagggaaactggatgcagagaccagatgaagtaagaaaaatagctatc gttttgagcaaaaatcactgaagtttcttgcatatgagagtgacataataaatagggaaacgtagaaaattgattcacatgtatatata tatatagaactgattagacaaagtctaacttgggtatagtcagaggagcttgctgtaattatattgaggtgatggataaagaactgaag ttgatgaaacaatgaagttaagaaaaaaaatcgagtaagagaccattgtggcagtgattgcacagaactggaaaacattgtgaaacag agagtcagagatgacagctaaaatccctgtctgtgaatgaaaagaaggaaatttattgacagaacagcaaatgcctacaagcccctgt ttggatctggcaatgaacgtagccattctgtggcaatcacttcaaactcctgtacccaagacccttaggaagtatgtagcaccctcaaa cctaaaacctcaaagaaagaggttttagaagatataatacccttcttctccagtttcattaatcccaaaacctcttctcaaagtatt
```

-continued

```
tcctctatgtgtccaccccaaagagctcacctcaccatatctcttgagtgggagcacatagataggcggtgctaccatctaacagcttc tgaaattcctttgtcatattttttgagtccccactaataacccacaaagcagaataaataccagttgctcatgtacaataatcactcaac tgctgtcttgtagcatacattaattaagcacattctttgaataattactgtgtccaaacaatcacactttaaaatctcacacttgtgct atcccttgcccttctgaatgtcactctgtattttaaatgaagagatgagggttgaatttcctgtgttacttattgttcatttctcgatg aggagttttcacattcaccttagtggaaaacacataagtacacatcttacaggaaaaatataccaaactgacatgtagcatgaatgct tgtgcatgtagtcatataaaatcttgtagcaatgtaaacattctctgatatacacatacagatgtgtctatatgtctacacaatttctt atgctccatgaacaaacattccatgcacacataagaacacacactgttacagatgcatacttgagtgcattgacaaaattacccagtc aatctagagaatttggatttctgcatttgactctgttagctttgtacatgctgttcatttactctgggtgatgtctttccctcattttg ccttgtctatcttgtactcatactttaagtcctaacttatatgttatctcaactaagaagctatttttttttaattttaactgggctta aagccctgtctataaactctgctacaattatgggctcttccttataatatttagtgttttcctactaatgtacttaatctgctcattg tatattcctaccactaaattttaacctcttttatggtagagacattgtcttgtaaactcttatttccctagtatttggagatgaaaaaa aagattaaattatccaaaattagatctctcttttctacattatgagtattacactatccatagagaagtttgtttgagacctaaactga ggaaccttttggttctaaaatgactatgtgatatcttagtatttataggtcatgaggttccttcctctgcctctgctatagtttgattag tcaacaagcatgtgtcatgcatttattcacatcagaatttcatacactaataagacatagtatcagaagtcagtttattagttatatca gttagggtccatcaaggaaaggacaaaccattatcagttactcaacctagaattaaatacagctcttaatagttaattatccttgtatt ggaagagctaaaatatcaaataaaggacagtgcagaaatctagatgttagtaacatcagaaaacctcttccgccattaggcctagaagg gcagaaggagaaaatgtttataccaccagagtccagaaccagagccataaccagaggtccactggattcagtgagctagtgggtgctc cttggagagagccagaactgtctaatgggggcatcaaagtatcagccataaaaaaccataaaaaagactgtctgctgtaggagatccgt tcagagagagagagagaccagaaataatcttgcttatgctttccctcagccagtgtttaccattgcagaatgtacatgcgactgaaagg gtgaggaaacctgggaaatgtcagttcctcaaatacagagaacactgagggaaggatgagaaataaatgtgaaagcagacatgaatggt aattgacagaaggaaactaggatgtgtccagtaaatgaataattacagtgtgcagtgattattgcaatgattaatgtattgataagata atatgaaaacacagaattcaaacagcagtgaactgagattagaattgtggagagcactggcatttaagaatgtcacacttagaatgtgt ctctaggcattgttctgtgcatatatcatctcaatattcattatctgaaaattatgaattaggtacaaagctcaaataatttatttttt caggttagcaagaacttttttttttttttttctgagatagagcattgctatggttgcccaggctggagtgcaatggcatgatccaggctc actgcaacatctgcctcccaggttcaagcgattctcctgcctcagcctcccaagtagctggcactacaggcatgtgccaccaccatgcc tggctaattttctattttagtagatagggggtttcaccatgttggtcaggctgatctcgaactcctaacatcaggtgatccaccctcc tcggcctctgaaagtgctgggatcacaggcgtgagccaccacacccagccaagaatgtgaattttgtagaaggatataacccatatttc tctgacctagagtccttagtatacctcccataccatgtggctcatcctccttacatacatttcccatcttcaccctacctttttcctt tttgtttcagcttttcactgtgtcaaaatctagaaccttatctcctacctgctctgaaaccaacagcaagttgacttccattctaaccc acattggcattacactaattaaaatcgatactgagttctaaaatcatcggggatttt gggactatgtcttacttcatacttccttgag atttcacattaaatgttggtgttcattaaaggtccttcatttaactttgtattcatcacactcttggattcacagttatatctaaactc ttaaatacagcctgtataatcccaattcccaactctgatttctaacctctgacctccaacctcagtgccaaacccatatatcaaacaat gtactgggcttatttatatagatgtcctataggcacctcagactcagcatgggtatttcacttgttatactaaaactgtttctcttcca gtgttttccattttagtcattagatagctacttgcccattccaaggtcacagattaaaatcatttccctacctctaatcaacagttc gattctgcttcaatttgtccctatctattaatcaccactcttactgcccagtcaggtcctcattgtttcctgaacaagagtagatgcta ttctttccacttttagaccttatcctggctggatgcggtggctcaggcttgtaaacccagcactttgggaggccaaggcaggcagatca cttgaggtcaggagttcaagaccagcctgaccaacatggtgaaaccccatctctactaaaaatacaaaatcagccgggcgtgtggtgca tgcctgcagtcccagctattcaggtggctgaggcaggagaattgcttgaacccaggaggcagaggttgcggtgagcctagattgcacca ttgcactctagcttgggcaatagggatgaaactccatctcagaagagaaaagaaaaaagaccttattctgttatacaaatcctctcaa tgcaatccatatagaataaacatgtaaccagatctcccaatgtgtaaaatcatttcaggtagaacagaattaaagtgaaaagccaagtc tttggaattaacagacaaagatcaaataacagtcctcatggcccttaagaatttacctaacatttttttttagaatcaattttcttatata
```

-continued

```
tgaattggaaacataattcctccctcacaaacacattctaagattttaaggagatattgatgaagtacatcatctgtcattttaacag gtagtggtagtgattcacacagcacattatgatctgttcttgtatgttctgttccattctgtattcttgacctggttgtattctttctg agctccagatccacatatctaagtacatcttttgcattttacaagagtgcatacaatacaatgtatccaagactgtatttctgatttt atcgtaccactaaactcacaaatgtggccctattcttgtgttcacgactgacatcaccgtcatggtccaagtctgataatagaaatggc attgtcactttcttccctactgcaacagaagcccagctatttgtctcccattttctctacttctaaaatacatttcttcactaagtgag aataatcttttaaagacacaaatcaaaccatgccaccacctttcttgaattattcaatatctttcgttggcttccaggttacagaaaaa taacttgtaacaaagtttaaaggtcattcatggctcctctctaccctattttataacatttccccttgtgatcagaatctcaggcacat catccatctttctatatacaaataaagtcatatagtttgaactcacctctggttacttttaatcaaccaaatgctgtaaaatgcatttg tatcgctacgtgttaagcagtagttgattcttttcatttctgtgtaatattctattctttgactataccgtaaatttatcaattctactg ttggtaagcatttaagtggctaccggtttgaggttttatgattattgctgtcataagcatttctatacatgtctttggatacacacat gcatgtgtttctgaatatctaaaaatgtaattgctaggtaatagacttatcaagcatccagcatttgtggatactattaaaggttttcc aaaggggttatactattgtacagtgtcaccaacagagtttgagtttctattgatccatatcaccaccaaaatttgaactgtcagtctta tctcttctcttgtctcttttttcctcttttttttccttcccttccctctcttcgtttcttttctctcctcttctcttctttcctctct tcccttcccttctctttctcttccctatcccttctcctctcctctccctccttttttctcctctcctctccattatttatttttcct tcttctcctccatcccttccatcctctctcttccctcttccttccttcctttctccatttcttcctcctcttccttcaatccttcct tttggatatgctcatgggtgtgtatttgtctgccattgtggcattatttgaattcagaaaagagtgaaaaactactgggatcttcattc ctgggtctaattccacatttttttttaagaacacatctgtaaaaatgttctgtactagcatattcccaggaacttcgttaaatttaatc tggctgaatatggtaaatctacttttcactttgcattctttctttagtcataccataattttaaacattcaaaatatttgtatataata tttgattttatctgtcattaaaatgttaaccttaaaattcatgtttccagaacctatttcaataactggtaaataaacactattcattt tttaaatattcttttaatggatatttatttcaatataataaaaaattagagttttattataggaagaatttaccaaaagaaggaggaag caagcaagtttaaactgcagcaatagatttgtccattccaacctctcaaaattcccttggagacaaaaatctctagaggcaaagaagaa ctttatattgagtcaacttgttaaaacatctgcttttagataagttttcttagtataaagtgacagaaacaaataagttaaactctaag atacattccactatattagcctaaaacacttctgcaaaaatgaaactaggaggatattttagaaacaactgctgaaagagatgcggtg gggagatatgtagaggagaacagggtttctgagtcaagacacacatgacagaacagccaatctcagggcaagttaagggaatagtggaa tgaaggttcattttcattctcacaaactaatgaaaccctgcttatcttaaaccaacctgctcactggagcagggaggacaggaccagc ataaaaggcagggcagagtcgactgttgcttacactttcttctgacataacagtgttcactagcaacctcaaacagacaccatggtgca tctgactcctgaggagaagactgctgtcaatgccctgtggggcaaagtgaacgtggatgcagttggtggtgaggccctgggcaggttgg tatcaaggttataagagaggctcaaggaggcaaatggaaactgggcatgtgtagacagagaagactcttgggtttctgataggcactga ctctctgtcccttggctgttttcctaccctcagattactggtggtctaccttggacccagaggttctttgagtccttggggatctg tcctctcctgatgctgttatgggcaaccctaaggtgaaggctcatggcaagaaggtgctaggtgcctttagtgatggcctggctcacct ggacaacctcaagggcacttttctcagctgagtgagctgcactgtgacaagctgcacgtggatcctgagaacttcagggtgagtccag gagatgcttcacttttctcttttactttctaatcttacattttggttcttttacctacctgctcttctcccacatttttgtcatttta ctatatttatcatttaatgcttctaaaatttgttaattttttatttaaatattctgcattttttccttcctcacaatcttgctattt taaattatttaatatcctgtctttctctcccaaccccctcccttcatttttccttctctaacaacaactcaaattatgcataccagctc tcacctgctaattctgcacttagaataatccttttgtctctccacatgggtatgggagaggctccaactcaaagatgagaggcatagaa tactgttttagaggctataaatcattttacaataaggaataattggaattttataaattctgtagtaaatggaatggaaggaaagtga atatttgattatgaaagactaggcagttacactggaggtggggcagaagtcgttgctaggagacagcccatcatcacactgattaatca attaatttgtatctattaatctgtttatagtaattaatttgtatatgctatatacacatacaaaattaaaactaatttggaattaattt gtatatagtattatacagcatatatagcatatatgtacatatatagactacatgctagttaagtacatagaggatgtgtgtgtatagat atatgttatatgtatgcattcatatatgtacttatttatgctgatgggaataacctggggatcagttttgtctaagatttgggcagaaa
```

```
aaaatgggtgttggctcagtttctcagaagccagtctttatttctctgttaaccatatgcatgtatctgcctacctcttctccgcagct
cttgggcaatgtgctggtgtgtgtgctggcccgcaactttggcaaggaattcacccacaaatgcaggctgcctatcagaaggtggtgg
ctggtgtggctaatgccctggctcacaagtaccattgagatcctggactgtttcctgataaccataagaagaccctatttccctagatt
ctattttctgaacttgggaacacaatgcctacttcaagggtatggcttctgcctaataaagaatgttcagctcaacttcctgattaatt
tcacttatttcatttttttgtccaggtgtgtaagaaggttcctgaggctctacagatagggagcacttgtttattttacaaagagtaca
tgggaaaagagaaaagcaagggaaccgtacaaggcattaatgggtgacacttctacctccaaagagcagaaattatcaagaactcttga
tacaaagataatactggcactgcagaggttctagggaagacctcaaccctaagacatagcctcaagggtaatgctacgattaaactcca
acaattactgagaaaataatgtgctcaattaaaggcataatgattactcaagacaatgttatgttgtctttcttcctccttcctttgcc
tgcacattgtagcccataatactatacccatcaagtgttcctgctccaagaaatagcttcctcctcttacttgcccagaacatctct
gtaaagaatttcctcttatcttcccatatttcagtcaagattcattgctcacgtattacttgtgacctctcttgaccccagccacaata
aacttctctatactacccaaaaaatctttccaaaccctcccccacaccattttttatattttatattttcttatttatttcatgcac
acacacactccgtgctttataagcaattctgcctattctctaccttcttacatgcctactgtgcctcatattaaattcatcaatggg
cagaaagaaaatatttattcaagaaaacagtgaatgaatgaacgaatgagtaaatgagtaaatgaaggaatgattattccttgctttag
aacttctggaattagaggacaatattaataataccatcgcacagtgtttctttgttgttaatgctacaacatacaaagaggaagcatgc
agtaaacaaccgaacagttatttcctttctgatcataggagtaatattttttccttgagcaccattttgccataggtaaaattagaa
ggattttagaactttctcagttgtatacattttaaaaatctgtattatatgcatgttgattaattttaaacttacttgaatacctaa
acagaatctgttgtttccttgtgtttgaaagtgctttcacagtaactctgtctgtactgccagaatatactgacaatgtgttatagtta
actgttttgatcacaacattttgaattgactggcagcagaagctcttttatatccatgtgttttccttaagtcattatacatagtaggc
actgagaactctttatatctgaataagatatttaggaaccactggtttacatatcagaagcagagctactcagggcatttggggaaga
tcactttcacattcctgagcatagggaagttctcataagagtaagatattaaaaggagatacttgtgtggtattcgaaagacagtaaga
gagattgtagacctatgatcttgatagggaaaacaaactacattcctttctccaaaagtcaaaaaaaaagagcaaatatagcttacta
taccttctattcctacaccattagaagtagtcagtgagtctaggcaagatgttggccctaaaaatccaaataccagagaattcatgaga
acatcacctggatgggacatgtgccgagcacacacaattactatatgctaggcattgctatcttcatattgaagatgaggaggtcaaga
gatgaaaaagacttggcaccttgttgttatattaaaattatttgttagagtagagcttttgtaagagtctaggagtgtgggagctaaa
tgatgatacacatggacacaaaaaatagatcaacagacacccaggcctacttgagggttgagggtgggaagagggagacgatgaaaaag
aacctatgggtattaagttcatcactgagtgatgaaataatctgtacatcaagacccagtgatatgcaatttacctatataacttgta
catgtaccccaaatttaaaatgaaagttaaaacaaagtataggaatggaattaattcctcaagatttggctttaattttatttgataa
tttatcaaatggttgtttttcttttctcactatggcgttgctttataaactatgttcagtatgtctgaatgaaagggtgtgtgtgtgtg
tgaaagagagggagagaggaagggaagagaggacgtaataatgtgaatttgagttcatgaaaattttcaataaaataatttaatgtca
ggagaattaagcctaatagtctcctaaatcatccatctcttgagcttcagagcagtcctctgaattaatgcctacatgtttgtaaggg
tgttcagactgaagccaagattctacctctaaagagatgcaatctcaaatttatctgaagactgtacctctgctctccataaattgaca
ccatggcccacttaatgaggttaaaaaaagctaattctgaatgaaaatctgagcccagtggaggaaatattaatgaacaaggtgcaga
ctgaaatataaattttctgtaataattatgcatatactttagcaaagttctgtctatgttgactttattgcttttggtaagaaatac
aactttttaaagtgaactaaactatcctatttccaaactattttgtgtgtgtgcggtttgtttctatgggttctggttttcttggagca
ttttatttcatttttaattaattaattctgagagctgctgagttgtgtttactgagagattgtgtatctgcgagagaagtctgtagcaa
gtagctagactgtgcttgacctaggaacatatacagtagattgctaaaatgtctcacttggggaattttagactaaacagtagagcatg
tataaaaatactctagtcaagtgctgcttttgaaacaaatgataaaaccacactcccatagatgagtgtcatgattttcatggaggaag
ttaatattcatcctctaagtatacccagactagggccattctgatataaaacattaggacttaagaaagattaatagactggagtaaag
gaaatggacctctgtctctctcgctgtctcttttttgaggacttgtgtgtgtgtgtgtgtgtgtgtgtgtgtgtgttgtggtcagtg
gggctggaataaaagtagaatagacctgcacctgctgtggcatccattcacagagtagaagcaagctcacaatagtgaagatgtcagta
agcttgaatagttttcaggaactttgaatgctgatttagatttgaaactgaggctctgaccataaccaaatttgcactatttattgct
```

-continued

```
tcttgaaacttatttgcctggtatgcctgggcttttgatggtcttagtatagcttgcagccttgtccctgcagggtattatgggtaata gaaagaaaagtctgcgttacactctagtcacactaagtaactaccattggaaaagcaacccctgccttgaagccaggatgatggtatct gcagcagttgccaacacaagagaaggatccatagttcatcatttaaaaaagaaaacaaatagaaaaggaaaactatttctgagcata agaagttgtagggtaagtctttaagaaggtgacaatttctgccaatcaggatttcaaagctcttgctttgacaattttggtctttcaga atactataaatataacctatattataatttcataaagtctgtgcattttctttgacccaggatatttgcaaaagacatattcaaacttc cgcagaacactttatttcacatatacatgcctcttatatcagggatgtgaaacagggtcttgaaaactgtctaaatctaaaacaatgct aatgcaggtttaaatttaataaaataaaatccaaaatctaacagccaagtcaaatctgcatgttttaacatttaaaatattttaaagac gtcttttcccaggattcaacatgtgaaatcttttctcagggatacacgtgtgcctagatcctcattgctttagttttttacagaggaat gaatataaaaagaaaatacttaaattttatccctcttacctctataatcatacataggcataatttttaacctaggctccagatagcc atagaagaaccaaacactttctgcgtgtgtgagaataatcagagtgagatttttcacaagtacctgatgagggttgagacaggtagaa aaagtgagagatctctatttatttagcaataatagagaaagcatttaagagaataaagcaatggaaataagaaatttgtaaatttcctt ctgataactagaaatagaggatccagtttcttttggttaacctaaattttatttcattttattgttttattttattttatttttatttta ttttgtgtaatcgtagtttcagagtgttagagctgaaaggaagaagtaggagaaacatgcaaagtaaaagtataacactttccttacta aaccgacatgggtttccaggtaggggcaggattcaggatgactgacagggcccttagggaacactgagaccctacgctgacctcataaa tgcttgctacctttgctgttttaattacatcttttaatagcaggaagcagaactctgcacttcaaaagttttcctcacctgaggagtt aatttagtacaaggggaaaaagtacaggggatgggagaaaggcgatcacgttgggaagctatagagaagaagagtaaattttagtaa aggaggtttaaacaaacaaaatataaagagaaataggaacttgaatcaaggaaatgattttaaaacgcagtattcttagtggactagag gaaaaaataatctgagccaagtagaagacctttcccctcctacccctactttctaagtcacagaggcttttgttccccagacact cttgcagattagtccaggcagaaacagttagatgtccccagttaacctcctatttgacaccactgattacccccattgatagtcacactt tgggttgtaagtgacttttatttatttgtattttttgactgcattaagaggtctctagtttttttatctcttgtttcccaaaacctaata agtaactaatgcacagagcacattgatttgtatttattctatttttagacataatttattagcatgcatgagcaaattaagaaaaacaa caacaaatgaatgcatatatatgtatatgtatgtgtgtatatatacacacatatatatatattttttcttttcttaccagaaggttt taatccaaataaggagaagatatgcttagaaccgaggtagagttttcatccattctgtcctgtaagtattttgcatattctggagacgc aggaagagatccatctacatatcccaaagctgaattatggtagacaaaactcttccacttttagtgcatcaacttcttatttgtgtaat aagaaaattgggaaaacgatcttcaatatgcttaccaagctgtgattccaaatattacgtaaatacacttgcaaaggaggatgttttta gtagcaatttgtactgatggtatggggccaagagatatcttagagggagggctgagggtttgaagtccaactcctaagccagtgcca gaagagccaaggacaggtacggctgtcatcacttagacctcaccctgtggagccacaccctagggttggccaatctactcccaggagca gggagggcaggagccagggctgggcataaaagtcagggcagagccatctattgcttacatttgcttctgacacaactgtgttcactagc aacctcaaacagacaccatggtgcatctgactcctgaggagaagtctgccgttactgccctgtggggcaaggtgaacgtggatgaagtt ggtggtgaggccctgggcaggttggtatcaaggttacaagacaggtttaaggagaccaatagaaactgggcatgtggagacagagaaga ctcttgggtttctgataggcactgactctctctgcctattggtctatttcccacccttaggctgctggtggtctaccttggacccag aggttctttgagtcctttggggatctgtccactcctgatgctgttatgggcaaccctaaggtgaaggctcatggcaagaaagtgctcgg tgcctttagtgatggcctggctcacctggacaacctcaagggcacctttgccacactgagtgagctgcactgtgacaagctgcacgtgg atcctgagaacttcagggtgagtctatgggacgcttgatgttttctttccccttcttttctatggttaagttcatgtcataggaagggg ataagtaacagggtacagtttagaatgggaaacagacgaatgattgcatcagtgtggaagtctcaggatcgttttagtttcttttattt gctgttcataacaattgttttcttttgtttaattcttgctttcttttttttcttctccgcaatttttactattatacttaatgcctta acattgtgtataacaaaaggaaatatctctgagatacattaagtaacttaaaaaaaaactttacacagtctgcctagtacattactatt tggaatatatgtgtgcttatttgcatattcataatctccctactttattttctttattttttaattgatacataatcattatacatatt tatgggttaaagtgtaatgttttaatatgtgtacacatattgaccaaatcagggtaattttgcatttgtaattttaaaaaatgctttct tcttttaatatacttttttgtttatcttatttctaatactttccctaatctctttctttcagggcaataatgatacaatgtatcatgcc
```

-continued

```
tctttgcaccattctaaagaataacagtgataattttctggggttaaggcaatagcaatatctctgcatataaatatttctgcatataaat tgtaactgatgtaagagggtttcatattgctaatagcagctacaatccagctaccattctgcttttatttttatggttgggataaggctgg attattctgagtccaagctaggccttttgctaatcatgttcatacctcttatcttcctcccacagctcctgggcaacgtgctggtctg tgtgctggcccatcactttggcaaagaattcaccccaccagtgcaggctgcctatcagaaagtggtggctggtgtggctaatgccctgg cccacaagtatcactaagctcgctttcttgctgtccaatttctattaaaggttcctttgttccctaagtccaactactaaactggggga tattatgaagggccttgagcatctggattctgcctaataaaaaacatttattttcattgcaatgatgtatttaaattatttctgaatat tttactaaaagggaatgtgggaggtcagtgcatttaaaacataaagaaatgaagagctagttcaaaccttgggaaaatacactatatc ttaaactccatgaaagaaggtgaggctgcaaacagctaatgcacattggcaacagccctgatgcatatgccttattcatccctcagaa aaggattcaagtagaggcttgatttggaggttaaagttttgctatgctgtattttacattacttattgtttagctgtcctcatgaatg tcttttcactacccatttgcttatcctgcatctctcagccttgactccactcagttctcttgctagagataccacctttcccctgaag tgttccttccatgttttacggcgagatggtttctcctcgcctggccactcagccttagttgtctctgttgtcttatagaggtctacttg aagaaggaaaaacagggtcatggtttgactgtcctgtgagcccttcttccctgcctcccccactcacagtgacccggaatctgcagtg ctagtctcccggaactatcactctttcacagtctgctttggaaggactgggcttagtatgaaaagttaggactgagaagaatttgaaag gcggcttttttgtagcttgatattcactactgtcttattaccctgtcataggcccaccccaaatggaagtcccattcttcctcaggatgt ttaagattagcattcaggaagagatcagaggtctgctggctcccttatcatgtcccttatggtgcttctggctctgcagttattagcat agtgttaccatcaaccaccttaacttcattttctttattcaatacctaggtaggtagatgctagattctggaaataaaatatgagtctc aagtggtccttgtcctctctcccagtcaaattctgaatctagttggcaagattctgaaatcaaggcatataatcagtaataagtgatga tagaagggtatatagaagaatttttattatatgagagggtgaaaccctcaaaatgaaatgaaatcagaccccttgtcttacaccataaaca aaaataaatttgaatgggttaaagaattaaactaagacctaaaaccataaaaattttaaagaaatcaaaagaagaaaattctaatatt cacgttgcagccgttttttgaattgatatgagaagcaaaggcaacaaaggaaaaataaagaagtgaggctacatcaaactaaaaat ttccacacaaaaaacaaacaatgaacaaatgaaaggtgaaccatgaaatggcatatttgcaaaccaaatatttcttaaatattttggt taatatccaaaatatataagaaacacagatgattcaataacaaacaaaaaattaaaaataggaaaataaaaaaattaaaaagaagaaaa tcctgccatttatggcagaattgatgaacctggaggatgtaaaactaagaaaaataagcctgacacaaaaagacaaatactacacaacc ttgctcatatgtgaaacataaaaaagtcactctcatggaaacagacagtagaggtatggtttccaggggttgggggtgggagaatcagg aaactattactcaaagggtataaaatttcagttatgtgggatgaataaattctagatatctaatgtacagcatcgtgactgtagttaat tgtactgtaagtatatttaaaatttgcaaagagagtagattttttttttttttagatggagttttgctcttgttgtccaggctggagt gcaatggcaagatcttggctcactgcaacctccgcctcctgggttcaagcaaatctcctgcctcagcctcccgagtagctgggattaca ggcatgcgacaccatgcccagctaattttgtattttagtagagacgggtttctccatgttggtcaggctgatccgcctgcctcggcc acccaaagggctgggattacaggcgtgagccaccgggcctggccgagagtagatcttaaaagcatttaccacaagaaaaaggtaactat gtgagataatgggtatgttaattagcttgattgtggtaatcatttcacaaggtatacatatattaaaacatcatgttgtacaccttaaa tatatacaattttttatttgtgaatgatacctcaataaagttgaagaataataaaaaagaatagacatcacatgaattaaaaaactaaaa aataaaaaaatgcatcttgatgattagaattgcattcttgattttcagatacaaatatccatttgactgtttactcttttccaaaaca atacaataaattttagcactttatcttcattttccccttcccaatctataattatatatatatatttttagatattttgtatagtttt actccctagattttctagtgttattattaaatagtgaagaaatgtttacacttatgtacaaaatgttttgcatgcttttcttcatttct aacattctctctaagtttattctattttttctgattatccttaatattatctctttctgctggaaatacattgttacttttggtttat ctaaaaatggcttcatttcttcattctaaaatcatgttaaattaataccactcatgtgtaagtaagatagtggaataaatagaaatcc aaaaactaaatctcactaaaatataataatgtgatatataaaaatatagcttttaaatttagcttggaaataaaaaacaaacagtaatt gaacaactatacttttttgaaaagagtaaagtgaaatgcttaactgcatataccacaatcgattacacaattaggtgtgaaggtaaaatt cagtcacgaaaaaactagaataaaaatatgggaagacatgtatataatcttagagataacactgttatttaattatcaacccaaagtag aaactatcaaggagaaataaattcagtcaacaataaaagcatttaagaagttattctaggctgggagcggtggctcacacctgcaatt gcagcactttgggaggcctagacaggcggatcacgacgtcaggagttcaagatcagcctggccaacatagtgaaaccctcatcgctacta
```

-continued

```
aaaatataaaaacttagcctggcgtggtggcaggcatgtgtaatcccagcaatttgggaggctgaggcaggagaatcgcttgatcctgg
gaggcagaggttgcagtgagccaagattgtgccactgcattccagcccaggtgacagcatgagactccgtcacaaaaaaaaagaaaaa
aaaaagggggggggagcggtggagccaagatgaccgaataggaacagctccagtctatagctcccatcgtgagtgacgcagaagacgg
gtgatttctgcatttccaactgaggtaccaggttcatctcacagggaagtgccaggcagtgggtgcaggacagtaggtgcagtgcactg
tgcatgagccaaagcagggcgaggcatcacctcacccgggaagcacaaggggtcagggaattcccttcctagtcaaagaaaagggtga
cagatggcacctggaaaatcgggtcactcccgccctaatactgcgctcttccaacaagcttaacaaatggcacaccaggagattatatc
ccatgcctggctcagagggtcctacgcccatggagcctcgctcattgctagcacagcagtctgaggtcaaactgcaaggtggcagtgag
gctgggggaggggtgcccaccattgtccaggcttgagcaggtaaacaaagccgcctggaagctcgaactgggtggagcccaccacagct
caaggaggcctgcctgcctctgtaggctccacctctaggggcagggcacagacaaacaaaagacaacaagaacctctgcagacttaaat
gtccctgtctgacagctttgaagagagtagtggttctcccagcacatagcttcagatctgagaacaggcagactgcctcctcaagtggg
tccctgaccccgagtagcctaactgggaggcatccccagtaggggcagactgacacctcacatggctggtactcctctaagacaaaa
cttccagaggaatgatcaggcagcagcatttgcggttcaccaatatccactgttctgcagccaccgctgttgatacccaggaaaacagc
ttctggagtggacctccagtaaactccaacagacctgcagctgagggtcctgactgttagaaggaaaactaacaaacagaaaggacatc
cacaccaaaaacccatctgtacatcgccatcatcaaagaccaaaggtagataaaaccataaagatggggaaaaagcagagcagaaaaac
tggacactctaaaaatgagagtgcctctcctcctccaaagtaacgcagctcctcaccagcaatggaacaaagctgggcagagaatgact
ttgacgagttgagagaggaaggcttcagaagatcaaactactccaagctaaaggaggaagttcgaacaaacggcaaagaagtaaaaaac
tttgaaaaaaaattagatgaatggataactagaataaccaatgcacagaagtccttaaaggacctgatggagctgaaaaccaaggcagg
agaactacgtgacaaatacacaagcctcagtaaccgatgagatcaactggaagaaagggtatcaatgacgaaagatgaaatgaatgaaa
tgaagcatgaagagaagtttagagaaaaaagaataaaaagaaacgaacaaagcctccaagaaatatgggactatgtgaaaagaccaaat
ctacatctaattggtgtagctgaaagtgatggggagaatggaaccaagttggaaaacactctgcaggatattatccaggagaacttccc
caatctagcaaggcaagcccaaattcacattcaggaaatacagagaacgccacaaagatactcctagagaaaagcaactccaagacaca
taactgtcagattcaccaaagttgaaatgaaggaaaaaatgttaagggcagccagagagagaaaggtcgggttacccacaaagggaagccc
atcagactaacagctgatctatcggcagaaactctacaagccagaagaaagtgggggccaatattcaacattgttaaagaaaagaattt
tcaacccagaatttcatatccagccaaactaagcttcataagtgaaggagaaataaaatcctttacagacaagcaaatgctgagagatt
ttgtcaccaccaggcctgccctacaagagctcctgaaggaagcactaaacatggaaaggaacaactagtatcagccactgcaaaaacat
gccaaattgtaaagaccatcaaggctaggaagaaactgcatcaacgagcaaaataaccagctaacatcataatgacaggatcaaattca
tacataacaatactcaccttaaatgtaaataggctaaatgctccaattaaaagacacagactggcaaattggataaggagtcaagaccc
atctgtgttctgtattcaggaaacccatctcacgtgcagagacacacataggctcgaaataaaaggatggaggaatatctaccaagcaa
atggaaaacaaaaaaggcaggggttgcaatcctagtctctgataaaacagattttaaaccaacaaagatcaaaagagacaaagaaggc
cattacataatggcaaagggatctattcaagaagaagaactaactatactaaatatatatgcacccaatacaggagcacccagattcat
aaaacaagtcctgagtgacctacaaagagacttagatgcccacacaataataatgggagactttaacaccccactgtcaacattagaca
gatcaacgagacagaaagttaacaaggatatccaggaattggactcagctctgcaccaagcagacctaatagacatctacagaactctc
caccccaaatcaacagaatatacattcttttcagcaccacaccacacctattccaaaactgaccacatagttggaagtaaagctctcct
cagcaaatgtaaaagaacagaaactataacaaactgtctctcagaccacagtgcaatcaaactagaactcaggattaagaaactcactc
aaaaccactcagctacatggaaactgaacagcctgctcctgaatgactactgggtacataacaaaatgaaggcagaaataaagatgttc
tttgaaaccaacgagaacaaagacacaacacaccagaatctctgagacacattcaaagcagtgtgtagagggaaatttatagcactaaa
tgcccacaagggaaagcaggaaagatctaaaattgacaccctaacatcacaattaaaaaactagagaagcaggagcaaacacattcaaa
agctaacagaagacaagaaataactaagatcagagcagaagtgaaggacatagagacacaaaaaaacccttcaaaaaaatcaatgaatc
cagaagctgttttttttgaaaagatcaacaaaattgatagactgctagcaagactaataaagaagaaaagagagaagaatcaaatagacg
caataaaaaatgacacgggggtatcaccactgatcccacagaaatacaaactaccgtcagagaatactataaacacctctacgcaaataa
```

-continued

```
actagaaaatctagaagaaatggataaattcctcgacacatacactctgccaagactaaaccaggaagaagttgtatctctgaatagac caataacaggctctgaaattgaggcaataattaatagcttatcaaccaaaaaaagtccgggaccagtaggattcatagccgaattctac cagaggtacaaggaggagctggtaccattccttctgaaactattccaatcaatagaaaaagagggaatcctccctaactcattttatga ggccagcatcatcctgataccaaagcctgacagagacacaacaaaaaaagagaatgttacaccaatatccttgatgaacattgatgcaa aaatcctcaataaaatactggcaaactgatccaccatgatcaagtgggcttcatccctgccatgcaaggctggttcaacatacgaaaat caataaacataatccagcatataaacagaaccaaagacacaaaccatatgattatctcaatagatgcagaaaaggcctttgacaaaatt caacaacgcttcatgctaaaaactctcaataaattaggtattgatgggacatatctcaaaataataagagctatctatgacaaacccac agccaatatcatactgagtggacaaaaactggaagcattccctttgaaaactggcacaaggcagggatgccctctctcaccactcctat tcaacatagtgttgtaagttctggccagggcaatcaggcaggagaaggaaataaagggcattcaattaggaaaagaggaagtgaaattg tccctgtttgcagatgacatgattgtatatctagaaaacccccattgtctcagcccaaaatctccttaagctgataagcaacttcagcaa agtctcaggatataaaatcagtgtgcaaaaatcacaagtattcctatgcaccaataacagacaaacagagagccaaatcatgagtgaac tcccattcacaattgcttcaaagagaataaaatacctaggaatccaacttacaagggatgtgaaggacctcttcaaggagaactacaaa ccactgctcaatgaaataaaagaggatacaaacaaatggaagaacattccatgctcatgggtaggaagaatcaatatcgtgaaaatggt catactgcccaaggtaatttatagattcaatgccatccccatcaagctaccaatgactttcttcacagaactggaaaaaactactttaa agttcatatggaaccaaaaagagcccacatcaccaaggcaatcctaagccaaaagaacaaagctggaggcatcacgctacctgacttc aaactatactacaatgctacggtaaccaaaacagcatggtactggtaccaaaacagagatctagaccaatggaacagaacagagccctc agaaataatgccgcatatctacaactatctgatctttgacaaacctgagagaaacaagcaatggggaaaggattccctatttaataat ggtgctgggaaaactggctagccatatgtagaaagctgaaactggatcccttccttacaccttatacaaaaattaattcaagatggatt aaagacttacatgttagacctaaaaccataaaaaccctagaaaaaaacctaggcaataccattcaggacataggcatgggcaaggactt catgtctaaaacaccaaaagcaatggcaacaaaagacaaaatggacaaacgggatctaattaaactaaagagcttctgcacagctaaag aaactaccatcagagtgaacaggcaacctacaaaatgggagaaaatttttgcaatctactcatctgacaaagggctaatatccagaatc tacaatgaactcaaacaaatttacaagaaaaaacaaacaaccccatcaaaaagtgggcaaaggatatgaacagacacttcgcaaaagaa gacatttatgtaatcaaaaaacacatgaaaaaatgctcatcatcactagccatcagagaaatgcaaatcaaaaccacaatgagatacca tctcacaccagttagaatggcgatcattaaaaagtcaggaaacaacaggtgctggagaggatgtggagaaacaggaacaacttttacac tgttggtgggactgtaaactagttcaaccattgcggaagtcagtgtggcaattcctcaggaatctagaactagaaataccatttgaccc agccatcccattactgggtacatacccaaaggattataaatcatgctgctataaagacacatgcacacgtatgtttattgcagcactat tcacaatagcaaagacttggaaccaacccaaatgtccaacaacgatagactggattaagaaaatgtggcacatatacaccatggaatac tatgcagccataaaaatgatgagttcatgtcctttgtagggacatggatgaagctggaaactatcattctcagcaaactatcacaagg agaataaaccaaacaccgcatgttctcactcataggtgggaattgaacaatgagaacacatggacacatgaagaggaacatcacactct ggggactgttatggggtgggggcaggggcagggatagcactaggagatatacctaatgctaaatgacgagttaatgggtgcagcacac caacatggcacatgtatacatatataacaaacctgcatgttgtgcacatgtaccctaaaacttgaagtataataataaaaaaaagttat cctattaaaactgatctcacacatccgtagagccattatcaagtctttctctttgaaatagacagaaatttagtgttttctcagtcagt taac
```

Five 5' hypersensitive site (HS) sites (HS1-HS5) and one 3' HS site have been identified in the human β-globin LCR (Stamatoyannopoulos et al., (2001)). The 5' HSs 1-4 are Dnase I hypersensitive sites. The HS2 and HS3 elements are the most powerful single elements within the LCR (Ellis et al., *EMBO J.* (1996), 15:562-568; Collis et al., *EMBO J.* (1990) 9:233-240), as corroborated by many groups. Deleting HS2 in the context of βYAC in transgenic mice severely affects HS site formation as well as expression of all of the human β-globin genes at every developmental stage (Bungert et al., *Mol. Cell Biol.* (1999); 19:3062-3072). It was reported that deletion of HS2 minimally reduced the expression of the embryonic εy and βhi globin genes in yolk sac-derived erythrocytes (Ley et al., Ann. N.Y. Acad. Sci. (1998); 850:45-53; Hug et al., *Mol. Cell Biol.* (1996); 26:2906-2912). HS2 functions primarily as an enhancer.

In certain embodiments, the β-globin LCR comprises a HS2 region. In non-limiting example, the β-globin LCR comprises a HS2 region, a HS3 region, and a HS4 region. In certain embodiments, the HS2 region, HS3 region and HS4 region within the β-globin LCR are contiguous. In certain embodiments, the β-globin LCR consists essentially of a HS2 region, a HS3 region and a HS4 region. In another embodiment, the β-globin LCR comprises two introduced GATA-1 binding sites at the junction between the HS3 region and the HS4 region. The HS3 region can lie between the HS2 region and the HS4 region. The length and the sequence of the HS2 region can vary. The HS2 region can have a length of from about 400 bp to about 1000 bp, e.g., from about 400 bp to about 500 bp, from about 500 bp to about 600 bp, from about 600 bp to about 700 bp, from about 700 bp to about 800 bp, from about 800 bp to about 850 bp, from about 800 bp to about 820 bp, from about 820 bp to about 830 bp, from about 830 bp to about 840 bp, from about 840 bp to about 850 bp, from about 850 bp to about 900 bp, from about 800 bp to about 900 bp, or from about 900 bp to about 1000 bp.

In certain embodiments, the HS2 region has a length of from about 850 bp to about 900 bp. In certain non-limiting embodiments, the HS2 region has a length of about 860 bp. In certain non-limiting embodiments, the HS2 region comprises or has the nucleotide sequence set forth in SEQ ID NO:9, which is provided below:

[SEQ ID NO: 9]
GTATATGTGTATATATATATATATATATTCAGGAAATAATATATTCTAGA

ATATGTCACATTCTGTCTCAGGCATCCATTTTCTTTATGATGCCGTTTGA

GGTGGAGTTTTAGTCAGGTGGTCAGCTTCTCCttttttttGCCATCTGCC

CTGTAAGCATCCTGCTGGGGACCCAGATAGGAGTCATCACTCTAGGCTGA

GAACATCTGGGCACACACCCTAAGCCTCAGCATGACTCATCATGACTCAG

CATTGCTGTGCTTGAGCCAGAAGGTTTGCTTAGAAGGTTACACAGAACCA

GAAGGCGGGGGTGGGGCACTGACCCCGACAGGGGCCTGGCCAGAACTGCT

CATGCTTGGACTATGGGAGGTCACTAATGGAGACACACAGAAATGTAACA

GGAACTAAGGAAAAACTGAAGCTTATTTAATCAGAGATGAGATGCTGGAA

GGGATAGAGGGAGCTGAGCTTGTAAAAAGTATAGTAATCATTCAGCAAAT

GGTTTTGAAGCACCTGCTGGATGCTAAACACTATTTTCAGTGCTTGAATC

ATAAATAAGAATAAAACATGTATCTTATTCCCCACAAGAGTCCAAGTAAA

AAATAACAGTTAATTATAATGTGCTCTGTCCCCCAGGCTGGAGTGCAGTG

GCACGATCTCAGCTCACTGCAACCTCCGCCTCCCGGGTTCAAGCAATTCT

CCTGCCTCAGCCACCCTAATAGCTGGGATTACAGGTGCACACCACCATGC

CAGGCTAATTTTTGTACTTTTTGTAGAGGCAGGGTATCACCATGTTGTCC

AAGATGGTCTTGAACTCCTGAGCTCCAAGCAGTCCACCCACCTCAGCCTC

CCAAAGTGCT

In certain embodiments, the HS2 region has a length of from about 800 bp to about 850 bp. In certain embodiments, the HS2 region has a length of about 840 bp. In certain embodiments, the HS2 region has a length of about 820 bp. In certain embodiments, the HS2 region has a length of about 816 bp.

In certain non-limiting embodiments, the HS2 region comprises or has the nucleotide sequence that is a consecutive portion of SEQ ID NO:9. In certain embodiments, the consecutive portion of SEQ ID NO: 9 is at least about 600 bp, or at least about 700 bp, or at least about 800 bp, or at least about 820 bp, and up to about 860 bp in length. Alternatively or additionally, in non-limiting various embodiments, the HS2 region comprises or has nucleotides 1 to 860, 20 to 860, 30 to 860, 40 to 860, 45 to 860, 50 to 860, 100 to 860, or 200 to 860 of SEQ ID NO: 9. In certain embodiments, the HS2 region comprises or has nucleotides 45 to 860 of SEQ ID NO: 9.

In certain embodiments, the HS2 region comprises or has a nucleotide sequence that is at least about 80%, at least about 85%, at least about 90%, at least about 99%, or at least about 100% homologous to the nucleotide sequence set forth in SEQ ID NO:9 or a consecutive portion thereof. In certain embodiments, the HS2 region comprises or has a nucleotide sequence that is at least about 99% homologous to the nucleotide sequence set forth in SEQ ID NO:9. In certain embodiments, the HS2 region comprises or has a nucleotide sequence that is about 100% homologous to nucleotides 45 to 860 of SEQ ID NO: 9, e.g., the HS2 region has a nucleotide sequence that includes up to 5, up to 4, up to 3, up to 2, or up to 1 mutations of nucleotides 45 to 860 of SEQ ID NO: 9. In certain embodiments, the HS2 region comprises or has the nucleotide sequence set forth in SEQ ID NO: 33, which is provided below.

(SEQ ID NO: 33)
TCTAGAATATGTCACATTCTGTCTCAGGCATCCATTTTCTTTATGATGCC

GTTTGAGGTGGAGTTTTAGTCAGGTGGTCAGCTTCTCCttttttttGCCA

TCTGCCCTGTAAGCATCCTGCTGGGGACCCAGATAGGAGTCATCACTCTA

GGCTGAGAACATCTGGGCACACACCCTAAGCCTCAGCATGACTCATCATG

ACTCAGCATTGCTGTGCTTGAGCCAGAAGGTTTGCTTAGAAGGTTACACA

GAACCAGAAGGCGGGGGTGGGGCACTGACCCCGACAGGGGCCTGGCCAGA

ACTGCTCATGCTTGGACTATGGGAGGTCACTAATGGAGACACACAGAAAT

GTAACAGGAACTAAGGAAAAACTGAAGCTTATTTAATCAGAGATGAGATG

CTGGAAGGGATAGAGGGAGCTGAGCTTGTAAAAAGTATAGTAATCATTCA

GCAAATGGTTTTGAAGCACCTGCTGGATGCTAAACACTATTTTCAGTGCT

TGAATCATAAATAAGAACAAAACATGTATCTTATTCCCCACAAGAGTCCA

AGTAAAAAATAACAGTTAATTATAATGTGCTCTGTCCCCCAGGCTGGAGT

GCAGTGGCACGATCTCAGCTCACTGCAACCTCCGCCTCCCGGGTTCAAGC

AATTCTCCTGCCTCAGCCACCCTAATAGCTGGGATTACAGGTGCACACCA

CCATGCCAGGCTAATTTTTGTACTTTTTGTAGAGGCAGGGTATCACCATG

TTGTCCAAGATGGTCTTGAACTCCTGAGCTCCAAGCAGTCCACCCACCTC

AGCCTCCCAAAGTGCT.

In certain embodiments, the HS2 region comprises or has a nucleotide sequence that is a modification of the nucleotide sequence set forth in SEQ ID NO: 9 or a consecutive portion thereof. Non-limiting modifications include deletion, mutations, additions, or combinations thereof. In certain embodiments, the modification comprises one or more mutation, e.g., up to 5, up to 4, up to 3, up to 2, or up to 1 mutations. In certain embodiments, the modification comprises one mutation. In certain embodiments, the one or more mutation is located within a polyadenylation site (or polyadenylation signal motif), e.g., a polyadenylation site on SEQ ID NO: 9. In certain embodiments, the polyadenylation site has the nucleotide sequence AATAAA. In certain embodiments, the one or more mutation comprises a mismatch mutation T>C at a polyadenylation site having the nucleotide sequence AATAAA, e.g., the mutated sequence is AACAAA. In certain embodiments, the polyadenylation site has the nucleotide sequence ATTAAA. In certain embodiments, the one or more mutation comprises a mismatch mutation T>C at a polyadenylation site having the nucleotide sequence ATTAAA, e.g., the mutated sequence is ATCAAA or ACTAAA. In certain embodiments, the one or more mutation comprises two mismatch mutations T>C at a polyadenylation site having the nucleotide sequence ATTAAA, e.g., the mutated sequence is ACCAAA. The inventors discovered that a modification (e.g., one or more mismatch mutation) at a polyadenylation site can preempt premature termination of RNA transcription, thereby increasing the titer of the expression cassette (e.g., expression vector) without compromising the expression of the globin gene.

In certain embodiments, the HS2 region has a length of about 650 bp (e.g., 646 bp). In certain embodiments, the HS2 region has a length of about 420 bp (e.g., 423 bp).

The length and the sequence of the HS3 region can vary. The HS3 region can have a length of from about 200 bp to about 1400 bp, e.g., from about 200 bp to about 300 bp, from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, from about 1100 bp to about 1200 bp, from about 1200 bp to about 1300 bp, or from about 1300 bp to about 1400 bp. In certain embodiments, the HS3 region has a length of about 1300 bp. In certain non-limiting embodiments, the HS3 region has a length of 1308 bp. In certain non-limiting embodiments, the HS3 region has a length of 1301 bp. In certain non-limiting embodiments, the HS3 region comprises or has the nucleotide sequence set forth in SEQ ID NO:5, which is provided below:

[SEQ ID NO: 5]
AAGCTTTCATTAAAAAAAGTCTAACCAGCTGCATTCGACTTTGACTGCAG

CAGCTGGTTAGAAGGTTCTACTGGAGGAGGGTCCCAGCCCATTGCTAAAT

TAACATCAGGCTCTGAGACTGGCAGTATATCTCTAACAGTGGTTGATGCT

ATCTTCTGGAACTTGCCTGCTACATTGAGACCACTGACCCATACATAGGA

AGCCCATAGCTCTGTCCTGAACTGTTAGGCCACTGGTCCAGAGAGTGTGC

ATCTCCTTTGATCCTCATAATAACCCTATGAGATAGACACAATTATTACT

CTTACTTTATAGATGATGATCCTGAAAACATAGGAGTCAAGGCACTTGCC

CCTAGCTGGGGTATAGGGGAGCAGTCCCATGTAGTAGTAGAATGAAAAA

TGCTGCTATGCTGTGCCTCCCCCACCTTTCCCATGTCTGCCCTCTACTCA

TGGTCTATCTCTCCTGGCTCCTGGGAGTCATGGACTCCACCCAGCACCAC

CAACCTGACCTAACCACCTATCTGAGCCTGCCAGCCTATAACCCATCTGG

GCCCTGATAGCTGGTGGCCAGCCCTGACCCCACCCCACCCTCCCTGGAAC

CTCTGATAGACACATCTGGCACACCAGCTCGCAAAGTCACCGTGAGGGTC

TTGTGTTTGCTGAGTCAAAATTCCTTGAAATCCAAGTCCTTAGAGACTCC

TGCTCCCAAATTTACAGTCATAGACTTCTTCATGGCTGTCTCCTTTATCC

ACAGAATGATTCCTTTGCTTCATTGCCCCATCCATCTGATCCTCCTCATC

AGTGCAGCACAGGGCCCATGAGCAGTAGCTGCAGAGTCTCACATAGGTCT

GGCACTGCCTCTGACATGTCCGACCTTAGGCAAATGCTTGACTCTTCTGA

GCTCAGTCTTGTCATGGCAAAATAAAGATAATAATAGTGTTTTTTTATGG

AGTTAGCGTGAGGATGGAAAACAATAGCAAAATTGATTAGACTATAAAAG

GTCTCAACAAATAGTAGTAGATTTTATCATCCATTAATCCTTCCCTCTCC

TCTCTTACTCATCCCATCACGTATGCCTCTTAATTTTCCCTTACCTATAA

TAAGAGTTATTCCTCTTATTATATTCTTCTTATAGTGATTCTGGATATTA

AAGTGGGAATGAGGGGCAGGCCACTAACGAAGAAGATGTTTCTCAAAGAA

GCCATTCTCCCCACATAGATCATCTCAGCAGGGTTCAGGAAGATAAAGGA

GGATCAAGGTCGAAGGTAGGAACTAAGGAAGAACACTGGGCAAGTGGATC

C

In certain embodiments, the HS2 region comprises or has the nucleotide sequence that is a consecutive portion of SEQ ID NO: 5. In certain embodiments, the consecutive portion of SEQ ID NO: 5 is at least about 600 bp, or at least about 700 bp, or at least about 800 bp, at least about 900 bp, at least about 1000 bp, at least about 1100 bp, or at least about 1200 bp, and up to about 1300 bp in length.

In certain embodiments, the HS3 region comprises or has a nucleotide sequence that is at least about 80%, at least about 85%, at least about 90%, at least about 99%, or at least about 100% homologous to the nucleotide sequence set forth in SEQ ID NO: 5 or a consecutive portion thereof. In certain embodiments, the HS3 region comprises or has a nucleotide sequence that is at least about 99% homologous to the nucleotide sequence set forth in SEQ ID NO: 5. In certain embodiments, the HS3 region comprises or has a nucleotide sequence that is about 100% homologous to the nucleotide sequence set forth in SEQ ID NO: 5, e.g., the HS3 region has a nucleotide sequence that includes up to 5, up to 4, up to 3, up to 2, or up to 1 mutations of SEQ ID NO: 5. In certain embodiments, the HS3 region comprises or has the nucleotide sequence set forth in SEQ ID NO: 34, which is provided below.

(SEQ ID NO: 34)
AAGCTTTCATCaaaaaaaGTCTAACCAGCTGCATTCGACTTTGACTGCAG

CAGCTGGTTAGAAGGTTCTACTGGAGGAGGGTCCCAGCCCATTGCTAAAT

TAACATCAGGCTCTGAGACTGGCAGTATATCTCTAACAGTGGTTGATGCT

ATCTTCTGGAACTTGCCTGCTACATTGAGACCACTGACCCATACATAGGA

AGCCCATAGCTCTGTCCTGAACTGTTAGGCCACTGGTCCAGAGAGTGTGC

ATCTCCTTTGATCCTCATAATAACCCTATGAGATAGACACAATTATTACT

CTTACTTTATAGATGATGATCCTGAAAACATAGGAGTCAAGGCACTTGCC

CCTAGCTGGGGTATAGGGGAGCAGTCCCATGTAGTAGTAGAATGAAAAA

TGCTGCTATGCTGTGCCTCCCCCACCTTTCCCATGTCTGCCCTCTACTCA

TGGTCTATCTCTCCTGGCTCCTGGGAGTCATGGACTCCACCCAGCACCAC

CAACCTGACCTAACCACCTATCTGAGCCTGCCAGCCTATAACCCATCTGG

GCCCTGATAGCTGGTGGCCAGCCCTGACCCCACCCCACCCTCCCTGGAAC

CTCTGATAGACACATCTGGCACACCAGCTCGCAAAGTCACCGTGAGGGTC

TTGTGTTTGCTGAGTCAAAATTCCTTGAAATCCAAGTCCTTAGAGACTCC

TGCTCCCAAATTTACAGTCATAGACTTCTTCATGGCTGTCTCCTTTATCC

ACAGAATGATTCCTTTGCTTCATTGCCCCATCCATCTGATCCTCCTCATC

AGTGCAGCACAGGGCCCATGAGCAGTAGCTGCAGAGTCTCACATAGGTCT

-continued
```
GGCACTGCCTCTGACATGTCCGACCTTAGGCAAATGCTTGACTCTTCTGA

GCTCAGTCTTGTCATGGCAAAACAAAGATAATAATAGTGttttttttATGG

AGTTAGCGTGAGGATGGAAAACAATAGCAAAATTGATTAGACTATAAAG

GTCTCAACAAATAGTAGTAGATTTTATCATCCATTAATCCTTCCCTCTCC

TCTCTTACTCATCCCATCACGTATGCCTCTTAATTTTCCCTTACCTATAA

TAAGAGTTATTCCTCTTATTATATTCTTCTTATAGTGATTCTGGATATCA

AAGTGGGAATGAGGGGCAGGCCACTAACGAAGAAGATGTTTCTCAAAGAA

GCCATTCTCCCCACATAGATCATCTCAGCAGGGTTCAGGAAGATAAAGGA

GGATCAAGGTCGAAGGTAGGAACTAAGGAAGAACACTGGGCAAGTGGATC

C.
```

In certain embodiments, the HS3 region comprises or has a nucleotide sequence that is a modification of the nucleotide sequence set forth in SEQ ID NO: 5 or a consecutive portion thereof. Non-limiting modifications include deletion, mutations, additions, or combinations thereof. In certain embodiments, the modification comprises one or more mutation, e.g., up to 5, up to 4, up to 3, up to 2, or up to 1 mutations. In certain embodiments, the modification comprises three mutations. In certain embodiments, the one or more mutation is located within a polyadenylation site (or polyadenylation signal motif), e.g., a polyadenylation site on SEQ ID NO: 5. In certain embodiments, the polyadenylation site has the nucleotide sequence AATAAA. In certain embodiments, the one or more mutation comprises a mismatch mutation T>C at a polyadenylation site having the nucleotide sequence AATAAA, e.g., the mutated sequence is AACAAA. In certain embodiments, the polyadenylation site has the nucleotide sequence ATTAAA. In certain embodiments, the one or more mutation comprises a mismatch mutation T>C at a polyadenylation site having the nucleotide sequence ATTAAA, e.g., the mutated sequence is ATCAAA or ACTAAA. In certain embodiments, the one or more mutation comprises two mismatch mutations T>C at a polyadenylation site having the nucleotide sequence ATTAAA, e.g., the mutated sequence is ACCAAA.

A modification (e.g., one or more mismatch mutation) at a polyadenylation site can preempt premature termination of RNA transcription, thereby increasing the titer of the expression cassette (e.g., expression vector) without compromising the expression of the globin gene.

In certain embodiments, the HS3 region has a length of about 850 bp (e.g., 845 bp). In certain embodiments, the HS3 region has a length of from about 280 bp to about 290 bp (e.g., 280 bp and 287 bp).

Similarly, the length and the sequence of the HS4 region can vary. The HS4 region can have a length of from about 200 bp to about 1200 bp, e.g., from about 200 bp to about 300 bp, from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, or from about 1100 bp to about 1200 bp.

In certain embodiments, the HS4 region has a length of about 1.0 kb or more. In certain embodiments, the HS4 region has a length of about 1.1 kb. In certain embodiments, the HS4 region has a length of about 1150 bp (e.g., 1153 bp). In certain non-limiting embodiments, the HS4 region has a length of 1100 bp. In certain non-limiting embodiments, the HS4 region has a length of 1065 bp. In certain non-limiting embodiments, the HS4 region has the nucleotide sequence set forth in SEQ ID NO:6, which is provided below:

```
                                          [SEQ ID NO: 6]
TGAGCCCCTTTTCCTCTAACTGAAAGAAGGAAAAAAAAAATGGAACCCAA

AATATTCTACATAGTTTCCATGTCACAGCCAGGGCTGGGCAGTCTCCTGT

TATTTCTTTTAAAATAAATATATCATTTAAATGCATAAATAAGCAAACCC

TGCTCGGGAATGGGAGGGAGAGTCTCTGGAGTCCACCCCTTCTCGGCCCT

GGCTCTGCAGATAGTGCTATCAAAGCCCTGACAGAGCCCTGCCCATTGCT

GGGCCTTGGAGTGAGTCAGCCTAGTAGAGAGGCAGGGCAAGCCATCTCAT

AGCTGCTGAGTGGGAGAGAGAAAAGGGCTCATTGTCTATAAACTCAGGTC

ATGGCTATTCTTATTCTCACACTAAGAAAAAGAATGAGATGTCTACATAT

ACCCTGCGTCCCCTCTTGTGTACTGGGGCCCCAAGAGCTCTCTAAAAGT

GATGGCAAAGTCATTGCGCTAGATGCCATCCCATCTATTATAAACCTGCA

TTTGTCTCCACACACCAGTCATGGACAATAACCCTCCTCCCAGGTCCACG

TGCTTGTCTTTGTATAATACTCAAGTAATTTCGGAAAATGTATTCTTTCA

ATCTTGTTCTGTTATTCCTGTTTCAATGGCTTAGTAGAAAAAGTACATAC

TTGTTTTCCCATAAATTGACAATAGACAATTTCACATCAATGTCTATATG

GGTCGTTGTGTTTGCTGTGTTTGCAAAAACTCACAATAACTTTATATTGT

TACTACTCTAAGAAAGTTACAACATGGTGAATACAAGAGAAAGCTATTAC

AAGTCCAGAAAATAAAAGTTATCATCTTGAGGCCTCAGCTTTCTAGGAAT

AATATCAATATTACAAAATTTAATCTAACAATTATGAACAGCAATGAGAT

AATATGTACAAAGTACCCAGACCTATGTGGTAGAGCATCAAGGAAGCGCA

TTGCGGAGCAGTTTTTTGTTTGTTTGTTTTTGTATTCTGTTTCGTGAGGC

AAGGTTTCACTCTGCTGTCCAGGCTGGAGTGCAGTGGCAAGATCATGTCT

CACTGCAGCCTTGAC
```

In certain non-limiting embodiments, the HS4 region has the nucleotide sequence set forth in SEQ ID NO:7, which is provided below:

```
                                          [SEQ ID NO: 7]
TGAGCCCCTTTTCCTCTAACTGAAAGAAGGAAAAAAAAAATGGAACCCAA

AATATTCTACATAGTTTCCATGTCACAGCCAGGGCTGGGCAGTCTCCTGT

TATTTCTTTTAAAATAAATATATCATTAAATGCATAAATAAGCAAACCCT

GCTCGGGAATGGGAGGGAGAGTCTCTGGAGTCCACCCCTTCTCGGCCCTG

GCTCTGCAGATAGTGCTATCAAAGCCCTGACAGAGCCCTGCCCATTGCTG

GGCCTTGGAGTGAGTCAGCCTAGTAGAGAGGCAGGGCAAGCCATCTCATA

GCTGCTGAGTGGGAGAGAGAAAAGGGCTCATTGTCTATAAACTCAGGTCA

TGGCTATTCTTATTCTCACACTAAGAAAAAGAATGAGATGTCTACATATA

CCCTGCGTCCCCTCTTGTGTACTGGGGCCCCAAGAGCTCTCTAAAAGTG

ATGGCAAAGTCATTGCGCTAGATGCCATCCCATCTATTATAAACCTGCAT

TTGTCTCCACACACCAGTCATGGACAATAACCCTCCTCCCAGGTCCACGT

GCTTGTCTTTGTATAATACTCAAGTAATTTCGGAAAATGTATTCTTTCAA

TCTTGTTCTGTTATTCCTGTTTCAATGGCTTAGTAGAAAAAGTACATACT
```

TGTTTTCCCATAAATTGACAATAGACAATTTCACATCAATGTCTATATGG

GTCGTTGTGTTTGCTGTGTTTGCAAAAACTCACAATAACTTTATATTGTT

ACTACTCTAAGAAAGTTACAACATGGTGAATACAAGAGAAAGCTATTACA

AGTCCAGAAAATAAAAGTTATCATCTTGAGGCCTCAGCTTTCTAGGaATA

ATATCAATATTACAAAATTAATCTAACAATTATGAACAGCAATGAGATAA

TATGTACAAAGTACCCAGACCTATGTGGTAGAGCATCAAGGAAGCGCATT

GCGGAGCAGTTTTTTGTTTGTTTGTTTTTGTATTCTGTTTCGTGAGGCAA

GGTTTCACTCTGCTGTCCAGGCTGGAGTGCAGTGGCAAGATCATGTCTCA

CTGCAGCCTTGACAC

In certain embodiments, the HS4 region has a length of less than about 1.0 kb, less than about 900 bp, or less than about 800 bp. In certain embodiments, the HS4 region has a length of from about 700 bp to about 800 bp, e.g., from about 700 bp to about 750 bp, or from about 750 bp to about 800 bp. In certain embodiments, the HS4 region has a length of about 750 bp. In certain embodiments, the HS4 region has a length of about 754 bp.

In certain embodiments, the HS4 region comprises or has the nucleotide sequence that is a consecutive portion of SEQ ID NO: 6 or 7. In certain embodiments, the consecutive portion of SEQ ID NO: 6 or 7 is at least about 600 bp or at least about 700 bp and up to about 800 bp or up to about 900 bp, or up to about 1.0 kb in length. Alternatively or additionally, in non-limiting various embodiments, the HS4 region comprises or has nucleotides 1 to 900, 100 to 900, 100 to 1000, 110 to 900, 115 to 900, 115 to 890, 115 to 880, 115 to 870, 115 to 868, 115 to 860, 115 to 1000 of SEQ ID NO: 6 or 7. In certain embodiments, the HS4 region comprises or has nucleotides 115 to 868 of SEQ ID NO: 6.

In certain embodiments, the HS4 region comprises or consists essentially of a core sequence of the HS4 region. In certain embodiments, the HS4 region or consists essentially of the full length of a 280 bp core sequence of a human HS4 region (e.g., the 280 bp core sequence of human HS4 disclosed in Pruzina et al., *Nucleic Acids Research* (1991); 19:7:1413-1419, which is incorporated by reference in its entirety).

In certain embodiments, the HS4 region does not comprise the nucleotide sequence set forth in SEQ ID NO: 50, which is provided below.

[SEQ ID NO: 50]
TGAGCCCCTTTTCCTCTAACTGAAAGAAGGAAAAAAAAAATGGAACC

CAAAATATTCTACATAGTTTCCATGTCACAGCCAGGGCTGGGCAGTC

TCCTGTTATTTCTTTTAAAA

In certain embodiments, the HS4 region does not comprise the nucleotide sequence set forth in SEQ ID NO: 51, which is provided below.

[SEQ ID NO: 51]
TTTAATCTAACAATTATGAACAGCAATGAGATAATATGTACAAAGTA

CCCAGACCTATGTGGTAGAGCATCAAGGAAGCGCATTGCGGAGCAGT

TTTTTGTTTGTTTGTTTTTGTATTCTGTTTCGTGAGGCAAGGTTTCA

CTCTGCTGTCCAGGCTGGAGTGCAGTGGCAAGATCATGTCTCACTGC

AGCCTTGAC

In certain embodiments, the HS4 region does not comprise the nucleotide sequence set forth in SEQ ID NO: 50 or the nucleotide sequence set forth in SEQ ID NO: 51.

In certain embodiments, the HS4 region comprises or has a nucleotide sequence that is at least about 80%, at least about 85%, at least about 90%, at least about 99%, or at least about 100% homologous to the nucleotide sequence set forth in SEQ ID NO: 6 or a consecutive portion thereof. In certain embodiments, the HS4 region comprises or has a nucleotide sequence that is at least about 80%, at least about 85%, at least about 90%, at least about 99%, or at least about 100% homologous to the nucleotide sequence set forth in SEQ ID NO: 7 or a consecutive portion thereof. In certain embodiments, the HS4 region comprises or has a nucleotide sequence that is at least about 99% homologous to the nucleotide sequence set forth in SEQ ID NO: 6 or 7. In certain embodiments, the HS4 region comprises or has a nucleotide sequence that is at least about 99% (e.g., about 100%) homologous to nucleotides 115 to 868 of SEQ ID NO: 6, e.g., the HS4 region has a nucleotide sequence that includes up to 5, up to 4, up to 3, up to 2, or up to 1 mutations of nucleotides 115 to 868 of SEQ ID NO: 6. In certain embodiments, the HS4 region comprises or has the nucleotide sequence set forth in SEQ ID NO: 35, which is provided below.

[SEQ ID NO: 35]
TAAATATATCATTTAAATGCATAAATAAGCAAACCCTGCTCGGGAAT

GGGAGGGAGAGTCTCTGGAGTCCACCCCTTCTCGGCCCTGGCTCTGC

AGATAGTGCTATCAAAGCCCTGACAGAGCCCTGCCCATTGCTGGGCC

TTGGAGTGAGTCAGCCTAGTAGAGAGGCAGGGCAAGCCATCTCATAG

CTGCTGAGTGGGAGAGAGAAAAGGGCTCATTGTCTATAAACTCAGGT

CATGGCTATTCTTATTCTCACACTAAGAAAAAGAATGAGATGTCTAC

ATATACCCTGCGTCCCCTCTTGTGTACTGGGGCCCCCAAGAGCTCTC

TAAAAGTGATGGCAAAGTCATTGCGCTAGATGCCATCCCATCTATTA

TAAACCTGCATTTGTCTCCACACACCAGTCATGGACAATAACCCTCC

TCCCAGGTCCACGTGCTTGTCTTTGTATAATACTCAAGTAATTTCGG

AAAATGTATTCTTTCAATCTTGTTCTGTTATTCCTGTTTCAATGGCT

TAGTAGAAAAAGTACATACTTGTTTTCCCATAAATTGACAATAGACA

ATTTCACATCAATGTCTATATGGGTCGTTGTGTTTGCTGTGTTTGCA

AAAACTCACAATAACTTTATATTGTTACTACTCTAAGAAAGTTACAA

CATGGTGAATACAAGAGAAAGCTATTACAAGTCCAGAAAACAAAAGT

TATCATCTTGAGGCCTCAGCTTTCTAGGAATAATATCAATATTACAA

AA.

In certain embodiments, the HS4 region comprises or has a nucleotide sequence that is a modification of the nucleotide sequence set forth in SEQ ID NO: 6 or a consecutive portion thereof. In certain embodiments, the HS4 region comprises or has a nucleotide sequence that is a modification of the nucleotide sequence set forth in SEQ ID NO: 7 or a consecutive portion thereof. Non-limiting modifications include deletion, mutations, additions, or combinations thereof. In certain embodiments, the modification comprises one or more mutation, e.g., up to 5, up to 4, up to 3, up to 2, or up to 1 mutations. In certain embodiments, the modification comprises one mutation. In certain embodiments, the one or more mutation is located within a polyadenylation site (or polyadenylation signal motif), e.g., a polyadenylation site on SEQ ID NO: 6 or a polyadenylation site on SEQ ID NO: 7. In certain embodiments, the polyadenylation site has the nucleotide sequence AATAAA. In certain embodiments, the one or more mutation comprises a mismatch mutation T>C at a polyadenylation site having the nucleotide sequence AATAAA, e.g., the mutated sequence is AACAAA. In certain embodiments, the polyadenylation site has the nucleotide sequence ATTAAA. In certain embodiments, the one or more mutation comprises a mismatch mutation T>C at a polyadenylation site having the nucleotide sequence ATTAAA, e.g., the mutated sequence is ATCAAA or ACTAAA. In certain embodiments, the one or more mutation comprises two mismatch mutations T>C at a polyadenylation site having the nucleotide sequence ATTAAA, e.g., the mutated sequence is ACCAAA. A modification (e.g., one or more mismatch mutation) at a polyadenylation site can preempt premature termination of RNA transcription, thereby increasing the titer of the expression cassette (e.g., expression vector) without compromising the expression of the globin gene.

In certain embodiments, the HS4 region has a length of less than about 500 bp. In certain embodiments, the HS4 region has a length of about 450 bp. In certain non-limiting embodiments, the HS4 region has a length of about 446 bp. In certain non-limiting embodiments, the HS4 region comprises or has the nucleotide sequence set forth in SEQ ID NO:8, which is provided below:

[SEQ ID NO: 8]
TGGAACCCAAAATATTCTACATAGTTTCCATGTCACAGCCAGGGCTG

GGCAGTCTCCTGTTATTTCTTTTAAAATAAATATATCATTTAAATGC

ATAAATAAGCAAACCCTGCTCGGGAATGGGAGGGAGAGTCTCTGGAG

TCCACCCCTTCTCGGCCCTGGCTCTGCAGATAGTGCTATCAAAGCCC

TGACAGAGCCCTGCCCATTGCTGGGCCTTGGAGTGAGTCAGCCTAGT

AGAGAGGCAGGGCAAGCCATCTCATAGCTGCTGAGTGGGAGAGAGAA

AAGGGCTCATTGTCTATAAACTCAGGTCATGGCTATTCTTATTCTCA

CACTAAGAAAAGAATGAGATGTCTACATATACCCTGCGTCCCCTCT

TGTGTACTGGGGTCCCCAAGAGCTCTCTAAAAGTGATGGCAAAGTCA

TTGCGCTAGATGCCATCCCATCT

In certain embodiments, the HS4 region has a length of about 280 bp (e.g., 283 bp). In certain embodiments, the HS4 region has a length of about 240 bp (e.g., 243 bp).

In certain non-limiting embodiments, the β-globin LCR comprises or consists essentially of a HS2 region having the nucleotide sequence set forth in SEQ ID NO:9 or a consecutive portion thereof, a modification of SEQ ID NO: 9, a modification of a consecutive portion of SEQ ID NO: 9 (e.g., SEQ ID NO: 33), SEQ ID NO:20, SEQ ID NO:21; a HS3 region having the nucleotide sequence set forth in SEQ ID NO:5 or a modification of SEQ ID NO: 5 (e.g., SEQ ID NO: 34); and a HS4 region having the nucleotide sequence set forth in SEQ ID NO:6 or a consecutive portion thereof, SEQ ID NO:7 or a consecutive portion thereof, a modification of SEQ ID NO: 6, a modification of a consecutive portion of SEQ ID NO: 6 (e.g., SEQ ID NO: 35), a modification of SEQ ID NO: 7, a modification of a consecutive portion of SEQ ID NO: 7, or SEQ ID NO:8, and the β-globin LCR does not comprise a HS1 region.

Figure 1:
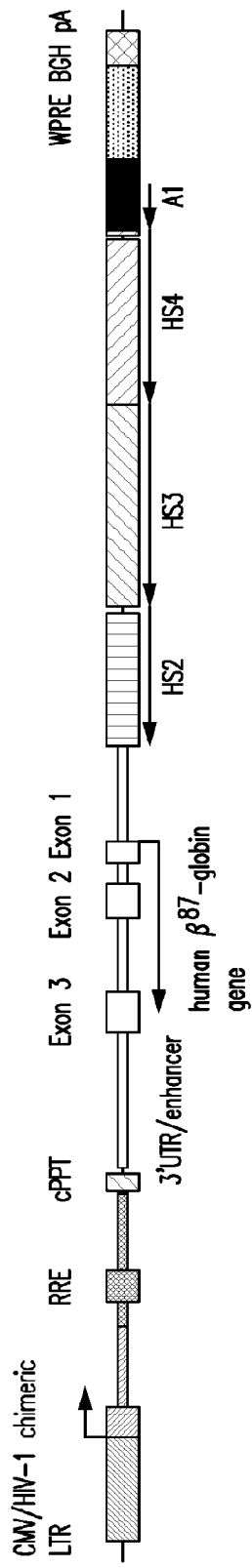
FIG. 1 depicts a recombinant vector comprising an expression cassette in accordance with one non-limiting embodiment of the presently disclosed subject matter.

In certain non-limiting embodiments, the β-globin LCR comprises or consists essentially of a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7, as shown in FIG. 1.

In certain non-limiting embodiments, the β-globin LCR comprises or consists essentially of a HS2 region having nucleotides 45 to 860 of SEQ ID NO: 9; a HS3 region having the nucleotide sequence set forth in SEQ ID NO: 5; and a HS4 region having nucleotides 115 to 868 of SEQ ID NO: 6, and the β-globin LCR does not comprise a HS1 region, e.g., the β-globin LCR of SNS23.B87.A1 shown in FIG. 15.

In certain non-limiting embodiments, the β-globin LCR comprises or consists essentially of a HS2 region having the nucleotide sequence set forth in SEQ ID NO: 33; a HS3 region having the nucleotide sequence set forth in SEQ ID NO: 34; and a HS4 region having the nucleotide sequence set forth in SEQ ID NO: 35, and the β-globin LCR does not comprise a HS1 region, e.g., the β-globin LCR of SNS23.2.B87.A1 shown in FIGS. 13 and 14.

In certain non-limiting embodiments, the β-globin LCR further comprises a HS1 region, i.e., a β-globin LCR comprising a HS1 region, a HS2 region, a HS3 region, and a HS4 region. In certain embodiments, the HS1 region, HS2 region, HS3 region and HS4 region within the β-globin LCR are contiguous. In certain non-limiting embodiments, the β-globin LCR consisting essentially of a HS1 region, a HS2 region, a HS3 region and a HS4 region. In certain embodiments, the β-globin LCR comprises two introduced GATA-1 binding sites at the junction between the HS3 region and the HS4 region.

The length and the sequence of the HS1 region can vary. In certain embodiments, the HS1 region is from about 300 bp to about 1500 bp in length, e.g., from about 300 bp to about 1100 bp in length. In certain embodiments, the HS1 region has a length of about 1.0 kb or more, e.g., about 1.1 kb, about 1.2 kb, about 1.3 kb, about 1.4 kb, or about 1.5 kb. In certain embodiments, the HS1 region has a length of about 1.1 kb. In certain non-limiting embodiments, the HS1 region has a length of 1074 bp. In certain non-limiting embodiments, the HS1 region comprises or has the nucleotide sequence set forth in SEQ ID NO:2, which is provided below:

[SEQ ID NO: 2]
AAGTAAACTTCCACAACCGCAAGCTTATTGAGGCTAAGGCATCTGTG

AAGGAAAGAAACATCTCCTCTAAACCACTATGCTGCTAGAGCCTCTT

TTCTGTACTCAAGCCTCATTCAGACACTAGTGTCACCAGTCTCCTCA

TATACCTATTGTATTTTCTTCTTCTTGCTGGTTTAGTCATGTTTTCT

GGGAGCTTAGGGGCTTATTTTATTTTGTTTTGTTTTCTAATCAACAG

AGATGGGCAAACCCATTATTTTTTTCTTTAGACTTGGGATGGTGATA

GCTGGGCAGCGTCAGAAACTGTGTGTGGATATAGATAAGAGCTCGGA

CTATGCTGAGCTGTGATGAGGGAGGGACCTAGCCAAAGGCAGTGAGA

-continued
GTCAGAATGCTCCTGCTATTGCCTTCTCAGTCCCCACGCTTGGTTTC

TACACAAGTAGATACATAGAAAAGGCTATAGGTTAGTGTTTGAGAGT

CCTGCATGAGTTAGTTGCTCAGAAATGCCCGATAAATATGTTATGTG

TGTTTATGTATATATATGTTTTATATATATATATGTGTGTGTGTGTG

TGTGTGTGTGTTGTGTTTACAAATATGTGATTATCATCAAAACGTGA

GGGCTAAAGTGACCAGATAACTTGCAGGTCCTAGGATACCAGGAAAA

TAAATTACATTCCAAAAATTTAACTGAGACTTTAAAAAAAAAAAAAA

AAAAAAAAAAAAAACCAGTGATCCATGGACACAGGGAGGGGAACATC

ACACACTGGGGCCTGTTGGGGGTGGGGGGCTAGGGGAAGGATAGCAT

TAGGAGAAATACCTAATGTAGATGACGGGTTGATGGGTGCAGCAAAC

CACCATGGCACATGTACCCCAGAACTTAAAGCATATTAAAAAAACAG

TGATCATAAAAGAAGCTCAAATTTAACTATAAGAGACGGAATGGCTC

CCACAATTCTTAACTATAATCTTACAGAATATTCTCATTGAATAGAA

GTATGCTTATCATTAGAGATTTGGACAGCCAGGAAAGCACAGAAAAA

AAAAAAAGGAGCTCTGTTGCCTTATAGCCTAGAGGTGTTT

In certain embodiments, the HS1 region has a length of less than about 1.0 kb, e.g., from about 400 bp to about 700 bp, from about 400 bp to about 500 bp, from about 500 bp to about 600 bp, from about 600 bp to about 700 bp, from about 700 bp to about 800 bp, from about 800 bp to about 900 bp, or from about 900 bp to about 1.0 kb. In certain embodiments, the HS1 region has a length of less than about 700 bp. In certain embodiments, the HS1 region has a length of about 600 bp. In certain non-limiting embodiments, the HS1 region has a length of 602 bp. In certain non-limiting embodiments, the HS1 region comprises or has the nucleotide sequence set forth in SEQ ID NO:3, which is provided below:

[SEQ ID NO: 3]
GGCATCTGTGAAGGAAAGAAACATCTCCTCTAAACCACTATGCTGCT

AGAGCCTCTTTTCTGTACTCAAGCCTCATTCAGACACTAGTGTCACC

AGTCTCCTCATATACCTATTGTATTTTCTTCTTCTTGCTGGTTTAGT

CATGTTTTCTGGGAGCTTAGGGGCTTATTTTATTTTGTTTTGTTTTC

TAATCAACAGAGATGGGCAAACCCATTATTTTTTTCTTTAGACTTGG

GATGGTGATAGCTGGGCAGCGTCAGAAACTGTGTGTGGATATAGATA

AGAGCTCGGACTATGCTGAGCTGTGATGAGGGAGGGACCTAGCCAAA

GGCAGTGAGAGTCAGAATGCTCCTGCTATTGCCTTCTCAGTCCCCAC

GCTTGGTTTCTACACAAGTAGATACATAGAAAAGGCTATAGGTTAGT

GTTTGAGAGTCCTGCATGAGTTAGTTGCTCAGAAATGCCCGATAAAT

ATGTTATGTGTGTTTATGTATATATATGTTTTATATATATATATGTG

TGTGTGTGTGTGTGTGTGTTGTGTTTACAAATATGTGATTATCAT

CAAAACGTGAGGGCTAAAGTGACCAGATAACTTGCAGG

In certain embodiments, the HS1 region has a length of less than about 500 bp. In certain embodiments, the HS1 region has a length of about 490 bp. In certain non-limiting embodiments, the HS1 region has a length of 489 bp. In certain non-limiting embodiments, the HS1 region comprises or has the nucleotide sequence set forth in SEQ ID NO:4, which is provided below:

[SEQ ID NO: 4]
GGCATCTGTGAAGGAAAGAAACATCTCCTCTAAACCACTATGCTGCT

AGAGCCTCTTTTCTGTACTCAAGCCTCATTCAGACACTAGTGTCACC

AGTCTCCTCATATACCTATTGTATTTTCTTCTTCTTGCTGGTTTAGT

CATGTTTTCTGGGAGCTTAGGGGCTTATTTTATTTTGTTTTGTTTTC

TAATCAACAGAGATGGGCAAACCCATTATTTTTTTCTTTAGACTTGG

GATGGTGATAGCTGGGCAGCGTCAGAAACTGTGTGTGGATATAGATA

AGAGCTCGGACTATGCTGAGCTGTGATGAGGGAGGGACCTAGCCAAA

GGCAGTGAGAGTCAGAATGCTCCTGCTATTGCCTTCTCAGTCCCCAC

GCTTGGTTTCTACACAAGTAGATACATAGAAAAGGCTATAGGTTAGT

GTTTGAGAGTCCTGCATGAGTTAGTTGCTCAGAAATGCCCGATAAAT

ATGTTATGTGTGTTTATGT

In certain non-limiting embodiments, the β-globin LCR comprises or consists essentially of a HS1 region disclosed herein, a HS2 region disclosed herein, a HS3 region disclosed herein, and a HS4 region disclosed herein.

In certain non-limiting embodiments, the β-globin LCR comprises or consists essentially of a HS1 region having the nucleotide sequence set forth in SEQ ID NO: 3, SEQ ID NO: 4, SEQ ID NO: 22 or SEQ ID NO: 23; a HS2 region having the nucleotide sequence set forth in SEQ ID NO: 9 or a consecutive portion thereof, a modification of SEQ ID NO: 9, a modification of a consecutive portion of SEQ ID NO: 9 (e.g., SEQ ID NO: 33), SEQ ID NO:20, SEQ ID NO:21; a HS3 region having the nucleotide sequence set forth in SEQ ID NO: 5 or a modification thereof (e.g., SEQ ID NO: 34); and a HS4 region having the nucleotide sequence set forth in SEQ ID NO: 6 or a consecutive portion thereof, SEQ ID NO: 7 or a consecutive portion thereof, a modification of SEQ ID NO: 6, a modification of a consecutive portion of SEQ ID NO: 6 (e.g., SEQ ID NO: 35), a modification of SEQ ID NO: 7, or a modification of a consecutive portion of SEQ ID NO: 7, or SEQ ID NO:8.

In certain non-limiting embodiments, the β-globin LCR comprises or consists essentially of a HS1 region having the nucleotide sequence set forth in SEQ ID NO: 3; a HS2 region having nucleotides 45 to 860 of SEQ ID NO: 9; a HS3 region having the nucleotide sequence set forth in SEQ ID NO: 5; and a HS4 region having nucleotides 115 to 868 of SEQ ID NO: 6 e.g., the β-globin LCR of SNS22.B87.A1 shown in FIG. 15.

In certain non-limiting embodiments, the β-globin LCR comprises or consists essentially of a HS1 region having the nucleotide sequence set forth in SEQ ID NO: 3; a HS2 region having nucleotide sequence set forth in SEQ ID NO: 33; a HS3 region having the nucleotide sequence set forth in SEQ ID NO: 34; and a HS4 region having the nucleotide sequence set forth in SEQ ID NO: 35, e.g., as the β-globin LCR of SNS22.2.B87.A1 shown in FIG. 13.

Recent studies have shown that HS2 is not erythroid-specific, but is expressed in other cell lines and lineages (See Example 3 and FIG. 7) and is also present in undifferentiated human embryonic stem cells (Chang et al., Stem cell reviews (2013); 9:397-407). Due to the non-erythroid activity of HS2, HS2-containing globin vectors may pose a risk for their safe use in clinical treatment, e.g., for treating thalassemia and sickle cell patients. In certain embodiments, the β-globin LCR does not comprise a HS2 region. In certain embodiments, the β-globin LCR does not comprise a core sequence of HS2. A core sequence of HS2 provides position independent, high level expression. In addition, a core sequence of HS2 sustains the enhancer activity of HS2. For example, the core sequence of HS2 enhances the transcription of a globin gene (e.g., human β-globin gene). Additionally, a core sequence of HS2 comprises one or more binding sites or binding motifs for ubiquitous as well as tissue-specific (e.g., erythroid-specific) proteins (e.g., transcription factors), including, but not limited to, members of AP1 family of proteins (e.g., NF-E2), GATA-1 (also known as "NF-E1" or "NFE1"), Krüppel-like Zn finger proteins (e.g., ubiquitous proteins Sp1 and YY1, and erythroid-restricted factor erythroid Krüppel-like factor (EKLF)), and basic helix-loop-helix (bHLH) proteins (E boxes) (e.g., USF and TAL1). AP1 binding sites are required for enhancement and induction (Moi and Kan (1990); Ney et al., (1990); Talbot and Grosveld (1991)). Furthermore, binding of NF-E2 can cause disruption of in vitro reconstituted chromatin at HS2 (Armstrong and Emerson (1996)). Mutations in the GATA-1 binding sites can cause a reduction in enhancer activity of HS2 in transgenic mice (Caterina et al., (1994)). Although both AP1 (e.g., AP1/NF-E2) and GATA1 binding sites are important for core function, mice lacking these factors do not show impaired globin gene expression (Weiss et al., 1994).

In certain embodiments, the β-globin LCR does not comprise the full length of a core sequence of HS2. In certain embodiments, the core sequence of a HS2 region is a core sequence of human HS2. In certain non-limiting embodiments, the core sequence of human HS2 comprises a tandem pair of binding sites for members of AP1 family of proteins (e.g., NF-E2) (referred to as "AP1/NF-E2" binding sites) (e.g., GCTGAGTCA, and GATGAGTCA), one binding site for Kruppel-like Zn finger proteins (e.g., AGGGTGTGT), one GATA-1 binding site (e.g., CTATCT), and three E boxes (CANNTG, e.g., CAGATG, and CACCTG). In certain non-limiting embodiments, the β-globin LCR does not comprise the full length of a 388 bp core sequence of human HS2, which has the nucleotide sequence set forth in SEQ ID NO:20 provided below:

[SEQ ID NO: 20]
TAAGCTTCAGTTTTTCCTTAGTTCCTGTTACATTTCTGTGTGTCTCC

ATTAGTGACCTCCCATAGTCCAAGCATGAGCAGTTCTGGCCAGGCCC

CTGTCGGGGTCAGTGCCCCACCCCCGCCTTCTGGTTCTGTGTAACCT

TCTAAGCAAACCTTCTGGCTCAAGCACAGCAATGCTGAGTCATGATG

AGTCATGCTGAGGCTTAGGGTGTGTGCCCAGATGTTCTCAGCCTAGA

GTGATGACTCCTATCTGGGTCCCCAGCAGGATGCTTACAGGGCAGAT

GGCAAAAAAAGGAGAAGCTGACCACCTGACTAAAACTCCACCTCAA

ACGGCATCATAAAGAAAATGGATGCCTGAGACAGAATGTGACATATT

CTAGAATATATT

The nucleotide sequence set forth in SEQ ID NO:20 corresponds to nucleotides position 16671 to position 17058 of SEQ ID NO:19 (GenBank Access No.: NG_000007.3). In SEQ ID NO:20, one AP1/NF-E2 binding site having the nucleotide sequence of GCTGAGTCA is located at position 175 to position 183, one AP1/NF-E2 binding site having the nucleotide sequence of GATGAGTCA is located at position 185 to position 193, one binding site for Krüppel-like Zn finger proteins having the nucleotide sequence of AGGGTGTGT is located as position 205 to position 213, two E boxes, each of which have the nucleotide sequence of CAGATG, is located at position 217 to position 222, and position 278 to position 283, one GATA-1 binding site having the nucleotide sequence of CTATCT is located at position 246 to position 251, one E box having the nucleotide sequence of CACCTG is located at position 306 to position 311.

In certain non-limiting embodiments, the β-globin LCR does not comprise the full length of a 387 bp core sequence of human HS2, which has the nucleotide sequence set forth in SEQ ID NO:21 provided below:

[SEQ ID NO: 21]
TAAGCTTCAGTTTTTCCTTAGTTCCTGTTACATTTCTGTGTGTCTCC

ATTAGTGACCTCCCATAGTCCAAGCATGAGCAGTTCTGGCCAGGCCC

CTGTCGGGGTCAGTGCCCCACCCCCGCCTTCTGGTTCTGTGTAACCT

TCTAAGCAAACCTTCTGGCTCAAGCACAGCAATGCTGAGTCATGATG

AGTCATGCTGAGGCTAGGGTGTGTGCCCAGATGTTCTCAGCCTAGAG

TGATGACTCCTATCTGGGTCCCCAGCAGGATGCTTACAGGGCAGATG

GCAAAAAAAGGAGAAGCTGACCACCTGACTAAAACTCCACCTCAAA

CGGCATCATAAAGAAAATGGATGCCTGAGACAGAATGTGACATATTC

TAGAATATATT

In SEQ ID NO:21, one AP1/NF-E2 binding site having the nucleotide sequence of GCTGAGTCA is located at position 175 to position 183, one AP1/NF-E2 binding site having the nucleotide sequence of GATGAGTCA is located at position 185 to position 193, one binding site for Krüppel-like Zn finger proteins having the nucleotide sequence of AGGGTGTGT is located as position 204 to position 212, two E boxes, each of which have the nucleotide sequence of CAGATG, is located at position 216 to position 221, and position 277 to position 282, one GATA-1 binding site having the nucleotide sequence of CTATCT is located at position 245 to position 250, one E box having the nucleotide sequence of CACCTG is located at position 305 to position 310.

In certain embodiments, the β-globin LCR does not comprise a HS2 region that comprises a core sequence of HS2. A HS2 region that comprises a core sequence of HS2 can vary in length and sequence. In non-limiting examples, a HS2 region that comprises a core sequence of HS2 is from about 400 bp to about 1000 bp, e.g., from about 400 bp to about 500 bp, from about 500 bp to about 600 bp, from about 600 bp to about 700 bp, from about 700 bp to about 800 bp, from about 800 bp to about 900 bp, or from about 900 bp to about 1000 bp, in length. In certain non-limiting embodiments, the β-globin LCR does not comprise a 840 bp HS2 region (e.g., the HS2 region comprised in the globin vector TNS9 disclosed in U.S. Pat. No. 7,541,179). In certain non-limiting embodiments, the β-globin LCR does not comprise a 860 bp HS2 region. In certain non-limiting embodiments, the β-globin LCR does not comprise an about 650 bp HS2 region. In certain non-limiting embodiments, the β-globin LCR does not comprise a 646 bp HS2 region (e.g., the HS2 region comprised in the globin vector Lenti-Globin™, also known as "β87"). In certain non-limiting embodiments, the β-globin LCR does not comprise an about 420 bp HS2 region. In certain non-limiting embodiments, the β-globin LCR does not comprise a 423 bp HS2 region (e.g., the HS2 region comprised in the globin vector disclosed in Sadelain et al., *Proc. Nat'l Acad. Sci. (USA)* (1995); 92:6728-6732).

In certain embodiments, the β-globin LCR does not comprise a HS2 region that sustains the enhancer activity of HS2. In certain embodiments, the β-globin LCR does not comprise a HS2 region that is capable of enhancing the transcription of a globin gene (e.g., human β-globin gene). In non-limiting examples, the β-globin LCR does not comprise a HS2 region whose ability to enhance the transcription of a globin gene (e.g., human β-globin gene) is no less than about 60%, no less than about 70%, no less than about 80%, no less than about 90%, or no less than about 95% in comparison to a native HS2 region.

In certain embodiments, the β-globin LCR does not comprise a HS2 region that comprises one, two, three, four, five, six or seven of the following binding sites: two (a tandem pair of) AP1/NF-E2 binding sites (e.g., GCTGAGTCA, and GATGAGTCA), one binding site for Kruppel-like Zn finger proteins (e.g., AGGGTGTGT), one GATA-1 binding site (e.g., CTATCT), and three E boxes (CANNTG, e.g., CAGATG, and CACCTG). In certain embodiments, the β-globin LCR does not comprise a HS2 region that comprises six of the above-described binding sites. For example, in certain embodiments, the β-globin LCR does not comprise a HS2 region that comprises two AP1/NF-E2 binding sites, one binding site for Kruppel-like Zn finger proteins, one GATA-1 binding site, and two not three E boxes. In certain embodiments, the β-globin LCR does not comprise a HS2 region that comprises one not two AP1/NF-E2 binding site, one binding site for Kruppel-like Zn finger proteins, one GATA-1 binding site, and three E boxes. In certain embodiments, the β-globin LCR does not comprise a HS2 region that comprises two AP1/NF-E2 binding sites, one GATA-1 binding site, and three E boxes and does not comprise one binding site for Kruppel-like Zn finger proteins. In certain embodiments, the β-globin LCR does not comprise a HS2 region that comprises two AP1/NF-E2 binding sites, one binding site for Kruppel-like Zn finger proteins, and three E boxes, and does not comprise one GATA-1 binding site.

In certain embodiments, the β-globin LCR comprises a HS1 region, a HS3 region, and a HS4 region, and does not comprise a HS2 region. In certain embodiments, the HS1 region, HS3 region and HS4 region within the β-globin LCR are contiguous. In certain non-limiting embodiments, the β-globin LCR consists essentially of a HS1 region, a HS3 region and a HS4 region. In certain embodiments, the β-globin LCR comprises two introduced GATA-1 binding sites at the junction between the HS3 region and the HS4 region. The HS3 region can lie between the HS1 region and the HS4 region. The HS1, HS3, and HS4 regions can be any HS1, HS3, and HS4 regions disclosed herein. The HS2 region can also be any HS2 region disclosed herein.

In certain non-limiting embodiments, the β-globin LCR comprises or consists essentially of a HS1 region disclosed herein, a HS3 region disclosed herein, and a HS4 region disclosed herein, and does not comprise a HS2 region.

In certain non-limiting embodiments, the β-globin LCR comprises or consists essentially of a HS1 region having the nucleotide sequence set forth in SEQ ID NO:2, SEQ ID NO:3, SEQ ID NO:4, SEQ ID NO:22 or SEQ ID NO:23; a HS3 region having the nucleotide sequence set forth in SEQ ID NO:5 or a modification thereof (e.g., SEQ ID NO: 34); and a HS4 region having the nucleotide sequence set forth in SEQ ID NO:6 or a consecutive portion thereof, SEQ ID NO:7 or a consecutive portion thereof, a modification of SEQ ID NO: 6, a modification of a consecutive portion of SEQ ID NO: 6 (e.g., SEQ ID NO: 35), a modification of SEQ ID NO: 7, or a modification of a consecutive portion of SEQ ID NO: 7, or SEQ ID NO:8, and the β-globin LCR does not comprise a HS2 region.

In certain non-limiting embodiments, the β-globin LCR comprises or consists essentially of a HS1 region having the nucleotide sequence set forth in SEQ ID NO:2, a HS3 region having the nucleotide sequence set forth in SEQ ID NO:5, and a HS4 region having the nucleotide sequence set forth in SEQ ID NO:6, and the β-globin LCR does not comprise a HS2 region, as shown in FIG. 2.

In certain non-limiting embodiments, the β-globin LCR comprises or consists essentially of a HS1 region having the nucleotide sequence set forth in SEQ ID NO:3, a HS3 region having the nucleotide sequence set forth in SEQ ID NO:5, and a HS4 region having the nucleotide sequence set forth in SEQ ID NO:8, and the β-globin LCR does not comprise a HS2 region, as shown in FIG. 3.

In certain non-limiting embodiments, the β-globin LCR comprises or consists essentially of a HS1 region having the nucleotide sequence set forth in SEQ ID NO:4, a HS3 region having the nucleotide sequence set forth in SEQ ID NO:5, and a HS4 region having the nucleotide sequence set forth in SEQ ID NO:8, and the β-globin LCR does not comprise a HS2 region.

In certain non-limiting embodiments, the β-globin LCR comprises or consists essentially of a HS1 region having the nucleotide sequence set forth in SEQ ID NO: 3; a HS3 region having the nucleotide sequence set forth in SEQ ID NO: 5; and a HS4 region having nucleotides 115 to 868 of SEQ ID NO: 6 e.g., the β-globin LCR of SNS24.B87.A1 shown in FIG. 15.

In certain non-limiting embodiments, the β-globin LCR comprises or consists essentially of a HS1 region having the nucleotide sequence set forth in SEQ ID NO: 3; a HS3 region having the nucleotide sequence set forth in SEQ ID NO: 34; and a HS4 region having the nucleotide sequence set forth in SEQ ID NO: 35, e.g., as the β-globin LCR of SNS24.2.B87.A1 shown in FIG. 13.

In certain embodiments, the β-globin LCR does not comprise a HS1 region or a HS2 region. In certain embodiments, the β-globin LCR does not comprise a core sequence of HS1. A core sequence of HS1 sustains the activity of HS1, e.g., enhancer activity, or functioning as a facilitator or regulatory element to tether the enhancer activity of other HS regions, e.g., HS2-4. In addition, a core sequence of HS1 comprises one or more binding sites or binding motifs for ubiquitous as well as tissue-specific (e.g., erythroid-specific) proteins (e.g., transcription factors), including, but not limited to, GATA-1, and Krüppel-like Zn finger proteins (e.g., erythroid-restricted factor EKLF).

In certain embodiments, the β-globin LCR does not comprise the full length of a core sequence of HS1. In certain embodiments, the core sequence of a HS1 region is a core sequence of human HS1. In certain non-limiting embodiments, the core sequence of human HS1 comprises two GATA-1 binding sites (e.g., TTATCT, and CTATCA), and one binding site for EKLF (e.g., CCACACACA). In certain embodiments, the β-globin LCR does not comprise the full length of a 286 bp core sequence of human HS1. In certain non-limiting embodiments, the 286 bp core sequence of human HS1 has the nucleotide sequence set forth in SEQ ID NO:22 provided below:

[SEQ ID NO: 22]
CTGAGCAACTAACTCATGCAGGACTCTCAAACACTAACCTATAGCCT

TTTCTATGTATCTACTTGTGTAGAAACCAAGCGTGGGGACTGAGAAG

GCAATAGCAGGAGCATTCTGACTCTCACTGCCTTTGGCTAGGTCCCT

CCCTCATCACAGCTCAGCATAGTCCGAGCTCTTATCTATATCCACAC

ACAGTTTCTGACGCTGCCCAGCTATCACCATCCCAAGTCTAAAGAAA

AAAATAATGGGTTTGCCCATCTCTGTTGATTAGAAAACAAAACAAAA

TAAA

In SEQ ID NO:22, one GATA-1 binding site having the nucleotide sequence of TTATCT is located at position 173 to position 178, one GATA-1 binding site having the nucleotide sequence of CTATCA located at position 210 to position 215, and one binding site for EKLF having the nucleotide sequence of CCACACACA is located at position 183 to position 191.

In certain non-limiting embodiments, the 286 bp core sequence of human HS1 has the nucleotide sequence set forth in SEQ ID NO:23 provided below:

[SEQ ID NO: 23]
CTGAGCAACTAATCATGCAGGACTCTCAAACACTAACCTATAGCCTT

TTCTATGTATCTACTTGTGTAGAAACCAAGCGTGGGGACTGAGAAGG

CAATAGCAGGAGCATTCTGACTCTCACTGCCTTTAGCTAGGCCCCTC

CCTCATCACAGCTCAGCATAGTCCTGAGCTCTTATCTATATCCACAC

ACAGTTTCTGACGCTGCCCAGCTATCACCATCCCAAGTCTAAAGAAA

AAAATAATGGGTTTGCCCATCTCTGTTGATTAGAAAACAAAACAAAA

TAAA

The nucleotide sequence set forth in SEQ ID NO:23 corresponds to nucleotides position 21481 to position 21766 of SEQ ID NO:19 (GenBank Access No.: NG_000007.3). In SEQ ID NO:23, one GATA-1 binding site having the nucleotide sequence of TTATCT is located at position 173 to position 178, one GATA-1 binding site having the nucleotide sequence of CTATCA located at position 210 to position 215, and one binding site for EKLF having the nucleotide sequence of CCACACACA is located at position 183 to position 191.

In certain embodiments, the β-globin LCR does not comprise a HS1 region that comprises a core sequence of HS1. A HS1 region that comprises a core sequence of HS1 can vary in length and sequence. In non-limiting examples, a HS1 region that comprises a core sequence of HS1 is from about 300 bp to about 1200 bp, e.g., from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, or from about 1100 bp to about 1200 bp, in length. In certain non-limiting embodiments, the β-globin LCR does not comprise an about 1.0 kb bp HS1 region. In certain non-limiting embodiments, the β-globin LCR does not comprise an about 1.1 kb HS1 region.

In certain embodiments, the β-globin LCR does not comprise a HS1 region that sustains the activity of HS1, e.g., enhancer activity, or functioning as a facilitator or regulatory element to tether the enhancer activity of other HS regions, e.g., HS2-4. In certain embodiments, the β-globin LCR does not comprise a HS1 region that is capable of enhancing the transcription of a globin gene (e.g., human β-globin gene). In non-limiting examples, the β-globin LCR does not comprise a HS1 region whose ability to enhance the transcription of a globin gene (e.g., human β-globin gene) is no less than about 60%, no less than about 70%, no less than about 80%, no less than about 90%, or no less than about 95% in comparison to a native HS1 region. In non-limiting examples, the β-globin LCR does not comprise a HS1 region whose ability to tether the enhancer activity of one or more of HS2-HS4 is no less than about 60%, no less than about 70%, no less than about 80%, no less than about 90%, or no less than about 95% in comparison to a native HS1 region.

In certain embodiments, the β-globin LCR does not comprise a HS1 region that comprises one, two, or three of the following binding sites: two GATA-1 binding sites (e.g., TTATCT, and CTATCA), and one binding site for EKLF (e.g., CCACACACA). In certain embodiments, the β-globin LCR does not comprise a HS1 region that comprises two of the above-described binding sites. For example, in certain embodiments, the β-globin LCR does not comprise a HS1 region that comprises two GATA-1 binding sites and does not comprise one binding site for EKLF. In certain embodiments, the β-globin LCR does not comprise a HS1 region that comprises one not two AP1/NF-E2 binding site and one binding site for EKLF.

In certain embodiments, the β-globin LCR comprises a HS3 region and a HS4 region, and the β-globin LCR does not comprise a HS1 region or a HS2 region. In certain embodiments, the HS3 region and HS4 region within the β-globin LCR are contiguous. In certain non-limiting embodiments, the β-globin LCR consisting essentially of a HS3 region and a HS4 region. In another embodiment, the β-globin LCR comprises two introduced GATA-1 binding sites at the junction between the HS3 region and the HS4 region. The HS3 region can lie between the globin gene or functional portion thereof and the HS4 region.

In certain embodiments, the β-globin LCR comprises a HS3 region having the nucleotide sequence set forth in SEQ ID NO:5 and a HS4 region having the nucleotide sequence set forth in SEQ ID NO:6, SEQ ID NO:7 or SEQ ID NO:8, and the β-globin LCR does not comprise a HS1 region or a HS2 region.

In certain non-limiting embodiments, the β-globin LCR comprises a HS3 region having the nucleotide sequence set forth in SEQ ID NO:5 and a HS4 region having the nucleotide sequence set forth in SEQ ID NO:6, and the β-globin LCR does not comprise a HS1 region or a HS2 region, as shown in FIG. 4.

In certain embodiments, the β-globin LCR does not comprise a HS1 region, a HS2 region, or a HS4 region. In certain embodiments, the β-globin LCR does not comprise the full length of a core sequence of HS4. In certain embodiments, the core sequence of a HS4 region is a core sequence of human HS4. In certain embodiments, the β-globin LCR does not comprise the full length of a 280 bp core sequence of human HS4 (e.g., the 280 bp core sequence of human HS4 disclosed in Pruzina et al., *Nucleic Acids Research* (1991); 19:7:1413-1419).

In certain embodiments, the β-globin LCR does not comprise a HS4 region that comprises a core sequence of HS4. A HS4 region that comprises a core sequence of HS4 can vary in length and sequence. In non-limiting examples, a HS4 region that comprises a core sequence of HS4 is from about 300 bp to about 1200 bp, e.g., from about 300 bp to about 400 bp, from about 400 bp to about 500 bp, from about 500 bp to about 600 bp, from about 600 bp to about 700 bp, from about 700 bp to about 760 bp, from about 700 bp to about 800 bp, from about 800 bp to about 900 bp, from about 900 bp to about 1000 bp, from about 1000 bp to about 1100 bp, or from about 1100 bp to about 1200 bp, in length. In certain non-limiting embodiments, the β-globin LCR does not comprise an about 1.0 kb HS4 region. In certain non-limiting embodiments, the β-globin LCR does not comprise an about 1.1 kb HS4 region. In certain non-limiting embodiments, the β-globin LCR does not comprise an about 760 bp HS4 region. In certain non-limiting embodiments, the β-globin LCR does not comprise an about 754 bp HS4 region.

In certain embodiments, the β-globin LCR does not comprise a HS4 region that sustains the activity of HS4, e.g., enhancer activity. In certain embodiments, the β-globin LCR does not comprise a HS4 region that is capable of enhancing the transcription of a globin gene (e.g., human β-globin gene), conferring position independent expression, and/or increasing β-globin transgene expression. In certain embodiments, the expression cassette comprises at least one erythroid-specific enhancer, which can compensate the activities of HS1, HS2, and/or HS4 regions.

In certain embodiments, the β-globin LCR comprises a HS3 region, and the β-globin LCR does not comprise a HS1 region, a HS2 region or a HS4 region. In certain embodiments, the β-globin LCR consisting essentially of a HS3 region. In certain embodiments, the β-globin LCR comprises a HS3 region having the nucleotide sequence set forth in SEQ ID NO: 5 and a HS4 region having the nucleotide sequence set forth in SEQ ID NO:6, SEQ ID NO:7 or SEQ ID NO:8, and the β-globin LCR does not comprise a HS1 region or a HS2 region. In certain embodiments, the expression cassette comprises at least one erythroid-specific enhancer.

In certain non-limiting embodiments, the β-globin LCR comprises a HS3 region having the nucleotide sequence set forth in SEQ ID NO:5, and the β-globin LCR does not comprise a HS1 region, a HS2 region or a HS4 region. In certain embodiments, the expression cassette comprises at least one erythroid-specific enhancer.

In certain non-limiting embodiments, the β-globin LCR comprises a HS3 region having the nucleotide sequence set forth in SEQ ID NO: 34, and the β-globin LCR does not comprise a HS1 region, a HS2 region or a HS4 region, e.g., the β-globin LCR of SNS27.2.B87.A1 shown in FIG. 13. In certain embodiments, the expression cassette comprises at least one erythroid-specific enhancer, e.g., SNS27.2.B87.A1 shown in FIG. 13.

3.2. Globin Gene

In accordance with the presently disclosed subject matter, the expression cassette comprises a globin gene or a functional portion thereof. The globin gene can be a β-globin gene, a γ-globin gene, or a δ-globin gene. In certain embodiments, the expression cassette comprises a human β-globin gene. In accordance with the presently disclosed subject matter, the human β-globin gene can be a wild-type human β-globin gene, a deleted human β-globin gene comprising one or more deletions of intron sequences, or a mutated human β-globin gene encoding at least one anti-sickling amino acid residue. In certain non-limiting embodiments, a presently disclosed expression cassette comprises a wild-type human β-globin gene. A wild-type human β-globin gene comprises three exons (exon 1, exon 2, and exon 3). In certain embodiments, a presently disclosed expression cassette comprises a non-wild-type (mutated or modified) human $β^A$-globin gene. In certain embodiments, a presently disclosed expression cassette comprises a human β-globin gene with a deletion in intron 2 (IVS2). In certain embodiments, the deletion in IVS2 is about 370 bp. The deletion in IVS2 can eliminate AT-rich (ATR) sequences that comprise a cryptic polyadenylation site responsible of premature termination of the transcription. In certain embodiments, a presently disclosed expression cassette comprises a human $β^A$-globin gene encoding a threonine to glutamine mutation at codon 87 ($β^{A-T87Q}$). The glutamine residue at position 87 in the gamma-globin chain augments the anti-sickling activity of the gamma chain relative to the beta chain, while preserving adult oxygen-binding characteristics of the beta chain (Nagel et al., *Proc. Natl. Acad. Sci. U.S.A.* (1979); 76:670-672). In certain embodiments, a functional portion of a globin gene has at least about 80%, at least about 90%, at least about 95%, at least about 99% or at least about 100% identity to a corresponding wild-type reference polynucleotide sequence.

In certain embodiments, the human $β^A$-globin gene is a human $β^A$-globin gene encoding a threonine to glutamine mutation at codon 87 ($β^{A-T87Q}$). In certain embodiments, the human $β^A$-globin gene encoding a threonine to glutamine mutation at codon 87 ($β^{A-T87Q}$) further comprises a deletion in intron 2 (e.g., an about 370 bp deletion). In certain embodiments, the human $β^A$-globin gene encoding a threonine to glutamine mutation at codon 87 ($β^{A-T87Q}$) comprises the nucleotide sequence set forth in SEQ ID NO: 36, which is provided below.

[SEQ ID NO: 36]
gc aatgaaaata aatgtttttt attaggcaga atccagatgc tcaaggccct tcataatatc ccccagttta gtagttggac ttagggaaca aaggaacctt taatagaaat tggacagcaa gaaagcgagc ttagtgatac ttgtgggcca gggcattagc cacaccagcc accactttct gataggcagc ctgcactggt ggggtgAATT CTTTGCCAAA GTGATGGGCC AGCACACAGA

CCAGCACGTT GCCCAGGAGC TGTGGGAGGA AGATAAGAGG

TATGAACATG ATTAGCAAAA GGGCCTAGCT TGGACTCAGA

ATAATCCAGC CTTATCCCAA CCATAAAATA AAAGCAGAAT

GGTAGCTGGA TTGTAGCTGC TATTAGCAAT ATGAAACCTC

TTACATCAGT TACAATTTAT ATGCAGAAAT ATTTATATGC

AGAAATATTG CTATTGCCTT AACCCAGAAA TTATCACTGT

TATTCTTTAG AATGGTGCAA AGAGGCATGA TACATTGTAT

CATTATTGCC CTGAAAGAAA GAGATTAGGG AAAGTATTAG

AAATAAGATA AACAAAAAAG TATATTAAAA GAAGAAAGCA

TTTTTTAAAA TTACAAATGC AAAATTACCC TGATTTGGTC

AATATGTGTA CCCTGTTACT TCTCCCCTTC CTATGACATG

AACTTAACCA TAGAAAAGAA GGGGAAAGAA AACATCAAGG

GTCCCATAGA CTCACCCTGA AGTTCTCAGG ATCCACGTGC

AGCTTGTCAC AGTGCAGCTC ACTCAGctgG GCAAAGGTGC

CCTTGAGGTT GTCCAGGTGA GCCAGGCCAT CACTAAAGGC

ACCGAGCACT TTCTTGCCAT GAGCCTTCAC CTTAGGGTTG

```
CCCATAACAG CATCAGGAGT GGACAGATCC CCAAAGGACT

CAAAGAACCT CTGGGTCCAA GGGTAGACCA CCAGCAGCCT

AAGGGTGGGA AAATAGACCA ATAGGCAGAG AGAGTCAGTG

CCTATCAGAA ACCCAAGAGT CTTCTCTGTC TCCACATGCC

CAGTTTCTAT TGGTCTCCTT AAACCTGTCT TGTAACCTTG

ATACCAACCT GCCCAGGGCC TCACCACCAA CTTCATCCAC

GTTCACCTTG CCCCACAGGG CAGTAACGGC AGACTTCTCC

TCAGGAGTCA GGTGCACCAT GGTGTCTGTT TGAGGTTGCT

AGTGAACACA GTTGTGTCAG AAGCAAATGT
```

In certain embodiments, the human β$^A$-globin gene encoding a threonine to glutamine mutation at codon 87 (β$^{A\text{-}T87Q}$) comprises the nucleotide sequence set forth in SEQ ID NO: 53, which is provided below.

```
                                        [SEQ ID NO: 53]
gc aatgaaaata aatgtttttt attaggcaga atccagatgc tcaaggccct tcataatatc ccccagttta gtagttggac ttagggaaca aaggaaccnt taatagaaat tggacagcaa gaaagcgagc ttagtgatac ttgtgggcca gggcattagc cacaccagcc accactttct gataggcagc ctgcactggt ggggtgAATT CTTTGCCAAA GTGATGGGCC AGCACACAGA

CCAGCACGTT GCCCAGGAGC TGTGGGAGGA AGATAAGAGG

TATGAACATG ATTAGCAAAA GGGCCTAGCT TGGACTCAGA

ATAATCCAGC CTTATCCCAA CCATAAAATA AAAGCAGAAT

GGTAGCTGGA TTGTAGCTGC TATTAGCAAT ATGAAACCTC

TTACATCAGT TACAATTTAT ATGCAGAAAT ATTTATATGC

AGAAATATTG CTATTGCCTT AACCCAGAAA TTATCACTGT

TATTCTTTAG AATGGTGCAA AGAGGCATGA TACATTGTAT

CATTATTGCC CTGAAAGAAA GAGATTAGGG AAAGTATTAG

AAATAAGATA AACAAAAAAG TATATTAAAA GAAGAAAGCA

TTTTTTAAAA TTACAAATGC AAAATTACCC TGATTTGGTC

AATATGTGTA CCCTGTTACT TCTCCCCTTC CTATGACATG

AACTTAACCA TAGAAAAGAA GGGGAAAGAA AACATCAAGG

GTCCCATAGA CTCACCCTGA AGTTCTCAGG ATCCACGTGC

AGCTTGTCAC AGTGCAGCTC ACTCAGTTGG GCAAAGGTGC

CCTTGAGGTT GTCCAGGTGA GCCAGGCCAT CACTAAAGGC

ACCGAGCACT TCTTGCCAT GAGCCTTCAC CTTAGGGTTG

CCCATAACAG CATCAGGAGT GGACAGATCC CCAAAGGACT

CAAAGAACCT CTGGGTCCAA GGGTAGACCA CCAGCAGCCT

AAGGGTGGGA AAATAGACCA ATAGGCAGAG AGAGTCAGTG

CCTATCAGAA ACCCAAGAGT CTTCTCTGTC TCCACATGCC

CAGTTTCTAT TGGTCTCCTT AAACCTGTCT TGTAACCTTG

ATACCAACCT GCCCAGGGCC TCACCACCAA CTTCATCCAC

GTTCACCTTG CCCCACAGGG CAGTAACGGC AGACTTCTCC

TCAGGAGTCA GGTGCACCAT GGTGTCTGTT TGAGGTTGCT

AGTGAACACA GTTGTGTCAG AAGCAAATGT
```

In certain non-limiting embodiments, the human β-globin gene is a human β$^A$-globin gene encoding a glutamic acid to alanine mutation at codon 22 (β$^{A\text{-}E22A}$). In certain embodiments, the human β$^A$-globin gene encoding a glutamic acid to alanine mutation at codon 22 (β$^{A\text{-}E22A}$) further comprises a deletion in intron 2 (e.g., an about 370 bp deletion). In certain embodiments, the human β$^A$-globin gene encoding a glutamic acid to alanine mutation at codon 22 (β$^{A\text{-}E22A}$) comprises the nucleotide sequence set forth in SEQ ID NO: 54, which is provided below:

```
                                        [SEQ ID NO: 54]
gcaatgaaaataaatgtttttattaggcagaatccagatgctcaag gcccttcataatatccccagtttagtagttggacttagggaacaaa ggaacctttaatagaaattggacagcaagaaagcgagcttagtgata cttgtgggccagggcattagccacaccagccaccactttctgatagg cagcctgcactggtggggtgAATTCTTTGCCAAAGTGATGGGCCAGC

ACACAGACCAGCACGTTGCCCAGGAGCTGTGGGAGGAAGATAAGAGG

TATGAACATGATTAGCAAAAGGGCCTAGCTTGGACTCAGAATAATCC

AGCCTTATCCCAACCATAAAATAAAAGCAGAATGGTAGCTGGATTGT

AGCTGCTATTAGCAATATGAAACCTCTTACATCAGTTACAATTTATA

TGCAGAAATATTTATATGCAGAAATATTGCTATTGCCTTAACCCAGA

AATTATCACTGTTATTCTTTAGAATGGTGCAAAGAGGCATGATACAT

TGTATCATTATTGCCCTGAAAGAAAGAGATTAGGGAAAGTATTAGAA

ATAAGATAAACAAAAAGTATATTAAAAGAAGAAAGCATTTTTTAAA

ATTACAAATGCAAAATTACCCTGATTTGGTCAATATGTGTACCCTGT

TACTTCTCCCCTTCCTATGACATGAACTTAACCATAGAAAAGAAGGG

GAAAGAAAACATCAAGGGTCCCATAGACTCACCCTGAAGTTCTCAGG

ATCCACGTGCAGCTTGTCACAGTGCAGCTCACTCAGtgtGGCAAAGG

TGCCCTTGAGgttGTCCAGGTGAGCCAGGCCATCACTAAAGGCACCG

AGCACTTCTTGCCATGAGCCTTCACCTTAGGGTTGCCCATAACAGC

ATCAGGAGTGGACAGATCCCCAAAGGACTCAAAGAACCTCTGGGTCC

AAGGGTAGACCACCAGCAGCCTAAGGGTGGGAAAATAGACCAATAGG

CAGAGAGAGTCAGTGCCTATCAGAAACCCAAGAGTCTTCTCTGTCTC

CACATGCCCAGTTTCTATTGGTCTCCTTAAACCTGTCTTGTAACCTT

GATACCAACCTGCCCAGGGCCTCACCACCAACggcATCCACGTTCAC

CTTGCCCCACAGGGCAGTAACGGCAGACTTCTCCTCAGGAGTCAGGT

GCACCATGGTGTCTGTTTGAGGTTGCTAGTGAACACAGTTGTGTCAG

AAGCAAATGT
```

In certain embodiments, the human β$^A$-globin gene encoding a glutamic acid to alanine mutation at codon 22 (β$^{A\text{-}E22A}$) comprises the nucleotide sequence set forth in SEQ ID NO: 55, which is provided below:

[SEQ ID NO: 55]
gcaatgaaaataaatgttttttattaggcagaatccagatgctcaag gcccttcataatatcccccagtttagtagttggacttagggaacaaa ggaacctttaatagaaattggacagcaagaaagcgagcttagtgata cttgtgggccagggcattagccacaccagccaccactttctgatagg cagcctgcactggtggggtgAATTCTTTGCCAAAGTGATGGGCCAGC

ACACAGACCAGCACGTTGCCCAGGAGCTGTGGGAGGAAGATAAGAGG

TATGAACATGATTAGCAAAAGGGCCTAGCTTGGACTCAGAATAATCC

AGCCTTATCCCAACCATAAAATAAAAGCAGAATGGTAGCTGGATTGT

AGCTGCTATTAGCAATATGAAACCTCTTACATCAGTTACAATTTATA

TGCAGAAATATTTATATGCAGAAATATTGCTATTGCCTTAACCCAGA

AATTATCACTGTTATTCTTTAGAATGGTGCAAAGAGGCATGATACAT

TGTATCATTATTGCCCTGAAAGAAAGAGATTAGGGAAAGTATTAGAA

ATAAGATAAACAAAAAGTATATTAAAAGAAGAAAGCATTTTTTAAA

ATTACAAATGCAAAATTACCCTGATTTGGTCAATATGTGTACCCTGT

TACTTCTCCCCTTCCTATGACATGAACTTAACCATAGAAAGAAGGG

GAAAGAAAACATCAAGGGTCCCATAGACTCACCCTGAAGTTCTCAGG

ATCCACGTGCAGCTTGTCACAGTGCAGCTCACTCAGtgtGGCAAAGG

TGCCCTTGAGgttGTCCAGGTGAGCCAGGCCATCACTAAAGGCACCG

AGCACTTTCTTGCCATGAGCCTTCACCTTAGGGTTGCCCATAACAGC

ATCAGGAGTGGACAGATCCCCAAAGGACTCAAAGAACCTCTGGGTCC

AAGGGTAGACCACCAGCAGCCTAAGGGTGGGAAAATAGACCAATAGG

CAGAGAGAGTCAGTGCCTATCAGAAACCCAAGAGTCTTCTCTGTCTC

CACATGCCCAGTTTCTATTGGTCTCCTTAAACCTGTCTTGTAACCTT

GATACCAACCTGCCCAGGGCCTCACCACCAACTGCATCCACGTTCAC

CTTGCCCCACAGGGCAGTAACGGCAGACTTCTCCTCAGGAGTCAGGT

GCACCATGGTGTCTGTTTGAGGTTGCTAGTGAACACAGTTGTGTCAG

AAGCAAATGT

In certain embodiments, the human β$^A$-globin gene encoding a glutamic acid to alanine mutation at codon 22 (β$^{A-E22A}$) comprises the nucleotide sequence set forth in SEQ ID NO: 56, which is provided below:

[SEQ ID NO: 56]
gcaatgaaaataaatgttttttattaggcagaatccagatgctcaaggcc cttcataatatcccccagtttagtagttggacttagggaacaaaggaacc tttaatagaaattggacagcaagaaagcgagcttagtgatacttgtgggc cagggcattagccacaccagccaccactttctgataggcagcctgcactg AgtggggtgAATTCTTTGCCAAAGTGATGGGCCAGCACACGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGtgtGGCAAAGGT

GCCCTTGAGgttGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACAGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT

In certain embodiments, the human β$^A$-globin gene encoding a glutamic acid to alanine mutation at codon 22 (β$^{A-E22A}$) comprises the nucleotide sequence set forth in SEQ ID NO: 57, which is provided below:

[SEQ ID NO: 57]
gcaatgaaaataaatgttttttattaggcagaatccagatgctcaaggccc ttcataatatcccccagtttagtagttggacttagggaacaaaggaacctt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGtgtGGCAAAGGTGCCCTTGAGgttGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACCGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT

In certain non-limiting embodiments, the human β-globin gene is a human β$^A$-globin gene encoding an asparagine to lysine mutation at codon 80 (β$^{-N80K}$). In certain embodiments, the human β$^A$-globin gene encoding an asparagine to lysine mutation at codon 80 (β$^{-N80K}$) further comprises a deletion in intron 2 (e.g., an about 370 bp deletion). In certain embodiments, the human β$^A$-globin gene encoding an asparagine to lysine mutation at codon 80 (β$^{-N80K}$) comprises the nucleotide sequence set forth in SEQ ID NO: 58, which is provided below:

[SEQ ID NO: 58]
gcaatgaaaataaatgttttttattaggcagaatccagatgctcaaggcc cttcataatatccccagtttagtagttggacttagggaacaaaggaacc tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGtgtGGCAAAGGT

GCCCTTGAGcttGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACttcATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT

In certain embodiments, the human β$^A$-globin gene encoding an asparagine to lysine mutation at codon 80 (β$^{-N80K}$) comprises the nucleotide sequence set forth in SEQ ID NO: 59, which is provided below:

[SEQ ID NO: 59]
gcaatgaaaataaatgttttttattaggcagaatccagatgctcaaggcc cttcataatatccccagtttagtagttggacttagggaacaaaggaacc tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGtgtGGCAAAGGT

GCCCTTGAGTTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACttcATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT

In certain non-limiting embodiments, the human β-globin gene is human β$^A$-globin gene encoding a glutamic acid to alanine mutation at codon 22 and an asparagine to lysine mutation at codon 80. In certain embodiments, the human β$^A$-globin gene encoding a glutamic acid to alanine mutation at codon 22 and an asparagine to lysine mutation at codon 80 further comprises a deletion in intron 2 (e.g., an about 370 bp deletion). In certain embodiments, the human β$^A$-globin gene encoding a glutamic acid to alanine mutation at codon 22 and an asparagine to lysine mutation at codon 80 comprises the nucleotide sequence set forth in SEQ ID NO: 60, which is provided below:

[SEQ ID NO: 60]
gcaatgaaaataaatgttttttattaggcagaatccagatgctcaaggcc cttcataatatccccagtttagtagttggacttagggaacaaaggaacc tttaatagaaattggacagcaagaaagcgagcttagtgatacttgtgggc cagggcattaGCCACACCAGCCACCACTTTCTGATAGGCAGCCTGCACTG

GTGGGGTGAATTCTTTGCCAAAGTGATGGGCCAGCACACAGACCAGCACG

TTGCCCAGGAGCTGTGGGAGGAAGATAAGAGGTATGAACATGATTAGCAA

```
AAGGGCCTAGCTTGGACTCAGAATAATCCAGCCTTATCCCAACCATAAAA
TAAAAGCAGAATGGTAGCTGGATTGTAGCTGCTATTAGCAATATGAAACC
TCTTACATCAGTTACAATTTATATGCAGAAATATTTATATGCAGAAATAT
TGCTATTGCCTTAACCCAGAAATTATCACTGTTATTCTTTAGAATGGTGC
AAAGAGGCATGATACATTGTATCATTATTGCCCTGAAAGAAAGAGATTAG
GGAAAGTATTAGAAATAAGATAAACAAAAAAGTATATTAAAAGAAGAAAG
CATTTTTTAAAATTACAAATGCAAAATTACCCTGATTTGGTCAATATGTG
TACCCTGTTACTTCTCCCCTTCCTATGACATGAACTTAACCATAGAAAAG
AAGGGGAAAGAAAACATCAAGGGTCCCATAGACTCACCCTGAAGTTCTCA
GGATCCACGTGCAGCTTGTCACAGTGCAGCTCACTCAGTGTGGCAAAGGT
GCCCTTGAGCTTGTCCAGGTGAGCCAGGCCATCACTAAAGGCACCGAGCA
CTTTCTTGCCATGAGCCTTCACCTTAGGGTTGCCCATAACAGCATCAGGA
GTGGACAGATCCCCAAAGGACTCAAAGAACCTCTGGGTCCAAGGGTAGAC
CACCAGCAGCCTAAGGGTGGGAAAATAGACCAATAGGCAGAGAGAGTCAG
TGCCTATCAGAAACCCAAGAGTCTTCTCTGTCTCCACATGCCCAGTTTCT
ATTGGTCTCCTTAAACCTGTCTTGTAACCTTGATACCAACCTGCCCAGGG
CCTCACCACCAACGGCATCCACGTTCACCTTGCCCCACAGGGCAGTAACG
GCAGACTTCTCCTCAGGAGTCAGGTGCACCATGGTGTCTGTTTGAGGTTG
CTAGTGAACACAGTTGTGTCAGAAGCAAATGT
```

In certain embodiments, the human $\beta^A$-globin gene encoding a glutamic acid to alanine mutation at codon 22 and an asparagine to lysine mutation at codon 80 comprises the nucleotide sequence set forth in SEQ ID NO: 61, which is provided below:

[SEQ ID NO: 61]
```
gcaatgaaaataaatgttttttattaggcagaatccagatgctcaaggccc
ttcataatatccccagtttagtagttggacttagggaacaaaggaacctt
taatagaaattggacagcaagaaagcgagcttagtgatacttgtgggccag
ggcattagccacaccagccaccactttctgataggcagcctgcactggtgg
ggtgAATTCTTTGCCAAAGTGATGGGCCAGCACACAGACCAGCACGTTGCC
CAGGAGCTGTGGGAGGAAGATAAGAGGTATGAACATGATTAGCAAAAGGGC
CTAGCTTGGACTCAGAATAATCCAGCCTTATCCCAACCATAAAATAAAAGC
AGAATGGTAGCTGGATTGTAGCTGCTATTAGCAATATGAAACCTCTTACAT
CAGTTACAATTTATATGCAGAAATATTTATATGCAGAAATATTGCTATTGC
CTTAACCCAGAAATTATCACTGTTATTCTTTAGAATGGTGCAAAGAGGCAT
GATACATTGTATCATTATTGCCCTGAAAGAAAGAGATTAGGGAAAGTATTA
GAAATAAGATAAACAAAAAGTATATTAAAAGAAGAAAGCATTTTTTAAAA
TTACAAATGCAAAATTACCCTGATTTGGTCAATATGTGTACCCTGTTACTT
CTCCCCTTCCTATGACATGAACTTAACCATAGAAAAGAAGGGGAAAGAAAA
CATCAAGGGTCCCATAGACTCACCCTGAAGTTCTCAGGATCCACGTGCAGC
TTGTCACAGTGCAGCTCACTCAGtgtGGCAAAGGTGCCCTTGAGTttGTCC
AGGTGAGCCAGGCCATCACTAAAGGCACCGAGCACTTTCTTGCCATGAGCC
TTCACCTTAGGGTTGCCCATAACAGCATCAGGAGTGGACAGATCCCCAAAG
GACTCAAAGAACCTCTGGGTCCAAGGGTAGACCACCAGCAGCCTAAGGGTG
GGAAAATAGACCAATAGGCAGAGAGAGTCAGTGCCTATCAGAAACCCAAGA
GTCTTCTCTGTCTCCACATGCCCAGTTTCTATTGGTCTCCTTAAACCTGTC
TTGTAACCTTGATACCAACCTGCCCAGGGCCTCACCACCAACggcATCCAC
GTTCACCTTGCCCCACAGGGCAGTAACGGCAGACTTCTCCTCAGGAGTCAG
GTGCACCATGGTGTCTGTTTGAGGTTGCTAGTGAACACAGTTGTGTCAGAA
GCAAATGT
```

In certain embodiments, the human $\beta^A$-globin gene encoding a glutamic acid to alanine mutation at codon 22 and an asparagine to lysine mutation at codon 80 comprises the nucleotide sequence set forth in SEQ ID NO: 62, which is provided below:

[SEQ ID NO: 62]
```
GCAATGAAAATAAATGTTTTTTATTAGGCAGAATCCAGATGCTCAAGGCC
CTTCATAATATCCCCCAGTTTAGTAGTTGGACTTAGGGAACAAAGGAACC
TTTAATAGAAATTGGACAGCAAGAAAGCGAGCTTAGTGATACTTGTGGGC
CAGGGCATTAGCCACACCAGCCACCACTTTCTGATAGGCAGCCTGCACTG
GTGGGGTGAATTCTTTGCCAAAGTGATGGGCCAGCACACAGACCAGCACG
TTGCCCAGGAGCTGTGGGAGGAAGATAAGAGGTATGAACATGATTAGCAA
AAGGGCCTAGCTTGGACTCAGAATAATCCAGCCTTATCCCAACCATAAAA
TAAAAGCAGAATGGTAGCTGGATTGTAGCTGCTATTAGCAATATGAAACC
TCTTACATCAGTTACAATTTATATGCAGAAATATTTATATGCAGAAATAT
TGCTATTGCCTTAACCCAGAAATTATCACTGTTATTCTTTAGAATGGTGC
AAAGAGGCATGATACATTGTATCATTATTGCCCTGAAAGAAAGAGATTAG
GGAAAGTATTAGAAATAAGATAAACAAAAAAGTATATTAAAAGAAGAAAG
CATTTTTTAAAATTACAAATGCAAAATTACCCTGATTTGGTCAATATGTG
TACCCTGTTACTTCTCCCCTTCCTATGACATGAACTTAACCATAGAAAAG
AAGGGGAAAGAAAACATCAAGGGTCCCATAGACTCACCCTGAAGTTCTCA
GGATCCACGTGCAGCTTGTCACAGTGCAGCTCACTCAGTGTGGCAAAGGT
GCCCTTGAGCTTGTCCAGGTGAGCCAGGCCATCACTAAAGGCACCGAGCA
CTTTCTTGCCATGAGCCTTCACCTTAGGGTTGCCCATAACAGCATCAGGA
GTGGACAGATCCCCAAAGGACTCAAAGAACCTCTGGGTCCAAGGGTAGAC
CACCAGCAGCCTAAGGGTGGGAAAATAGACCAATAGGCAGAGAGAGTCAG
TGCCTATCAGAAACCCAAGAGTCTTCTCTGTCTCCACATGCCCAGTTTCT
ATTGGTCTCCTTAAACCTGTCTTGTAACCTTGATACCAACCTGCCCAGGG
CCTCACCACCAACTGCATCCACGTTCACCTTGCCCCACAGGGCAGTAACG
GCAGACTTCTCCTCAGGAGTCAGGTGCACCATGGTGTCTGTTTGAGGTTG
CTAGTGAACACAGTTGTGTCAGAAGCAAATGT
```

In certain embodiments, the human $\beta^A$-globin gene encoding a glutamic acid to alanine mutation at codon 22 and an asparagine to lysine mutation at codon 80 comprises the nucleotide sequence set forth in SEQ ID NO: 63, which is provided below:

[SEQ ID NO: 63]
gcaatgaaaataaatgttttttattaggcagaatccagatgctcaaggccc ttcataatatcccccagtttagtagttggacttagggaacaaaggaaccttt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGTGTGGCAAAGGTGCCCTTGAGCTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACAGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT

In certain embodiments, the human β$^A$-globin gene encoding a glutamic acid to alanine mutation at codon 22 and an asparagine to lysine mutation at codon 80 comprises the nucleotide sequence set forth in SEQ ID NO: 64, which is provided below:

[SEQ ID NO: 64]
gcaatgaaaataaatgttttttattaggcagaatccagatgctcaaggccc ttcataatatcccccagtttagtagttggacttagggaacaaaggaaccttt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGTGTGGCAAAGGTGCCCTTGAGCTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACCGCATCCAC

GTTCACCTTGCCCCACAGGGCAGTAACGGCAGACTTCTCCTCAGGAGTCAG

GTGCACCATGGTGTCTGTTTGAGGTTGCTAGT-
GAACACAGTTGTGTCAGAA

GCAAATGT

In certain embodiments, the human β$^A$-globin gene encoding a glutamic acid to alanine mutation at codon 22 and an asparagine to lysine mutation at codon 80 comprises the nucleotide sequence set forth in SEQ ID NO: 65, which is provided below:

[SEQ ID NO: 65]
gcaatgaaaataaatgttttttattaggcagaatccagatgctcaaggcc cttcataatatcccccagtttagtagttggacttagggaacaaaggaacc tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGTGTGGCAAAGGT

GCCCTTGAGTTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACTGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT

In certain embodiments, the human β$^A$-globin gene encoding a glutamic acid to alanine mutation at codon 22 and an asparagine to lysine mutation at codon 80 comprises the nucleotide sequence set forth in SEQ ID NO: 66, which is provided below:

[SEQ ID NO: 66]

gcaatgaaaataaatgttttttattaggcagaatccagatgctcaaggccc ttcataatatcccccagtttagtagttggACTTAGGGAACAAAGGAACCTT

TAATAGAAATTGGACAGCAAGAAAGCGAGCTTAGTGATACTTGTGGGCCAG

GGCATTAGCCACACCAGCCACCACTTTCTGATAGGCAGCCTGCACTGGTGG

GGTGAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAGTATATTAAAAGAAGAAAGCATTTTTTAAAA

TTACAAATGCAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGTGTGGCAAAGGTGCCCTTGAGTTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACAGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT

In certain embodiments, the human β$^A$-globin gene encoding a glutamic acid to alanine mutation at codon 22 and an asparagine to lysine mutation at codon 80 comprises the nucleotide sequence set forth in SEQ ID NO: 67, which is provided below:

[SEQ ID NO: 67]

gcaatgaaaataaatgttttttattaggcagaatccagatgctcaaggcc cttcataatatcccccagtttagtagttggacttagggaacaaaggaacc tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGTGTGGCAAAGGT

GCCCTTGAGTTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACCGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT

In certain non-limiting embodiments, the human β-globin gene is a human β$^A$-globin gene encoding a glutamic acid to alanine mutation at codon 22 and a threonine to glutamine mutation at codon 87. In certain embodiments, the human β$^A$-globin gene encoding a glutamic acid to alanine mutation at codon 22 and a threonine to glutamine mutation at codon 87 further comprises a deletion in intron 2 (e.g., an about 370 bp deletion). In certain embodiments, the human β$^A$-globin gene encoding a glutamic acid to alanine mutation at codon 22 and a threonine to glutamine mutation at codon 87 comprises the nucleotide sequence set forth in SEQ ID NO: 68, which is provided below:

[SEQ ID NO: 68]

gcaatgaaaataaatgttttttattaggcagaatccagatgctcaaggcc cttcataatatcccccagtttagtagttggacttagggaacaaaggaacc tttaatagaaattggacagcaagaaagcgagcttagtgatacttgtgggc cagggcattagccacaccagccaccactttctgataggcagcctgcactg gtggggtgAATTCTTTGCCAAAGTGATGGGCCAGCACACAGACCAGCACG

TTGCCCAGGAGCTGTGGGAGGAAGATAAGAGGTATGAACATGATTAGCAA

AAGGGCCTAGCTTGGACTCAGAATAATCCAGCCTTATCCCAACCATAAAA

TAAAAGCAGAATGGTAGCTGGATTGTAGCTGCTATTAGCAATATGAAACC

```
TCTTACATCAGTTACAATTTATATGCAGAAATATTTATATGCAGAAATAT

TGCTATTGCCTTAACCCAGAAATTATCACTGTTATTCTTTAGAATGGTGC

AAAGAGGCATGATACATTGTATCATTATTGCCCTGAAAGAAAGAGATTAG

GGAAAGTATTAGAAATAAGATAAACAAAAAAGTATATTAAAAGAAGAAAG

CATTTTTTAAAATTACAAATGCAAAATTACCCTGATTTGGTCAATATGTG

TACCCTGTTACTTCTCCCCTTCCTATGACATGAACTTAACCATAGAAAAG

AAGGGGAAAGAAAACATCAAGGGTCCCATAGACTCACCCTGAAGTTCTCA

GGATCCACGTGCAGCTTGTCACAGTGCAGCTCACTCAGCTGGGCAAAGGT

GCCCTTGAGGTTGTCCAGGTGAGCCAGGCCATCACTAAAGGCACCGAGCA

CTTTCTTGCCATGAGCCTTCACCTTAGGGTTGCCCATAACAGCATCAGGA

GTGGACAGATCCCCAAAGGACTCAAAGAACCTCTGGGTCCAAGGGTAGAC

CACCAGCAGCCTAAGGGTGGGAAAATAGACCAATAGGCAGAGAGAGTCAG

TGCCTATCAGAAACCCAAGAGTCTTCTCTGTCTCCACATGCCCAGTTTCT

ATTGGTCTCCTTAAACCTGTCTTGTAACCTTGATACCAACCTGCCCAGGG

CCTCACCACCAACGGCATCCACGTTCACCTTGCCCCACAGGGCAGTAACG

GCAGACTTCTCCTCAGGAGTCAGGTGCACCATGGTGTCTGTTTGAGGTTG

CTAGTGAACACAGTTGTGTCAGAAGCAAATGT
```

In certain embodiments, the human β$^A$-globin gene encoding a glutamic acid to alanine mutation at codon 22 and a threonine to glutamine mutation at codon 87 comprises the nucleotide sequence set forth in SEQ ID NO: 69, which is provided below:

```
                                            [SEQ ID NO: 69]
gcaatgaaaataaatgttttttattaggcagaatccagatgctcaaggccc ttcataatatccccagtttagtagttggacttagggaacaaaggaacctt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGTTGGGCAAAGGTGCCCTTGAGGTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACGGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT
```

In certain embodiments, the human β$^A$-globin gene encoding a glutamic acid to alanine mutation at codon 22 and a threonine to glutamine mutation at codon 87 comprises the nucleotide sequence set forth in SEQ ID NO: 70, which is provided below:

```
                                            [SEQ ID NO: 70]
gcaatgaaaataaatgttttttattaggcagaatccagatgctcaaggccc ttcataatatccccagtttagtagttggacttagggaacaaaggaacctt taatagaaattggacagcaagaaagcgagcttagtgatacttgtgggccag ggcattagccacaccagccaccactttctgataggcagcctgcactggtgg ggtgAATTCTTTGCCAAAGTGATGGGCCAGCACACAGACCAGCACGTTGCC

CAGGAGCTGTGGGAGGAAGATAAGAGGTATGAACATGATTAGCAAAAGGGC

CTAGCTTGGACTCAGAATAATCCAGCCTTATCCCAACCATAAAATAAAAGC

AGAATGGTAGCTGGATTGTAGCTGCTATTAGCAATATGAAACCTCTTACAT

CAGTTACAATTTATATGCAGAAATATTTATATGCAGAAATATTGCTATTGC

CTTAACCCAGAAATTATCACTGTTATTCTTTAGAATGGTGCAAAGAGGCAT

GATACATTGTATCATTATTGCCCTGAAAGAAAGAGATTAGGGAAAGTATTA

GAAATAAGATAAACAAAAAAGTATATTAAAAGAAGAAAGCATTTTTTAAAA

TTACAAATGCAAAATTACCCTGATTTGGTCAATATGTGTACCCTGTTACTT

CTCCCCTTCCTATGACATGAACTTAACCATAGAAAAGAAGGGGAAAGAAAA

CATCAAGGGTCCCATAGACTCACCCTGAAGTTCTCAGGATCCACGTGCAGC

TTGTCACAGTGCAGCTCACTCAGCTGGGCAAAGGTGCCCTTGAGGTTGTCC

AGGTGAGCCAGGCCATCACTAAAGGCACCGAGCACTTTCTTGCCATGAGCC

TTCACCTTAGGGTTGCCCATAACAGCATCAGGAGTGGACAGATCCCCAAAG

GACTCAAAGAACCTCTGGGTCCAAGGGTAGACCACCAGCAGCCTAAGGGTG

GGAAAATAGACCAATAGGCAGAGAGAGTCAGTGCCTATCAGAAACCCAAGA

GTCTTCTCTGTCTCCACATGCCCAGTTTCTATTGGTCTCCTTAAACCTGTC

TTGTAACCTTGATACCAACCTGCCCAGGGCCTCACCACCAACTGCATCCAC

GTTCACCTTGCCCCACAGGGCAGTAACGGCAGACTTCTCCTCAGGAGTCAG

GTGCACCATGGTGTCTGTTTGAGGTTGCTAGTGAACACAGTTGTGTCAGAA

GCAAATGT
```

In certain embodiments, the human β$^A$-globin gene encoding a glutamic acid to alanine mutation at codon 22 and a threonine to glutamine mutation at codon 87 comprises the nucleotide sequence set forth in SEQ ID NO: 71, which is provided below:

[SEQ ID NO: 71]
gcaatgaaaataaatgttttttattaggcagaatccagatgctcaagg cccttcataatatcccccagtttagtagttggacttagggaacaaagg aacctttaatagaaattggacagcaagaaagcgagcttagtgatactt gtgggccagggcattagccacaccagccaccactttctgataggcagc ctgcactggtggggtgAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGCTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC

CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACCGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT

In certain embodiments, the human β$^4$-globin gene encoding a glutamic acid to alanine mutation at codon 22 and a threonine to glutamine mutation at codon 87 comprises the nucleotide sequence set forth in SEQ ID NO: 72, which is provided below:

[SEQ ID NO: 72]
gcaatgaaaataaatgttttttattaggcagaatccagatgctcaagg cccttcataatatcccccagtttagtagttggacttagggaacaaagg aacctttaatagaaattggacagcaagaaagcgagcttagtgatactt gtgggccagggcattagccacaccagccaccactttctgataggcagc ctgcactggtggggtgAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGCTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC

CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACCGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT

In certain embodiments, the human β$^4$-globin gene encoding a glutamic acid to alanine mutation at codon 22 and a threonine to glutamine mutation at codon 87 comprises the nucleotide sequence set forth in SEQ ID NO: 73, which is provided below:

[SEQ ID NO: 73]
gcaatgaaaataaatgttttttattaggcagaatccagatgctcaagg cccttcataatatcccccagtttagtagttggacttagggaacaaagg aacctttaatagaaattggacagcaagaaagcgagcttagtgatactt gtgggccagggcattagccacaccagccaccactttctgataggcagc ctgcactggtggggtgAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGTTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC

CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACTGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT

In certain embodiments, the human β$^A$-globin gene encoding a glutamic acid to alanine mutation at codon 22 and a threonine to glutamine mutation at codon 87 comprises the nucleotide sequence set forth in SEQ ID NO: 74, which is provided below:

[SEQ ID NO: 74]
gcaatgaaaataaatgttttttattaggcagaatccagatgctcaagg cccttcataatatcccccagtttagtagttggacttagggaacaaagg aacctttaatagaaattggacagcaagaaagcgagcttagtgatactt gtgggccagggcattaGCCACACCAGCCACCACTTTCTGATAGGCAGC

CTGCACTGGTGGGGTGAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGTTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC

CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACAGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT

In certain embodiments, the human β$^A$-globin gene encoding a glutamic acid to alanine mutation at codon 22 and a threonine to glutamine mutation at codon 87 comprises the nucleotide sequence set forth in SEQ ID NO: 75, which is provided below:

[SEQ ID NO: 75]
gcaatgaaaataaatgttttttattaggcagaatccagatgctcaagg cccttcataatatcccccagtttagtagttggACTTAGGGAACAAAGG

AACCTTTAATAGAAATTGGACAGCAAGAAAGCGAGCTTAGTGATACTT

GTGGGCCAGGGCATTAGCCACACCAGCCACCACTTTCTGATAGGCAGC

CTGCACTGGTGGGTGAATTCTTTGCCAAAGTGATGGGCCAGCACACA

GACCAGCACGTTGCCCAGGAGCTGTGGGAGGAAGATAAGAGGTATGAA

CATGATTAGCAAAAGGGCCTAGCTTGGACTCAGAATAATCCAGCCTTA

TCCCAACCATAAAATAAAAGCAGAATGGTAGCTGGATTGTAGCTGCTA

TTAGCAATATGAAACCTCTTACATCAGTTACAATTTATATGCAGAAAT

ATTTATATGCAGAAATATTGCTATTGCCTTAACCCAGAAATTATCACT

GTTATTCTTTAGAATGGTGCAAAGAGGCATGATACATTGTATCATTAT

TGCCCTGAAAGAAAGAGATTAGGGAAAGTATTAGAAATAAGATAAACA

AAAAAGTATATTAAAAGAAGAAAGCATTTTTTAAAATTACAAATGCAA

AATTACCCTGATTTGGTCAATATGTGTACCCTGTTACTTCTCCCCTTC

CTATGACATGAACTTAACCATAGAAAAGAAGGGGAAAGAAAACATCAA

GGGTCCCATAGACTCACCCTGAAGTTCTCAGGATCCACGTGCAGCTTG

TCACAGTGCAGCTCACTCAGTTGGGCAAAGGTGCCCTTGAGGTTGTCC

AGGTGAGCCAGGCCATCACTAAAGGCACCGAGCACTTTCTTGCCATGA

GCCTTCACCTTAGGGTTGCCCATAACAGCATCAGGAGTGGACAGATCC

CCAAAGGACTCAAAGAACCTCTGGGTCCAAGGGTAGACCACCAGCAGC

CTAAGGGTGGGAAAATAGACCAATAGGCAGAGAGAGTCAGTGCCTATC

AGAAACCCAAGAGTCTTCTCTGTCTCCACATGCCCAGTTTCTATTGGT

CTCCTTAAACCTGTCTTGTAACCTTGATACCAACCTGCCCAGGGCCTC

ACCACCAACCGCATCCACGTTCACCTTGCCCCACAGGGCAGTAACGGC

AGACTTCTCCTCAGGAGTCAGGTGCACCATGGTGTCTGTTTGAGGTTG

CTAGTGAACACAGTTGTGTCAGAAGCAAATGT

In certain embodiments, the site of the human β-globin gene IVS2 deletion is located at nucleotides 650-652 of SEQ ID NO: 36. In certain embodiments, nucleotides 1 to 261 of SEQ ID NO: 36 is the nucleotide sequence of exon 3 of the human β-globin gene. In certain embodiments, nucleotides 738 to 960 of SEQ ID NO: 36 is the nucleotide sequence of exon 2 of the human β-globin gene. certain embodiments, nucleotides 1091 to 1232 of SEQ ID NO: 36 is the nucleotide sequence of exon 1 of the human β-globin gene.

3.3. Promoters

In accordance with the presently disclosed subject matter, the expression cassette can further comprise a β-globin promoter. In certain embodiments, the β-globin promoter is positioned between the globin gene or functional portion thereof and the β-globin LCR. The length and the sequence of the β-globin promoter can vary. In certain embodiments, the β-globin promoter is from about 100 bp to about 1600 bp in length, e.g., from about 200 bp to about 700 bp, from about 100 bp to about 200 bp, from about 200 bp to about 300 bp, from about 300 bp to about 400 bp, from about 400 bp to about 500 bp, from about 500 bp to about 600 bp, from about 600 bp to about 700 bp, from about 700 bp to about 800 bp, from about 800 bp to about 900 bp, from about 900 bp to about 1000 bp, from about 1000 bp to about 1100 bp, from about 1100 bp to about 1200 bp, from about 1200 bp to about 1300 bp, from about 1300 bp to about 1400 bp, from about 1400 bp to about 1500 bp, or from about 1500 bp to about 1600 bp in length. In certain embodiments, the β-globin promoter a human β-globin promoter that is about 130 bp, about 613 bp, about 265 bp, or about 1555 bp, in length. In certain embodiments, the β-globin promoter is a human β-globin promoter that is about 613 bp in length. In certain non-limiting embodiments, the human β-globin promoter has the nucleotide sequence set forth in SEQ ID NO:10, which is provided below:

[SEQ ID NO: 10]
AAGCAATAGATGGCTCTGCCCTGACTTTTATGCCCAGCCCTGGCTCCT

GCCCTCCCTGCTCCTGGGAGTAGATTGGCCAACCCTAGGGTGTGGCTC

CACAGGGTGAGGTCTAAGTGATGACAGCCGTACCTGTCCTTGGCTCTT

CTGGCACTGGCTTAGGAGTTGGACTTCAAACCCTCAGCCCTCCCTCTA

AGATATATCTCTTGGCCCCATACCATCAGTACAAATTGCTACTAAAAA

CATCCTCCTTTGCAAGTGTATTTACGTAATATTTGGAATCACAGCTTG

GTAAGCATATTGAAGATCGTTTTCCCAATTTTCTTATTACACAAATAA

GAAATTGATGCACTAAAAGTGGAAGAGTTTTGTCTACCATAATTCAGC

TTTGGGATATGTAGATGGATCTCTTCCTGCGTCTCCAGAATATGCAAA

ATACTTACAGGACAGAATGGATGAAAACTCTACCTCAGTTCTAAGCAT

ATCTTCTCCTTATTTGGATTAAAACCTTCTGGTAAGAAAAGAAAAAAA

ATATATATATATATGTGTATATATACACACATACATATACATATATAT

GCATTCATTTGTTGTTGTTTTTCTTAATTTGCTCATG

In certain embodiments, the β-globin promoter is a human β-globin promoter that is about 265 bp in length. In certain non-limiting embodiments, the human β-globin promoter has the nucleotide sequence set forth in SEQ ID NO:11.

[SEQ ID NO: 11]
AAGCAATAGATGGCTCTGCCCTGACTTTTATGCCCAGCCCTGGCTCCT

GCCCTCCCTGCTCCTGGGAGTAGATTGGCCAACCCTAGGGTGTGGCTC

CACAGGGTGAGGTCTAAGTGATGACAGCCGTACCTGTCCTTGGCTCTT

CTGGCACTGGCTTAGGAGTTGGACTTCAAACCCTCAGCCCTCCCTCTA

AGATATATCTCTTGGCCCCATACCATCAGTACAAATTGCTACTAAAAA

CATCCTCCTTTGCAAGTGTATTTAC

3.4. Human β-globin 3' Enhancers

Additionally or alternatively, a presently disclosed expression cassette can further comprise a human β-globin 3' enhancer. In certain embodiments, the human β-globin 3' enhancer is positioned in the upstream of the globin gene or functional portion thereof. In certain embodiments, the β-globin 3' enhancer is from about 500 bp to about 1000 bp in length, e.g., from about 500 bp to about 600 bp, from about 600 bp to about 700 bp, from about 700 bp to about 800 bp, or from about 800 bp to about 900 bp in length. In certain embodiments, the human β-globin 3' enhancer is about 879 bp in length. In certain embodiments, the human β-globin 3' enhancer has the nucleotide sequence set forth in SEQ ID NO:12, which is provided below.

[SEQ ID NO: 12]
TAGGTATTGAATAAGAAAAATGAAGTTAAGGTGGTTGATGGTAACACT

ATGCTAATAACTGCAGAGCCAGAAGCACCATAAGGGACATGATAAGGG

AGCCAGCAGACCTCTGATCTCTTCCTGAATGCTAATCTTAAACATCCT

GAGGAAGAATGGGACTTCCATTTGGGGTGGGCCTATGATAGGGTAATA

AGACAGTAGTGAATATCAAGCTACAAAAAGCCCCCTTTCAAATTCTTC

TCAGTCCTAACTTTTCATACTAAGCCCAGTCCTTCCAAAGCAGACTGT

GAAAGAGTGATAGTTCCGGGAGACTAGCACTGCAGATTCCGGGTCACT

GTGAGTGGGGAGGCAGGGAAGAAGGGCTCACAGGACAGTCAAACCAT

GCCCCCTGTTTTTCCTTCTTCAAGTAGACCTCTATAAGACAACAGAGA

CAACTAAGGCTGAGTGGCCAGGCGAGGAGAAACCATCTCGCCGTAAAA

CATGGAAGGAACACTTCAGGGGAAAGGTGGTATCTCTAAGCAAGAGAA

CTGAGTGGAGTCAAGGCTGAGAGATGCAGGATAAGCAAATGGGTAGTG

AAAAGACATTCATGAGGACAGCTAAAACAATAAGTAATGTAAAATACA

GCATAGCAAAACTTTAACCTCCAAATCAAGCCTCTACTTGAATCCTTT

TCTGAGGGATGAATAAGGCATAGGCATCAGGGGCTGTTGCCAATGTGC

ATTAGCTGTTTGCAGCCTCACCTTCTTTCATGGAGTTTAAGATATAGT

GTATTTTCCCAAGGTTTGAACTAGCTCTTCATTTCTTTATGTTTTAAA

TGCACTGACCTCCCACATTCCCTTTTTAGTAAAATATTCAGAAATAAT

TTAAATACATCATTG

In certain embodiments, the human β-globin 3' enhancer has the nucleotide sequence set forth in SEQ ID NO: 78, which is provided below.

[SEQ ID NO: 78]
CTAGGTATTGA ATAAGAAAAA TGAAGTTAAG GTGGTTGATG

GTAACACTAT GCTAATAACT GCAGAGCCAG AAGCACCATA

AGGGACATGA TAAGGGAGCC AGCAGACCTC TGATCTCTTC

CTGAATGCTA ATCTTAAACA TCCTGAGGAA GAATGGGACT

TCCATTTGGG GTGGGCCTAT GATAGGGTAA TAAGACAGTA

GTGAATATCA AGCTACAAAA AGCCCCCTTT CAAATTCTTC

TCAGTCCTAA CTTTTCATAC TAAGCCCAGT CCTTCCAAAG

CAGACTGTGA AAGAGTGATA GTTCCGGGAG ACTAGCACTG

CAGATTCCGG GTCACTGTGA GTGGGGAGG CAGGGAAGAA

GGGCTCACAG GACAGTCAAA CCATGCCCCC TGTTTTTCCT

TCTTCAAGTA GACCTCTATA AGACAACAGA GACAACTAAG

GCTGAGTGGC CAGGCGAGGA GAAACCATCT CGCCGTAAAA

CATGGAAGGA ACACTTCAGG GGAAAGGTGG TATCTCTAAG

CAAGAGAACT GAGTGGAGTC AAGGCTGAGA GATGCAGGAT

AAGCAAATGG GTAGTGAAAA GACATTCATG AGGACAGCTA

AAACAATAAG TAATGTAAAA TACAGCATAG CAAAACTTTA

ACCTCCAAAT CAAGCCTCTA CTTGAATCCT TTTCTGAGGG

ATGAATAAGG CATAGGCATC AGGGGCTGTT GCCAATGTGC

-continued

ATTAGCTGTT TGCAGCCTCA CCTTCTTTCA TGGAGTTTAA

GATATAGTGT ATTTTCCCAA GGTTTGAACT AGCTCTTCAT

TTCTTTATGT TTTAAATGCA CTGACCTCCC ACATTCCCTT

TTTAGTAAAA TATTCAGAAA TAATTTAAAT ACATCATT

3.5. Erythroid-Specific Enhancers

Furthermore, a presently disclosed expression cassette can further comprise at least one erythroid-specific enhancer. The presently disclosed expression cassette allows for expression of a globin gene (e.g., human β-globin gene) in erythroid-specific fashion. The erythroid-specific enhancer can enhance the expression of the globin gene in erythroid-specific fashion. For example, the erythroid-specific enhancer lack enhancer activity in non-erythroid tissues. In particularly, for the β-globin LCR that lacks a HS2 region, which primarily functions as an expression enhancer, the addition of one or more erythroid-specific enhancers can compensate the enhancing activity of a HS2 region. Additionally, for an expression cassette that lacks a β-globin LCR (e.g., SNS26.B87.A1) or the β-globin LCR consists essentially of a HS3 region and does not comprise a HS1 region, a HS2 region, or a HS4 region (e.g., SN27.2B87.A1), the addition of one or more erythroid-specific enhancers are capable of driving the expression of the β-globin gene. See e.g., Table 1 and FIG. 16. Furthermore, the presently disclosed erythroid-specific enhancers do not decrease or reduce the titer of a vector comprising the expression cassette. The length of the erythroid-specific enhancer can vary, e.g., from about 100 bp to about 200 bp, from about 100 bp to about 120 bp, from about 120 bp to about 140 bp, from about 140 bp to about 200 (e.g., from about 140 bp to about 150 bp, from about 150 bp to about 160 bp, from about 160 bp to about 170 bp, from about 170 bp to about 180 bp, from about 180 bp to about 190 bp, or from about 190 bp to about 200 bp). In certain embodiments, the erythroid-specific enhancer has a length of from about 140 bp to about 200 bp. In certain non-limiting embodiments, the erythroid-specific enhancer has a length of 152 bp, which has the nucleotide sequence set forth in SEQ ID NO:13, which is provided below:

[SEQ ID NO: 13]
TCTCCCACGCCCTGGTCTCAGCTTGGGGAGTGGTCAGACCCCAATGGC

GATAAACTCTGGCAACTTTATCTGTGcaCTGCAGGCTCAGCCCCAAca

GCTTTAGCTTTCACAAGCAGGCAGGGGAAGGGAAACACATATCTCCAG

ATATGAGG

In certain non-limiting embodiments, the erythroid-specific enhancer has a length of 157 bp, which has the nucleotide sequence set forth in SEQ ID NO:14, which is provided below:

[SEQ ID NO: 14]
CTAAACCCCTCCCCCACCCTAGCCCCAAGCTTCATCTTAGCTCCACTC

CTGACCCTATCCAGCTAAAGGTCCCCACCCAGCTCCTGCCTATCTAGT

CATTGCATATGGCAAGACTTGAAAGTCCTATCTCAAAGCAGCAGAATT

ATCAGCTACGACT

In certain non-limiting embodiments, the erythroid-specific enhancer has a length of 141 bp, which has the nucleotide sequence set forth in SEQ ID NO:15, which is provided below:

[SEQ ID NO: 15]
CCATCCCCCAGCACTCCCTGCCCCCACAGCCCAGACTTGACCAACTCC

CAGCTcCGCCTGGGACTTCCAGATATGGGGCCCCACCCTTGCAGGCCT

TGGGGACGCTGAAGATATTGACTATCTGCGTGCCggAAAAGGGTG

In certain non-limiting embodiments, the erythroid-specific enhancer has a length of 171 bp, which has the nucleotide sequence set forth in SEQ ID NO:16, which is provided below:

[SEQ ID NO: 16]
AAAGGCTGGGGGTGGGAGTAGCGGATTTGAAGCACTTGTTGGCCTACA

GAGGTGTGGCAAGCAGAGCACCTCAGAACTCAGGCGTACTGCCCGCCG

CCCGAGCCCTGCGAGGGCCGATAGCGAGGGTGTGGCCCTTATCTGCAC

CCAGCAGAGCGCCGGCGGGGTACGGTC

In certain non-limiting embodiments, the erythroid-specific enhancer has a length of 195 bp, which has the nucleotide sequence set forth in SEQ ID NO:17, which is provided below:

[SEQ ID NO: 17]
CAGTTGCCTCAGCTGAGTATGTCTTCTAAAGATAATGTCGATTGTGTA

TGGCTGATGGGATTCTAGGACCAAGCAAGAGGTTTTTTTTTTCCCCC

ACATACTTAACGTTTCTATATTTCTATTTGAATTCGACTGGACAGTTC

CATTTGAATTATTTCTCTCTCTCTCTCTCTCTGACACATTTTATCTTG

CCA

The erythroid-specific enhancer can be located within the β-globin LCR, e.g., between any two of the HS1, HS2, HS3, and HS4 regions. In certain embodiments, the erythroid-specific enhancer is located between the HS1 and HS3 regions within the β-globin LCR.

Alternatively, the erythroid-specific enhancer can be located upstream or downstream of the insulator, e.g., where the expression cassette does not comprise a β-globin LCR. In certain embodiments, the erythroid-specific enhancer is located upstream of the erythroid-specific enhancer.

Furthermore, the erythroid-specific enhancer can be located upstream or downstream of any of the HS1, HS2, HS3, and HS4 regions. In certain embodiments, the erythroid-specific enhancer is located upstream of the HS3 region.

In certain embodiments, the β-globin LCR comprises or consists essentially of a HS1 region having the nucleotide sequence set forth in SEQ ID NO: 3; a HS3 region having the nucleotide sequence set forth in SEQ ID NO: 5; a HS4 region having nucleotides 115 to 868 of SEQ ID NO: 6; and an erythroid-specific enhancer having the nucleotide sequence set forth in SEQ ID NO: 15, wherein the erythroid-specific enhancer is positioned between the HS1 region and the HS3 region, e.g., the β-globin LCR of SNS24.B87.A1 shown in FIG. 15.

In certain non-limiting embodiments, the β-globin LCR comprises or consists essentially of a HS1 region having the nucleotide sequence set forth in SEQ ID NO: 3; a HS3 region having the nucleotide sequence set forth in SEQ ID NO: 34; and a HS4 region having the nucleotide sequence set forth in SEQ ID NO: 35; and an erythroid-specific enhancer having the nucleotide sequence set forth in SEQ ID NO: 15, wherein the erythroid-specific enhancer is positioned between the HS1 region and the HS3 region, e.g., as the β-globin LCR of SNS22.2.B87.A1 shown in FIG. 13.

Erythroid-specific enhancers can be identified and determined by any suitable methods known in the art. The erythroid-specific enhancers can be positioned at the 3' UTR (downstream) or the 5' UTR (downstream) of the β-globin LCR. In certain embodiments, the at least one erythroid-specific enhancer is positioned in the 5' UTR of the β-globin LCR, e.g., the upstream of the HS3 region. The expression cassette can comprise one, two, three, four, or five erythroid-specific enhancers. In certain embodiments, the expression cassette comprises one erythroid-specific enhancer. In certain embodiments, the expression cassette comprises two erythroid-specific enhancers. In certain embodiments, the expression cassette comprises three erythroid-specific enhancers. In certain embodiments, the expression cassette comprises four erythroid-specific enhancers. In certain non-limiting embodiments, the expression cassette comprises five erythroid-specific enhancers.

3.6. Insulators

In accordance with the presently disclosed subject matter, the expression cassette comprises at least one of the above-described insulators. In certain embodiments, a presently disclosed expression cassette comprises at least one insulator comprising the CTCF binding site sequence set forth in SEQ ID NO:18, for example, but not limited to, an insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32 or a fragment thereof. In certain embodiments, a presently disclosed expression cassette comprises at least one insulator comprising or having the nucleotide sequence set forth in SEQ ID NO: 1. In various non-limiting embodiments, the insulator can be incorporated or inserted into one or both LTRs or elsewhere in the region of a presently disclosed expression cassette that integrates into the cellular genome. In certain embodiments, the insulator is positioned at the 3' end of the expression cassette. In certain embodiments, the insulator is positioned at the 5' end of the expression cassette. In certain embodiments, the expression cassette comprises two of the insulator disclosed herein, e.g., an insulator comprising the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, SEQ ID NO: 31, or SEQ ID NO: 32 or a fragment thereof, where one insulator is positioned at the 3' end and the other insulator is positioned at the 5' end of the expression cassette.

The presently disclosed insulators possess powerful enhancer blocking activity. In certain embodiments, the insulators possess barrier activity in addition to enhancer blocking activity. The presently disclosed insulators substantially decrease the risks of insertional mutagenesis and genotoxicity associated with viral vectors. Furthermore, when a presently disclosed insulator is incorporated into a vector, the insulator does not adversely effect vector titers of the vector. In certain embodiments, the insulators increase the in vivo expression of the globin gene or functional portion thereof.

3.7. Exemplary Expression Cassettes

For the purpose of illustration and not limitation, FIGS. 1-4, 13, 14, and 15 show recombinant vectors comprising exemplary expression cassettes in accordance with certain embodiments of the presently disclosed subject matter.

FIG. 1 shows a recombinant vector comprising a presently disclosed expression cassette that comprises a human $\beta^{A-T87Q}$ globin gene, which is operably linked to a β-globin LCR that comprises a 860 bp HS2 region (e.g., one having the nucleotide sequence set forth in SEQ ID NO:9), a 1301 bp HS3 region (e.g., one having the nucleotide sequence set forth in SEQ ID NO:5), and a 1065 bp HS4 region (e.g., one having the nucleotide sequence set forth in SEQ ID NO:7).

FIG. 2 shows one exemplary recombinant vector comprising an expression cassette in accordance with one embodiment of the presently disclosed subject matter. FIG. 2 shows a recombinant vector comprising a presently disclosed expression cassette that comprises a human $\beta^{A-T87Q}$ globin gene, which is operably linked to a β-globin LCR that comprises a 1.1 kb HS1 region (e.g., one having the nucleotide sequence set forth in SEQ ID NO:2), a 1301 bp HS3 region (e.g., one having the nucleotide sequence set forth in SEQ ID NO:5), and a 1065 bp HS4 region (e.g., one having the nucleotide sequence set forth in SEQ ID NO:6).

FIG. 3 shows one exemplary recombinant vector comprising an expression cassette in accordance with one embodiment of the presently disclosed subject matter. FIG. 3 shows a recombinant vector comprising a presently disclosed expression cassette that comprises a human $\beta^{A-T87Q}$ globin gene, which is operably linked to a β-globin LCR that comprises a 602 bp HS1 region (e.g., one having the nucleotide sequence set forth in SEQ ID NO:3), a 1301 bp HS3 region (e.g., one having the nucleotide sequence set forth in SEQ ID NO:5), and a 446 bp HS4 region (e.g., one having the nucleotide sequence set forth in SEQ ID NO:8).

FIG. 4 shows one exemplary recombinant vector comprising an expression cassette in accordance with one embodiment of the presently disclosed subject matter. FIG. 4 shows a recombinant vector comprising a presently disclosed expression cassette that comprises a human $\beta^{A-T87Q}$ globin gene, which is operably linked to a β-globin LCR that comprises a 1301 bp HS3 region (e.g., one having the nucleotide sequence set forth in SEQ ID NO:5), and a 1065 bp HS4 region (e.g., one having the nucleotide sequence set forth in SEQ ID NO:6). The expression cassette shown in FIG. 4 also comprises the following five erythroid-specific enhancers (shown as "EE5" in FIG. 4): one erythroid-specific enhancer having the nucleotide sequence set forth in SEQ ID NO:13, one erythroid-specific enhancer having the nucleotide sequence set forth in SEQ ID NO:14, one erythroid-specific enhancer having the nucleotide sequence set forth in SEQ ID NO:15, one erythroid-specific enhancer having the nucleotide sequence set forth in SEQ ID NO:16, and one erythroid-specific enhancer having the nucleotide sequence set forth in SEQ ID NO:17.

FIG. 13 shows the following five exemplary recombinant vectors: SNS22.2.B87A1, which comprises an expression cassette that comprises a human $\beta^{A-T87Q}$ globin gene, which is operably linked to a β-globin LCR that comprises a 602 bp HS1 region (e.g., one having the nucleotide sequence set forth in SEQ ID NO:3), a 816 bp HS2 region (e.g., one having the nucleotide sequence set forth in SEQ ID NO:33), a 1301 bp HS3 region (e.g., one having the nucleotide sequence set forth in SEQ ID NO:34), and a 754 bp HS4 region (e.g., one having the nucleotide sequence set forth in SEQ ID NO:35);

SNS23.2.B87A1, which comprises an expression cassette that comprises a human $\beta^{A-T87Q}$ globin gene, which is operably linked to a β-globin LCR that comprises a 816 bp HS2 region (e.g., one having the nucleotide sequence set forth in SEQ ID NO:33), a 1301 bp HS3 region (e.g., one having the nucleotide sequence set forth in SEQ ID NO:34), and a 754 bp HS4 region (e.g., one having the nucleotide sequence set forth in SEQ ID NO:35), wherein the β-globin LCR does not comprise a HS1 region;

SNS24.2.B87A1, which comprises an expression cassette that comprises a human $β^{A-T87Q}$ globin gene, which is operably linked to a β-globin LCR that comprises a 602 bp HS1 region (e.g., one having the nucleotide sequence set forth in SEQ ID NO:3), a 1301 bp HS3 region (e.g., one having the nucleotide sequence set forth in SEQ ID NO:34), a 754 bp HS4 region (e.g., one having the nucleotide sequence set forth in SEQ ID NO:35); and an erythroid-specific enhancer having the nucleotide sequence set forth in SEQ ID NO:15, wherein the β-globin LCR does not comprise a HS2 region;

SNS26.B87A1, which comprises an expression cassette that comprises a human $β^{A-T87Q}$ globin gene, and an erythroid-specific enhancer having the nucleotide sequence set forth in SEQ ID NO:15, wherein the expression cassette does not comprise a β-globin LCR; and SNS27.2.B87.A1, which comprises an expression cassette that comprises an insulator comprising the nucleotide sequence set forth in SEQ ID NO: 1, and a human $β^{A-T87Q}$ globin gene that is operably linked to a β-globin LCR comprising a 1301 bp HS3 region (e.g., one having the nucleotide sequence set forth in SEQ ID NO:34), and an erythroid-specific enhancer having the nucleotide sequence set forth in SEQ ID NO:15, wherein the β-globin LCR does not comprise a HS1 region, a HS2 region, or a HS4 region.

FIG. 15 shows five exemplary recombinant vectors including SNS22.B87A1, which comprises an expression cassette that comprises a human $β^{A-T87Q}$ globin gene, which is operably linked to a β-globin LCR that comprises a 602 bp HS1 region (e.g., one having the nucleotide sequence set forth in SEQ ID NO:3), a 816 bp HS2 region (e.g., one having nucleotides 45 to 860 of SEQ ID NO: 9), a 1301 bp HS3 region (e.g., one having the nucleotide sequence set forth in SEQ ID NO:5), and a 754 bp HS4 region (e.g., one having nucleotides 115 to 868 of SEQ ID NO: 6);

SNS23.B87A1, which comprises an expression cassette that comprises a human $β^{A-T87Q}$ globin gene, which is operably linked to a β-globin LCR that comprises a 816 bp HS2 region (e.g., one having nucleotides 45 to 860 of SEQ ID NO: 9), a 1301 bp HS3 region (e.g., one having the nucleotide sequence set forth in SEQ ID NO:5), and a 754 bp HS4 region (e.g., one having nucleotides 115 to 868 of SEQ ID NO: 6); SNS24.B87A1, which comprises an expression cassette that comprises a human $β^{A-T87Q}$ globin gene, which is operably linked to a β-globin LCR that comprises a 602 bp HS1 region (e.g., one having the nucleotide sequence set forth in SEQ ID NO:3), a 1301 bp HS3 region (e.g., one having the nucleotide sequence set forth in SEQ ID NO:5), a 754 bp HS4 region (e.g., one having nucleotides 115 to 868 of SEQ ID NO: 6); and an erythroid-specific enhancer having the nucleotide sequence set forth in SEQ ID NO:15; and SNS26.B87.A1, which is also disclosed in FIG. 13 as described above.

As shown in FIGS. 1-4, 13, and 15, each of the expression cassettes comprises an insulator, wherein the insulator has the nucleotide sequence set forth in SEQ ID NO:1 (i.e., insulator A1). In addition, as shown in FIGS. 1-4, 13, 15, each of the expression cassettes comprises a human β-globin 3' enhancer that is positioned upstream of the human β-globin gene, wherein the human β-globin 3' enhancer has a length of 879 bp and has the nucleotide sequence set forth in SEQ ID NO: 12. Additionally, as shown in FIGS. 13 and 15, each of SNS22.B87.A1, SNS23.B87.A1, SNS24.B87.A1, SNS22.2.B87.A1, SNS23.2.B87.A1, SNS24.2.B87.A1, SNS26.B87.A1, and SNS27.2B87.A1 comprises a 265 bp human β-globin promoter, wherein the human β-globin promoter has the nucleotide sequence set forth in SEQ ID NO: 11. TNS9.B87.A1 shown in FIG. 15 comprises a 613 bp human β-globin promoter, wherein the human β-globin promoter has the nucleotide sequence set forth in SEQ ID NO: 10.

III. Vectors, Nucleases and CRISPR-Cas Systems

The presently disclosed subject matter provides vectors and delivery systems (e.g., a non-naturally occurring or engineered nucleases or a CRISPR-Cas system) comprising the above-described expression cassettes. The vectors and delivery systems are suitable delivery vehicles for the stable introduction of globin gene (e.g., human β-globin) into the genome of a broad range of target cells to increase expression of the globin protein (human β-globin protein) in the cell.

In certain embodiments, the vector is a retroviral vector (e.g., gamma retroviral vector or a lentiviral vector) that is employed for the introduction or transduction of the above-described expression cassette into the genome of a host cell (e.g., a hematopoietic stem cell, an embryonic stem cell, an induced pluripotent stem cell, or a hemogenic endothelium cell). In certain embodiments, the retroviral vector comprises an expression cassette that comprises one of the above-described insulators, e.g., insulator A1. The insulator can be positioned at the 3' or the 5' end of the expression cassette. In certain embodiments, the insulator is positioned at the 3' end of the expression cassette. During reverse transcription and vector integration, the insulator positioned at the 3' end is copied into the 5' end of the expression cassette. The resulting topology places copies of the insulator between the genomic regions located at the 5' LTR and the 3' LTR of the integrated virus and enhancer activity from the 5' LTR and internal package promoter, but does not contain the enhancer in the 3' LTR. This topology can decrease genotoxicity, thereby resulting in decreased tumor formation and increased survival of the animals.

In certain embodiments, the vector is an Adeno-associated virus (AAV) vector. Non-limiting examples of AAV vectors include AAV1, AAV2, AAV3, AAV4, AAV5, AAV6, AAV7, AAV8, AAV9, AAV10, and AAV11. In certain embodiments, the vector is an AAV6 vector.

In certain embodiments, the recombinant vector is a retroviral vector. In certain embodiments, the retroviral vector is a lentiviral vector. In certain embodiments, the recombinant vector is a self-inactivating (SIN) lentiviral vector in which the enhancer and promoter region of the 3' long terminal repeat ("LTR") is modified (e.g., a 133 bp deletion in the U3 region). SIN vectors can infect and integrate into the genome of non-dividing cells in vivo with an efficacy similar to that of wild-type vectors. SIN lentivirus vectors are disclosed in Miyoshi et al., *J. Virol.* (October 1998); 72:8150-8157, which is incorporated by reference in its entirety. SIN vectors can reduce the risk of creating undesired replication-competent virus because there is no complete U3 region in the 3' LTR, thereby eliminating the ability of the virus to be passed (see Miyoshi 1998).

In certain embodiments, the retroviral vector is a gamma-retroviral vector. In certain embodiments, the retroviral vector is a SIN gamma-retroviral vector.

In certain embodiments, the recombinant vector further comprises one or more of a rev-responsive element ("RRE"), a central polypurine tract ("cPPT"), a 5' LTR (in which the U3 region of the 5' LTR comprises a heterologous promoter (e.g., replaced with a cytomegalovirus (CMV) HIV heterologous promoter) resulting in Tat-independent transcription with no decreases in virus titer), and a 3' SIN LTR (e.g., a 3' SIN LTR comprising a 389 bp deletion in the U3 region).

In certain embodiments, the recombinant vector further comprises a Woodchuck hepatitis post-regulatory element (WPRE) in the 3' long terminal repeat (LTR) of the vector (e.g., 3' to the R region in the 3' LTR of the vector). In certain embodiments, the recombinant vector further comprises a bovine growth hormone polyadenylation signal in addition to the WPRE in the 3' long terminal repeat (LTR) of the vector (e.g., 3' to the R region in the 3' LTR of the vector). The WPRE can increase the titer of the recombinant vector (e.g., can increase the vector titer by at least about 5 folds). Addition of a bovine growth hormone ("BGH") polyadenylation ("polyA") signal ("BGH/polyA") to the WPRE can further increase the titer of the recombinant vector. In certain embodiments, the WPRE and BGH/polyA are eliminated after the vector is transfused to target cells, and thus, are not present in the proviruses. In certain embodiments, the WPRE and the BGH/polyA are not comprised within the expression cassette, and thus, not transferred to the cells transduced with the recombinant vector.

As shown in FIGS. 1-4, 13, and 15, the recombinant vector can further comprises a rev-responsive element ("RRE"), a central polypurine tract ("cPPT"), a 5' LTR (in which the U3 region of the 5' LTR comprises a heterologous promoter (e.g., replaced with a cytomegalovirus (CMV) HIV heterologous promoter) resulting in Tat-independent transcription with no decreases in virus titer), a 3' SIN LTR comprising a 389 bp deletion in the U3 region, a WPRE, and a BGH/polyA in the 3' long terminal repeat (LTR) of the vector (e.g., 3' to the R region in the 3' LTR). The heterologous promoter (e.g., a CMV/HIV heterologous promoter) can increase the RNA transcription and the production of the vector. The heterologous promoter (e.g., a CMV/HIV heterologous promoter) is eliminated after reverse transcription, and thus, is not present in the proviruses.

In certain non-limiting embodiments, a presently disclosed expression cassette can be cloned into a retroviral vector and expression can be driven from its endogenous promoter, from the retroviral long terminal repeat, or from an alternative internal promoter. Combinations of retroviral vector and an appropriate packaging line are also suitable, where the capsid proteins will be functional for infecting human cells. Various amphotropic virus-producing cell lines are known, including, but not limited to, PA12 (Miller, et al. (1985) *Mol. Cell. Biol.* 5:431-437); PA317 (Miller, et al. (1986) *Mol. Cell. Biol.* 6:2895-2902); and CRIP (Danos, et al. (1988) *Proc. Natl. Acad. Sci. USA* 85:6460-6464). Non-amphotropic particles are suitable too, e.g., particles pseudo-typed with VSVG, RD114 or GALV envelope and any other known in the art.

Suitable methods of transduction also include direct co-culture of the cells with producer cells, e.g., by the method of Bregni, et al. (1992) *Blood* 80:1418-1422, or culturing with viral supernatant alone or concentrated vector stocks with or without appropriate growth factors and polycations, e.g., by the method of Xu, et al. (1994) *Exp. Hemat.* 22:223-230; and Hughes, et al. (1992) *J. Clin. Invest.* 89:1817.

Transducing viral vectors can be used to express a globin gene (e.g., a human β-globin gene) in a host cell (e.g., hematopoietic stem cells, an embryonic stem cell, or an induced pluripotent stem cell). In certain embodiments, the chosen vector exhibits high efficiency of infection and stable integration and expression (see, e.g., Cayouette et al., Human Gene Therapy (1997); 8:423-430; Kido et al., Current Eye Research (1996); 15:833-844; Bloomer et al., Journal of Virology (1997); 71:6641-6649; Naldini et al., Science (1996); 272:263 267; and Miyoshi et al., Proc. Natl. Acad. Sci. U.S.A. 94:10319, 1997). Other viral vectors that can be used include, for example, adenoviral, lentiviral, and adeno-associated viral vectors, vaccinia virus, a bovine papilloma virus, or a herpes virus, such as Epstein-Barr Virus (also see, for example, the vectors of Miller, *Human Gene Therapy* (1990); 15-14; Friedman, *Science* (1989); 244:1275-1281; Eglitis et al., *BioTechniques* 6:608-614, 1988; Tolstoshev et al., *Current Opinion in Biotechnology* (1990); 1:55-61; Sharp, *The Lancet* (1991); 337: 1277-1278; Cornetta et al., *Nucleic Acid Research and Molecular Biology* (1987) 36:311-322; Anderson, *Science* (1984); 226:401-409; Moen, *Blood Cells* (1991); 17:407-416; Miller et al., *Biotechnology* (1989); 7:980-990; Le Gal La Salle et al., *Science* (1993); 259:988-990; and Johnson, *Chest* (1995); 107:775-83S). Retroviral vectors are particularly well developed and have been used in clinical settings (Rosenberg et al., *N. Engl. J. Med* (1990); 323:370; Anderson et al., U.S. Pat. No. 5,399,346).

The requirement for efficient delivery and integration make retroviral vectors suitable for transducing a presently disclosed expression cassette. Retroviral vectors can be derived from three genera of the retroviridae: the γ-retroviruses (also known as C-type murine retroviruses or oncoretroviruses), the lentiviruses, and the spumaviruses (also known as foamy viruses). Several reviews detailing molecular approaches for the generation of replication-defective retroviral particles are available (Cornetta et al. (2005); Cockrell & Kafri (2007)). The vector itself, which encodes the therapeutic transgene or cDNA, retains the minimal viral sequences needed to enable packaging in viral particles in a packaging cell line, reverse transcription, and integration. The packaging cell expresses the necessary structural proteins and enzymes that are required to assemble an infectious recombinant particle that contains the vector sequence and the machinery needed for its reverse transcription and integration in the transduced cell.

While the manufacturing aspects of all retroviral vector types follow the same general principles, γ-retroviral, lentiviral and spumaviral vectors differ in some of their intrinsic biological properties. Gamma-retroviruses, including the prototypic murine leukaemia viruses (MLV), effectively infect many cell types but are unable to integrate in cells that do not proceed to S phase soon after infection. In contrast, lentiviruses and their vector derivatives can transduce non-dividing cells (Follenzi & Naldini, 2002; Salmon & Trono, 2002) owing to their ability to translocate to the nucleus and integrate in the absence of cell division (Lewis & Emerman, 1994; Goff, 2001). Another fundamental attribute of lentiviral vectors is their relative genomic stability, as established for globin lentiviral vectors (May et al., 2000), which contrasts with the genomic instability of MLV-based globin vectors (Leboulch et al., 1994; Sadelain et al., 1995). Lentiviral and foamy vectors further provide a greater packaging capacity (Kumar et al., 2001; Rethwilm, 2007). All three vector types have been used successfully for the transduction of cytokineactivated HSCs (Miyoshi et al., 1999; Josephson et al., 2002; Leurs et al., 2003).

These three vector systems differ in their integration patterns. The integration pattern of retroviruses is semi-random and biased towards genes and their vicinity in approximately two-thirds of all integration events (Schroder et al., 2002; Wu et al., 2003; Mitchell et al., 2004; De Palma et al., 2005; Trobridge et al., 2006). There are however subtle and possibly significant differences in their exact distribution. Gamma-retroviruses have a propensity to integrate upstream of transcribed genes, whereas lentiviruses and lentiviral vectors target the entire transcribed gene sequence. Foamy vectors appear to be less prone to intragenic integration (Trobridge et al., 2006). In certain embodiments, the vector comprising the expression cassette is a lentivirus vector. The vectors can be derived from human immunodeficiency-1 (HIV-1), human immunodeficiency-2 (HIV-2), simian immunodeficiency virus (SIV), feline immunodeficiency virus (Hy), bovine immunodeficiency virus (BIV), Jembrana Disease Virus (JDV), equine infectious anemia virus (EIAV), caprine arthritis encephalitis virus (CAEV) and the like. In one non-limiting embodiment, the lentiviral vector is an HIV vector. HIV-based constructs are the most efficient at transduction of human cells.

The semi-random pattern of vector integration exposes patients to the risk of insertional oncogenesis when the vector trans-activates a neighboring oncogene. This may result in clonal expansion (Ott et al, 2006; Cavazzana-Calvo et al, 2010), myelodysplasia (Stein et al, 2010) or leukaemia (Hacein-Bey-Abina et al, 2003, 2008; Howe et al, 2008). Targeted gene delivery strategies, utilizing a non-naturally occurring or engineered nuclease (including, but not limited to, Zinc-finger nuclease (ZNFs), meganuclease, transcription activator-like effector nuclease (TALEN)), or a CRISPR-Cas system, can reduce or even eliminate the concern of insertional oncogenesis that is inherent to the use of retroviral vectors.

Eukaryotic cells utilize two distinct DNA repair mechanisms in response to DNA double strand breaks (DSBs): Homologous recombination (HR) and non-homologous end-joining (NHEJ). The activation of the HR repair machinery depends on the cell cycle status, and it is restricted to the S and G2 phases; in contrast, the NHEJ pathway is active throughout the cell cycle. Mechanistically, HR is an error-free DNA repair mechanism, because it requires a homologous template to repair the damaged DNA strand. On the other hand, NHEJ is a template-independent repair mechanism that is imprecise, due to DNA end processing during repair that leads to insertions or deletions at the DNA break site (Moynahan & Jasin, 2010). Because of its homology-based mechanism, HR has been used as a tool to site-specifically engineer the genome of different species. From a therapeutic perspective, HR has been successfully used to repair mutated genes, thus offering a promising approach to cell-mediated treatment of monogenic diseases (Porteus et al, 2006).

Gene targeting by HR requires the use of two homology arms that flank the transgene/target site of interest. Generally, standard plasmid DNAs have been used to deliver 5-10 kb homology arms along with transgenes for positive and negative selection. This method is commonly used to knock-out/knockin genes in mouse embryonic stem (mES) cells (Capecchi, 2005; FIG. 2B). In human cells, the use of this approach has allowed gene targeting with efficiencies in the order of $10^{-6}$, which are lower than in mES cells and are not therapeutically practical. HR efficiency can be increased by the introduction of DNA-doubled stranded breaks (DSBs) at the target site using specific rare-cutting endonucleases, resulting in over 1,000-fold increase in correct gene targeting (Jasin, 1996). The discovery of this phenomenon prompted the development of methods to create site-specific DSBs in the genome of different species. Various chimeric enzymes have been designed for this purpose over the last decade, namely zinc-finger nucleases (ZFNs), meganucleases, and transcription activator-like effector nucleases (TALENs).

ZFNs are modular chimeric proteins that contain a ZF-based DNA binding domain (DBD) and a FokI nuclease domain (Porteus & Carroll, 2005). DBD is usually composed of three ZF domains, each with 3-base pair specificity; the FokI nuclease domain provides a DNA nicking activity, which is targeted by two flanking ZFNs. Owing to the modular nature of the DBD, any site in a genome could be targeted in principle. However, as a single ZFN can bind and nick DNA, there is potential for a high number of off-target effects, resulting in the activation of the NHEJ pathway that may either introduce insertions/deletions or integrate the targeting vector in a non-specific manner. Obligate FokI domains that can nick their respective DNA strand only when they form a heterodimer were recently reported (Doyon et al, 2011). The use of such obligate ZFNs can reduce the genotoxic effects of this approach.

Meganucleases (MNs)/homing endonucleases (HEs) are dsDNA nucleases that recognize and cleave large DNA sites (14-40 bp) with low cleavage frequencies in eukaryotic genomes (Paques & Duchateau, 2007). Although this limits the potential target sites, MN-DNA structures have been used as a guide to specifically modify DNA-interacting residues in order to change the MN specificity (Marcaida et al, 2010). I-CreI has been successfully engineered to generate chimeric meganucleases that target the human XPC and RAG1 genes, and they have been shown to stimulate HR activity in mammalian cells with no evident genotoxicity (Redondo et al, 2008; Grizot et al, 2009). The genotoxicity of this approach will need to be compared to that of ZFNs and TALE nucleases.

TALENs are similar ZFN except that the DBD is derived from transcription activator-like effcetors (TALEs), which are virulent factors used by phytopathogenic bacteria (Herbers, 1992). The TALE DBD is modular, and it is composed of 34-residue repeats, and its DNA specificity is determined by the number and order of repeats (Herbers, 1992). Each repeat binds a single nucleotide in the target sequence through only two residues (Boch, 2011). The advantage over ZFN technology is the rapid construction of DBDs.

A number of studies have used these chimeric enzymes to stimulate HR for either gene addition or gene repair at their target site (Paques & Duchateau, 2007; Urnov et al, 2010). Porteus designed a ZFN to a half site sequence from the human HBB that surrounds the sickle cell mutation nucleotide (Porteus, 2006). This ZFN targets the sequence and stimulates HR at a chimeric DNA target when combined with a ZFN targeting the Zif268 binding site. There have been recent advances in targeting genes in cord blood CD34+ cells. Use of non-integrating lentiviruses to deliver ZFNs and the donor DNA in these cells to target the CCR5 gene was reported in Lombardo et al, 2007. Lombardo et al, 2007 showed gene addition at this locus with correct targeting in 80% of the positively selected cells.

The presently disclosed subject matter provides a non-naturally occurring or engineered nuclease comprising a presently disclosed expression cassette, as described above. Suitable nucleases include, but are not limited to, ZFNs, meganucleases, and TALENs. A presently disclosed nuclease comprises a DNA binding domain and a nuclease cleavage domain. The DNA binding domain of the nuclease can be engineered to bind to a sequence of choice, e.g., a predetermined site. An engineered DNA binding domain can have a distinct binding specificity, compared to a naturally occurring nuclease. Engineering methods include, but are not limited to, rational design and various types of selection. Any suitable cleavage domain can be operatively linked to a DNA-binding domain to form a nuclease. For example, Zinc-finger protein (ZFP) DNA-binding domains can be fused to nuclease cleavage domains to create ZFNs—a functional entity that is able to recognize its intended nucleic acid target through its engineered ZFP DNA binding domain and cause the DNA to be cut near the ZFP binding site via the nuclease activity. See, e.g., Kim et al. *Proc Nat'l Acad Sci USA* (1996); 93(3):1156-1160. Likewise, TALE DNA-binding domains can be fused to nuclease cleavage domains to create TALENs. See, e.g., U.S. Publication No. 20110301073.

The cleavage domain can be heterologous to the DNA-binding domain, e.g., a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalog, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional regions thereof) can be used as a source of cleavage domains and cleavage half-domains.

Similarly, a cleavage half-domain can be derived from the above-described nuclease that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional portions thereof), or each cleavage half-domain can be derived from a different endonuclease (or functional portions thereof).

In certain embodiments, the nuclease comprises an expression cassette that comprises two of the insulators disclosed herein, e.g., two of the insulator having the nucleotide sequence set forth in SEQ ID NO: 1, SEQ ID NO: 24, SEQ ID NO: 25, SEQ ID NO: 27, SEQ ID NO: 28, SEQ ID NO: 29, SEQ ID NO: 30, or SEQ ID NO: 31. One of the two insulators is positioned at the 3' end of the expression cassette, and the other insulator is positioned at the 5' end of the expression cassette.

The presently disclosed subject matter also provides a non-naturally occurring or engineer CRISPR-Cas system comprising the above-described expression cassette. The CRISPR (Clustered Regularly Interspaced Short Palindromic Repeats)-Cas (CRISPR Associated) system is an engineered nuclease system based on a bacterial system that can be used for genome engineering. It is based on part of the adaptive immune response of many bacteria and archea. When a virus or plasmid invades a bacterium, segments of the invader's DNA are converted into CRISPR RNAs (crRNA) by the "immune" response. The crRNA then associates, through a region of partial complementarity, with another type of RNA called tracrRNA to guide a CRISPR-Cas nuclease to a region homologous to the crRNA in the target DNA called a "proto spacer". The CRISPR-Cas nuclease cleaves the DNA to generate blunt ends at the DSB at sites specified by a 20-nucleotide guide sequence contained within the crRNA transcript. The CRISPR-Cas nuclease requires both the crRNA and the tracrRNA for site specific DNA recognition and cleavage. This system has been engineered such that the crRNA and tracrRNA can be combined into one molecule (the "single guide RNA"); and the crRNA equivalent portion of the single guide RNA can be engineered to guide the CRISPR-Cas nuclease to target any desired sequence (see Jinek et al., *Science* (2012); 337:816-821). Thus, the CRISPR-Cas system can be engineered to create a DSB at a desired target in a genome. In certain embodiments, the CRISPR-Cas system comprises a CRISPR-Cas nuclease and a single-guide RNA. Suitable examples of CRISPR-Cas nucleases include, but are not limited to, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These CRISPR-Cas nucleases are known; for example, the amino acid sequence of *S. pyogenes* Cas9 protein may be found in the SwissProt database under accession number Q99ZW2. In some embodiments, the CRISPR-Cas nuclease has DNA cleavage activity, e.g., Cas9. In certain embodiments, the CRISPR-Cas nuclease is Cas9. The CRISPR-Cas nuclease can direct cleavage of one or both strands at the location of a target sequence (e.g., a genomic safe harbor site). Additionally, the CRISPR-Cas nuclease can direct cleavage of one or both strands within about 1, 2, 3, 4, 5, 6, 7, 8, 9, 10, 15, 20, 25, 50, 100, 200, 500, or more base pairs from the first or last nucleotide of a target sequence.

The presently disclosed nucleases and CRISPR-Cas system allow for targeted delivery of the expression cassette. In certain embodiments, a presently disclosed CRISPR-Cas system or the DNA binding domain of a presently disclosed nuclease binds to a genomic safe harbor site. A nuclease or the CRISPR-Cas system generates a double strand break at the genomic safe harbor site. Genomic safe harbor sites are intragenic or extragenic regions of the human genome that are able to accommodate the predictable expression of newly integrated DNA without adverse effects on the host cell or organism. A useful safe harbor must permit sufficient transgene expression to yield desired levels of the vector-encoded protein or non-coding RNA. A genomic safe harbor site also must not predispose cells to malignant transformation nor alter cellular functions. Methods for identifying genomic safe harbor sites are described in Sadelain et al., "Safe Harbours for the integration of new DNA in the human genome," Nature Reviews (2012); 12:51-58; Papapetrou et al., "Genomic safe harbors permit high β-globin transgene expression in thalassemia induced pluripotent stem cells" *Nat Biotechnol.* (2011) January; 29(1):73-8, which are incorporated by reference in their entireties. A presently disclosed genomic safe harbor site meets one or more (one, two, three, four, or five) of the following five criteria: (1) distance of at least 50 kb from the 5' end of any gene (e.g., from the 5' end of the gene), (ii) distance of at least 300 kb from any cancer-related gene, (iii) within an open/accessible chromatin structure (measured by DNA cleavage with natural or engineered nucleases), (iv) location outside a gene transcription unit and (v) location outside ultraconserved regions (UCRs), microRNA or long non-coding RNA of the human genome. As the most common insertional oncogenesis event is transactivation of neighboring tumor-promoting genes, the first two criteria exclude the portion of the human genome located near promoters of genes, in particular, cancer-related genes, which are genes functionally implicated in human cancers or the human homologs of genes implicated in cancer in model organisms. Proximity to miRNA genes is one exclusion criterion because miRNAs are implicated in the regulation of many cellular processes, including cell proliferation and differentiation. As vector integration within a transcription unit can disrupt gene function through the loss of function of a tumor suppressor gene or the generation of an aberrantly spliced gene product, the fourth (iv) criterion excludes all sites located inside transcribed genes. UCRs, which are regions that are highly conserved over multiple vertebrates and known to be enriched for enhancers and exons, and long non-coding RNAs, are also excluded. In certain embodiments, the genomic safe harbor site is an extragenic genomic safe harbor site. In certain embodiments, the genomic safe harbor site is located on chromosome 1.

The presently disclosed subject matter also provides polynucleotides encoding the above-described nucleases, vectors comprising the polynucleotides encoding the above-described nucleases, polynucleotides encoding the above-described CRISPR-Cas system, and vectors comprising the polynucleotides encoding the above-described CRISPR-Cas system.

The nucleases and polynucleotides encoding these nucleases, and the CRISPR-Cas system and polynucleotides encoding the CRISPR-Cas system can be delivered in vivo or ex vivo by any suitable means. For example, nucleases and CRISPR-Cas system as described herein can be delivered to a cell (e.g., a hematopoietic stem cell, an embryonic stem cell, an induced pluripotent stem cell, or an hemogenic endothelium cell) by a vector comprising polynucleotides encoding the nuclease or the CRISPR-Cas system. Any vectors can be used including, but not limited to, plasmid vectors, retroviral vectors (e.g., γ-retroviral vectors, lentiviral vectors and foamy viral vectors), adenovirus vectors, poxvirus vectors; herpes virus vectors and adena-associated virus vectors, etc. In certain embodiments, the vector comprising a polynucleotide encoding an above-described nuclease or an above-described CRISPR-Cas system is a lentiviral vector. In one particular embodiment, the lentiviral vector is a non-integrating lentiviral vector. Examples of non-integrating lentiviral vector are described in Ory et al. (1996) *Proc. Natl. Acad. Sci. USA* 93:11382-11388; Dull et al., (1998) *J. Virol.* 72:8463-8471; Zuffery et al. (1998) *J. Virol.* 72:9873-9880; Follenzi et al., (2000) *Nature Genetics* 25:217-222; U.S. Patent Publication No 2009/054985.

Additionally, non-viral approaches (e.g., single-stranded DNA) can also be employed for the expression of a globin gene in cells. For example, a nucleic acid molecule can be introduced into a cell by administering the nucleic acid in the presence of lipofection (Feigner et al., *Proc. Natl. Acad. Sci. U.S.A.* 84:7413, 1987; Ono et al., *Neuroscience Letters* 17:259, 1990; Brigham et al., *Am. J. Med. Sci.* 298:278, 1989; Staubinger et al., *Methods in Enzymology* 101:512, 1983), asialoorosomucoid-polylysine conjugation (Wu et al., Journal of Biological Chemistry 263:14621, 1988; Wu et al., *Journal of Biological Chemistry* 264:16985, 1989), or by micro-injection under surgical conditions (Wolff et al., Science 247:1465, 1990). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases. Transient expression may be obtained by RNA electroporation.

IV. Cells

Genetic modification of cells (e.g., hematopoietic stem cells, embryonic stem cells, induced pluripotent stem cells, and hemogenic endothelium cells) can be accomplished by transducing a substantially homogeneous cell composition with a recombinant DNA or RNA construct (e.g., a vector or a delivery system comprising the above-described expression cassette). The presently disclosed subject matter provides cells transduced with the above-described expression cassettes, cells transduced with the above-described vectors, and cells transduced with the above-described nucleases or with vectors comprising polynucleotides encoding the nucleases, and cell transduced with the above-described CARISPR-Cas system or with vectors comprising polynucleotides encoding the CARISPR-Cas system, which are collectively referred to as "transduced cells". As described above, the vectors, nucleases and CRISPR-Cas system are employed for transduction of the expression cassette to the cells to express a globin gene (e.g., a human β-globin gene). In certain embodiments, the transduced cells are administered to a subject to treat and/or prevent a hematopoietic disease, disorder, or condition. The presently disclosed insulators can enhance the efficiency of the transduction of the expression cassette to cells.

Suitable transduced cells include, but are not limited to, stem cells, progenitor cells, and differentiated cells. As used herein, the term "progenitor" or "progenitor cells" refers to cells that have the capacity to self-renew and to differentiate into more mature cells. Progenitor cells have a reduced potency compared to pluripotent and multipotent stem cells. Many progenitor cells differentiate along a single lineage, but may also have quite extensive proliferative capacity.

In certain embodiments, the transduced cells are stem cells. Stem cells have the ability to differentiate into the appropriate cell types when administered to a particular biological niche, in vivo. A stem cell is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. Stem cells are subclassified according to their developmental potential as totipotent, pluripotent, multipotent and oligo/unipotent. As used herein, the term "pluripotent" means the ability of a cell to form all lineages of the body or soma (i.e., the embryo proper). For example, embryonic stem cells are a type of pluripotent stem cells that are able to form cells from each of the three germs layers, the ectoderm, the mesoderm, and the endoderm. As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

In certain embodiments, the transduced cells are embryonic stem cells, bone marrow stem cells, umbilical cord stem cells, placental stem cells, mesenchymal stem cells, neural stem cells, liver stem cells, pancreatic stem cells, cardiac stem cells, kidney stem cells, and/or hematopoietic stem cells. In certain embodiments, the transduced cells are hematopoietic stem cells (HSCs). HSCs give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to all blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells). When transplanted into lethally irradiated animals or humans, hematopoietic stem and progenitor cells can repopulate the erythroid, neutrophil-macrophage, megakaryocyte and lymphoid hematopoietic cell pool.

HSCs can be isolated or collected from bone marrow, umbilical cord blood, or peripheral blood. HSCs can be identified according to certain phenotypic or genotypic markers. For example, HSCs can be identified by their small size, lack of lineage (lin) markers, low staining (side population) with vital dyes such as rhodamine 123 (rhodamineDULL, also called rholo) or Hoechst 33342, and presence of various antigenic markers on their surface, many of which belong to the cluster of differentiation series (e.g., CD34, CD38, CD90, CD133, CD105, CD45, Ter1 19, and c-kit, the receptor for stem cell factor). In certain embodiments, the transduced cell is a CD34$^+$ HSC.

In certain embodiments, the transduced cell is an embryonic stem cell. In certain embodiments, the transduced cell is an induced pluripotent stem cell. In certain embodiments, the transduced cell is a hemogenic endothelium cell.

While HSCs are the natural vehicle for restoring long-term hematopoiesis, their use has some important limitations. The first is their relative scarcity, which can eventually preclude autologous HSC therapy when the harvested cellular product is too small. The second is the difficulty to perform biosafety testing such as integration site analysis and consequently to select cells with chosen integration sites, because adult HSCs cannot be replicated in vitro. The third limitation is that homologous recombination using current technologies is practically impossible thus compromising the advent of gene correction. All of these limitations are ultimately due to the fact that adult HSCs cannot be expanded in vitro without losing their stem cell potency. These limitations explain the importance of viral vectors such as gamma-retroviral and lentiviral vectors, which are remarkably quick and efficient in achieving stable gene transfer.

Use of ESs and induced pluripotent stem (iPS) cells for globin gene therapy is disclosed in Moi et al., *Haematol* Mar. 1, 2008; 93(3):325-330. Embryonic stem (ES) cells are amenable to gene targeting and correction, which requires unlimited in vitro cell division without losing multipotency. Chang et al., *Proc Natl Acad Sci USA* 2006; 103:1036-40 provided proof of principle of the feasibility of the homologous recombination approach in mice with sickle cell anemia. Takahashi et al. *Cell* 2006; 126:663-76 reported the successful reprogramming of fibroblasts to an embryonic stem-like state. Cells obtained by this reverse-differentiation process, called induced pluripotent stem (iPS) cells, were produced by exposing embryonic or young adult bulk fibroblast cultures to gamma-retroviral vectors encoding 4 transcription factors, which are physiologically active in the embryonic stem cells, but generally turned off when differentiation progresses. The cultured cells formed colonies similar to ES cell colonies. These findings have been confirmed and extended by others to both mouse and human fibroblasts (Meissner et al., Nat Biotechnol 2007; 25:1177-81; Nakagawa et al., Nat Biotechnol 2007; 26:101-6; Okita et al., Nature 2007; 448:313-7; Park et al., Nature 2007; 451:141-6; Takahashi et al., Nat Protoc 2007; 2:3081-9; Takahashi K et al., *Cell* 2007; 131:861-72; Wernig et al., Nature 2007; 448:318-24; Yu J et al., Science 2007; 318: 1917-20). Rudolf Jaenisch and co-workers achieved a successful gene therapy in a mouse model of sickle cell disease, using homologous recombination in ES-like iPS cells (Hanna et al., Science 2007; 318:1920-3). The process has so far been mostly applied to fibroblast harvested from a skin biopsy, which are then induced to become iPS by transduction with retroviral vectors that encode four stem cell transcription factors. iPS are amenable to the correction of the SC mutation by standard homologous recombination techniques and can then be differentiated in vitro into unlimited amounts of hematopoietic stem cells. The whole process ends with the autologous transplantation of the corrected HSC into the original mouse donor, which will now be cured of its SC disease. This technique is not only useful for homologous recombination, but can also enhance lentiviral-mediated globin gene transfer for the treatment of β-thalassemia by providing a means to perform detailed integration site analysis and adequate in vitro cell expansion before infusing cells into the recipient.

The cell of the presently disclosed subject matter can be autologous ("self") or non-autologous ("non-self," e.g., allogeneic, syngeneic or xenogeneic). As used herein, "autologous" refers to cells from the same subject. As used herein, "allogeneic" refers to cells of the same species that differ genetically to the cell in comparison. As used herein, "syngeneic" refers to cells of a different subject that are genetically identical to the cell in comparison. As used herein, "xenogeneic" refers to cells of a different species to the cell in comparison. In certain embodiments, the cell is autologous, e.g., a cell transduced with the presently disclosed expression cassette is administered to a subject from whom the cell is collected, e.g., the cell is collected from bone marrow, umbilical cord blood, peripheral blood, and/or adipose tissue of the subject. In certain embodiments, the cell is obtained or collected from bone marrow of a subject.

In certain embodiments, prior to transduction with the expression cassette, the cell is pre-stimulated, e.g., in the presence of one or more cytokines (e.g., IL-3, IL-1α, IL-6, Kit ligand (also known as "Stem Cell Factor (SCF)"), and Flt-3 ligand), and/or one or more glycoproteins (e.g., thrombopoietin and fibronectin). In certain embodiments, the cell is pre-stimulated in the presence of Flt-3 ligand, SCF, thrombopoietin, interleukin-3, and fibronectin. The cell can be pre-stimulated for about 24 hours or longer, e.g., about 48 hours, or about 36 hours. Subsequently, the cell is transduced with a presently disclosed expression cassette, or a vector or another delivery system comprising such expression cassette. Transduction can be performed on a fresh cell, or on a frozen cell. Genomic DNA of the cell is isolated to determine the vector copy number and analyze the integration site or integrated vector structure, e.g., by South blot analysis and/or by Quantitative PCR. For quantification of globin mRNA (e.g., human β-globin transgene analysis), total RNA is extracted from the cell. Quantitative primer extension assay can be used for quantification of globin mRNA.

V. Compositions and Formulations

The presently disclosed subject matter provides pharmaceutical compositions comprising a presently disclosed transduced cell as described above and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible, including pharmaceutically acceptable cell culture media. The pharmaceutically acceptable carrier can be suitable for parenteral (e.g., intravenous, intramuscular, subcutaneous, or intraperitoneal), spinal or epidermal administration (e.g., by injection, infusion or implantation). Depending on the route of administration, the active compound, e.g., the transduced cell, may be coated in a material to protect the compound from the action of acids and other natural conditions that may inactivate the compound.

Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the transduced cells, use thereof in the pharmaceutical compositions of the invention is contemplated.

The pharmaceutical compositions of the presently disclosed subject matter can further comprise one or more polypeptides, polynucleotides, vectors comprising the same, transduced cells, etc., as described herein, formulated in pharmaceutically-acceptable or physiologically-acceptable solutions for administration to a cell or an animal, either alone, or in combination with one or more other modalities of therapy. If desired, the pharmaceutical compositions of the presently disclosed subject matter can be administered in combination with other agents, including, but not limited to, cytokines, growth factors, hormones, small molecules or various pharmaceutically-active agents. Any additional agents that do not adversely affect the ability of the composition to deliver the intended gene therapy can be included in the compositions.

In the pharmaceutical compositions of the presently disclosed subject matter, formulation of pharmaceutically-acceptable excipients and carrier solutions is well known to those of ordinary skill in the art, as is the development of suitable dosing and treatment regimens for using the particular compositions described herein in a variety of treatment regimens, including, e.g., oral, parenteral, intravenous, intranasal, and intramuscular administration and formulation.

The pharmaceutical compositions of the presently disclosed subject matter can be delivered parenterally (e.g., intravenously, intramuscularly, or intraperitoneally) as described, for example, in U.S. Pat. Nos. 5,543,158; 5,641,515 and 5,399,363. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

The pharmaceutical compositions of the presently disclosed subject matter can be conveniently provided as sterile liquid preparations, e.g., isotonic aqueous solutions, suspensions, emulsions, dispersions, or viscous compositions, which can be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Sterile injectable solutions can be prepared by incorporating the compositions of the presently disclosed subject matter in the required amount of the appropriate solvent with various amounts of the other ingredients, as desired. Such compositions may be in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, alum inurn monostearate and gelatin.

The compositions can be isotonic, i.e., they can have the same osmotic pressure as blood and lacrimal fluid. The desired isotonicity of the compositions of the presently disclosed subject matter can be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

For parenteral administration in an aqueous solution, for example, the solution should be suitably buffered if necessary and the liquid diluent first rendered isotonic with sufficient saline or glucose. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

In certain embodiments, the compositions can be delivered by intranasal sprays, inhalation, and/or other aerosol delivery vehicles. Methods for delivering genes, polynucleotides, and peptide compositions directly to the lungs via nasal aerosol sprays are described, e.g., in U.S. Pat. Nos. 5,756,353 and 5,804,212. Methods of delivering drugs using lysophosphatidyl-glycerol compounds are described, e.g., in U.S. Pat. No. 5,725,871. Transmucosal drug delivery in the form of a polytetrafluoroetheylene support matrix is described, e.g., in U.S. Pat. No. 5,780,045. The compositions of the presently disclosed subject matter can be formulated for delivery either encapsulated in a lipid particle, a liposome, a vesicle, a nanosphere, a nanoparticle or the like. The formulation and use of such delivery vehicles can be carried out using known and conventional techniques. The formulations and compositions of the presently disclosed subject matter can comprise one or more repressors and/or activators comprising a combination of any number of polypeptides, polynucleotides, and small molecules, as described herein, formulated in pharmaceutically-acceptable or physiologically-acceptable solutions (e.g., culture medium) for administration to a cell or an animal, either alone, or in combination with one or more other modalities of therapy.

In certain aspects, the presently disclosed subject matter provides formulations or compositions suitable for the delivery of viral vector systems (i.e., viral-mediated transduction) including, but not limited to, retroviral (e.g., lentiviral) vectors. Exemplary formulations for ex vivo delivery can also include the use of various transfection agents known in the art, such as calcium phosphate, electoporation, heat shock and various liposome formulations (i.e., lipid-mediated transfection). Liposomes are lipid bilayers entrapping a fraction of aqueous fluid. DNA spontaneously associates to the external surface of cationic liposomes (by virtue of its charge) and these liposomes will interact with the cell membrane.

The skilled artisan can readily determine the amount of cells and optional additives, vehicles, and/or carrier in compositions and to be administered in methods of the presently disclosed subject matter. Typically, any additives (in addition to the transduced cell(s) and/or agent(s)) are present in an amount of from about 0.001% to about 50% by weight) solution in phosphate buffered saline, and the active ingredient is present in the order of micrograms to milligrams, such as from about 0.0001 wt % to about 5 wt %, from about 0.0001 wt % to about 1 wt %, from about 0.0001 wt % to about 0.05 wt %, from about 0.001 wt % to about 20 wt %, from about 0.01 wt % to about 10 wt %, or from about 0.05 wt % to about 5 wt %. For any composition to be administered to an animal or human, and for any particular method of administration, toxicity should be determined, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

VI. Uses and Methods

Vectors and other delivery systems (nucleases and CRISPR-Cas systems) comprising the presently disclosed expression cassette provide improved methods of gene therapy. As used herein, the term "gene therapy" refers to the introduction of a polynucleotide into a cell's genome that restores, corrects, or modifies the gene and/or expression of the gene. In various non-limiting embodiments, a presently disclosed vector or other delivery system (e.g., a nuclease or a CRISPR-Cas system) comprises an expression cassette comprising a globin gene or a functional portion thereof that encodes a globin protein (e.g., human β globin protein), which provides curative, preventative, or ameliorative benefits to a subject diagnosed with or that is suspected of having a disease, disorder, or condition of the hematopoietic system. The vector or other delivery systems (e.g., a nuclease and the CRISPR-Cas system) can infect and transduce the cell in vivo, ex vivo, or in vitro. In ex vivo and in vitro embodiments, the transduced cells can then be administered to a subject in need of therapy. The presently disclosed subject matter contemplates that the vectors and other delivery systems (e.g., nucleases or CRISPR-Cas systems), viral particles, and transduced cells of the presently disclosed subject matter are be used to treat, prevent, and/or ameliorate a disease, disorder, or condition of the hematopoietic system in a subject, e.g., a hemoglobinopathy.

As used herein, the term "hemoglobinopathy" or "hemoglobinopathic condition" includes any disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. Also included are hemoglobinopathies in which a combination of abnormal hemoglobins are present in the blood (e.g., sickle cell/Hb-C disease).

As used herein, "thalassemia" refers to a hereditary disorder characterized by defective production of hemoglobin. Examples of thalassemias include α- and β-thalassemia. β-thalassemias are caused by a mutation in the beta globin chain, and can occur in a major or minor form. In the major form of β-thalassemia, children are normal at birth, but develop anemia during the first year of life. The mild form of β-thalassemia produces small red blood cells and the thalassemias are caused by deletion of a gene or genes from the globin chain. α-thalassemia typically results from deletions involving the HBA1 and HBA2 genes. Both of these genes encode α-globin, which is a component (subunit) of hemoglobin. There are two copies of the HBA1 gene and two copies of the HBA2 gene in each cellular genome. As a result, there are four alleles that produce α-globin. The different types of a thalassemia result from the loss of some or all of these alleles. Hb Bart syndrome, the most severe form of a thalassemia, results from the loss of all four α-globin alleles. HbH disease is caused by a loss of three of the four [alpha]-globin alleles. In these two conditions, a shortage of [alpha]-globin prevents cells from making normal hemoglobin. Instead, cells produce abnormal forms of hemoglobin called hemoglobin Bart (Hb Bart) or hemoglobin H (HbH). These abnormal hemoglobin molecules cannot effectively carry oxygen to the body's tissues. The substitution of Hb Bart or HbH for normal hemoglobin causes anemia and the other serious health problems associated with a thalassemia.

As used herein, the term "sickle cell disease" refers to a group of autosomal recessive genetic blood disorders, which results from mutations in a globin gene and which is characterized by red blood cells that assume an abnormal, rigid, sickle shape. They are defined by the presence of $\beta^S$-gene coding for a β-globin chain variant in which glutamic acid is substituted by valine at amino acid position 6 of the peptide, and second β-gene that has a mutation that allows for the crystallization of HbS leading to a clinical phenotype. As used herein, the term "sickle cell anemia" refers to a specific form of sickle cell disease in patients who are homozygous for the mutation that causes HbS. Other common forms of sickle cell disease include HbS/β-thalassemia, HbS/HbC and HbS/HbD.

In certain embodiments, gene therapy methods of the presently disclosed subject mater are used to treat, prevent, or ameliorate a hemoglobinopathy that is selected from the group consisting of: hemoglobin C disease, hemoglobin sickle cell disease (SCD), sickle cell anemia, hereditary anemia, thalassemia, β-thalassemia, thalassemia major, thalassemia intermedia, α-thalassemia, and hemoglobin H disease. In certain embodiments, the hemoglobinopathy is β-thalassemia. In certain embodiments, the hemoglobinopathy is sickle cell anemia In various non-limiting embodiments, vectors or other delivery systems (e.g., nucleases or CRISPR-Cas systems) comprising a presently disclosed expression cassette are administered by direct injection to a cell, tissue, or organ of a subject in need of gene therapy, in vivo. In certain embodiments, cells are transduced in vitro or ex vivo with vectors or other delivery systems (e.g., nucleases or CRISPR-Cas systems) of the presently disclosed subject matter, and optionally expanded ex vivo. The transduced cells are then administered to a subject in need of gene therapy, e.g., within a pharmaceutical formulation disclosed herein.

The presently disclosed subject matter provides a method of providing a transduced cell to a subject. In various non-limiting embodiments, the method comprises administering (e.g., parenterally) one or more cells (a population of cells) transduced with a presently disclosed expression cassette or a vector or another delivery system (e.g., a nuclease or CRISPR-Cas system) comprising such expression cassette to the subject.

The presently disclosed subject matter provides a method of treating a hemoglobinopathy in a subject. In various non-limiting embodiments, the method comprises administering an effective amount of a presently disclosed transduced cell or a population of the presently disclosed transduced cells (e.g., HSCs, embryonic stem cells, or iPSCs) to the subject.

For treatment, the amount administered is an amount effective in producing the desired effect. An effective amount can be provided in one or a series of administrations. An effective amount can be provided in a bolus or by continuous perfusion. An "effective amount" (or "therapeutically effective amount") is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

In certain embodiments, following administration of one or more of the presently disclosed transduced cells, peripheral blood of the subject is collected and hemoglobin levels is measured. A therapeutically relevant level of hemoglobin is produced following administration of one or more of the presently disclosed transduced cells. Therapeutically relevant level of hemoglobin is a level of hemoglobin that is sufficient (1) to improve or correct anemia, (2) to restore the ability of the subject to produce red blood cells containing normal hemoglobin, (3) to correct ineffective erythropoiesis in the subject, (4) to correct extra-medullary hematopoiesis (e.g., splenic and hepatic extra-medullary hematopoiesis), and/or (5) to reduce iron accumulation, e.g., in peripheral tissues and organs. Therapeutically relevant level of hemoglobin can be at least about 7 g/dL Hb, at least about 7.5 g/dL Hb, at least about 8 g/dL Hb, at least about 8.5 g/dL Hb, at least about 9 g/dL Hb, at least about 9.5 g/dL Hb, at least about 10 g/dL Hb, at least about 10.5 g/dL Hb, at least about 11 g/dL Hb, at least about 11.5 g/dL Hb, at least about 12 g/dL Hb, at least about 12.5 g/dL Hb, at least about 13 g/dL Hb, at least about 13.5 g/dL Hb, at least about 14 g/dL Hb, at least about 14.5 g/dL Hb, or at least about 15 g/dL Hb. Additionally or alternatively, therapeutically relevant level of hemoglobin can be from about 7 g/dL Hb to about 7.5 g/dL Hb, from about 7.5 g/dL Hb to about 8 g/dL Hb, from about 8 g/dL Hb to about 8.5 g/dL Hb, from about 8.5 g/dL Hb to about 9 g/dL Hb, from about 9 g/dL Hb to about 9.5 g/dL Hb, from about 9.5 g/dL Hb to about 10 g/dL Hb, from about 10 g/dL Hb to about 10.5 g/dL Hb, from about 10.5 g/dL Hb to about 11 g/dL Hb, from about 11 g/dL Hb to about 11.5 g/dL Hb, from about 11.5 g/dL Hb to about 12 g/dL Hb, from about 12 g/dL Hb to about 12.5 g/dL Hb, from about 12.5 g/dL Hb to about 13 g/dL Hb, from about 13 g/dL Hb to about 13.5 g/dL Hb, from about 13.5 g/dL Hb to about 14 g/dL Hb, from about 14 g/dL Hb to about 14.5 g/dL Hb, from about 14.5 g/dL Hb to about 15 g/dL Hb, from about 7 g/dL Hb to about 8 g/dL Hb, from about 8 g/dL Hb to about 9 g/dL Hb, from about 9 g/dL Hb to about 10 g/dL Hb, from about 10 g/dL Hb to about 11 g/dL Hb, from about 11 g/dL Hb to about 12 g/dL Hb, from about 12 g/dL Hb to about 13 g/dL Hb, from about 13 g/dL Hb to about 14 g/dL Hb, from about 14 g/dL Hb to about 15 g/dL Hb, from about 7 g/dL Hb to about 9 g/dL Hb, from about 9 g/dL Hb to about 11 g/dL Hb, from about 11 g/dL Hb to about 13 g/dL Hb, or from about 13 g/dL Hb to about 15 g/dL Hb. In certain embodiments, the therapeutically relevant level of hemoglobin is maintained in the subject for at least about 6 months, for at least about 12 months (or 1 year), for at least about 24 months (or 2 years). In certain embodiments, the therapeutically relevant level of hemoglobin is maintained in the subject for up to about 6 months, for up to about 12 months (or 1 year), for up to about 24 months (or 2 years). In certain embodiments, the therapeutically relevant level of hemoglobin is maintained in the subject for about 6 months, for about 12 months (or 1 year), for about 24 months (or 2 years). In certain embodiments, the therapeutically relevant level of hemoglobin is maintained in the subject for from about 6 months to about 12 months (e.g., from about 6 months to about 8 months, from about 8 months to about 10 months, from about 10 months to about 12 months), from about 12 months to about 18 months (e.g., from about 12 months to about 14 months, from about 14 months to about 16 months, or from about 16 months to about 18 months), or from about 18 months to about 24 months (e.g., from about 18 months to about 20 months, from about 20 months to about 22 months, or from about 22 months to about 24 months).

In certain embodiments, the method comprises administering one or more cells transduced with a recombinant vector comprising a presently disclosed expression cassette as described above. The vector copy number of the recombinant vector in the cells that provide for the therapeutically relevant level of hemoglobin (e.g., 9-10 g/dL) in the subject is from about 0.5 to about 2, from about 0.5 to about 1, or from about 1 to about 2 vector copy number per cell. In certain embodiments, the vector copy number of the presently disclosed vector is about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, or about 2.0 vector copy number per cell.

In certain embodiments, the subject lacks a human leukocyte antigen (HLA)-matched donor. In certain embodiments, the transduced cell is from the same subject. In certain embodiments, the transduced cell is from bone marrow of the same subject. Thus, administration of the transduced cells do not incur the risk of graft-versus host disease in the subject. The method does not require immune suppression to prevent graft rejection, e.g., the method does not comprise administering an immunosuppressive agent to the subject.

The present disclosed subject matter also provides a method of increasing the proportion of red blood cells or erythrocytes compared to white blood cells or leukocytes in a subject. In various non-limiting embodiments, the method comprises administering an effective amount of a presently disclosed transduced cell or a population of the presently disclosed transduced cells (e.g., HSCs, embryonic stem cells, or iPSCs) to the subject, wherein the proportion of red blood cell progeny cells of the hematopoietic stem cells are increased compared to white blood cell progeny cells of the hematopoietic stem cells in the subject.

An important advantage provided by the expression cassette, vectors and other delivery systems (e.g., nucleases and CRISPR-Cas systems), compositions, and methods of the presently disclosed subject is the high efficacy of globin gene therapy that can be achieved by administering populations of cells comprising lower percentages of transduced cells compared to existing methods. This provides important safety advantages associated with reduced chances of deleterious mutation, transformation, or oncogene activation of cellular genes in transduced cells. The transduced cells can be administered as part of a bone marrow or cord blood transplant in an individual that has or has not undergone bone marrow ablative therapy.

One consideration concerning the therapeutic use of the presently disclosed cells transduced with the expression cassette described herein ("transduced cells") is the quantity of cells necessary to achieve an optimal effect. The quantity of transduced cells to be administered will vary for the subject being treated. In certain embodiments, from about $1 \times 10^4$ to about $1 \times 10^5$ cells/kg, from about $1 \times 10^5$ to about $1 \times 10^6$ cells/kg, from about $1 \times 10^6$ to about $1 \times 10^7$ cells/kg, from about $1 \times 10^7$ to about $1 \times 10^8$ cells/kg, from about $1 \times 10^8$ to about $1 \times 10^9$ cells/kg, or from about $1 \times 10^9$ to about $1 \times 10^{10}$ cells/kg of the presently disclosed transduced cells are administered to a subject. More effective cells may be administered in even smaller numbers. In certain embodiments, at least about $1 \times 10^8$ cells/kg, at least about $2 \times 10^8$ cells/kg, at least about $3 \times 10^8$ cells/kg, at least about $4 \times 10^8$ cells/kg, or at least about $5 \times 10^8$ cells/kg of the presently disclosed transduced cells are administered to a subject. The precise determination of what would be considered an effective dose may be based on factors individual to each subject, including their size, age, sex, weight, and condition of the particular subject. Dosages can be readily ascertained by those skilled in the art from this disclosure and the knowledge in the art.

In certain embodiments, the expression cassettes, vectors and other delivery systems (nucleases and CRISPR-Cas systems), compositions, and methods of the presently disclosed subject matter offer improved methods of gene therapy using ex vivo gene therapy and autologous transplantation. Transplantation of cells transduced with the expression cassette or into subjects having a hemoglobinopathy results in long-term correction of the disease.

One or more presently disclosed transduced cells can be administered by any methods known in the art, including, but not limited to, parenteral administration (e.g., intramuscular administration, intravenous administration, subcutaneous administration, or intraperitoneal administration), spinal administration, and epidermal administration. In certain embodiments, one or more transduced cells are delivered to a subject intravenously. One or more presently disclosed transduced cells can be administered by injection, infusion, or implantation. In certain embodiments, one or more transduced cells are administered by injection. In certain embodiments, one or more transduced cells are administered by intravenous injection.

The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

VII. Kits

The presently disclosed subject matter provides kits for the treatment or prevention of a hemoglobinopathy. In certain embodiments, the kit comprises a therapeutic or prophylactic composition containing an effective amount of a cell transduced with the presently disclosed expression cassette in unit dosage form. In certain embodiments, the kit comprises one or more expression cassettes disclosed herein. In certain embodiments, the kit comprises one or more vectors comprising an expression cassette disclosed herein. In certain embodiments, the kit comprises a sterile container, which can be a box, an ampule, a bottle, a vial, a tube, a bag, a pouch, a blister-pack, or other suitable container forms known in the art. Such containers can be made of plastic, glass, laminated paper, metal foil, or other materials suitable for holding medicaments.

If desired, the transduced cell is provided together with instructions for administering the cell to a subject having or at risk of developing a hemoglobinopathy. The instructions will generally include information about the use of the composition for the treatment or prevention of a hemoglobinopathy. In certain embodiments, the instructions include at least one of the following: description of the therapeutic agent; dosage schedule and administration for treatment or prevention of a hemoglobinopathy or symptoms thereof; precautions; warnings; indications; counter-indications; overdosage information; adverse reactions; animal pharmacology; clinical studies; and/or references. Alternatively or additionally, the kit can include instructions for transducing a cell with the one or more expression cassettes and/or vectors comprising such expression cassettes. The instructions may be printed directly on the container (when present), or as a label applied to the container, or as a separate sheet, pamphlet, card, or folder supplied in or with the container.

EXAMPLES

The practice of the presently disclosed subject matter employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the presently disclosed subject matter, and, as such, may be considered in making and practicing the presently disclosed subject matter. Particularly useful techniques for particular embodiments will be discussed in the sections that follow.

The following examples are put forth so as to provide those of ordinary skill in the art with a complete disclosure and description of how to make and use the expression cassettes, vectors, delivery systems, and therapeutic methods of the presently disclosed subject matter, and are not intended to limit the scope of what the inventors regard as their invention.

Example 1: Discovery of Novel Insulators

The problems created by insertional mutagenesis of viral vectors are widely known (Nienhuis (2013), Baum et al. (2006), Nienhuis et al. (2006)) as is the evidence that the risks of genotoxicity can be reduced by the use of chromatin insulators (Arumugam et al. (2007), Emery (2011), Evans-Galea et al. (2007), Rivella et al. (2000), Emery et al. (2000), Emery et al. (2002), Yannaki et al. (2002), Hino et al. (2004), Ramezani et al. (2003), Ramezani et al. (2008)). Approaches allowing the efficient identification of enhancer blocking insulators in the human genome have been developed. These new insulators are short, on the average 150 bp, and they do not affect adversely the titers of viral vectors and they are several times more powerful than the insulator cHS4. Genomic approaches were used to discover the most powerful enhancer blocker and barrier insulators of the human genome. For gene therapy of the hemoglobinopathies, powerful enhancers are required to achieve therapeutic levels of globin gene expression. Powerful insulators may thus provide one means to protect the genomic environment from the powerful enhancers of the integrating vectors.

Several studies have demonstrated the ability of the cHS4 insulator to reduce position-effect silencing of gammaretroviral vectors (Evans-Galea et al. (2007), Rivella et al. (2000), Emery et al. (2000), Emery et al. (2002), Yannaki et al. (2002), Hino et al. (2004), Ramezani et al. (2006), Yao et al. (2003), Nishino et al. (2006), Aker et al. (2007), Li and Emery (2008)), and lentiviral vectors (Evans-Galea et al. (2007), Ramezani et al. (2003), Puthenveetil et al. (2004), Arumugam et al. (2007), Bank et al. (2005), Aker et al. (2007), Ma et al. (2003), Chang et al. (2005), Pluta et al. (2005)). Those studies that were appropriately designed demonstrated that inclusion of the 1.2 kb version of the cHS4 insulator increased the likelihood and/or consistency of vector transgene expression in at least some settings (Arumugam et al. (2007), Evans-Galea et al. (2007), Emery et al. (2002), Yannaki et al. (2002), Hino et al. (2004), Ramezani et al. (2006), Aker et al. (2007), Li and Emery (2008), Pluta et al. (2005), Jakobsson et al. (2004)). Nevertheless, the degree of protection afforded by the cHS4 insulator is far from complete. In addition, the inclusion of the 1.2 Kb cHS4 can adversely affect vector titers while the smallest cHS4 core has been proven ineffective (Aker et al. (2007), Jakobsson et al. (2004)).

Effects on genotoxicity were tested using an in vivo assay based on quantitation of tumor formation in mice. Vectors insulated by insulator A1 decreased tumor formation induced by random vector integration in hematopoietic chimeras compared to mice that received uninsulated or cHS4-insulated controls.

To assess effects on vector titers, insulator A1 was introduced into the double-copy region of a third-generation lentiviral vector expressing GFP from a constitutive package promoter, and the viral titers and GFP expression were measured. Insulator A1 did not affect adversely vector GFP expression.

In the in vivo genotoxicity assay, a cell line transduced with gammaretroviral vectors produced tumors after transplantation in mice and allowed quantitation of genotoxic effects by measuring rates of tumor free survival. Effects of an insulator on genotoxicity were quantitated by the number of tumors formed in the mice and the rates of tumor free survival. Insulator A1 was inserted in the proximal portion of the 3' LTR, from which it is copied into the 5' LTR during reverse transcription and vector integration. The resulting topology places copies of the insulator between the genomic regions located 5' and 3' of the integrated provirus and enhancer activity from the 5' viral LTR and internal Pgk promoter, but does not contain the enhancer in the 3' LTR. This can decrease genotoxicity thus resulting in decreased tumor formation and increased survival of the animals. Gamma-retroviral reporter vectors flanked with insulator A1 or control regions were used to transduce the growth factor-dependent cell line 32D, and 10 independent sub-pools for each vector were transplanted into syngeneic C3H/HeJ mice. All 10 mice transplanted with mock-transduced cells remained free of 32D cell-derived tumors, while nearly all mice transplanted with 32D cells transduced with vectors containing no inserts or a 790 bp neutral spacer developed tumors within a median of 16 weeks (FIG. 5B). Flanking this vector with the cHS4 insulator delayed the onset of tumor formation by several weeks, and reduced the frequency of animals that developed tumors to 6 of 10. In contrast, only two of 10 animals developed tumors following transplantation with 32D cells transduced with the vector flanked with insulator A1 (FIG. 5B). The frequency of animals with tumors and the number of vector transduction events in the original sub-pools suggested that flanking the vector with insulator A1 reduced the overall rate of tumor formation 12-fold, from 46.9 tumors per $10^5$ provirus to 3.9 tumors per $10^5$ provirus (FIG. 5C). In comparison, the cHS4 insulator reduced the overall rate of tumor formation 2.8-fold (to 16.9 tumors per $10^5$ provirus), while the neutral spacer had no statistically discernable effect on the rate of tumor formation. These results indicate that the discovered enhancer blocking insulators can decrease substantially the risks of insertional mutagenesis and genotoxicity.

Example 2: Characterization of Globin Vectors Comprising at Least One Insulator

A presently disclosed expression cassette (designated as "Expression Cassette 1"; as shown in FIG. 1), which comprises insulator A1, and a human $\beta^A$-globin gene encoding a threonine to glutamine mutation at codon 87 ($\beta^{A-T87Q}$) operably linked to a β-globin LCR comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7, was generated. The rationale for using the variant β chain ($\beta^A$) is to facilitate the detection of the vector-encoded β-globin gene, distinguishing it from endogenous or transfused beta chains. The glutamine (GLN) residue at position 87 in the γ-globin chain augments the anti-sickling activity of the gamma chain relative to the β chain, while preserving adult oxygen-binding characteristics of the β chain (Nagel et al. (1979)). In Vector 1, a point mutation altering codon 87 ($\beta^{A-T87Q}$, or β87) replaces the normal threonine with glutamine and augments anti-sickling activity of the vector-encoded β chain. This β87 chain has been safely used in a patient with HbE-thalassemia (Cavazzana-Calvo et al. (2010)).

Expression cassette 1 was incorporated or introduced to a lentivirus vector (designated as "Vector 1"). Vector 1 was introduced in bone marrow cells of C57BL/6-Hbb th3/+ mice and transplanted to syngeneic lethally irradiated recipients as previously described (May et al. (2000), May et al. (2002), Lisowski et al. (2007)). The vector titer of V1 was comparable to that of a lentivirus vector comprising an expression cassette lacking insulator A1. The β-globin expression of Vector 1 was compared to that of a lentivirus vector (designated as "Vector 2") comprising an expression cassette that lacks an insulator and comprises a wild human β-globin gene operably linked to a β-globin LCR comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:6. In comparison to Vector 2, β-globin expression of Vector 1 normalized to vector copy was equivalent or slightly increased, suggesting an added benefit for in vivo expression provided by the flanking barrier elements, as shown in FIG. 6.

Example 3: Evaluation of Enhancer Activity in Non-Erythroid K562 Cells

The enhancer activity of HS2 was evaluated in Non-erythroid K562 Cells. As shown in FIG. 7, GFP expression in K562 cells transduced with vectors driven by a minimal promoter linked to no enhancer ("Empty", HS2, HS3-4, HS2-3-4 or the runx1 enhancer used as positive control ("RUNX1"). Background expression was on the order or 0.01% ("empty), but increased over 10-fold with HS2-3-4 ("Lcr9", 0.17%). This enhancement was mostly due to HS2 (0.15%) but not HS3-4 (0.05%). All cell lines were comparably transduced (mean vector copy number 2.5). The results support that HS2 but not HS3-HS4 may pose an oncogenic risk in non-erythroid hematopoietic stem and progenitor cells.

Example 4: Novel Erythroid-Specific Enhancers

As shown in FIGS. 8 and 9, five erythroid-specific enhancers were substituted for HS2: ALAS Intron 1, ALAS Intron 8, BLVRB, PPDX, and Spectrin-alpha. The inventors have shown that all these five enhancers are powerful enhancers, and lack enhancer activity in non-erythroid tissues, and do not reduce the vector titer.

Example 5: Increasing Globin Lentiviral Vector Production Through 3' LTR Modifications An essential feature of therapeutic globin vectors is to achieve a high titer, sufficient for effective transduction of patient cells. By virtue of their large cargo, comprising a gene, promoter, enhancers and/or LCR elements, globin lentiviral vectors inherently have low titer, complicating their manufacture and limiting their clinical use. This problem is further compounded by the incorporation of additional genomic elements such as an insulator, which further increase the size of the vector.

The inventors explored different modifications of the 3' long terminal repeat (LTR) of globin vectors to increase the titer of globin vectors. Over 62 variations were evaluated, numbered 1 through 62, modeled on a lentivirus vector comprising a human β-globin gene operably linked to a β-globin LCR comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7. In other words, all of Vectors #1 through Vector 62 comprise a β-globin LCR comprising a HS2 region having the nucleotide sequence set forth in SEQ ID NO:9, a HS3 region having the nucleotide sequence set forth in SEQ ID NO:5, and a HS4 region having the nucleotide sequence set forth in SEQ ID NO:7. Vector #18 served as a baseline, comprising a standard U3 deletion in the 3'LTR. Vector #1 (not depicted) comprised a full, i.e., wild-type LTR, which cannot be used clinically. Modifications to the 3'LTR are depicted in FIGS. 10A and 10B, and their titers shown in FIGS. 11 and 12 (the Y axis shows the vector copy number of vector stocks manufactured and tested under strictly identical conditions). Titrations were measured in triple replicas, performed in parallel by two operators, and repeated in multiple experiments.

As shown in FIGS. 11 and 12, Vector #55 repeatedly showed a higher titer. This vector comprises a Woodchuck hepatitis post-regulatory element (WPRE) and a bovine growth hormone polyadenylation signal 3' to the R region in the 3' LTR. The WPRE element is therefore not transferred to the transduced cells.

Example 6: Generation of Globin Vectors

Methods and Materials
Vector Production
Various lentiviral vectors were produced, including TNS9.B87.A1, SNS22.2.B87.A1, SNS23.2.B87.A1, and SNS24.2.B87.A1. The nucleotide sequences of TNS9.B87.A1, SNS22.2.B87.A1, SNS23.2.B87.A1, SNS24.2.B87.A1, SNS26.B87.A1 and SNS27.2.B87.A1 are set forth in SEQ ID NO: 37, SEQ ID NO: 38, SEQ ID NO: 39, SEQ ID NO: 40, SEQ ID NO: 76, and SEQ ID NO: 77, respectively.

[SEQ ID NO: 37]

```
attggccattgcatacgttgtatccatatcataatatgtacatttatattggctcatgtccaacattaccgccatgttga
cattgattattgactagttattaatagtaatcaattacggggtcattagttcatagcccatatatggagttccgcgttac
ataacttacggtaaatggcccgcctggctgaccgcccaacgaccccgcccattgacgtcaataatgacgtatgttccca
tagtaacgccaatagggactttccattgacgtcaatggtggagtatttacggtaaactgcccacttggcagtacatcaa
gtgtatcatatgccaagtacgccccctattgacgtcaatgacggtaaatggcccgcctggcattatgcccagtacatgac
cttatgggactttcctacttggcagtacatctacgtattagtcatcgctattaccatggtgatgcggttttggcagtaca
tcaatgggcgtggatagcggtttgactcacggggatttccaagtctccacccattgacgtcaatgggagtttgttttgg
caccaaaatcaacgggactttccaaaatgtcgtaacaactccgccccattgacgcaaatgggcggtaggcgtgtacggtg
ggaggtctatataagcagagctcgtttagtgaaccgggtctctctggttagaccagatctgagcctgggagctctctgg
ctaactagggaacccactgcttaagcctcaataaagcttgccttgagtgcttcaagtagtgtgtgcccgtctgttgtgtg
actctggtaactagagatccctcagacccttttagtcagtgtggaaaatctctagcagtggcgcccgaacagggacttga
aagcgaaagggaaaccagaggagctctctcgacgcaggactcggcttgctgaagcgcgcacggcaagaggcgaggggcgg
cgactggtgagtacgccaaaaattttgactagcggaggctagaaggagagagacgggtgcgagagcgtcagtattaagcg
ggggtgaataagatcgcgatgggaaaaaattcggttaaggccaggggggaaagaaaaaatataaattaaaacatatagtat
gggcaagcagggagctagaacgattcgcagttaatcctggcctgttagaaacatcagaaggctgtagacaaatactggga
cagctacaaccatcccttcagacaggatcagaagaacttagatcattatataatacagtagcaaccctctattgtgtgca
tcaaaggatagagataaaagacaccaaggaagctttagacaagatagaggaagagcaaaacaaaagtaagaccaccgcac
agcaagcggccgctgatcttcagacctggaggaggagatatgagggacaattggagaagtgaattatataaatataaagt
agtaaaaattgaaccattaggagtagcacccaccaaggcaaagagaagagtggtgcagagagaaaaaagagcagtgggaa
taggagctttgttccttgggttcttgggagcagcaggaagcactatgggcgcagcgtcaatgacgctgacggtacaggcc
agacaattattgtctggtatagtgcagcagcagaacaatttgctgagggctattgaggcgcaacagcatctgttgcaact
cacagtctggggcatcaagcagctccaggcaagaatcctggctgtggaaagatacctaaaggatcaacagctcctgggga
tttgggggttgctctggaaaactcatttgcaccactgctgtgccttggaatgctagttggagtaataaatctctggaacag
atttggaatcacacgacctggatggagtgggacagagaaattaacaattacacaagcttaatacactccttaattgaaga
atcgcaaaaccagcaagaaaagaatgaacaagaattattggaattagataaatgggcaagtttgtggaattggtttaaca
taacaaattggctgtggtatataaaattattcataatgatagtaggaggcttggtaggtttaagaatagttttgctgta
ctttctatagtgaatagagttaggcagggatattcaccattatcgtttcagacccacctcccaaccccgaggggacccga
caggcccgaaggaatagaagaagaaggtggagagagagacagagacagatccattcgattagtgaacggatctcgacggt
atcgttttaaaagaaaagggggggattgggggtacagtgcaggggaaagaatagtagacataatagcaacagacatacaa
actaaagaattacaaaaacaaattacaaaaattcaaaattttatcggcgtgttgggggtggaccatcctctaggtattga
ataagaaaatgaagttaaggtggttgatggtaacactatgctaataactgcagagccagaagcaccataagggacatga
taagggagccagcagacctctgatctcttcctgaatgctaatcttaaacatcctgaggaagaatgggacttccatttggg
gtgggcctatgataggtaataagacagtagtgaatatcaagctacaaaaagccccctttcaaattcttctcagtcctaa
cttttcatactaagcccagtccttccaaagcagactgtgaaagagtgatagttccgggagactagcactgcagattccgg
gtcactgtgagtgggggaggcagggaagaagggctcacaggacagtcaaaccatgcccctgttttccttcttcaagta
gacctctataagacaacagagacaactaaggctgagtggccaggcgaggagaaaccatctcgccgtaaaacatggaagga
acacttcaggggaaaggtggtatctctaagcaagagaactgagtggagtcaaggctgagagatgcaggataagcaaatgg
gtagtgaaaagacattcatgaggacagctaaaacaataagtaatgtaaaatacagcatagcaaaactttaacctccaaat
```

-continued caagcctctacttgaatccttttctgagggatgaataaggcataggcatcagggctgttgccaatgtgcattagctgtt tgcagcctcaccttctttcatggagtttaagatatagtgtattttcccaaggtttgaactagctcttcatttctttatgt tttaaatgcactgacctcccacattccttttagtaaaatattcagaaataatttaaatacatcattgcaatgaaaata aatgttttttattaggcagaatccagatgctcaaggcccttcataatatcccccagtttagtagttggacttagggaaca aaggaaccttaatagaaattggacagcaagaaagcgagcttagtgatacttgtgggccagggcattagccacaccagcc accactttctgataggcagcctgcactggtggggtgAATTCTTTGCCAAAGTGATGGGCCAGCACACAGACCAGCACGTT

GCCCAGGAGCTGTGGGAGGAAGATAAGAGGTATGAACATGATTAGCAAAAGGGCCTAGCTTGGACTCAGAATAATCCAGC

CTTATCCCAACCATAAAATAAAAGCAGAATGGTAGCTGGATTGTAGCTGCTATTAGCAATATGAAACCTCTTACATCAGT

TACAATTTATATGCAGAAATATTTATATGCAGAAATATTGCTATTGCCTTAACCCAGAAATTATCACTGTTATTCTTTAG

AATGGTGCAAAGAGGCATGATACATTGTATCATTATTGCCCTGAAAGAAAGAGATTAGGGAAAGTATTAGAAATAAGATA

AACAAAAAGTATATTAAAAGAAGAAAGCATTTTTTAAAATTACAAATGCAAAATTACCCTGATTTGGTCAATATGTGTA

CCCTGTTACTTCTCCCCTTCCTATGACATGAACTTAACCATAGAAAAGAAGGGGAAAGAAAACATCAAGGGTCCCATAGA

CTCACCCTGAAGTTCTCAGGATCCACGTGCAGCTTGTCACAGTGCAGCTCACTCAGctgGGCAAAGGTGCCCTTGAGGTT

GTCCAGGTGAGCCAGGCCATCACTAAAGGCACCGAGCACTTTCTTGCCATGAGCCTTCACCTTAGGGTTGCCCATAACAG

CATCAGGAGTGGACAGATCCCCAAAGGACTCAAAGAACCTCTGGGTCCAAGGGTAGACCACCAGCAGCCTAAGGGTGGGA

AAATAGACCAATAGGCAGAGAGAGTCAGTGCCTATCAGAAACCCAAGAGTCTTCTCTGTCTCCACATGCCCAGTTTCTAT

TGGTCTCCTTAAACCTGTCTTGTAACCTTGATACCAACCTGCCCAGGGCCTCACCACCAACTTCATCCACGTTCACCTTG

CCCCACAGGGCAGTAACGGCAGACTTCTCCTCAGGAGTCAGGTGCACCATGGTGTCTGTTTGAGGTTGCTAGTAACACA

GTTGTGTCAGAAGCAAATGTAAGCAATAGATGGCTCTGCCCTGACTTTTATGCCCAGCCCTGGCTCCTGCCCTCCCTGCT

CCTGGGAGTAGATTGGCCAACCctagggtgtggctccacagggtgaggtctaagtgatgacagccgtacctgtccttggc tcttctggcactggcttaggagttggacttcaaaccctcagccctccctctaagatatatctcttggccccataccatca gtacaaattgctactaaaaacatcctcctttgcaagtgtatttacgtaatatttggaatcacagcttggtaagcatattg aagatcgttttcccaattttcttattacacaaataagaaattgatgcactaaaagtggaagagttttgtctaccataatt cagctttgggatatgtagatggatctcttcctgcgtctccagaatatgcaaaatacttacaggacagaatggatgaaaac tctacctcagttctaagcatatcttctccttatttggattaaaaaccttctggtaagaaaagaaaaaaaatatatatatat atgtgtatatatacacacatacatatacatatatatgcattcatttgttgttgttttcttaatttgctcatggtatatg tgtatatatatatatatattcaggaaataatatattctagaatatgtcacattctgtctcaggcatccatttctctta tgatgccgtttgaggtggagttttagtcaggtggtcagcttctcctttttttgccatctgccctgtaagcatcctgctg gggacccagataggagtcatcactctaggctgagaacatctgggcacacaccctaagcctcagcatgactcatcatgact cagcattgctgtgcttgagccagaaggtttgcttagaaggttacacagaaccagaaggcgggggtggggcactgaccccg acaggggcctggccagaactgctcatgcttggactatgggaggtcactaatggagacacacagaaatgtaacaggaacta aggaaaaactgaagcttatttaatcagagatgagatgctggaagggatagagggagctgagcttgtaaaaagtatagtaa tcattcagcaaatggttttgaagcacctgctggatgctaaacactattttcagtgcttgaatcataaataagaataaaac atgtatcttattccccacaagagtccaagtaaaaaataacagttaattataatgtgctctgtccccaggctggagtgca gtggcacgatctcagctcactgcaacctccgcctcccgggttcaagcaattctcctgcctcagccaccctaatagctggg attacaggtgcacaccaccatgccaggctaatttttgtactttttgtagaggcagggtatcaccatgttgtccaagatgg tcttgaactcctgagctccaagcagtccacccacctcagcctcccaaagtgctatctgcggccgcctatctgtaccacta gtctcgagaagctttcattaaaaaagtctaaccagctgcattcgactttgactgcagcagctggttagaaggttctact ggaggagggtcccagcccattgctaaattaacatcaggctctgagactggcagtatatctctaacagtggttgatgctat cttctggaacttgcctgctacattgagaccactgacccatacataggaagcccatagctctgtcctgaactgttaggcca -continued

```
ctggtccagagagtgtgcatctcctttgatcctcataataaccctatgagatagacacaattattactcttactttatag atgatgatcctgaaaacataggagtcaaggcacttgcccctagctgggggtataggggagcagtcccatgtagtagtaga atgaaaaatgctgctatgctgtgcctcccccacctttcccatgtctgccctctactcatggtctatctctcctggctcct gggagtcatggactccaccagcaccaccaacctgacctaaccacctatctgagcctgccagcctataacccatctgggc cctgatagctggtggccagccctgacccaccccaccctccctggaacctctgatagacacatctggcacaccagctcgc aaagtcaccgtgagggtcttgtgtttgctgagtcaaaattccttgaaatccaagtccttagagactcctgctcccaaatt tacagtcatagacttcttcatggctgtctcctttatccacagaatgattcctttgcttcattgcccatcctcatctgatcc tcctcatcagtgcagcacagggcccatgagcagtagctgcagagtctcacataggtctggcactgcctctgacatgtccg acctaggcaaatgcttgactcttctgagctcagtcttgtcatggcaaaataaagataataatagtgttttttatggag ttagcgtgaggatggaaaacaatagcaaaattgattagactataaaaggtctcaacaaatagtagtagattttatcatcc attaatccttccctctcctctcttactcatcccatcacgtatgcctcttaattttcccttacctataataagagttattc ctcttattatattcttcttatagtgattctggatattaaagtgggaatgaggggcaggccactaacgaagaagatgtttc tcaaagaagccattctccccacatagatcatctcagcagggttcaggaagataaaggaggatcaaggtcgaaggtaggaa ctaaggaagaacactgggcaagtggatcctgagcccctttcctctaactgaaagaaggaaaaaaaaaatggaacccaaa atattctacatagtttccatgtcacagccagggctgggcagtctcctgttatttcttttaaaataaatatatcatttaaa tgcataaataagcaaaccctgctcgggaatgggagggagagtctctggagtccacccctctcggccctggctctgcaga tagtgctatcaaagccctgacagagccctgcccattgctgggccttggagtgagtcagcctagtagagaggcagggcaag ccatctcatagctgctgagtgggagagagaaagggctcattgtctataaactcaggtcatggctattcttattctcaca ctaagaaaagaatgagatgtctacatatacccctgcgtcccctcttgtgtactgggcccccaagagctctctaaaagtg atggcaaagtcattgcgctagatgccatcccatctattataaacctgcatttgtctccacacaccagtcatggacaataa ccctcctcccaggtccacgtgcttgtctttgtataatactcaagtaatttcggaaaatgtattctttcaatcttgttctg ttattcctgtttcaatggcttagtagaaaaagtacatacttgttttcccataaattgacaatagacaatttcacatcaat gtctatatgggtcgttgtgtttgctgtgttttgcaaaaactcacaataactttatattgttactactctaagaaagttaca acatggtgaatacaagagaaagctattacaagtccagaaaataaaagttatcatcttgaggcctcagctttctaggaata atatcaatattacaaaatttaatctaacaattatgaacagcaatgagataatatgtacaaagtacccagacctatgtggt agagcatcaaggaagcgcattgcggagcagttttttgtttgtttgtttttgtattctgtttcgtgaggcaaggtttcact ctgctgtccaggctggagtgcagtggcaagatcatgtctcactgcagccttgacacgcgtcgacggtaccgttaacgatc ttagccactttttaaaagaaaaggggggactggaagggctaattcactcccaacgaagacaagatatcctgCTAGTCCTT

CCTTTCTAAATGACGAGAGAGACAGAAGAATTCTTCAAGGTTAGTGTGTCCAGCATGCAACCTTTCCTTCCTGGATGAGC

ATCCCTGGAGTAGGAGAGCCAGCCTGCCTCCTGCGCTGGCACAGAGCCCGGTTCCCTAGACAACTGCCTCTCCAAATCTG

ATGTCCAGCGCCACCTGGTGTCCACATCAAGCAGACACAATTAATAGTCAACCTGTTCAGGAAAACTGTGAGGGGGAAAA

AAAAGAAAGAGGATTTATGAAGGGAAAAGAAAGTTTAGAGGATATGCCACGATTGGctagcagctgcttttttgcctgtac tgggtctctctggttagaccagatctgagcctgggagctctctggctaactagggaacccactgcttaagcctcaataaa gcttgccttgagtgcttcatccggAATCAACCTCTGGATTACAAAATTTGTGAAAGATTGACTGGTATTCTTAACTATGT

TGCTCCTTTTACGCTATGTGGATACGCTGCTTTAATGCCTTTGTATCATGCTATTGCTTCCCGTATGGCTTTCATTTTCT

CCTCCTTGTATAAATCCTGGTTGCTGTCTCTTTATGAGGAGTTGTGGCCCGTTGTCAGGCAACGTGGCGTGGTGTGCACT

GTGTTTGCTGACGCAACCCCCACTGGTTGGGGCATTGCCACCACCTGTCAGCTCCTTTCCGGGACTTTCGCTTTCCCCCT

CCCTATTGCCACGGCGGAACTCATCGCCGCCTGCCTTGCCCGCTGCTGGACAGGGGCTCGGCTGTTGGGCACTGACAATT

CCGTGGTGTTGTCGGGGAAGCTGACGTCCTTTCCATGGCTGCTCGCCTGTGTTGCCACCTGGATTCTGCGCGGGACGTCC

TTCTGCTACGTCCCTTCGGCCCTCAATCCAGCGGACCTTCCTTCCCGCGGCCTGCTGCCGGCTCTGCGGCCTCTTCCGCG

TCTTCGCCTTCGCCCTCAGACGAGTCGGATCTCCCTTTGGGCCGCCTCCCCGCCTGtccggtAGCTTGCCAGCCTCGACT
```

-continued

```
GTGCCTTCTAGTTGCCAGCCGTCTGTTGTTTGCCCCTCCCCCGTGCCTTCCTTGACCCTGGAAGGTGCCACTCCCACTGT
CCTTTCCTAATAAAATGAGGAAATTGCATCGCATTGTCTGAGTAGGTGTCATTCTATTCTGGGGGGTGGGGTGGGGCAGG
ACAGCAAGGGGGAGGATTGGGAAGACAATAGCAGGCATGcaagcttggcgtaatcatggtcatagctgtttcctgtgtga
aattgttatccgctcacaattccacacaacatacgagccggaagcataaagtgtaaagcctggggtgcctaatgagtgag
ctaactcacattaattgcgttgcgctcactgcccgctttccagtcgggaaacctgtcgtgccagctgcattaatgaatcg
gccaacgcgcggggagaggcggtttgcgtattgggcgctcttccgcttcctcgctcactgactcgctgcgctcggtcgtt
cggctgcggcgagcggtatcagctcactcaaaggcggtaatacggttatccacagaatcaggggataacgcaggaaagaa
catgtgagcaaaaggccagcaaaaggccaggaaccgtaaaaaggccgcgttgctggcgtttttccataggctccgccccc
ctgacgagcatcacaaaaatcgacgctcaagtcagaggtggcgaaacccgacaggactataaagataccaggcgtttccc
cctggaagctccctcgtgcgctctcctgttccgaccctgccgcttaccggatacctgtccgcctttctcccttcgggaag
cgtggcgctttctcatagctcacgctgtaggtatctcagttcggtgtaggtcgttcgctccaagctgggctgtgtgcacg
aaccccccgttcagcccgaccgctgcgccttatccggtaactatcgtcttgagtccaacccggtaagacacgacttatcg
ccactggcagcagccactggtaacaggattagcagagcgaggtatgtaggcggtgctacagagttcttgaagtggtggcc
taactacggctacactagaagaacagtatttggtatctgcgctctgctgaagccagttaccttcggaaaaagagttggta
gctcttgatccggcaaacaaaccaccgctggtagcggtggtttttttgtttgcaagcagcagattacgcgcagaaaaaaa
ggatctcaagaagatcctttgatcttttctacggggtctgacgctcagtggaacgaaaactcacgttaagggattttggt
catgagattatcaaaaaggatcttcacctagatccttttaaattaaaaatgaagttttaaatcaatctaaagtatatatg
agtaaacttggtctgacagttaccaatgcttaatcagtgaggcacctatctcagcgatctgtctatttcgttcatccata
gttgcctgactccccgtcgtgtagataactacgatacgggagggcttaccatctggccccagtgctgcaatgataccgcg
agacccacgctcaccggctccagatttatcagcaataaaccagccagccggaagggccgagcgcagaagtggtcctgcaa
ctttatccgcctccatccagtctattaattgttgccgggaagctagagtaagtagttcgccagttaatagtttgcgcaac
gttgttgccattgctacaggcatcgtggtgtcacgctcgtcgtttggtatggcttcattcagctccggttcccaacgatc
aaggcgagttacatgatcccccatgttgtgcaaaaaagcggttagctccttcggtcctccgatcgttgtcagaagtaagt
tggccgcagtgttatcactcatggttatggcagcactgcataattctcttactgtcatgccatccgtaagatgcttttct
gtgactggtgagtactcaaccaagtcattctgagaatagtgtatgcggcgaccgagttgctcttgcccggcgtcaatacg
ggataataccgcgccacatagcagaactttaaaagtgctcatcattggaaaacgttcttcggggcaaaactctcaaggat
cttaccgctgttgagatccagttcgatgtaacccactcgtgcacccaactgatcttcagcatcttttactttcaccagcg
tttctgggtgagcaaaaacaggaaggcaaaatgccgcaaaaaagggaataagggcgacacggaaatgttgaatactcata
ctcttcctttttcaatattattgaagcatttatcagggttattgtctcatgagcggatacatatttgaatgtatttagaa
aaataaacaaataggggttccgcgcacatttccccgaaaagtgccacctgacgtctaagaaaccattattatcatgacat
taacctataaaaataggcgtatcacgaggcccttcgtctcgcgcgtttcggtgatgacggtgaaaacctctgacacatg
cagctcccggagacggtcacagcttgtctgtaagcggatgccgggagcagacaagcccgtcagggcgcgtcagcgggtgt
tggcgggtgtcggggctggcttaactatgcggcatcagagcagattgtactgagagtgcacc
```

[SEQ ID NO: 38]
```
ATTGGCCATTGCATACGTTGTATCCATATCATAATATGTACATTTATATTGGCTCATGTCCAACATTACCGCCATGTTGA
CATTGATTATTGACTAGTTATTAATAGTAATCAATTACGGGGTCATTAGTTCATAGCCCATATATGGAGTTCCGCGTTAC
ATAACTTACGGTAAATGGCCCGCCTGGCTGACCGCCCAACGACCCCCGCCCATTGACGTCAATAATGACGTATGTTCCCA
TAGTAACGCCAATAGGGACTTTCCATTGACGTCAATGGGTGGAGTATTTACGGTAAACTGCCCACTTGGCAGTACATCAA
GTGTATCATATGCCAAGTACGCCCCCTATTGACGTCAATGACGGTAAATGGCCCGCCTGGCATTATGCCCAGTACATGAC
CTTATGGGACTTTCCTACTTGGCAGTACATCTACGTATTAGTCATCGCTATTACCATGGTGATGCGGTTTTGGCAGTACA
TCAATGGGCGTGGATAGCGGTTTGACTCACGGGGATTTCCAAGTCTCCACCCCATTGACGTCAATGGGAGTTTGTTTTGG
```

-continued

```
CACCAAAATCAACGGGACTTTCCAAAATGTCGTAACAACTCCGCCCCATTGACGCAAATGGGCGGTAGGCGTGTACGGTG

GGAGGTCTATATAAGCAGAGCTCGTTTAGTGAACCGGGGTCTCTCTGGTTAGACCAGATCTGAGCCTGGGAGCTCTCTGG

CTAACTAGGGAACCCACTGCTTAAGCCTCAATAAAGCTTGCCTTGAGTGCTTCAAGTAGTGTGTGCCCGTCTGTTGTGTG

ACTCTGGTAACTAGAGATCCCTCAGACCCTTTTAGTCAGTGTGGAAAATCTCTAGCAGTGGCGCCCGAACAGGGACTTGA

AAGCGAAAGGGAAACCAGAGGAGCTCTCTCGACGCAGGACTCGGCTTGCTGAAGCGCGCACGGCAAGAGGCGAGGGGCGG

CGACTGGTGAGTACGCCAAAAATTTTGACTAGCGGAGGCTAGAAGGAGAGAGACGGGTGCGAGAGCGTCAGTATTAAGCG

GGGGTGAATAAGATCGCGATGGGAAAAAATTCGGTTAAGGCCAGGGGGAAAGAAAAAATATAAATTAAAACATATAGTAT

GGGCAAGCAGGGAGCTAGAACGATTCGCAGTTAATCCTGGCCTGTTAGAAACATCAGAAGGCTGTAGACAAATACTGGGA

CAGCTACAACCATCCCTTCAGACAGGATCAGAAGAACTTAGATCATTATATAATACAGTAGCAACCCTCTATTGTGTGCA

TCAAAGGATAGAGATAAAAGACACCAAGGAAGCTTTAGACAAGATAGAGGAAGAGCAAAACAAAAGTAAGACCACCGCAC

AGCAAGCGGCCGCTGATCTTCAGACCTGGAGGAGGAGATATGAGGGACAATTGGAGAAGTGAATTATATAAATATAAAGT

AGTAAAAATTGAACCATTAGGAGTAGCACCCACCAAGGCAAAGAGAAGAGTGGTGCAGAGAGAAAAAAGAGCAGTGGGAA

TAGGAGCTTTGTTCCTTGGGTTCTTGGGAGCAGCAGGAAGCACTATGGGCGCAGCGTCAATGACGCTGACGGTACAGGCC

AGACAATTATTGTCTGGTATAGTGCAGCAGCAGAACAATTTGCTGAGGGCTATTGAGGCGCAACAGCATCTGTTGCAACT

CACAGTCTGGGGCATCAAGCAGCTCCAGGCAAGAATCCTGGCTGTGGAAAGATACCTAAAGGATCAACAGCTCCTGGGA

TTTGGGGTTGCTCTGGAAAACTCATTTGCACCACTGCTGTGCCTTGGAATGCTAGTTGGAGTAATAAATCTCTGGAACAG

ATTTGGAATCACACGACCTGGATGGAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGGCAAGTTTGTGGAATTGGTTTAACA

TAACAAATTGGCTGTGGTATATAAAATTATTCATAATGATAGTAGGAGGCTTGGTAGGTTTAAGAATAGTTTTTGCTGTA

CTTTCTATAGTGAATAGAGTTAGGCAGGGATATTCACCATTATCGTTTCAGACCCACCTCCCAACCCCGAGGGGACCCGA

CAGGCCCGAAGGAATAGAAGAAGAAGGTGGAGAGAGAGACAGAGACAGATCCATTCGATTAGTGAACGGATCTCGACGGT

ATCGTTTTAAAAGAAAAGGGGGGATTGGGGGGTACAGTGCAGGGGAAAGAATAGTAGACATAATAGCAACAGACATACAA

ACTAAAGAATTACAAAAACAAATTACAAAAATTCAAAATTTTATCGGCGTGTTGGGGGTGGACCATCCTCTAGGTATTGA

ATAAGAAAATGAAGTTAAGGTGGTTGATGGTAACACTATGCTAATAACTGCAGAGCCAGAAGCACCATAAGGGACATGA

TAAGGGAGCCAGCAGACCTCTGATCTCTTCCTGAATGCTAATCTTAAACATCCTGAGGAAGAATGGGACTTCCATTTGGG

GTGGGCCTATGATAGGGTAATAAGACAGTAGTGAATATCAAGCTACAAAAAGCCCCCTTTCAAATTCTTCTCAGTCCTAA

CTTTTCATACTAAGCCCAGTCCTTCCAAAGCAGACTGTGAAAGAGTGATAGTTCCGGGAGACTAGCACTGCAGATTCCGG

GTCACTGTGAGTGGGGGAGGCAGGGAAGAAGGGCTCACAGGACAGTCAAACCATGCCCCCTGTTTTTCCTTCTTCAAGTA

GACCTCTATAAGACAACAGAGACAACTAAGGCTGAGTGGCCAGGCGAGGAGAAACCATCTCGCCGTAAAACATGAAGGA

ACACTTCAGGGGAAAGGTGGTATCTCTAAGCAAGAGAACTGAGTGGAGTCAAGGCTGAGAGATGCAGGATAAGCAAATGG

GTAGTGAAAAGACATTCATGAGGACAGCTAAAACAATAAGTAATGTAAAATACAGCATAGCAAAACTTTAACCTCCAAAT

CAAGCCTCTACTTGAATCCTTTTCTGAGGGATGAATAAGGCATAGGCATCAGGGGCTGTTGCCAATGTGCATTAGCTGTT

TGCAGCCTCACCTTCTTTCATGGAGTTTAAGATATAGTGTATTTTCCCAAGGTTTGAACTAGCTCTTCATTTCTTTATGT

TTTAAATGCACTGACCTCCCACATTCCCTTTTTAGTAAAATATTCAGAAATAATTTAAATACATCATTGCAATGAAAATA

AATGTTTTTTATTAGGCAGAATCCAGATGCTCAAGGCCCTTCATAATATCCCCAGTTTAGTAGTTGGACTTAGGGAACA

AAGGAACCTTTAATAGAAATTGGACAGCAAGAAAGCGAGCTTAGTGATACTTGTGGGCCAGGGCATTAGCCACACCAGCC

ACCACTTTCTGATAGGCAGCCTGCACTGGTGGGGTGAATTCTTTGCCAAAGTGATGGGCCAGCACACAGACCAGCACGTT

GCCCAGGAGCTGTGGGAGGAAGATAAGAGGTATGAACATGATTAGCAAAAGGGCCTAGCTTGGACTCAGAATAATCCAGC

CTTATCCCAACCATAAAATAAAAGCAGAATGGTAGCTGGATTGTAGCTGCTATTAGCAATATGAAACCTCTTACATCAGT

TACAATTTATATGCAGAAATATTTATATGCAGAAATATTGCTATTGCCTTAACCCAGAAATTATCACTGTTATTCTTTAG
```

-continued

```
AATGGTGCAAAGAGGCATGATACATTGTATCATTATTGCCCTGAAAGAAAGAGATTAGGGAAAGTATTAGAAATAAGATA
AACAAAAAAGTATATTAAAAGAAGAAAGCATTTTTTAAAATTACAAATGCAAAATTACCCTGATTTGGTCAATATGTGTA
CCCTGTTACTTCTCCCCTTCCTATGACATGAACTTAACCATAGAAAAGAAGGGGAAAGAAAACATCAAGGGTCCCATAGA
CTCACCCTGAAGTTCTCAGGATCCACGTGCAGCTTGTCACAGTGCAGCTCACTCAGCTGGGCAAAGGTGCCCTTGAGGTT
GTCCAGGTGAGCCAGGCCATCACTAAAGGCACCGAGCACTTTCTTGCCATGAGCCTTCACCTTAGGGTTGCCCATAACAG
CATCAGGAGTGGACAGATCCCCAAAGGACTCAAAGAACCTCTGGGTCCAAGGGTAGACCACCAGCAGCCTAAGGGTGGGA
AAATAGACCAATAGGCAGAGAGAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCAACTTCATCCACGTTCACCTTG
CCCCACAGGGCAGTAACGGCAGACTTCTCCTCAGGAGTCAGGTGCACCATGGTGTCTGTTTGAGGTTGCTAGTGAACACA
GTTGTGTCAGAAGCAAATGTAAGCAATAGATGGCTCTGCCCTGACTTTTATGCCCAGCCCTGGCTCCTGCCCTCCCTGCT
CCTGGGAGTAGATTGGCCAACCCTAGGGTGTGGCTCCACAGGGTGAGGTCTAAGTGATGACAGCCGTACCTGTCCTTGGC
TCTTCTGGCACTGGCTTAGGAGTTGGACTTCAAACCCTCAGCCCTCCCTCTAAGATATATCTCTTGGCCCCATACCATCA
GTACAAATTGCTACTAAAAACATCCTCCTTTGCAAGTGTATTTACGGCATCTGTGAAGGAAAGAAACATCTCCTCTAAAC
CACTATGCTGCTAGAGCCTCTTTTCTGTACTCAAGCCTCATTCAGACACTAGTGTCACCAGTCTCCTCATATACCTATTG
TATTTTCTTCTTCTTGCTGGTTTAGTCATGTTTTCTGGGAGCTTAGGGGCTTATTTTATTTTGTTTTGTTTTCTAATCAA
CAGAGATGGGCAAACCCATTATTTTTTTCTTTAGACTTGGGATGGTGATAGCTGGGCAGCGTCAGAAACTGTGTGTGGAT
ATAGATAAGAGCTCGGACTATGCTGAGCTGTGATGAGGGAGGGACCTAGCCAAAGGCAGTGAGAGTCAGAATGCTCCTGC
TATTGCCTTCTCAGTCCCCACGCTTGGTTTCTACACAAGTAGATACATAGAAAAGGCTATAGGTTAGTGTTTGAGAGTCC
TGCATGAGTTAGTTGCTCAGAAATGCCCGATAAATATGTTATGTGTGTTTATGTATATATATGTTTTATATATATATATG
TGTGTGTGTGTGTGTGTGTGTTGTGTTTACAAATATGTGATTATCATCAAAACGTGAGGGCTAAAGTGACCAGATAAC
TTGCAGGTCTAGAATATGTCACATTCTGTCTCAGGCATCCATTTTCTTTATGATGCCGTTTGAGGTGGAGTTTTAGTCAG
GTGGTCAGCTTCTCCTTTTTTTTGCCATCTGCCCTGTAAGCATCCTGCTGGGGACCCAGATAGGAGTCATCACTCTAGGC
TGAGAACATCTGGGCACACACCCTAAGCCTCAGCATGACTCATCATGACTCAGCATTGCTGTGCTTGAGCCAGAAGGTTT
GCTTAGAAGGTTACACAGAACCAGAAGGCGGGGGTGGGGCACTGACCCCGACAGGGGCCTGGCCAGAACTGCTCATGCTT
GGACTATGGGAGGTCACTAATGGAGACACACAGAAATGTAACAGGAACTAAGGAAAAACTGAAGCTTATTTAATCAGAGA
TGAGATGCTGGAAGGGATAGAGGGAGCTGAGCTTGTAAAAAGTATAGTAATCATTCAGCAAATGGTTTTGAAGCACCTGC
TGGATGCTAAACACTATTTTCAGTGCTTGAATCATAAATAAGAACAAAACATGTATCTTATTCCCCACAAGAGTCCAAGT
AAAAAATAACAGTTAATTATAATGTGCTCTGTCCCCAGGCTGGAGTGCAGTGGCACGATCTCAGCTCACTGCAACCTCC
GCCTCCCGGGTTCAAGCAATTCTCCTGCCTCAGCCACCCTAATAGCTGGGATTACAGGTGCACACCACCATGCCAGGCTA
ATTTTTGTACTTTTTGTAGAGGCAGGGTATCACCATGTTGTCCAAGATGGTCTTGAACTCCTGAGCTCCAAGCAGTCCAC
CCACCTCAGCCTCCCAAAGTGCTATCTGCGGCCGCCTATCTGTACCACTAGTCTCGAGAAGCTTTCATCAAAAAAAGTCT
AACCAGCTGCATTCGACTTTGACTGCAGCAGCTGGTTAGAAGGTTCTACTGGAGGAGGGTCCCAGCCCATTGCTAAATTA
ACATCAGGCTCTGAGACTGGCAGTATATCTCTAACAGTGGTTGATGCTATCTTCTGGAACTTGCCTGCTACATTGAGACC
ACTGACCCATACATAGGAAGCCCATAGCTCTGTCCTGAACTGTTAGGCCACTGGTCCAGAGAGTGTGCATCTCCTTTGAT
CCTCATAATAACCCTATGAGATAGACACAATTATTACTCTTACTTTATAGATGATGATCCTGAAAACATAGGAGTCAAGG
CACTTGCCCCTAGCTGGGGGTATAGGGGAGCAGTCCCATGTAGTAGTAGAATGAAAAATGCTGCTATGCTGTGCCTCCCC
CACCTTTCCCATGTCTGCCCTCTACTCATGGTCTATCTCTCCTGGCTCCTGGGAGTCATGGACTCCACCCAGCACCACCA
ACCTGACCTAACCACCTATCTGAGCCTGCCAGCCTATAACCCATCTGGGCCCTGATAGCTGGTGGCCAGCCCTGACCCCA
CCCCACCCTCCCTGGAACCTCTGATAGACACATCTGGCACACCAGCTCGCAAAGTCACCGTGAGGGTCTTGTGTTTGCTG
AGTCAAAATTCCTTGAAATCCAAGTCCTTAGAGACTCCTGCTCCCAAATTTACAGTCATAGACTTCTTCATGGCTGTCTC
CTTTATCCACAGAATGATTCCTTTGCTTCATTGCCCCATCCATCTGATCCTCCTCATCAGTGCAGCACAGGGCCCATGAG
```

-continued

```
CAGTAGCTGCAGAGTCTCACATAGGTCTGGCACTGCCTCTGACATGTCCGACCTTAGGCAAATGCTTGACTCTTCTGAGC

TCAGTCTTGTCATGGCAAAACAAAGATAATAATAGTGTTTTTTTATGGAGTTAGCGTGAGGATGGAAAACAATAGCAAAA

TTGATTAGACTATAAAAGGTCTCAACAAATAGTAGTAGATTTTATCATCCATTAATCCTTCCCTCTCCTCTCTTACTCAT

CCCATCACGTATGCCTCTTAATTTTCCCTTACCTATAATAAGAGTTATTCCTCTTATTATATTCTTCTTATAGTGATTCT

GGATATCAAAGTGGGAATGAGGGGCAGGCCACTAACGAAGAAGATGTTTCTCAAAGAAGCCATTCTCCCCACATAGATCA

TCTCAGCAGGGTTCAGGAAGATAAAGGAGGATCAAGGTCGAAGGTAGGAACTAAGGAAGAACACTGGGCAAGTGGATCCT

AAATATATCATTTAAATGCATAAATAAGCAAACCCTGCTCGGGAATGGGAGGGAGAGTCTCTGGAGTCCACCCCTTCTCG

GCCCTGGCTCTGCAGATAGTGCTATCAAAGCCCTGACAGAGCCCTGCCCATTGCTGGGCCTTGGAGTGAGTCAGCCTAGT

AGAGAGGCAGGGCAAGCCATCTCATAGCTGCTGAGTGGGAGAGAGAAAAGGGCTCATTGTCTATAAACTCAGGTCATGGC

TATTCTTATTCTCACACTAAGAAAAAGAATGAGATGTCTACATATACCCTGCGTCCCCTCTTGTGTACTGGGGCCCCCAA

GAGCTCTCTAAAAGTGATGGCAAAGTCATTGCGCTAGATGCCATCCCATCTATTATAAACCTGCATTTGTCTCCACACAC

CAGTCATGGACAATAACCCTCCTCCCAGGTCCACGTGCTTGTCTTTGTATAATACTCAAGTAATTTCGGAAAATGTATTC

TTTCAATCTTGTTCTGTTATTCCTGTTTCAATGGCTTAGTAGAAAAAGTACATACTTGTTTTCCCATAAATTGACAATAG

ACAATTTCACATCAATGTCTATATGGGTCGTTGTGTTTGCTGTGTTTGCAAAAACTCACAATAACTTTATATTGTTACTA

CTCTAAGAAAGTTACAACATGGTGAATACAAGAGAAAGCTATTACAAGTCCAGAAAACAAAAGTTATCATCTTGAGGCCT

CAGCTTTCTAGGAATAATATCAATATTACAAAACGCGTCGACGGTACCGTTAACGATCTTAGCCACTTTTTAAAAGAAAA

GGGGGGACTGGAAGGGCTAATTCACTCCCAACGAAGACAAGATATCCTGCTAGTCCTTCCTTTCTAAATGACGAGAGAGA

CAGAAGAATTCTTCAAGGTTAGTGTGTCCAGCATGCAACCTTTCCTTCCTGGATGAGCATCCCTGGAGTAGGAGAGCCAG

CCTGCCTCCTGCGCTGGCACAGAGCCCGGTTCCCTAGACAACTGCCTCTCCAAATCTGATGTCCAGCGCCACCTGGTGTC

CACATCAAGCAGACACAATTAATAGTCAACCTGTTCAGGAAAACTGTGAGGGGGAAAAAAAAGAAAGAGGATTTATGAAG

GGAAAAGAAAGTTTAGAGGATATGCCACGATTGGCTAGCAGCTGCTTTTTGCCTGTACTGGGTCTCTCTGGTTAGACCAG

ATCTGAGCCTGGGAGCTCTCTGGCTAACTAGGGAACCCACTGCTTAAGCCTCAATAAAGCTTGCCTTGAGTGCTTCATCC

GGAATCAACCTCTGGATTACAAAATTTGTGAAAGATTGACTGGTATTCTTAACTATGTTGCTCCTTTTACGCTATGTGGA

TACGCTGCTTTAATGCCTTTGTATCATGCTATTGCTTCCCGTATGGCTTTCATTTTCTCCTCCTTGTATAAATCCTGGTT

GCTGTCTCTTTATGAGGAGTTGTGGCCCGTTGTCAGGCAACGTGGCGTGGTGTGCACTGTGTTTGCTGACGCAACCCCCA

CTGGTTGGGGCATTGCCACCACCTGTCAGCTCCTTTCCGGGACTTTCGCTTTCCCCCTCCCTATTGCCACGGCGGAACTC

ATCGCCGCCTGCCTTGCCCGCTGCTGGACAGGGGCTCGGCTGTTGGGCACTGACAATTCCGTGGTGTTGTCGGGGAAGCT

GACGTCCTTTCCATGGCTGCTCGCCTGTGTTGCCACCTGGATTCTGCGCGGGACGTCCTTCTGCTACGTCCCTTCGGCCC

TCAATCCAGCGGACCTTCCTTCCCGCGGCCTGCTGCCGGCTCTGCGGCCTCTTCCGCGTCTTCGCCTTCGCCCTCAGACG

AGTCGGATCTCCCTTTGGGCCGCCTCCCCGCCTGTCCGGTAGCTTGCCAGCCTCGACTGTGCCTTCTAGTTGCCAGCCGT

CTGTTGTTTGCCCCTCCCCCGTGCCTTCCTTGACCCTGGAAGGTGCCACTCCCACTGTCCTTTCCTAATAAAATGAGGAA

ATTGCATCGCATTGTCTGAGTAGGTGTCATTCTATTCTGGGGGGTGGGGTGGGGCAGGACAGCAAGGGGGAGGATTGGGA

AGACAATAGCAGGCATGCAAGCTTGGCGTAATCATGGTCATAGCTGTTTCCTGTGTGAAATTGTTATCCGCTCACAATTC

CACACAACATACGAGCCGGAAGCATAAAGTGTAAAGCCTGGGGTGCCTAATGAGTGAGCTAACTCACATTAATTGCGTTG

CGCTCACTGCCCGCTTTCCAGTCGGGAAACCTGTCGTGCCAGCTGCATTAATGAATCGGCCAACGCGCGGGGAGAGGCGG

TTTGCGTATTGGGCGCTCTTCCGCTTCCTCGCTCACTGACTCGCTGCGCTCGGTCGTTCGGCTGCGGCGAGCGGTATCAG

CTCACTCAAAGGCGGTAATACGGTTATCCACAGAATCAGGGGATAACGCAGGAAAGAACATGTGAGCAAAAGGCCAGCAA

AAGGCCAGGAACCGTAAAAAGGCCGCGTTGCTGGCGTTTTTCCATAGGCTCCGCCCCCCTGACGAGCATCACAAAAATCG

ACGCTCAAGTCAGAGGTGGCGAAACCCGACAGGACTATAAAGATACCAGGCGTTTCCCCCTGGAAGCTCCCTCGTGCGCT

CTCCTGTTCCGACCCTGCCGCTTACCGGATACCTGTCCGCCTTTCTCCCTTCGGGAAGCGTGGCGCTTTCTCATAGCTCA
```

-continued

```
CGCTGTAGGTATCTCAGTTCGGTGTAGGTCGTTCGCTCCAAGCTGGGCTGTGTGCACGAACCCCCCGTTCAGCCCGACCG

CTGCGCCTTATCCGGTAACTATCGTCTTGAGTCCAACCCGGTAAGACACGACTTATCGCCACTGGCAGCAGCCACTGGTA

ACAGGATTAGCAGAGCGAGGTATGTAGGCGGTGCTACAGAGTTCTTGAAGTGGTGGCCTAACTACGGCTACACTAGAAGA

ACAGTATTTGGTATCTGCGCTCTGCTGAAGCCAGTTACCTTCGGAAAAAGAGTTGGTAGCTCTTGATCCGGCAAACAAAC

CACCGCTGGTAGCGGTGGTTTTTTTGTTTGCAAGCAGCAGATTACGCGCAGAAAAAAAGGATCTCAAGAAGATCCTTTGA

TCTTTTCTACGGGGTCTGACGCTCAGTGGAACGAAAACTCACGTTAAGGGATTTTGGTCATGAGATTATCAAAAAGGATC

TTCACCTAGATCCTTTTAAATTAAAAATGAAGTTTTAAATCAATCTAAAGTATATATGAGTAAACTTGGTCTGACAGTTA

CCAATGCTTAATCAGTGAGGCACCTATCTCAGCGATCTGTCTATTTCGTTCATCCATAGTTGCCTGACTCCCCGTCGTGT

AGATAACTACGATACGGGAGGGCTTACCATCTGGCCCCAGTGCTGCAATGATACCGCGAGACCCACGCTCACCGGCTCCA

GATTTATCAGCAATAAACCAGCCAGCCGGAAGGGCCGAGCGCAGAAGTGGTCCTGCAACTTTATCCGCCTCCATCCAGTC

TATTAATTGTTGCCGGGAAGCTAGAGTAAGTAGTTCGCCAGTTAATAGTTTGCGCAACGTTGTTGCCATTGCTACAGGCA

TCGTGGTGTCACGCTCGTCGTTTGGTATGGCTTCATTCAGCTCCGGTTCCCAACGATCAAGGCGAGTTACATGATCCCCC

ATGTTGTGCAAAAAAGCGGTTAGCTCCTTCGGTCCTCCGATCGTTGTCAGAAGTAAGTTGGCCGCAGTGTTATCACTCAT

GGTTATGGCAGCACTGCATAATTCTCTTACTGTCATGCCATCCGTAAGATGCTTTTCTGTGACTGGTGAGTACTCAACCA

AGTCATTCTGAGAATAGTGTATGCGGCGACCGAGTTGCTCTTGCCCGGCGTCAATACGGGATAATACCGCGCCACATAGC

AGAACTTTAAAAGTGCTCATCATTGGAAAACGTTCTTCGGGGCAAAACTCTCAAGGATCTTACCGCTGTTGAGATCCAGT

TCGATGTAACCCACTCGTGCACCCAACTGATCTTCAGCATCTTTTACTTTCACCAGCGTTTCTGGGTGAGCAAAAACAGG

AAGGCAAAATGCCGCAAAAAAGGGAATAAGGGCGACACGGAAATGTTGAATACTCATACTCTTCCTTTTTCAATATTATT

GAAGCATTTATCAGGGTTATTGTCTCATGAGCGGATACATATTTGAATGTATTTAGAAAAATAAACAAATAGGGGTTCCG

CGCACATTTCCCCGAAAAGTGCCACCTGACGTCTAAGAAACCATTATTATCATGACATTAACCTATAAAAATAGGCGTAT

CACGAGGCCCTTTCGTCTCGCGCGTTTCGGTGATGACGGTGAAAACCTCTGACACATGCAGCTCCCGGAGACGGTCACAG

CTTGTCTGTAAGCGGATGCCGGGAGCAGACAAGCCCGTCAGGGCGCGTCAGCGGGTGTTGGCGGGTGTCGGGCTGGCTT

AACTATGCGGCATCAGAGCAGATTGTACTGAGAGTGCACC
```

[SEQ ID NO: 39]
```
ATTGGCCATTGCATACGTTGTATCCATATCATAATATGTACATTTATATTGGCTCATGTCCAACATTACCGCCATGTTGA

CATTGATTATTGACTAGTTATTAATAGTAATCAATTACGGGGTCATTAGTTCATAGCCCATATATGGAGTTCCGCGTTAC

ATAACTTACGGTAAATGGCCCGCCTGGCTGACCGCCCAACGACCCCCGCCCATTGACGTCAATAATGACGTATGTTCCCA

TAGTAACGCCAATAGGGACTTTCCATTGACGTCAATGGGTGGAGTATTTACGGTAAACTGCCCACTTGGCAGTACATCAA

GTGTATCATATGCCAAGTACGCCCCCTATTGACGTCAATGACGGTAAATGGCCCGCCTGGCATTATGCCCAGTACATGAC

CTTATGGGACTTTCCTACTTGGCAGTACATCTACGTATTAGTCATCGCTATTACCATGGTGATGCGGTTTTGGCAGTACA

TCAATGGGCGTGGATAGCGGTTTGACTCACGGGGATTTCCAAGTCTCCACCCCATTGACGTCAATGGGAGTTTGTTTTGG

CACCAAAATCAACGGGACTTTCCAAAATGTCGTAACAACTCCGCCCCATTGACGCAAATGGGCGGTAGGCGTGTACGGTG

GGAGGTCTATATAAGCAGAGCTCGTTTAGTGAACCGGGGTCTCTCTGGTTAGACCAGATCTGAGCCTGGGAGCTCTCTGG

CTAACTAGGGAACCCACTGCTTAAGCCTCAATAAAGCTTGCCTTGAGTGCTTCAAGTAGTGTGTGCCCGTCTGTTGTGTG

ACTCTGGTAACTAGAGATCCCTCAGACCCTTTTAGTCAGTGTGGAAAATCTCTAGCAGTGGCGCCCGAACAGGGACTTGA

AAGCGAAAGGGAAACCAGAGGAGCTCTCTCGACGCAGGACTCGGCTTGCTGAAGCGCGCACGGCAAGAGGCGAGGGGCGG

CGACTGGTGAGTACGCCAAAAATTTTGACTAGCGGAGGCTAGAAGGAGAGAGACGGGTGCGAGAGCGTCAGTATTAAGCG

GGGGTGAATAAGATCGCGATGGGAAAAAATTCGGTTAAGGCCAGGGGGAAAGAAAAAATATAAATTAAAACATATAGTAT

GGGCAAGCAGGGAGCTAGAACGATTCGCAGTTAATCCTGGCCTGTTAGAAACATCAGAAGGCTGTAGACAAATACTGGGA

CAGCTACAACCATCCCTTCAGACAGGATCAGAAGAACTTAGATCATTATATAATACAGTAGCAACCCTCTATTGTGTGCA

TCAAAGGATAGAGATAAAAGACACCAAGGAAGCTTTAGACAAGATAGAGGAAGAGCAAAACAAAGTAAGACCACCGCAC
```

-continued

```
AGCAAGCGGCCGCTGATCTTCAGACCTGGAGGAGGAGATATGAGGGACAATTGGAGAAGTGAATTATATAAATATAAAGT
AGTAAAAATTGAACCATTAGGAGTAGCACCCACCAAGGCAAAGAGAAGAGTGGTGCAGAGAGAAAAAAGAGCAGTGGGAA
TAGGAGCTTTGTTCCTTGGGTTCTTGGGAGCAGCAGGAAGCACTATGGGCGCAGCGTCAATGACGCTGACGGTACAGGCC
AGACAATTATTGTCTGGTATAGTGCAGCAGCAGAACAATTTGCTGAGGGCTATTGAGGCGCAACAGCATCTGTTGCAACT
CACAGTCTGGGGCATCAAGCAGCTCCAGGCAAGAATCCTGGCTGTGGAAAGATACCTAAAGGATCAACAGCTCCTGGGGA
TTTGGGGTTGCTCTGGAAAACTCATTTGCACCACTGCTGTGCCTTGGAATGCTAGTTGGAGTAATAAATCTCTGGAACAG
ATTTGGAATCACACGACCTGGATGGAGTGGGACAGAGAAATTAACAATTACACAAGCTTAATACACTCCTTAATTGAAGA
ATCGCAAACCAGCAAGAAAAGAATGAACAAGAATTATTGGAATTAGATAAATGGGCAAGTTTGTGGAATTGGTTTAACA
TAACAAATTGGCTGTGGTATATAAAATTATTCATAATGATAGTAGGAGGCTTGGTAGGTTTAAGAATAGTTTTTGCTGTA
CTTTCTATAGTGAATAGAGTTAGGCAGGGATATTCACCATTATCGTTTCAGACCCACCTCCCAACCCCGAGGGGACCCGA
CAGGCCCGAAGGAATAGAAGAAGAAGGTGGAGAGAGAGACAGAGACAGATCCATTCGATTAGTGAACGGATCTCGACGGT
ATCGTTTTAAAAGAAAAGGGGGGATTGGGGGGTACAGTGCAGGGGAAAGAATAGTAGACATAATAGCAACAGACATACAA
ACTAAAGAATTACAAAAACAAATTACAAAAATTCAAAATTTTATCGGCGTGTTGGGGGTGGACCATCCTCTAGGTATTGA
ATAAGAAAAATGAAGTTAAGGTGGTTGATGGTAACACTATGCTAATAACTGCAGAGCCAGAAGCACCATAAGGGACATGA
TAAGGGAGCCAGCAGACCTCTGATCTCTTCCTGAATGCTAATCTTAAACATCCTGAGGAAGAATGGGACTTCCATTTGGG
GTGGGCCTATGATAGGGTAATAAGACAGTAGTGAATATCAAGCTACAAAAAGCCCCCTTTCAAATTCTTCTCAGTCCTAA
CTTTTCATACTAAGCCCAGTCCTTCCAAAGCAGACTGTGAAAGAGTGATAGTTCCGGGAGACTAGCACTGCAGATTCCGG
GTCACTGTGAGTGGGGGAGGCAGGGAAGAAGGGCTCACAGGACAGTCAAACCATGCCCCCTGTTTTTCCTTCTTCAAGTA
GACCTCTATAAGACAACAGAGACAACTAAGGCTGAGTGGCCAGGCGAGGAGAAACCATCTCGCCGTAAAACATGGAAGGA
ACACTTCAGGGGAAAGGTGGTATCTCTAAGCAAGAGAACTGAGTGGAGTCAAGGCTGAGAGATGCAGGATAAGCAAATGG
GTAGTGAAAAGACATTCATGAGGACAGCTAAAACAATAAGTAATGTAAAATACAGCATAGCAAAACTTTAACCTCCAAAT
CAAGCCTCTACTTGAATCCTTTTCTGAGGGATGAATAAGGCATAGGCATCAGGGGCTGTTGCCAATGTGCATTAGCTGTT
TGCAGCCTCACCTTCTTTCATGGAGTTTAAGATATAGTGTATTTTCCCAAGGTTTGAACTAGCTCTTCATTTCTTTATGT
TTTAAATGCACTGACCTCCCACATTCCCTTTTTAGTAAAATATTCAGAAATAATTTAAATACATCATTGCAATGAAAATA
AATGTTTTTTATTAGGCAGAATCCAGATGCTCAAGGCCCTTCATAATATCCCCCAGTTTAGTAGTTGGACTTAGGGAACA
AAGGAACCTTTAATAGAAATTGGACAGCAAGAAAGCGAGCTTAGTGATACTTGTGGGCCAGGGCATTAGCCACACCAGCC
ACCACTTTCTGATAGGCAGCCTGCACTGGTGGGGTGAATTCTTTGCCAAAGTGATGGGCCAGCACACAGACCAGCACGTT
GCCCAGGAGCTGTGGGAGGAAGATAAGAGGTATGAACATGATTAGCAAAAGGGCCTAGCTTGGACTCAGAATAATCCAGC
CTTATCCCAACCATAAAATAAAAGCAGAATGGTAGCTGGATTGTAGCTGCTATTAGCAATATGAAACCTCTTACATCAGT
TACAATTTATATGCAGAAATATTTATATGCAGAAATATTGCTATTGCCTTAACCCAGAAATTATCACTGTTATTCTTTAG
AATGGTGCAAAGAGGCATGATACATTGTATCATTATTGCCCTGAAAGAAAGAGATTAGGGAAAGTATTAGAAATAAGATA
AACAAAAAGTATATTAAAAGAAGAAAGCATTTTTTAAAATTACAAATGCAAAATTACCCTGATTTGGTCAATATGTGTA
CCCTGTTACTTCTCCCCTTCCTATGACATGAACTTAACCATAGAAAAGAAGGGGAAAGAAAACATCAAGGGTCCCATAGA
CTCACCCTGAAGTTCTCAGGATCCACGTGCAGCTTGTCACAGTGCAGCTCACTCAGCTGGGCAAAGGTGCCCTTGAGGTT
GTCCAGGTGAGCCAGGCCATCACTAAAGGCACCGAGCACTTTCTTGCCATGAGCCTTCACCTTAGGGTTGCCCATAACAG
CATCAGGAGTGGACAGATCCCCAAAGGACTCAAAGAACCTCTGGGTCCAAGGGTAGACCACCAGCAGCCTAAGGGTGGGA
AAATAGACCAATAGGCAGAGAGAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCAACTTCATCCACGTTCACCTTG
CCCCACAGGGCAGTAACGGCAGACTTCTCCTCAGGAGTCAGGTGCACCATGGTGTCTGTTTGAGGTTGCTAGTGAACACA
GTTGTGTCAGAAGCAAATGTAAGCAATAGATGGCTCTGCCCTGACTTTTATGCCCAGCCCTGGCTCCTGCCCTCCCTGCT
CCTGGGAGTAGATTGGCCAACCCTAGGGTGTGGCTCCACAGGGTGAGGTCTAAGTGATGACAGCCGTACCTGTCCTTGGC
```

```
TCTTCTGGCACTGGCTTAGGAGTTGGACTTCAAACCCTCAGCCCTCCCTCTAAGATATATCTCTTGGCCCCATACCATCA
GTACAAATTGCTACTAAAAACATCCTCCTTTGCAAGTGTATTTACTCTAGAATATGTCACATTCTGTCTCAGGCATCCAT
TTTCTTTATGATGCCGTTTGAGGTGGAGTTTTAGTCAGGTGGTCAGCTTCTCCTTTTTTTTGCCATCTGCCCTGTAAGCA
TCCTGCTGGGGACCCAGATAGGAGTCATCACTCTAGGCTGAGAACATCTGGGCACACACCCTAAGCCTCAGCATGACTCA
TCATGACTCAGCATTGCTGTGCTTGAGCCAGAAGGTTTGCTTAGAAGGTTACACAGAACCAGAAGGCGGGGGTGGGGCAC
TGACCCCGACAGGGGCCTGGCCAGAACTGCTCATGCTTGGACTATGGGAGGTCACTAATGGAGACACACAGAAATGTAAC
AGGAACTAAGGAAAAACTGAAGCTTATTTAATCAGAGATGAGATGCTGGAAGGGATAGAGGGAGCTGAGCTTGTAAAAAG
TATAGTAATCATTCAGCAAATGGTTTTGAAGCACCTGCTGGATGCTAAACACTATTTTCAGTGCTTGAATCATAAATAAG
AACAAAACATGTATCTTATTCCCCACAAGAGTCCAAGTAAAAAATAACAGTTAATTATAATGTGCTCTGTCCCCCAGGCT
GGAGTGCAGTGGCACGATCTCAGCTCACTGCAACCTCCGCCTCCCGGGTTCAAGCAATTCTCCTGCCTCAGCCACCCTAA
TAGCTGGGATTACAGGTGCACACCACCATGCCAGGCTAATTTTTGTACTTTTTGTAGAGGCAGGGTATCACCATGTTGTC
CAAGATGGTCTTGAACTCCTGAGCTCCAAGCAGTCCACCCACCTCAGCCTCCCAAAGTGCTATCTGCGGCCGCCTATCTG
TACCACTAGTCTCGAGAAGCTTTCATCAAAAAAGTCTAACCAGCTGCATTCGACTTTGACTGCAGCAGCTGGTTAGAAG
GTTCTACTGGAGGAGGGTCCCAGCCCATTGCTAAATTAACATCAGGCTCTGAGACTGGCAGTATATCTCTAACAGTGGTT
GATGCTATCTTCTGGAACTTGCCTGCTACATTGAGACCACTGACCCATACATAGGAAGCCCATAGCTCTGTCCTGAACTG
TTAGGCCACTGGTCCAGAGAGTGTGCATCTCCTTTGATCCTCATAATAACCCTATGAGATAGACACAATTATTACTCTTA
CTTTATAGATGATGATCCTGAAAACATAGGAGTCAAGGCACTTGCCCCTAGCTGGGGGTATAGGGGAGCAGTCCCATGTA
GTAGTAGAATGAAAAATGCTGCTATGCTGTGCCTCCCCCACCTTTCCCATGTCTGCCCTCTACTCATGGTCTATCTCTCC
TGGCTCCTGGGAGTCATGGACTCCACCCAGCACCACCAACCTGACCTAACCACCTATCTGAGCCTGCCAGCCTATAACCC
ATCTGGGCCCTGATAGCTGGTGGCCAGCCCTGACCCCACCCCACCCTCCCTGGAACCTCTGATAGACACATCTGGCACAC
CAGCTCGCAAAGTCACCGTGAGGGTCTTGTGTTTGCTGAGTCAAAATTCCTTGAAATCCAAGTCCTTAGAGACTCCTGCT
CCCAAATTTACAGTCATAGACTTCTTCATGGCTGTCTCCTTTATCCACAGAATGATTCCTTTGCTTCATTGCCCCATCCA
TCTGATCCTCCTCATCAGTGCAGCACAGGGCCCATGAGCAGTAGCTGCAGAGTCTCACATAGGTCTGGCACTGCCTCTGA
CATGTCCGACCTTAGGCAAATGCTTGACTCTTCTGAGCTCAGTCTTGTCATGGCAAAACAAAGATAATAATAGTGTTTTT
TTATGGAGTTAGCGTGAGGATGGAAAACAATAGCAAAATTGATTAGACTATAAAAGGTCTCAACAAATAGTAGTAGATTT
TATCATCCATTAATCCTTCCCTCTCCTCTCTTACTCATCCCATCACGTATGCCTCTTAATTTTCCCTTACCTATAATAAG
AGTTATTCCTCTTATTATATTCTTCTTATAGTGATTCTGGATATCAAAGTGGGAATGAGGGGCAGGCCACTAACGAAGAA
GATGTTTCTCAAAGAAGCCATTCTCCCCACATAGATCATCTCAGCAGGGTTCAGGAAGATAAAGGAGGATCAAGGTCGAA
GGTAGGAACTAAGGAAGAACACTGGGCAAGTGGATCCTAAATATATCATTTAAATGCATAAATAAGCAAACCCTGCTCGG
GAATGGGAGGGAGAGTCTCTGGAGTCCACCCCTTCTCGGCCCTGGCTCTGCAGATAGTGCTATCAAAGCCCTGACAGAGC
CCTGCCCATTGCTGGGCCTTGGAGTGAGTCAGCCTAGTAGAGAGGCAGGGCAAGCCATCTCATAGCTGCTGAGTGGGAGA
GAGAAAAGGGCTCATTGTCTATAAACTCAGGTCATGGCTATTCTTATTCTCACACTAAGAAAAAGAATGAGATGTCTACA
TATACCCTGCGTCCCCTCTTGTGTACTGGGGCCCCAAGAGCTCTCTAAAAGTGATGGCAAAGTCATTGCGCTAGATGCC
ATCCCATCTATTATAAACCTGCATTTGTCTCCACACACCAGTCATGGACAATAACCCTCCTCCCAGGTCCACGTGCTTGT
CTTTGTATAATACTCAAGTAATTTCGGAAAATGTATTCTTTCAATCTTGTTCTGTTATTCCTGTTTCAATGGCTTAGTAG
AAAAAGTACATACTTGTTTTCCCATAAATTGACAATAGACAATTTCACATCAATGTCTATATGGGTCGTTGTGTTTGCTG
TGTTTGCAAAAACTCACAATAACTTTATATTGTTACTACTCTAAGAAAGTTACAACATGGTGAATACAAGAGAAAGCTAT
TACAAGTCCAGAAAACAAAAGTTATCATCTTGAGGCCTCAGCTTTCTAGGAATAATATCAATATTACAAAACGCGTCGAC
GGTACCGTTAACGATCTTAGCCACTTTTTAAAAGAAAAGGGGGACTGGAAGGGCTAATTCACTCCCAACGAAGACAAGA
TATCCTGCTAGTCCTTCCTTTCTAAATGACGAGAGAGACAGAAGAATTCTTCAAGGTTAGTGTGTCCAGCATGCAACCTT
```

-continued

```
TCCTTCCTGGATGAGCATCCCTGGAGTAGGAGAGCCAGCCTGCCTCCTGCGCTGGCACAGAGCCCGGTTCCCTAGACAAC
TGCCTCTCCAAATCTGATGTCCAGCGCCACCTGGTGTCCACATCAAGCAGACACAATTAATAGTCAACCTGTTCAGGAAA
ACTGTGAGGGGGAAAAAAAAGAAAGAGGATTTATGAAGGGAAAAGAAAGTTTAGAGGATATGCCACGATTGGCTAGCAGC
TGCTTTTTGCCTGTACTGGGTCTCTCTGGTTAGACCAGATCTGAGCCTGGGAGCTCTCTGGCTAACTAGGGAACCCACTG
CTTAAGCCTCAATAAAGCTTGCCTTGAGTGCTTCATCCGGAATCAACCTCTGGATTACAAAATTTGTGAAAGATTGACTG
GTATTCTTAACTATGTTGCTCCTTTTACGCTATGTGGATACGCTGCTTTAATGCCTTTGTATCATGCTATTGCTTCCCGT
ATGGCTTTCATTTTCTCCTCCTTGTATAAATCCTGGTTGCTGTCTCTTTATGAGGAGTTGTGGCCCGTTGTCAGGCAACG
TGGCGTGGTGTGCACTGTGTTTGCTGACGCAACCCCCACTGGTTGGGGCATTGCCACCACCTGTCAGCTCCTTTCCGGGA
CTTTCGCTTTCCCCCTCCCTATTGCCACGGCGGAACTCATCGCCGCCTGCCTTGCCCGCTGCTGGACAGGGGCTCGGCTG
TTGGGCACTGACAATTCCGTGGTGTTGTCGGGGAAGCTGACGTCCTTTCCATGGCTGCTCGCCTGTGTTGCCACCTGGAT
TCTGCGCGGGACGTCCTTCTGCTACGTCCCTTCGGCCCTCAATCCAGCGGACCTTCCTTCCCGCGGCCTGCTGCCGGCTC
TGCGGCCTCTTCCGCGTCTTCGCCTTCGCCCTCAGACGAGTCGGATCTCCCTTTGGGCCGCCTCCCCGCCTGTCCGGTAG
CTTGCCAGCCTCGACTGTGCCTTCTAGTTGCCAGCCGTCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGAGTAGGTGTCATTCTATTCTGGGG
GGTGGGGTGGGGCAGGACAGCAAGGGGGAGGATTGGGAAGACAATAGCAGGCATGCAAGCTTGGCGTAATCATGGTCATA
GCTGTTTCCTGTGTGAAATTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCGGGAAACCTGTCGTGCCAG
CTGCATTAATGAATCGGCCAACGCGCGGGGAGAGGCGGTTTGCGTATTGGGCGCTCTTCCGCTTCCTCGCTCACTGACTC
GCTGCGCTCGGTCGTTCGGCTGCGGCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGACCCTGCCGCTTACCGGATACCTGTCCGCCT
TTCTCCCTTCGGGAAGCGTGGCGCTTTCTCATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATCCGGTAACTATCGTCTTGAGTCCAACCCGGT
AAGACACGACTTATCGCCACTGGCAGCAGCCACTGGTAACAGGATTAGCAGAGCGAGGTATGTAGGCGGTGCTACAGAGT
TCTTGAAGTGGTGGCCTAACTACGGCTACACTAGAAGAACAGTATTTGGTATCTGCGCTCTGCTGAAGCCAGTTACCTTC
GGAAAAAGAGTTGGTAGCTCTTGATCCGGCAAACAAACCACCGCTGGTAGCGGTGGTTTTTTTGTTTGCAAGCAGCAGAT
TACGCGCAGAAAAAAAGGATCTCAAGAAGATCCTTTGATCTTTTCTACGGGGTCTGACGCTCAGTGGAACGAAAACTCAC
GTTAAGGGATTTTGGTCATGAGATTATCAAAAAGGATCTTCACCTAGATCCTTTTAAATTAAAAATGAAGTTTTAAATCA
ATCTAAAGTATATATGAGTAAACTTGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGGAGGGCTTACCATCTGGCCCCAGTG
CTGCAATGATACCGCGAGACCCACGCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAAGCTAGAGTAAGTAGTTCGCCAGT
TAATAGTTTGCGCAACGTTGTTGCCATTGCTACAGGCATCGTGGTGTCACGCTCGTCGTTTGGTATGGCTTCATTCAGCT
CCGGTTCCCAACGATCAAGGCGAGTTACATGATCCCCCATGTTGTGCAAAAAAGCGGTTAGCTCCTTCGGTCCTCCGATC
GTTGTCAGAAGTAAGTTGGCCGCAGTGTTATCACTCATGGTTATGGCAGCACTGCATAATTCTCTTACTGTCATGCCATC
CGTAAGATGCTTTTCTGTGACTGGTGAGTACTCAACCAAGTCATTCTGAGAATAGTGTATGCGGCGACCGAGTTGCTCTT
GCCCGGCGTCAATACGGGATAATACCGCGCCACATAGCAGAACTTTAAAAGTGCTCATCATTGGAAAACGTTCTTCGGGG
CAAAACTCTCAAGGATCTTACCGCTGTTGAGATCCAGTTCGATGTAACCCACTCGTGCACCCAACTGATCTTCAGCATCT
TTTACTTTCACCAGCGTTTCTGGGTGAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATTGTCTCATGAGCGGATACATAT
```

-continued

TTGAATGTATTTAGAAAAATAAACAAATAGGGGTTCCGCGCACATTTCCCCGAAAAGTGCCACCTGACGTCTAAGAAACC

ATTATTATCATGACATTAACCTATAAAAATAGGCGTATCACGAGGCCCTTTCGTCTCGCGCGTTTCGGTGATGACGGTGA

AAACCTCTGACACATGCAGCTCCCGGAGACGGTCACAGCTTGTCTGTAAGCGGATGCCGGGAGCAGACAAGCCCGTCAGG

GCGCGTCAGCGGGTGTTGGCGGGTGTCGGGGCTGGCTTAACTATGCGGCATCAGAGCAGATTGTACTGAGAGTGCACC

[SEQ ID NO: 40]

ATTGGCCATTGCATACGTTGTATCCATATCATAATATGTACATTTATATTGGCTCATGTCCAACATTACCGCCATGTTGA

CATTGATTATTGACTAGTTATTAATAGTAATCAATTACGGGGTCATTAGTTCATAGCCCATATATGGAGTTCCGCGTTAC

ATAACTTACGGTAAATGGCCCGCCTGGCTGACCGCCCAACGACCCCCGCCCATTGACGTCAATAATGACGTATGTTCCCA

TAGTAACGCCAATAGGGACTTTCCATTGACGTCAATGGGTGGAGTATTTACGGTAAACTGCCCACTTGGCAGTACATCAA

GTGTATCATATGCCAAGTACGCCCCCTATTGACGTCAATGACGGTAAATGGCCCGCCTGGCATTATGCCCAGTACATGAC

CTTATGGGACTTTCCTACTTGGCAGTACATCTACGTATTAGTCATCGCTATTACCATGGTGATGCGGTTTTGGCAGTACA

TCAATGGGCGTGGATAGCGGTTTGACTCACGGGGATTTCCAAGTCTCCACCCCATTGACGTCAATGGGAGTTTGTTTTGG

CACCAAAATCAACGGGACTTTCCAAAATGTCGTAACAACTCCGCCCCATTGACGCAAATGGGCGGTAGGCGTGTACGGTG

GGAGGTCTATATAAGCAGAGCTCGTTTAGTGAACCGGGGTCTCTCTGGTTAGACCAGATCTGAGCCTGGGAGCTCTCTGG

CTAACTAGGGAACCCACTGCTTAAGCCTCAATAAAGCTTGCCTTGAGTGCTTCAAGTAGTGTGTGCCCGTCTGTTGTGTG

ACTCTGGTAACTAGAGATCCCTCAGACCCTTTTAGTCAGTGTGGAAAATCTCTAGCAGTGGCGCCCGAACAGGGACTTGA

AAGCGAAAGGGAAACCAGAGGAGCTCTCTCGACGCAGGACTCGGCTTGCTGAAGCGCGCACGGCAAGAGGCGAGGGGCGG

CGACTGGTGAGTACGCCAAAAATTTTGACTAGCGGAGGCTAGAAGGAGAGAGACGGGTGCGAGAGCGTCAGTATTAAGCG

GGGGTGAATAAGATCGCGATGGGAAAAAATTCGGTTAAGGCCAGGGGGAAAGAAAAAATATAAATTAAAACATATAGTAT

GGGCAAGCAGGGAGCTAGAACGATTCGCAGTTAATCCTGGCCTGTTAGAAACATCAGAAGGCTGTAGACAAATACTGGGA

CAGCTACAACCATCCCTTCAGACAGGATCAGAAGAACTTAGATCATTATATAATACAGTAGCAACCCTCTATTGTGTGCA

TCAAAGGATAGAGATAAAAGACACCAAGGAAGCTTTAGACAAGATAGAGGAAGAGCAAAACAAAAGTAAGACCACCGCAC

AGCAAGCGGCCGCTGATCTTCAGACCTGGAGGAGGAGATATGAGGGACAATTGGAGAAGTGAATTATATAAATATAAAGT

AGTAAAAATTGAACCATTAGGAGTAGCACCCACCAAGGCAAAGAGAAGAGTGGTGCAGAGAGAAAAAAGAGCAGTGGGAA

TAGGAGCTTTGTTCCTTGGGTTCTTGGGAGCAGCAGGAAGCACTATGGGCGCAGCGTCAATGACGCTGACGGTACAGGCC

AGACAATTATTGTCTGGTATAGTGCAGCAGCAGAACAATTTGCTGAGGGCTATTGAGGCGCAACAGCATCTGTTGCAACT

CACAGTCTGGGGCATCAAGCAGCTCCAGGCAAGAATCCTGGCTGTGGAAAGATACCTAAAGGATCAACAGCTCCTGGGGA

TTTGGGGTTGCTCTGGAAAACTCATTTGCACCACTGCTGTGCCTTGGAATGCTAGTTGGAGTAATAAATCTCTGGAACAG

ATTTGGAATCACACGACCTGGATGGAGTGGGACAGAGAAATTAACAATTACACAAGCTTAATACACTCCTTAATTGAAGA

ATCGCAAAACCAGCAAGAAAAGAATGAACAAGAATTATTGGAATTAGATAAATGGGCAAGTTTGTGGAATTGGTTTAACA

TAACAAATTGGCTGTGGTATATAAAATTATTCATAATGATAGTAGGAGGCTTGGTAGGTTTAAGAATAGTTTTTGCTGTA

CTTTCTATAGTGAATAGAGTTAGGCAGGGATATTCACCATTATCGTTTCAGACCCACCTCCCAACCCCGAGGGGACCCGA

CAGGCCCGAAGGAATAGAAGAAGAAGGTGGAGAGAGAGACAGAGACAGATCCATTCGATTAGTGAACGGATCTCGACGGT

ATCGTTTTAAAAGAAAAGGGGGGATTGGGGGGTACAGTGCAGGGGAAAGAATAGTAGACATAATAGCAACAGACATACAA

ACTAAAGAATTACAAAAACAAATTACAAAAATTCAAAATTTTATCGGCGTGTTGGGGGTGGACCATCCTCTAGGTATTGA

ATAAGAAAATGAAGTTAAGGTGGTTGATGGTAACACTATGCTAATAACTGCAGAGCCAGAAGCACCATAAGGGACATGA

TAAGGGAGCCAGCAGACCTCTGATCTCTTCCTGAATGCTAATCTTAAACATCCTGAGGAAGAATGGGACTTCCATTTGGG

GTGGGCCTATGATAGGGTAATAAGACAGTAGTGAATATCAAGCTACAAAAAGCCCCCTTTCAAATTCTTCTCAGTCCTAA

CTTTTCATACTAAGCCCAGTCCTTCCAAAGCAGACTGTGAAAGAGTGATAGTTCCGGGAGACTAGCACTGCAGATTCCGG

GTCACTGTGAGTGGGGAGGCAGGGAAGAAGGGCTCACAGGACAGTCAAACCATGCCCCCTGTTTTTCCTTCTTCAAGTA

GACCTCTATAAGACAACAGAGACAACTAAGGCTGAGTGGCCAGGCGAGGAGAAACCATCTCGCCGTAAAACATGGAAGGA

-continued

```
ACACTTCAGGGGAAAGGTGGTATCTCTAAGCAAGAGAACTGAGTGGAGTCAAGGCTGAGAGATGCAGGATAAGCAAATGG

GTAGTGAAAAGACATTCATGAGGACAGCTAAAACAATAAGTAATGTAAAATACAGCATAGCAAAACTTTAACCTCCAAAT

CAAGCCTCTACTTGAATCCTTTTCTGAGGGATGAATAAGGCATAGGCATCAGGGGCTGTTGCCAATGTGCATTAGCTGTT

TGCAGCCTCACCTTCTTTCATGGAGTTTAAGATATAGTGTATTTTCCCAAGGTTTGAACTAGCTCTTCATTTCTTTATGT

TTTAAATGCACTGACCTCCCACATTCCCTTTTTAGTAAAATATTCAGAAATAATTTAAATACATCATTGCAATGAAAATA

AATGTTTTTTATTAGGCAGAATCCAGATGCTCAAGGCCCTTCATAATATCCCCAGTTTAGTAGTTGGACTTAGGGAACA

AAGGAACCTTTAATAGAAATTGGACAGCAAGAAAGCGAGCTTAGTGATACTTGTGGGCCAGGGCATTAGCCACACCAGCC

ACCACTTTCTGATAGGCAGCCTGCACTGGTGGGGTGAATTCTTTGCCAAAGTGATGGGCCAGCACACAGACCAGCACGTT

GCCCAGGAGCTGTGGGAGGAAGATAAGAGGTATGAACATGATTAGCAAAAGGGCCTAGCTTGGACTCAGAATAATCCAGC

CTTATCCCAACCATAAAATAAAAGCAGAATGGTAGCTGGATTGTAGCTGCTATTAGCAATATGAAACCTCTTACATCAGT

TACAATTTATATGCAGAAATATTTATATGCAGAAATATTGCTATTGCCTTAACCCAGAAATTATCACTGTTATTCTTTAG

AATGGTGCAAAGAGGCATGATACATTGTATCATTATTGCCCTGAAAGAAAGAGATTAGGGAAAGTATTAGAAATAAGATA

AACAAAAAGTATATTAAAAGAAGAAAGCATTTTTAAAATTACAAATGCAAAATTACCCTGATTTGGTCAATATGTGTA

CCCTGTTACTTCTCCCCTTCCTATGACATGAACTTAACCATAGAAAAGAAGGGGAAAGAAAACATCAAGGGTCCCATAGA

CTCACCCTGAAGTTCTCAGGATCCACGTGCAGCTTGTCACAGTGCAGCTCACTCAGCTGGGCAAAGGTGCCCTTGAGGTT

GTCCAGGTGAGCCAGGCCATCACTAAAGGCACCGAGCACTTTCTTGCCATGAGCCTTCACCTTAGGGTTGCCCATAACAG

CATCAGGAGTGGACAGATCCCCAAAGGACTCAAAGAACCTCTGGGTCCAAGGGTAGACCACCAGCAGCCTAAGGGTGGGA

AAATAGACCAATAGGCAGAGAGAGTCAGTGCCTATCAGAAACCCAAGAGTCTTCTCTGTCTCCACATGCCCAGTTTCTAT

TGGTCTCCTTAAACCTGTCTTGTAACCTTGATACCAACCTGCCCAGGGCCTCACCACCAACTTCATCCACGTTCACCTTG

CCCCACAGGGCAGTAACGGCAGACTTCTCCTCAGGAGTCAGGTGCACCATGGTGTCTGTTTGAGGTTGCTAGTAACACA

GTTGTGTCAGAAGCAAATGTAAGCAATAGATGGCTCTGCCCTGACTTTTATGCCCAGCCCTGGCTCCTGCCCTCCCTGCT

CCTGGGAGTAGATTGGCCAACCCTAGGGTGTGGCTCCACAGGGTGAGGTCTAAGTGATGACAGCCGTACCTGTCCTTGGC

TCTTCTGGCACTGGCTTAGGAGTTGGACTTCAAACCCTCAGCCCTCCCTCTAAGATATATCTCTTGGCCCCATACCATCA

GTACAAATTGCTACTAAAAACATCCTCCTTTGCAAGTGTATTTACGGCATCTGTGAAGGAAAGAAACATCTCCTCTAAAC

CACTATGCTGCTAGAGCCTCTTTTCTGTACTCAAGCCTCATTCAGACACTAGTGTCACCAGTCTCCTCATATACCTATTG

TATTTTCTTCTTCTTGCTGGTTTAGTCATGTTTTCTGGGAGCTTAGGGGCTTATTTTATTTTGTTTTGTTTTCTAATCAA

CAGAGATGGGCAAACCCATTATTTTTTTCTTTAGACTTGGGATGGTGATAGCTGGGCAGCGTCAGAAACTGTGTGTGGAT

ATAGATAAGAGCTCGGACTATGCTGAGCTGTGATGAGGGAGGGACCTAGCCAAAGGCAGTGAGAGTCAGAATGCTCCTGC

TATTGCCTTCTCAGTCCCCACGCTTGGTTTCTACACAAGTAGATACATAGAAAAGGCTATAGGTTAGTGTTTGAGAGTCC

TGCATGAGTTAGTTGCTCAGAAATGCCCGATAAATATGTTATGTGTGTTTATGTATATATATGTTTTATATATATATATG

TGTGTGTGTGTGTGTGTGTTGTGTTTACAAATATGTGATTATCATCAAAACGTGAGGGCTAAAGTGACCAGATAAC

TTGCAGGTCTAGACACCCTTTTCCGGCACGCAGATAGTCAATATCTTCAGCGTCCCCAAGGCCTGCAAGGGTGGGCCCC

ATATCTGGAAGTCCCAGGCGGAGCTGGGAGTTGGTCAAGTCTGGGCTGTGGGGCAGGGAGTGCTGGGGATGGCTCGAG

AAGCTTTCATCAAAAAAGTCTAACCAGCTGCATTCGACTTTGACTGCAGCAGCTGGTTAGAAGGTTCTACTGGAGGAGG

GTCCCAGCCCATTGCTAAATTAACATCAGGCTCTGAGACTGGCAGTATATCTCTAACAGTGGTTGATGCTATCTTCTGGA

ACTTGCCTGCTACATTGAGACCACTGACCCATACATAGGAAGCCCATAGCTCTGTCCTGAACTGTTAGGCCACTGGTCCA

GAGAGTGTGCATCTCCTTTGATCCTCATAATAACCCTATGAGATAGACACAATTATTACTCTTACTTTATAGATGATGAT

CCTGAAAACATAGGAGTCAAGGCACTTGCCCCTAGCTGGGGGTATAGGGGAGCAGTCCCATGTAGTAGTAGAATGAAAAA

TGCTGCTATGCTGTGCCTCCCCCACCTTTCCCATGTCTGCCCTCTACTCATGGTCTATCTCCTGGCTCCTGGGAGTCA

TGGACTCCACCCAGCACCACCAACCTGACCTAACCACCTATCTGAGCCTGCCAGCCTATAACCCATCTGGGCCCTGATAG
```

-continued

```
CTGGTGGCCAGCCCTGACCCCACCCCACCCTCCCTGGAACCTCTGATAGACACATCTGGCACACCAGCTCGCAAAGTCAC

CGTGAGGGTCTTGTGTTTGCTGAGTCAAAATTCCTTGAAATCCAAGTCCTTAGAGACTCCTGCTCCCAAATTTACAGTCA

TAGACTTCTTCATGGCTGTCTCCTTTATCCACAGAATGATTCCTTTGCTTCATTGCCCCATCCATCTGATCCTCCTCATC

AGTGCAGCACAGGGCCCATGAGCAGTAGCTGCAGAGTCTCACATAGGTCTGGCACTGCCTCTGACATGTCCGACCTTAGG

CAAATGCTTGACTCTTCTGAGCTCAGTCTTGTCATGGCAAAACAAAGATAATAATAGTGTTTTTTTATGGAGTTAGCGTG

AGGATGGAAAACAATAGCAAAATTGATTAGACTATAAAAGGTCTCAACAAATAGTAGTAGATTTTATCATCCATTAATCC

TTCCCTCTCCTCTCTTACTCATCCCATCACGTATGCCTCTTAATTTTCCCTTACCTATAATAAGAGTTATTCCTCTTATT

ATATTCTTCTTATAGTGATTCTGGATATCAAAGTGGGAATGAGGGGCAGGCCACTAACGAAGAAGATGTTTCTCAAAGAA

GCCATTCTCCCCACATAGATCATCTCAGCAGGGTTCAGGAAGATAAAGGAGGATCAAGGTCGAAGGTAGGAACTAAGGAA

GAACACTGGGCAAGTGGATCCTAAATATATCATTTAAATGCATAAATAAGCAAACCCTGCTCGGGAATGGGAGGGAGAGT

CTCTGGAGTCCACCCCTTCTCGGCCCTGGCTCTGCAGATAGTGCTATCAAAGCCCTGACAGAGCCCTGCCCATTGCTGGG

CCTTGGAGTGAGTCAGCCTAGTAGAGAGGCAGGGCAAGCCATCTCATAGCTGCTGAGTGGGAGAGAGAAAAGGGCTCATT

GTCTATAAACTCAGGTCATGGCTATTCTTATTCTCACACTAAGAAAAAGAATGAGATGTCTACATATACCCTGCGTCCCC

TCTTGTGTACTGGGGCCCCCAAGAGCTCTCTAAAAGTGATGGCAAAGTCATTGCGCTAGATGCCATCCCATCTATTATAA

ACCTGCATTTGTCTCCACACACCAGTCATGGACAATAACCCTCCTCCCAGGTCCACGTGCTTGTCTTTGTATAATACTCA

AGTAATTTCGGAAAATGTATTCTTTCAATCTTGTTCTGTTATTCCTGTTTCAATGGCTTAGTAGAAAAAGTACATACTTG

TTTTCCCATAAATTGACAATAGACAATTTCACATCAATGTCTATATGGGTCGTTGTGTTTGCTGTGTTTGCAAAAACTCA

CAATAACTTTATATTGTTACTACTCTAAGAAAGTTACAACATGGTGAATACAAGAGAAAGCTATTACAAGTCCAGAAAAC

AAAAGTTATCATCTTGAGGCCTCAGCTTTCTAGGAATAATATCAATATTACAAAACGCGTCGACGGTACCGTTAACGATC

TTAGCCACTTTTTAAAAGAAAAGGGGGGACTGGAAGGGCTAATTCACTCCCAACGAAGACAAGATATCCTGCTAGTCCTT

CCTTTCTAAATGACGAGAGAGACAGAAGAATTCTTCAAGGTTAGTGTGTCCAGCATGCAACCTTTCCTTCCTGGATGAGC

ATCCCTGGAGTAGGAGAGCCAGCCTGCCTCCTGCGCTGGCACAGAGCCCGGTTCCCTAGACAACTGCCTCTCCAAATCTG

ATGTCCAGCGCCACCTGGTGTCCACATCAAGCAGACACAATTAATAGTCAACCTGTTCAGGAAAACTGTGAGGGGGAAAA

AAAAGAAAGAGGATTTATGAAGGGAAAAGAAAGTTTAGAGGATATGCCACGATTGGCTAGCAGCTGCTTTTTGCCTGTAC

TGGGTCTCTCTGGTTAGACCAGATCTGAGCCTGGGAGCTCTCTGGCTAACTAGGGAACCCACTGCTTAAGCCTCAATAAA

GCTTGCCTTGAGTGCTTCATCCGGAATCAACCTCTGGATTACAAAATTTGTGAAAGATTGACTGGTATTCTTAACTATGT

TGCTCCTTTTACGCTATGTGGATACGCTGCTTTAATGCCTTTGTATCATGCTATTGCTTCCCGTATGGCTTTCATTTTCT

CCTCCTTGTATAAATCCTGGTTGCTGTCTCTTTATGAGGAGTTGTGGCCCGTTGTCAGGCAACGTGGCGTGGTGTGCACT

GTGTTTGCTGACGCAACCCCCACTGGTTGGGGCATTGCCACCACCTGTCAGCTCCTTTCCGGGACTTTCGCTTTCCCCCT

CCCTATTGCCACGGCGGAACTCATCGCCGCCTGCCTTGCCCGCTGCTGGACAGGGGCTCGGCTGTTGGGCACTGACAATT

CCGTGGTGTTGTCGGGGAAGCTGACGTCCTTTCCATGGCTGCTCGCCTGTGTTGCCACCTGGATTCTGCGCGGGACGTCC

TTCTGCTACGTCCCTTCGGCCCTCAATCCAGCGGACCTTCCTTCCCGCGGCCTGCTGCCGGCTCTGCGGCCTCTTCCGCG

TCTTCGCCTTCGCCCTCAGACGAGTCGGATCTCCCTTTGGGCCGCCTCCCCGCCTGTCCGGTAGCTTGCCAGCCTCGACT

GTGCCTTCTAGTTGCCAGCCGTCTGTTGTTTGCCCCTCCCCCGTGCCTTCCTTGACCCTGGAAGGTGCCACTCCCACTGT

CCTTTCCTAATAAAATGAGGAAATTGCATCGCATTGTCTGAGTAGGTGTCATTCTATTCTGGGGGGTGGGTGGGGCAGG

ACAGCAAGGGGGAGGATTGGGAAGACAATAGCAGGCATGCAAGCTTGGCGTAATCATGGTCATAGCTGTTTCCTGTGTGA

AATTGTTATCCGCTCACAATTCCACACAACATACGAGCCGGAAGCATAAAGTGTAAAGCCTGGGGTGCCTAATGAGTGAG

CTAACTCACATTAATTGCGTTGCGCTCACTGCCCGCTTTCCAGTCGGGAAACCTGTCGTGCCAGCTGCATTAATGAATCG

GCCAACGCGCGGGGAGAGGCGGTTTGCGTATTGGGCGCTCTTCCGCTTCCTCGCTCACTGACTCGCTGCGCTCGGTCGTT

CGGCTGCGGCGAGCGGTATCAGCTCACTCAAAGGCGGTAATACGGTTATCCACAGAATCAGGGGATAACGCAGGAAAGAA

CATGTGAGCAAAAGGCCAGCAAAAGGCCAGGAACCGTAAAAAGGCCGCGTTGCTGGCGTTTTTCCATAGGCTCCGCCCCC
```

-continued

```
CTGACGAGCATCACAAAAATCGACGCTCAAGTCAGAGGTGGCGAAACCCGACAGGACTATAAAGATACCAGGCGTTTCCC

CCTGGAAGCTCCCTCGTGCGCTCTCCTGTTCCGACCCTGCCGCTTACCGGATACCTGTCCGCCTTTCTCCCTTCGGGAAG

CGTGGCGCTTTCTCATAGCTCACGCTGTAGGTATCTCAGTTCGGTGTAGGTCGTTCGCTCCAAGCTGGGCTGTGTGCACG

AACCCCCCGTTCAGCCCGACCGCTGCGCCTTATCCGGTAACTATCGTCTTGAGTCCAACCCGGTAAGACACGACTTATCG

CCACTGGCAGCAGCCACTGGTAACAGGATTAGCAGAGCGAGGTATGTAGGCGGTGCTACAGAGTTCTTGAAGTGGTGGCC

TAACTACGGCTACACTAGAAGAACAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGCAGCAGATTACGCGCAGAAAAAA

GGATCTCAAGAAGATCCTTTGATCTTTTCTACGGGGTCTGACGCTCAGTGGAACGAAAACTCACGTTAAGGGATTTTGGT

CATGAGATTATCAAAAGGATCTTCACCTAGATCCTTTTAAATTAAAAATGAAGTTTTAAATCAATCTAAAGTATATATG

AGTAAACTTGGTCTGACAGTTACCAATGCTTAATCAGTGAGGCACCTATCTCAGCGATCTGTCTATTTCGTTCATCCATA

GTTGCCTGACTCCCCGTCGTGTAGATAACTACGATACGGGAGGGCTTACCATCTGGCCCCAGTGCTGCAATGATACCGCG

AGACCCACGCTCACCGGCTCCAGATTTATCAGCAATAAACCAGCCAGCCGGAAGGGCCGAGCGCAGAAGTGGTCCTGCAA

CTTTATCCGCCTCCATCCAGTCTATTAATTGTTGCCGGGAAGCTAGAGTAAGTAGTTCGCCAGTTAATAGTTTGCGCAAC

GTTGTTGCCATTGCTACAGGCATCGTGGTGTCACGCTCGTCGTTTGGTATGGCTTCATTCAGCTCCGGTTCCCAACGATC

AAGGCGAGTTACATGATCCCCCATGTTGTGCAAAAAAGCGGTTAGCTCCTTCGGTCCTCCGATCGTTGTCAGAAGTAAGT

TGGCCGCAGTGTTATCACTCATGGTTATGGCAGCACTGCATAATTCTCTTACTGTCATGCCATCCGTAAGATGCTTTTCT

GTGACTGGTGAGTACTCAACCAAGTCATTCTGAGAATAGTGTATGCGGCGACCGAGTTGCTCTTGCCCGGCGTCAATACG

GGATAATACCGCGCCACATAGCAGAACTTTAAAAGTGCTCATCATTGGAAAACGTTCTTCGGGGCAAAACTCTCAAGGAT

CTTACCGCTGTTGAGATCCAGTTCGATGTAACCCACTCGTGCACCCAACTGATCTTCAGCATCTTTTACTTTCACCAGCG

TTTCTGGGTGAGCAAAAACAGGAAGGCAAATGCCGCAAAAAAGGGAATAAGGGCGACACGGAAATGTTGAATACTCATA

CTCTTCCTTTTCAATATTATTGAAGCATTTATCAGGGTTATTGTCTCATGAGCGGATACATATTTGAATGTATTTAGAA

AAATAAACAAATAGGGGTTCCGCGCACATTTCCCCGAAAAGTGCCACCTGACGTCTAAGAAACCATTATTATCATGACAT

TAACCTATAAAAATAGGCGTATCACGAGGCCCTTTCGTCTCGCGCGTTTCGGTGATGACGGTGAAAACCTCTGACACATG

CAGCTCCCGGAGACGGTCACAGCTTGTCTGTAAGCGGATGCCGGGAGCAGACAAGCCCGTCAGGGCGCGTCAGCGGGTGT

TGGCGGGTGTCGGGGCTGGCTTAACTATGCGGCATCAGAGCAGATTGTACTGAGAGTGCACC
```

[SEQ ID NO: 76]

```
attggccattgcatacgttgtatccatatcataatatgtacatttatattggctcatgtccaacattaccgccatgttga cattgattattgactagttattaatagtaatcaattacggggtcattagttcatagcccatatatggagttccgcgttac ataacttacggtaaatggcccgcctggctgaccgcccaacgacccccgcccattgacgtcaataatgacgtatgttccca tagtaacgccaatagggactttccattgacgtcaatgggtggagtatttacggtaaactgcccacttggcagtacatcaa gtgtatcatatgccaagtacgccccctattgacgtcaatgacggtaaatggcccgcctggcattatgcccagtacatgac cttatgggactttcctacttggcagtacatctacgtattagtcatcgctattaccatggtgatgcggttttggcagtaca tcaatgggcgtggatagcggtttgactcacggggatttccaagtctccaccccattgacgtcaatgggagtttgttttgg caccaaaatcaacgggactttccaaaatgtcgtaacaactccgccccattgacgcaaatgggcggtaggcgtgtacggtg ggaggtctatataagcagagctcgtttagtgaaccggggtctctctggttagaccagatctgagcctgggagctctctgg ctaactagggaacccactgcttaagcctcaataaagcttgccttgagtgcttcaagtagtgtgtgcccgtctgttgtgtg actctggtaactagagatccctcagacccttttagtcagtgtggaaaatctctagcagtggcgcccgaacagggacttga aagcgaaagggaaaccagaggagctctctcgacgcaggactcggcttgctgaagcgcgcacggcaagaggcgaggggcgg cgactggtgagtacgccaaaattttgactagcggaggctagaaggagagacgggtgcgagagcgtcagtattaagcg ggggtgaataagatcgcgatggaaaaaattcggttaaggccaggggaagaaaaaatataaattaaaacatatagtat gggcaagcagggagctagaacgattcgcagttaatcctggcctgttagaaacatcagaaggctgtagacaaatactggga
```

-continued

```
cagctacaaccatcccttcagacaggatcagaagaacttagatcattatataatacagtagcaaccctctattgtgtgca tcaaaggatagagataaaagacaccaaggaagctttagacaagatagaggaagagcaaaacaaaagtaagaccaccgcac agcaagcggccgctgatcttcagacctggaggaggagatatgagggacaattggagaagtgaattatataaatataaagt agtaaaaattgaaccattaggagtagcacccaccaaggcaaagagaagagtggtgcagagagaaaaaagagcagtgggaa taggagctttgttccttgggttcttgggagcagcaggaagcactatgggcgcagcgtcaatgacgctgacggtacaggcc agacaattattgtctggtatagtgcagcagcagaacaatttgctgagggctattgaggcgcaacagcatctgttgcaact cacagtctgggcatcaagcagctccaggcaagaatcctggctgtggaaagatacctaaaggatcaacagctcctgggga tttggggttgctctggaaaactcatttgcaccactgctgtgccttggaatgctagttggagtaataaatctctggaacag atttggaatcacacgacctggatggagtgggacagagaaattaacaattacacaagcttaatacactccttaattgaaga atcgcaaaaccagcaagaaaagaatgaacaagaattattggaattagatgaatgggcaagtttgtggaattggtttaaca taacaaattggctgtggtatataaaattattcataatgatagtaggaggcttggtaggtttaagaatagttttgctgta ctttctatagtgaatagagttaggcagggatattccacaattatcgtttcagacccacctcccaaccccgagggaccga caggcccgaaggaatagaagaagaaggtggagagagagacagagacagatccattcgattagtgaacggatctcgacggt atcgttttaaaagaaaaggggggattgggggtacagtgcaggggaaagaatagtagacataatagcaacagacatacaa actaaagaattacaaaaacaaattacaaaaattcaaaattttatcggcgtgttgggggtggaccatcctctaggtattga ataagaaaatgaagttaaggtggttgatggtaacactatgctaataactgcagagccagaagcaccataagggacatga taagggagccagcagacctctgatctcttcctgaatgctaatcttaaacatcctgaggaagaatgggacttccatttggg gtgggcctatgatagggtaataagacagtagtgaatatcaagctacaaaaagcccccttttcaaattcttctcagtcctaa cttttcatactaagcccagtccttccaaagcagactgtgaaagagtgatagttccgggagactagcactgcagattccgg gtcactgtgagtgggggaggcagggaagaagggctcacaggacagtcaaaccatgccccctgtttttccttcttcaagta gacctctataagacaacagagacaactaaggctgagtggccaggcgaggagaaaccatctcgccgtaaaacatggaagga acacttcaggggaaaggtggtatctctaagcaagagaactgagtggagtcaaggctgagagatgcaggataagcaaatgg gtagtgaaaagacattcatgaggacagctaaaacaataagtaatgtaaaatacagcatagcaaaactttaacctccaaat caagcctctacttgaatccttttctgagggatgaataaggcataggcatcagggctgttgccaatgtgcattagctgtt tgcagcctcaccttctttcatggagtttaagatatagtgtattttcccaaggtttgaactagctcttcatttctttatgt tttaaatgcactgacctcccacattcccttttagtaaaatattcagaaataattaaatacatcattgcaatgaaaata aatgttttttattaggcagaatccagatgctcaaggcccttcataatatcccccagtttagtagttggacttagggaaca aaggaacctttaatagaaattggacagcaagaaagcgagcttagtgatacttgtgggccagggcattagccacaccagcc accactttctgataggcagcctgcactggtggggtgAATTCTTTGCCAAAGTGATGGGCCAGCACACAGACCAGCACGTT

GCCCAGGAGCTGTGGGAGGAAGATAAGAGGTATGAACATGATTAGCAAAAGGGCCTAGCTTGGACTCAGAATAATCCAGC

CTTATCCCAACCATAAAATAAAAGCAGAATGGTAGCTGGATTGTAGCTGCTATTAGCAATATGAAACCTCTTACATCAGT

TACAATTTATATGCAGAAATATTTATATGCAGAAATATTGCTATTGCCTTAACCCAGAAATTATCACTGTTATTCTTTAG

AATGGTGCAAAGAGGCATGATACATTGTATCATTATTGCCCTGAAAGAAAGAGATTAGGGAAAGTATTAGAAATAAGATA

AACAAAAAGTATATTAAAAGAAGAAAGCATTTTTTAAAATTACAAATGCAAAATTACCCTGATTTGGTCAATATGTGTA

CCCTGTTACTTCTCCCCTTCCTATGACATGAACTTAACCATAGAAAAGAAGGGGAAAGAAAACATCAAGGGTCCCATAGA

CTCACCCTGAAGTTCTCAGGATCCACGTGCAGCTTGTCACAGTGCAGCTCACTCAGctgGGCAAAGGTGCCCTTGAGGTT

GTCCAGGTGAGCCAGGCCATCACTAAAGGCACCGAGCACTTTCTTGCCATGAGCCTTCACCTTAGGGTTGCCCATAACAG

CATCAGGAGTGGACAGATCCCCAAAGGACTCAAAGAACCTCTGGGTCCAAGGGTAGACCACCAGCAGCCTAAGGGTGGGA

AAATAGACCAATAGGCAGAGAGTCAGTGCCTATCAGAAACCCAAGAGTCTTCTCTGTCTCCACATGCCCAGTTTCTAT

TGGTCTCCTTAAACCTGTCTTGTAACCTTGATACCAACCTGCCCAGGGCCTCACCACCAACTTCATCCACGTTCACCTTG
```

-continued

```
CCCCACAGGGCAGTAACGGCAGACTTCTCCTCAGGAGTCAGGTGCACCATGGTGTCTGTTTGAGGTTGCTAGTGAACACA

GTTGTGTCAGAAGCAAATGTAAGCAATAGATGGCTCTGCCCTGACTTTTATGCCCAGCCCTGGCTCCTGCCCTCCCTGCT

CCTGGGAGTAGATTGGCCAACCctagggtgtggctccacagggtgaggtctaagtgatgacagccgtacctgtccttggc tcttctggcactggcttaggagttggacttcaaaccctcagccctccctctaagatatatctcttggcccccataccatca gtacaaattgctactaaaaacatcctcctttgcaagtgtatttacCACCCTTTTCCGGCACGCAGATAGTCAATATCTTC

AGCGTCCCCAAGGCCTGCAAGGGTGGGGCCCCATATCTGGAAGTCCCAGGCGGAGCTGGGAGTTGGTCAAGTCTGGGCTG

TGGGGGCAGGGAGTGCTGGGGGATGGacgcgtcgacggtaccgttaacgatcttagccactttttaaaagaaaagggggg actggaagggctaattcactcccaacgaagacaagatatcctgCTAGTCCTTCCTTTCTAAATGACGAGAGAGACAGAAG

AATTCTTCAAGGTTAGTGTGTCCAGCATGCAACCTTTCCTTCCTGGATGAGCATCCCTGGAGTAGGAGAGCCAGCCTGCC

TCCTGCGCTGGCACAGAGCCCGGTTCCCTAGACAACTGCCTCTCCAAATCTGATGTCCAGCGCCACCTGGTGTCCACATC

AAGCAGACACAATTAATAGTCAACCTGTTCAGGAAAACTGTGAGGGGGAAAAAAAAGAAAGAGGATTTATGAAGGGAAAA

GAAAGTTTAGAGGATATGCCACGATTGGctagcagctgcttttttgcctgtactgggtctctctggttagaccagatctga gcctgggagctctctggctaactagggaacccactgcttaagcctcaataaagcttgccttgagtgcttcatccggAATC

AACCTCTGGATTACAAAATTTGTGAAAGATTGACTGGTATTCTTAACTATGTTGCTCCTTTTACGCTATGTGGATACGCT

GCTTTAATGCCTTTGTATCATGCTATTGCTTCCCGTATGGCTTTCATTTTCTCCTCCTTGTATAAATCCTGGTTGCTGTC

TCTTTATGAGGAGTTGTGGCCCGTTGTCAGGCAACGTGGCGTGGTGTGCACTGTGTTTGCTGACGCAACCCCCACTGGTT

GGGGCATTGCCACCACCTGTCAGCTCCTTTCCGGGACTTTCGCTTTCCCCCTCCCTATTGCCACGGCGGAACTCATCGCC

GCCTGCCTTGCCCGCTGCTGGACAGGGGCTCGGCTGTTGGGCACTGACAATTCCGTGGTGTTGTCGGGGAAGCTGACGTC

CTTTCCATGGCTGCTCGCCTGTGTTGCCACCTGGATTCTGCGCGGGACGTCCTTCTGCTACGTCCCTTCGGCCCTCAATC

CAGCGGACCTTCCTTCCCGCGGCCTGCTGCCGGCTCTGCGGCCTCTTCCGCGTCTTCGCCTTCGCCCTCAGACGAGTCGG

ATCTCCCTTTGGGCCGCCTCCCCGCCTGtccggtAGCTTGCCAGCCTCGACTGTGCCTTCTAGTTGCCAGCCGTCTGTTG

TTTGCCCCTCCCCCGTGCCTTCCTTGACCCTGGAAGGTGCCACTCCCACTGTCCTTTCCTAATAAAATGAGGAAATTGCA

TCGCATTGTCTGAGTAGGTGTCATTCTATTCTGGGGGGTGGGGTGGGCAGGACAGCAAGGGGGAGGATTGGGAAGACAA

TAGCAGGCATGcaagcttggcgtaatcatggtcatagctgtttcctgtgtgaaattgttatccgctcacaattccacaca acatacgagccggaagcataaagtgtaaagcctggggtgcctaatgagtgagctaactcacattaattgcgttgcgctca ctgcccgctttccagtcgggaaacctgtcgtgccagctgcattaatgaatcggccaacgcgcggggagaggcggtttgcg tattgggcgctcttccgcttcctcgctcactgactcgctgcgctcggtcgttcggctgcggcgagcggtatcagctcact caaaggcggtaatacggttatccacagaatcagggataacgcaggaaagaacatgtgagcaaaaggccagcaaaaggcc aggaaccgtaaaaaggccgcgttgctggcgtttttccataggctccgcccccctgacgagcatcacaaaaatcgacgctc aagtcagaggtggcgaaacccgacaggactataaagataccaggcgtttccccctggaagctccctcgtgcgctctcctg ttccgaccctgccgcttaccggatacctgtccgcctttctcccttcgggaagcgtggcgctttctcatagctcacgctgt aggtatctcagttcggtgtaggtcgttcgctccaagctgggctgtgtgcacgaaccccccgttcagcccgaccgctgcgc cttatccggtaactatcgtcttgagtccaacccggtaagacacgacttatcgccactggcagcagccactggtaacagga ttagcagagcgaggtatgtaggcggtgctacagagttcttgaagtggtggcctaactacggctacactagaagaacagta tttggtatctgcgctctgctgaagccagttaccttcggaaaaagagttggtagctcttgatccggcaaacaaaccaccgc tggtagcggtggtttttttgtttgcaagcagcagattacgcgcagaaaaaaaggatctcaagaagatcctttgatcttt ctacggggtctgacgctcagtggaacgaaaactcacgttaagggattttggtcatgagattatcaaaaaggatcttcacc tagatccttttaaattaaaaatgaagttttaaatcaatctaaagtatatatgagtaaacttggtctgacagttaccaatg cttaatcagtgaggcacctatctcagcgatctgtctatttcgttcatccatagttgcctgactccccgtcgtgtagataa ctacgatacgggagggcttaccatctggccccagtgctgcaatgataccgcgagacccacgctcaccggctccagattta tcagcaataaaccagccagccggaagggccgagcgcagaagtggtcctgcaactttatccgcctccatccagtctattaa
```

-continued ttgttgccgggaagctagagtaagtagttcgccagttaatagtttgcgcaacgttgttgccattgctacaggcatcgtgg tgtcacgctcgtcgtttggtatggcttcattcagctccggttcccaacgatcaaggcgagttacatgatcccccatgttg tgcaaaaaagcggttagctccttcggtcctccgatcgttgtcagaagtaagttggccgcagtgttatcactcatggttat ggcagcactgcataattctcttactgtcatgccatccgtaagatgcttttctgtgactggtgagtactcaaccaagtcat tctgagaatagtgtatgcggcgaccgagttgctcttgcccggcgtcaatacgggataataccgcgccacatagcagaact ttaaaagtgctcatcattggaaaacgttcttcggggcaaaactctcaaggatcttaccgctgttgagatccagttcgatg taacccactcgtgcacccaactgatcttcagcatcttttactttcaccagcgtttctgggtgagcaaaaacaggaaggca aaatgccgcaaaaagggaataagggcgacacggaaatgttgaatactcatactcttccttttcaatattattgaagca tttatcagggttattgtctcatgagcggatacatatttgaatgtatttagaaaaataaacaatagggttccgcgcaca tttccccgaaaagtgccacctgacgtctaagaaaccattattatcatgacattaacctataaaaataggcgtatcacgag gccctttcgtctcgcgcgtttcggtgatgacggtgaaaacctctgacacatgcagctcccggagacggtcacagcttgtc tgtaagcggatgccgggagcagacaagcccgtcagggcgcgtcagcgggtgttggcgggtgtcggggctggcttaactat gcggcatcagagcagattgtactgagagtgcacc

[SEQ ID NO: 77]
attggccattgcatacgttgtatccatatcataatatgtacatttatattggctcatgtccaacattaccgccatgttga cattgattattgactagttattaatagtaatcaattacggggtcattagttcatagcccatatatggagttccgcgttac ataacttacggtaaatggcccgcctggctgaccgcccaacgaccccccgcccattgacgtcaataatgacgtatgttccca tagtaacgccaatagggactttccattgacgtcaatgggtggagtatttacggtaaactgcccacttggcagtacatcaa gtgtatcatatgccaagtacgccccctattgacgtcaatgacggtaaatggcccgcctggcattatgcccagtacatgac cttatgggactttcctacttggcagtacatctacgtattagtcatcgctattaccatggtgatgcggttttggcagtaca tcaatgggcgtggatagcggtttgactcacggggatttccaagtctccaccccattgacgtcaatgggagtttgttttgg caccaaaatcaacgggactttccaaaatgtcgtaacaactccgccccattgacgcaaatgggcggtaggcgtgtacggtg ggaggtctatataagcagagctcgtttagtgaaccggggtctctctggttagaccagatctgagcctgggagctctctgg ctaactagggaacccactgcttaagcctcaataaagcttgccttgagtgcttcaagtagtgtgtgcccgtctgttgtgtg actctggtaactagagatccctcagacccttttagtcagtgtggaaaatctctagcagtggcgcccgaacagggacttga aagcgaaagggaaaccagaggagctctctcgacgcaggactcggcttgctgaagcgcgcacggcaagaggcgaggggcgg cgactggtgagtacgccaaaaattttgactagcggaggctagaaggagagagacgggtgcgagagcgtcagtattaagcg ggggtgaataagatcgcgatgggaaaaaattcggttaaggccaggggggaagaaaaaatataaattaaaacatatagtat gggcaagcagggagctagaacgattcgcagttaatcctggcctgttagaaacatcagaaggctgtagacaaatactggga cagctacaaccatcccttcagacaggatcagaagaacttagatcattatataatacagtagcaaccctctattgtgtgca tcaaaggatagagataaaagacaccaaggaagctttagacaagatagaggaagagcaaaacaaaagtaagaccaccgcac agcaagcggccgctgatcttcagacctggaggaggagatatgagggacaattggagaagtgaattatataaatataaagt agtaaaaattgaaccattaggagtagcacccaccaaggcaaagagaagagtggtgcagagagaaaaaagagcagtgggaa taggagctttgttccttgggttcttgggagcagcaggaagcactatgggcgcagcgtcaatgacgctgacggtacaggcc agacaattattgtctggtatagtgcagcagcagaacaatttgctgagggctattgaggcgcaacagcatctgttgcaact cacagtctggggcatcaagcagctccaggcaagaatcctggctgtggaaagatacctaaaggatcaacagctcctgggga tttggggttgctctggaaaactcatttgcaccactgctgtgccttggaatgctagttggagtaataaatctctggaacag atttggaatcacacgacctggatggagtgggacagagaaattaacaattacacaagcttaatacactccttaattgaaga atcgcaaaaccagcaagaaaagaatgaacaagaattattggaattagataaatgggcaagtttgtggaattggtttaaca taacaaattggctgtggtatataaaattattcataatgatagtaggaggcttggtaggtttaagaatagtttttgctgta cttTctatagtgaatagagttaggcagggatattcaccattatcgtttcagacccacctcccaaccccgaggggacccga -continued

```
caggcccgaaggaatagaagaagaaggtggagagagagacagagacagatccattcgattagtgaacggatctcgacggt
atcgttttaaaagaaaaggggggattgggggtacagtgcagggaaagaatagtagacataatagcaacagacatacaa
actaaagaattacaaaaacaaattacaaaaattcaaaattttatcggcgtgttgggggtggaccatcctctaggtattga
ataagaaaatgaagttaaggtggttgatggtaacactatgctaataactgcagagccagaagcaccataagggacatga
taagggagccagcagacctctgatctcttcctgaatgctaatcttaaacatcctgaggaagaatgggacttccatttggg
gtgggcctatgatagggtaataagacagtagtgaatatcaagctacaaaaagcccctttcaaattcttctcagtcctaa
cttttcatactaagcccagtccttccaaagcagactgtgaaagagtgatagttccgggagactagcactgcagattccgg
gtcactgtgagtgggggaggcagggaagaagggctcacaggacagtcaaaccatgcccctgtttttccttcttcaagta
gacctctataagacaacagagacaactaaggctgagtggccaggcgaggagaaaccatctcgccgtaaaacatggaagga
acacttcaggggaaaggtggtatctctaagcaagagaactgagtggagtcaaggctgagagatgcaggataagcaaatgg
gtagtgaaaagacattcatgaggacagctaaaacaataagtaatgtaaaatacagcatagcaaaactttaacctccaaat
caagcctctacttgaatccttttctgagggatgaataaggcataggcatcaggggctgttgccaatgtgcattagctgtt
tgcagcctcaccttctttcatggagtttaagatatagtgtattttcccaaggtttgaactagctcttcatttctttatgt
tttaaatgcactgacctcccacattccctttttagtaaaatattcagaaataatttaaatacatcattgcaatgaaaata
aatgtttttattaggcagaatccagatgctcaaggcccttcataatatcccccagtttagtagttggacttagggaaca
aaggaacctttaatagaaattggacagcaagaaagcgagcttagtgatacttgtgggccagggcattagccacaccagcc
accactttctgataggcagcctgcactggtggggtgAATTCTTTGCCAAAGTGATGGGCCAGCACACAGACCAGCACGTT
GCCCAGGAGCTGTGGGAGGAAGATAAGAGGTATGAACATGATTAGCAAAAGGGCCTAGCTTGGACTCAGAATAATCCAGC
CTTATCCCAACCATAAAATAAAAGCAGAATGGTAGCTGGATTGTAGCTGCTATTAGCAATATGAAACCTCTTACATCAGT
TACAATTTATATGCAGAAATATTTATATGCAGAAATATTGCTATTGCCTTAACCCAGAAATTATCACTGTTATTCTTTAG
AATGGTGCAAAGAGGCATGATACATTGTATCATTATTGCCCTGAAAGAAAGAGATTAGGGAAAGTATTAGAAATAAGATA
AACAAAAAGTATATTAAAAGAAGAAAGCATTTTTTAAAATTACAAATGCAAAATTACCCTGATTTGGTCAATATGTGTA
CCCTGTTACTTCTCCCCTTCCTATGACATGAACTTAACCATAGAAAAGAAGGGGAAAGAAAACATCAAGGGTCCCATAGA
CTCACCCTGAAGTTCTCAGGATCCACGTGCAGCTTGTCACAGTGCAGCTCACTCAGctgGGCAAAGGTGCCCTTGAGGTT
GTCCAGGTGAGCCAGGCCATCACTAAAGGCACCGAGCACTTTCTTGCCATGAGCCTTCACCTTAGGGTTGCCCATAACAG
CATCAGGAGTGGACAGATCCCCAAAGGACTCAAAGAACCTCTGGGTCCAAGGGTAGACCACCAGCAGCCTAAGGGTGGGA
AAATAGACCAATAGGCAGAGAGAGTCAGTGCCTATCAGAAACCCAAGAGTCTTCTCTGTCTCCACATGCCCAGTTTCTAT
TGGTCTCCTTAAACCTGTCTTGTAACCTTGATACCAACCTGCCCAGGGCCTCACCACCAACTTCATCCACGTTCACCTTG
CCCCACAGGGCAGTAACGGCAGACTTCTCCTCAGGAGTCAGGTGCACCATGGTGTCTGTTTGAGGTTGCTAGTGAACACA
GTTGTGTCAGAAGCAAATGTAAGCAATAGATGGCTCTGCCCTGACTTTTATGCCCAGCCCTGGCTCCTGCCCTCCCTGCT
CCTGGGAGTAGATTGGCCAACCctagggtgtggctccacagggtgaggtctaagtgatgacagccgtacctgtccttggc
tcttctggcactggcttaggagttggacttcaaaccctcagccctccctctaagatatatctcttggcccccataccatca
gtacaaattgctactaaaaacatcctccttttgcaagtgtatttacCACCCTTTTCCGGCACGCAGATAGTCAATATCTTC
AGCGTCCCCAAGGCCTGCAAGGGTGGGCCCCATATCTGGAAGTCCCAGGCGGAGCTGGGAGTTGGTCAAGTCTGGGCTG
TGGGGGCAGGGAGTGCTGGGGGATGGacgcgtatctgcggccgcctatctgtaccactagtctcgagaagctttcatcaa
aaaagtctaaccagctgcattcgactttgactgcagcagctggttagaaggttctactggaggagggtcccagcccatt
gctaaattaacatcaggctctgagactggcagtatatctctaacagtggttgatgctatcttctggaacttgcctgctac
attgagaccactgacccatacataggaagcccatagctctgtcctgaactgttaggccactggtccagagagtgtgcatc
tcctttgatcctcataataaccctatgagatagacacaattattactcttactttatagatgatgatcctgaaaacatag
gagtcaaggcacttgcccctagctgggggtataggggagcagtcccatgtagtagtagaatgaaaaatgctgctatgctg
```

-continued tgcctcccccacctttcccatgtctgccctctactcatggtctatctctcctggctcctgggagtcatggactccaccca gcaccaccaacctgacctaaccacctatctgagcctgccagcctataacccatctgggcctgatagctggtggccagcc ctgaccccaccccaccctccctggaacctctgatagacacatctggcacaccagctcgcaaagtcaccgtgagggtcttg tgtttgctgagtcaaaattccttgaaatccaagtccttagagactcctgctcccaaatttacagtcatagacttcttcat ggctgtctcctttatccacagaatgattcctttgcttcattgccccatccatctgatcctcctcatcagtgcagcacagg gcccatgagcagtagctgcagagtctcacataggtctggcactgcctctgacatgtccgaccttaggcaaatgcttgact cttctgagctcagtcttgtcatggcaaaacaaagataataatagtgttttttatggagttagcgtgaggatggaaaaca atagcaaaattgattagactataaaaggtctcaacaaatagtagtagattttatcatccattaatccttccctctcctct cttactcatcccatcacgtatgcctcttaattttcccttacctataataagagttattcctcttattatattcttcttat agtgattctggatatcaaagtgggaatgagggcaggccactaacgaagaagatgtttctcaaagaagccattctcccca catagatcatctcagcagggttcaggaagataaaggaggatcaaggtcgaaggtaggaactaaggaagaacactgggcaa gtgacgcgtcgacggtaccgttaacgatcttagccactttttaaaagaaaagggggggactggaagggctaattcactccc aacgaagacaagatatcctgCTAGTCCTTCCTTTCTAAATGACGAGAGAGACAGAAGAATTCTTCAAGGTTAGTGTGTCC

AGCATGCAACCTTTCCTTCCTGGATGAGCATCCCTGGAGTAGGAGAGCCAGCCTGCCTCCTGCGCTGGCACAGAGCCCGG

TTCCCTAGACAACTGCCTCTCCAAATCTGATGTCCAGCGCCACCTGGTGTCCACATCAAGCAGACACAATTAATAGTCAA

CCTGTTCAGGAAAACTGTGAGGGGGAAAAAAAAGAAAGAGGATTTATGAAGGGAAAAGAAAGTTTAGAGGATATGCCACG

ATTGGctagcagctgcttttttgcctgtactgggtctctctggttagaccagatctgagcctgggagctctctggctaact agggaacccactgcttaagcctcaataaagcttgccttgagtgcttcatccggaATCAACCTCTGGATTACAAAATTTGT

GAAAGATTGACTGGTATTCTTAACTATGTTGCTCCTTTTACGCTATGTGGATACGCTGCTTTAATGCCTTTGTATCATGC

TATTGCTTCCCGTATGGCTTTCATTTTCTCCTCCTTGTATAAATCCTGGTTGCTGTCTCTTTATGAGGAGTTGTGGCCCG

TTGTCAGGCAACGTGGCGTGGTGTGCACTGTGTTTGCTGACGCAACCCCCACTGGTTGGGGCATTGCCACCACCTGTCAG

CTCCTTTCCGGGACTTTCGCTTTCCCCCTCCCTATTGCCACGGCGGAACTCATCGCCGCCTGCCTTGCCCGCTGCTGGAC

AGGGGCTCGGCTGTTGGGCACTGACAATTCCGTGGTGTTGTCGGGGAAGCTGACGTCCTTTCCATGGCTGCTCGCCTGTG

TTGCCACCTGGATTCTGCGCGGGACGTCCTTCTGCTACGTCCCTTCGGCCCTCAATCCAGCGGACCTTCCTTCCCGCGGC

CTGCTGCCGGCTCTGCGGCCTCTTCCGCGTCTTCGCCTTCGCCCTCAGACGAGTCGGATCTCCCTTTGGGCCGCCTCCCC

GCCTGtccggtAGCTTGCCAGCCTCGACTGTGCCTTCTAGTTGCCAGCCGTCTGTTGTTTGCCCCTCCCCCGTGCCTTCC

TTGACCCTGGAAGGTGCCACTCCCACTGTCCTTTCCTAATAAAATGAGGAAATTGCATCGCATTGTCTGAGTAGGTGTCA

TTCTATTCTGGGGGGTGGGGTGGGGCAGGACAGCAAGGGGGAGGATTGGGAAGACAATAGCAGGCATGcaagcttggcgt aatcatggtcatagctgtttcctgtgtgaaattgttatccgctcacaattccacacaacatacgagccggaagcataaag tgtaaagcctggggtgcctaatgagtgagctaactcacattaattgcgttgcgctcactgcccgctttccagtcgggaaa cctgtcgtgccagctgcattaatgaatcggccaacgcgcggggagaggcggtttgcgtattgggcgctcttccgcttcct cgctcactgactcgctgcgctcggtcgttcggctgcggcgagcggtatcagctcactcaaaggcggtaatacggttatcc acagaatcaggggataacgcaggaaagaacatgtgagcaaaaggccagcaaaaggccaggaaccgtaaaaaggccgcgtt gctggcgtttttccataggctccgcccccctgacgagcatcacaaaaatcgacgctcaagtcagaggtggcgaaacccga caggactataaagataccaggcgtttccccctggaagctccctcgtgcgctctcctgttccgaccctgccgcttaccgga tacctgtccgcctttctcccttcgggaagcgtggcgctttctcatagctcacgctgtaggtatctcagttcggtgtaggt cgttcgctccaagctgggctgtgtgcacgaaccccccgttcagcccgaccgctgcgccttatccggtaactatcgtcttg agtccaacccggtaagacacgacttatcgccactggcagcagccactggtaacaggattagcagagcgaggtatgtaggc ggtgctacagagttcttgaagtggtggcctaactacggctacactagaagaacagtatttggtatctgcgctctgctgaa gccagttaccttcggaaaaagagttggtagctcttgatccggcaaacaaaccaccgctggtagcggtggtttttttgttt gcaagcagcagattacgcgcagaaaaaaaggatctcaagaagatcctttgatcttttctacggggtctgacgctcagtgg -continued

```
aacgaaaactcacgttaagggattttggtcatgagattatcaaaaaggatcttcacctagatccttttaaattaaaaatg aagttttaaatcaatctaaagtatatatgagtaaacttggtctgacagttaccaatgcttaatcagtgaggcacctatct cagcgatctgtctatttcgttcatccatagttgcctgactcccgtcgtgtagataactacgatacgggagggcttacca tctggcccagtgctgcaatgataccgcgagacccacgctcaccggctccagatttatcagcaataaaccagccagccgg aagggccgagcgcagaagtggtcctgcaactttatccgcctccatccagtctattaattgttgccgggaagctagagtaa gtagttcgccagttaatagtttgcgcaacgttgttgccattgctacaggcatcgtggtgtcacgctcgtcgtttggtatg gcttcattcagctccggttcccaacgatcaaggcgagttacatgatccccatgttgtgcaaaaaagcggttagctcctt cggtcctccgatcgttgtcagaagtaagttggccgcagtgttatcactcatggttatggcagcactgcataattctctta ctgtcatgccatccgtaagatgcttttctgtgactggtgagtactcaaccaagtcattctgagaatagtgtatgcggcga ccgagttgctcttgcccggcgtcaatacgggataataccgcgccacatagcagaactttaaaagtgctcatcattggaaa acgttcttcggggcaaaactctcaaggatcttaccgctgttgagatccagttcgatgtaacccactcgtgcacccaactg atcttcagcatcttttactttcaccagcgtttctgggtgagcaaaaacaggaaggcaaaatgccgcaaaaaagggaataa gggcgacacggaaatgttgaatactcatactcttcctttttcaatattattgaagcatttatcagggttattgtctcatg agcggatacatatttgaatgtatttagaaaaataaacaatagggggttccgcgcacatttccccgaaaagtgccacctga cgtctaagaaaccattattatcatgacattaacctataaaaataggcgtatcacgaggccctttcgtctcgcgcgtttcg gtgatgacggtgaaaacctctgacacatgcagctcccggagacggtcacagcttgtctgtaagcggatgccgggagcaga caagcccgtcagggcgcgtcagcgggtgttggcgggtgtcggggctggcttaactatgcggcatcagagcagattgtact gagagtgcacc
```

These vectors were produced by transient triple transfection of the recombinant vector, pCMVΔR8.9 and pMD.G into 293T cells. A total of $5 \times 10^6$ 293 T cells were seeded in 10-cm-diameter dishes 24 h prior to transfection in DMEM with 10% fetal bovine serum, penicillin (100 IU/ml), and streptomycin (100 μg/ml) in a 5% $CO_2$ incubator. A total of 20 μg of plasmid DNA was used for the transfection of one 10 cm dish: 3.5 μg of the envelope plasmid pMD.G, 6.5 μg of packaging plasmid, and 10 μg of transfer vector plasmid. The medium (10 ml) was replaced after 14 to 16 h; the conditioned medium was collected after another 24 h, cleared by low-speed centrifugation, and filtered through 0.45-μm-pore-size cellulose acetate filters. The pseudotyped virions were than concentrated by ultracentrifugation and resuspended for frozen down in aliquots for subsequent titration and stem cell transduction.

Titration Assay

These vectors were produced by transient triple transfection of the recombinant vector, pCMVΔR8.9 and pMD.G into 293T cells. A total of $5 \times 10^6$ 293 T cells were seeded in 10-cm-diameter dishes 24 h prior to transfection in DMEM with 10% fetal bovine serum, penicillin (100 IU/ml), and streptomycin (100 μg/ml) in a 5% $CO_2$ incubator. A total of 20 μg of plasmid DNA was used for the transfection of one 10 cm dish: 3.5 μg of the envelope plasmid pMD.G, 6.5 μg of packaging plasmid, and 10 μg of transfer vector plasmid. The medium (10 ml) was replaced after 14 to 16 h; the conditioned medium was collected after another 24 h, cleared by low-speed centrifugation, and filtered through 0.45-μm-pore-size cellulose acetate filters. The pseudotyped virions were than used directly for titration assays in Hela cells. Serial dilutions of un-concentrated virus were used to infect $20^5$ cells in a six-well plate in the presence of Polybrene (8 μg/ml). each dilution was tested in triplicate. The cells were kept in culture for no less than 15 days, harvested and genomic DNA were extracted, quantified and used to Vector Copy Number (VCN) quantification. Transducing activity was expressed in transducing units (TU). VCN analysis was performed by TaqMan PCR analysis using:

Gag-specific probe—5'-acagccttctgatgtttctaacaggccagg-3' (SEQ ID NO: 41)

Gag-primer-Forward:—5'-ggagctagaacgattcgcagtt-3' (SEQ ID NO: 42)

Gag-primer-Reverse:—5'-gttgtagctgtcccagtatttgtc-3' (SEQ ID NO: 43)

Human Albumin Probe—5'-tgctgaaacattcaccttccatgcagt-3' (SEQ ID NO: 44)

Human Albumin Forward—5'tgaaacatacgttcccaaagagttt-3' (SEQ ID NO: 45)

Human Albumin Reverse—5' ctctccttctcagaaagtgtgcatat-3' (SEQ ID NO: 46)

Hematopoietic Stem Cell Transduction and Transplantation

Donor bone marrow was flushed from the femurs of 8- to 16-week-old male Hbb$^{th3/+}$ thalassemic mice that had been injected intravenously (i.v.) 6 days earlier with 5-flurouracil (5-FU, Pharmacia; 150 mg kg$^{-1}$ body weight). Bone marrow cells were resuspended in serum-free medium, and supplemented with rmSCF (100 ng ml$^{-1}$), rmTPO (100 ng ml$^{-1}$), β-mercaptoethanol (55 μM; Sigma), L-glutamine (2 mM), pen/strep (10 IU ml$^{-1}$), and cultured for 18 h. Bone marrow cells were pelleted and resuspended in serum-free medium containing concentrated lentiviral supernatant at a multiplicity of infection (MOI) of 25 and supplemented with polybrene (8 μg ml$^{-1}$), L-glutamine (2 mM), pen/strep (100 IU ml$^{-1}$) and incubated for 8 h. Transduced bone marrow cells ($5 \times 10^5$) were then i.v. injected into each of the irradiated female recipients to establish bone marrow chimaeras.

Recipient mice (11- to 14-week-old C57/Hbb$^{th3/+}$ mice) were irradiated with 10.5 Gy (split dose 2×5.25 Gy) on the day of transplantation.

Post-Transplant Vector Studies

Peripheral Blood was collected periodically starting 5-6 weeks after hematopoietic stem cell transplantation. Blood samples were obtained by retro-orbital puncture under ether anesthesia, according to MSKCC animal protocol. Total hemoglobin levels, red cell counts, hematocrit levels, neutrophil counts, platelet counts, and reticulocyte counts were measured on a blood cell count analyzer.

VCN analysis: To evaluate the integrated vector copy number in peripheral blood, mouse genomic DNA was isolated, quantified and analyzed with multiplex real-time TaqMan PCR using following probes and primer:

Gag-specific probe—5'-acagccttctgatgtactaacaggccagg-3' (SEQ ID NO: 41)

Gag-primer-Forward—5'-ggagctagaacgattcgcagtt-3' (SEQ ID NO: 42)

Gag-primer-Reverse—5'-gttgtagctgtcccagtatttgtc-3' (SEQ ID NO: 43)

Mouse β-actin Probe—5'-tacgagggctatgctctccctcacgc-3' (SEQ ID NO: 47)

Mouse β-actin-primer-Forward—5'-tcacccacactgtgcccat-3' (SEQ ID NO: 48)

Mouse β-actin-primer-reverse—5'-agccaggtccagacgcag-3' (SEQ ID NO: 49)

Hemoglobin assays: automated hemoglobin (Hb) quantification; based line anemia in Hbb$^{th3/+}$ mice is 7.5-8.5 g/dL. Vector performance, i.e., protein output per vector copy, was determined as the ratio of gain in hemoglobin expression (i.e., correction of anemia), ΔHb g/dL, per vector copy number (VCN) measured in circulating blood cells.

Results and Discussion

As shown in FIG. 17, the SNS22.2.B87.A1, SNS23.2.B87.A1, SNS24.2.B87.A1, SNS26.B87.A1 and SNS27.2.B87.A1 vectors achieved higher titer than the TNS9.B87.A1 vector. Moreover, as shown in FIG. 16 and Table 1, the multiple mutations and/or deletions introduced into the promoter, HS2, HS3, and HS4 regions of the β-globin LCR of SNS23.2.B87.A1 did not affect (e.g., did not reduce) globin expression in mice. Furthermore, vectors lacking HS2 or all LCR elements but including an BLV enhancer and flanked by the A1 insulator, e.g., SNS26.B87.A1 and SNS27.2.B87.A1, can effectively treat anemia in thalassemic mice. While the globin protein output per copy of the SNS26.B87.A1 vector or the SNS27.2.B87.A1 vector was less than that of the SNS23.2.B87.A1 vector (see FIG. 18 and Table 1), SNS26.B87.A1 and SNS27.2.B87.A1 vectors were able to correct the disease with a higher vector copy number (see FIG. 16). The higher titer of the SNS26.B87.A1 and SNS27.2.B87.A1 vectors facilitated higher gene transfer, resulting in a higher vector copy number (VCN) and therapeutic activity.

As shown in FIG. 16, the expression of an incomplete or lacking LCR required 0.8 or higher copies of vector per cell, while in the case of SNS23.2.B87.A1, a VCN of 0.3 copies was sufficient to achieve correction of anemia

TABLE 1

Vector copy number (VCN) and Hb levels in long-term hematopoietic chimeras. Total Hb level [g/dL] in peripheral blood (PB) of chimeric mice. Representative data for week 6 after transplant is shown. ΔHb level was obtained by subtracting Th3/+ hemoglobin (value = 9 g/dL) from total Hb level for each animal tested. ΔHb/copy = Correlation between delta(Δ)Hb and vector copy number.

| mouse ID | VCN | HGB (g/dL) | Δ(HGB-9) | ΔHGB/copy |
|---|---|---|---|---|
| TNS9.B87.A1 #1 | 0.2 | 11.3 | 2.3 | 11.5 |
| TNS9.B87.A1 #2 | 0.2 | 12.0 | 3.0 | 16.7 |
| TNS9.B87.A1 #3 | 0.2 | 8.5 | −0.5 | −2.5 |
| TNS9.B87.A1 #4 | 0.2 | 13.5 | 4.5 | 30.0 |
| SNS23.2.B87.A1 #1 | 0.3 | 13.1 | 4.1 | 15.8 |
| SNS23.2.B87.A1 #2 | 0.3 | 13.3 | 4.3 | 13.0 |
| SNS23.2.B87.A1 #3 | 0.3 | 13.2 | 4.2 | 14.5 |
| SNS23.2.B87.A1 #4 | 0.3 | 13.0 | 4.0 | 13.8 |
| SNS23.2.B87.A1 #5 | 0.3 | 13.2 | 4.2 | 13.5 |
| SNS26.B87.A1 #1 | 1.2 | 11.4 | 2.4 | 2.0 |
| SNS26.B87.A1 #2 | 1.2 | 11.9 | 2.9 | 2.3 |
| SNS26.B87.A1 #3 | 1.3 | 9.7 | 0.7 | 0.6 |
| SNS26.B87.A1 #4 | 1.7 | 11.9 | 2.9 | 1.8 |
| SNS26.B87.A1 #5 | 1.3 | 11.3 | 2.3 | 1.8 |
| SNS27.2.B87.A1 #1 | 0.8 | 11.7 | 2.7 | 3.3 |
| SNS27.2.B87.A1 #2 | 0.8 | 13.0 | 4.0 | 5.3 |
| SNS27.2.B87.A1 #3 | 0.9 | 11.5 | 2.5 | 2.7 |
| SNS27.2.B87.A1 #4 | 0.9 | 11.5 | 2.5 | 2.7 |
| SNS27.2.B87.A1 #5 | 0.7 | 11.3 | 2.3 | 3.2 |
| TH3/+ MOCK #1 | — | 7.5 | −1.5 | |

Example 7: Evaluation of Globin Production at Different Time Points

Additional experiments were conducted to measure the globin production at different time points in thalassemic mice transfected with vectors disclosed herein. The methods used in Example 6 were applied in this Example. Average total Hb levels and average gains in Hb levels (ΔHb) in peripheral blood were measured in thalassemic mice transfected with vectors for 6-week, 5-month, or 9-month. ΔHb was normalized to vector copy (VCN), and ΔHb=Hb level–7.5 (baseline level in thalassemic mice, as all the time points consistently show an HGB value of 7.5 g/dL in the Thalassemic mice used as controls, this value was used). As shown in FIG. 19 and Table 2, globin productions from all vectors, including SNS23.2.B87A1, were stable over time. As shown in FIG. 20, SNS23.2.B87.A1 exhibited equal or better output of B-globin relative to TNS9.B87.A1, especially at late time points.

TABLE 2

Representative data for three different time points after transplant

| Vectors | VCN | HGB (g/dL) | Δ(HGB-7.5) | ΔHGB/copy |
|---|---|---|---|---|
| TNS9.B87.A1 (6 weeks) | 0.5 | 10.6 | 3.8 | 8.6 |
| TNS9.B87.A1 (5 months) | 0.5 | 10.7 | 3.2 | 5.1 |
| TNS9.B87.A1 (9 months) | 0.4 | 9.8 | 2.3 | 6.4 |
| SNS23.2.B87.A1 (6 weeks) | 1.1 | 13.2 | 5.7 | 6.0 |
| SNS23.2.B87.A1 (5 months) | 1.1 | 11.3 | 3.8 | 4.3 |
| SNS23.2.B87.A1 (9 months) | 0.5 | 11.6 | 4.1 | 8.3 |
| SNS26.B87.A1 (6 weeks) | 2.0 | 11.2 | 3.7 | 2.0 |
| SNS26.B87.A1 (5 months) | 3.0 | 11.1 | 3.6 | 1.5 |
| SNS26.B87.A1 (9 months) | 3.1 | 11.1 | 3.6 | 1.4 |
| SNS27.2.B87.A1 (6 weeks) | 0.8 | 11.8 | 4.3 | 5.3 |

TABLE 2-continued

Representative data for three different time points after transplant

| Vectors | VCN | HGB (g/dL) | Δ(HGB-7.5) | ΔHGB/ copy |
|---|---|---|---|---|
| SNS27.2.B87.A1 (5 months) | 1.5 | 12.1 | 4.6 | 3.5 |
| SNS27.2.B87.A1 (9 months) | 1.1 | 10.4 | 2.7 | 2.4 |
| TH3/+ MOCK (6 weeks) | 0 | 7.5 | 0 | 0 |
| TH3/+ MOCK (5 months) | 0 | 7.5 | 0 | 0 |
| TH3/+ MOCK (9 months) | 0 | 7.5 | 0 | 0 |

Average of Vector copy number (VCN) in long-term hematopoietic chimeras. Average Hb level [g/dL] in peripheral blood (PB) of chimeric mice. ΔHGb level was obtained by subtracting Th3/+ hemoglobin (value=7.5 g/dL) from total Hb level for each animal tested. ΔHGb/copy=Correlation between delta(Δ)Hb and vector copy number.
All the ΔHGb calculations are made using TH3/+ MOCK (7.5 g/dL) as basal HGB, value that is consistent in all the time points.

Example 8: Human Primary CD34+ Cells Transduced with Vectors Disclosed Herein

Human primary CD34$^+$ cells were isolated by centrifugation on a gradient of Ficoll-Hypaque Plus density. CD34+ cells were purified by positive selection using separation columns and beads. After one day of cytokine stimulation the CD34$^+$ cells were transduced with SNS.23.2.B87.A1 or TNS9.B87.A1 vectors disclosed herein using 4 different MOI. 10 and 15 days after transduction, the cells were harvested and the Vector copy number (VCN) was measured using the methods disclosed in Example 6. As shown in Table 3, at MOIs from 20×1 to 100×1, a linearly increased VCN response was observed in cells transduced with SNS.23.2.B87.A1 vector, with maximum VCN>2. By contrast, cells transduced with TNS9.B87.A1 vector did not exhibit proportional increases in VCN at MOIs from 20×1 to 100×1. Unlike TNS9.B87.A1 vector, the SNS23.2.B87.A1 vector resulted in an increased globin gene transduction in CD34$^+$ cells up to >2 VCN per cell (2.33 at MOI 100, day 15, Table 3).

TABLE 3

Transduction of human primary CD34+ cells

| Groups | MOI | VCN day10 | VCN day15 |
|---|---|---|---|
| SNS23.2.B87.A1 | 10 × 1 | 1 | 0.21 |
| Concentrate virus | 20 × 1 | 1.78 | 0.56 |
| | 40 × 1 | 3.35 | 0.86 |
| | 100 × 1 | 7.33 | 2.33 |
| TNS9.B87.A1 | 10 × 1 | 0.47 | 0.38 |
| Concentrate virus | 20 × 1 | 0.52 | 0.44 |
| | 40 × 1 | 0.48 | 0.40 |
| | 100 × 1 | 0.60 | 0.44 |
| UT | NA | 0.00 | 0.00 |

REFERENCES

1. Weatherall, D. J. & Clegg, J. B. The Thalassemia Syndrome. *Blackwell Scientific Oxford* (1981).
2. Stamatoyannopoulos, G., Nienhuis, A. W., Majerus, P. & Varmus, H. The Molecular Basis of Blood Diseaes. *W B Saunders, Philadelfphia* (1994).
3. Weatherall, D. J. Phenotype-genotype relationships in monogenic disease: lessons from the thalassaemias. *Nat Rev Genet* 2, 245-255. (2001).
4. Steinberg, M. H., Forget, B. G., Higgs, D. R. & Nagel, R. L. *Molecular Mechanism of β Thalassemia*; Bernard G. Forget, (Cambridge University Press, Cambridge, UK, 2001).
5. Cooley, T. B. & Lee, P. A series of cases of splenomegaly in children with anemia and peculiar bone changes. *Trans. Am. Pediatr. Soc.* 37, 29 (1925).
6. Giardina, P. J. & Grady, R. W. Chelation therapy in beta-thalassemia: an optimistic update. *Semin Hematol* 38, 360-366. (2001).
7. Giardini, C. & Lucarelli, G. Bone marrow transplantation in the treatment of thalassemia. *Current opinion in hematology* 1, 170-176. (1994).
8. Boulad, F., Giardina, P., Gillio, A., Kernan, N., Small, T., Brochstein, J., Van Syckle, K., George, D., Szabolcs, P. & O'Reilly, R. J. Bone marrow transplantation for homozygous beta-thalassemia. The Memorial Sloan-Kettering Cancer Center experience. *Ann NY Acad Sci* 850, 498-502. (1998).
9. Lucarelli, G., Clift, R. A., Galimberti, M., Angelucci, E., Giardini, C., Baronciani, D., Polchi, P., Andreani, M., Gaziev, D., Erer, B., Ciaroni, A., D'Adamo, F., Albertini, F. & Muretto, P. Bone marrow transplantation in adult thalassemic patients. *Blood* 93, 1164-1167. (1999).
10. Tisdale, J. & Sadelain, M. Toward gene therapy for disorders of globin synthesis. *Semin Hematol* 38, 382-392 (2001).
11. Pauling, L., Itano, H. A., Singer, S. J. & Wells, I. C. Sickle cell anemia, a molecular disease. *Science* 110, 543-546 (1949).
12. Swank, R. A. & Stamatoyannopoulos, G. Fetal gene reactivation. *Curr Opin Genet Dev* 8, 366-370 (1998).
13. Platt, O. S., Orkin, S. H., Dover, G., Beardsley, G. P., Miller, B. & Nathan, D. G. Hydroxyurea enhances fetal hemoglobin production in sickle cell anemia. *J Clin Invest* 74, 652-656. (1984).
14. Charache, S., Dover, G. J., Moore, R. D., Eckert, S., Ballas, S. K., Koshy, M., Milner, P. F., Orringer, E. P., Phillips, G., Jr., Platt, O. S. & et al. Hydroxyurea: effects on hemoglobin F production in patients with sickle cell anemia. *Blood* 79, 2555-2565. (1992).
15. Atweh, G. F. & Loukopoulos, D. Pharmacological induction of fetal hemoglobin in sickle cell disease and beta-thalassemia. *Semin Hematol* 38, 367-373. (2001).
16. Perrine, S. P., Castaneda, S. A., Boosalis, M. S., White, G. L., Jones, B. M. & Bohacek, R. Induction of fetal globin in beta-thalassemia: Cellular obstacles and molecular progress. *Ann NY Acad Sci* 1054, 257-265 (2005).
17. Stamatoyannopoulos, G. Prospects for developing a molecular cure for thalassemia. *Hematology* 10 Suppl 1, 255-257 (2005).
18. Vermylen, C., Cornu, G., Ferster, A., Brichard, B., Ninane, J., Ferrant, A., Zenebergh, A., Maes, P., Dhooge, C., Benoit, Y., Beguin, Y., Dresse, M. F. & Sariban, E. Haematopoietic stem cell transplantation for sickle cell anaemia: the first 50 patients transplanted in Belgium. *Bone Marrow Transplant* 22, 1-6 (1998).
19. Luzzatto, L. & Goodfellow, P. Sickle cell anaemia. A simple disease with no cure. *Nature* 337, 17-18 (1989).
20. Sadelain, M. Genetic treatment of the haemoglobinopathies: recombinations and new combinations. *Br J Haematol* 98, 247-253 (1997).
21. Sadelain, M., Boulad, F., Galanello, R., Giardina, P., Locatelli, F., Maggio, A., Rivella, S., Riviere, I. & Tisdale, J. Therapeutic options for patients with severe beta-thalassemia: the need for globin gene therapy. *Hum Gene Ther* 18, 1-9 (2007).
22. Borgna-Pignatti, C., Rugolotto, S., De Stefano, P., Zhao, H., Cappellini, M. D., Del Vecchio, G. C., Romeo, M. A., Forni, G. L., Gamberini, M. R., Ghilardi, R., Piga, A. & Cnaan, A. Survival and complications in patients with thalassemia major treated with transfusion and deferoxamine. *Haematologica* 89, 1187-1193 (2004).
23. Telfer, P. T., Warburton, F., Christou, S., Hadjigavriel, M., Sitarou, M., Kolnagou, A. & Angastiniotis, M. Improved survival in thalassemia major patients on switching from desferrioxamine to combined chelation therapy with desferrioxamine and deferiprone. *Haematologica* 94, 1777-1778 (2009).
24. Ladis, V., Chouliaras, G., Berdoukas, V., Chatziliami, A., Fragodimitri, C., Karabatsos, F., Youssef, J., Kattamis, A. & Karagiorga-Lagana, M. Survival in a large cohort of Greek patients with transfusion-dependent beta thalassaemia and mortality ratios compared to the general population. *European journal of haematology* 86, 332-338 (2011).
25. Mancuso, A., Sciarrino, E., Renda, M. C. & Maggio, A. A prospective study of hepatocellular carcinoma incidence in thalassemia. *Hemoglobin* 30, 119-124 (2006).
26. Persons, D. A. & Tisdale, J. F. Gene therapy for the hemoglobin disorders. *Semin Hematol* 41, 279-286 (2004).
27. Sadelain, M. Recent advances in globin gene transfer for the treatment of beta-thalassemia and sickle cell anemia. *Current opinion in hematology* 13, 142-148 (2006).
28. May, C., Rivella, S., Callegari, J., Heller, G., Gaensler, K. M., Luzzatto, L. & Sadelain, M. Therapeutic haemoglobin synthesis in beta-thalassaemic mice expressing lentivirus-encoded human beta-globin. *Nature* 406, 82-86 (2000).
29. May, C., Rivella, S., Chadburn, A. & Sadelain, M. Successful treatment of murine beta-thalassemia intermedia by transfer of the human beta-globin gene. *Blood* 99, 1902-1908 (2002).
30. Rivella, S., May, C., Chadburn, A., Riviere, I. & Sadelain, M. A novel murine model of Cooley anemia and its rescue by lentiviral-mediated human beta-globin gene transfer. *Blood* 101, 2932-2939 (2003).
31. Sadelain, M., Boulad, F., Lisowki, L., Moi, P. & Riviere, I. Stem cell engineering for the treatment of severe hemoglobinopathies. *Curr Mol Med* 8, 690-697 (2008).
32. Bank, A., Dorazio, R. & Leboulch, P. A phase I/II clinical trial of beta-globin gene therapy for beta-thalassemia. *Ann NY Acad Sci* 1054, 308-316 (2005).
33. Cavazzana-Calvo, M., Payen, E., Negre, O., Wang, G., Hehir, K., Fusil, F., Down, J., Denaro, M., Brady, T., Westerman, K., Cavallesco, R., Gillet-Legrand, B., Caccavelli, L., Sgarra, R., Maouche-Chretien, L., Bernaudin, F., Girot, R., Dorazio, R., Mulder, G. J., Polack, A., Bank, A., Soulier, J., Larghero, J., Kabbara, N., Dalle, B., Gourmel, B., Socie, G., Chretien, S., Cartier, N., Aubourg, P., Fischer, A., Cornetta, K., Galacteros, F., Beuzard, Y., Gluckman, E., Bushman, F., Hacein-Bey-Abina, S. & Leboulch, P. Transfusion independence and HMGA2 activation after gene therapy of human beta-thalassaemia. *Nature* 467, 318-322 (2010).
34. Braun, C. J., Bortug, K., Paruzynski, A., Witzel, M., Schwarzer, A., Rothe, M., Modlich, U., Beier, R., Gohring, G., Steinemann, D., Fronza, R., Ball, C. R., Haemmerle, R., Naundorf, S., Kuhlcke, K., Rose, M., Fraser, C., Mathias, L., Ferrari, R., Abboud, M. R., Al-Herz, W., Kondratenko, I., Marodi, L., Glimm, H., Schlegelberger, B., Schambach, A., Albert, M. H., Schmidt, M., von Kalle, C. & Klein, C. Gene therapy for Wiskott-Aldrich syndrome—long-term efficacy and genotoxicity. *Sci Transl Med* 6, 227ra233 (2014).
35. Chang, A. H. & Sadelain, M. The genetic engineering of hematopoietic stem cells: the rise of lentiviral vectors, the conundrum of the ltr, and the promise of lineage-restricted vectors. *Mol Ther* 15, 445-456 (2007).
36. Pawliuk, R., Westerman, K. A., Fabry, M. E., Payen, E., Tighe, R., Bouhassira, E. E., Acharya, S. A., Ellis, J., London, I. M., Eaves, C. J., Humphries, R. K., Beuzard, Y., Nagel, R. L. & Leboulch, P. Correction of sickle cell disease in transgenic mouse models by gene therapy. *Science* 294, 2368-2371 (2001).
37. Emery, D. W., Chen, H., Li, Q. & Stamatoyannopoulos, G. Development of a condensed locus control region cassette and testing in retrovirus vectors for A gamma-globin. *Blood Cells Mol Dis* 24, 322-339 (1998).
38. Miccio, A., Cesari, R., Lotti, F., Rossi, C., Sanvito, F., Ponzoni, M., Routledge, S. J., Chow, C. M., Antoniou, M. N. & Ferrari, G. In vivo selection of genetically modified erythroblastic progenitors leads to long-term correction of beta-thalassemia. *Proc Natl Acad Sci USA* 105, 10547-10552 (2008).
39. Sadelain, M., Wang, C. H., Antoniou, M., Grosveld, F. & Mulligan, R. C. Generation of a high-titer retroviral vector capable of expressing high levels of the human beta-globin gene. *Proc Natl Acad Sci USA* 92, 6728-6732 (1995).
40. Samakoglu, S., Lisowski, L., Budak-Alpdogan, T., Usachenko, Y., Acuto, S., Di Marzo, R., Maggio, A., Zhu, P., Tisdale, J. F., Riviere, I. & Sadelain, M. A genetic strategy to treat sickle cell anemia by coregulating globin transgene expression and RNA interference. *Nat Biotechnol* 24, 89-94 (2006).
41. Pestina, T. I., Hargrove, P. W., Jay, D., Gray, J. T., Boyd, K. M. & Persons, D. A. Correction of murine sickle cell disease using gamma-globin lentiviral vectors to mediate high-level expression of fetal hemoglobin. *Mol Ther* 17, 245-252 (2009).
42. Hanawa, H., Yamamoto, M., Zhao, H., Shimada, T. & Persons, D. A. Optimized lentiviral vector design improves titer and transgene expression of vectors containing the chicken beta-globin locus HS4 insulator element. *Mol Ther* 17, 667-674 (2009).
43. Arumugam, P. I., Scholes, J., Perelman, N., Xia, P., Yee, J. K. & Malik, P. Improved human beta-globin expression from self-inactivating lentiviral vectors carrying the chicken hypersensitive site-4 (cHS4) insulator element. *Mol Ther* 15, 1863-1871 (2007).
44. Fraser, P., Pruzina, S., Antoniou, M. & Grosveld, F. Each hypersensitive site of the human beta-globin locus control region confers a different developmental pattern of expression on the globin genes. *Genes & development* 7, 106-113 (1993).
45. Navas, P. A., Peterson, K. R., Li, Q., Skarpidi, E., Rohde, A., Shaw, S. E., Clegg, C. H., Asano, H. & Stamatoyannopoulos, G. Developmental specificity of the interaction between the locus control region and embryonic or fetal globin genes in transgenic mice with an HS3 core deletion. *Molecular and cellular biology* 18, 4188-4196 (1998).
46. Li, Q. & Stamatoyannopoulos, G. Hypersensitive site 5 of the human beta locus control region functions as a chromatin insulator. *Blood* 84, 1399-1401 (1994).

47. Li, Q., Zhang, M., Han, H., Rohde, A. & Stamatoyannopoulos, G. Evidence that DNase I hypersensitive site 5 of the human beta-globin locus control region functions as a chromosomal insulator in transgenic mice. *Nucleic Acids Res* 30, 2484-2491 (2002).
48. Puthenveetil, G., Scholes, J., Carbonell, D., Qureshi, N., Xia, P., Zeng, L., Li, S., Yu, Y., Hiti, A. L., Yee, J. K. & Malik, P. Successful correction of the human beta-thalassemia major phenotype using a lentiviral vector. *Blood* 104, 3445-3453 (2004).
49. Wilber, A., Nienhuis, A. W. & Persons, D. A. Transcriptional regulation of fetal to adult hemoglobin switching: new therapeutic opportunities. *Blood* 117, 3945-3953 (2011).
50. Arumugam, P. I., Higashimoto, T., Urbinati, F., Modlich, U., Nestheide, S., Xia, P., Fox, C., Corsinotti, A., Baum, C. & Malik, P. Genotoxic potential of lineage-specific lentivirus vectors carrying the beta-globin locus control region. *Mol Ther* 17, 1929-1937 (2009).
51. Chang, K. H., Fang, X., Wang, H., Huang, A., Cao, H., Yang, Y., Bonig, H., Stamatoyannopoulos, J. A. & Papayannopoulou, T. Epigenetic modifications and chromosome conformations of the beta globin locus throughout development. *Stem cell reviews* 9, 397-407 (2013).
52. Papayannopoulou, T., Priestley, G. V., Rohde, A., Peterson, K. R. & Nakamoto, B. Hemopoietic lineage commitment decisions: in vivo evidence from a transgenic mouse model harboring micro LCR-betapro-LacZ as a transgene. *Blood* 95, 1274-1282 (2000).
53. Nienhuis, A. W. Development of gene therapy for blood disorders: an update. *Blood* 122, 1556-1564 (2013).
54. Baum, C., Kustikova, O., Modlich, U., Li, Z. & Fehse, B. Mutagenesis and oncogenesis by chromosomal insertion of gene transfer vectors. *Hum Gene Ther* 17, 253-263 (2006).
55. Nienhuis, A. W., Dunbar, C. E. & Sorrentino, B. P. Genotoxicity of retroviral integration in hematopoietic cells. *Mol Ther* 13, 1031-1049 (2006).
56. Emery, D. W. The use of chromatin insulators to improve the expression and safety of integrating gene transfer vectors. *Hum Gene Ther* 22, 761-774 (2011).
57. Evans-Galea, M. V., Wielgosz, M. M., Hanawa, H., Srivastava, D. K. & Nienhuis, A. W. Suppression of clonal dominance in cultured human lymphoid cells by addition of the cHS4 insulator to a lentiviral vector. *Mol Ther* 15, 801-809 (2007).
58. Rivella, S., Callegari, J. A., May, C., Tan, C. W. & Sadelain, M. The cHS4 insulator increases the probability of retroviral expression at random chromosomal integration sites. *J Virol* 74, 4679-4687 (2000).
59. Emery, D. W., Yannaki, E., Tubb, J. & Stamatoyannopoulos, G. A chromatin insulator protects retrovirus vectors from chromosomal position effects. *Proc Natl Acad Sci USA* 97, 9150-9155 (2000).
60. Emery, D. W., Yannaki, E., Tubb, J., Nishino, T., Li, Q. & Stamatoyannopoulos, G. Development of virus vectors for gene therapy of beta chain hemoglobinopathies: flanking with a chromatin insulator reduces gamma-globin gene silencing in vivo. *Blood* 100, 2012-2019 (2002).
61. Yannaki, E., Tubb, J., Aker, M., Stamatoyannopoulos, G. & Emery, D. W. Topological constraints governing the use of the chicken HS4 chromatin insulator in oncoretrovirus vectors. *Mol Ther* 5, 589-598 (2002).
62. Hino, S., Fan, J., Taguwa, S., Akasaka, K. & Matsuoka, M. Sea urchin insulator protects lentiviral vector from silencing by maintaining active chromatin structure. *Gene Ther* 11, 819-828 (2004).
63. Ramezani, A., Hawley, T. S. & Hawley, R. G. Performance- and safety-enhanced lentiviral vectors containing the human interferon-beta scaffold attachment region and the chicken beta-globin insulator. *Blood* 101, 4717-4724 (2003).
64. Ramezani, A., Hawley, T. S. & Hawley, R. G. Combinatorial incorporation of enhancer-blocking components of the chicken beta-globin 5'HS4 and human T-cell receptor alpha/delta BEAD-1 insulators in self-inactivating retroviral vectors reduces their genotoxic potential. *Stem Cells* 26, 3257-3266 (2008).
65. Yannaki, E., Emery, D. W. & Stamatoyannopoulos, G. Gene therapy for beta-thalassaemia: the continuing challenge. *Expert reviews in molecular medicine* 12, e31 (2010).
66. Persons, D. A. The challenge of obtaining therapeutic levels of genetically modified hematopoietic stem cells in beta-thalassemia patients. *Ann NY Acad Sci* 1202, 69-74 (2010).
67. Perumbeti, A. & Malik, P. Therapy for beta-globinopathies: a brief review and determinants for successful and safe correction. *Ann NY Acad Sci* 1202, 36-44 (2010).
68. Johnson, K. D., Grass, J. A., Park, C., Im, H., Choi, K. & Bresnick, E. H. Highly restricted localization of RNA polymerase II within a locus control region of a tissue-specific chromatin domain. *Molecular and cellular biology* 23, 6484-6493 (2003).
69. Vieira, K. F., Levings, P. P., Hill, M. A., Crusselle, Kang, S. H., Engel, J. D. & Bungert, J. Recruitment of transcription complexes to the beta-globin gene locus in vivo and in vitro. *J Biol Chem* 279, 50350-50357 (2004).
70. Levings, P. P., Zhou, Z., Vieira, K. F., Crusselle-Davis, V. J. & Bungert, J. Recruitment of transcription complexes to the beta-globin locus control region and transcription of hypersensitive site 3 prior to erythroid differentiation of murine embryonic stem cells. *The FEBS journal* 273, 746-755 (2006).
71. Felsenfeld, G. & Groudine, M. Controlling the double helix. *Nature* 421, 448-453 (2003).
72. Felsenfeld, G. Chromatin as an essential part of the transcriptional mechanism. *Nature* 355, 219-224 (1992).
73. Brownell, J. E. & Allis, C. D. Special HATs for special occasions: linking histone acetylation to chromatin assembly and gene activation. *Curr Opin Genet Dev* 6, 176-184 (1996).
74. Kingston, R. E. & Narlikar, G. J. ATP-dependent remodeling and acetylation as regulators of chromatin fluidity. *Genes & development* 13, 2339-2352 (1999).
75. Tsukiyama, T. & Wu, C. Chromatin remodeling and transcription. *Curr Opin Genet Dev* 7, 182-191 (1997).
76. Wolffe, A. P., Wong, J. & Pruss, D. Activators and repressors: making use of chromatin to regulate transcription. *Genes to cells: devoted to molecular & cellular mechanisms* 2, 291-302 (1997).
77. Kadonaga, J. T. Eukaryotic transcription: an interlaced network of transcription factors and chromatin-modifying machines. *Cell* 92, 307-313 (1998).
78. Struhl, K. Histone acetylation and transcriptional regulatory mechanisms. *Genes & development* 12, 599-606 (1998).
79. Gross, D. S. & Garrard, W. T. Nuclease hypersensitive sites in chromatin. *Annual review of biochemistry* 57, 159-197 (1988).
80. Elgin, S. C. Anatomy of hypersensitive sites. *Nature* 309, 213-214 (1984).

81. Wu, C. The 5' ends of *Drosophila* heat shock genes in chromatin are hypersensitive to DNase I. *Nature* 286, 854-860 (1980).
82. Felsenfeld, G., Boyes, J., Chung, J., Clark, D. & Studitsky, V. Chromatin structure and gene expression. *Proc Natl Acad Sci USA* 93, 9384-9388 (1996).
83. Burgess-Beusse, B., Farrell, C., Gaszner, M., Litt, M., Mutskov, V., Recillas-Targa, F., Simpson, M., West, A. & Felsenfeld, G. The insulation of genes from external enhancers and silencing chromatin. *Proc Natl Acad Sci USA* 99 Suppl 4, 16433-16437 (2002).
84. Elgin, S. C. DNAase I-hypersensitive sites of chromatin. *Cell* 27, 413-415 (1981).
85. McGhee, J. D., Wood, W. I., Dolan, M., Engel, J. D. & Felsenfeld, G. A 200 base pair region at the 5' end of the chicken adult beta-globin gene is accessible to nuclease digestion. *Cell* 27, 45-55 (1981).
86. Lowrey, C. H., Bodine, D. M. & Nienhuis, A. W. Mechanism of DNase I hypersensitive site formation within the human globin locus control region. *Proc Natl Acad Sci USA* 89, 1143-1147 (1992).
87. Adams, C. C. & Workman, J. L. Binding of disparate transcriptional activators to nucleosomal DNA is inherently cooperative. *Molecular and cellular biology* 15, 1405-1421 (1995).
88. McArthur, M., Gerum, S. & Stamatoyannopoulos, G. Quantification of DNaseI-sensitivity by real-time PCR: quantitative analysis of DNaseI-hypersensitivity of the mouse beta-globin LCR. *J Mol Biol* 313, 27-34 (2001).
89. Dorschner, M. O., Hawrylycz, M., Humbert, R., Wallace, J. C., Shafer, A., Kawamoto, J., Mack, J., Hall, R., Goldy, J., Sabo, P. J., Kohli, A., Li, Q., McArthur, M. & Stamatoyannopoulos, J. A. High-throughput localization of functional elements by quantitative chromatin profiling. *Nat Methods* 1, 219-225 (2004).
90. Sabo, P. J., Kuehn, M. S., Thurman, R., Johnson, B. E., Johnson, E. M., Cao, H., Yu, M., Rosenzweig, E., Goldy, J., Haydock, A., Weaver, M., Shafer, A., Lee, K., Neri, F., Humbert, R., Singer, M. A., Richmond, T. A., Dorschner, M. O., McArthur, M., Hawrylycz, M., Green, R. D., Navas, P. A., Noble, W. S. & Stamatoyannopoulos, J. A. Genome-scale mapping of DNase I sensitivity in vivo using tiling DNA microarrays. *Nat Methods* 3, 511-518 (2006).
91. Sabo, P. J., Hawrylycz, M., Wallace, J. C., Humbert, R., Yu, M., Shafer, A., Kawamoto, J., Hall, R., Mack, J., Dorschner, M. O., McArthur, M. & Stamatoyannopoulos, J. A. Discovery of functional noncoding elements by digital analysis of chromatin structure. *Proc Natl Acad Sci USA* 101, 16837-16842 (2004).
92. Sabo, P. J., Humbert, R., Hawrylycz, M., Wallace, J. C., Dorschner, M. O., McArthur, M. & Stamatoyannopoulos, J. A. Genome-wide identification of DNaseI hypersensitive sites using active chromatin sequence libraries. *Proc Natl Acad Sci USA* 101, 4537-4542 (2004).
93. Thurman, R. E., Rynes, E., Humbert, R., Vierstra, J., Maurano, M. T., Haugen, E., Sheffield, N.C., Stergachis, A. B., Wang, H., Vernot, B., Garg, K., John, S., Sandstrom, R., Bates, D., Boatman, L., Canfield, T. K., Diegel, M., Dunn, D., Ebersol, A. K., Frum, T., Giste, E., Johnson, A. K., Johnson, E. M., Kutyavin, T., Lajoie, B., Lee, B. K., Lee, K., London, D., Lotakis, D., Neph, S., Neri, F., Nguyen, E. D., Qu, H., Reynolds, A. P., Roach, V., Safi, A., Sanchez, M. E., Sanyal, A., Shafer, A., Simon, J. M., Song, L., Vong, S., Weaver, M., Yan, Y., Zhang, Z., Zhang, Z., Lenhard, B., Tewari, M., Dorschner, M. O., Hansen, R. S., Navas, P. A., Stamatoyannopoulos, G., Iyer, V. R., Lieb, J. D., Sunyaev, S. R., Akey, J. M., Sabo, P. J., Kaul, R., Furey, T. S., Dekker, J., Crawford, G. E. & Stamatoyannopoulos, J. A. The accessible chromatin landscape of the human genome. *Nature* 489, 75-82 (2012).
94. Stergachis, A. B., Neph, S., Reynolds, A., Humbert, R., Miller, B., Paige, S. L., Vernot, B., Cheng, J. B., Thurman, R. E., Sandstrom, R., Haugen, E., Heimfeld, S., Murry, C. E., Akey, J. M. & Stamatoyannopoulos, J. A. Developmental fate and cellular maturity encoded in human regulatory DNA landscapes. *Cell* 154, 888-903 (2013).
95. Neph, S., Stergachis, A. B., Reynolds, A., Sandstrom, R., Borenstein, E. & Stamatoyannopoulos, J. A. Circuitry and dynamics of human transcription factor regulatory networks. *Cell* 150, 1274-1286 (2012).
96. Maurano, M. T., Humbert, R., Rynes, E., Thurman, R. E., Haugen, E., Wang, H., Reynolds, A. P., Sandstrom, R., Qu, H., Brody, J., Shafer, A., Neri, F., Lee, K., Kutyavin, T., Stehling-Sun, S., Johnson, A. K., Canfield, T. K., Giste, E., Diegel, M., Bates, D., Hansen, R. S., Neph, S., Sabo, P. J., Heimfeld, S., Raubitschek, A., Ziegler, S., Cotsapas, C., Sotoodehnia, N., Glass, I., Sunyaev, S. R., Kaul, R. & Stamatoyannopoulos, J. A. Systematic localization of common disease-associated variation in regulatory DNA. *Science* 337, 1190-1195 (2012).
97. Stergachis, A. B., Haugen, E., Shafer, A., Fu, W., Vernot, B., Reynolds, A., Raubitschek, A., Ziegler, S., LeProust, E. M., Akey, J. M. & Stamatoyannopoulos, J. A. Exonic transcription factor binding directs codon choice and affects protein evolution. *Science* 342, 1367-1372 (2013).
98. Neph, S., Vierstra, J., Stergachis, A. B., Reynolds, A. P., Haugen, E., Vernot, B., Thurman, R. E., John, S., Sandstrom, R., Johnson, A. K., Maurano, M. T., Humbert, R., Rynes, E., Wang, H., Vong, S., Lee, K., Bates, D., Diegel, M., Roach, V., Dunn, D., Neri, J., Schafer, A., Hansen, R. S., Kutyavin, T., Giste, E., Weaver, M., Canfield, T., Sabo, P., Zhang, M., Balasundaram, G., Byron, R., MacCoss, M. J., Akey, J. M., Bender, M. A., Groudine, M., Kaul, R. & Stamatoyannopoulos, J. A. An expansive human regulatory lexicon encoded in transcription factor footprints. *Nature* 489, 83-90 (2012).
99. Ramezani, A., Hawley, T. S. & Hawley, R. G. Stable gammaretroviral vector expression during embryonic stem cell-derived in vitro hematopoietic development. *Mol Ther* 14, 245-254 (2006).
100. Recillas-Targa, F., Pikaart, M. J., Burgess-Beusse, B., Bell, A. C., Litt, M. D., West, A. G., Gaszner, M. & Felsenfeld, G. Position-effect protection and enhancer blocking by the chicken beta-globin insulator are separable activities. *Proc Natl Acad Sci USA* 99, 6883-6888 (2002).
101. Gaszner, M. & Felsenfeld, G. Insulators: exploiting transcriptional and epigenetic mechanisms. *Nat Rev Genet* 7, 703-713 (2006).
102. Wallace, J. A. & Felsenfeld, G. We gather together: insulators and genome organization. *Curr Opin Genet Dev* 17, 400-407 (2007).
103. Chung, J. H., Bell, A. C. & Felsenfeld, G. Characterization of the chicken beta-globin insulator. *Proc Natl Acad Sci USA* 94, 575-580 (1997).
104. Bell, A. C., West, A. G. & Felsenfeld, G. The protein CTCF is required for the enhancer blocking activity of vertebrate insulators. *Cell* 98, 387-396 (1999).
105. Ryu, B. Y., Persons, D. A., Evans-Galea, M. V., Gray, J. T. & Nienhuis, A. W. A chromatin insulator blocks interactions between globin regulatory elements and cellular promoters in erythroid cells. *Blood Cells Mol Dis* 39, 221-228 (2007).

106. Ryu, B. Y., Evans-Galea, M. V., Gray, J. T., Bodine, D. M., Persons, D. A. & Nienhuis, A. W. An experimental system for the evaluation of retroviral vector design to diminish the risk for proto-oncogene activation. *Blood* 111, 1866-1875 (2008).

107. Yao, S., Osborne, C. S., Bharadwaj, R. R., Pasceri, P., Sukonnik, T., Pannell, D., Recillas-Targa, F., West, A. G. & Ellis, J. Retrovirus silencer blocking by the cHS4 insulator is CTCF independent. *Nucleic Acids Res* 31, 5317-5323 (2003).

108. Nishino, T., Tubb, J. & Emery, D. W. Partial correction of murine beta-thalassemia with a gammaretrovirus vector for human gamma-globin. *Blood Cells Mol Dis* 37, 1-7 (2006).

109. Aker, M., Tubb, J., Groth, A. C., Bukovsky, A. A., Bell, A. C., Felsenfeld, G., Kiem, H. P., Stamatoyannopoulos, G. & Emery, D. W. Extended core sequences from the cHS4 insulator are necessary for protecting retroviral vectors from silencing position effects. *Hum Gene Ther* 18, 333-343 (2007).

110. Li, C. L. & Emery, D. W. The cHS4 chromatin insulator reduces gammaretroviral vector silencing by epigenetic modifications of integrated provirus. *Gene Ther* 15, 49-53 (2008).

111. Ma, Y., Ramezani, A., Lewis, R., Hawley, R. G. & Thomson, J. A. High-level sustained transgene expression in human embryonic stem cells using lentiviral vectors. *Stem Cells* 21, 111-117 (2003).

112. Chang, L. J., Liu, X. & He, J. Lentiviral siRNAs targeting multiple highly conserved RNA sequences of human immunodeficiency virus type 1. *Gene Ther* 12, 1133-1144 (2005).

113. Pluta, K., Luce, M. J., Bao, L., Agha-Mohammadi, S. & Reiser, J. Tight control of transgene expression by lentivirus vectors containing second-generation tetracycline-responsive promoters. *J Gene Med* 7, 803-817 (2005).

114. Jakobsson, J., Rosenqvist, N., Thompson, L., Barraud, P. & Lundberg, C. Dynamics of transgene expression in a neural stem cell line transduced with lentiviral vectors incorporating the cHS4 insulator. *Experimental cell research* 298, 611-623 (2004).

115. Leboulch, P., Huang, G. M., Humphries, R. K., Oh, Y. H., Eaves, C. J., Tuan, D. Y. & London, I. M. Mutagenesis of retroviral vectors transducing human beta-globin gene and beta-globin locus control region derivatives results in stable transmission of an active transcriptional structure. *EMBO J* 13, 3065-3076 (1994).

116. Kim, T. H., Abdullaev, Z. K., Smith, A. D., Ching, K. A., Loukinov, D. I., Green, R. D., Zhang, M. Q., Lobanenkov, V. V. & Ren, B. Analysis of the vertebrate insulator protein CTCF-binding sites in the human genome. *Cell* 128, 1231-1245 (2007).

117. Yusufzai, T. M. & Felsenfeld, G. The 5'-HS4 chicken beta-globin insulator is a CTCF-dependent nuclear matrix-associated element. *Proc Natl Acad Sci USA* 101, 8620-8624 (2004).

118. Phillips, J. E. & Corces, V. G. CTCF: master weaver of the genome. *Cell* 137, 1194-1211 (2009).

119. Giles, K. E., Gowher, H., Ghirlando, R., Jin, C. & Felsenfeld, G. Chromatin boundaries, insulators, and long-range interactions in the nucleus. *Cold Spring Harbor symposia on quantitative biology* 75, 79-85 (2010).

120. Barski, A., Cuddapah, S., Cui, K., Roh, T. Y., Schones, D. E., Wang, Z., Wei, G., Chepelev, I. & Zhao, K. High-resolution profiling of histone methylations in the human genome. *Cell* 129, 823-837 (2007).

121. Wang, H., Maurano, M. T., Qu, H., Varley, K. E., Gertz, J., Pauli, F., Lee, K., Canfield, T., Weaver, M., Sandstrom, R., Thurman, R. E., Kaul, R., Myers, R. M. & Stamatoyannopoulos, J. A. Widespread plasticity in CTCF occupancy linked to DNA methylation. *Genome research* 22, 1680-1688 (2012).

122. Schmidt, D., Schwalie, P. C., Wilson, M. D., Ballester, B., Goncalves, A., Kutter, C., Brown, G. D., Marshall, A., Flicek, P. & Odom, D. T. Waves of retrotransposon expansion remodel genome organization and CTCF binding in multiple mammalian lineages. *Cell* 148, 335-348 (2012).

123. Renda, M., Baglivo, I., Burgess-Beusse, B., Esposito, S., Fattorusso, R., Felsenfeld, G. & Pedone, P. V. Critical DNA binding interactions of the insulator protein CTCF: a small number of zinc fingers mediate strong binding, and a single finger-DNA interaction controls binding at imprinted loci. *J Biol Chem* 282, 33336-33345 (2007).

124. Dickson, J., Gowher, H., Strogantsev, R., Gaszner, M., Hair, A., Felsenfeld, G. & West, A. G. VEZF1 elements mediate protection from DNA methylation. *PLoS Genet* 6, e1000804 (2010).

125. Li, C. L., Xiong, D., Stamatoyannopoulos, G. & Emery, D. W. Genomic and functional assays demonstrate reduced gammaretroviral vector genotoxicity associated with use of the cHS4 chromatin insulator. *Mol Ther* 17, 716-724 (2009).

126. Lisowski, L. & Sadelain, M. Locus control region elements HS1 and HS4 enhance the therapeutic efficacy of globin gene transfer in beta-thalassemic mice. *Blood* 110, 4175-4178 (2007).

127. Nagel, R. L., Bookchin, R. M., Johnson, J., Labie, D., Wajcman, H., Isaac-Sodeye, W. A., Honig, G. R., Schiliro, G., Crookston, J. H. & Matsutomo, K. Structural bases of the inhibitory effects of hemoglobin F and hemoglobin A2 on the polymerization of hemoglobin S. *Proc Natl Acad Sci USA* 76, 670-672 (1979).

128. Sadelain et al., *Proc. Nat'l Acad. Sci. (USA)* (1995); 92:6728-6732.

129. Armstrong, J. A., Emerson, B. M., 1996. NFE2 disrupts chromatin structure at human fl-globin locus control region hypersensitive site 2 in vitro. *Mol. Cell. Biol.* 16, 5634-5644.

130. Caterina, J. J., Ciavatta, D. J., Donze, D., Behringer, R. R., Townes, T. M., 1994. Multiple elements in human fl-globin locus control region 5' HS2 are involved in enhancer activity and position-independent transgene expression. *Nucleic Acids Res.* 22, 1006 1011.

131. Moi, P., Kan, Y. W., 1990. Synergistic enhancement of globin gene expression by activator protein-1-like proteins. *Proc. Natl. Acad, Sci. USA* 87, 9000-9004.

132. Ney, P., Sorrentino, B., McDonagh, K., Nienhuis, A., 1990. Tandem AP-1-binding sites within the human /j-globin dominant control region function as an inducible enhancer in erythroid cells. *Genes Dev.* 4, 993 1006.

133. Shivdasani, R. A., Rosenblatt, M. F., Zucker-Franklin, D., Jackson, C. W., Hunt, P., Saris, C. J. M., Orkin, S. H., 1995. Transcription factor NF-E2 is required for platelet formation independent of the actions of thrombopoietin/MGDF in megakaryocyte development. *Cell* 81, 695-704.

134. Talbot, D., Grosveld, F., 1991. The 5'HS2 of the globin locus control region enhances transcription through the interaction of a multimeric complex binding at two functionally distinct NF-E2 binding sites. *EMBO J.* 10, 1391-1398.

135. Hardison et al., *Gene* (1997); 205:73-94.

136. Elnitski et al., *The Journal of Biological Chemistry* (1997); 272(1):369-378; Horak et al., *PNAS* (2002); 99(5):2924-2929.

137. Shimotsuma et al., *Journal of Biological Chemistry* (2010); 285(19):14495-14503.

From the foregoing description, it will be apparent that variations and modifications may be made to the presently disclosed subject matter described herein to adopt it to various usages and conditions. Such embodiments are also within the scope of the following claims.

All patents and publications and sequences referred to by accession or reference number mentioned in this specification are herein incorporated by reference to the same extent as if each independent patent and publication and sequence was specifically and individually indicated to be incorporated by reference.

What is claimed is:

1. An expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, and wherein the β-globin LCR comprises:
  (a) a HS2 region consisting of nucleotides 45-860 of SEQ ID NO: 9, a HS3 region consisting of the nucleotide sequence set forth in SEQ ID NO: 5, and a HS4 region consisting of nucleotides 115-868 of SEQ ID NO: 6;
  (b) a HS2 region consisting of the nucleotide sequence set forth in SEQ ID NO: 33, a HS3 region consisting of the nucleotide sequence set forth in SEQ ID NO: 34, and a HS4 region consisting of the nucleotide sequence set forth in SEQ ID NO: 35;
  (c) a HS1 region consisting of the nucleotide sequence set forth in SEQ ID NO: 3, a HS2 region consisting of nucleotides 45-860 of SEQ ID NO: 9, a HS3 region consisting of the nucleotide sequence set forth in SEQ ID NO: 5, and a HS4 region consisting of nucleotides 115-868 of SEQ ID NO: 6; or
  (d) a HS1 region consisting of the nucleotide sequence set forth in SEQ ID NO: 3, a HS2 region consisting of the nucleotide sequence set forth in SEQ ID NO: 33, a HS3 region consisting of the nucleotide sequence set forth in SEQ ID NO: 34, and a HS4 region consisting of the nucleotide sequence set forth in SEQ ID NO: 35.

2. An expression cassette comprising a globin gene or a functional portion thereof operably linked to a β-globin locus control region (LCR) that comprises a HS1 region, a HS3 region, and a HS4 region and does not comprise a core sequence of HS2 region, wherein the HS4 region has a length of less than about 800 bp and does not comprise the nucleotide sequence set forth in SEQ ID NO:50, wherein the β-globin LCR comprises:
  (a) a HS1 region consisting of the nucleotide sequence set forth in SEQ ID NO: 3, a HS3 region consisting of the nucleotide sequence set forth in SEQ ID NO: 5, and a HS4 region consisting of nucleotides 115-868 of SEQ ID NO: 6; or
  (b) a HS1 region consisting of the nucleotide sequence set forth in SEQ ID NO: 3, a HS3 region consisting of the nucleotide sequence set forth in SEQ ID NO: 34, and a HS4 region consisting of the nucleotide sequence set forth in SEQ ID NO: 35.

3. An expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, wherein the β-globin LCR comprises; a HS2 region consisting of nucleotides 45-860 of SEQ ID NO: 9, a HS3 region consisting of the nucleotide sequence set forth in SEQ ID NO: 5, and a HS4 region consisting of nucleotides 115-868 of SEQ ID NO: 6.

4. An expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, and wherein the β-globin LCR comprises; a HS2 region consisting of the nucleotide sequence set forth in SEQ ID NO: 33, a HS3 region consisting of the nucleotide sequence set forth in SEQ ID NO: 34, and a HS4 region consisting of the nucleotide sequence set forth in SEQ ID NO: 35.

5. An expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, and wherein the β-globin LCR comprises; a HS1 region consisting of the nucleotide sequence set forth in SEQ ID NO: 3, a HS2 region consisting of nucleotides 45-860 of SEQ ID NO: 9, a HS3 region consisting of the nucleotide sequence set forth in SEQ ID NO: 5, and a HS4 region consisting of nucleotides 115-868 of SEQ ID NO: 6.

6. An expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, and wherein the β-globin LCR comprises; a HS1 region consisting of the nucleotide sequence set forth in SEQ ID NO: 3, a HS2 region consisting of the nucleotide sequence set forth in SEQ ID NO: 33, a HS3 region consisting of the nucleotide sequence set forth in SEQ ID NO: 34, and a HS4 region consisting of the nucleotide sequence set forth in SEQ ID NO: 35.

7. An expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, and wherein the β-globin LCR consists essentially of; a HS2 region consisting of nucleotides 45-860 of SEQ ID NO: 9, a HS3 region consisting of the nucleotide sequence set forth in SEQ ID NO: 5, and a HS4 region consisting of nucleotides 115-868 of SEQ ID NO: 6.

8. An expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, and wherein the β-globin LCR consists essentially of; a HS2 region consisting of the nucleotide sequence set forth in SEQ ID NO: 33, a HS3 region consisting of the nucleotide sequence set forth in SEQ ID NO: 34, and a HS4 region consisting of the nucleotide sequence set forth in SEQ ID NO: 35.

9. An expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, and wherein the β-globin LCR consists essentially of; a HS1 region consisting of the nucleotide sequence set forth in SEQ ID NO: 3, a HS2 region consisting of nucleotides 45-860 of SEQ ID NO: 9, a HS3 region consisting of the nucleotide sequence set forth in SEQ ID NO: 5, and a HS4 region consisting of nucleotides 115-868 of SEQ ID NO: 6.

10. An expression cassette comprising a globin gene or a functional portion thereof operably linked to a β-globin locus control region (LCR) that comprises a Dnase I hypersensitive site-2 (HS2) region, a Dnase I hypersensitive site-3 (HS3) region, and a Dnase I hypersensitive site-4 (HS4) region, wherein the HS4 region has a length of less than about 800 bp and does not comprise the nucleotide sequence set forth in SEQ ID NO: 50, wherein the β-globin LCR consists essentially of; a HS1 region consisting of the nucleotide sequence set forth in SEQ ID NO: 3, a HS2 region consisting of the nucleotide sequence set forth in SEQ ID NO: 33, a HS3 region consisting of the nucleotide sequence set forth in SEQ ID NO: 34, and a HS4 region consisting of the nucleotide sequence set forth in SEQ ID NO: 35.

11. An expression cassette comprising a globin gene or a functional portion thereof operably linked to a β-globin locus control region (LCR) that comprises a HS1 region, a HS3 region, and a HS4 region and does not comprise a core sequence of HS2 region, wherein the HS4 region has a length of less than about 800 bp and does not comprise the nucleotide sequence set forth in SEQ ID NO:50, and wherein the β-globin LCR comprises; a HS1 region consisting of the nucleotide sequence set forth in SEQ ID NO: 3, a HS3 region consisting of the nucleotide sequence set forth in SEQ ID NO: 5, and a HS4 region consisting of nucleotides 115-868 of SEQ ID NO: 6.

12. An expression cassette comprising a globin gene or a functional portion thereof operably linked to a β-globin locus control region (LCR) that comprises a HS1 region, a HS3 region, and a HS4 region and does not comprise a core sequence of HS2 region, wherein the HS4 region has a length of less than about 800 bp and does not comprise the nucleotide sequence set forth in SEQ ID NO:50, and wherein the β-globin LCR comprises; a HS1 region consisting of the nucleotide sequence set forth in SEQ ID NO: 3, a HS3 region consisting of the nucleotide sequence set forth in SEQ ID NO: 34, and a HS4 region consisting of the nucleotide sequence set forth in SEQ ID NO: 35.

13. An expression cassette comprising a globin gene or a functional portion thereof operably linked to a β-globin locus control region (LCR) that comprises a HS1 region, a HS3 region, and a HS4 region and does not comprise a core sequence of HS2 region, wherein the HS4 region has a length of less than about 800 bp and does not comprise the nucleotide sequence set forth in SEQ ID NO:50, and wherein the β-globin LCR consists essentially of; a HS1 region consisting of the nucleotide sequence set forth in SEQ ID NO: 3, a HS3 region consisting of the nucleotide sequence set forth in SEQ ID NO: 5, and a HS4 region consisting of nucleotides 115-868 of SEQ ID NO: 6.

14. An expression cassette comprising a globin gene or a functional portion thereof operably linked to a β-globin locus control region (LCR) that comprises a HS1 region, a HS3 region, and a HS4 region and does not comprise a core sequence of HS2 region, wherein the HS4 region has a length of less than about 800 bp and does not comprise the nucleotide sequence set forth in SEQ ID NO:50, and wherein the β-globin LCR consists essentially of; a HS1 region consisting of the nucleotide sequence set forth in SEQ ID NO: 3, a HS3 region consisting of the nucleotide sequence set forth in SEQ ID NO: 34, and a HS4 region consisting of the nucleotide sequence set forth in SEQ ID NO: 35.

* * * * *